US006878700B1

(12) United States Patent
Link et al.

(10) Patent No.: US 6,878,700 B1
(45) Date of Patent: Apr. 12, 2005

(54) CELL ADHESION-INHIBITING ANTIINFLAMMATORY AND IMMUNE-SUPPRESSIVE COMPOUNDS

(75) Inventors: James Link, Evanston, IL (US); Gang Liu, Gurnee, IL (US); ZhongHua Pei, Libertyville, IL (US); Tom von Geldern, Richmond, IL (US); Martin Winn, Deerfield, IL (US); Zhili Xin, Lake Bluff, IL (US); Steven A. Boyd, Mundelein, IL (US); Gui-Dong Zhu, Gurnee, IL (US); Jennifer C. Freeman, Grayslake, IL (US); Indrani W. Gunawardana, Libertyville, IL (US); Michael A. Staeger, Greenfield, WI (US); Hwan-Soo Jae, Glencoe, IL (US); John K. Lynch, Kenosha, WI (US); Sheldon Wang, Carmel, IN (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/541,795

(22) Filed: Mar. 31, 2000

Related U.S. Application Data

(63) Continuation-in-part of application No. 09/474,517, filed on Dec. 29, 1999.
(60) Provisional application No. 60/114,097, filed on Dec. 29, 1998.

(51) Int. Cl.[7] .................... A61K 31/33; A61K 31/415; C07D 265/30; C07D 221/02; C07D 319/00
(52) U.S. Cl. .................... 514/183; 514/295; 514/395; 514/415; 514/712; 544/106; 544/253; 544/283; 544/282; 546/183; 548/306.4; 549/362; 549/469
(58) Field of Search .................... 514/183, 295, 514/395, 415, 712; 544/106, 253, 283, 282; 546/183; 548/306.4; 549/362, 469; 568/38, 58

(56) References Cited

U.S. PATENT DOCUMENTS

| 4,808,582 A | * | 2/1989 | Platel et al. ............... 514/212 |
|---|---|---|---|
| 4,973,599 A | | 11/1990 | Gilman et al. ............. 514/398 |
| 5,028,629 A | | 7/1991 | Hite et al. .................. 514/575 |
| 5,208,253 A | | 5/1993 | Boschelli et al. .......... 574/443 |
| 5,776,951 A | | 7/1998 | Arrowsmith et al. ...... 514/328 |
| 5,817,862 A | | 10/1998 | Poetsch et al. |
| 5,883,106 A | | 3/1999 | Stevens et al. ............ 514/277 |
| 5,883,133 A | | 3/1999 | Schwark et al. ........... 514/619 |
| 5,912,266 A | | 6/1999 | Perez ....................... 514/460 |
| 6,110,922 A | * | 8/2000 | Link et al. ................. 514/259 |
| 6,329,362 B1 | | 12/2001 | Archibald et al. ......... 514/188 |

FOREIGN PATENT DOCUMENTS

| DE | 2123383 | | 12/1971 |
|---|---|---|---|
| DE | 4030041 | * | 3/1992 |
| EP | 0081321 | * | 6/1983 |
| EP | 0219756 | | 10/1986 |
| EP | 722928 | * | 7/1996 |
| EP | 835 867 | | 4/1998 |
| EP | 887 340 | | 12/1998 |
| GB | 2 117 760 A | | 10/1983 |
| JP | 12072766 | | 3/2000 |
| WO | 9813347 | * | 4/1998 |
| WO | 9822423 | * | 5/1998 |
| WO | WO98/39303 | | 9/1998 |
| WO | 98/54207 | | 12/1998 |
| WO | 9911258 | | 3/1999 |
| WO | WO99/20617 | | 4/1999 |
| WO | WO99/20618 | | 4/1999 |
| WO | WO99/49856 | | 10/1999 |
| WO | WO00/15604 | | 3/2000 |
| WO | WO00/15645 | | 3/2000 |
| WO | WO00/21920 | | 4/2000 |
| WO | WO00/48989 | | 8/2000 |
| WO | WO01/06984 | | 2/2001 |
| WO | WO01/07052 | | 2/2001 |

OTHER PUBLICATIONS

Chemical Abstract DN 117:111634, also cited as DE 4030041.*
Chemical Abstract DN 129:40990, also cited as WO 9822423.*
Chemical Abstract DN 125:167598, also cited as EP 722928.*
Franke et al,Helkvetica Chimica Acta,58/1,268–78(1975), also cited as Chemical Abstract Dn 82:124989. See CAS RN # 54875 53–5.*
Kelly et al.,PubMed Abstr.:10553036;also cited as J Immunol, 163/10,5173–7(1999).*
Zhou et al,PubMed Abstr.:11776041;also cited as Chin Med J 113/7,654–6(2000).*
Pillinger et al,PubMed Abstr.:9826736; also cited as Proc Natl Acad Sci. USA,95/24, 14540–5(1998).*
Emond et al,PubMed.Abstr.:11881994;also cited as J Med Chem.,45/6,1253–8(2002).*
Fujita et al.,PubMed Abst.:11408364;also cited as Drug Metab Dispos, 19/7,983–9(2001).*
Franke et al:"Synthetische Juvenilhormone"; Helv. Chim. Acta vol. 58 Fasc. 1 p 268–278 (1975).*
U.S. Appl. No. 09/285,477, filed Apr. 2, 1999, Staunton et al.
U.S. Appl. No. 09/285,325, filed Apr. 2, 1999, Fowler et al.
U.S. Appl. No. 09/606,770, filed Jun. 29, 2000, Link et al.
U.S. Appl. No. 09/606,717, filed Jun. 29, 2000, Wang et al.

(Continued)

*Primary Examiner*—Richard L. Raymond
*Assistant Examiner*—Sudhaker B. Patel
(74) *Attorney, Agent, or Firm*—Finnegan, Henderson, Farabow, Garrett & Dunner LLP

(57) ABSTRACT

The present invention relates to novel cinnamide compounds that are useful for treating inflammatory and immunune diseases, to pharmaceutical compositions containing these compounds, and to methods of inhibiting inflammation or suppressing immune response in a mammal.

7 Claims, No Drawings

OTHER PUBLICATIONS

U.S. Appl. No. 09/695,040, filed Oct. 24, 2000, Gunawardana.

Ali, R. et al., *Mechanisms of inflammation and Leukocyte Activation*, Med. Clin. North America (1997) 81:1–28.

Bella, J., et al., *The Structure of the Two Amino–terminal Domains of Human ICAM–1 Suggests How it Functions as a Rhinovirus Receptor and As An LFA–1 Integrin Ligand*, Proc. Natl. Acad. Sci., USA (1998) 95:4140–4145.

Binnerts, M.E., et al., *How LFA–1 Binds to Different Ligands*, Immunol. Today (1999) 20:240–245.

Boschelli, D.H., et al., *Inhibition of E–Selectin–, ICAM–1–, and VCAM–1–Mediated Cell Adhesion by Benzo(b)thiophene–, Benzofuran–, Indole–, and Naphthalene–2–Carboxamides: Identification of PD 144795 as an Anti–inflammatory Agent*, J. Med. Chem. (1995) 38:4597–4614.

Carlos, T.M., *Leukocyte–Endothelial Adhesion Molecules*, Blood (1994) 84:2068–2101.

Edwards, C.P. et al., *Mapping the Intercellular Adhesion Molecule–1 and –2 Binding Site on the Inserted Domain of Leukocyte Function–associated Antigen–1*, J. Biol. Chem. (1998) 273:28937–28944.

Emeigh, J.E., et al., *Small Molecule Antagonists of LFA–1–Mediated Cell Adhesion*, 221st ACS National Meeting, San Diego, CA, USA (2001) MEDI 256.

Fisher, K.L., et al., *Identification of the Binding Site in Intercellular Adhesion Molecule 1 for its Receptor, Leukocyte Function associated Antigen 1*, Mol. Biol. Cell (1997) 8:501–515.

Gadek, T.R., et al., *Identification and Characterization of Antagonists of the LFA–1/1CAM–1 Protein–Protein Interaction as Novel Immunomodulatory Agents*, 220th ACS National Meeting, Washington, D.C., USA (2000) MEDI 177.

Gahmberg, C.G., *Leukocyte Adhesion: CD11/CD18 Integrins and Intercullular Adhesion Molecules*, Curr. Opin. Cell Biol. (1997) 9:643–650.

Gahmberg, C.G., *Leukocyte Adhesion: Structure and Function of Human Leukocyte $\beta_2$–integrins and Their Cellular Ligands*, Eur. J. Biochem. (1997) 245:215–232.

Green, J.M., *T Cell Receptor Stimulation, But Not CD28 Costimulation, Is Dependent on LFA–1–Mediated Events*, Eur. J. Immunology (1994) 24:265–272.

Hamilton, G.S., et al., *Fluorenylalkanoic and Benzoic Acids as Novel Inhibitors of Cell Adhesion Processes in Leukocytes*, J. Med. Chem. (1995) 38:1650–1656.

Henricks, P.A., *Pharmacological modulation of cell adhesion molecules*, Eur. J. Pharmcol. (1998) 344:1–13.

Huang, C., *A Binding Interface on the I Domain of Lymphocyte Function–associated Antigen–1 (LFA–1) Required for Specific Interaction with Intercellular Adhesion Molecule 1 (ICAM–1)*, J. Biol. Chem. (1995) 270:19008–19016.

Huth, J.R., *NMR and Mutagenesis Evidence for an I Domain Allosteric Site That Regulates Lymphocyte Function–associated Antigen 1 Ligand Binding.* Proc. Natl. Acad. Sci,, USA (2000) 97:5231–5236.

Kallen, J., et al., *Structural Basis for LFA–1 Inhibition upon Lovastatin Binding to the CD1 1a I–Domain*, J. Mol. Biol. (1999) 292–1–9.

Kelly, T.A., *Cutting Edge: A Small Molecule Antagonist of LFA–1–Mediated Cell Adhesion*, J. Immunol. (1999) 163:5173–5177.

Kishimoto, T.K., *Integrins, ICAMs and Selectins: Role and Regulation of Adhesion Molecules in Neutrophil Recruitment to Inflammatory Sites*, Adv. Pharmacol. (1994) 25:117–169.

Landis, R.C., *Involvement of The "I" domain of LFA–1 in Selective Binding to Ligands ICAM–I and ICAM–3*, J. Cell Biol. (1994) 126:529–537.

Link, J.T., et al., *Discovery and SAR of Diarylsulfide Cyclopropylamide LFA–1/ICAM–1 Interaction Antagonists*, Bioorg. Med. Chem Lett. (2001) 11:973–976.

Liu, G., *Small Molecule Antagonists of the LFA–1/CAM–1 Interaction as Potential Therapeutic Agents*, Expert Opin. Ther. Patents (2001) 11(9):1383–1393.

Liu, G., et al., *Discovery of Novel P–arylthio Cinnamides as Antogonists of Leukocyte Function–associated Antigen–1/intracellular Adhesion Molecule–1 Interaction, 1. Identification of an Additional Binding Pocket Based on an Anilino Diaryl Sulfide Lead.* J. Med. Chem. (2000) 43:4025–4040.

Liu, G., et al., *Novel P–arylthio Cinnamides as Antagonists of Leukocyte Function–associated Antigen–1/intracellular Adhesion Molecule–1 Interaction. 2. Mechanism of Inhibition and Structure–based Improvement of Pharmaceutical Properties.* (2001) J. Med. Chem. 44:1202–1210.

Lu, C., et al., *An Isolated, Surface–expressed I Domain of the Integrin AI$\beta$2 Is Sufficient for Strong Adhesive Function When Locked in the Open Conformation with a Disulfide Bond.* Proc. Natl. Acad. Sci. USA (2001) 98–2387–2392.

Nakano, T., et al., *Adxanthromycins A and B, New Inhibitors of ICAM–1/ILFA–1 Mediated Cell Adhesion Molecule from Streptomyces sp. NA–148*, J. Antibos. (Tokyo) (2000) 53:12–18.

Pei, Z., et al., *Discovery of Potent Antagonists of Leukocyte Function–associated Antigen–1/intercellular Adhesion Molecule–1 Interaction. 3. Amide (C–ring) Structure–activity Relationship and Improvement of Overall Properties of Arylthio Cinnamides.* J. Med. Chem. (2001) 44:2913–2920.

Qu, A., et al., *The Role of the Divalent Cation in the Structure of the I Domain from the CD11a/CD18 Integrin*, Structure (1996) 4:931–942.

Sanfilippo, P.J., *Novel Thiazole Based Heterocycles as Inhibitors of LFA–1/ICAM–1 Mediated Cell Adhesion*, J. Med. Chem. (1995) 38:1057–1059.

Springer, T.A., *Adhesion Receptors of the Immune System*, Nature (1990) 346:425–434.

Stanley, P., et al., *The I Domain of Integrin LFA–1 interacts with ICAM–1 Domain 1 at Residue Glu–34 But Not GIn–73*, J. Biol. Chem. (1998) 273:3358–3362.

Winn, Martin et al., *Discovery of Novel p–Arylthio Cinnamides as Antagolists of Leukocyte Function–Associated Antigen–1/Intercellular Adhesion Molecule–1 Interaction. 4. Structure–Activity Relationship of Substituents on the Benzene Ring of the Cinnamide*, J. Med. Chem. (2001) 44:4393.

Zhu, G., et al., *Diels–Alder Reactions of Hexafluoro–w–butyne with 2–Heterosubstituted Furans: A Facile and General Synthesis of 1,4 Disubstituted 2,3–Di(trifluoromethyl) benzenes*, Organic Letters (2000) 2(21):3345.

Springer, T.A., 1994, *Traffic Signals for Lymphocyte Recirculation and Leukocyte Emigration: The Multistep Paradigm*, CELL, 76: 301–314.

Lawrence, M.B., Springer, T.A., 1991, *Leukocytes' Roll on a Selectin in Physiologic Flow Rate: Distinction from and Prerequisite for Adhesion Through Integrins*, CELL, 65:859–873.

Von Adrian, V., Chambers, J.D., McEnvoy, L.M. Bargatze, R.F., Arfos, K.E., Butcher, E.C., 1991, Two–Step Model of Leukocyte–Endothelial Cell Interactions in Inflammation, Proc. National Acad. Sci. USA, 88:7538–7542.
Ley, K., Gaehtgens, P., Fennie, C., Singer, M.S., Lasky, L.H., Rosen, S.D., 1991, Lectin–Like Cell Adhesion Molecule 1 Mediates Rolling in Mesenteric Venules, in vivo, BLOOD, 77:2553–2555.
Higuchi, T., Stella, V., Pro–drugs as Novel Delivery Systems, vol. 14 of the A.C.S. Symposium Series.
Roche, E.B., Bioreversible Carriers in Drug Design, American Pharmaceutical Association and Pergamon Press, 1987.
Prescott, E., Methods in Cell Biology, vol. XIV, Academic Press, New York, NY (1976), p. 33 et seq.
Berge, S.M., et al., J. Pharmaceutical Sciences, 1977, 66:1 et seq.
Kakimoto, et al., Cell Immunol 142:326–337, 1992.
Knoerzer, et al., Toxical Pathol 25:13–19, 1997.
Halloran, et al., Arthritis Rheum 39:810–819, 1996.
Schimmer, et al., J. Immunol 160: 1455–1477, 1998.
Oppenheimer–Marks, et al., J. Clin Invest 101:1261–1272, 1998.
Wegner, et al., Science 247:456–459, 1990.
Bloemen, et al., Am J. Respir Crit Care Med 153:521–529, 1996.
Wegner, et al., LUNG 170: 267–279, 1992.
Mulligan, et al., J Immunol 154:1350–1363, 1995.
Nagase, et al., Am J Respir Crit Care Med 154:504–510, 1996.
Bennet, et al., J Pharmacol Exp Ther, 280:988–1000, 1997.
Hasagawa, et al., Int Immunol, 6:831–838, 1994.
Herrold, et al., Cell Immunol, 157:489–500, 1994.
Tanaka, et al., J. Immunol, 151:5088–5095, 1993.
Kawasaki, et al., J. Immunol, 150:1074–1083, 1993.
Panes, et al., Gastroenterology, 108:1761–1769, 1995.
Hallahan, et al., Proc Natl Acad Sci USA, 94:6432–6437, 1997.
Tamiya, et al., Immunopharmacology, 29(1):53–63, 1995.
Hartman, et al., Cardiovasc Res, 30(1): 47–54, 1995.
DeMeester, et al., Transplantation, 62(10): 1477–1485, 1996.
Horgan, et al., Am J Physiol, 261(5):H1578–H1584, 1991.
Nakanishai, et al., Exp Neurol, 121:215–219, 1993.
Chopp, et al., STROKE, 25(4):869–875, 1994.
Clark, et al., NEUROSURG, 75(4): 623–627, 1991.
Gute, et al., Mol Cell Biochem, 179: 169–187, 1998.
Isobe, et al., SCIENCE, 255: 1125–1127, 1992.
Talento, et al., TRANSPLANTATION, 55: 418–422, 1993.
Cosimi, et al., J. IMMUNOL, 144: 4606–4612, 1990.
Nakao, et al., Muscle Nerve, 18:93–102, 1995.
Gorczynski, Wojcik, J. IMMUNOL, 152:2011–2019, 1994.
He, et al., Opthalmol Vis Sci, 35: 3218–3225, 1994.
Zeng, et al., TRANSPLANTATION, 58: 681–689, 1994.
Harning, et al., TRANSPLANTATION, 52: 842–845, 1991.
Aoudjit, et al., J. IMMUNOL, 161: 2333–2338, 1998.
Gross, et al., SCIENCE 281, 703–706, 1998.
Franke, et al., "Synthetische Juvenilhormone", *Helvetica Chimica Acta,* vol. 58, Fasc. 1, 1975—Nr. 32, pp. 268–278.

* cited by examiner

CELL ADHESION-INHIBITING ANTIINFLAMMATORY AND IMMUNE-SUPPRESSIVE COMPOUNDS

This application is a continuation-in-part of application Ser. No. 09/474,517, filed Dec. 29, 1999, which is a continuation-in-part of provisional Application Ser. No. 60/114,097, filed Dec. 29, 1998.

TECHNICAL FIELD

The present invention relates to compounds that are useful for treating inflammatory and immune diseases, to pharmaceutical compositions comprising these compounds, and to methods of inhibiting inflammation or suppressing immune response in a mammal.

BACKGROUND

Inflammation results from a cascade of events that includes vasodilation accompanied by increased vascular permeability and exudation of fluid and plasma proteins. This disruption of vascular integrity precedes or coincides with an infiltration of inflammatory cells. Inflammatory mediators generated at the site of the initial lesion serve to recruit inflammatory cells to the site of injury. These mediators (chemokines such as IL-8, MCP-1, MIP-1, and RANTES, complement fragments and lipid mediators) have chemotactic activity for leukocytes and attract the inflammatory cells to the inflamed lesion. These chemotactic mediators which cause circulating leukocytes to localize at the site of inflammation require the cells to cross the vascular endothelium at a precise location. This leukocyte recruitment is accomplished by a process called cell adhesion.

Cell adhesion occurs through a coordinately regulated series of steps that allow the leukocytes to first adhere to a specific region of the vascular endothelium and then cross the endothelial barrier to migrate to the inflamed tissue (Springer, T. A., 1994, "Traffic Signals for Lymphocyte Recirculation and Leukocyte Emigration: The Multistep Paradigm," Cell 76: 301–314; Lawrence, M. B., and Springer, T. A., 1991, "Leukocytes Roll on a Selectin at Physiologic Flow Rates: Distinction from and Prerequisite for Adhesion Through Integrins," Cell 65: 859–873; von Adrian, U., Chambers, J. D., McEnvoy, L. M., Bargatze, R. F., Arfos, K. E, and Butcher, E. C., 1991, "Two-Step Model of Leukocyte-Endothelial Cell Interactions in Inflammation," Proc. Natl. Acad. Sci. USA 88: 7538–7542; and Ley, K., Gaehtgens, P., Fennie, C., Singer, M. S., Lasky, L. H. and Rosen, S. D.,1991, "Lectin-Like Cell Adhesion Molecule 1 Mediates Rolling in Mesenteric Venules In Vivo," Blood 77: 2553–2555). These steps are mediated by families of adhesion molecules such as integrins, Ig supergene family members, and selectins which are expressed on the surface of the circulating leukocytes and on the vascular endothelial cells. The first step consists of leukocytes rolling along the vascular endothelial cell lining in the region of inflammation. The rolling step is mediated by an interaction between a leukocyte surface oligosaccharide, such as Sialylated Lewis-X antigen (SLe$^x$), and a selectin molecule expressed on the surface of the endothelial cell in the region of inflammation. The selectin molecule is not normally expressed on the surface of endothelial cells but rather is induced by the action of inflammatory mediators such as TNF-α and interleukin-1. Rolling decreases the velocity of the circulating leukocytes in the region of inflammation and allows the cells to more firmly adhere to the endothelial cell.

The firm adhesion is accomplished by the interaction of integrin molecules that are present on the surface of the rolling leukocytes and their counter-receptors (the Ig superfamily molecules) on the surface of the endothelial cell. The Ig superfamily molecules or CAMs (Cell Adhesion Molecules) are either not expressed or are expressed at low levels on normal vascular endothelial cells. The CAMs, like the selectins, are induced by the action of inflammatory mediators like TNF-alpha and IL-1. The final event in the adhesion process is the extravasation of leukocytes through the endothelial cell barrier and their migration along a chemotactic gradient to the site of inflammation. This transmigration is mediated by the conversion of the leukocyte integrin from a low avidity state to a high avidity state. The adhesion process relies on the induced expression of selectins and CAMs on the surface of vascular endothelial cells to mediate the rolling and firm adhesion of leukocytes to the vascular endothelium.

The interaction of the intercellular adhesion molecule ICAM-1 (cd54) on endothelial cells with the integrin LFA-1 on leukocytes plays an important role in endothelial-leukocyte contact. Leukocytes bearing high-affinity LFA-1 adhere to endothelial cells through interaction with ICAM-1, initiating the process of extravasation from the vasculature into the surrounding tissues. Thus, an agent which blocks the ICAM-1/LFA-1 interaction suppresses these early steps in the inflammatory response. Consistent with this background, ICAM-1 knockout mice have numerous abnormalities in their inflammatory responses.

The present application discloses compounds which bind to the interaction-domain (I-domain) of LFA-1, thus interrupting endothelial cell-leukocyte adhesion by blocking the interaction of LFA-1 with ICAM-1, ICAM-3, and other adhesion molecules. These compounds are useful for the treatment or prophylaxis of diseases in which leukocyte trafficking plays a role, notably acute and chronic inflammatory diseases, autoimmune diseases, tumor metastasis, allograft rejection, and reperfusion injury. The compounds of this invention are diaryl sulfides, which are substituted with a cinnamide moiety. The cinnamide functionality may be placed either ortho- or para- to the linking sulfur atom, although para-substitution is preferable. Appropriate substitution of both aromatic rings is tolerated, and can be used to modulate a variety of biochemical, physicochemical and pharmacokinetic properties. In particular the amide moiety is readily modified; a variety of secondary and tertiary amides are active, and alternatively a heterocyclic ring may be attached at this position. Modifications of this amide functionality are particularly useful in modulating physicochemical and pharmacokinetic properties.

SUMMARY OF THE INVENTION

The present application provides compounds of formula I, below,

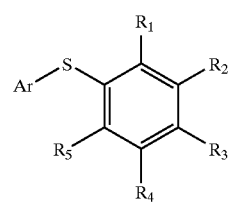

or a pharmaceutically-acceptable salt or prodrug thereof, where $R_1$, $R_2$, $R_3$, $R_4$, and $R_5$ are each independently selected from a. hydrogen,
b. halogen,
c. alkyl,
d. haloalkyl,
e. alkoxy,
f. cyano,
g. nitro,
h. carboxaldehyde,
i. heterocyclylsulfanyl,
j. "cis-cinnamide", and
k. "trans-cinnamide", where $R_1$ and $R_3$ are defined as

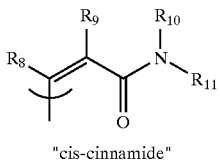 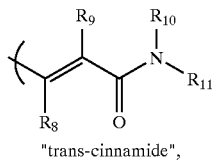

"cis-cinnamide"        "trans-cinnamide", where $R_8$ and $R_9$ are each independently selected from
a. hydrogen,
b. alkyl,
c. carboxy alkyl,
d. monoalkylaminocarbonyl alkyl, and
e. dialkylaminocarbonyl alkyl, and $R_{10}$ and $R_{11}$ are each independently selected from
a. hydrogen,
b. alkyl,
c. cycloalkyl,
d. alkoxycarbonylalkyl,
e. hydroxyalkyl,
f. substituted aryl,
g. unsubstituted heterocyclyl,
h. unsubstituted heterocyclylalkyl,
i. heterocyclylamino,
j. substituted heterocyclyl,
k. substituted heterocyclylalkyl,
l. unsubstituted aryl,
m. arylalkyl,
n. carboxyalkyl, and
o. alkoxyalkyl, or $R_{10}$ and $R_{11}$ are taken together with N to form an unsubstituted heterocyclyl or substituted heterocyclyl group, substituted by one or more than one substituent, each substitutent independently selected from
1) alkyl
2) alkoxy,
3) alkoxyalkyl,
4) cycloalkyl,
5) aryl,
6) heterocyclyl,
7) heterocyclylcarbonyl,
8) heterocyclylalkylaminocarbonyl,
9) hydroxy,
10) hydroxyalkyl,
11) hydroxyalkoxyalkyl,
12) carboxy,
13) carboxyalkyl,
14) carboxycarbonyl,
15) carboxaldehyde,
16) alkoxycarbonyl,
17) arylalkoxycarbonyl,
18) aminoalkyl,
19) aminoalkanoyl,
20) carboxamido,
21) alkoxycarbonylalkyl,
22) carboxamidoalkyl,
23) cyano,
24) unsubstituted tetrazolyl,
25) substituted tetrazolyl,
26) alkanoyl,
27) hydroxyalkanoyl,
28) alkanoyloxy,
29) alkanoylamino,
30) alkanoyloxyalkyl,
31) alkanoylaminoalkyl,
32) sulfonate,
33) alkylsulfonyl,
34) alkylsulfonylaminocarbonyl,
35) arylsulfonylaminocarbonyl,
36) heterocyclylsulfonylaminocarbonyl,
37) alkenoxycarbonyl,
38) alkoxycarbonylalkylaminocarbonyl,
39) aryl(carboxy)alkylaminocarbonyl,
40) carboxyalkylaminocarbonyl,
41) heterocyclylalkyl,
42) hydroxyalkylaminocarbonyl,
43) hydroxyaminocarbonyl,
44) hydroxy(carboxy)alkylaminocarbonyl,
45) hydroxy(carboxy)alkylcarbonyl, and
46) sulfoalkylaminocarbonyl, and where Ar is an unsubstituted aryl or unsubstituted heteroaryl group, or a substituted aryl or substituted heteroaryl group, substituted by one or more than one substituent, each substituent independently selected from
a. halogen,
b. alkyl,
c. aryl,
d. haloalkyl,
e. hydroxy,
f. alkoxy,
g. alkoxyalkyl,
h. alkoxycarbonyl,
i. alkoxyalkoxy,
j. hydroxyalkyl,
k. aminoalkyl,
l. aminocarbonyl,
m. alkyl(alkoxycarbonylalkyl)aminoalkyl,
n. unsubstituted heterocyclyl,
o. substituted heterocyclyl,
p. unsubstituted heterocyclylalkyl,
q. substituted heterocyclylalkyl,
r. carboxaldehyde,
s. carboxaldehyde hydrazone,
t. carboxamide,
u. alkoxycarbonylalkyl,
v. carboxy,
w. carboxyalkyl,
x. carboxyalkoxy,
y. carboxythioalkoxy,
z. carboxycycloalkoxy,
aa. alkylsulfanyl,
bb. hydroxycarbonylalkyl (carboxyalkyl),
cc. hydroxyalkylaminocarbonyl,
dd. cyano,
ee. amino,
ff. heterocyclylalkylamino,
gg. carboxyalkylamino,
hh. carboxyalkenyl,
ii. alkoxycarbonylalkenyl jj. heterocyclylalkylaminocarbonyl, and
kk. "trans-cinnamide",
subject to the provisos that:
i) one or more than one of $R_1$ or $R_3$ is a "cis-cinnamide" or a "trans-cinnamide", as defined above, and
ii) when R3 is a "cis-cinnamide" or a "trans-cinnamide," and $R_8$ is alkyl, then
(A) one or more than one of $R_1$, $R_2$, $R_4$, and $R_5$ is other than hydrogen when Ar is an unsubstituted aryl group, or
(B) Ar is a substituted aryl group, when all of $R_1$, $R_2$, $R_4$, and $R_5$ are hydrogen Additionally provided are methods of treatment or prophylaxis in which the inhibition of inflammation or suppression of immune response is desired, comprising administering an effective amount of a compound of formula I.

Still further provided are pharmaceutical compositions containing compounds of formula I.

DETAILED DESCRIPTION

The term "alkanoyl" as used herein refers to an alkyl group attached to the parent molecular group through a carbonyl group.

The term "alkanoylamino" as used herein refers to an alkanoyl group attached to the parent molecular group though an amino group.

The term "alkanoylaminoalkyl" as used herein refers to an alkanoylamino group attached to the parent molecular group through an alkyl group.

The term "alkanoyloxy" as used herein refers to an alkanoyl group attached to the parent molecular group through an oxygen radical.

The term "alkanoyloxyalkyl" as used herein refers to an alkanoyloxy group attached to the parent molecular group through an alkyl group.

The term "alkoxy" as used herein refers to an alkyl group attached to the parent molecular group through an oxygen atom.

The term "alkoxyalkoxy" as used herein refers to an alkoxy group attached to the parent molecular group through an alkoxy group.

The term "alkoxyalkyl" as used herein refers to an alkoxy group attached to the parent molecular group through an alkyl group.

The term "alkoxycarbonyl" as used herein refers to an alkoxy group attached to the parent molecular group through a carbonyl group.

The term "alkoxycarbonylalkyl" as used herein refers to an alkoxycarbonyl group attached to the parent molecular group through an alkyl group.

The term "alkyl" as used herein refers to a saturated straight or branched chain radical group of 1–10 carbon atoms derived from an alkane by the removal of one hydrogen. The alkyl groups of this invention can be optionally substituted with one or more than one substituent, including but not limited to, alkanoylamido, alkanoyloxy, alkoxycarbonylalkyl, alkoxy, alkoxycarbonyl, amino, aryl, arylalkyl, carboxamido, carboxy, heterocyclyl, hydroxy, hydroxyalkoxy, heterocyclyl, and sulfonate, where the aryl, and heterocyclyl groups alone, or as joined with another radical, can be optionally substituted with one or more than one substituent as described herein.

The term "alkyl(alkoxycarbonylalkyl)amino" as used herein refers to an amino group substituted with one alkyl group and one alkoxycarbonylalkyl group.

The term "alkyl(alkoxycarbonylalkyl)aminoalkyl" as used herein refers to an alkyl(alkoxycarbonylalkyl)amino group attached to the parent molecular group through an alkyl group.

The term "alkylene" as used herein refers to a divalent group of 1–10 carbon atoms derived from a straight or branched chain alkane by the removal of two hydrogen atoms.

The term "alkylsulfonyl" as used herein refers to an alkyl radical attached to the parent molecular group through an —$SO_2$— group.

The term "alkylsulfonylaminocarbonyl" as used herein refers to an alkylsulfonyl group attached to the parent molecular group through an aminocarbonyl group.

The term "amino" as used herein refers to a radical of the form —$NR_{18}R_{19}$, or to a radical of the form $NR_{18}$, where $R_{18}$ and $R_{19}$ are independently selected from hydrogen, alkyl, alkylsulfonyl, cycloalkyl, alkanoyl, alkoxyalkyl, alkoxycarbonylalkyl, hydroxy, hydroxyalkyl, hydroxy (carboxy)alkyl, aryl, arylalkyl, arylsulfonyl, aryl(carboxy) alkyl, heterocyclyl, heterocyclylalkyl, heterocyclylamino, heterocyclylsulfonyl, carboxyalkyl, and sulfoalkyl, where the alkyl, cycloalkyl, aryl, and heterocyclyl groups alone, or as joined with another radical, can be optionally substituted with one or more than one substituent as described herein.

The term "aminoalkanoyl" as used herein refers to to an amino group attached to the parent molecular group through an alkanoyl group.

The term "aminoalkyl" as used herein refers to an amino group attached to the parent molecular group through an alkyl group.

The term "aminocarbonyl" as used herein refers to an amino group attached to the parent molecular group through a carbonyl group.

The term "aryl" as used herein refers to a mono- or bicyclic carbocyclic ring system having one or two aromatic rings. The aryl group can also be fused to a cyclohexane, cyclohexene, cyclopentane or cyclopentene ring. The aryl groups of this invention, unless otherwise specified, can be optionally substituted with one or more than one substituent, including but not limited to, alkyl, haloalkyl, halogen, hydroxy, carboxy, alkoxy, alkoxyalkyl, alkoxycarbonyl, alkoxyalkoxy, hydroxyalkyl, aminoalkyl, aminocarbonyl, alkyl(alkoxycarbonylalkyl)aminoalkyl, unsubstituted heterocyclyl, substituted heterocyclyl, unsubstituted heterocyclylalkyl, substituted heterocyclylalkyl, carboxaldehyde, carboxaldehyde hydrazone, carboxamide, alkoxycarbonylalkyl, carboxyalkyl, carboxyalkoxy, carboxythioalkoxy, carboxycycloalkoxy, alkylsulfanyl, sulfonate, hydroxycarbonylalkyl (carboxyalkyl), hydroxyalkylaminocarbonyl, cyano, amino, heterocyclylalkylamino, carboxyalkylamino, carboxyalkenyl, alkoxycarbonylalkenyl, heterocyclylalkyl-aminocarbonyl, and "trans-cinnamide" substituents, where the alkyl, aryl, and heterocyclyl groups alone, or as joined with another radical, can be optionally substituted with one or more than one substituent as described herein.

The term "arylalkoxy" as used herein refers to an aryl group attached to the parent molecular group through an alkoxy group.

The term "arylalkoxycarbonyl" as used herein refers to an arylalkoxy group attached to the parent molecular group through a carbonyl group.

The term "arylsulfonyl" as used herein refers to an aryl radical attached to the parent molecular group through an —$SO_2$— group.

The term "arylsulfonylaminocarbonyl" as used herein refers to an arylsulfonyl group attached to the parent molecular group through an aminocarbonyl group.

The term "carboxaldehyde" as used herein refers to the radical —CHO.

The term "carboxaldehyde hydrazone" as used herein refers to the radical —CH=N—NR$_{20}$R$_{21}$, where R$_{20}$ and R$_{21}$ are independently selected from hydrogen, alkyl or cycloalkyl.

The terms "carboxamide" or "carboxamido" as used herein refer to an amino group attached to the parent molecular group through a carbonyl group.

The term "carboxamidoalkyl" as used herein refers to a carboxamido group attached to the parent molecular group through an alkyl group.

The term "carboxy" as used herein refers to the radical —COOH.

The term "carboxyalkyl" as used herein refers to a carboxy group attached to the parent molecular group through a alkyl group.

The term "carboxycarbonyl" as used herein refers to a carboxy group attached to the parent molecular group through a carbonyl group.

The term "cyano" as used herein refers to the radical —CN.

The term "cycloalkyl" as used herein refers to a monovalent saturated cyclic or bicyclic hydrocarbon group of 3–12 carbons derived from a cycloalkane by the removal of a single hydrogen atom. Cycloalkyl groups may be optionally substituted with alkyl, alkoxy, halo, or hydroxy substituents.

The terms "halo" or "halogen" as used herein refers to F, Cl, Br, or I.

The term "haloalkyl" as used herein refers to an alkyl group substituted with one or more halogen atoms.

The terms "heterocycle" or "heterocyclyl" represent a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" or "heterocyclic" as used herein additionally refers to bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, oxopyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, dioxaspirodecanyl, dioxotriazaspirodecanyl and the like.

Heterocyclics also include bridged bicyclic groups where a monocyclic heterocyclic group is bridged by an alkylene group such as

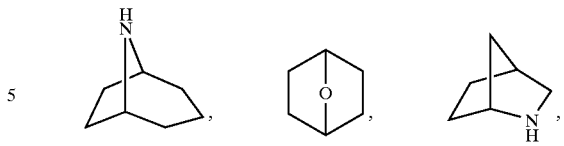

and the like.

Heterocyclics also include compounds of the formula

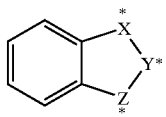

where X* and Z* are independently selected from —CH$_2$—, —CH$_2$NH—, —CH$_2$O—, —NH— and —O—, with the proviso that at least one of X* and Z* is not —CH$_2$—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, 2,3-dihydro-1H-benzimidazol-2-one and the like. The heterocycle groups of this invention, unless otherwise specified, can be optionally substituted with one or more than one substituent, including but not limited to, alkanoyl, alkanoylamino, alkanoylaminoalkyl, alkanoyloxy, alkanoyloxyalkyl, alkenoxycarbonyl, alkoxy, alkoxyalkyl, alkoxyalkoxy, alkoxyalkylaminocarbonyl, alkoxycarbonyl, alkoxycarbonylalkenyl, alkoxycarbonylalkyl, alkyl, alkyl(alkoxycarbonylalkyl)aminoalkyl, alkylsulfanyl, alkylsulfonyl, alkylsulfonylaminocarbonyl, amino, aminoalkanoyl, aminoalkyl, aminocarbonyl, aryl, arylalkoxycarbonyl, aryl(carboxy)alkylaminocarbonyl arylsulfonylaminocarbonyl, carboxaldehyde, carboxaldehyde hydrazone, carboxamide, carboxamidoalkyl, carboxy, carboxyalkoxy, carboxyalkenyl, carboxyalkyl, carboxyalkylamino, carboxyalkylaminocarbonyl, carboxycarbonyl, carboxycycloalkoxy, carboxythioalkoxy, cyano, cycloalkyl, haloalkyl, halogen, unsubstituted heterocyclyl, substituted heterocyclyl, unsubstituted heterocyclylalkyl, substituted heterocyclylalkylamino, heterocyclylalkylaminocarbonyl, heterocyclylcarbonyl, heterocyclylsulfonylaminocarbonyl, hydroxy, hydroxyalkanoyl, hydroxyalkoxyalkyl, hydroxyalkyl, hydroxyalkylaminocarbonyl, hydroxyaminocarbonyl, hydroxy(carboxy)alkylaminocarbonyl, hydroxy(carboxy)alkylcarbonyl, hydroxycarbonylalkyl(carboxyalkyl), sulfonate, unsubstituted tetrazolyl, substituted tetrazolyl, sulfoalkylaminocarbonyl, and "trans-cinnamide," substituents where the alkyl, aryl, and heterocyclyl groups alone, or as joined with another radical, can be optionally substituted with one or more than one substituent as described herein.

The term "heterocyclylalkyl" as used herein refers to an heterocyclic group attached to the parent molecular group through an alkyl group.

The term "heterocyclylalkylamino" as used herein refers to an heterocyclylalkyl group attached to the parent molecular group through an amino group.

The term "heterocyclylalkylaminocarbonyl" as used herein refers to a heterocyclylalkylamino group attached the parent molecular group through a carbonyl group.

The term "heterocyclylamino" as used herein refers to a heterocyclyl group attached to the parent molecular group through a amino group.

The term "heterocyclylcarbonyl" as used herein refers to a heterocyclyl group attached to the parent molecular group through a carbonyl group.

The term "heterocyclylsulfonyl" as used herein refers to a heterocyclyl radical attached to the parent molecular group through an —SO₂— group.

The term "heterocyclylsulfonylaminocarbonyl" as used herein refers to a heterocyclylsulfonyl group attached to the parent molecular group through an aminocarbonyl group.

The term "hydroxyalkanoyl" as used herein refers to an hydroxy radical attached to the parent molecular group through an alkanoyl group.

The term "hydroxyalkoxy" as used herein refers to an hydroxy radical attached to the parent molecular group through an alkoxy group.

The term "hydroxyalkoxyalkyl" as used herein refers to an hydroxyalkoxy group attached to the parent molecular group through an alkyl group.

The term "hydroxyalkyl" as used herein refers to an hydroxy radical attached to the parent molecular group through an alkyl group.

The term "hydroxyalkylaminocarbonyl" as used herein refers to an hydroxyalkyl group attached to the parent molecular group through an aminocarbonyl group.

The term "perfluoroalkyl" as use herein refers to an alkyl group in which all of the hydrogen atoms have been replaced by fluoride atoms.

The term "phenyl" as used herein refers to a monocyclic carbocyclic ring system having one aromatic ring. The phenyl group can also be fused to a cyclohexane or cyclopentane ring. The phenyl groups of this invention can be optionally substituted with alkyl, halogen, hydroxy or alkoxy substituents.

The term "pharmaceutically-acceptable prodrugs" as used herein represents those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "sulfonate," or "sulfo" as used herein refers to the radical —SO₃H.

The term "tetrazole" or "tetrazolyl" as used herein refers to the heterocyclic radical —CN₄H.

The term "thioalkoxy" as used herein refers to an alkyl group attached to the parent molecular group through a sulfur atom.

Compounds of the present invention can exist as stereoisomers wherein asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring. Substituents around a carbon-carbon double bond are designated as being in the Z or E configuration wherein the term "Z" represents substituents on the same side of the carbon-carbon double bond and the term "E" represents substituents on opposite sides of the carbon-carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated cis/trans.

As is apparent from the foregoing descriptions, the compounds of Formula I are useful in a variety of forms, i.e., with various substitutions as identified. Examples of particularly desirable compounds are quite diverse, and many are mentioned herein. Included are compounds in which $R_1$ is a "cis-cinnamide" or a "trans-cinnamide", and $R_3$ is hydrogen; or where $R_3$ is a "cis-cinnamide" or a "trans-cinnamide", and $R_1$ is hydrogen, or $R_1$, $R_2$, and $R_4$ are each independently hydrogen or alkyl, and $R_5$ is halogen, haloalkyl or nitro. Further preferred compounds include those as above wherein Rio and Ran are each independently hydrogen, alkyl, cycloalkyl, alkoxycarbonylalkyl, hydroxyalkyl, or heterocyclylalkyl, or where $NR_{10}R_{11}$ is heterocyclyl or substituted heterocyclyl, and where Ar is aryl, substituted aryl, heteroaryl, or substituted heteroaryl.

Compounds of the present invention include:

(2,4Dichlorophenyl)[2-(E-((6-hydroxyhexylamino)carbonyl)ethenyl)phenyl]sulfide;
(2,4Dichlorophenyl)[2-(E-((3-(1-imidazolyl)propylamino)carbonyl)ethenyl)phenyl]sulfide;
(2,4Dichlorophenyl)[2-chloro-4-(E(2-hydroxyethylamino)carbonyl)ethenyl)phenyl]sulfide;

Compounds of the present invention include:

(2,4-Dichlorophenyl)[2-(E-((6-hydroxyhexylamino)carbonyl)ethenyl)phenyl]sulfide;
(2,4-Dichlorophenyl)[2-(E-((3-(1-imidazolyl)propylamino)carbonyl)ethenyl)phenyl]sulfide;
(2,4-Dichlorophenyl)[2-chloro-4-(E-((2-hydroxyethyl-amino)carbonyl)ethenyl)phenyl]sulfide;
(2,4-Dichlorophenyl)[2-chloro-4-(E-((6-hydroxyhexyl-amino)carbonyl)ethenyl)phenyl]sulfide;
(2,4-Dichlorophenyl)[2-chloro-4-(E-((bis-(2-hydroxyethyl)amino)carbonyl)ethenyl)phenyl]sulfide;
(2,4-Dichlorophenyl)[2-chloro-4-(E-((3-(2-oxopyrrolidin-1-yl)propylamino)carbonyl)ethenyl)phenyl]sulfide;
(2,4-Dichlorophenyl)[2-chloro-4-(E-((1-morpholinyl)carbonyl)ethenyl)phenyl]sulfide;
(2,4-Dichlorophenyl)[2-chloro-4-(E-((4-methylpiperazin-1-yl)carbonyl)ethenyl)phenyl]sulfide;

(2,4-Dichlorophenyl)[2-chloro-4-(E-((4-acetylpiperazin-1-yl)carbonyl)ethenyl)phenyl]sulfide;
(2,4-Dichlorophenyl)[2-chloro-4-(E-((4-(2-pyridyl)piperazin-1-yl)carbonyl)ethenyl)phenyl]sulfide;
(2-(Hydroxymethyl)phenyl)[2-chloro-4-(E-((1-morpholinyl)carbonyl)ethenyl)phenyl]sulfide;
(2-Bromophenyl)[2-chloro-4-(E-((1-morpholinyl)carbonyl)ethenyl)phenyl]sulfide;
(2,4-Dichlorophenyl)[2-chloro-4-(E((4-(2-hydroxyethyl)piperazin-1-yl)carbonyl)ethenyl)phenyl]sulfide;
(2,4-Dichlorophenyl)[2-chloro-4-(E-((4-(2-hydroxyethoxyethyl)piperazin-1-yl)carbonyl)ethenyl)phenyl]sulfide;
(2-Bromophenyl)[2-chloro-4-(E-((3-(hydroxyethyl)piperidin-1-yl)carbonyl)ethenyl)phenyl]sulfide;
(2-Bromophenyl)[2-chloro-4-(E-((2-(hydroxymethyl)piperidin-1-yl)carbonyl)ethenyl)phenyl]sulfide;
(2-Bromophenyl)[2-chloro-4-(E-((3-acetamidopyrrolidin-1-yl)carbonyl)ethenyl)phenyl]sulfide;
(2-Bromophenyl)[2-chloro-4-(E-((4-hydroxypiperidin-1-yl)carbonyl)ethenyl)phenyl]sulfide;
(2-Bromophenyl)[2-chloro-4-(E-((piperidin-1-yl)carbonyl)ethenyl)phenyl]sulfide;
(2,4-Dichlorophenyl)[2-chloro-4-(E-((3-carboxypiperidin-1-yl)carbonyl)ethenyl)phenyl]sulfide;
(2,4-Dichlorophenyl)[2-chloro-4-E-((4-carboxypiperidin-1-yl)carbonyl)ethenyl)phenyl]sulfide;
(2-Bromophenyl)[2-chloro-4-(E-((4-acetylhomopiperazin-1-yl)carbonyl)ethenyl)phenyl]sulfide;
(2-Bromophenyl)[2-chloro-4-(E-((thiomorpholin-1-yl)carbonyl)ethenyl)phenyl]sulfide;
(2-Bromophenyl)[2-chloro-4-(E-((4-(2-oxo-2,3-dihydro-1H-benzimidazol-1-yl)piperidin-1-yl)carbonyl)ethenyl)phenyl]sulfide;
(2-Bromophenyl)[2-chloro-4-(E-((2-tetrahydroisoquinolinyl)carbonyl)ethenyl)phenyl]sulfide;
(2-Methylphenyl)[2-trifluoromethyl-4-(E-((4-acetylpiperazin-1-yl)carbonyl)ethenyl)phenyl]sulfide;
(2-Methylphenyl)[2-trifluoromethyl-4-(E-((1-morpholinyl)carbonyl)ethenyl)phenyl]sulfide;
(2-Methylphenyl)[2-trifluoromethyl-4-(E-((2-(1-morpholinyl)ethylamino)carbonyl)ethenyl)phenyl]sulfide;
(2-Methylphenyl)[2-trifluoromethyl-4-(E-((4-phenylpiperazin-1-yl)carbonyl)ethenyl)phenyl]sulfide;
(2-Methylphenyl)[2-trifluoromethyl-4-(E-((3-(2-oxopyrrolidin-1-yl)propylamino)carbonyl)ethenyl)phenyl]sulfide;
(2-Methylphenyl)[2-trifluoromethyl-4-(E-((cyclopropylamino)carbonyl)ethenyl)phenyl]sulfide;
(2,4-Dichlorophenyl)[2-nitro-4-(E-((4-acetylpiperazin-1-yl)carbonyl)ethenyl)phenyl]sulfide;
(2,4-Dichlorophenyl)[2-nitro-4-(E-((3-(2-oxopyrrolidin-1-yl)propylamino)carbonyl)ethenyl)phenyl]sulfide;
(2,3-Dichlorophenyl)[2-nitro-4-(E-((4-acetylpiperazin-1-yl)carbonyl)ethenyl)phenyl]sulfide;
(4Bromophenyl)[2-nitro-4-(E-((4-acetylpiperazin-1-yl)carbonyl)ethenyl)phenyl]sulfide;
(4-Methylphenyl)[2-nitro-4-(E-((4-acetylpiperazin-1-yl)carbonyl)ethenyl)phenyl]sulfide;
(2,4-Dichlorophenyl)[2-nitro-4-(E-((4-(tert-butoxycarbonyl)piperazin-1-yl)carbonyl)ethenyl)phenyl]sulfide;
(2,4-Dichlorophenyl)[2-nitro-4-(E-((4-(2-furoylcarbonyl)piperazin-1-yl)carbonyl)ethenyl)phenyl]sulfide;
(2,4-Dichlorophenyl)[2-nitro-4-(E-((4-(methanesulfonyl)piperazin-1-yl)carbonyl)ethenyl)phenyl]sulfide;
(2,4-Dichlorophenyl)[2-nitro-4-(E-((4-(diethylaminocarbonylmethyl)piperazin-1-yl)carbonyl)ethenyl)phenyl]sulfide;
(2,4-Dichlorophenyl)[2-nitro-4-(E-((4-(diethylaminocarbonyl)piperazin-1-yl)carbonyl)ethenyl)phenyl]sulfide;
(2,4-Dichlorophenyl)[2-nitro-4-(E-((4-(tert-butoxycarbonylmethyl)piperazin-1-yl)carbonyl)ethenyl)phenyl]sulfide;
(2,4-Dichlorophenyl)[(2-nitro-4-(E-((4-(carboxycarbonyl)piperazin-1-yl)carbonyl)ethenyl)phenyl]sulfide;
(2,4-Dichlorophenyl)[2-nitro-4-(E-((4-(carboxyethyl)piperazin-1-yl)carbonyl)ethenyl)phenyl]sulfide;
(2-Methylphenyl)[2-nitro-4-(E-((4-acetylpiperazin-1-yl)carbonyl)ethenyl)phenyl]sulfide;
(2-Chlorophenyl)[2-nitro-4-(E-((4-acetylpiperazin-1-yl)carbonyl)ethenyl)phenyl]sulfide;
(2-Aminophenyl)[2-nitro-4-(E-((4-acetylpiperazin-1-yl)carbonyl)ethenyl)phenyl]sulfide;
(2-Hydroxymethylphenyl)[2-nitro-4-(E-((4-acetylpiperazin-1-yl)carbonyl)ethenyl) phenyl]sulfide;
(2-Ethylphenyl)[2-nitro-4-(E-((4-acetylpiperazin-1-yl)carbonyl)ethenyl)phenyl]sulfide;
(2-iso-Propylphenyl)[2-nitro-4-(E-((4-acetylpiperazin-1-yl)carbonyl)ethenyl)phenyl]sulfide;
(2-tert-Butylphenyl)[2-nitro-4-(E-((4-acetylpiperazin-1-yl)carbonyl)ethenyl)phenyl]sulfide;
(2-Chlorophenyl)[2-chloro-4-(E-((4-acetylpiperazin-1-yl)carbonyl))2-propenyl)phenyl]sulfide;
(2-(1-Morpholinylmethyl)phenyl)[2-chloro-4-(E-((1-morpholinyl)carbonyl)ethenyl)phenyl]sulfide;
(2-(4-(1,3-Benzodioxolyl-5-methyl)piperazin-1-ylmethyl)phenyl)[2-chloro-4-(E-((1-morpholinyl)carbonyl)ethenyl)phenyl]sulfide;
(2-(4-(iso-Propylaminocarbonylmethyl)piperazin-1-ylmethyl)phenyl)[2-chloro-4-(E-((1-morpholinyl)carbonyl)ethenyl)phenyl]sulfide;
(2-((N-Ethoxycarbonylmethyl-N-methyl)aminomethyl)phenyl)[2-chloro-4-(E-((1-morpholinyl)carbonyl)ethenyl)phenyl]sulfide;
(2-Formylphenyl)[2-chloro-4-(E-((1-morpholinyl)carbonyl)ethenyl)phenyl]sulfide;
(2-(4-Formylpiperazin-1-ylmethyl)phenyl)[2-chloro-4-(E-((1-morpholinyl)carbonyl)ethenyl)phenyl]sulfide;
(2-(E-((1-Morpholinyl)carbonyl)ethenyl)phenyl)[2-chloro-4-(E-((1-morpholinyl)carbonyl)ethenyl)phenyl]sulfide;
(2-Formylphenyl)[2-nitro-4-(E-((4-acetylpiperazin-1-yl)carbonyl)ethenyl)phenyl]sulfide;
(2-Formylphenyl)[2-chloro-4-(E-((1-morpholinyl)carbonyl)ethenyl)phenyl]sulfide, N,N-dimethyl hydrazone;
(2-((3-(1-Morpholinyl)propyl)-1-amino)phenyl)[2-chloro-4-(E-((1-morpholinyl)carbonyl)ethenyl)phenyl]sulfide;
(2,4-Dichlorophenyl)[2-bromo-4-(E-((3-(2-oxopyrrolidin-1-yl)propylamino)carbonyl)ethenyl)phenyl]sulfide;
(2,4-Dichlorophenyl)[2-formyl-4-(E-((1-morpholinyl)carbonyl)ethenyl)phenyl]sulfide;
(2-Chloro-6-formylphenyl)[2-chloro-4-(E-((4-acetylpiperazin-1-yl)carbonyl)ethenyl)phenyl]sulfide;
(2-Cyanophenyl)[2-chloro-4-(E-((4-acetylpiperazin-1-yl)carbonyl)ethenyl)phenyl]sulfide;
(2-Isopropylphenyl)[2-cyano-4-(E-(morpholin-1-yl)carbonyl)ethenyl)phenyl]sulfide;
(2-Bromophenyl)[2-nitro-4-(E-((4-acetylpiperazin-1-yl)carbonyl)ethenyl)phenyl]sulfide;
(2-(Pyrrolidin-1-yl)phenyl)[2-chloro-4-(E-((morpholin-1-yl)carbonyl)ethenyl)phenyl]sulfide;
(2-Methoxyphenyl)-[2-chloro-4-(E-[(morpholin-1-yl)carbonyl]ethenyl)phenyl]sulfide;

(2-Isopropylphenyl)[2-nitro-4-(E-((3-carbomethoxy-piperazin-1-yl)carbonyl)ethenyl)phenyl]sulfide;
(2-Methylphenyl)[2-nitro-4-(E-((3-carboxamido-4-carbobenzoxypiperazin-1-yl)carbonyl)ethenyl)phenyl]sulfide;
(2-Isopropylphenyl)[2-nitro-4-(E-((2-carbomethoxy-4-tert-butoxycarbonylpiperazin-1-yl)carbonyl)ethenyl)phenyl]sulfide;
(2-Isopropylphenyl)[2-nitro-4-(E-((2-carboxy-4-tert-butoxycarbonylpiperazin-1-yl)carbonyl)ethenyl)phenyl]sulfide;
(2-Isopropylphenyl)[2-trifluoromethyl-4-(E-((4-acetylpiperazin-1-yl)carbonyl)ethenyl)phenyl]sulfide;
(2-Isopropylphenyl)[2-trifluoromethyl-4-(E-((morpholin-1-yl)carbonyl)ethenyl)phenyl]sulfide;
(2-Isopropylphenyl)[2-trifluoromethyl-4-(E-((3-(2-oxopyrrolidin-1-yl)prop-1-ylamino)carbonyl)ethenyl)phenyl]sulfide;
(2-Isopropylphenyl)[2-trifluoromethyl-4-(E-((cyclobutylamino)carbonyl)ethenyl)phenyl]sulfide;
(2-Isopropylphenyl)[2-trifluoromethyl-4-(E-((cyclopentylamino)carbonyl)ethenyl)phenyl]sulfide;
(2-Isopropylphenyl)[2-trifluoromethyl-4-(E-((5-hydroxypent-1-ylamino)carbonyl)ethenyl)phenyl]sulfide;
(2-Isopropylphenyl)[2-nitro-4-(E-((3-carbomethoxy-4-acetylpiperazin-1-yl)carbonyl)ethenyl)phenyl]sulfide;
(2-Biphenyl)[2-chloro-4-(E-((morpholin-1-yl)carbonyl)ethenyl)phenyl]sulfide;
(3,4-Dimethylphenyl)[2-nitro-4-(E-((4-acetylpiperazin-1-yl)carbonyl)ethenyl)phenyl]sulfide;
(2-Bromophenyl)[2-trifluoromethyl-4-(E-((4-acetylpiperazin-1-yl)carbonyl)ethenyl)phenyl]sulfide;
(5-Indolyl)[2-chloro-4-(E-((4-acetylpiperazin-1-yl)carbonyl)ethenyl)phenyl]sulfide;
(5-Benzodioxolyl)[2-chloro-4-(E-((4-acetylpiperazin-1-yl)carbonyl)ethenyl)phenyl]sulfide;
(2-Isopropylphenyl)[2-nitro-4-(E-((2-carbomethoxy-piperazin-1-yl)carbonyl)ethenyl)phenyl]sulfide;
(2,3-Dimethoxyphenyl)-[2-chloro-4-(E-[(morpholin-1-yl)carbonyl]ethenyl)phenyl]sulfide;
(2-Fluorophenyl)[2-nitro-4-(E-((4-acetylpiperazin-1-yl)carbonyl)ethenyl)phenyl]sulfide;
(2-Bromophenyl)[2-trifluoromethyl-4-(E-((4-(tert-butoxycarbonyl)piperazin-1-yl)carbonyl)ethenyl)phenyl]sulfide;
(2-(Pyrrolidin-1-yl)phenyl)[2-trifluoromethyl-4-(E-((4-(tert-butoxycarbonyl)piperazin-1-yl)carbonyl)ethenyl)phenyl]sulfide;
(3-Carboxamidophenyl)[2-nitro-4-(E-((4-acetylpiperazin-1-yl)carbonyl)ethenyl)phenyl]sulfide;
(3-(Hydroxymethyl)phenyl)[2-nitro-4-(E-((4-acetylpiperazin-1-yl)carbonyl)ethenyl)phenyl]sulfide;
Phenyl[2-trifluoromethyl-4-(E-((4-(tert-butoxycarbonyl)piperazin-1-yl)carbonyl)ethenyl)phenyl]sulfide;
(2-Isopropylphenyl)[2-trifluoromethyl-4-(E-((2-carbomethoxy-4-(tert-butoxycarbonyl)piperazin-1-yl)carbonyl)ethenyl)phenyl]sulfide;
(2-Isopropylphenyl)[2-nitro-4-(E-((3-(pyridine-4-methylaminocarbonyl)-4-tert-butoxycarbonylpiperazin-1-yl)carbonyl)ethenyl)phenyl]sulfide;
(2-Ethoxyphenyl)-[2-chloro-4-(E-[(morpholin-1-yl)carbonyl]ethenyl)phenyl]sulfide;
(2-Methoxyphenyl)[2-nitro-4-(E-((4-acetylpiperazin-1-yl)carbonyl)ethenyl)phenyl]sulfide;
(2-(Azetidin-1-yl)phenyl)[2-trifluoromethyl-4-(E-((4-(tert-butoxycarbonyl)piperazin-1-yl)carbonyl)ethenyl)phenyl]sulfide;
(2-(Piperidin-1-yl)phenyl)[2-trifluoromethyl-4-(E-((4-(tert-butoxycarbonyl)piperazin-1-yl)carbonyl)ethenyl)phenyl]sulfide;
(3-Chloro-2-formylphenyl)[2-chloro-4-(E-((4-acetylpiperazin-1-yl)carbonyl)ethenyl)phenyl]sulfide;
(2-Trifluoromethylphenyl)[2-trifluoromethyl-4-(E-((4-acetylpiperazin-1-yl)carbonyl)ethenyl)phenyl]sulfide;
(3-Bromophenyl)[2-trifluoromethyl-4-(E-((4-acetylpiperazin-1-yl)carbonyl)ethenyl)phenyl]sulfide;
(3,5-Dimethylphenyl)[2-trifluoromethyl-4-(E-((4-acetylpiperazin-1-yl)carbonyl)ethenyl)phenyl]sulfide;
(2-Isopropylphenyl)[2-nitro-4-(E-((3-dimethylamino-carbonyl-4-(pyridine-4-carbonyl)piperazin-1-yl)carbonyl)ethenyl)phenyl]sulfide;
(2-Isopropylphenyl)[2-nitro-4-(E-((3-dimethylamino-carbonyl-4-carbomethoxypiperazin-1-yl)carbonyl)ethenyl)phenyl]sulfide;
(2-Isopropylphenyl)[2-nitro-4-(E-((3-dimethylamino-carbonyl-4-acetylpiperazin-1-yl)carbonyl)ethenyl)phenyl]sulfide;
(2-Isopropylphenyl)[2-nitro-4-(E-((3-(1-morpholino-carbonyl)-4-tert-butoxycarbonylpiperazin-1-yl)carbonyl)ethenyl)phenyl]sulfide;
(2-Isopropylphenyl)[2-nitro-4-(E-((3-(pyridine-4-methylaminocarbonyl)piperazin-1-yl)carbonyl)ethenyl)phenyl]sulfide;
(2-Isopropylphenyl)[2-nitro-4-(E-(((3-dimethylamino-carbonyl)piperazin-1-yl)carbonyl)ethenyl)phenyl]sulfide;
(2-Isopropylphenyl)[2nitro-4-(E-((3-(benzylamino-carbonyl)-4-tert-butoxycarbonylpiperazin-1-yl)carbonyl)ethenyl)phenyl]sulfide;
(2-Isopropylphenyl)[2-nitro-4-(E-((3-(dimethylamino-carbonyl)-4-tert-butoxycarbonylpiperazin-1-yl)carbonyl)ethenyl)phenyl]sulfide;
(2-Bromophenyl)[2-chloro-4-(E-((3-(5S-hydroxymethyl-2-oxopyrrolidin-1-yl)prop-1-ylamino)carbonyl)ethenyl)phenyl]sulfide;
(2-Bromophenyl)[2-chloro-4-(E-((3-(2-oxopyrrolidin-1-yl)prop-1-ylamino)carbonyl)ethenyl)phenyl]sulfide;
(2-Bromophenyl)[2-chloro-4-(E-(N-methyl-N-(3-(2-oxopyrrolidin-1-yl)prop-1-yl)amino)carbonyl)ethenyl)phenyl]sulfide;
(2-[2-Methoxy]ethoxyphenyl)-[2-chloro-4-(E-[(morpholin-1-yl)carbonyl]ethenyl)phenyl]sulfide;
(2-Isopropylphenyl)[2-nitro-4-E-((3-(morpholinocarbonyl)piperazin-1-yl)carbonyl)ethenyl)phenyl]sulfide;
(2-Isopropylphenyl)[2-nitro-4E-((4-tert-butoxycarbonyl-piperazin-1-yl)carbonyl)ethenyl)phenyl]sulfide;
(2-Isopropylphenyl)[2-nitro-4-(E-((4-methoxycarbonyl-piperazin-1-yl)carbonyl)ethenyl)phenyl]sulfide;
(2-Isopropylphenyl)[2-nitro-4-(E-(4-(pyridine-4-carbonyl)piperazin-1-yl)carbonyl)ethenyl)phenyl]sulfide;
(2-Isopropylphenyl)[2-nitro-4-(E-((3-(pyridine-3-methylaminocarbonyl)-4-tert-butoxycarbonylpiperazin-1-yl)carbonyl)ethenyl)phenyl]sulfide;
(2-Isopropylphenyl)[2-nitro-4-(E-((3-(pyridine-2-methylaminocarbonyl)piperazin-1-yl)carbonyl)ethenyl)phenyl]sulfide;
(2-Isopropylphenyl)[2-nitro-4-(E-((3-(pyridine-3-methylaminocarbonyl)piperazin-1-yl)carbonyl)ethenyl)phenyl]sulfide;
(4-Hydroxyphenyl)[2-nitro-4-(E-((4-acetylpiperazin-1-l)carbonyl)ethenyl)phenyl]sulfide;

(3,5-Dichlorophenyl)[2-nitro-4-(E-((4-acetylpiperazin-1-yl)carbonyl)ethenyl)phenyl]sulfide;
(2-Bromophenyl)[2-chloro-4-(E-((3-(5S-acetoxymethyl-2-oxopyrrolidin-1-yl)prop-1-ylamino)carbonyl)ethenyl)phenyl]sulfide;
(2-Bromophenyl)[2-chloro-4-(E-((3-(5S-methoxymethyl-2-oxopyrrolidin-1-yl)prop-1-ylamino)carbonyl)ethenyl)phenyl]sulfide;
(2-Bromophenyl)[2-chloro-4-(E-((3-(4R-hydroxy-2-oxopyrrolidin-1-yl)prop-1-ylamino)carbonyl)ethenyl)phenyl]sulfide;
Phenyl[2-nitro-4-(E-((4-acetylpiperazin-1-yl)carbonyl)ethenyl)phenyl]sulfide;
(2-Dimethylaminophenyl)[2-nitro-4-(E-((4-acetylpiperazin-1-yl)carbonyl)ethenyl)phenyl]sulfide;
(3-((2-Hydroxyethyl)aminocarbonyl)phenyl)[2-nitro-4-(E-((4-acetylpiperazin-1-yl)carbonyl)ethenyl)phenyl]sulfide;
(3-((3-(1-Imidazolyl)propyl)aminocarbonyl)phenyl)[2-nitro-4-(E-((4-acetylpiperazin-1-yl)carbonyl)ethenyl)phenyl]sulfide;
(3-((2-(1-Morpholinyl)ethyl)aminocarbonyl)phenyl)[2-nitro-4-(E-((4-acetylpiperazin-1-yl)carbonyl)ethenyl)phenyl]sulfide;
(2-Isopropylphenyl)[2-nitro-4-(E-((3-hydroxymethyl-4-tert-butoxycarbonylpiperazin-1-yl)carbonyl)ethenyl)phenyl]sulfide;
(2-Isopropylphenyl)[2-nitro-4-(E-((4-formylpiperazin-1-yl)carbonyl)ethenyl)phenyl]sulfide;
(2-Isopropylphenyl)[2-nitro-4-(E-((2-hydroxymethyl-4-tert-butoxycarbonylpiperazin-1-yl)carbonyl)ethenyl)phenyl]sulfide;
(2-Ethoxyphenyl)-[2-chloro-4-(E-[(3-ethoxycarbonyl-piperidin-1-yl)carbonyl]ethenyl)phenyl]sulfide;
(3-Aminophenyl)[2-nitro-4-(E-((4-acetylpiperazin-1-yl)carbonyl)ethenyl)phenyl]sulfide;
(4-Aminophenyl)[2-nitro-4-(E-((4-acetylpiperazin-1-yl)carbonyl)ethenyl)phenyl]sulfide;
(2,4-Dimethylphenyl)[2-nitro-4-(E-((4-acetylpiperazin-1-yl)carbonyl)ethenyl)phenyl]sulfide;
(2,5-Dimethylphenyl)[2-nitro-4-(E-((4-acetylpiperazin-1-yl)carbonyl)ethenyl)phenyl]sulfide;
(4-Methoxyphenyl)[2-nitro-4-(E-((4-acetylpiperazin-1-yl)carbonyl)ethenyl)phenyl]sulfide;
(3-Chlorophenyl)[2-nitro-4-(E-((4-acetylpiperazin-1-yl)carbonyl)ethenyl)phenyl]sulfide;
(2-Chloro-4,5-diaminophenyl)[2-chloro-4-(E-((4-acetylpiperazin-1-yl)carbonyl)ethenyl)phenyl]sulfide;
(3,4-Diaminophenyl)[2-chloro-4-(E-((4-acetylpiperazin-1-yl)carbonyl)ethenyl)phenyl]sulfide;
(6-Chloro-2-oxo-2,3-dihydro-1H-benzimidazol-5-yl)[2-chloro-4-(E-((4-acetylpiperazin-1-yl)carbonyl)ethenyl)phenyl]sulfide;
(1-Methylindol-7-yl)[2-chloro-4-(E-((4-acetylpiperazin-1-yl)carbonyl)ethenyl)phenyl]sulfide;
(2-Hydroxy-4-aminophenyl)[2-chloro-4-(E-((4-acetylpiperazin-1-yl)carbonyl)ethenyl)phenyl]sulfide;
(2-Isopropylphenyl)[2-nitro-4-(E-((4-methylpiperazin-1-yl)carbonyl)ethenyl)phenyl]sulfide;
(2-Isopropylphenyl)[2-nitro-4-(E-((4-(pyridine-2-carbonyl)piperazin-1-yl)carbonyl)ethenyl)phenyl]sulfide;
(2-Isopropylphenyl)[2-nitro-4-(E-((4-(pyridine-3-carbonyl)piperazin-1-yl)carbonyl)ethenyl)phenyl]sulfide;
(2-Isopropylphenyl)[2-nitro-4-(E-((2-carbomethoxy-4-methoxycarbonylpiperazin-1-yl)carbonyl)ethenyl)phenyl]sulfide;
(2-Isopropylphenyl)[2-nitro-4-(E-((2-carboxy-4-methoxycarbonylpiperazin-1-yl)carbonyl)ethenyl)phenyl]sulfide;
(2-Isopropylphenyl)[2-nitro-4-(E-((3-carbomethoxy-4-methylpiperazin-1-yl)carbonyl)ethenyl)phenyl]sulfide;
(2-Ethoxyphenyl)-[2-chloro-4-(E-[(3-carboxypiperidin-1-yl)carbonyl]ethenyl)phenyl]sulfide;
(2-Ethoxyphenyl)-[2-chloro-4-(E-[(2-ethoxycarbonyl-piperidin-1-yl)carbonyl]ethenyl)phenyl]sulfide;
(2-Ethoxyphenyl)[2-trifluoromethyl-4-(E-((1-(tert-butoxycarbonyl)-4-hydroxypyrrolidin-3-ylamino)carbonyl)ethenyl)phenyl]sulfide;
(2-Ethoxyphenyl)-[2-chloro-4-(E-[(2-carboxypiperidin-1-yl)carbonyl]ethenyl)phenyl]sulfide;
(2-Ethoxyphenyl)[2-trifluoromethyl-4-(E-(((pyrrolidin-3-ene-1-yl)carbonyl)ethenyl)phenyl]sulfide;
(2-Ethoxyphenyl)[2-trifluoromethyl-4-(E-((3-(2-oxopyrrolidin-1-yl)prop-1-ylamino)carbonyl)ethenyl)phenyl]sulfide;
(2-Ethoxyphenyl)[2-trifluoromethyl-4-(E-((4-acetylpiperazin-1-yl)carbonyl)ethenyl)phenyl]sulfide;
(2-Ethoxyphenyl)[2-trifluoromethyl-4-(E-((4-(ethoxycarbonyl)piperazin-1-yl)carbonyl)ethenyl)phenyl]sulfide;
(2-Ethoxyphenyl)[2-trifluoromethyl-4-(E-((4-(2-furylcarbonyl)piperazin-1-yl)carbonyl)ethenyl)phenyl]sulfide;
(2-Ethoxyphenyl)-[2-chloro-4-(E-[(3-ethoxycarbonyl-piperidin-1-yl)carbonyl]ethenyl)phenyl]sulfide;
(2-Ethoxyphenyl)-[2-chloro-4-(E-[(4-carboxypiperidin-1-yl)carbonyl]ethenyl)phenyl]sulfide;
(Benzodioxan-6-yl)[2-chloro-4-(E-((4-acetylpiperazin-1-yl)carbonyl)ethenyl)phenyl]sulfide;
(2-Isopropylphenyl)[2-nitro-4-(E-((4-ethoxycarbonyl-piperazin-1-yl)carbonyl)ethenyl)phenyl]sulfide;
(2-Isopropylphenyl)[2-nitro-4-(E-((4-isopropoxycarbonyl-piperazin-1-yl)carbonyl)ethenyl)phenyl]sulfide;
(2-Isopropylphenyl)[2-nitro-4-(E-((4-isobutoxycarbonyl-piperazin-1-yl)carbonyl)ethenyl)phenyl]sulfide;
(2-Isopropylphenyl)[2-nitro-4-(E-((4-((1-propen-2-oxy)carbonyl)piperazin-1-yl)carbonyl)ethenyl)phenyl]sulfide;
(2-Isopropylphenyl)[2-nitro-4-(E-((4-propionylpiperazin-1-yl)carbonyl)ethenyl)phenyl]sulfide;
(2-Isopropylphenyl)[2-nitro-4-(E-((4-carboxamidopiperazin-1-yl)carbonyl)ethenyl)phenyl]sulfide;
(2-Isopropylphenyl)[2-nitro-4-(E-((4-methylaminocarbonylpiperazin-1-yl)carbonyl)ethenyl)phenyl]sulfide;
(2-Isopropylphenyl)[2-nitro-4-(E-((4-(pyrimidin-2-yl)piperazin-1-yl)carbonyl)ethenyl)phenyl]sulfide;
(2-Isopropylphenyl)[2-nitro-4-(E-((4-hydroxyacetyl-piperazin-1-yl)carbonyl)ethenyl)phenyl]sulfide;
(2-Isopropylphenyl)[2-nitro-4-(E-((4-(pyrazine-2-carbonyl)piperazin-1-yl)carbonyl)ethenyl)phenyl]sulfide;
(2-Isopropylphenyl)[2-trifluoromethyl-4-(E-(((2-carboxypyrrol-3-ene-1-yl)carbonyl)ethenyl)phenyl]sulfide methyl ester;
(2-Isopropylphenyl)[2-nitro-4-(E-((3-hydroxymethyl-4-methylpiperazin-1-yl)carbonyl)ethenyl)phenyl]sulfide;
(2-Isopropylphenyl)[2-trifluoromethyl-4-(E-(((2-carboxypyrrol-3-ene-1-yl)carbonyl)ethenyl)phenyl]sulfide;
(2-Isopropylphenyl)[2-trifluoromethyl-4-(E-(((2-hydroxymethylpyrrolidin-1-yl)carbonyl)ethenyl)phenyl]sulfide;

(2-Isopropylphenyl)[2-nitro-4-(E-((3-methylamino-carbonyl)piperazin-1-yl)carbonyl)ethenyl)phenyl]sulfide;
(2-Isopropylphenyl)[2-nitro-4-(E-(((3-cyclopropylamino-carbonyl)piperazin-1-yl)carbonyl)ethenyl)phenyl]sulfide;
(2-Isopropylphenyl)[2-nitro-4-(E-((3-carboxamido-piperazin-1-yl)carbonyl)ethenyl)phenyl]sulfide;
(2-Isopropylphenyl)[2-nitro-4-(E-((3-carbomethoxy-4-oxopiperidin-1-yl)carbonyl)ethenyl)phenyl]sulfide;
(2-Isopropylphenyl)[2-nitro-4-(E-((3,5-dimethylpiperazin-1-yl)carbonyl)ethenyl)phenyl]sulfide;
(1-Ethylindol-7-yl)[2-chloro-4-(E-((4-acetylpiperazin-1-yl)carbonyl)ethenyl)phenyl]sulfide;
(3-[2-Methoxy]ethoxyphenyl)-[2-chloro-4-(E-[(morpholin-1-yl)carbonyl]ethenyl)phenyl]sulfide;
(2-Bromophenyl)[2-chloro-4-(E-((4,4'-S-dioxythio-morpholin-1-yl)carbonyl)ethenyl)phenyl]sulfide;
(2-Bromophenyl)[2-chloro-4-(E-(N-carbomethoxymethyl-N-(3-(2-oxopyrrolidin-1-yl)prop-1-yl)amino)carbonyl)ethenyl)phenyl]sulfide;
(2-Bromophenyl)[2-chloro-4-(E-((4-S-oxythiomorpholin-1-yl)carbonyl)ethenyl)phenyl]sulfide;
(2-Methoxy-5-chlorophenyl)[2-nitro-4-(E-((4-acetylpiperazin-1-yl)carbonyl)ethenyl)phenyl]sulfide;
(2-Isopropylphenyl)[2-nitro-4-(E-((3-acetoxymethyl)piperazin-1-yl)carbonyl)ethenyl)phenyl]sulfide;
(2-Isopropylphenyl)[2-nitro-4-(E-(3,5-dimethyl-4-acetyl-piperazin-1-yl)carbonyl)ethenyl)phenyl]sulfide;
(1-Methylindol-5-yl)[2-chloro-4-(E-((4-acetylpiperazin-1-yl)carbonyl)ethenyl)phenyl]sulfide;
(Benzodioxan-6-yl)[2-nitro-4-(E-((4-acetylpiperazin-1-yl)carbonyl)ethenyl)phenyl]sulfide;
(Benzodioxan-6-yl)[2-nitro-4-(E-((3-(2-oxopyrrolidin-1-yl)prop-1-ylamino)carbonyl)ethenyl)phenyl]sulfide;
(Benzodioxan-6-yl)[2-nitro-4-(E-((3-carboethoxypiperidin-1-yl)carbonyl)ethenyl)phenyl]sulfide;
(Benzodioxan-6-yl)[2-nitro-4-(E-((4-carboethoxypiperidin-1-yl)carbonyl)ethenyl)phenyl]sulfide;
(2-Ethoxyphenyl)[2-trifluoromethyl-4-(Z-((4-acetylpiperazin-1-yl)carbonyl)ethenyl)phenyl]sulfide;
(2-Ethoxyphenyl)[2-trifluoromethyl-4-(E-((6-methylpyrid-2-ylamino)carbonyl)ethenyl)phenyl]sulfide;
(2-Methyl-3chlorophenyl)[2-nitro-4-(E-((4-acetylpiperazin-1-yl)carbonyl)ethenyl)phenyl]sulfide;
(Benzodioxan-6-yl)[2-nitro-4-(E-((3-carboxamido-piperidin-1-yl)carbonyl)ethenyl)phenyl]sulfide;
(Benzodioxan-6-yl)[2-nitro-4-(E-((2-carboethoxypiperidin-1-yl)carbonyl)ethenyl)phenyl]sulfide;
(Benzodioxan-6-yl)[2-nitro-4-(E-((4-carboxamido-piperidin-1-yl)carbonyl)ethenyl)phenyl]sulfide;
(Benzodioxan-6-yl)[2-nitro-4-(E-((4-tert-butoxycarbonyl-piperazin-1-yl)carbonyl)ethenyl)phenyl]sulfide;
(2-Isopropylphenyl)[(2-nitro-4-(E-((syn-3,5-dimethylmorpholin-1-yl)carbonyl)ethenyl)phenyl]sulfide;
(2-Isopropylphenyl)[2-nitro-4-(E-((anti-3,5-dimethylmorpholin-1-yl)carbonyl)ethenyl)phenyl]sulfide;
(2-Isopropylphenyl)[2-nitro-4-(E-((3-carboethoxypip-erazin-1-yl)carbonyl)ethenyl)phenyl]sulfide;
(2-Isopropylphenyl)[2-nitro-4-(E-((3-isopropoxycarbo-nylpiperazin-1-yl)carbonyl)ethenyl)phenyl]sulfide;
(2-Isopropylphenyl)[2-nitro-4-(E-((3-(dimethylamino-carbonyl)-4-methylpiperazin-1-yl)carbonyl)ethenyl)phenyl]sulfide;
(2-Isopropylphenyl)[2-nitro-4-(E-((3-carbomethoxy-4-hydroxypiperidin-1-yl)carbonyl)ethenyl)phenyl]sulfide;
(2-Isopropylphenyl)[2-nitro-4-(E-((3-hydroxymethyl-4-hydroxypiperidin-1-yl)carbonyl)ethenyl)phenyl]sulfide;
(2-Ethoxyphenyl)[2-trifluoromethyl-4-E-((2-carbomethoxy-4-(methoxycarbonyl)piperazin-1-yl)carbonyl)ethenyl)phenyl]sulfide;
(2-Ethoxyphenyl)[2-trifluoromethyl-4-(E-((2-carbomethoxy-4-methylpiperazin-1-yl)carbonyl)ethenyl)phenyl]sulfide;
(2-Ethoxyphenyl)[2-trifluoromethyl-4-(E-((2-carboxy-4-(methoxycarbonyl)piperazin-1-yl)carbonyl)ethenyl)phenyl]sulfide;
(Indol-6-yl)[2-chloro-4-(E-((4-acetylpiperazin-1-yl)carbonyl)ethenyl)phenyl]sulfide;
(1-Ethyl-3-(dimethylaminomethyl)indol-7-yl)[2-chloro-4-(E-((4-acetylpiperazin-1-yl)carbonyl)ethenyl)phenyl]sulfide;
(5-Ethoxybenzodioxan-6-yl)[2-chloro-4-(E-((4-acetylpiperazin-1-yl)carbonyl)ethenyl)phenyl]sulfide;
(2-Ethyl-4-bromophenyl)[2-nitro-4-(E-((4-acetylpiperazin-1-yl)carbonyl)ethenyl)phenyl]sulfide;
(Benzodioxan-6-yl)[2-nitro-4-(E-((2-carboxypiperidin-1-yl)carbonyl)ethenyl)phenyl]sulfide;
(Benzodioxan-6-yl)[2-nitro-4-(E-((4-carboxymethyl-piperazin-1-yl)carbonyl)ethenyl)phenyl]sulfide;
3-Morpholinophenyl)[2-nitro-4-(E-((4-acetylpiperazin-1-yl)carbonyl)ethenyl)phenyl]sulfide;
5-Ethoxybenzodioxan-8-yl)[2-chloro-4-(E-((4-acetylpiperazin-1-yl)carbonyl)ethenyl)phenyl]sulfide;
(5-Chloro-8-ethoxyquinolin-7-yl)[2-chloro-4-(E-((4-acetylpiperazin-1-yl)carbonyl)ethenyl)phenyl]sulfide;
(2-Isopropylphenyl)[2-nitro-4-(E-((3-carboethoxypiperidin-1-yl)carbonyl)ethenyl)phenyl]sulfide;
(2-Isopropylphenyl)[2-nitro-4-(E-((3-carboxypiperidin-1-yl)carbonyl)ethenyl)phenyl]sulfide;
(2-Isopropylphenyl)[2-nitro-4-(E-(((3-ethanesulfonyl-aminocarbonyl)piperidin-1-yl)carbonyl)ethenyl)phenyl]sulfide;
(2-Isopropylphenyl)[2-nitro-4-(E-(((3-(4-methylpiperazine)sulfonylaminocarbonyl)piperidin-1-yl)carbonyl)ethenyl)phenyl]sulfide;
(2-Isopropylphenyl)[2-nitro-4-(E-(((3-p-toluenesulfonyl-aminocarbonyl)piperidin-1-yl)carbonyl)ethenyl)phenyl]sulfide;
(2-Isopropylphenyl)[2-nitro-4-(E-((3-methyl-4-acetylpiperazin-1-yl)carbonyl)ethenyl)phenyl]sulfide;
(2-Hydroxyphenyl)-[2-chloro-4-(E-[(morpholin-1-yl)carbonyl]ethenyl)phenyl]sulfide;
(1-(Carboxymethyl)indol-5-yl)[2-chloro-4-(E-((4-acetylpiperazin-1-yl)carbonyl)ethenyl)phenyl]sulfide;
(Benzodioxan-6-yl)[2-trifluoromethyl-4-(E-((4-acetylpiperazin-1-yl)carbonyl)ethenyl)phenyl]sulfide;
(2-Isopropylphenyl)[2-nitro-4-(E-((3-(2-oxopyrrolidin-1-yl)prop-1-ylamino)carbonyl)ethenyl)phenyl]sulfide;
(3-(2-Morpholinoethylamino)phenyl)[2-trifluoromethyl-4-(E-((4-acetylpiperazin-1-yl)carbonyl)ethenyl)phenyl]sulfide;
(2-Pyrrolidin-1-ylphenyl)[2-nitro-4-(E-((4-acetylpiperazin-1-yl)carbonyl)ethenyl)phenyl]sulfide;

(3-Bromophenyl)[2-nitro-4-(E-((3-carboethoxypyrrolidin-1-yl)carbonyl)ethenyl)phenyl]sulfide;

(3-Bromophenyl)[2-nitro-4-(E-((4-carboethoxypyrrolidin-1-yl)carbonyl)ethenyl)phenyl]sulfide;

(2-(Hydroxymethyl)-benzodioxan-6-yl)[2-chloro-4-(E-((4-acetylpiperazin-1-yl)carbonyl)ethenyl)phenyl]sulfide;

(Benzodioxan-6-yl)[2-trifluoromethyl-4-(E-((3-(2-oxopyrrolidin-1-yl)prop-1-ylamino)carbonyl)ethenyl)phenyl]sulfide;

3-(Dimethylaminomethyl)indol-5-yl)[2-chloro-4-(E-((4-acetylpiperazin-1-yl)carbonyl)ethenyl)phenyl]sulfide;

(2-Isopropylphenyl)[2-nitro-4-(E-((2-carboethoxypiperidin-1-yl)carbonyl)ethenyl)phenyl]sulfide;

(2-Isopropylphenyl)[2-nitro-4-(E-((2-carboxypiperidin-1-yl)carbonyl)ethenyl)phenyl]sulfide;

(2-Isopropylphenyl)[2-nitro-4-(E-((4-carboethoxypiperidin-1-yl)carbonyl)ethenyl)phenyl]sulfide;

(2-Isopropylphenyl)[2-nitro-4-E-((4-carboxypiperidin-1-yl)carbonyl)ethenyl)phenyl]sulfide;

(2-Isopropylphenyl)[2-nitro-4-(E-(((4-p-toluenesulfonylaminocarbonyl)piperidin-1-yl)carbonyl)ethenyl)phenyl]sulfide;

(2-Isopropylphenyl)[2-nitro-4-(E-((3-carboxy-4-hydroxypiperidin-1-yl)carbonyl)ethenyl)phenyl]sulfide;

(Benzodioxan-6-yl)[2-trifluoromethyl-4-(E-((3-carboethoxypiperidin-1-yl)carbonyl)ethenyl)phenyl]sulfide;

Benzodioxan-6-yl)[2-trifluoromethyl-4-(E-((2-carboethoxypiperidin-1-yl)carbonyl)ethenyl)phenyl]sulfide;

(Benzodioxan-6-yl)[2-nitro-4-(E-((4-carboxypiperidin-1-yl)carbonyl)ethenyl)phenyl]sulfide;

(Benzodioxan-6-yl)[2-trifluoromethyl-4-(E-((3-carboxypyrrolidin-1-yl)carbonyl)ethenyl)phenyl]sulfide;

(Benzodioxan-6-yl)[2-trifluoromethyl-4-(E-((4-carboethoxypiperidin-1-yl)carbonyl)ethenyl)phenyl]sulfide;

(Benzodioxan-6-yl)[2-trifluoromethyl-4-(E-((2-carbomethoxy-4-tert-butoxycarbonylpiperazin-1-yl)carbonyl)ethenyl)phenyl]sulfide;

(Benzodioxan-6-yl)[2-trifluoromethyl-4-(E-((2-carbomethoxy-4-methoxycarbonylpiperazin-1-yl)carbonyl)ethenyl)phenyl]sulfide;

(Benzodioxan-6-yl)[2-trifluoromethyl-4-(E-((2-carbomethoxypiperazin-1-yl)carbonyl)ethenyl)phenyl]sulfide;

(2-Methyl-3-(carboethoxyethyl)indol-5-yl)[2-trifluoromethyl-4-(E-((morpholin-1-yl)carbonyl)ethenyl)phenyl]sulfide;

(1-(2-Methoxyethyl)indol-5-yl)[2-chloro-4-(E-((4-acetylpiperazin-1-yl)carbonyl)ethenyl)phenyl]sulfide;

(2-Isopropylphenyl)[2-nitro-4-(E-((3-acetoxymethyl-4-hydroxypiperidin-1-yl)carbonyl)ethenyl)phenyl]sulfide;

(2-Isopropylphenyl)[2-nitro-4-(E-((3-(dimethylaminocarbonyl)-4-hydroxypiperidin-1-yl)carbonyl)ethenyl)phenyl]sulfide;

(2-Isopropylphenyl)[2-nitro-4-(E-((3-cyanomorpholin-1-yl)carbonyl)ethenyl)phenyl]sulfide;

(2-Isopropylphenyl)[2-nitro-4-(E-((3-carboethoxymorpholin-1-yl)carbonyl)ethenyl)phenyl]sulfide;

(2-Isopropylphenyl)[2-nitro-4-(E-((3-(tetrazol-5-yl)morpholin-1-yl)carbonyl)ethenyl)phenyl]sulfide;

(Benzodioxan-6-yl)[2-trifluoromethyl-4-(E-((4-carboxypiperidin-1-yl)carbonyl)ethenyl)phenyl]sulfide;

(Benzodioxan-6-yl)[2-trifluoromethyl-4-(E-((2-carboxypiperidin-1-yl)carbonyl)ethenyl) phenyl]sulfide;

(Benzodioxan-6-yl)[2-trifluoromethyl-4-(E-((4-carbomethoxypiperazin-1-yl)carbonyl)ethenyl)phenyl]sulfide;

(Benzodioxan-6-yl)[2-trifluoromethyl-4-(E-((3-aza-6,9-dioxaspiro[5.4]decan-1-yl)carbonyl)ethenyl)phenyl]sulfide;

(Benzodioxan-6-yl)[2-trifluoro-4-(E-((4-(2-oxo-2,3-dihydro-1H-benzimidazole-1-yl)piperidin-1-yl)carbonyl)ethenyl)phenyl]sulfide;

(Benzodioxan-6-yl)[2-trifluoromethyl-4-(E-((4-(methylaminocarbonyl)piperidin-1-yl)carbonyl)ethenyl)phenyl]sulfide;

(Benzodioxan-6-yl)[2-trifluoromethyl-4-(E-((3-carbomethoxy-4-methoxycarbonylpiperazin-1-yl)carbonyl)ethenyl)phenyl]sulfide;

(2-Isopropylphenyl)[2-nitro-4-(E-((3-carboxymorpholin-1-yl)carbonyl)ethenyl)phenyl]sulfide;

(Benzodioxan-6-yl)[2-trifluoromethyl-4-(E-((2-carboxy-4-methoxycarbonylpiperazin-1-yl)carbonyl)ethenyl)phenyl]sulfide;

(Benzodioxan-6-yl)[2-trifluoromethyl-4-(E-((morpholin-1-yl)carbonyl)ethenyl)phenyl]sulfide;

(Benzodioxan-6-yl)[2-trifluoromethyl-4-(E-((4-(pyrrolidin-1-yl)piperidin-1-yl)carbonyl)ethenyl)phenyl]sulfide;

(2-Isopropylphenyl)[2-nitro-4-(E-((3-aza-6,9-dioxaspiro[5.4]decan-1-yl)carbonyl)ethenyl)phenyl]sulfide;

(2-Isopropylphenyl)[2-nitro-4-(E-((2-(dimethylaminomethyl)piperidin-1-yl)carbonyl)ethenyl)phenyl]sulfide;

(2-Isopropylphenyl)[2-nitro-4-(E-((piperidin-1-ylamino)carbonyl)ethenyl)phenyl]sulfide;

(Benzodioxan-6-yl)[2-trifluoromethyl-4-(E-((3-carboxy-4-methoxycarbonylpiperazin-1-yl)carbonyl)ethenyl)phenyl]sulfide;

(2-(Dimethylaminocarbonyl)-benzodioxan-6-yl)[2-chloro-4-(E-((4-acetylpiperazin-1-yl)carbonyl)ethenyl)phenyl]sulfide;

(2-Isopropylphenyl)[2-nitro-4-(E-((3-(2-(methoxymethyl)tetrazol-5-yl)piperidin-1-yl)carbonyl)ethenyl)phenyl]sulfide;

(2-Isopropylphenyl)[2-nitro-4-(E-((3-(1-(methoxymethyl)tetrazol-5-yl)piperidin-1-yl)carbonyl)ethenyl)phenyl]sulfide;

(1-Methylindol-5-yl)[2-chloro-4-(E-((3-(2-oxopyrrolidin-1-yl)propylamino)carbonyl)ethenyl)phenyl]sulfide;

(2-Isopropylphenyl)[2-nitro-4-(E-((3-(tetrazol-5-yl)piperidin-1-yl)carbonyl)ethenyl)phenyl]sulfide;

(1-Methylindol-5-yl)[2-chloro-4-(E-((3-carboethoxypiperidin-1-yl)carbonyl)ethenyl)phenyl]sulfide;

(1-Methylindol-5-yl)[2-chloro-4-(E-((3-carboxypiperidin-1-yl)carbonyl)ethenyl)phenyl]sulfide;

(1-Methylindol-5-yl)[2-chloro-4-(E-((4-carboethoxypiperidin-1-yl)carbonyl)ethenyl)phenyl]sulfide;

(1-Methylindol-5-yl)[2-chloro-4-(E-((4-carboxypiperidin-1-yl)carbonyl)ethenyl)phenyl]sulfide;

(2-Isopropylphenyl)[2-nitro-4-(E-((2-(1-methylpyrrolidin-2-yl)ethylamino)carbonyl)ethenyl)phenyl]sulfide;

(2-Isopropylphenyl)[2-nitro-4-(E-((4-(pyrrolidin-1-yl)piperidin-1-yl)carbonyl)ethenyl)phenyl]sulfide;

(2-Isopropylphenyl)[2-nitro-4-(E-((4-sulfopiperidin-1-yl)carbonyl)ethenyl)phenyl]sulfide;

(2-Isopropylphenyl)[2-nitro-4-(E-((3-hydroxypiperidin-1-yl)carbonyl)ethenyl)phenyl]sulfide;

(Benzodioxan-6-yl)[2-trifluoromethyl-4-(E-((3-((ethanesulfonylamino)carbonyl)piperidin-1-yl)carbonyl)ethenyl)phenyl]sulfide;

(Benzodioxan-6-yl)[2-trifluoromethyl-4-(E-((3-((p-toluenesulfonylamino)carbonyl)piperidin-1-yl)carbonyl)ethenyl)phenyl]sulfide;

(Benzodioxan-6-yl)[2-trifluoromethyl-4-(E-((4-((ethanesulfonylamino)carbonyl)piperidin-1-yl)carbonyl)ethenyl)phenyl]sulfide;

(Benzodioxan-6-yl)[2-trifluoromethyl-4-(E-((2-(tetrazol-5-yl)morpholin-1-yl)carbonyl)ethenyl)phenyl]sulfide;

(2-Isopropylphenyl)[2-nitro-4-(E-((2-butyl-5-(tetrazol-5-yl)morpholin-1-yl)carbonyl)ethenyl)phenyl]sulfide;

(2-(and 3-)(Hydroxymethyl)-benzodioxan-6-yl)[2-nitro-4-(E-((4-acetylpiperazin-1-yl)carbonyl)ethenyl)phenyl]sulfide;

(2-(and 3-)(Hydroxyethyl)-benzodioxan-6-yl)[2-nitro-4-(E-((3-(2-oxopyrrolidin-1-yl)prop-1-ylamino)carbonyl)ethenyl)phenyl]sulfide;

(2-(and 3-)(Hydroxymethyl)-benzodioxan-6-yl)[2-trifluoromethyl-4-(E-((3-(2-oxopyrrolidin-1-yl)prop-1-ylamino)carbonyl)ethenyl)phenyl]sulfide;

(3-Hydroxymethyl)-benzodioxan-6-yl)[2-nitro-4-(E-((3-(2-oxopyrrolidin-1-yl)prop-1-ylamino)carbonyl)ethenyl)phenyl]sulfide;

(Benzodioxan-6-yl)[2-chloro-4-(E-((3-carboxypiperidin-1-yl)carbonyl)ethenyl)phenyl]sulfide;

(2 and 3-)(Aminomethyl)-benzodioxan-6-yl)[2-trifluoromethyl-4-(E-((3-(2-oxopyrrolidin-1-yl)prop-1-ylamino)carbonyl)ethenyl)phenyl]sulfide;

(2-Isopropylphenyl)[2-nitro-4-(E-((3-(methylaminocarbonyl)morpholin-1-yl)carbonyl)ethenyl)phenyl]sulfide;

(2-Isopropylphenyl)[2-nitro-4-(E-((3-(hydroxymethyl)morpholin-1-yl)carbonyl)ethenyl)phenyl]sulfide;

(2-Isopropylphenyl)[2-nitro-4-(E-((3-(acetoxymethyl)morpholin-1-yl)carbonyl)ethenyl)phenyl]sulfide;

(2-Isopropylphenyl)[2-nitro-4-(E-((3-(aminomethyl)morpholin-1-yl)carbonyl)ethenyl)phenyl]sulfide;

(2-Isopropylphenyl)[2-nitro-4-(E-((3-(acetamidomethyl)morpholin-1-yl)carbonyl)ethenyl)phenyl]sulfide;

(Benzodioxan-6-yl)[2-chloro-4-(E-((3-(2-oxopyrrolidin-1-yl)prop-1-ylamino)carbonyl)ethenyl)phenyl]sulfide;

(Benzodioxan-6-yl)[2-chloro-4-(E-((3-carboethoxy-piperidin-1-yl)carbonyl)ethenyl)phenyl]sulfide;

Benzodioxan-6-yl)[2-chloro-4-(E-((2-carboethoxy-piperidin-1-yl)carbonyl)ethenyl)phenyl]sulfide;

(2-Methoxyphenyl)-[2,3-dichloro-4-(E-[(morpholin-1-yl)carbonyl]ethenyl)phenyl]sulfide;

(2-Methoxyphenyl)-[2,3-dimethyl-4-(E-[(morpholin-1-yl)carbonyl]ethenyl)phenyl]sulfide;

(2-Isopropylphenyl)[2-nitro-4-(E-(indol-5-ylamino)carbonyl)ethenyl)phenyl]sulfide;

(Benzodioxan-6-yl)[2-chloro-4-(E-((3-carboxypiperidin-1-yl)carbonyl)ethenyl)phenyl]sulfide;

(Benzodioxan-6-yl)[2-chloro-4-(E-((3-(tetrazol-5-yl)piperidin-1-yl)carbonyl)ethenyl)phenyl]sulfide;

(Benzodioxan-6-yl)[2-chloro-4-(E-((4-(tert-butoxycarbonyl)piperazin-1-yl)carbonyl)ethenyl)phenyl]sulfide;

(Benzodioxan-6-yl)[2-chloro-4-(E-((2-carboxypiperidin-1-yl)carbonyl)ethenyl)phenyl]sulfide;

(Benzodioxan-6-yl)[2-chloro-4-(E-((3-(tetrazol-5-yl)morpholin-1-yl)carbonyl)ethenyl)phenyl]sulfide;

(Benzodioxan-6-yl)[2-chloro-4-(E-((4-(methylaminocarbonyl)piperazin-1-yl)carbonyl)ethenyl)phenyl]sulfide;

(2-Methoxyphenyl)-[2,3-dichloro-4-(E-[(4-carboxypiperidin-1-yl)carbonyl]ethenyl)phenyl]sulfide;

(Benzodioxan-6-yl)[2-chloro-4-(E-((4-(tetrazol-5-yl)piperidin-1-yl)carbonyl)ethenyl)phenyl]sulfide;

(2-Methoxyphenyl)-[3-chloro-4-(E-[(morpholin-1-yl)carbonyl]ethenyl)phenyl]sulfide;

(2-Isopropylphenyl)[2-nitro-4-(E-((4-oxopiperidin-1-yl)carbonyl)ethenyl)phenyl]sulfide;

(Benzodioxan-6-yl)[2-trifluoromethyl-4-(E-((3-R-carboethoxypiperidin-1-yl)carbonyl)ethenyl)phenyl]sulfide;

(Benzodioxan-6-yl)[2-trifluoromethyl-4-(E-((3-R-carboxypiperidin-1-yl)carbonyl)ethenyl)phenyl]sulfide;

(Benzodioxan-6-yl)[2,3-dichloro-4-(E-((3-(2-oxopyrrolidin-1-yl)prop-1-ylamino)carbonyl)ethenyl)phenyl]sulfide;

(Benzodioxan-6-yl)[2,3-dichloro-4-(E-((4-acetylpiperazin-1-yl)carbonyl)ethenyl)phenyl]sulfide;

(Benzodioxan-6-yl)[2,3-dichloro-4-(E-((3-carboethoxypiperidin-1-yl)carbonyl)ethenyl)phenyl]sulfide;

(Benzodioxan-6-yl)[2,3-dichloro-4-(E-((4-carboethoxypiperidin-1-yl)carbonyl)ethenyl)phenyl]sulfide;

(Benzodioxan-6-yl)[2,3-dichloro-4-(E-((3-carboxypiperidin-1-yl)carbonyl)ethenyl)phenyl]sulfide;

(Benzodioxan-6-yl)[2,3-dichloro-4-(E-((4-carboxypiperidin-1-yl)carbonyl)ethenyl)phenyl]sulfide;

(2-Isopropylphenyl)[2,3-dichloro-4-(E-((3-(2-oxopyrrolidin-1-yl)propylamino)carbonyl)ethenyl)phenyl]sulfide;

(2-Isopropylphenyl)[2,3-dichloro-4-(E-((4-acetylpiperazin-1-yl)carbonyl)ethenyl)phenyl]sulfide;

(2-Isopropylphenyl)[2,3-dichloro-4-(E-((3-carboethoxypiperidin-1-yl)carbonyl)ethenyl)phenyl]sulfide;

(2-Isopropylphenyl)[2,3-dichloro-4-(E-((4-carboethoxypiperidin-1-yl)carbonyl)ethenyl)phenyl]sulfide;

(2-Isopropylphenyl)[2,3-dichloro-4-(E-((3-carboxypiperidin-1-yl)carbonyl)ethenyl)phenyl]sulfide;

(2-Isopropylphenyl)[2,3-dichloro-4-(E-((4-carboxypiperidin-1-yl)carbonyl)ethenyl)phenyl]sulfide;

(1-Methylindol-5-yl)[2,3-dichloro-4-(E-((3-carboethoxypiperidin-1-yl)carbonyl)ethenyl)phenyl]sulfide;

(1-Methylindol-5-yl)[2,3-dichloro-4-(E-((3-carboxypiperidin-1-yl)carbonyl)ethenyl)phenyl]sulfide;

(1-Methylindol-5-yl)[2,3-dichloro-4-(E-((4-carboethoxypiperidin-1-yl)carbonyl)ethenyl)phenyl]sulfide;

(1-Methylindol-5-yl)[2,3-dichloro-4-(E-((4-carboxypiperidin-1-yl)carbonyl)ethenyl)phenyl]sulfide;

(2-Ethoxyphenyl)-[2,3-dichloro-4-(E-[(4-carboxypiperidin-1-yl)carbonyl]ethenyl)phenyl]sulfide;

(2-Ethoxyphenyl)-[2,3-dichloro-4-(E-[(morpholin-1-yl)carbonyl]ethenyl)phenyl]sulfide;

(2-Ethoxyphenyl)-[2,3-dichloro-4-(E-[(3-carboxypiperidin-1-yl)carbonyl]ethenyl)phenyl]sulfide;

(2-Isopropylphenyl)[2-nitro-4-(E-((3-carboethoxy-pyrrolidin-1-yl)carbonyl)ethenyl)phenyl]sulfide;

(2-Isopropylphenyl)[2-nitro-4-(E-((3-carboxypyrrolidin-1-yl)carbonyl)ethenyl)phenyl]sulfide;

(2-Isopropylphenyl)[2,3-difluoro-4-(E-((3-carboethoxypiperidin-1-yl)carbonyl)ethenyl)phenyl]sulfide;

(2-Isopropylphenyl)[2,3-difluoro-4-(E-((3-carboxypiperidin-1-yl)carbonyl)ethenyl)phenyl]sulfide;

(2-Isopropylphenyl)[2,3-difluoro-4-(E-((4-carboxy-piperidin-1-yl)carbonyl)ethenyl)phenyl]sulfide;
(Benzodioxan-6-yl)[2-trifluoromethyl-4-(E-((3-ethoxycarbonylpyrrolidin-1-yl)carbonyl)ethenyl)phenyl]sulfide;
(Benzodioxan-6-yl)[2-trifluoromethyl-4-(E-((3-carboxypyrrolidin-1-yl)carbonyl)ethenyl)phenyl]sulfide;
(2-Methoxyphenyl)[2-chloro-3-trifluoromethyl-4-(E-((4-carboethoxypiperidin-1-yl)carbonyl)ethenyl)phenyl]sulfide;
(2-Methoxyphenyl)[2-chloro-3-trifluoromethyl-4-(E-((4-carboxypiperidin-1-yl)carbonyl)ethenyl)phenyl]sulfide;
(2-Methoxyphenyl)[2-chloro-3-trifluoromethyl-4-(E-((morpholin-1-yl)carbonyl)ethenyl)phenyl]sulfide;
(Benzodioxan-6-yl)[4-(E-((4-carboxypiperidin-1-yl)carbonyl)ethenyl)naphthyl]sulfide;
(2-Methoxyphenyl)[2,3-dichloro-4-(E-((4-2,4-dioxo-1,3,8-triazaspiro[4.5])-piperidin-1-yl)carbonyl)ethenyl)phenyl]sulfide;
(2-Methoxyphenyl)[2,3-dichloro-4-(E-((4-ethylpiperazin-1-yl)carbonyl)ethenyl)phenyl]sulfide;
(2-Isopropylphenyl)[2,3-dichloro-4-(E-((4-(2-(2-hydroxyethoxy)ethyl)piperazin-1-yl)carbonyl)ethenyl)phenyl]sulfide;
(Benzodioxan-6-yl)[2,3-bis(trifluoromethyl)-4-(E-((4-carboxypiperidin-1-yl)carbonyl)ethenyl)phenyl]sulfide;
(2-Methoxyphenyl)[2,3-dichloro-4-(E-((4-(carboxy-methylamino)carbonyl-piperidin-1-yl)carbonyl)ethenyl)phenyl]sulfide;
(2-Methoxyphenyl)[2,3-bis(trifluoromethyl)-4-(E-((4-carboxymethylpiperazin-1-yl)carbonyl)ethenyl)phenyl]sulfide;
(2-Methoxyphenyl)[2,3-bis(trifluoromethyl)-4-(E-((4-N-(2-hydroxyethyl)piperazin-1-yl)carbonyl)ethenyl)phenyl]sulfide;
(1-Methylindol-5-yl)[2,3-dichloro-4-(E-((4-(carbon-2,3-dihydroxypropylamino)piperidin-1-yl)carbonyl)ethenyl)phenyl]sulfide;
(2-Methoxyphenyl)[2,3-dichloro-4-(E-(4-(2,3-dihydroxypropionyl)piperazin-1-yl)carbonyl)ethenyl)phenyl]sulfide;
(2-Methoxyphenyl)[2,3-dichloro-4-E-(4-(2,3-dihydroxy-3-carboxypropionyl)piperazin-1-yl)carbonyl)ethenyl)phenyl]sulfide;
(1-Methylindol-5-yl)[2,3-dichloro-4-(E-((4-(carboxymethylamino)carbonyl-piperidin-1-yl)carbonyl)ethenyl)phenyl]sulfide;
(1-Methylindol-5-yl)[2,3-dichloro-4-(E-((4-sulfopiperidin-1-yl)carbonyl)ethenyl)phenyl]sulfide;
(1-Methylindol-5-yl)[2,3-dichloro-4-(E-(4-methylhomopiperazin-1-ylcarbonyl)ethenyl)phenyl]sulfide;
(1-Methylindol-5-yl)[2,3-dichloro-4-(E-(4-tetrahydrofuroylpiperazin-1-yl)carbonyl)ethenyl)phenyl]sulfide;
(Benzodioxan-6-yl)[2-(benzodioxan-6-sulfanyl)-4-(E-((4-morpholino)carbonyl)ethenyl)phenyl]sulfide;
(2-Methoxyphenyl)[2,3-dichloro-4-(E-((4-amino-4-carboxypiperidin-1-yl)carbonyl)ethenyl)phenyl]sulfide;
(2-Methoxyphenyl)[2,3-dichloro-4-((4-furoylpiperazin-1-yl)carbonyl)ethenyl)phenyl]sulfide;
(1-Methylindol-5-yl)[2,3-dichloro-4-(E-(4-(carbony-3-sulfopropylamino)piperidin-1-yl)carbonyl)ethenyl)phenyl]sulfide;
(2-Methoxyphenyl)[2,3-dichloro-4-(E-(4-acetylamino-4-carboxypiperidin-1-ylcarbonyl)ethenyl)phenyl]sulfide;
(2-Methoxyphenyl)[2,3-bis(trifluoromethyl)-4-(E-((4-carboxypiperidin-1-yl)carbonyl)ethenyl)phenyl]sulfide;
(2-Methoxyphenyl)5-[8-(E-((4-(aminocarbonyl)piperidin-1-yl)carbonyl)ethenyl)quinolinyl]sulfide;
(2-Methoxyphenyl)[2-trifluoromethyl-4-(E-((4-carboxypiperidin-1-yl)carbonyl)ethenyl)phenyl]sulfide;
(1-Methylindol-5-yl)[2,3-dichloro-4-(E-(((1S,4S)-5-tert-butyloxycarbonyl-2,5-diazabicyclo(2.2.1)heptan-2-yl)carbonyl)ethenyl)phenyl]sulfide;
(1-Methylindol-5-yl)[2,3-dichloro-4-(E/Z-((1S,4S)-2,5-diazabicyclo(2.2.1)heptan-2-ylcarbonyl)ethenyl)phenyl]sulfide;
(1-Methylindol-5-yl)[2,3-dichloro-4-(E-(4-hydroxy-3-carboxypiperidin-1-ylcarbonyl)ethenyl)phenyl]sulfide;
(1-Methylindol-5-yl)[2,3-dichloro-4-(E-(S-oxothiomorpholin-1-ylcarbonyl)ethenyl)phenyl]sulfide;
(2-Methoxyphenyl)[2,3-dichloro-4-(E-((4-sulfophenyl-amino)carbonyl)ethenyl)phenyl]sulfide;
(2-Methoxyphenyl)[2,3-dichloro-4-(E-((4-carboxy-phenylamino)carbonyl)ethenyl)phenyl]sulfide;
[3-(4-Morpholino)phenyl][2,3-dichloro-4-(E-[(4-carboxypiperidin-1-yl)carbonyl]ethenyl)phenyl]sulfide;
(2-Methoxyphenyl)[2,3-bis(trifluoromethyl)-4-(E-((4-phenylcarboxypiperidin-1-yl)carbonyl)ethenyl)phenyl]sulfide;
(2-Methoxyphenyl)[2,3-dichloro-4-(E-(((4-hydroxyl-aminocarbonyl)piperidin-1-yl)carbonyl)ethenyl)phenyl]sulfide;
(2-Methoxyphenyl)[2,3-dichloro-4-(E-((N-carboxymethyl-N-phenylamino)carbonyl)ethenyl)phenyl]sulfide;
(2-Methoxyphenyl)[3-chloro-6-hydroxy-4-(E-((3-carboxypiperidin-1-yl)carbonyl)ethenyl)phenyl]sulfide;
(2-Methoxyphenyl)[2,3-dichloro-4-(E-(4-((1-(2-phenyl-1-carboxyethyl)amino)carbonyl)piperidin-1-yl)carbonyl)ethenyl)phenyl]sulfide;
(2-Methoxyphenyl)[2,3-dichloro-4-(E-(4-((1-(2-hydroxy-1-carboxyethyl)amino)carbonyl)piperidin-1-yl)carbonyl)ethenyl)phenyl]sulfide;
(3-(1-(3-Carboxypiperidinyl)phenyl)[2,3-dichloro-4-(E-((1,2,5,6-tetrahydropyridin-1-yl)carbonyl)ethenyl)phenyl]sulfide;
(3-(4-Pyrrolidin-1-yl)piperidin-1-yl)phenyl)[2,3-dichloro-4-(E-(((3-(2-oxopyrrolidin-1-yl)propylamino)carbonyl)ethenyl)phenyl]sulfide;
[3-(4-(Spiro-2,2-dioxolanyl)piperidin-1-yl)phenyl][2,3-dichloro-4-(E-((4-morpholinyl)carbonyl)ethenyl)phenyl]sulfide;
[3-(3-Carboxylpiperidin-1-yl)phenyl][2,3-dichloro-4-(E-[(4-carboxypiperidin-1-yl)carbonyl]ethenyl)phenyl]sulfide;
(2-(2-Carboxy)ethenyl)phenyl)[2,3-dichloro-4-(E-((4-morpholinyl)carbonyl)ethenyl)phenyl]sulfide;
[3-(4-Carboxylpiperidin-1-yl)phenyl][2,3-dichloro-4-(E-[(1,2,3,6-tetrahydropyridin-1-yl)carbonyl]ethenyl)phenyl]sulfide;
[3-(4-Carboxylpiperidinyl)phenyl][2,3-dichloro-4-(E-[(4-morpholinyl)carbonyl]ethenyl)phenyl]sulfide;
[2-(4-Acetylpiperazin-1-yl)phenyl][2,3-dichloro-4-(E-[(4-carboxypiperidin-1-yl)carbonyl]ethenyl)phenyl]sulfide;
[3-(3-Carboxypiperidin-1-yl)phenyl][2,3-dichloro-4-(E-[(4-morpholinyl)carbonyl]ethenyl)phenyl]sulfide;
[3-(4-Carboxypiperidin-1-yl)phenyl][2,3-dichloro-4-(E-[(4-(dimethylaminosulfamoyl)piperazin-1-yl)carbonyl]ethenyl)phenyl]sulfide;
(2-Methoxyphenyl)[2,3-bis(trifluoromethyl)-4-(E-((3-carboxypiperidin-1-yl)carbonyl)ethenyl)phenyl]sulfide;
(2-Methoxyphenyl)[2,3-bis(trifluoromethyl)-4-(E-((2-carboxypyrrolidin-1-yl)carbonyl)ethenyl)phenyl]sulfide;
[3-(4-Carboxypiperidin-1-yl)phenyl][2,3-dichloro-4-(E-((4-((trifluoromethylsulfonyl)piperazin-1-yl)carbonyl)ethenyl)phenyl]sulfide;

(2-Methoxyphenyl)[2,3-dichloro-4-(E-(piperidin-1-ylcarbonyl)ethenyl)phenyl]sulfide;
(2-Hydroxyphenyl)[2,3-dichloro-4-(E-((4-morpholino)carbonyl)ethenyl)phenyl]sulfide;
(2-Methoxyphenyl)[2,3-dichloro-4-(E-((((4-carboxyphenyl)methyl)amino)carbonyl)ethenyl)phenyl]sulfide;
(2-Methoxyphenyl)[2,3-dichloro-4-(E-(((4-pyrrolidin-1-yl)piperidin-1-yl)carbonyl)ethenyl)phenyl]sulfide;
(2-Hydroxyphenyl)[2,3-dichloro-4-(E-((4-carboxypiperidin-1-yl)carbonyl)ethenyl)phenyl]sulfide;
[3-(4-Carboxypiperidin-1-yl)phenyl][2,3-dichloro-4-(E-((4-((methylsulfonyl)piperazin-1-yl)carbonyl)ethenyl)phenyl]sulfide;
(2-Aminophenyl)[2,3-dichloro-4-(E-((4-morpholinyl)carbonyl)ethenyl)phenyl]sulfide;
(3-(4-carboxypiperidin-1-yl)phenyl)[2,3-dichloro-4-(E-((S-oxothiomorpholin-1-yl)carbonyl)ethenyl)phenyl]sulfide;
[3-(4-Carboxypiperidin-1-yl)phenyl][2,3-dichloro-4-(E-((4-hydroxypiperidin-1-yl)carbonyl)ethenyl)phenyl]sulfide;
(2-Glycoxyphenyl)[2,3-dichloro-4-(E-((4-morpholino)carbonyl)ethenyl)phenyl]sulfide;
(2-(4-Butyroxy)phenyl)[2,3-dichloro-4-(E-((4-morpholino)carbonyl)ethenyl)phenyl]sulfide;
[3-(4-Carboxypiperidin-1-yl)phenyl][2,3-dichloro-4-(E-((4-hydroxyethylpiperazin-1-yl)carbonyl)ethenyl)phenyl]sulfide;
[3-(4-Carboxypiperidin-1-yl)phenyl][2,3-dichloro-4-(E-((4-furoylpiperazin-1-yl)carbonyl)ethenyl)phenyl]sulfide;
[3-(4-Carboxypiperidin-1-yl)phenyl][2,3-dichloro-4-(E-((pyrrolidin-1-yl)carbonyl)ethenyl)phenyl]sulfide;
[3-(4-Carboxypiperidin-1-yl)phenyl][2,3-dichloro-4-(E-((diethylaminocarbonyl)ethenyl)phenyl]sulfide;
[3-(4-Carboxypiperidin-1-yl)phenyl][2,3-dichloro-4-(E-((4-ethylpiperazin-yl)carbonyl)ethenyl)phenyl]sulfide;
[3-(4-Carboxypiperidin-1-yl)phenyl][2,3-dichloro-4-(E-((4-(aminocarbonyl)piperidin-1-yl)carbonyl)ethenyl)phenyl]sulfide;
[3-(4-Carboxypiperidin-1-yl)phenyl][2,3-dichloro-4-(E-((4-(2-(ethoxyethyl)piperidin-1-yl)carbonyl)ethenyl)phenyl]sulfide;
[3-((4-Carboxymethyl)piperazin-1-yl)phenyl][(2,3-dichloro-4-(E-(4-morpholinyl)carbonyl)ethenyl)phenyl]sulfide;
[3-(4-Carboxypiperidin-1-yl)phenyl][2,3-bis(trifluoromethyl)-4-(E-((4-morpholino)carbonyl)ethenyl)phenyl]sulfide;
(3-Hydroxyphenyl)[2,3-dichloro-4-(E-((4-morpholino)carbonyl)ethenyl)phenyl]sulfide;
[3-(4-Butyroxy)phenyl][2,3-dichloro-4-(E-((4-morpholino)carbonyl)ethenyl)phenyl]sulfide;
(2-Hydroxyphenyl)[(2,3-bis(trifluoromethyl)-4-(E-((4-morpholino)carbonyl)ethenyl)phenyl]sulfide;
(3-Hydroxyphenyl)[2,3-bis(trifluoromethyl)-4-(E-((4-morpholino)carbonyl)ethenyl)phenyl]sulfide;
[3-(4-Carboxypiperidin-1-yl)phenyl][2,3-bis(trifluoromethyl-4-(E-((4-hydroxypiperidin-1-yl)carbonyl)ethenyl)phenyl]sulfide;
[3-(4-Carboxypiperidin-1-yl)phenyl][2,3-bis(trifluoromethyl-4-(E-((1,2,5,6-tetrahydropyridin-1-yl)carbonyl)ethenyl)phenyl]sulfide;
[2-((4-Carboxy)butyloxy)phenyl][2,3-dichloro-4-(E-((4-morpholino)carbonyl)ethenyl)phenyl]sulfide;
(2-Glycoxyphenyl)[2,3-bis(trifluoromethyl)-4-(E-((4-morpholino)carbonyl)ethenyl)phenyl]sulfide;
(2-(4-Butyroxy)phenyl)[2,3-bis(trifluoromethyl)-4-(E-((4-morpholino)carbonyl)ethenyl)phenyl]sulfide;
[3-(4-Carboxypiperidin-1-yl)phenyl][2,3-bis(trifluoromethyl)-4-(E-((bis-(2-ethoxyethyl)amino)carbonyl)ethenyl)phenyl]sulfide;
[3-(4-Carboxypiperidin-1-yl)phenyl][2,3-bis-(trifluoromethyl)-4-(E-((bis-(2-hydroxypropyl)amino)carbonyl)ethenyl)phenyl]sulfide;
[3-(4-Carboxypiperidin-1-yl)phenyl][2,3-bis-(trifluoromethyl)-4-(E-((piperazin-1-yl)carbonyl)ethenyl)phenyl]sulfide;
(3-(4-Butyroxy)phenyl)[2,3-bis(trifluoromethyl)-4-(E-((4-morpholino)carbonyl)ethenyl)phenyl]sulfide;
[2-(3-Carboxypiperidin-1-yl)phenyl][2,3-dichloro-4-(E-((3-(2-oxopyrrolidin-1-yl)propylaminocarbonyl)ethenyl)phenyl]sulfide;
[2-(3-Carboxypiperidin-1-yl)phenyl][2,3-bis(trifluoromethyl)-4-(E-((3-(2-oxopyrrolidin-1-yl)propylaminocarbonyl)ethenyl)phenyl]sulfide;
[2-(3-Carboxypiperidin-1-yl)phenyl][2,3-dichloro-4-(E-((4-(2-hydroxyethyl)piperazin-1-yl)carbonyl)ethenyl)phenyl]sulfide;
[2-(3-Carboxypiperidin-1-yl)phenyl][2,3-bis(trifluoromethyl)-4-(E-((1,2,5,6-tetrahydropyridin-1-yl)carbonyl)ethenyl)phenyl]sulfide;
[2-(3-Carboxypiperidin-1-yl)phenyl][2,3-bis(trifluoromethyl)-4-(E-((4-(2-hydroxyethyl)piperazin-1-yl)carbonyl)ethenyl)phenyl]sulfide;
[2-(3-Carboxypiperidin-1-yl)phenyl][2,3-bis(trifluoromethyl)-4-(E-((4-(2-(hydroxyethoxy)ethyl)piperazin-1-yl)carbonyl)ethenyl)phenyl]sulfide; and
(3-(3-Propioxy)phenyl)[2,3-dichloro-4-(E-((4-morpholino)carbonyl)ethenyl)phenyl]sulfide.

Pharmaceutical Compositions and Methods of Treatment

The present invention also provides pharmaceutical compositions which comprise compounds of the present invention formulated together with one or more pharmaceutically-acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art . For example, S. M. Berge, et al. describe pharmaceutically-acceptable salts in detail in J. Pharmaceutical Sciences, 1977, 66:1 et seq. The salts may be prepared in situ during the final isolation and purification of the compounds of the invention or separately by reacting a free base function with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, paoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water-soluble, or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include cations based on alkali metals or alkaline earth metals such as lithium, sodium, potassium, calcium, magnesium, aluminum and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically-acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.1 to about 50 mg, more preferably of about 5 to about 20 mg of active compound per kilogram of body weight per day are administered orally or intravenously to a mammalian patient. If desired, the effective daily dose may be divided into multiple doses for purposes of administration, e.g. two to four separate doses per day.

Preparation of Compounds of the Invention

The compounds and processes of the present invention may be better understood in connection with the following synthetic Schemes which illustrate the methods by which the compounds of the invention can be prepared.

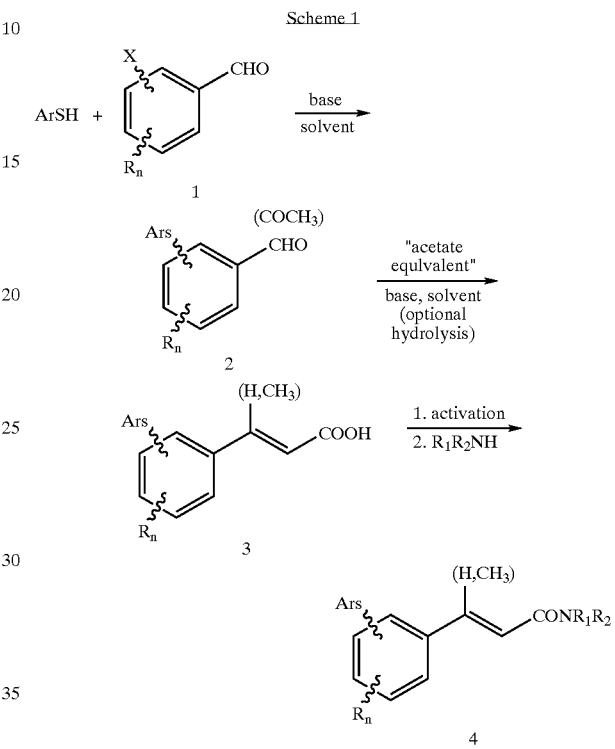

Scheme 1 describes the synthesis of a typical cinnamide-substituted diaryl sulfide 4 through an aldehyde intermediate 2. Aldehyde 2 is prepared by reaction of a thiophenol (for example 2,4-dichlorothiophenol, 2-bromothiophenol, or the like) with halo-substituted benzaldehyde derivative 1 (e.g. 2-chlorobenzaldehyde, 3-chloro,4-fluorobenzaldehyde, or the like) in the presence of base (e.g. sodium carbonate, triethylamine, or the like) and a polar solvent (e.g. dimethylformamide, dimethylsulfoxide, or the like). The aldehyde group is homologated to the corresponding cinnamic acid 3, using an acetate equivalent (for example, malonic acid, triethoxyphosphonoacetate, or the like) in the presence of an appropriate base and solvent. In some cases, it may be necessary to hydrolyze an intermediate ester (for example using sodium hydroxide in alcohol). The acid group is activated (for example using thionyl chloride, or dicyclohexylcarbodiimide and N-hydroxysuccinimide, or the like) and reacted with a primary or secondary amine (for example, 6-aminohexanol, pyrrolidone-3-propylamine, or the like) to provide the desired analog 4. In one variant, a halo-acetophenone can replace benzaldehyde 2; the resultant cinnamides 4 are substituted with a methyl group at the 3-position.

Scheme 2

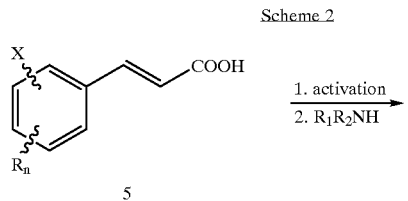
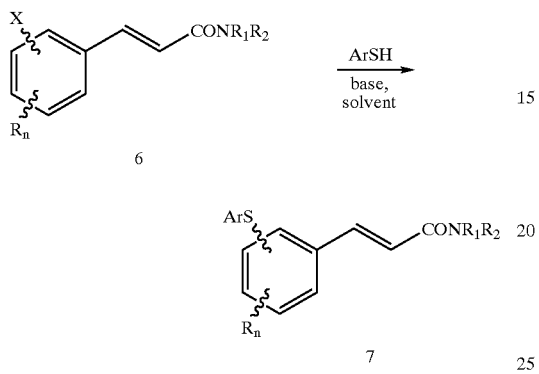

A number of the compounds described herein may be prepared from intermediate benzylic alcohols like 8 (Scheme 3) Activation of the alcohol moiety (for example, using phosphorus tribromide or methanesulfonyl chloride and lithium halide in dimethylformamide) and displacement with a primary or secondary amine (e.g. morpholine, N-formylpiperazine or the like) provides analogs with structures related to 9. Alternatively the alcohol may be oxidized (for example using TPAP or PCC or the like) to give aldehyde 10.

Scheme 4

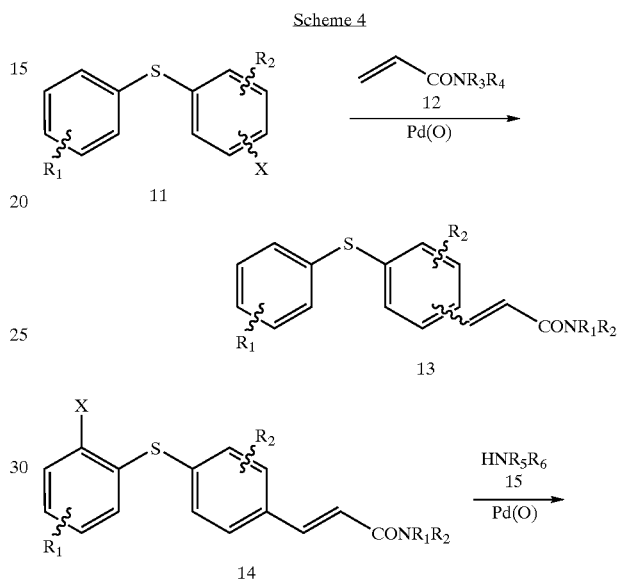

Alternatively, the order of these coupling steps may be reversed (Scheme 2). A substituted halocinnamic acid 5 (e.g. 3-chloro-2-nitrocinnamic acid or the like) may be coupled with a primary or secondary amine (e.g. N-acetylpiperazine or the like) as described above to give the corresponding amide 6. The halo-group can then be displaced with a substituted thiophenol in the presence of base to provide the product 7.

Scheme 3

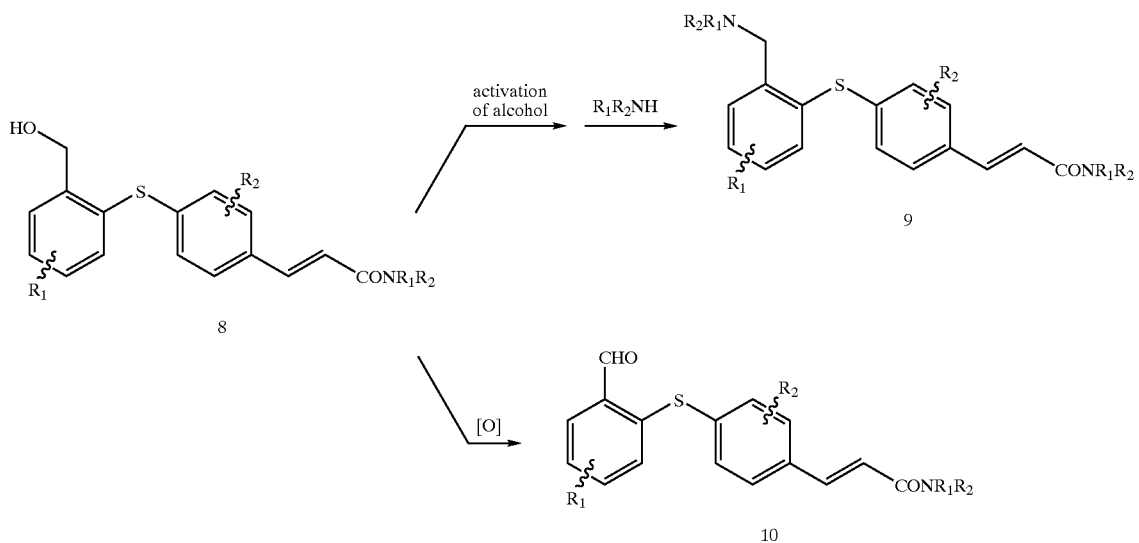

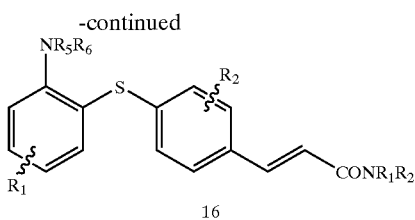

16

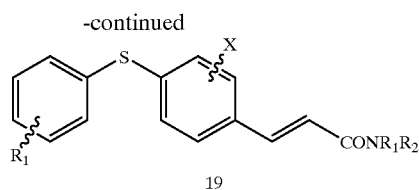

19

Cinnamides like 13 may be prepared from halo-substituted derivatives 11 by palladium-mediated coupling [e.g. using tetrakis (o-tolyl phosphine) palladium (0), Pd$_2$(dba)$_3$, or the like] with acrylamide derivatives 12 (Scheme 4). In similar manner, anilino-cinnamides like 16 can be prepared by palladium-mediated coupling of amines 15 with halo-cinnamides 14.

In some cases, functional groups on the aromatic rings can be modified to produce new analogs (Scheme 5). For example, a nitro group in compounds like 17 may be reduced (for example, with tin(II) chloride, or by catalytic hydrogenation, or the like) to the corresponding amine 18. This amine may then itself be converted to a halogen, for example by diazotization using nitrous acid or t-butyl nitrite in the presence of a metal halide salt like cupric bromide, providing analog 19.

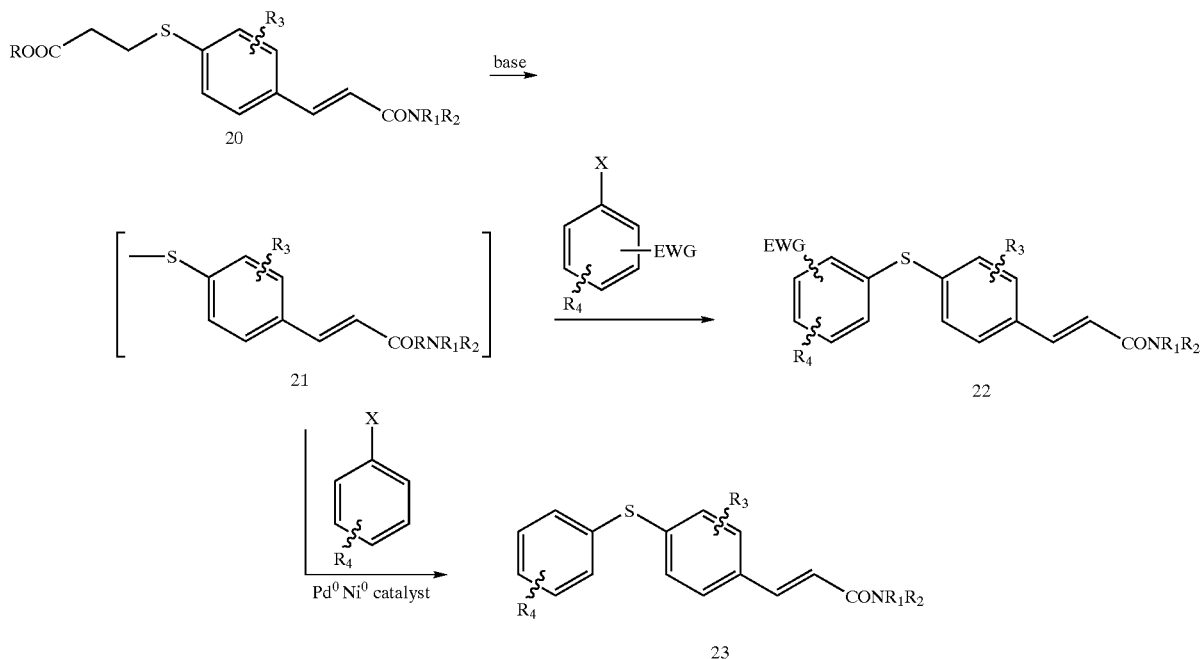

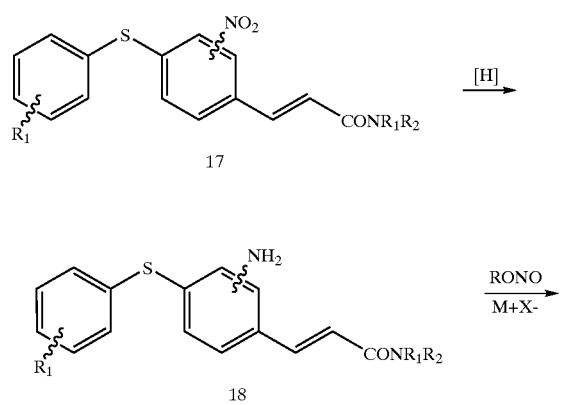

It is also possible to assemble cinnamide-substituted diaryl sulfides in a "reverse" sense (Scheme 6). Thus, for example, compound 20, prepared as described in Scheme 1, may be deprotected by treatment with base (e.g. potassium t-butoxide or the like) to provide thiolate anion 21, which may be reacted with an activated haloarene (e.g. 2,3-dichlorobenzaldehyde, 3-chloro,4-fluorobenzaldehyde or the like) to provide the corresponding product 22. Alternatively, this same thiolate anion may be coupled with unactivated aryl halides (e.g. aryl bromide or Aryl iodides) using a metal-catalyzed Ullman coupling procedure (for example, using a palladium or nickel catalyst) to give product 23.

A further method for producing diarylsulfide cinnamides is shown in Scheme 7, wherein the diaryl sulfide is formed through coupling of a suitably protected aryl thiol 28 to an activated cinnamate ester 27. Substituted phenol 24 may be brominated to give bromophenol 25. Heck-type coupling of bromide 25 with an appropriate olefinic substrate, for example methyl acrylate, is effected with palladium catalysis, leading to the cinnamate ester 26. The phenol is then activated towards further reaction, for example by conversion to the corresponding triflate 27 under standard conditions. The required protected thiol 28 may be prepared by the method of Soderquist, et al. (*Tetrahedron Lett.* 1994, 35, 3221–3224), by coupling an aryl halide or triflate with triisopropylsilyl thiol under palladium catalysis. The two partners 27 and 28 are then reacted in the presence of a fluoride source, for example cesium fluoride, to provide the diarylsulfide cinnamate 29. Hydrolysis is accomplished by basic media, such as lithium or sodium hydroxide in water-THF, and the resulting acid 30 is coupled to amines under standard amide-bond forming conditions (for example, EDC/HOBt) to produce the amides 31.

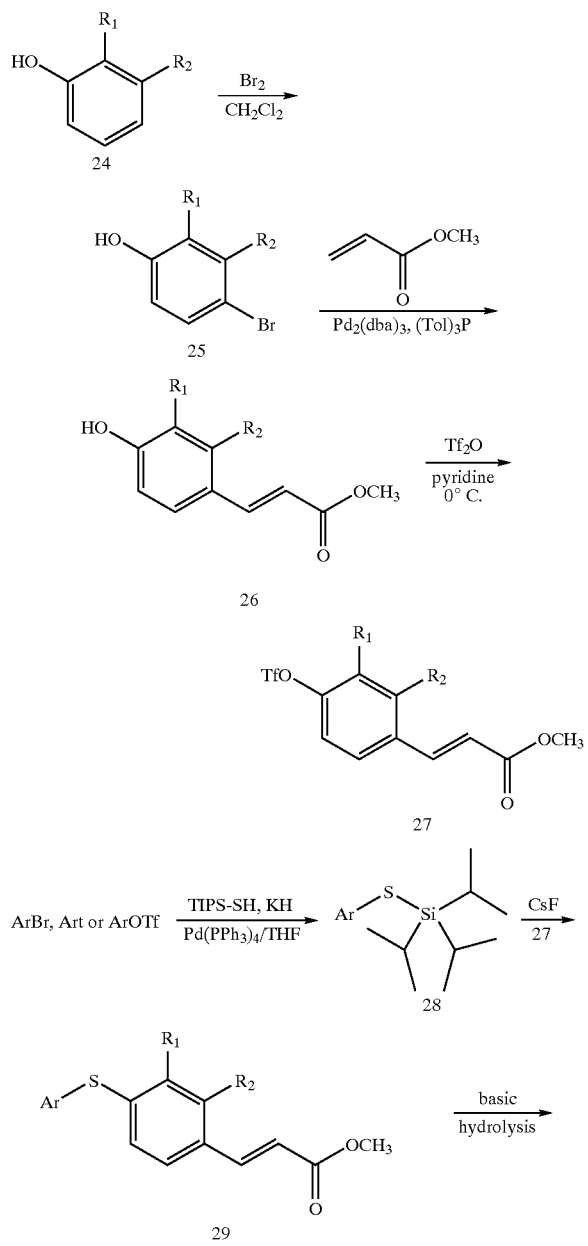

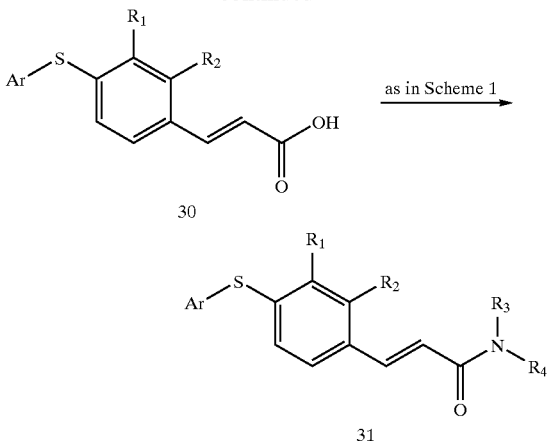

A method for preparing cinnamides bearing two arylthio groups is outlined in Scheme 8. Commercially available difluoro cinnamic acid 32 was coupled with an amine, using standard conditions, and this derived amide 33 was reacted with excess aryl thiol to provide the bis-sulfide 34.

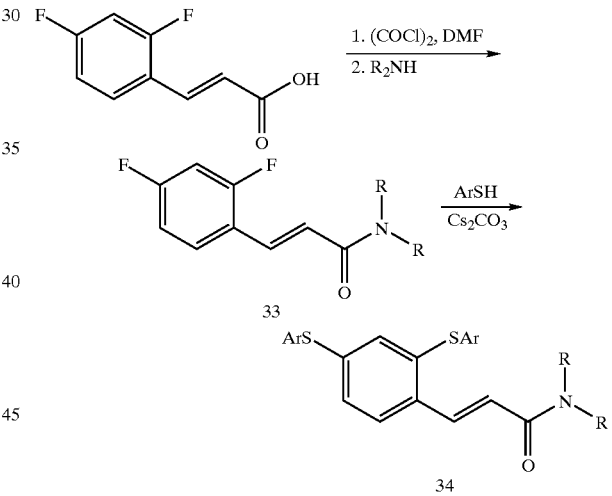

Compounds which contain trifluoromethyl groups on the cinnamide-portion of the compounds were made by the method shown in Scheme 9. According to the method of Chambers (Chambers,R. D.; Roche, A.; and Rock,M. H. (*J. Chem. Soc., Perkin Trans. I* 1 1996, 1095) (Ref), Diels-Alder reaction between 1,1,1,4,4,4-hexafluoro-2-butyne and 2-methylfuran led to bicyclic ether 35, which was rearranged with Lewis acid (for example, boron trifluoride etherate) to the phenol 36. The methyl group is then converted to the corresponding aldehyde 37 by bromination followed by reaction with dimethylsulfoxide. Using the analogous procedures described for Scheme 1 above, the phenol was activated and condensed with thiols under basic conditions to afford diarylsulfide aldehydes 38, and further converted to cinnamides 39 by the previously described procedures.

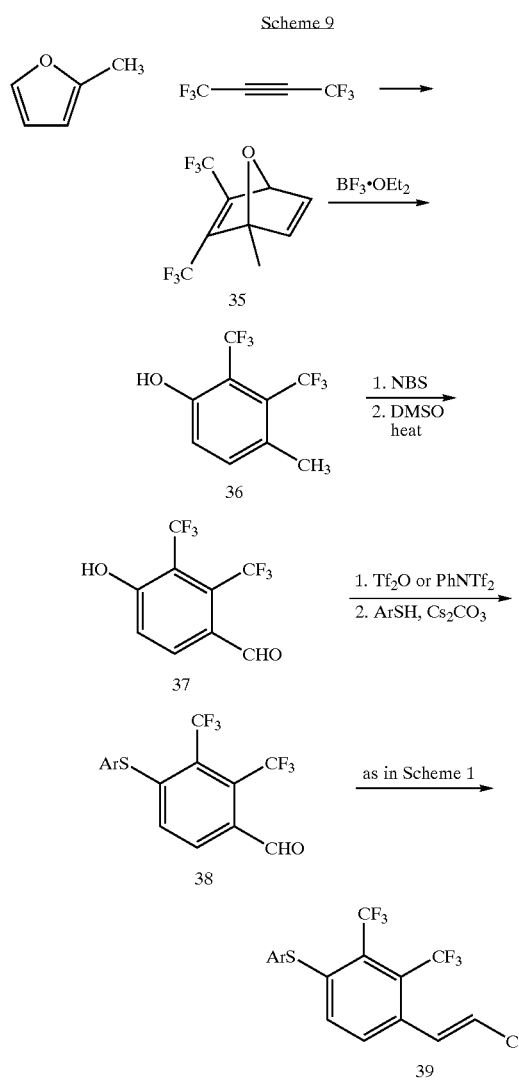

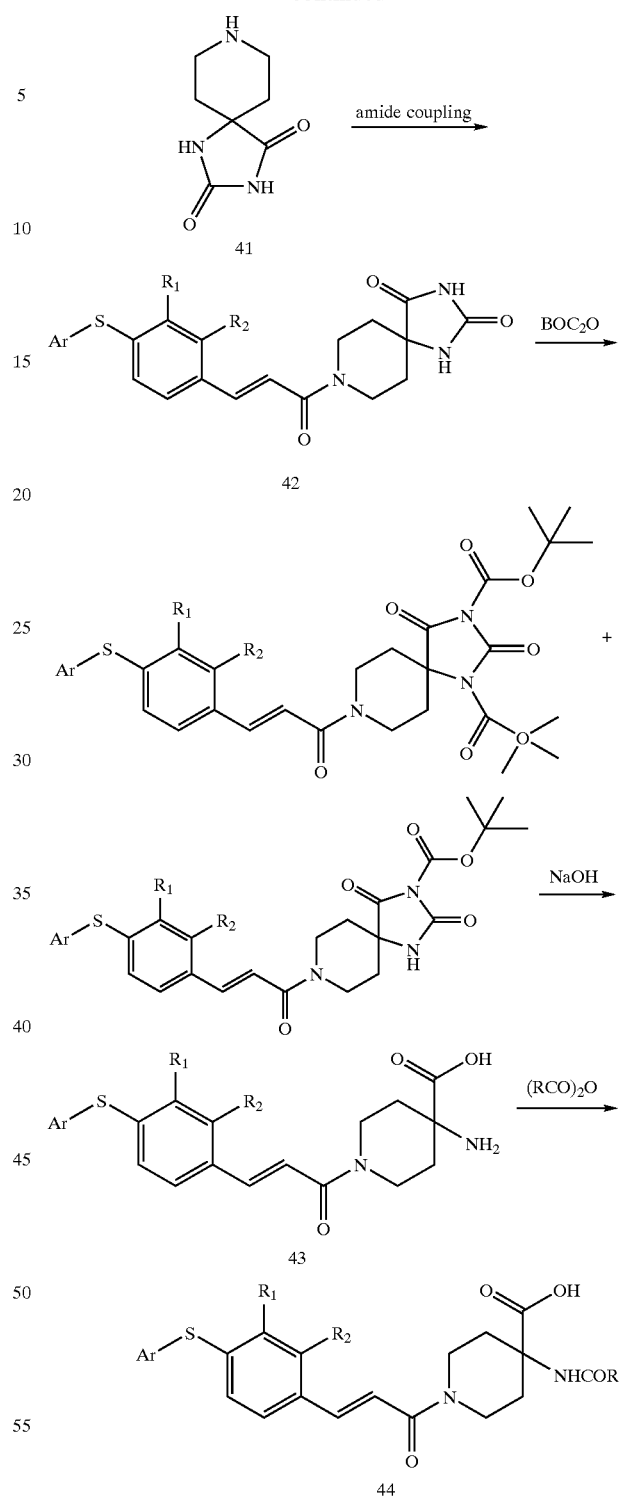

Cinnamides bearing more complex substituted piperidine amides can be produced by the methods outlined in Scheme 10 and 11. Cinnamic acids 40 are coupled to spirohydantoin piperidine 41, and the derived amide 42 is first reacted with an activating reagent (for example di-tert-butyl dicarbonate), and then hydrolyzed to the amino acid 43. The derived amino group may then be reacted further, for example with acid anhydrides or acid chlorides, to produce amides 44.

Scheme 10

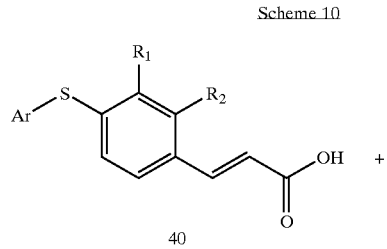

Further derivatives of piperidine amides can be obtained by coupling of piperidinone 45 with cinnamic acids 40, as shown in Scheme 11. Standard coupling conditions lead to amide 46, which is first reduced to the corresponding alcohol, then hydrolyzed to afford hydroxy acid 47.

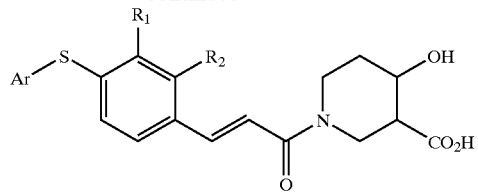

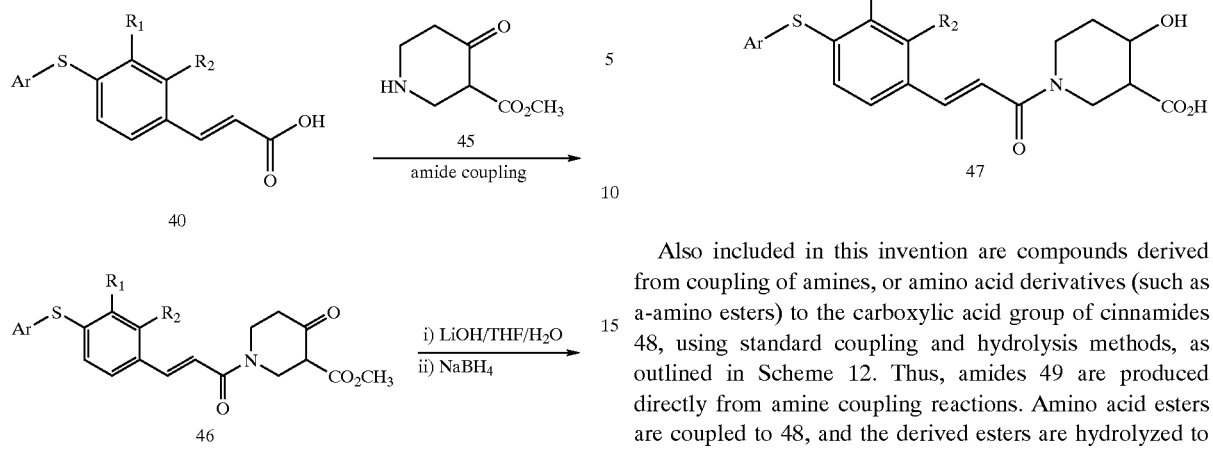

Also included in this invention are compounds derived from coupling of amines, or amino acid derivatives (such as a-amino esters) to the carboxylic acid group of cinnamides 48, using standard coupling and hydrolysis methods, as outlined in Scheme 12. Thus, amides 49 are produced directly from amine coupling reactions. Amino acid esters are coupled to 48, and the derived esters are hydrolyzed to the corresponding acids 50.

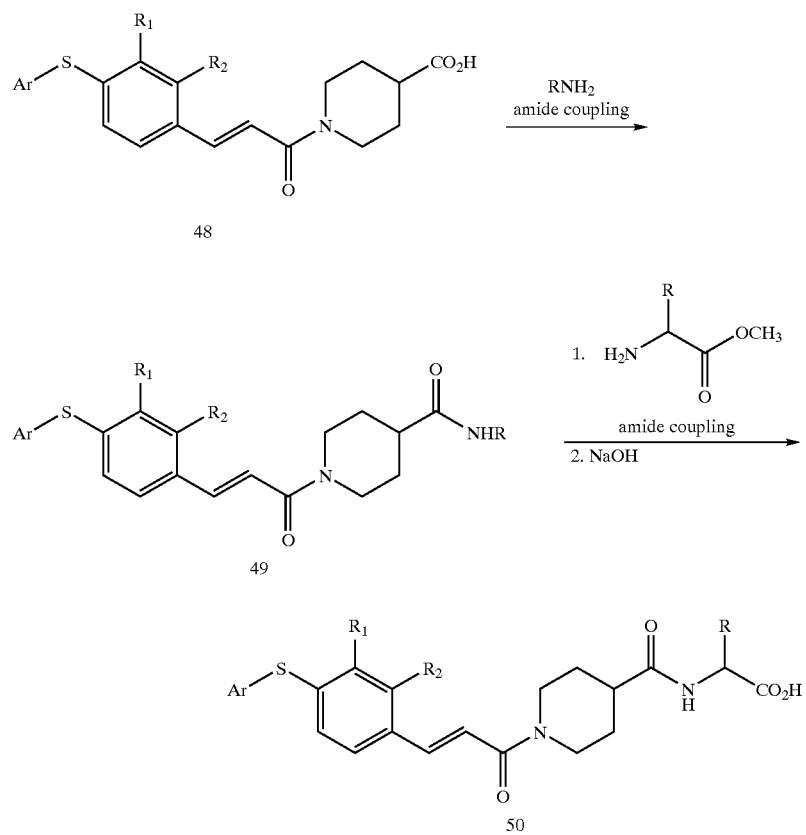

Inhibitors bearing substituted piperazine (or homopiperazine) cinnamides may be produced by the methods described in Scheme 13. The methods described may be utilized to produce piperazine amide 51. Secondary amine 51 then serves as educt for preparing amides 52, through standard coupling reactions. Alternatively, 51 may be converted to tertiary amines 53, through standard reductive alkylation methods (for example, condensation with an aldehyde in the presence of a reducing agent such as sodium triacetoxyborohydride).

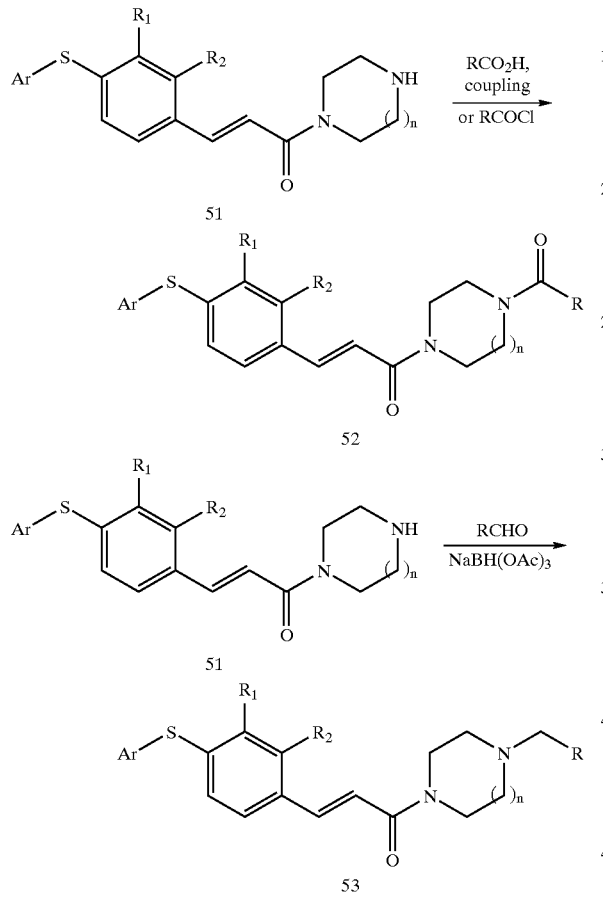

Scheme 13

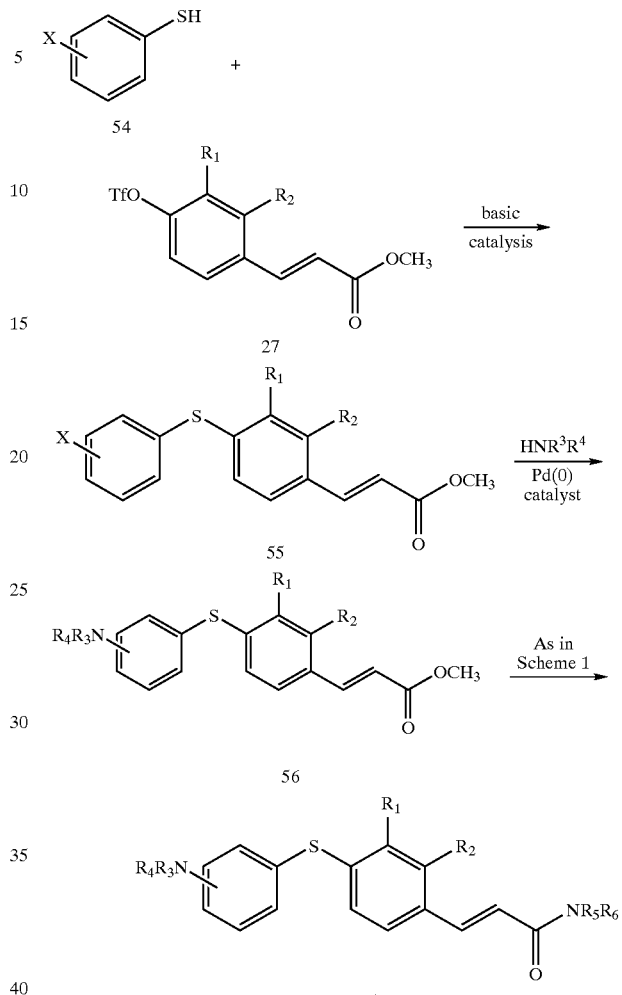

Scheme 14

A process for preparing analogs with amino substitutions of the aryl portion of the sulfides is illustrated in Scheme 14. The intermediate triflate 27 is reacted with halo-substituted thiophenols 54 (X=Br, Cl, OTf, OTs) under basic catalysis, to provide the sulfide derivative 55. The halogen or activated hydroxyl is then substituted with an amine, using the method of Buchwald (Old, D. W.; Wolfe, J. P.; Buchwald, S. L. *J. Am. Chem. Soc.* 1998, 120, 9722–9723). Similar transition-metal catalyzed reactions may be applied, see, for example, the method of Hartwig (Hamann, B. C.; Hartwig, J. F. *J. Am. Chem. Soc.* 1998, 120, 7369–7370). The $NR_3R_4$ group may constitute a cyclic or acyclic group, optionally substituted with additional functionalities that may enhance the activities of the compounds, and further synthetic transformations familiar to those skilled in the art may be applied. For instance, ester groups may be hydrolyzed to the corresponding carboxylic acids or amides. The derived anilino sulfides may then be processed as described above to produce the cinnamides 57.

Scheme 15 presents a synthesis of a particular class of substituted aniline derivatives bearing a carboxylic acid. A cyclic amino acid 58 may be converted into the corresponding t-butyl ester 61, through the intermediacy of carbamate 59 and ester 60, using standard synthetic methods. The amino ester 61 was then reacted with 2-fluoronitrobenzene with mild basic catalysis (for example, cesium fluoride, potassium bicarbonate), to provide the aniline derivative 62. The nitro group may then be transformed into an iodo-substituted derivative 64, by first conversion to the aniline 63, followed by standard diazotization and reaction of the diazonium salt with potassium iodide (among other similar methods for this Sandmeyer reaction). Using the method outlined in Scheme 7, the iodide 64 may be converted to the TIPS-protected arylthiol 65. In a sequence analogous with that described in Scheme 7, silyl thioether 65 may be reacted with cinnamide triflate 27 in the presence of a fluoride Ia source (for example, cesium fluoride), and thus converted to the diarylsulfide 66. Standard synthetic transformations (ester hydrolysis, amide coupling, and tert-butyl ester cleavage) provides the desired acid 68, through intermediate ester 67.

Compounds bearing elaborated ether groups on the aryl-sulfide ring were made according to Scheme 16. Methyl ether cinnamate esters such as 69 were hydrolyzed to the corresponding acids, and then the methyl ether was cleaved with boron tribromide (or alternatively using similar ether cleaving agents, such as trimethylsilyl iodide) to provide the hydroxy acids 70. Standard coupling methods provided the amides 71, which were then alkylated on the phenolic group using an appropriate alkyl halide 72 (where L is a linking group consisting of an acyclic or cyclic alkyl, or heterocyclic group) or lactone (m=1,2) in the presence of a base (such as potassium tert-butoxide, sodium hydride, or cesium carbonate). Alternatively, the phenolic group was alkylated with an ester-bearing alcohol 73, using Mitsunobu conditions. The resulting ester-bearing ethers 74 were then hydrolyzed to the corresponding acids 75 using standard hydrolysis conditions. Alternatively, the ester of 74 may be tert-butyl, in which case acidic deprotection to acid 75 would be employed (for example, using trifluoroacetic acid in dichloromethane, or hydrochloric acid in dioxane).

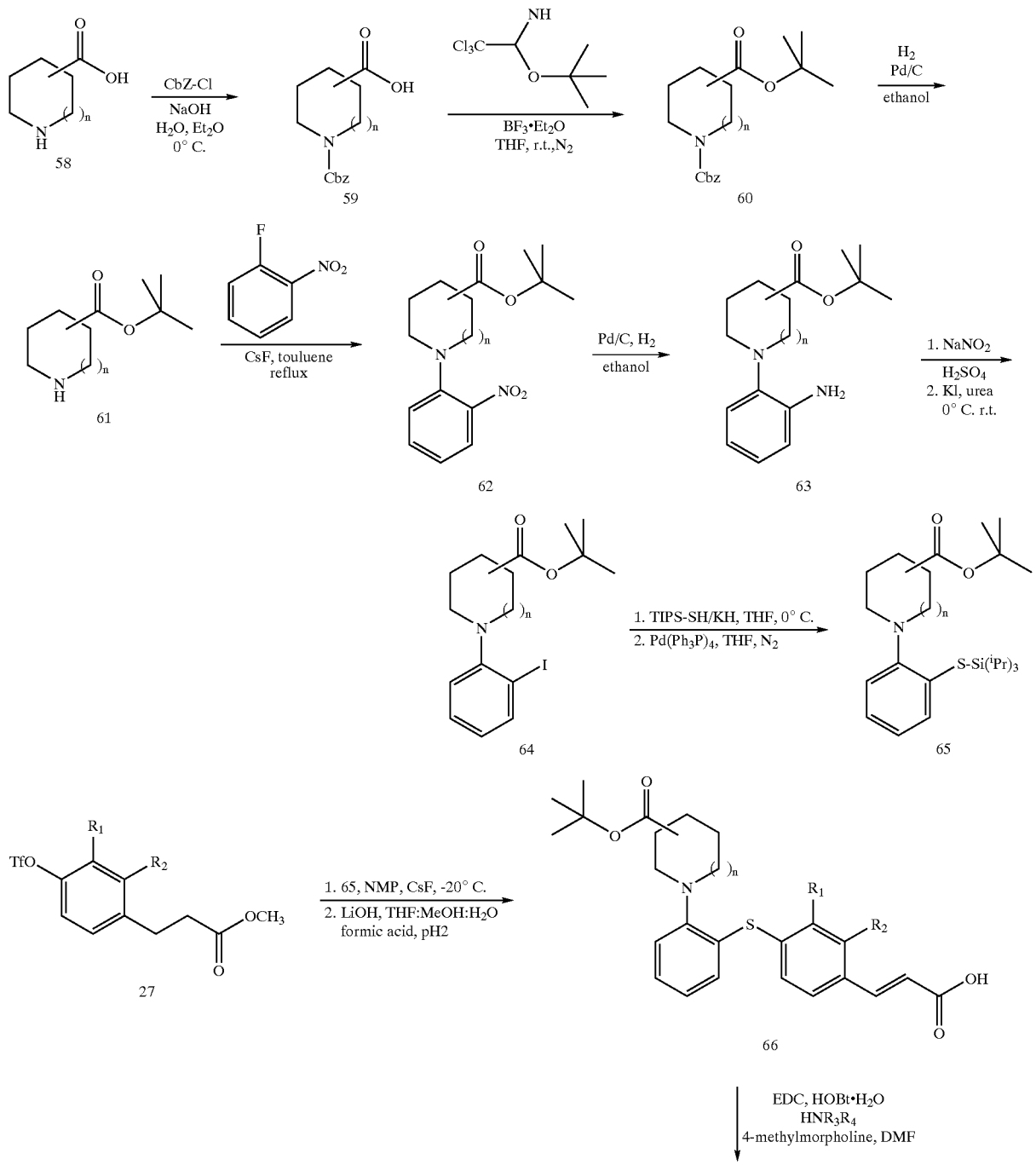

Scheme 15

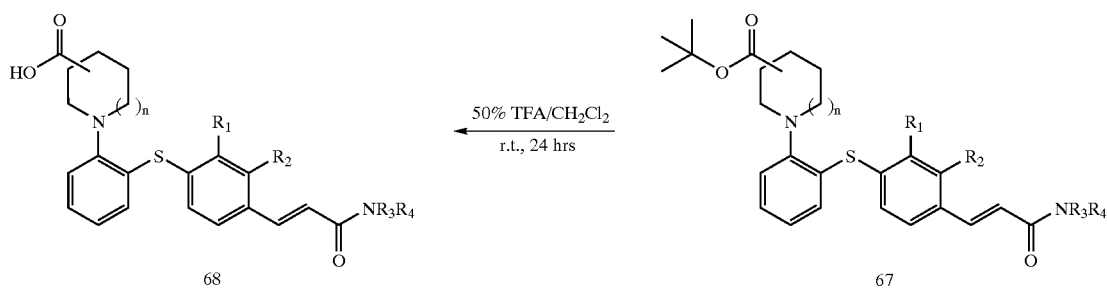

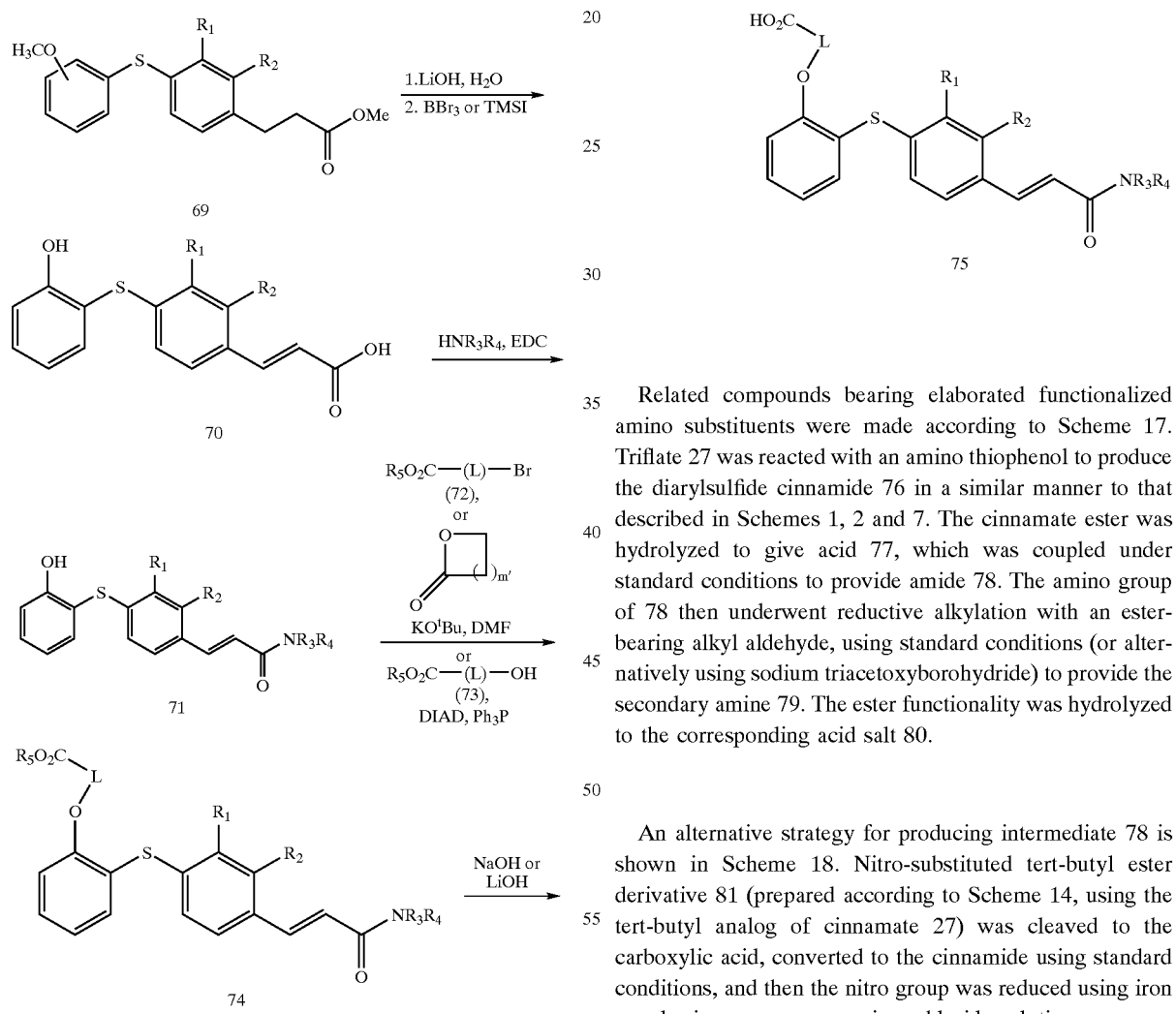

Related compounds bearing elaborated functionalized amino substituents were made according to Scheme 17. Triflate 27 was reacted with an amino thiophenol to produce the diarylsulfide cinnamide 76 in a similar manner to that described in Schemes 1, 2 and 7. The cinnamate ester was hydrolyzed to give acid 77, which was coupled under standard conditions to provide amide 78. The amino group of 78 then underwent reductive alkylation with an ester-bearing alkyl aldehyde, using standard conditions (or alternatively using sodium triacetoxyborohydride) to provide the secondary amine 79. The ester functionality was hydrolyzed to the corresponding acid salt 80.

An alternative strategy for producing intermediate 78 is shown in Scheme 18. Nitro-substituted tert-butyl ester derivative 81 (prepared according to Scheme 14, using the tert-butyl analog of cinnamate 27) was cleaved to the carboxylic acid, converted to the cinnamide using standard conditions, and then the nitro group was reduced using iron powder in aqueous ammonium chloride solution.

Scheme 17

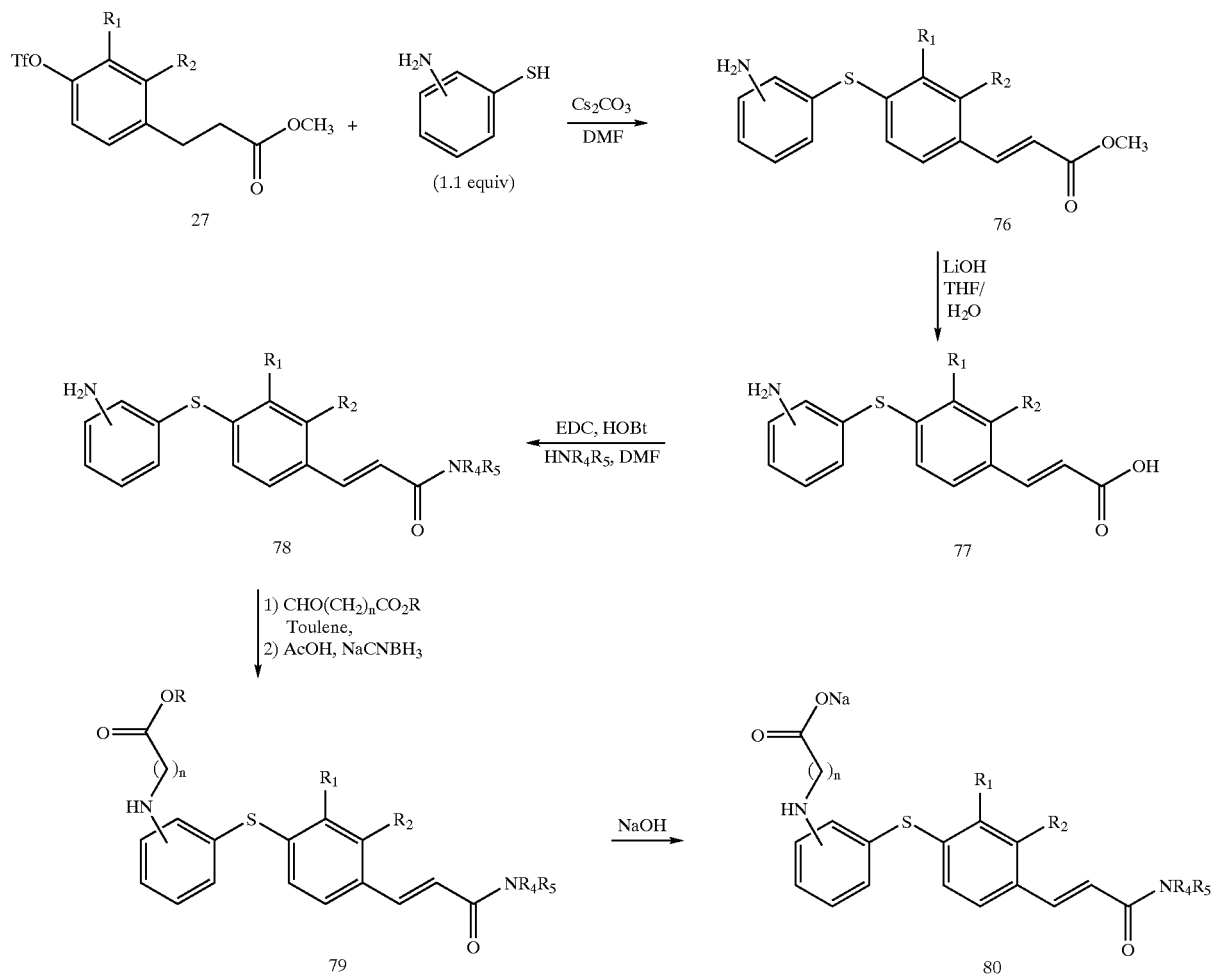

Scheme 18

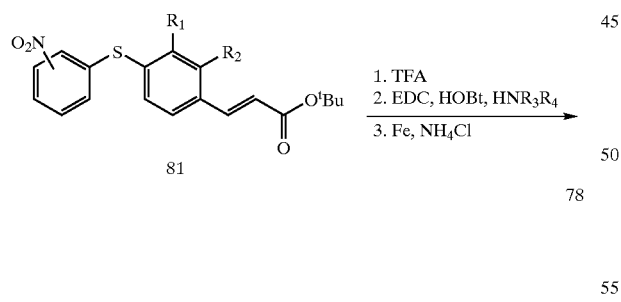

Scheme 19

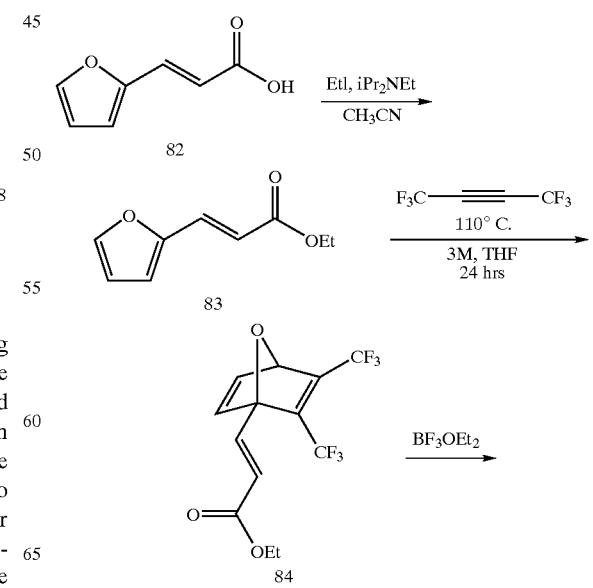

A modified method for the preparation of analogs bearing 2,3-bis-(trifluoromethyl)cinnamides is illustrated in Scheme 19. Commercially available acrylic acid 82 was esterified with ethyl iodide, and the ester 83 was condensed with 1,1,1,4,4,4-hexafluoro-2-butyne at 110° C. to give the bicyclic adduct 84. The bicyclic ether was then converted to the corresponding phenol 85 using a Lewis acid (for example boron trifluoride-etherate). Phenol 85 was then utilized as illustrated in Scheme 7 or Scheme 14 to prepare the desired inhibitors.

-continued

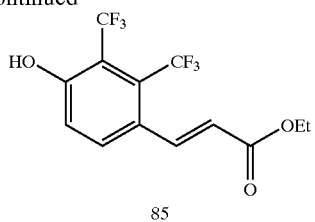

85

Scheme 20 illustrates an alternative method for preparing substituted anilinosulfides 57. Cinnamate ester 55 was converted to the corresponding tert-butyl ester 87, via reaction of acid 86 with tert-butyl trichloroacetimidate under Lewis acid catalysis. The bromide 87 was then coupled with an appropriately functionalized amine (illustrated in Scheme 20 with ethyl pyrrolidinecarboxylates) using palladium catalysis (for example, using the conditions of Buchwald or Hartwig noted for Scheme 14). The resultant substituted anilines 88 were then first cleaved to acids 89 using acidic conditions (FFA, HCl, or similar known deprotections for tert-butyl esters), then the acids 89 were coupled to amines $HNR_3R_4$ using standard conditions to provide amides 90. The ethyl ester group of 90 was then hydrolyzed using lithium or sodium hydroxide in aqueous media to produce acids 91.

Compounds with a 2,6-disubstitution pattern on the cinnamide ring system were made according to the method of Scheme 21. Commercially available 4,6-dichlorosalicylaldehyde was condensed with arylthiols under basic conditions to provide the diarylsulfide 92. The phenolic group was protected with allyl bromide, providing the O-allyl derivative 93. The method outlined in Scheme 1 was used to prepare the corresponding cinnamic acid 94, then the allyl group was removed using palladium(0)-catalyzed transfer to morpholine, thus producing hydroxy cinnamic acid 95. The acid group was coupled to a cyclic amino ester (n=0, 1, 2; R=Me, Et) under standard conditions to yield the amide 96. Basic hydrolysis conditions reveal the acid 97.

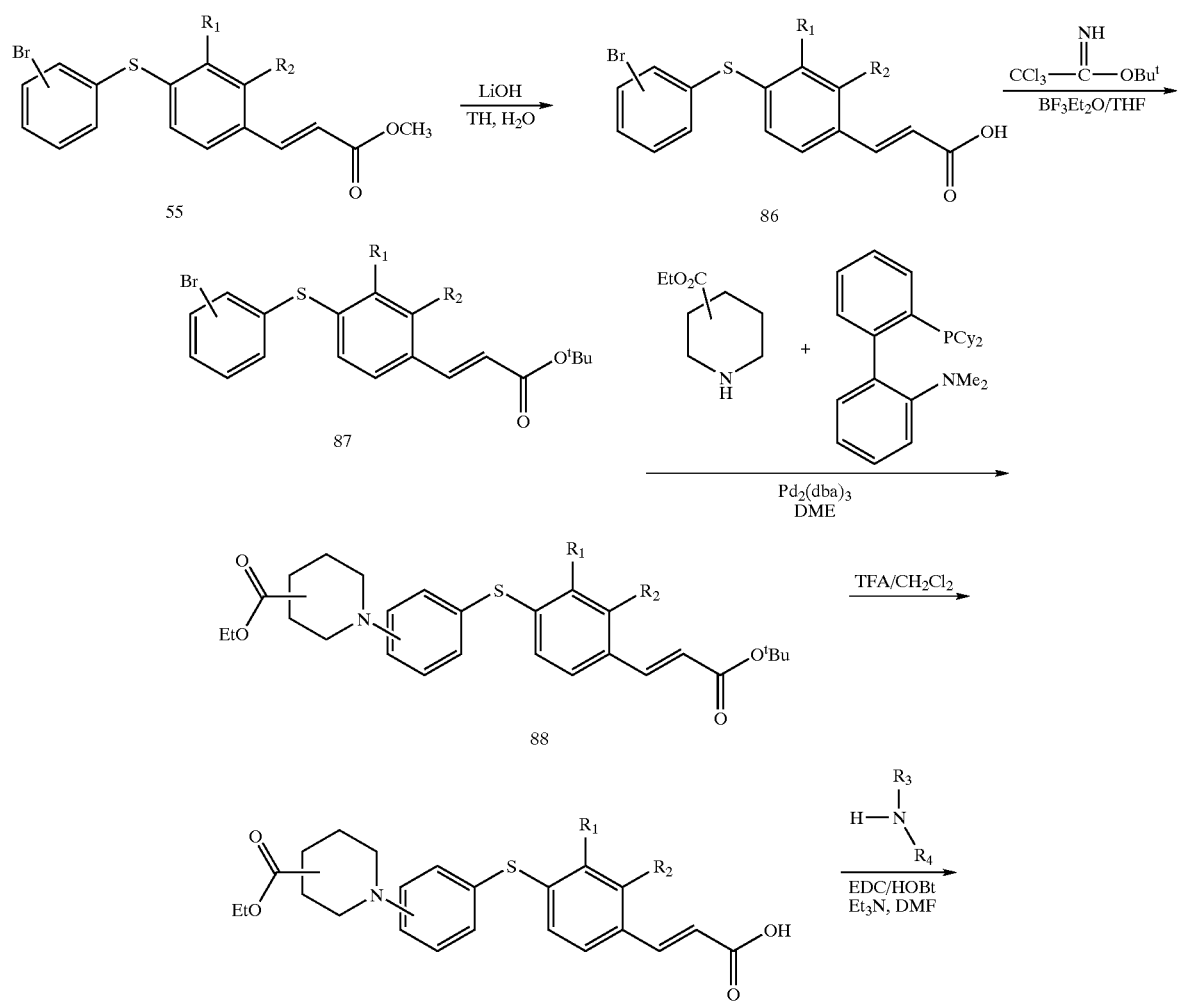

Scheme 20

-continued

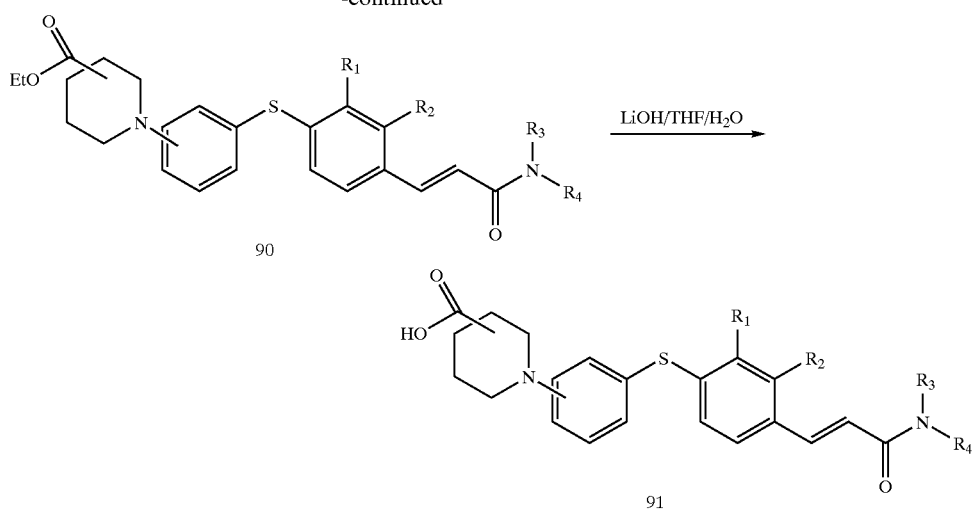

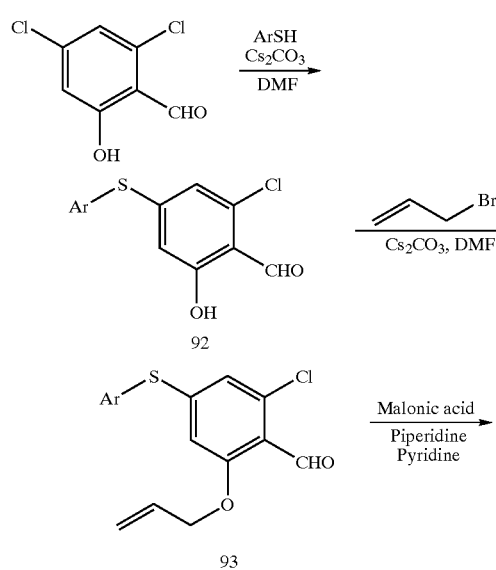

Scheme 21

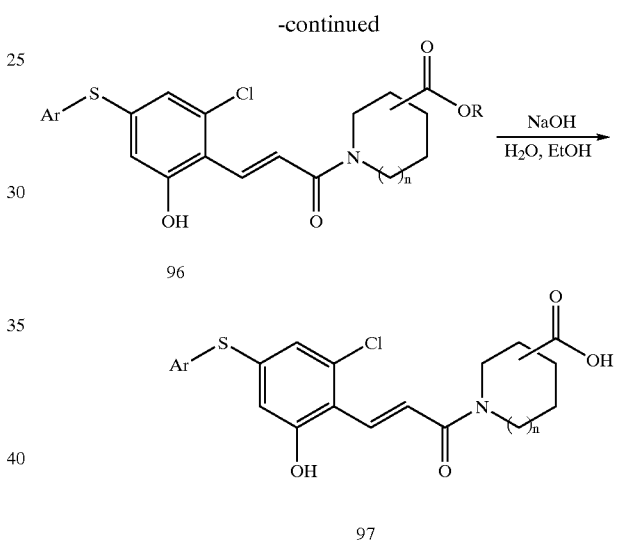

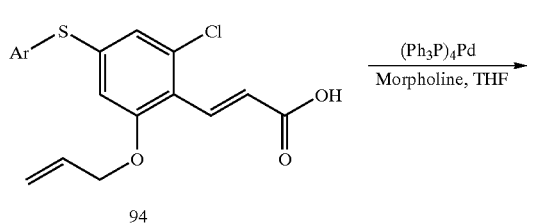

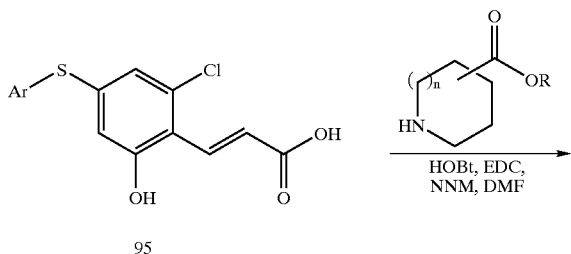

EXAMPLES

The compounds and processes of the present invention may be better understood in connection with the following Examples, which are intended as an illustration of and not a limitation upon the scope of the invention.

Example 1

(2,4-Dichlorophenyl)[2-(E-((6-hydroxyhexylamino)carbonyl)ethenyl)phenyl]sulfide

Example 1A

2-[(2,4-Dichlorophenyl)thio]benzaldehyde

To a stirred solution of 2,4-dichlorothiophenol (2.0 g, 11.2 mmol) in 25 mL of anhydrous DMF was added potassium carbonate (3.09 g, 22.4 mmol), followed by 2-chlorobenzaldehyde (1.26 mL, 11.3 mmol). The mixture was then heated under nitrogen atmosphere at 70° C. for 5 hours. The reaction mixture was then allowed to cool to room temperature and partitioned between ether and water.

The aqueous layer was extracted with ether once and the combined organic layer was washed with water and brine, dried over sodium sulfate and condensed in vacuo. The crude product was purified via silica gel flash chromatography, eluting with 5–10% ether/hexanes, to give 2.62 g (9.25 mmol, 83%) of the desired aldehyde as a colorless oil, which solidified slowly upon standing at room temperature.

Example 1B trans-2-[(2,4-Dichlorophenyl)thio]cinnamic acid

A mixture of the aldehyde (1.50 g, 5.3 mmol) from Example 1A, malonic acid (1.21 g, 11.6 mmol), piperidine (78.6 μL, 0.80 mmol) in 8.0 mL of anhydrous pyridine was heated at 110° C. for 2 hours. Gas evolution ceased during this period. Pyridine was then removed under vacuum. Water and 3N aq. HCl were then added with stirring. The desired cinnamic acid was then collected through filtration, washed with cold water and dried in a vacuum oven overnight to give 1.56 g (4.8 mmol, 91%) of white solid.

Example 1C (2,4-Dichlorophenyl)[2(E-((6-hydroxyhexylamino)carbonyl)ethenyl)phenyl]sulfide A suspension of the acid (284 mg, 0.87 mmol) from Example 1B in 5 mL of methylene chloride was stirred with $(COCl)_2$ (84 μL, 0.97 mmol), and one drop of DMF under nitrogen atmosphere for 90 minutes. The solvent was then removed under vacuum. The residue $(COCl)_2$ was removed with benzene (2×) in vacuo. To a separate flask, previously filled with 6-amino-1-hexanol (12 mg, 0.10 mmol), Hunig's base (22.8 μL, 0.13 mmol) and DMAP (1.1 mg, 0.008 mmol) in 2.0 mL of $CH_2Cl_2$, the acid chloride (30 mg, 0.087 mmol) in 1.0 mL of $CH_2Cl_2$ was then dropped in slowly. After 30 minutes, the reaction mixture was poured into 3N HCl and extracted with ethyl aceetate (EtOAc). The organic layer was washed with brine, dried with $Na_2SO_4$, condensed under reduced pressure. The crude product was purified by preparative TLC to give 21.0 mg (90%) of the title compound as a colorless oil. $^1$H NMR (CDCl$_3$, 300 MHz) δ 1.31–1.48 (m, 4H), 1.48–1.70 (m, 4H), 3.37 (q, J=6.7 Hz, 2H), 3.65 (t, J=6.3 Hz, 2H), 5.63 (br s, 1H), 6.36 (d, J=15.9 Hz, 1H), 6.71 (d, J=9.3 Hz, 1H), 7.05 (dd, J=2.4, 8.7 Hz, 1H), 7.31–7.49 (m, 4H), 7.65 (dd, J=2.1, 7.5 Hz, 1H), 7.99 (d, J=15.9 Hz, 1H). MS (DCI/NH$_3$) (M+NH$_4$)$^+$ at m/z 441, 443, 445.

Example 2

(2,4-Dichlorophenyl)[2-(E-((3-(1-imidazolyl)propylamino)carbonyl)ethenyl)phenyl]sulfide The title compound was prepared by the procedures described in Example 1C substituting 6-amino-1-hexanol with 1-(3-aminopropyl)imidazole. White powder; $^1$H NMR (d$^6$-DMSO, 300 MHz) δ 1.88 (p, J=7.7 Hz, 2H), 3.11 (q, J=7.7 Hz, 2H), 3.97 (t, J=7.7 Hz, 2H), 6.63 (d, J=15.9 Hz, 1H), 6.70 (d, J=8.7 Hz, 1H), 6.89 (d, J=0.9 Hz, 1H), 7.17 (d, J=0.9 Hz, 1H), 7.33 (dd, J=2.7, 8.7 Hz, 1H), 7.46–7.65 (m, 4H), 7.72 (d, J=2.7 Hz, 1H), 7.78 (d, J=15.9 Hz, 1H), 7.80 (d, J=8.7 Hz, 1H), 8.24 (t, J=5.9 Hz, 1H). MS (DCI/NH$_3$) (M+H)$^+$ at m/z 448, 450, 452. Analysis calculated for $C_{21}H_{19}N_3O_1Cl_2S_1$.0.87 $H_2O$: C, 56.30; H, 4.67; N, 9.38. Found: C, 56.30; H, 4.56; N, 9.27.

Example 3

(2,4-Dichlorophenyl)[2-chloro-4-(E-((2-hydroxyethylamino)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with ethanolamine. Colorless oil; $^1$H NMR (CDCl$_3$, 300 MHz) δ 3.57 (q, J=7.65 Hz, 2H), 3.71 (q, J=7.65 Hz, 2H), 6.06 (br s, 1H), 6.40 (d, J=15.3 Hz, 1H), 6.96 (d, J=8.7 Hz, 1H), 7.22–7.30 (m, 4H), 7.49–7.60 (m, 1H), 7.55 (d, J=15.3 Hz,1H). MS (APCI) (M+H)$^+$ at m/z 402, 404, 406, 408. Analysis calculated for $C_{17}H_{14}N_1O_2Cl_3S_1$ 0.25$H_2O$: C, 50.14; H, 3.59; N, 3.44. Found: C, 50.16; H, 3.62; N, 3.29.

Example 4

(2,4-Dichlorophenyl)[2-chloro-4-(E-((6-hydroxyhexylamino)carbonyl)ethenyl)phenyl]sulfide The title compound was prepared by the procedures described in Example 1 substituting 2-chlorobenzaldehyde with 3-chloro-4-fluoro-benzaldehyde. Colorless oil; $^1$H NMR (CDCl$_3$, 300 MHz) δ 1.42 (m, 4H), 1.58 (m, 4H), 3.40 (q, J=6.7 Hz, 2H), 3.65 (br m, 2H), 5.60 (br t, 1H), 6.35 (d, J=15.3 Hz, 1H), 6.98 (d, J=8.7 Hz, 1H), 7.22–7.30 (m, 4H), 7.49–7.60 (m, 1H), 7.55 (d, J=15.3 Hz, 1H). MS (APCI) (M+H)$^+$ at m/z 458, 460, 462, 464. Analysis calculated for $C_{21}H_{22}N_1O_2Cl_3S_1$ 0.27$H_2O$: C, 54.39; H, 4.90; N, 3.02. Found: C, 54.40; H, 4.85; N, 2.71.

Example 5

(2,4-Dichlorophenyl)[2-chloro-4-(E-((bis-(2-hydroxyethyl)amino)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with diethanolamine. Colorless oil; $^1$H NMR (CDCl$_3$, 300 MHz) δ 2.99 (br s, 2H), 3.67 (br m, 4H), 3.88 (t, J=5.1 Hz, 2H), 3.94 (t, J=5.1 Hz, 2H), 6.94 (d, J=15.3 Hz, 1H), 6.97 (d, J=8.7 Hz, 1H), 7.21–7.32 (m, 3H), 7.50–7.54 (m, 1H), 7.58 (d, J=2.4 Hz, 1H), 7.58 (d, J=15.3 Hz, 1H). MS (APCI) (M+H)$^+$ at m/z 446, 448, 450, 452. Analysis calculated for $C_{19}H_{18}N_1O_3Cl_3S_1$ 1.09$H_2O$: C, 48.93; H, 4.36; N, 3.00. Found: C, 48.88; H, 4.00; N, 3.01.

Example 6

(2,4-Dichlorophenyl)[2-chloro-4-(E-((3-(2-oxopyrrolidin-1-yl)propylamino)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with 1-(3-aminopropyl)-2-pyrrolidinone. Colorless oil; $^1$H NMR (CDCl$_3$, 300 MHz) δ 1.74 (qu, J=6.0 Hz, 2H), 2.09 (qu, J=7.5 Hz, 2H), 2.45 (t, J=8.25 Hz, 2H), 3.33 (q, J=6.0 Hz, 2H), 3.42 (q, J=8.25 Hz, 4H), 6.46 (d, J=15.6 Hz, 1H), 7.02 (d, J=8.7 Hz, 1H), 7.14–7.23 (m, 2H), 7.30 (dd, J=2.4, 8.7 Hz, 1H), 7.51 (d, J=2.4 Hz, 1H), 7.51 (d, J=15.6 Hz, 1H), 7.60 (d, J=2.1 Hz, 1H). MS (DCI/NH$_3$) (M+H)$^+$ at m/z 483, 485, 487, 489. Analysis calculated for $C_{22}H_{21}N_2O_2Cl_3S_1$ 0.57$H_2O$: C, 53.48; H, 4.52; N, 5.67. Found: C, 53.49; H, 4.60; N, 5.65.

Example 7

(2,4-Dichlorophenyl)[2-chloro-4-E-((1-monpholinyl)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1- hexanol with morpholine. White solid; $^1$H NMR (CDCl$_3$, 300 MHz) δ 3.59–3.80 (m, 8H), 6.83 (d, J=15.6 Hz, 1H), 6.97 (d, J=8.7 Hz, 1H), 7.16–7.32 (m, 3H), 7.49–7.53 (m, 1H), 7.59 (d, J=2.4 Hz, 1H), 7.59 (d, J=15.6 Hz, 1H). MS (DCI/NH$_3$) (M+H)$^+$ at m/z 428, 430, 432, 434. Analysis calculated for C$_{19}$H$_{16}$N$_1$O$_2$Cl$_3$S$_1$ 0.46H$_2$O: C, 52.22; H, 3.90; N, 3.20. Found: C, 52.20; H, 3.76; N, 3.12.

Example 8

(2,4-Dichlorophenyl)[2-chloro-4-(E-((4-methylpiperazin-1-yl)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with 1-methylpiperazine. Colorless oil; $^1$H NMR (CDCl$_3$, 300 MHz) δ 2.37 (s, 3H), 2.51 (br m, 4H), 3.63–3.87 (br m, 4H), 6.85 (d, J=15.6 Hz, 1H), 6.98 (d, J=8.7 Hz, 1H), 7.19–7.25 (m, 2H), 7.27 (dd, J=2.1, 8.7 Hz, 1H), 7.52 (t, J=0.9 Hz, 1H), 7.57 (d, J=15.6 Hz, 1H), 7.60 (d, J=2.1 Hz, 1H) MS (DCI/NH$_3$) (M+H)$^+$ at m/z 441, 443, 445, 447. Analysis calculated for C$_{20}$H$_{19}$N$_2$O$_1$Cl$_3$S$_1$ 0.45H$_2$O: C, 53.39; H, 4.46; N, 6.23. Found: C, 53.37; H, 4.46; N, 6.07.

Example 9

(2,4-Dichlorophenyl)[2-chloro-4-(E-((4-acetylpiperazin-1-yl)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with 1-acetylpiperazine. White solid; $^1$H NMR (CDCl$_3$, 300 MHz) δ 2.15 (s, 3H), 3.50–3.58 (m, 2H), 3.58–3.85 (m, 6H), 6.85 (d, J=15.3 Hz, 1H), 6.96 (d, J=8.7 Hz, 1H), 7.24–7.36 (m, 3H), 7.54 (d, J=2.4 Hz, 1H), 7.61 (d, J=15.3 Hz, 1H), 7.61 (d, J=2.1 Hz, 1H). MS (DCI/NH$_3$) (M+H)$^+$ at m/z 486, 488, 490, 492. Analysis calculated for C$_{21}$H$_{19}$N$_2$O$_2$Cl$_3$S$_1$ 0.85H$_2$O: C, 51.99; H, 4.30; N, 5.77. Found: C, 52.03; H, 4.27; N, 5.67.

Example 10

(2,4-Dichlorophenyl)[2-chloro-4-(E-((4-(2-pyridyl)piperazin-1-yl)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with 1-(2-pyridyl)piperazine. White solid; $^1$H NMR (CDCl$_3$, 300 MHz) δ 3.59 (br m, 2H), 3.69 (br m, 2H), 3.78 (br m, 2H), 3.86 (br m, 2H), 6.64–6.72 (m, 2H), 6.90 (d, J=15.6 Hz, 1H), 6.99 (d, J=8.7 Hz, 1H), 7.22–7.25 (m, 2H), 7.31(dd, J=2.4, 8.7 Hz, 1H), 7.49–7.57 (m, 2H), 7.61 (d, J=15.6 Hz, 1H), 7.62 (d, J=2.4 Hz, 1H), 8.19–8.24 (m, 1H). MS (DCI/NH$_3$) (M+H)$^+$ at m/z 504, 506, 508, 510. Analysis calculated for C$_{24}$H$_{20}$N$_3$O$_1$Cl$_3$S$_1$: C, 57.10; H, 3.99; N, 8.32. Found: C, 57.12; H, 4.06; N, 8.29.

Example 11

(2-(Hydroxymethyl)phenyl)[2-chloro-4-(E-((1-morpholinyl)carbonyl)ethenyl)phenyl]sulfide The title compound was prepared by the procedures described in Example 1 substituting 2,4-dichlorothiophenol with 2-mercaptobenzyl alcohol, 2-chlorobenzaldehyde with 3-chloro-4-fluoro-benzaldehyde, and 6-amino-1-hexanol with morpholine. White solid; $^1$H NMR (CDCl$_3$, 300 MHz) δ 3.50–3.62 (br m, 6H), 3.65–3.74 (br m, 2H), 4.54 (d, J=5.7 Hz, 2H), 5.33 (t, J=5.7 Hz, 1H), 6.62 (d, J=8.7 Hz, 1H), 7.28 (d, J=15.0 Hz, 1H), 7.36 (d, J=7.8 Hz, 1H), 7.42 (d, J=15.0 Hz, 1H), 7.43 (dd, J=1.8, 8.7 Hz, 1H), 7.50 (dd, J=2.1, 8.7 Hz, 1H), 7.55 (dd, J=2.1, 7.8 Hz, 1H), 7.68 (dd, J=1.5, 8.1 Hz, 1H), 8.02 (d, J=2.1 Hz, 1H). MS (DCI/NH$_3$) (M+H)$^+$ at m/z 390, 392. Analysis calculated for C$_{20}$H$_{20}$N$_1$O$_3$Cl$_1$S$_1$.0.09H$_2$O: C, 61.35; H, 5.20; N, 3.58. Found: C, 61.37; H, 5.48; N, 3.81.

Example 12

(2-Bromophenyl)[2-chloro-4-(E-((1-morpholinyl)carbonyl)ethenyl)phenyl]sulfide

The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with morpholine. White solid; $^1$H NMR (d$^6$-DMSO, 300 MHz) δ 3.50–3.66 (br m, 6H), 3.66–3.79 (br m, 2H), 7.05 (d, J=8.7 Hz, 1H), 7.26 (dd, J=2.1, 8.1 Hz, 1H), 7.33 (dd, J=2.1, 8.1 Hz, 1H), 7.36 (d, J=15.6 Hz, 1H), 7.39 (dd, J=1.8, 12.0 Hz, 1H), 7.45 (dd, J=1.8, 6.3 Hz, 1H), 7.48 (d, J=15.6 Hz, 1H), 7.64 (dd, J=2.1, 8.7 Hz, 1H), 7.80 (dd, J=2.8, 8.7 Hz, 1H), 8.09 (d, J=2.1 Hz, 1H). MS (DCI/NH$_3$) (M+H)$^+$ at m/z 438, 440, 442.

Example 13

(2,4-Dichlorophenyl)[2-chloro-4-(E-((4-(2-hydroxyethyl)piperazin-1-yl)carbonyl)ethenyl)phenyl]sulfide The title compound was prepared by the procedures described in Example 1 substituting 2-chlorobenzaldehyde with 3-chloro-4-fluoro-benzadehyde, and 6-amino-1-hexanol with 1-hydroxyethylpiperazine. Colorless oil; $^1$H NMR (CDCl$_3$, 300 MHz) δ 2.85–3.20 (br m, 6H), 3.84–4.19 (m, 6H), 6.80 (d, J=15.3 Hz, 1H), 6.94 (d, J=8.7 Hz, 1H), 7.22–7.38 (m, 3H), 7.50–7.56 (m, 1H), 7.56–7.62 (m, 1H), 7.60 (d, J=15.3 Hz, 1H). MS (DCI/NH$_3$) (M+H)$^+$ at m/z 471, 473, 475, 477.

Example 14

(2,4-Dichlorophenyl)[2-chloro-4-(E-((4-(2-hydroxyethoxyethyl)piperazin-1-yl)carbonyl)ethenyl)phenyl]sulfide The title compound was prepared by the procedures described in Example 1 substituting 2-chlorobenzaldehyde with 3-chloro-4-fluoro-benzaldehyde, and 6-amino-1-hexanol with 1-[2-(2-hydroxyethoxy)ethyl]piperazine. Colorless oil; $^1$H NMR (CDCl$_3$, 300 MHz) δ 2.73 (br m, 6H), 3.58–3.68 (m, 2H), 3.68–4.00 (m, 8H), 6.84 (d, J=15.3 Hz, 1H), 6.97 (d, J=8.7 Hz, 1H), 7.20–7.34 (m, 3H), 7.54 (d, J=7.5 Hz, 1H), 7.58 (d, J=15.3 Hz, 1H), 7.58–7.65 (overlapping d, 1H). MS (DCI/NH$_3$) (M+H)$^+$ at m/z 515, 517, 519,521.

Example 15

(2-Bromophenyl)[2-chloro-4-(E-((3-(hydroxymethyl)piperidin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with 3-hydroxymethylpiperidine. $^1$H NMR (DMSO-d$_6$, 300 MHz) δ 8.07 (d, J=17.7 Hz, 1H), 7.80 (d, J=7.7 Hz, 1H), 7.63 (br d, J=7.7 Hz, 1H), 7.44 (d, J=7.0 Hz, 1H), 7.40 (br s, 2H), 7.35 (m, 1H), 7.25 (dd 7.7, 1.5, 1H), 7.06 (dd, J=8.1, 2.9, 1H), 4.57 (m, 1H), 4.45 (m, 1H), 4.16 (br m, 2H), 1.2–1.8 (m, 8H). HRMS calculated for C$_{21}$H$_{21}$N$_1$O$_2$S$_1$Br$_1$Cl$_1$: 466.0243. Observed: 466.0247.

Example 16

(2-Bromophenyl)[2-chloro-4-(E-((2-(hydroxymethyl)piperidin-1-yl)carbonyl)ethenyl) phenyl]sulfide The title compound was prepared by the procedures described in Example 1 substituting 2,4-dichlorothiophenol with 2-bromothiophenol, 2-chlorobenzaldehyde with 3-chloro-4fluoro-benzaldehyde, and 6-amino-1-hexanol with 2-hydroxymethylpiperidine. $^1$H NMR (DMSO-d$_6$, 300 MHz) δ 8.03 (m, 1H), 7.79 (d, J=7.8 Hz, 1H), 7.61 (m, 1H), 7.30–7.45 (m, 4H), 7.23 (m, 1H), 7.07 (m, 1H), 4.79 (m, 2H), 4.61 (m, 2H), 4.10 (m, 1H), 1.50 (m, 6H). HRMS calculated for C$_{21}$H$_{21}$N$_1$O$_2$S$_1$Br$_1$Cl$_1$: 466.0243. Observed: 466.0247.

Example 17

(2-Bromophenyl)[2-chloro-4-(E-((3-acetamidopyrrolidin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with 3-acetamidopyrrolidine. $^1$H NMR (DMSO-d$_6$, 300 MHz) δ 8.14 (m, 1H), 8.07 (dd, J=9.8, 1.7Hz, 1H), 7.80 (d, J=7.8Hz, 1H), 7.64 (dd, J=8.1, 1.7 Hz, 1H), 7.25–7.47 (m, 4H), 7.10 (t, J=7.8 Hz, 1H), 7.03 (dd, J=8.1, 1.7 Hz, 1H), 3.45–4.34 (m, 6H), 2.02 (m, 1.81 (ap d, J=1.4 Hz, 1H). HRMS calculated for C$_{21}$H$_{20}$N$_2$O$_2$S$_1$Br$_1$Cl$_1$: 479.0196. Observed: 479.0183.

Example 18

(2-Bromophenyl)[2-chloro-4-(E-((4-hydroxypiperidin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with 4-hydroxypiperidine. $^1$H NMR (DMSO-d$_6$, 300 MHz) δ 8.08 (d, J=1.7 Hz, 1H), 7.80 (dd, J=8.0, 1.5 Hz, 1H), 7.63 (dd, J=8.3, 1.9 Hz, 1H), 7.44 (ap dd, J=7.5, 1.4 Hz, 2H), 7.40 (ap d, J=3.7 Hz, 2H), 7.34 (dt, J=7.6, 1.8 Hz, 1H), 7.25 (dd, J=7.5,1.7 Hz 1H), 7.05 (d, J=8.1 Hz, 1H), 4.76 (br s, 1H), 4.01 (m, 2H), 3.72 (m, 1H), 3.12 (m, 1H), 1.75 (m, 2H), 1.32 (m, 2H). HRMS calculated for C$_{20}$H$_{19}$N$_1$O$_2$S$_1$Br$_1$Cl$_1$: 452.0087. Observed: 452.0076.

Example 19

(2-Bromophenyl)[2-chloro-4-(E-((piperidin-1-yl) carbonyl)ethenyl)phenyl]sulfide

The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with piperidine. $^1$H NMR (DMSO-d$_6$, 300 MHz) δ 8.08 (d, J=1.7 Hz, 1H), 7.80 (dd, J=8.1, 1.4 Hz, 1H), 7.63 (dd, J=8.1, 1.7 Hz, 1H), 7.44 (ap dd, J=7.6, 1.5 Hz, 1H), 7.39 (ap d, J=4.8 Hz, 2H), 7.34 (dt, J=7.5, 1.6, 1H), 7.24 (dd, J=7.5, 1.7, 1H), 7.05 (d, J=8.1 Hz, 1H), 3.65 (br m, 2H), 3.53 (br m, 2H), 1.62 (br m, 2H), 1.50 (br m, 4H). HRMS calculated for C$_{20}$H$_{19}$N$_1$O$_1$S$_1$Br$_1$Cl$_1$: 436.0130. Observed: 436.0122.

Example 20

(2,4-Dichlorophenyl)[2-chloro-4-(E-((3-carboxypiperidin-1-yl)carbonyl)ethenyl)phenyl] sulfide The title compound was prepared by the procedures described in Example 1 substituting 2-chlorobenzaldehyde with 3-chloro-4-fluoro-benzaldehyde, and 6-amino-1-hexanol with nipecotic acid. Colorless oil; $^1$H NMR (CDCl$_3$, 300 MHz) δ 1.44–1.68 (br m, 1H), 1.68–2.00 (br m, 2H), 2.51–2.67 (br m, 1H), 3.13–3.37 (br m, 1H), 3.80–4.12 (br m, 1H), 4.30–5.00 (br m, 3H), 6.86 (d, J=15.3 Hz, 1H), 6.99 (d, J=8.7 Hz, 1H), 7.16–7.24 (m, 2H), 7.29 (d, J=8.7 Hz, 1H), 7.47–7.55 (m, 1H), 7.55 (d, J=15.3 Hz, 1H), 7.60 (br d, 1H). MS (APCI) (M+H)$^+$ at m/z 470, 472, 474, 476.

Example 21

(2,4-Dichlorophenyl)[2-chloro-4-(E-((4carboxypiperidin-1-yl)carbonyl)ethenyl)phenyl] sulfide The title compound was prepared by the procedures described in Example 1 substituting 2-chlorobenzaldehyde with 3-chloro-4-fluoro-benzaldehyde, and 6-amino-1-hexanol with isonipecotic acid. Colorless oil; $^1$H NMR (CDCl$_3$, 300 MHz) δ 1.68–1.85 (m, 2H), 1.98–2.09 (m, 2H), 2.60–2.72 (m, 1H), 2.90–3.13 (br m, 1H), 3.17–3.38 (br m, 1H), 3.93–4.12 (br m, 1H), 4.38–4.59 (br m, 1H), 6.86 (d, J=15.3 Hz, 1H), 6.99 (dd, J=8.7 Hz, 1H), 7.20–7.25 (m, 2H), 7.28 (dd, J=1.8, 8.7 Hz, 1H), 7.49–7.53 (m, 1H), 7.56 (d, J=15.3 Hz, 1H), 7.60 (d, J=1.8 Hz, 1H). MS (APCI) (M+H)$^+$ at m/z 470, 472, 474, 476.

Example 22

(2-Bromophenyl)[2-chloro-4-(E-((4-acetylhomopiperazin-1-yl)carbonyl)ethenyl)phenyl] sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with 4-acetylhomopiperazine. $^1$H NMR (DMSO-d$_6$, 300 MHz) δ 8.10 (m, 1H), 7.81 (d, J=7.7 Hz, 1H), 7.64 (m, 1H), 7.24–7.51 (m, 5H), 7.05 (m, 1H), 3.39–3.77 (m, 8H), 1.97 (m, 3H), 1.68 (m, 2H). HRMS calculated for C$_{22}$H$_{22}$N$_2$O$_2$S$_1$Br$_1$Cl$_1$: 493.0352. Observed: 493.0352.

Example 23

(2-Bromophenyl)[2-chloro-4-(E-((thiomorpholin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with thiomorpholine. $^1$H NMR (DMSO-d$_6$, 300 MHz) δ 8.10 (d, J=1.5 Hz, 1H), 7.80 (d, J=8.5 Hz, 1H), 7.64 (dd, J=8.1, 1.5 Hz, 1H), 7.31–7.48 (m, 4H), 7.36 (m, 1H), 7.26 (dd, J=8.1, 1.8 Hz, 1H), 7.05 (d J=8.1 Hz, 1H), 3.96 (m, 2H), 3.82 (m, 2H), 2.62 (m, 4H). HRMS calculated for C$_{19}$H$_{17}$N$_1$O$_1$S$_2$Br$_1$Cl$_1$: 455.9681. Observed: 455.9676.

Example 24

(2-Bromophenyl)[2-chloro-4-(E-((4-([2-oxo-2,3,dihydro-1H-benzimidazol-1-yl)piperidin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with 4-(2-oxo-2,3-dihydro-1H-benzimidazol-1-yl)piperidine. $^1$H NMR (DMSO-d$_6$ 300 MHz) δ 8.14 (d, J=1.5 Hz, 1H), 7.80 (dd, J=7.9, 1.3 Hz, 1H), 7.67 (dd, J=8.1, 1.8 Hz, 1H), 7.48 (ap s, 2H), 7.44 (dt, J=7.5, 1.2, 1H), 7.34 (dt, J=7.6, 1.6, 1H), 7.26 (dd, J=7.7, 1.8 Hz, 1H), 7.22 (m, 1H), 7.06 (d, J=8.1, 1H), 6.97 (ap d, J=2.6, 3H), 4.64 (m, 1H), 4.48 (m, 2H), 2.79 (m, 2H), 2.29 (m, 2H), 1.78 (m, 2H). HRMS calculated for C$_{27}$H$_{23}$N$_3$O$_2$S$_1$Br$_1$Cl$_1$: 568.0461. Observed: 568.0477.

Example 25

(2-Bromophenyl)[2-chloro-4-(E-((2-tetrahydroisoquinolinyl)carbonyl)ethenyl)phenyl]sulfide The title compound was prepared by the procedures described in Example 1 substituting 2,4-dichlorothiophenol with 2-bromothiophenol, 2-chlorobenzaldehyde with 3-chloro-4-fluoro-benzaldehyde, and 6-amino-1-hexanol with tetrahydroisoquinoline. $^1$H NMR (DMSO-d$_6$, 300 MHz) δ 8.12 (d, J=7.4 Hz, 1H), 7.81 (dd, J=7.7, 1.1 Hz, 1H), 7.67 (dd, J=8.3, 1.3 Hz, 1H), 7.47 (m, 2H), 7.43 (dd, J=7.5, 1.3 Hz, 2H), 7.34 (dt, J=7.6, 1.7 Hz, 1H), 7.27 (d 7.7 Hz, 1H), 7.19 (m, 4H), 7.05 (d, J=8.1 Hz, 1H), 4.92 (s, 1H), 4.72 (s, 1H), 3.95 (t, J=5.9 Hz, 1H), 3.78 (t, J=5.7 Hz, 1H), 2.89 (t, J=5.3 Hz, 1H), 2.83 (t, J=3.7, 1H). HRMS calculated for C$_{24}$H$_{19}$N$_1$O$_2$S$_1$Br$_1$Cl$_1$: 484.0138. Observed: 484.0128.

Example 26

(2-Methylphenyl)[2-trifluoromethyl-4-(E-((4-acetylpiperazin-1-yl)carbonyl)ethenyl)phenyl]sulfide The title compound was prepared by the procedures described in Example 1 substituting 2,4-dichlorothiophenol with 2-methylthiophenol, 2-chlorobenzaldehyde with 4-fluoro-3-trifluoromethyl benzaldehyde, and 6-amino-1-hexanol with 1-acetylpiperazine. $^1$H NMR (CDCl$_3$, 300 MHz) δ 7.79 (s, 1H); 7.63 (d, J=15.4 Hz, 1H); 7.51 (d, J=6.8 Hz, 1H); 7.41–7.33 (m, 3H); 7.28 (m, 1H); 6.83 (d, J=15.4 Hz, 1H); 6.79 (d, J=6.8 Hz, 1H); 3.80–3.60 (m, 6H); 3.57–3.50 (m, 2H); 2.34 (s, 3H); 2.14 (s, 3H). MS (ESI) m/z 919 (2M+Na)$^+$, 897 (2M+H)$^+$, 471 (M+Na)$^+$, 449 (M+H)$^+$.

Example 27

(2-Methylphenyl)[2-trifluoromethyl-4-(E-((1-morpholinyl)carbonyl)ethenyl)phenyl]sulfide The title compound was prepared by the procedures described in Example 1 substituting 2,4dichlorothiophenol with 2-methylthiophenol, 2-chlorobenzaldehyde with 4-fluoro-3-trifluoromethyl benzaldehyde, and 6-amino-I1-hexanol with morpholine. $^1$H NMR (CDCl$_3$, 300MHz) δ 7.79 (s, 1H); 7.63 (d, J=14.0 Hz, 1H); 7.52 (d, J=7.6 Hz, 1H); 7.40–7.30 (m, 3H); 7.28 (mi, 1H); 6.87 (d, J=14.0 Hz, 1H); 6.84 (d, J=7.6 Hz, 1H); 3.73 (br s, 8H); 2.34 (s, 3H). MS (ESI) m/z 837 (2M+Na)$^+$, 815 (2M+H)$^+$, 408 (M+H)$^+$.

Example 28

(2-Methylphenyl)[2-trifluoromethyl-4-(E-((2-(1-morpholinyl)ethylamino)carbonyl)ethenyl)phenyl]sulfide The title compound was prepared by the procedures described in Example 1 substituting 2,4-dichlorothiophenol with 2-methylthiophenol, 2-chlorobenzaldehyde with 4-fluoro-3-trifluoromethyl benzaldehyde, and 6-amino1-hexanol with 2-(1-morpholinyl)ethylamine. $^1$H NMR (CDCl$_3$, 300 MHz) δ 7.80 (s, 1H); 7.56 (d, J=15.8 Hz, 1H); 7.50 (d, J=8.1 Hz, 1H); 7.40–7.32 (m, 3H); 7.28 (m, 1H); 6.79 (d, J=15.8 Hz, 1H); 6.40 (d, J=8.1 Hz, 1H); 3.75 (t, J=4.6 Hz, 4H); 3.51 (q, J=5.5 Hz, 2H), 2.57 (t, J=5.8 Hz, 2H); 2.55–2.48 (m, 4H); 2.34 (s, 3H). MS (ESI) m/z 923 (2M+Na)$^+$,473 (M+Na)$^+$, 451 (M+H)$^+$.

Example 29

(2-Methylphenyl)[2-trifluoromethyl-4-(E-((4-phenylpiperazin-1-yl)carbonyl)ethenyl)phenyl]sulfide The title compound was prepared by the procedures described in Example 1 substituting 2,4-dichlorothiophenol with 2-methylthiophenol, 2-chlorobenzaldehyde with 4fluoro-3-trifluoromethyl benzaldehyde, and 6-amino-1-hexanol with 4-phenylpiperazine. $^1$H NMR (CDCl$_3$, 300 MHz) δ 7.81 (s, 1H); 7.64 (d, J=16.0 Hz, 1H); 7.51 (d, J=8.2 Hz, 1H); 7.40–7.27 (m, 6H); 6.98–6.90 (m, 4H); 6.80 (d, J=8.2 Hz, 1H); 3.88 (br s, 4H); 2.23 (br s, 4H); 2.34 (s, 3H). MS (ESI) m/z 987 (2M+Na)$^+$, 965 (2M+H)$^+$, 505 (M+Na)$^+$, 483 (M+H)$^+$, 451.

Example 30

(2-Methylphenyl)[2-trifluoromethyl-4-(E-((3-(2-oxopyrrolidin-1-yl)propylamino)carbonyl)ethenyl)phenyl]sulfide The title compound was prepared by the procedures described in Example 1 substituting 2,4-dichlorothiophenol with 2-methylthiophenol, 2-chlorobenzaldehyde with 4-fluoro-3-trifluoromethyl benzaldehyde, and 6-amino-1-hexanol with 3-(2-oxopyrrolidin-1-yl)propylamine. $^1$H NMR (CDCl$_3$, 300 MHz) δ 7.78 (s, 1H); 7.53 (d, J=15.6 Hz, 1H); 7.49 (d, J=7.2 Hz, 1H); 7.40–7.33 (m, 3H); 7.14 (m, 1H); 6.80 (d, J=8.2 Hz, 1H); 6.43 (d, J=15.6 Hz, 1H); 3.41 (m, 4H); 3.32 (q, J=6.1 Hz, 2H); 2.43 (t, J=6.6 Hz, 2H); 2.34 (s, 3H), 2.08 (m, 2H), 1.75 (m, 2H). MS (ESI) m/z 947 (2M+Na)$^+$, 925 (2M+H)$^+$, 485 (M+Na)$^+$, 463 (M+H)$^+$.

Example 31

(2-Methylphenyl)[2-trifluoromethyl-4-(E-((cyclopropylamino)carbonyl)ethenyl)phenyl]sulfide The title compound was prepared by the procedures described in Example 1 substituting 2,4-dichlorothiophenol with 2-methylthiophenol, 2-chlorobenzaldehyde with 4-fluoro-3-trifluoromethyl benzaldehyde, and 6-amino-1-hexanol with cyclopropylamine. $^1$H NMR (CDCl$_3$, 300

MHz) δ 7.76 (s, 1H); 7.56 (d, J=15.4 Hz, 1H); 7.50 (d, J=8.4 Hz, 1H); 7.40–7.30 (m, 3H); 7.28 (m, 1H); 6.88 (d, J=8.4 Hz, 1H); 6.30 (d, J=15.4 Hz, 1H); 5.70 (br s, 1H), 2.95 (m, 1H); 2.34 (s, 3H); 0.85 (m, 2H); 0.57 (m, 2H). MS (ESI) m/z 777 (2M+Na)$^+$, 755 (2M+H)$^+$, 400 (M+Na)$^+$, 378 (M+H)$^+$.

Example 32

(2,4-Dichlorophenyl)[2-nitro-4-(E-((4-acetylpiperazin-1-yl)carbonyl)ethenyl)phenyl]sulfide Example 32A 1-Chloro-2-nitro-4-(E-((4acetylpiperazin-1-yl)carbonyl)ethenyl)benzene To a stirred solution of trans-4-chloro-3-nitrocinnamic acid (1.50 g, 6.59 mmol) and 1-acetylpiperazine (0.89 g, 6.94 mmol) in 20 mL of DMF at room temperature was added EDAC (1.4 g, 7.30 mmol). The mixture was then stirred at room temperature for 2 hours. TLC indicated the complete consumption of the acid. Water was then added to quench the reaction and to precipitate out the product. Cinnamide was then collected through filtration and washed with cold water. The light yellow product was dried in a vacuum oven overnight at 40° C. to give 2.04 g (6.03 mmol, 91.6%) of the title compound.

Example 32B (2,4-Dichlorophenyl)[2-nitro-4-(E-((4-acetylpiperazin-1-yl)carbonyl)ethenyl)phenyl]sulfide To a stirred solution of 4-chloro-3-nitrocinnamide (275 mg, 0.814 mmol) from Example 32A in 1.0 mL of DMF was added potassium carbonate (169 mg, 1.22 mmol), followed by the dropwise addition of 2,4-dichlorothiophenol (146 mg, 0.815 mmol). The mixture was then stirred at room temperature for 60 minutes. Completion of the reaction was indicated by the TLC. Water was then added to precipitate the product. Filtration, washing with cold water, and drying in a vacuum oven afforded 350 mg (0.728 mmol, 89%) of the title compound as a light yellow solid. $^1$H NMR (d$^6$-DMSO, 300 MHz) δ 2.05 (s, 3H), 3.42–3.50 (br m, 4H), 3.50–3.64 (br m, 2H), 3.64–3.79 (br m, 2H), 6.83 (d, J=8.7 Hz, 1H), 7.44 (d, J=15.3 Hz, 1H), 7.55 (d, J=15.3 Hz, 1H), 7.63 (dd, J=2.7, 8.7 Hz, 1H), 7.83 (d, J=8.7 Hz, 1H), 7.93 (d, J=8.7 Hz, 1H), 7.96 (d, J=2.7 Hz, 1H), 8.69 (d, J=1.8 Hz, 1H). MS (DCI/NH$_3$) (M+H)$^+$ at m/z 497, 499, 501. Analysis calculated for C$_{21}$H$_{19}$N$_3$O$_4$Cl$_2$S$_1$ 0.82H$_2$O: C, 50.94; H, 4.20; N, 8.49. Found: C, 50.91; H, 4.21; N, 8.69.

Example 33

(2,4-Dichlorophenyl)[2-nitro-4-(E-((3-(2-oxopyrrolidin-1-yl)propylamino)carbonyl)ethenyl)phenyl]sulfide The crude product was purified with Gilson HPLC system, YMC C-18 column, 75×30 mm I.D., S-5 μM, 120 Å, and a flow rate of 25 mL/min, λ=214, 245 nm; mobile phase A, 0.05 M NH$_4$Oac, and B, CH$_3$CN; linear gradient 20–100% of B in 20 minutes to give the title compound (24 mg, 67%) as a light-yellow powder; $^1$H NMR (d$^6$-DMSO, 300 MHz) δ 1.64 (p, J=7.1 Hz, 2H), 1.91 (p, J=7.5 Hz, 2H), 2.21 (t, J=8.3 Hz, 2H), 3.15 (q, J=6.3 Hz, 2H), 3.21 (dd, J=9.9, 17.7 Hz, 2H), 3.32 (overlapping t, J=8.4 Hz, 2H), 6.72 (d, J=15.6 Hz, 1H), 6.86 (d, J=8.7 Hz, 1H), 7.46 (d, J=15.6 Hz, 1H), 7.63 (dd, J=2.4, 8.1 Hz, 1H), 7.79 (dd, J=2.4, 8.7 Hz, 1H), 7.84 (d, J=8.7 Hz, 1H), 7.96 (d, J=2.4 Hz, 1H), 8.18 (t, J=6.0 Hz, 1H), 8.46 (d, J=2.1 Hz, 1H). MS (DCI/NH$_3$) (M+H)$^+$ at m/z 494,496.

Example 34

(2,3-Dichlorophenyl)[2-nitro-4-(E-((4-acetylpiperazin-1-yl)carbonyl)ethenyl)phenyl]sulfide The title compound was prepared by the procedures described in Example 32B substituting 2,4-dichlorothiophenol with 2,3-dichlorothiophenol. Light-yellow powder; $^1$H NMR (d$^6$-DMSO, 300 MHz) δ 2.04 (s, 3H), 3.42–3.50 (br m, 4H), 3.50–3.64 (br m, 2H), 3.64–3.79 (br m, 2H), 6.88 (d, J=8.7 Hz, 1H), 7.45 (d, J=15.6 Hz, 1H), 7.55 (t, J=7.65 Hz, 1H), 7.57 (d, J=15.6 Hz, 1H), 7.78 (dd, J=1.8, 8.1 Hz, 1H), 7.87 (dd, J=1.8, 8.1 Hz, 1H), 7.95 (dd, J=2.7, 9.0 Hz, 1H), 8.69 (d, J=1.8 Hz, 1H). MS (DCI/NH$_3$) (M+H)$^+$ at m/z 497, 499, 501.

Example 35

(4-Bromophenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 4-bromothiophenol. Light-yellow powder; $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 6.90 (d, J=8.7 Hz, 1H), 7.43 (d, J=15.0 Hz, 1H), 7.54 (d, J=15.0 Hz, 1H), 7.58 (d, J=9.0 Hz, 2H), 7.78 (d, J=9.0 Hz, 2H), 7.92 (dd, J=2.1, 9.0 Hz, 1H), 8.65 (d, J=2.1 Hz, 1H). MS (DCI/NH$_3$) (M+H)$^+$ at m/z 507, 509.

Example 36

(4Methylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with p-thiocresol. Light-yellow powder; $^1$H NMR (d$^6$-DMSO, 300 MHz) δ 2.04 (s, 3H), 2.39 (s, 3H), 3.47 (br m, 4H), 3.52 (br m, 1H), 3.60 (br m, 1H), 3.68 (br m, 1H), 6.89 (d, J=8.7 Hz, 1H), 7.20 (d, J=8.1 Hz, 1H), 7.39 (d, J=8.4 Hz, 2H), 7.40 (d, J=15.0 Hz, 1H), 7.53 (d, J=15.0 Hz, 1H), 7.54 (d, J=8.4 Hz, 2H), 7.89 (dd, J=2.1, 8.7 Hz, 1H), 8.64 (d, J=2.1 Hz, 1H). MS (DCI/NH$_3$) (M+NH$_4$)$^+$ at m/z 443.

Example 37

(2,4-Dichlorophenyl)[2-nitro-4-(E-((4-(tert-butoxycarbonyl)piperazin-1-yl)carbonyl)ethenyl)phenyl]sulfide The title compound was prepared by the procedures described in Example 32 substituting 1-acetylpiperazine with tert-butyl piperazine carboxylate. Light-yellow powder; $^1$H NMR (d$^6$-DMSO, 300 MHz) δ 1.42 (s, 9H), 3.36 (overlapping m, 4H), 3.55 (br m, 2H), 3.70 (br m, 2H), 6.83 (d, J=8.7 Hz, 1H), 7.42 (d, J=15.6 Hz, 1H) 7.54 (d, J=15.6 Hz, 1H), 7.63 (dd, J=2.4, 8.4 Hz, 1H), 7.83 (d, J=8.7 Hz, 1H), 7.92 (dd, J=2.4, 8.7 Hz, 1H), 7.96 (d, J=2.7 Hz, 1H), 8.68 (d, J=2.4 Hz, 1H). MS (APCI) (M+H)$^+$ at m/z 538, 540, 542.

Example 38

(2,4-Dichlorophenyl)[2-nitro-4-(E-((4-(2-furoylcarbonyl)pipierazin-1-yl)carbonyl)ethenyl)phenyl]sulfide Example 38A (2,4-Dichlorophenyl)[2-nitro-4-(E-((piperazin-1-yl)carbonyl)ethenyl)phenyl]sulfide Trifluoroacetic Acid Salt The compound (100 mg, 0.186 mmol) from Example 37 was dissolved in 0.5 mL of neat trifluoroacetic acid (TFA).

The mixture was stirred at room temperature for 1 hour. The TFA was then removed under vacuum to give the title compound (105 mg) as a yellow solid.

Example 38B (2,4-Dichlorophenyl)[2-nitro-4-(E-((4-(2-furoylcarbonyl)piperazin-1-yl)carbonyl)ethenyl)phenyl]sulfide To a stirred solution of piperazine TFA salt (35 mg, 0.067 mmol) from Example 38A in 2.0 mL of $CH_2Cl_2$ was added $Et_3N$ (23 µL, 0.17 mmol), 4-dimethylaminopyridine (DMAP) (1.0 mg, 0.0082 mmol), and furyl chloride (8.0 µL, 0.080 mmol). The mixture was then stirred at room temperature for 30 minutes before the solvent was removed. The crude product was purified with Gilson HPLC system, YMC C-18 column, 75×30 mm I.D., S-5 µM, 120 Å, and a flow rate of 25 mL/min, λ=214, 245 nm; mobile phase A, 0.05 M $NH_4OAc$, and B, $CH_3CN$; linear gradient 20–100% of B in 20 minutes to give the title compound (24 mg, 67%) as a light-yellow powder; $^1H$ NMR ($d^6$-DMSO, 300 MHz) δ 3.62–3.87 (br m, 8H), 6.66 (q, J=2.1 Hz, 1H), 6.84 (d, J=8.7 Hz, 1H), 7.04 (d, J=3.3 Hz, 1H), 7.44 (d, J=15.3 Hz, 1H), 7.56 (d, J=15.3 Hz, 1H), 7.63 (dd, J=2.4, 8.1 Hz, 1H), 7.83 (d, J=8.4 Hz, 1H), 7.87 (d, J=2.1 Hz, 1H), 7.92 (dd, J=2.1, 12.0 Hz, 1H), 7.96 (d, J=2.1 Hz, 1H), 8.70 (d, J=2.1 Hz, 1H). MS (APCI) $(M+H)^+$ at m/z 532, 534, 536.

Example 39

(2,4-Dichlorophenyl)[2-nitro-4-(E-((4-(methanesulfonyl)piperazin-1-yl)carbonyl)ethenyl)phenyl]sulfide The title compound was prepared by the procedures described in Example 38B substituting furoyl chloride with methanesulfonyl chloride. Light-yellow powder; $^1H$ NMR ($d^6$-DMSO, 300 MHz) δ 2.90 (s, 3H), 3.25 (br m, 4H), 3.68 (br m, 2H), 3.83 (br m, 2H), 6.84 (d, J=9.0 Hz, 1H), 7.45 (d, J=15.6 Hz, 1H), 7.56 (d, J=15.6 Hz, 1H), 7.63 (dd, J=2.4, 8.7 Hz, 1H), 7.83 (d, J=9.0 Hz, 1H), 7.93 (dd, J=2.1, 9.0 Hz, 1H), 7.95 (d, J=2.7 Hz, 1H), 8.70 (d, J=2.1 Hz, 1H). MS (ESI) $(M+H)^+$ at m/z 516, 518, 520.

Example 40

(2,4-Dichlorophenyl)[2-nitro-4-(E-((4-(diethylaminocarbonylmethyl)piperazin-1-yl)carbonyl)ethenyl)phenyl]sulfide The title compound was prepared by the procedures described in Example 38B substituting furoyl chloride with 2-chloro-N,N-diethylacetamide. Light-yellow powder; $^1H$ NMR ($d^6$-DMSO, 300 MHz) δ 1.01 (t, J=7.2 Hz, 3H), 1.13 (t, J=7.2 Hz, 3H), 2.46 (br m, 4H), 3.16 (s, 2H), 3.24 (q, J=7.2 Hz, 2H), 3.37 (q, J=7.2 Hz, 2H), 3.56 (br m, 2H), 3.69 (br m, 2H), 6.83 (d, J=9.0 Hz, 1H), 7.46 (d, J=15.3 Hz, 1H), 7.52 (d, J=15.3 Hz, 1H), 7.62 (dd, J=2.4, 8.7 Hz, 1H), 7.82 (d, J=9.0 Hz, 1H), 7.92 (dd, J=2.1, 9.0 Hz, 1H), 7.95 (d, J=2.7 Hz, 1H), 8.67 (d, J=2.1 Hz, 1H). MS (ESI) $(M+NH_4)^+$ at m/z 573, 575, 577.

Example 41

(2,4-Dichlorophenyl)[2-nitro-4-(E-((4-(diethylaminocarbonyl)piperazin-1-yl)carbonyl)ethenyl)phenyl]sulfide The title compound was prepared by the procedures described in Example 38B substituting furoyl chloride with N,N-diethylcarbamyl chloride. Light-yellow powder; $^1H$ NMR ($d^6$-DMSO, 300 MHz) δ 1.06 (t, J=6.9 Hz, 6H), 3.12 (br m, 4H), 3.15 (q, J=6.9 Hz, 4H), 3.58 (br m, 2H), 3.72 (br m, 2H), 6.83 (d, J=8.7 Hz, 1H), 7.42 (d, J=15.6 Hz, 1H), 7.53 (d, J=15.6 Hz, 1H), 7.63 (dd, J=2.7, 9.0 Hz, 1H), 7.82 (d, J=8.7 Hz, 1H), 7.92 (dd, J=2.4, 8.7 Hz, 1H), 7.95 (d, J=2.7 Hz, 1H), 8.68 (d, J=2.1 Hz, 1H). MS (APCI) $(M+H)^+$ at m/z 537, 539, 541.

Example 42

(2,4-Dichlorophenyl)[2-nitro-4-(E-((4-(tert-butoxycarbonylmethyl)piperazin-1-yl)carbonyl)ethenyl)phenyl]sulfide The title compound was prepared by the procedures described in Example 38B substituting $CH_2CL_2$ with $CH_3CN$ as solvent, and furoyl chloride with tert-butyl bromoacetate. Light-yellow powder; $^1H$ NMR ($CDCl_3$, 300 MHz) δ 1.47 (s, 9H), 2.70 (br m, 4H), 3.21 (s, 2H), 3.74 (br m, 2H), 3.82 (br m, 2H), 6.73 (d, J=8.7 Hz, 1H), 6.92 (d, J=15.0 Hz, 1H), 7.39 (dd, J=2.4, 8.7 Hz, 1H), 7.47 (d, J=8.7 Hz, 1H), 7.61 (d, J=15.0 Hz, 1H), 7.62 (d, J=2.4 Hz, 1H), 7.66 (d, J=8.7 Hz, 1H), 8.43 (br d, 1H). MS (APCI) $(M+H)^+$ at m/z 552, 554, 556.

Example 43

(2,4-Dichlorophenyl)[2-nitro-4-(E-((4-(carboxycarbonyl)piperazin-1-yl)carbonyl)ethenyl)phenyl]sulfide

Example 43A (2,4-Dichlorophenyl)[2-nitro-4-(E-((4-(carbethoxycarbonyl)piperazin-1-yl)carbonyl)ethenyl)phenyl]sulfide The title compound was prepared by the procedures described in Example 38B substituting furoyl chloride with ethyl oxalyl chloride.

Example 43B (2,4-Dichlorophenyl)[2-nitro-4-(E-((4-(carboxycarbonyl)piperazin-1-yl)carbonyl)ethenyl)phenyl]sulfide To a stirred solution of the ethyl ester (40 mg, 0.074 mmol) from Example 43A in 2 mL of ethanol was added saturated LiOH (0.25 mL). The mixture was then stirred at room temperature for 2 hours. Water (2 mL) was then added to the reaction mixture, which was then acidified to pH=2 with concentrated HCl. The precipitates were collected through filtration, washed with cold water, dried under vacuum to give the title compound (30 mg, 79%) as a light yellow solid. $^1H$ NMR ($d^6$-DMSO, 300 MHz) δ 3.52 (br m, 4H), 3.62 (br m, 2H), 3.76 (br m, 2H), 6.84 (d, J=9.0 Hz, 1H), 7.46 (d, J=15.3 Hz,1H), 7.56 (d, J=15.3 Hz, 1H), 7.63 (dd, J=2.7, 8.7 Hz, 1H), 7.83 (d, J=9.0 Hz, 1H), 7.93 (d, J=9.0 Hz, 1H), 7.96 (d, J=2.7 Hz, 1H), 8.70 (br d, 1H). MS (APCI) $(M-COO)^+$ at m/z 466, 468, 470.

Example 44

(2,4-Dichlorophenyl)[2-nitro-4-(E-((4-(carboxymethyl)piperazin-1-yl)carbonyl)ethenyl)phenyl]sulfide The title compound was prepared by the procedures described in Example 38A substituting compound from Example 37 with compound from Example 42. Light-yellow powder; $^1$H NMR (d$^6$-DMSO, 300 MHz) δ 3.14 (s, 2H), 3.40 (overlapping br m, 4H), 3.44 (br m, 1H), 3.51 (br m, 1H), 3.57 (br m, 1H), 3.71 (br m, 1H), 6.82 (d, J=8.7 Hz, 1H), 7.42 (d, J 15.6 Hz, 1H), 7.52 (d, J=15.6 Hz, 1H), 7.63 (dd, J=2.4, 8.7 Hz, 1H), 7.83 (d, J=8.7 Hz, 1H), 7.92 (dd, J=2.4, 8.7 Hz, 1H), 7.96 (d, J=2.4 Hz, 1H), 8.68 (d, J=2.4 Hz, 1). MS (APCI) (M+H)$^+$ at m/z 496, 498, 500.

Example 45

(2-Methylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with o-thiocresol. Light-yellow powder; $^1$H NMR (d$^6$-DMSO, 300 MHz) δ 2.03 (s, 3H), 2.29 (s, 3H), 3.47 (br m, 4H), 3.53 (br m, 1H), 3.60 (br m, 1H), 3.67 (br m, 1H), 3.83 (br m, 1H), 6.64 (d, J=8.7 Hz, 1H), 7.40 (d, J=15.0 Hz, 1H), 7.36–7.42 (m, 1H), 7.46–7.57 (m, 3H), 7.63 (d, J=6.9 Hz, 1H), 7.89 (dd, J=2.4, 9.0 Hz, 1H), 8.66 (d, J=2.4 Hz, 1H). MS (APCI) (M+H)$^+$ at m/z 426.

Example 46

(2-Chlorophenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-chlorothiophenol. Light-yellow powder, $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.73 (br m, 1H), 6.75 (d, J=9.0 Hz, 1H), 7.43 (d, J=15.3 Hz, 1H), 7.54 (d, J=15.3 Hz, 1H), 7.55 (dd, J=1.8, 8.1 Hz, 1H), 7.64 (t, J=1.8, 8.1 Hz, 1H), 7.76 (d, J=1.8, 8.1 Hz, 1H), 7.82 (d, J=1.8, 8.1 Hz, 1H), 7.93 (dd, J=2.4, 9.0 Hz, 1H), 8.68 (d, J=2.4 Hz, 1H). MS (APCI) (M+H)$^+$ at m/z 446, 448, 450.

Example 47

(2-Aminophenyl)[2-nitro-4-(E-((4-acetylpiperazin-1-yl)carbonyl)ethenyl)]phenyl]sulfide The title compound was prepared by the procedures described in Example 32 substituting 2,4-dichlorothiophenol with 2-aminothiophenol. Light-yellow powder; $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 5.58 (s, 2H), 6.65 (td, J=1.5, 15.0 Hz, 1H), 6.72 (dd, J=1.5, 8.7 Hz, 1H), 7.00 (dd, J=1.8, 8.7 Hz, 1H), 7.27 (t, J=1.5, 8.6 Hz, 1H), 7.36 (dd, J=1.5, 8.7 Hz, 1H), 7.39 (d, J=15.3 Hz, 1H), 7.53 (d, J=15.3 Hz, 1H), 7.89 (dd, J=1.8, 8.7 Hz, 1H), 8.64 (d, J=1.8 Hz, 1H). MS (APCI) (M+H)$^+$ at m/z 427.

Example 48

(2-Hydroxymethylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-mercaptobenzyl alcohol. Light-yellow powder; $^1$H NMR (d$^6$-DMSO, 300 MHz) δ 2.03 (s, 3H), 3.47 (br m, 4H), 3.52 (br m, 1H), 3.60 (br m, 1H), 3.67 (br m, 1H), 3.73 (br m, 1H), 4.53 (d, J=5.7 Hz, 1H), 5.34 (t, J=5.7 Hz, 1H), 6.65 (d, J=8.7 Hz, 1H), 7.40 (d, J=15.3 Hz, 1H), 7.46 (d, J=7.8 Hz, 1H), 7.53 (d, J=15.3 Hz, 1H), 7.59 (d, J=7.5 Hz, 1H), 7.64 (d, J=7.5 Hz, 1H), 7.87 (dd, J=2.1, 8.7 Hz, 1H), 8.65 (d, J=2.1 Hz, 1H). MS (APCI) (M+NH$_4$)$^+$ at m/z 459.

Example 49

(2-Ethylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-ethylthiophenol. Light-yellow powder; $^1$H NMR (d$^6$-DMSO, 300 MHz) δ 1.01 (t, J=7.65 Hz, 3H), 2.04 (s, 3H), 2.69 (q, J=7.65 Hz, 2H), 3.47 (br m, 4H), 3.52 (br m, 1H), 3.59 (br m, 1H), 3.67 (br m, 1H), 3.73 (br m, 1H), 6.64 (d, J=8.7 Hz, 1H), 7.38 (dd, J=2.4, 7.5 Hz, 1H), 7.40 (d, J=15.6 Hz, 1H), 7.50–7.61 (m, 3H), 7.53 (d, J=15.6 Hz, 1H), 7.89 (dd, J=2.4, 8.7 Hz, 1H), 8.64 (d, J=2.4 Hz, 1H). MS (APCI) (M+Cl)$^-$ at m/z 474, 476.

Example 50

(2-iso-Propylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-isopropylthiophenol. Light-yellow powder; $^1$H NMR (d$^6$-DMSO, 300 MHz) δ 1.05 (d, J=6.9 Hz, 6H), 2.04 (s, 3H), 3.47 (br m, 4H), 3.52 (br m, 1H), 3.60 (br m, 1H), 3.67 (br m, 1H), 3.72 (br m, 1H), 6.64 (d, J=8.4 Hz, 1H), 7.34–7.41 (m, 2H), 7.39 (d, J=15.3 Hz, 1H), 7.52 (d, J=15.3 Hz, 1H), 7.56–7.73 (m, 2H), 7.90 (dd, J=2.1, 8.7 Hz, 1H), 8.64 (d, J=2.1 Hz, 1H). MS (APCI) (M+NH$_4$)$^+$ at m/z 471. Analysis calculated for C$_{24}$H$_{27}$N$_3$O$_4$S$_1$.0.21H$_2$O: C, 63.03; H, 5.96; N, 9.13. Found: C, 63.03; H, 6.04; N, 9.19.

Example 51

(2-tert-Butylphenyl)[2-nitro-4-(E-((4-acetylpiperazin-1-yl)carbonyl)ethenyl)phenyl]sulfide The title compound was prepared by the procedures described in Example 32 substituting 2,4-dichlorothiophenol with 2-tert-butylthiophenol. Light-yellow powder; $^1$H NMR (d$^6$-DMSO, 300 MHz) δ 1.46 (s, 9H), 2.04 (s, 3H), 3.47 (br m, 4H), 3.52 (br m, 1H), 3.60 (br m, 1H), 3.67 (br m, 1H), 3.73 (br m, 1H), 6.68 (d, J=8.7 Hz, 1H), 7.35 (t, J=7.5 Hz, 1H), 7.39 (d, J=15.3 Hz, 1H), 7.45–7.57 (m, 2H), 7.50 (d, J=15.3 Hz, 1H), 7.65 (d, J=8.1 Hz, 1H), 7.88 (dd, J=2.4, 8.7 Hz, 1H), 8.64 (d, J=2.4 Hz, 1H). MS (APCI) (M+NH$_4$)$^+$ at m/z 485.

Example 52

(2-Chlorophenyl)[2-chloro-4-(E-((4-acetylpiperazin-1-yl)carbonyl))2-propenyl)phenyl]sulfide

Example 52A

3'-Chloro-4'-[(2-chlorophenyl)thio]acetophenone

The title compound was prepared by the procedures described in Example 1A substituting 2,4-dichlorothiophenol with 2-chlorothiophenol, and 2-chlorobenzaldehyde with 4'-fluoro-3'-chloroacetophenone.

Example 52B (2-Chlorophenyl)[2-chloro-4-(E-(1-ethoxycarbonyl)2-propenyl)phenyl]sulfide To a stirred suspension of NaH (60% in mineral oil, 121 mg, 3.03 mmol) in 20 mL of anhydrous THF under nitrogen atmosphere was added triethyl phosphonoacetate dropwise. After 20 minutes, the acetophenone (600 mg, 2.02 mmol) from Example 52A in THF (5 mL) was added in one portion. The resulting clear solution was then stirred at room temperature for 7 hours. Reaction was then stopped, most of the solvent was evaporated, and the residue was partitioned between EtOAc (2×20 mL) and water. The combined organic layer was washed with water and brine, dried over $Na_2SO_4$, concentrated in vacuo. The crude product was purified using silica gel flash column chromatography eluting with 5–10% $Et_2O$ in hexanes to give the (E)-isomer of the cinnamate (500 mg, 68%) as a white solid.

Example 52C (2-Chlorophenyl)[2-chloro-4-(E-(1-carboxy)2-propenyl)phenyl]sulfide A mixture of the cinnamate (500 mg, 1.37 mmol) from Example 52B in 5 mL of EtOH/THF (4: 1) was stirred with sat. LiOH solution (0.50 mL) at 50° C. for 2 hours. The mixture was then acidified with 3N HCl and extracted with $CH_2Cl_2$ (3×10 mL). The combined organic layer was dried over $MgSO_4$, concentrated under reduced pressure to give the title compound (450 mg, 97%) as a white solid.

Example 52D (2-Chlorophenyl)[2-chloro-4-(E-((4-acetylpiperazin-1-yl)carbonyl))2-propenyl)phenyl]sulfide The title compound was prepared using the cinnamic acid from Example 52C by the procedures described in Example 1C substituting 6-amino-1-hexanol with 1-acetylpiperazine. White solid; $^1$H NMR ($CDCl_3$, 300 MHz) δ 2.10–2.20 (m, 3H), 2.25 (s, 3H), 3.40–3.80 (m, 8H), 6.28 (s, 1H), 7.00 (d, J=8.7 Hz, 1H), 7.19–7.36 (m, 4H), 7.46–7.56 (m, 2H). MS (APCI) $(M+NH_4)^+$ at m/z 466, 468, 470.

Example 53

(2-(1-Morpholinylmethyl)phenyl)[2-chloro-4-(E-((1-morpholinyl)carbonyl)ethenyl)phenyl]sulfide

Example 53A (2-(1-Bromomethyl)phenyl)[2-chloro-4-(E-((1-morpholinyl)carbonyl)ethenyl)phenyl]sulfide To a stirred solution of benzyl alcohol (195 mg, 0.32 mmol) from Example 11 in 2.0 mL of anhydrous DMF was added LiBr (48 mg, 0.35 mmol). The mixture was then cooled in an ice-water bath, and $PBr_3$ (60 μL, 0.40 mmol) was dropped in slowly. The ice bath was then removed and the mixture was stirred at room temperature for 1 hour. Water was then added, the mixture was then partitioned between EtOAc and aqueous $NaHCO_3$. The aqueous layer was extracted with EtOAc once. The combined organic layer was washed with water and brine, dried over $Na_2SO_4$, concentrated on a rotavap. The crude bromide (230 mg) was used directly for the alkylation without purification.

Example 53B (2-(1-Morpholinylmethyl)phenyl)[2-chloro-4-(E-((1-morpholinyl)carbonyl)ethenyl)phenyl]sulfide To a stirred solution of morpholine (10 μL, 0.11 mmol) in 0.5 mL of $CH_3CN$ was added Hunig's base (23.7 μL, 0.14 mmol), followed by the bromide (40 mg, 0.091 mmol). The mixture was then stirred at room temperature for 2 hours. Solvent was then removed and the crude product was purified with Gilson Preparative HPLC as described in Example 38B to give the title compound as a white solid. $^1$H NMR ($d^6$-DMSO, 300 MHz) δ 2.33 (br t, 4H), 3.45 (br t, 4H), 3.50–3.65 (m, 6H), 3.56 (s, 2H),3.65–3.80 (br m, 2H), 6.74 (d, J=8.7 Hz, 1H), 7.30 (d, J=15.3 Hz, 1H), 7.35–7.41 (m, 2H), 7.43 (d, J=15.3 Hz, 1H), 7.46 (td, J=2.4, 8.1 Hz, 1H), 7.52 (dd, J=2.1, 8.7 Hz, 1H), 7.56 (d, J=8.1 Hz, 1H), 8.02 (d, J=2.1 Hz, 1H). MS ($DCI/NH_3$) $(M+H)^+$ at m/z 459, 461.

Example 54

(2-(4-(1,3-Benzodioxolyl-5-methyl)piperazin-1-ylmethyl)phenyl)[2-chloro-4-(E-((1-morpholinyl)carbonyl)ethenyl)phenyl]sulfide The title compound was prepared by the procedures described in Example 53B substituting morpholine with 1-piperonylpiperazine. White solid; $^1$H NMR ($d^6$-DMSO, 300 MHz) δ 2.13–2.40 (br m, 8H), 3.28 (s, 2H), 3.49–3.64 (br m, 6H), 3.54 (s, 2H), 3.70 (br m, 2H), 5.97 (s, 2H), 6.69 (dd, J=1.8, 8.1 Hz, 1H), 6.74 (d, J=8.7 Hz, 1H), 6.79 (d, J=1.8 Hz, 1H), 6.81 (d, J=8.1 Hz, 1H), 7.39 (d, J=15.3 Hz, 1H), 7.33–7.38 (m, 2H), 7.38–7.50 (m, 2H), 7.43 (d, J=15.3 Hz, 1H), 7.53 (d, J=8.4 Hz, 1H), 8.00 (d, J=2.1 Hz, 1H). MS ($DCI/NH_3$) $(M+H)^+$ at m/z 592, 594.

Example 55

(2-(4-(iso-Propylaminocarbonylmethyl)piperazin-1-ylmethyl)phenyl)[2-chloro-4-(E-((1-morpholinyl)carbonyl)ethenyl)phenyl]sulfide The title compound was prepared by the procedures described in Example 53B substituting morpholine with N-isopropyl-1-piperazineacetamide. White solid; $^1$H NMR ($d^6$-DMSO, 300 MHz) δ 1.04 (d, J=6.3 Hz, 6H), 2.20–2.42 (br m, 8H), 2.78 (s, 2H), 3.47–3.64 (br m, 6H), 3.56 (s, 2H), 3.64–3.76 (br m, 2H), 3.85 (qd, J=6.3, 8.1 Hz, 1H), 6.73 (d, J=8.7 Hz, 1H), 7.29 (d, J=15.6 Hz, 1H), 7.31–7.39 (m, 2H), 7.43 (d, J=15.6 Hz, 1H), 7.45 (td, J=2.7, 6.3 Hz, 1H), 7.50 (dd, J=2.1, 8.7 Hz, 1H), 7.55 (d, J=7.8 Hz, 1H), 8.00 (d, J=2.1 Hz, 1H). MS ($DCI/NH_3$) $(M+H)^+$ at m/z 557, 559.

Example 56

(2-((N-Ethoxycarbonylmethyl-N-methyl)aminomethyl)phenyl)[2-chloro-4-(E-((1-morpholinyl)carbonyl)ethenyl)phenyl]sulfide The title compound was prepared by the procedures described in Example 53B substituting morpholine with ethyl sarcosinate hydrochloride. White solid; $^1$H NMR ($d^6$-DMSO, 300 MHz) δ 1.16 (t, J=7.2 Hz, 3H), 2.27 (s, 2H), 3.30 (s, 2H), 3.51–3.66 (br m, 6H), 3.66–3.75 (br m, 2H), 3.78 (s, 2H), 4.05 (q, J=7.2 Hz, 2H), 6.75 (d, J=8.7 Hz, 1H), 7.30 (d, J=15.3 Hz, 1H), 7.33–7.38 (m, 2H), 7.42–7.50 (m, 2H), 7.43 (d, J=15.3 Hz, 1H), 7.53 (dd, J=2.1, 8.7 Hz, 1H), 7.60 (d, J=7.8 Hz, 1H), 8.02 (d, J=2.1 Hz, 1H). MS ($DCI/NH_3$) $(M+H)^+$ at m/z 489, 491.

Example 57

(2-Formylphenyl)[2-chloro-4-(E-((1-morpholinyl)carbonyl)ethenyl)phenyl]sulfide

To a stirred solution of the alcohol (368 mg, 0.94 mmol) from Example 11 in 5 mL of anhydrous acetonitrile was added activated 4 Å molecular sieves, TPAP (3.3 mg, 0.0094 mmol), and NMO (110 mg, 1.03 mmol). The mixture was then stirred at room temperature for 3 hours. The reaction mixture was then quenched with dimethyl sulfide (100 µL). The crude product was filtered through celite, washed with acetonitrile, condensed in vacuo. The title compound was purified by silica gel column chromatography to give a white solid (216 mg, 59%). $^1$H NMR (d$^6$-DMSO, 300 MHz) δ 3.60 (br m, 6H), 3.73 (br m, 2H), 7.00 (d, J=8.4 Hz, 1H), 7.40 (d, J=15.3 Hz, 1H), 7.42 (d, J=8.4 Hz, 1H), 7.51 (d, J=15.3 Hz, 1H), 7.52 (td, J=1.8, 8.1 Hz, 1H), 7.61 (td, J=1.8, 8.1 Hz, 1H), 7.71 (dd, J=2.1, 8.4 Hz, 1H), 8.02 (dd, J=2.1, 8.4 Hz, 1H), 8.14 (d, J=2.1 Hz, 1H). MS (DCI/NH$_3$) (M+H)$^+$ at m/z 388, 390.

Example 58

(2-(4-Formylpiperazin-1-ylmethyl)phenyl)[2-chloro-4-(E-((1-morpholinyl)carbonyl)ethenyl)phenyl] sulfide The title compound was prepared by the procedures described in Example 53B substituting morpholine with 1-formyl piperazine. White solid; $^1$H NMR (d$^6$-DMSO, 300 MHz) δ 2.20–2.32 (m, 6H), 2.74 (br m, 2H), 3.48 (s, 2H), 3.59 (m, 6H), 3.70 (br m, 2H), 6.74 (d, J=8.7 Hz, 1H), 7.29 (d, J=15.6 Hz, 1H), 7.35–7.41 (m, 2H), 7.42 (d, J=15.6 Hz, 1H), 7.45–7.52 (m, 3H), 7.98 (d, J=2.1, 1H). MS (DCI/NH$_3$) (M+H)$^+$ at m/z 486, 488.

Example 59

(2-(E-((1-Morpholinyl)carbonyl)ethenyl)phenyl)[2-chloro-4-(E-((1-morpholinyl)carbonyl)ethenyl) phenyl]sulfide A mixture of bromide (80 mg, 0.18 mmol) from Example 12, acryloylmorpholine (33 mg, 0.23 mmol), Pd(OAc)$_2$ (2.0 mg, 0.009 mmol), P(o-tolyl)$_3$ (17 mg, 0.056 mmol), Et$_3$N (39 µL, 0.27 mmol), and anhydrous DMF (1.0 mL) in a pressure tube was flushed with nitrogen for 5 minutes before it was capped and heated at 110° C. overnight. TLC indicated almost complete consumption of the starting bromide. The reaction mixture was then allowed to cool to room temperature, partitioned between EtOAc and water. The aqueous layer was extracted once with EtOAc. The combined organic layer was washed with water and brine, dried over Na$_2$SO$_4$, condensed under reduced pressure. The crude product was purified with Gilson Preparative HPLC as described in Example 38B to give the title compound as a light-brown solid (35 mg, 39%). $^1$H NMR (d$^6$-DMSO, 300 MHz) δ 3.43–3.88 (m, 16H), 6.58 (d, J=8.7 Hz, 1H), 7.30 (d, J=15.3 Hz, 2H), 7.43 (d, J=15.3 Hz, 1H), 7.47–7.64 (m, 4H), 7.86 (d, J=15.3 Hz, 1H), 8.06 (d, J=2.1 Hz, 1H), 8.14 (d, J=7.5 Hz, 1H). MS (DCI/NH$_3$) (M+NH$_4$)$^+$ at m/z 516, 518. Analysis calculated for C$_{26}$H$_{27}$N$_2$O$_4$Cl$_1$S$_1$·0.46H$_2$O: C, 61.56; H, 5.55; N, 5.21. Found: C, 61.56; H, 5.50; N, 5.43.

Example 60

(2-Formylphenyl)[2-nitro-4-(E-((4-acetylpiperazin-1-yl)carbonyl)ethenyl)phenyl]sulfide The title compound was prepared by the procedures described in Example 57 substituting compound from Example 11 with compound from Example 48. Yellow solid; $^1$H NMR (d$^6$-DMSO, 300 MHz) δ 2.04 (s, 3H), 3.47 (br m, 4H), 3.52 (br m, 1H), 3.60 (br m, 1H), 3.68 (br m, 1H), 3.74 (br m, 1H), 6.85 (d, J=8.4Hz, 1H), 7.44 (d, J=15.6 Hz, 1H), 7.55 (d, J=15.6 Hz, 1H), 7.61 (d, J=7.5 Hz, 1H), 7.73 (t, J=7.5 Hz, 1H), 7.80 (td, J=2.4, 7.5 Hz, 1H), 7.92 (dd, J=2.1, 9.0 Hz, 1H), 8.04 (dd, J=2.4, 7.5 Hz, 1H), 8.66 (d, J=2.1 Hz, 1H), 10.29 (s, 1H). MS (APCI) (M+Cl)$^-$ at m/z 474, 476.

Example 61

(2-Formylphenyl)[2-chloro-4-(E-((1-morpholinyl) carbonyl)ethenyl)phenyl]sulfide, N,N-dimethyl hydrazone A mixture of the aldehyde (20 mg, 0.052 mmol) from Example 57, 1,1-dimethyl hydrazine (3.9 µL, 0.052 mmol) in 0.5 mL of EtOH with a tiny amount of AcOH was stirred at room temperature overnight. The solvent was then removed and the product was purified by preparative TLC to give the title compound (20 mg, 90%) as a white solid.

Example 62

(2-((3-(1-Morpholinyl)propyl)-1-amino)phenyl)[2-chloro-4-(E-((1-morpholinyl)carbonyl)ethenyl) phenyl]sulfide A mixture of bromide (60 mg, 0.14 mmol) from Example 12, aminopropylmorpholine (24 µL, 0.17 mmol), Pd$_2$(dba)$_3$ (1.2 mg, 0.0013 mmol), BINAP (2.5 mg, 0.004 mmol), NaOt-Bu (19 mg, 0.20 mmol), 18-crown-6 (50 mg, 0.20 mmol), and anhydrous toluene (1 mL) in a pressure tube was flushed with nitrogen for 3 minutes before it was capped and heated at 80° C. overnight. The reaction was then stopped, and allowed to cool to room temperature. The reaction mixture was partitioned between EtOAc and water, and the aqueous layer was extracted once with EtOAc. The combined organic layer was then washed with water and brine, dried over Na$_2$SO$_4$, condensed under reduced pressure. The crude product was purified with Gilson Preparative HPLC as described in Example 38B to give the title compound as a light-brown oil (30 mg, 44%). $^1$H NMR(d$^6$-DMSO, 300 MHz) δ 1.62 (quintet, J=6.5 Hz, 2H), 2.15–2.26 (m, 8H), 3.17 (q, J=6.5 Hz, 2H), 3.22–3.76 (m, 12 H), 3.50 (t, J=6.5 Hz, 2H), 5.72 (t, J=5.7 Hz, 1H), 6.47 (d, J=8.7 Hz, 1H), 6.68 (t, J=7.2 Hz, 1H), 6.81 (d, J=8.4 Hz, 1H), 7.26 (d, J=15.6 Hz, 1H), 7.35–7.42 (m, 2H), 7.43 (d, J=15.6 Hz, 1H), 7.44 (d, J=8.4 Hz, 1H), 7.49 (d, J=8.4 Hz, 1H), 8.00 (d, J=2.1 Hz, 1H). MS (APCI) (M+H)$^+$ at m/z 502, 504.

Example 63

(2,4-Dichlorophenyl)[2-bromo-4-(E-((3-(2-oxopyrrolidin-1-yl)propylamino)carbonyl)ethenyl) phenyl]sulfide A mixture of nitro compound (780 mg, 1.58 mmol) from Example 33, SnCl$_2$ (1.50 g, 7.91 mmol) in 25 mL of anhydrous EtOH was refluxed under nitrogen atmosphere for 90 minutes. The reaction was then allowed to cool to room temperature, quenched with sat. NaHCO$_3$, extracted with EtOAc (2×50 mL). The combined organic layer was washed with water and brine, dried over Na$_2$SO$_4$, condensed in vacuo to give the crude aniline as yellowish brown solid, which was converted to the bromide without purification.

Example 63A (2,4-Dichlorophenyl)[2-amino-4-(E-((3-(2-oxopyrrolidin-1-yl)propylamino)carbonyl)ethenyl) phenyl]sulfide A mixture of nitro compound (780 mg, 1.58 mmol) from Example 33, SnCl$_2$ (1.50 g, 7.91 mmol) in 25 mL of anhydrous EtOH was refluxed under nitrogen atmosphere for 90 minutes. The reaction was then allowed to cool to room temperature, quenched with sat. NaHCO$_3$, extracted with EtOAc.(2×50 mL). The combined organic layer was washed with water and brine, dried over Na$_2$SO$_4$, condensed in vacuo to give the crude aniline as yellowish brown solid, which was converted to the bromide without purification.

Example 63B (2,4-Dichlorophenyl)[2-bromo-4-(E-((3-(2-oxopyrrolidin-1-yl)propylamino)carbonyl)ethenyl)phenyl]sulfide To a stirred solution of t-butyl nitrite (57 μL, 0.48 mmol), CuBr$_2$ (87 mg, 0.39 mmol) in 2.0 mL of CH$_3$CN at room temperature was added a solution of aniline from Example 63A (150 mg, 0.323 mmol) in 1.0 mL of CH$_3$CN. The dark green solution was then heated at 65° C. under nitrogen atmosphere for 90 minutes. The reaction mixture was then allowed to cool to room temperature, partitioned between EtOAc and 3N HCl. The organic layer was then washed with brine, dried over Na$_2$SO$_4$, condensed in vacuo. The crude product was then purified with Gilson Preparative HPLC as described in Example 38B to give the title compound as a light-brown solid (50 mg, 29%). Colorless oil; $^1$H NMR (d$^6$-DMSO, 300 MHz) δ 1.63 (quintet, J=7.2 Hz, 2H), 1.91 (quintet, J=8.4 Hz, 2H), 2.22 (t, J=8.4 Hz, 2H), 3.09–3.47 (m, 6H), 6.67 (d, J=15.3 Hz, 1H), 7.07 (d, J=8.4 Hz, 1H), 7.32 (d, J=8.7 Hz, 1H), 7.38 (d, J=15.3 Hz, 1H), 7.50 (dd, J=2.4, 8.7 Hz, 1H), 7.57 (dd, J=2.1, 8.4 Hz, 1H), 7.86 (d, J=2.4 Hz, 1H), 7.96 (d, J=2.1 Hz, 1H), 8.13 (t, J=6.0 Hz, 1H). MS (ESI) (M+H)$^+$ at m/z 527, 529, 531, 533.

Example 64

(2,4-Dichlorophenyl)[2-formyl-4-(E-((1-morpholinyl)carbonyl)ethenyl)phenyl]sulfide

Example 64A

[1-Fluoro-2-formyl-4-(E-((1-morpholinyl)carbonyl)ethenyl)benzene

The title compound was prepared by the procedures described in Example 59 substituting the bromide from Example 12 with 2-fluoro-5-bromobenzaldehyde.

Example 64B (2,4-Dichlorophenyl)[2-formyl-4-(E-((1-morpholinyl)carbonyl)ethenyl)phenyl]sulfide The title compound was prepared by the procedures described in Example 32 substituting 4-chloro-3-nitrocinnamide with the compound from Example 64A. White solid; $^1$H NMR (d$^6$-DMSO, 300 MHz) δ 3.60 (br m, 6H), 3.71 (br m, 2H), 6.82 (d, J=8.7 Hz, 1H), 7.35 (d, J=15.6 Hz, 1 H), 7.54 (d, J=15.6 Hz, 1H), 7.55 (dd, J=2.4, 8.7 Hz, 1H), 7.61 (d, J=8.7 Hz, 1H), 7.86 (dd, J=2.4, 8.4 Hz, 1H), 7.91 (d, J=2.4 Hz, 1H), 8.41 (d, J=2.1 Hz, 1H), 10.19 (s, 1 H). MS (DCI/NH$_3$) (M+H)$^+$ at m/z 422, 424, 426, 428.

Example 65

(2-Chloro-6-formylphenyl)[2-chloro-4-(E-((4-acetylpiperazin-1-yl)carbonyl)ethenyl)phenyl]sulfide

Example 65A (2-Carbomethoxyethyl)[2-chloro-4-(E-((4-acetylpiperazin-1-yl)carbonyl)ethenyl)phenyl]sulfide The title compound was prepared by the procedures described in Example 1 substituting 2,4-dichlorothiophenol with methyl 3-mercaptopropionate, and 6-amino-1-hexanol with 1-acetyl piperazine.

Example 65B (2-Chloro-6-formylphenyl)[2-chloro-4-(E-((4-acetylpiperazin-1-yl)carbonyl)ethenyl)phenyl]sulfide To a stirred solution of the compound (105 mg, 0.26 mmol) from Example 65A in 2 mL of THF under nitrogen atmosphere at 0° C. was added t-BuOK solution (1.0M, 281 μL, 0.29 mmol). Light orange precipitates appeared immediately. After completion of the addition, the reaction mixture was stirred at room temperature for 1 hour before the solvent was removed on a rotavap under reduced pressure.

The yellow thiolate thus obtained was dissolved in 0.5 mL of DMF, and 2,3-dichlorobenzaldehyde was then added. The mixture was then heated at 80° C. under nitrogen for 2 hours. Reaction was then stopped and the solvent was removed under vacuum. The crude product was purified with Gilson Preparative HPLC as described in Example 38B to give the title compound as a white solid (25 mg, 21%). $^1$H NMR (CDCl$_3$, 300 MHz) δ 2.05 (s, 3H), 3.48–3.58 (m, 2H), 3.58–3.84 (m, 6H), 6.53 (d, J=8.7 Hz, 1H), 6.80 (d, J=15.3 Hz, 1H), 7.19 (dd, J=1.8, 8.7 Hz, 1H), 7.51–7.62 (m, 2H), 7.60 (d, J=15.3 Hz, 1H), 7.84 (dd, J=1.8, 8.4 Hz, 1H), 7.99 (dd, J=1.8, 8.4 Hz, 1H). MS (APCI) (M+NH$_4$)$^+$ at m/z 480, 482, 484.

Example 66

(2-Cyanophenyl)[2-chloro-4-(E-((4-acetylpiperazin-1-yl)carbonyl)ethenyl)phenyl]sulfide The title compound was prepared by the procedures described in Example 65B substituting 2,3-dichlorobenzaldehyde with 2-fluorobenzonitrile, giving a white solid. $^1$H NMR (CDCl$_3$, 300 MHz) δ 2.15 (s, 3H), 3.48–3.57 (m, 2H), 3.59–3.84 (m, 6H), 6.86 (d, J=15.6 Hz, 1H), 7.12 (d, J=8.4 Hz, 1H), 7.32 (d, J=8.4 Hz, 1H), 7.41 (d, J=6.6 Hz, 1H), 7.46 (dd, J=1.8, 8.4 Hz, 1H), 7.55 (dd, J=1.8, 8.1 Hz, 1H), 7.61 (d, J=15.6 Hz, 1H), 7.64 (d, J=1.8 Hz, 1H), 7.75 (dd, J=1.8, 8.4 Hz, 1H). MS (DCI/NH$_3$) (M+NH$_4$)$^+$ at m/z 443.

Example 67

(2-Isopropylphenyl)[2-cyano-4-(E-((morpholin-1-yl)carbonyl)ethenyl)phenyl]sulfide

Example 67A (2-Isopropylphenyl)(4-bromo-2-cyanophenyl)sulfide

The title compound was prepared by the procedures described in Example 1A substituting 2,4-dichlorothiophenol with isopropylthiophenol, and 2-chlorobenzaldehyde with 2-fluorobenzonitrile.

Example 67B (2-Isopropylphenyl)[2-cyano-4-(E-((morpholin-1-yl)carbonyl)ethenyl)phenyl]sulfide The title compound was prepared by the procedures described in Example 59 substituting the bromide from Example 12 with the bromide from Example 67A, giving a white solid. $^1$H NMR (CDCl$_3$, 300 MHz) δ 1.19 (d, J=6.9 Hz, 6H), 3.49 (septet, J=6.9 Hz, 1H), 3.58–3.87 (m, 8H), 6.73 (d, J=8.4 Hz, 1H), 6.83 (d, J=15.6 Hz, 1 H), 7.20–7.30

(m, 1H), 7.42 (dd, J=2.4, 8.4 Hz, 1H), 7.46 (d, J=3.0 Hz, 2H), 7.49 (dd, J=1.8, 6.9 Hz, 1H), 7.57 (d, J=15.6 Hz, 1H), 7.76 (d, J=1.8 Hz, 1H). MS (APCI$^+$) (M+H)$^+$ at m/z 393.

Example 68

(2-Bromophenyl)[2-nitro-4-(E-((4-acetylpiperazin-1-yl)carbonyl)ethenyl)phenyl]sulfide The title compound was prepared by the procedures described in Example 32B substituting 2,4-dichlorothiophenol with 2-bromothiophenol, providing a light-yellow solid; $^1$H NMR (d$^6$-DMSO, 300 MHz) δ 2.04 (s, 3H), 3.40–3.65 (m, 8H), 6.75 (d, J=8.7 Hz, 1H), 7.42 (d, J=15.6 Hz, 1H), 7.51 (dd, J=2.1, 6.9 Hz ,1H), 7.54 (d, J=15.6 Hz, 1H), 7.55 (t, J=2.1 Hz, 1H), 7.59 (dd, J=2.1, 6.9 Hz ,1H), 7.82 (dd, J=2.4, 7.8 Hz, 1H), 7.92(td, J=2.4, 8.4 Hz, 1H), 8.67 (d, J=2.4 Hz, 1H). MS (APCI$^-$) (M+Cl)$^-$ at m/z 524, 526, 528.

Example 69

(2-(Pyrrolidin-1-yl)phenyl)[2-chloro-4-(E-((morpholin-1-yl)carbonyl)ethenyl)phenyl]sulfide To a stirred solution of bromide (75 mg, 0.17 mmol) from Example 12 in toluene in a sealed tube was added sequentially pyrrolidine (18.4 mL, 0.22 mmol), Pd$_2$(dba)$_3$ (3.0 mg, 0.0034mmol), BINAP (6.0 mg, 0.010 mmol), followed by NaOt-Bu (26 mg, 0.27 mmol). The resulting mixture was then flushed with anhydrous N$_2$ for 2 minutes before it was capped and heated at 90° C. for 24 hours. The reaction mixture was then allowed to cool to room temperature and partitioned between ethyl acetate and brine. The organic layer was then dried with Na$_2$SO$_4$, filtered, and concentrated in vacuo. The crude product was purified using Gilson Preparative HPLC as described in Example 38B to give the title compound (40 mg, 55% yield) as a white solid; $^1$H NMR (CDCl$_3$, 300 MHz) δ 1.83 (br s, 4H), 3.40 (br s, 4H), 3.56–3.80 (m, 8H), 6.57 (d, J=8.4 Hz, 1H), 6.75 (d, J=15.6 Hz, 1H), 6.81 (br t, J=8.4 Hz, 1H), 6.90 (br s, 1H), 7.15 (dd, J=2.1, 8.4 Hz, 1H), 7.18–7.27 (m, 1H), 7.32 (td, J=1.8, 8.4 Hz, 1H), 7.42 (dd, J=1.8, 7.8 Hz, 1H), 7.50 (d, J=1.8 Hz, 1H), 7.55 (d, J=15.6 Hz, 1H). MS (APCI$^+$) (M+H)$^+$ at m/z 429, 431.

Example 70

(2-Methoxyphenyl)-[2-chloro-4-(E-[(morpholin-1-yl)carbonyl]ethenyl)phenyl]sulfide The title compound was prepared according to the procedures of Example 1, giving a white solid, m.p. 162–164C. $^1$H NMR (CDCl$_3$, 300 MHz) δ 3.60–3.78 (m, 8H), 3.84 (s, 3H), 6.72 (d, J=9Hz, 1H), 6.78 (d, J=16 Hz, 1H), 6.96–7.04 (m, 2H), 7.16 (dd, J=9 Hz, 2 Hz, 1H), 7.40–7.46 (, 2H), 7.55 (d, J=2H, 1H), 7.58 (d, J=16 Hz, 1H). Anal. Calcd. for C$_{20}$H$_{20}$ClNO$_3$S: C, 61.61; H, 5.17; N, 3.59. Found: C, 61.53; H, 5.22; N, 3.50.

Example 71

(2-Isopropylphenyl)[2-nitro-4-(E-((3-carbomethoxypiperazin-1-yl)carbonyl)ethenyl)phenyl]sulfide Example 71A 1-tert-Butoxycarbonyl-2-carbomethoxypiperazine 2-Carbomethoxypiperazine was treated with benzyl chloroformate (1.0 eq) in aqueous NaHCO$_3$ to give 1-benzyloxycarbonyl-3-carbomethoxypiperazine. This material was treated with di-tert-butyldicarbonate (1.1 eq) and triethylamine (1.0 eq) in THF to produce 1-tert-butoxycarbonyl-4-benzyloxycarbonyl-2-carbomethoxypiperazine. Hydrogenation of this compound in methanol using 10% Pd—C gave the title compound after filtration and solvent removal.

Example 71B (2-Isopropylphenyl)[2-nitro-4-(E-((3-carbomethoxypiperazin-1-yl)carbonyl)ethenyl)phenyl]sulfide A mixture of (2-isopropylphenyl)[2-nitro-4-E-(carboxyethenyl)phenyl]sulfide (prepared according to the procedures of Example 32), the amine from Example 71A (1.0 eq), 2-(1H-benzotriazol-1-yl)-1,1,3,3-tetramethyluronium tetrafluoroborate (1.0 eq), and diisopropylethylamine (2.0 eq) in DMF was stirred at ambient temperature for 4 hours. Ethyl acetate was added, and the mixture was washed sequentially with 1N HCl, aqueous NaHCO$_3$, and brine. The resultant yellow solid was treated with 1:1 TFA/dichloromethane at ambient temperature to give the title compound as a yellow solid. $^1$H NMR (DMSO-d$_6$, 300 MHz) δ 1.15 (d, J=6.6 Hz, 6H); 2.52–3.16 (br m, 4H); 3.25–3.47 (m, 1H); 3.60–3.65 (br d, 3H); 3.60, 3.66 (br s, br s, 3H); 6.61–6.67 (br m, 1H); 7.30–7.62 (m, 6H); 7.88–7.93 (br m, 1H); 8.58–8.65 (br m, 1H). MS (APCI) (M+H)$^+$ at m/z 470. Anal calcd for C$_{24}$H$_{27}$N$_3$S$_1$O$_5$: C, 61.39; H, 5.80; N, 8.95. Found: C, 61.51; H, 5.87; N, 8.68.

Example 72

(2-Methylphenyl)[2-nitro-4-(E-((3-carboxamido-4-carbobenzoxypiperazin-1-yl)carbonyl)ethenyl)phenyl]sulfide Prepared according to the procedures of Example 71, giving a yellow solid. $^1$H NMR (DMSO-D$_6$, 300 MHz) δ 2.30 (s, 3H); 2.80–4.80 (br m, 7H); 5.05–5.15 (br m, 2H); 6.61–6.67 (br m, 1H); 7.02–7.64 (m, 13H); 7.80–7.90 (br m, 1H); 8.56–8.65 (br m, 1H). MS (APCI) (M+H)$^+$ at m/z 561. Anal calcd for C$_{29}$H$_{28}$N$_4$S$_1$O$_6$0.42CH$_3$COOCH$_2$CH$_3$: C, 61.66; H, 5.29; N, 9.38. Found: C, 61.41; H, 5.28; N, 9.53.

Example 73

(2-Isopropylphenyl)[2-nitro-4-(E-((2-carbomethoxy4-tert-butoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.13 (d, J=6.6 Hz, 6H); 1.40, 1.41 (s, s, 9H); 2.72–3.08 (br m, 1H); 3.17–3.24 (m, 1H); 3.30–3.40 (m, 1H); 3.68 (br s, 3H); 3.79–4.51 (br m, 4H); 5.06, 5.36 (br s, br s, 1H); 6.61–6.67 (m, 1H); 7.30–7.62 (m, 6H); 7.85–7.93 (br m, 1H); 8.64–8.69 (br m, 1H). MS (APCI) (M+H)$^-$ at m/z 570. Anal calcd for C$_{29}$H$_{35}$N$_3$S$_1$O$_7$0.15C$_6$H$_{14}$: C, 61.66; H, 6.43; N, 7.21. Found: C, 61.69; H, 6.35; N, 7.02.

Example 74

(2-Isopropylphenyl)[2-nitro-4-(E-((2 carboxy-4-tert-butoxycarbonylpiperazin-1-yl)carbonyl)ethenyl)phenyl]sulfide Prepared according to the procedures of Example 71, giving a yellow solid. $^1$H NMR (CDCl$_3$, 300 MHz) δ 1.14

(d, J=6.6 Hz, 6H); 1.45 (s, 9H); 2.72–4.75 (br m, 6H); 3.38–3.49 (m, 1H); 5.78 (br s, 1H); 6.68, 6.72 (s, s, 1H); 6.88, 6.94 (br s, br, s, 1H); 7.26–7.71 (m, 6H); 8.44 (br s, 1H). MS (APCI) (M–H)$^+$ at m/z 554. Anal calcd for $C_{28}H_{33}N_3S_1O_7$: C, 60.53; H, 5.99; N, 7.56. Found: C, 60.42; H, 6.21; N, 7.31.

Example 75

(2-Isopropylphenyl)[2-trifluoromethyl-4-(E-((4-acetylpiperazin-1-yl)carbonyl)ethenyl)phenyl]sulfide The title compound was prepared according to the procedures of Example 1. $^1$H NMR (CDCl$_3$, 300 MHz) δ 7.78 (s, 1H), 7.62 (d, 1H, J=15.5 Hz), 7.43–7.49 (m, 3H), 7.37 (d, 1H, J=8.1 Hz), 7.23 (m, 1H), 6.85 (d, 1H, J=15.5 Hz), 6.82 (d, 1H, J=8.5 Hz), 3.63–3.77 (m, 6H), 3.45–3.55 (m, 3H), 2.14 (s, 3H), 1.17 (d, 6H, J=6.6 Hz). MS (ESI) m/z 477, 499, 975, 953. Anal. Calcd for $C_{25}H_{27}F_3N_2O_2S\cdot0.5$ EtOAc: C, 62.29; H, 6.00; N, 5.38. Found: C, 62.40; H, 6.21; N, 5.35.

Example 76

(2-Isopropylphenyl)[2-trifluoromethyl-4-(E-((morpholin -1-yl)carbonyl)ethenyl)phenyl]sulfide The title compound was prepared according to the procedures of Example 1. $^1$H NMR (CDCl$_3$, 300 MHz) 7.78 (s, 1H), 7.62 (br, 1H), 7.33–7.48 (m, 3H), 7.22 (m, 1H), 6.85 (m, 1H), 6.80 (d, 1H, J=8.5 Hz), 3.73 (br, 8H), 3.49 (dq, 1H, $J_1=J_2=6.9$ Hz), 1.17 (d, 6H, J=7.1 Hz). MS (ESI) m/z 436, 871, 893. Anal. Calcd for $C_{23}H_{24}F_3N_1O_2S$: C, 63.43; H, 5.55; N, 3.22. Found: C, 63.12; H, 5.81; N, 3.10.

Example 77

(2-Isopropylphenyl)[2-trifluoromethyl-4-(E-((3-(2-oxopyrrolidin-1-yl)prop-1-ylamino)carbonyl)ethenyl)phenyl]sulfide The title compound was prepared according to the procedures of Example 1. $^1$H NMR (CDCl$_3$, 300 MHz) δ 7.77 (s, 1H), 7.52(d, 1H, J=15.4 Hz), 7.43–7.51 (m, 3H), 7.36 (d, 1H, J=8.8 Hz), 7.22 (m, 1H), 7.10 (br, 1H), 6.80 (d, 1H, J=8.4 Hz), 6.44 (d, 1H, J=15.4 Hz), 3.49 (dq, 1H, $J_1=J_2=6.9$ Hz), 3.40 (m, 4H), 3.31 (dd, 2H, $J_1=5.7$ Hz, $J_2 =12.0$ Hz), 2.44 (t, 2H, J=8.1 Hz), 2.08 (tt, 2H, $J_1=J_2=7.5$ Hz), 1.74 (m, 2H), 1.18 (d, 6H, J=6.9 Hz). MS (ESI) m/z 491, 513, 981, 1003. Anal. Calcd for $C_{26}H_{29}F_3N_2O_2S$: C, 63.66; H, 5.96; N, 5.71. Found: C, 64.00; H, 6.12, N, 5.68.

Example 78

(2-Isopropylphenyl)[2-trifluoromethyl-4-(E-((cyclobutylamino)carbonyl)ethenyl)phenyl]sulfide The title compound was prepared according to the procedures of Example 1. $^1$H NMR (CDCl$_3$, 300 MHz) δ 7.76 (s, 1H), 7.52 (d, 1H, J=15.4 Hz), 7.43–7.49 (m, 3H), 7.33 (d, 1H, J=7.7 Hz), 7.22 (m, 1H), 6.79 (d, 1H, J=8.1 Hz), 6.33 (d, 1H, J=15.4 Hz), 5.72 (br, 1H), 4.52 (m, 1H), 3.49 (dq, 1H, $J_1=J_2=6.9$ Hz), 2.40 (m, 2H), 1.90 (m, 2H), 1.74 (m, 2H), 1.17 (d, 6H, J=6.6 Hz). MS (ESI) m/z 420, 839, 861. Anal. Calcd for $C_{23}H_{24}F_3N_1O_1S$: C, 65.85; H, 5.77; N, 3.34. Found: C,65.53; H, 5.83, N, 3.21.

Example 79

(2-Isopropylphenyl)[2-trifluoromethyl-4-(E-((cyclopentylamino)carbonyl)ethenyl)phenyl]sulfide The title compound was prepared according to the procedures of Example 1. $^1$H NMR (CDCl$_3$, 300 MHz) δ 7.77 (s, 1H), 7.52 (d, 1H, J=15.5 Hz), 7.43–7.48 (m, 3H), 7.33 (d, 1H, J=8.8 Hz), 7.22 (m, 1H), 6.79 (d, 1H, J=8.1 Hz), 6.33 (d, 1H, 15.5 Hz), 5.54 (d, J=7.7, 1 H), 4.35 (m, 1 H), 3.49 (dq, 1H, $J_1=J_2=6.9$ Hz), 2.05 (m, 2H), 1.68 (m, 4H), 1.44(m, 2H), 1.17 (d, 6H, J=7.0 Hz). MS (ESI) m/z 434, 867, 889. Anal. Calcd for $C_{24}H_{26}F_3N_1O_1S$: C, 66.49; H, 6.04; N, 3.23. Found: C, 66.24; H, 6.14, N, 3.06.

Example 80

(2-Isopropylphenyl)[2-trifluoromethyl4-(E-((5-hydroxypent-1-ylamino)carbonyl)ethenyl)phenyl] sulfide The title compound was prepared according to the procedures of Example 1. $^1$H NMR (CDCl$_3$, 300 MHz) δ 7.77 (s, 1H), 7.54 (d, 1H, J=15.5 Hz), 7.43–7.49 (m, 3H), 7.33 (d, 1H, J=8.0 Hz), 7.22 (m, 1H), 6.79 (d, 1H, J=8.4 Hz), 6.35 (d, 1H, J=15.6 Hz), 5.67 (br, 1H), 3.67 (t, 2H, J=6.4 Hz), 3.49 (dq, 1H, $J_1=J_2=6.9$ Hz), 2.40 (m, 2H), 1.45–1.62 (m, 6H), 1.17 (d, 6H, J=7.0 Hz). MS (ESI) m/z 452, 474, 903, 925. Anal. Calcd for $C_{24}H_{28}F_3NO_2S$ 0.56 EtOAc: C, 62.92; H, 6.54; N, 2.80. Found: C, 62.86; H. 6.53; N, 2.96.

Example 81

(2-Isopropylphenyl)[2-nitro-4-(E-((3-carbomethoxy-4-acetylpiperazin-1-yl)carbonyl)ethenyl)phenyl] sulfide Prepared according to the procedures of Example 71, giving a yellow solid. $^1$H NMR (CDCl$_3$, 300 MHz) δ 1.14 (d, J=6.6 Hz, 6H); 2.20 (s, 3H); 2.75–3.80 (br m, 4H); 3.39–3.50 (m, 1H); 3.70, 3.77 (br s, br s, 3H); 4.49–4.75 (br m, 2H); 5.39 (br s, 1H); 6.71(m, 1H); 6.91–7.04 (br m, 1H); 7.25–7.64 (m, 6H); 8.42 (br m, 1H). MS (APCI) (M+H)$^+$ at m/z 512. Anal calcd for $C_{26}H_{29}N_3S_1O_6$: C, 61.04; H, 5.71; N, 8.21. Found: C, 61.40; H, 6.05; N, 7.88.

Example 82

(2-Biphenyl)[2-chloro-4-(E-((morpholin-1-yl) carbonyl)ethenyl)ethenyl]sulfide

To a stirred solution of bromide from Example 12 (60 mg, 0.14 mmol) in 1 mL of toluene was added 0.5 mL of sat. Na$_2$CO$_3$, Pd(PPh$_3$)$_4$ (8 mg, 0.007 mmol), phenylboronic acid (17 mg, 0.14 mmol). The mixture was flushed with nitrogen and heated at 100° C. for 3 hours. The reaction mixture was then allowed to cool to room temperature and partitioned between ethyl acetate and brine. The organic layer was then dried with Na$_2$SO$_4$, filtered, and concentrated in vacuo. The crude product was purified using Gilson Preparative HPLC as described in Example 38B to give the title compound as a colorless oil (40 mg, 67% yield); $^1$H NMR (CDCl$_3$, 300 MHz) δ 3.58–3.86 (m, 8H), 6.77 (d, J=15.6 Hz, 1H), 6.86 (d, J=8.4 Hz, 1H), 7.67 (dd, J=2.1, 8.4 Hz, 1H), 7.29–7.40 (m, 3H), 7.40–7.48 (m, 6H), 7.56 (d, J=15.6 Hz, 1H), 7.65 (d, J=1.8 Hz, 1H). MS (APCI$^+$) (M+H)$^+$ at m/z 436, 438.

Example 83

(3.4-Dimethylphenyl)[2-nitro-4-(E-((4-acetylpiperazin-1-yl)carbonyl)ethenyl)1phenyl] sulfide To a solution of the compound of Example 32A (40 mg, 0.12 mmol) in 2.5 mL of dimethylformamide was added 3,4-dimethylthiophenol (17 mg, 0.12 mmol), followed by potassium carbonate powder (20 mg, 0.14 mmol). The mixture was heated at 100° C. for 20 hours. The solvent was removed using $N_2$ gas flow. Water (5 mL) was then added to the residue, the resulting precipitate was collected through filtration, washed with cold water, and air dried to give the title compound (42 mg, 81%) as light yellow solid. $^1$H-NMR (CDCl$_3$, 400 MHz) δ 2.08 (s, 3H), 2.23 (s, 3H), 2.27 (s, 3H), 3.45 (br, m, 2H), 3.63 (br, m, 6H), 6.79 (s, 1H), 6.82 (d, J=19 Hz, 1H), 7.18 (d, J=19 Hz, 1H), 7.24 (dd, J=4, 19 Hz, 1H), 7.27 (s, 1H), 7.34 (d, J=21 Hz, 1H), 7.56 (d, J=39 Hz, 1H), 8.32 (d, J=4 Hz, 1H). MS (APCI) (M+H)$^+$ at m/z 440. FAB High Resolution MS calculated m/z for $C_{23}H_{26}N_3O_4S$ (M+H)$^+$: 440.1644. Observed m/z: 440.1646.

Example 84

(2-Bromophenyl)[2-trifluoromethyl-4-(E-((4-acetylpiperazin-1-yl)carbonyl)ethenyl)phenyl]sulfide The title compound was prepared by the procedures described in Example 9 substituting 2,4-dichlorothiophenol with 2-bromothiophenol, and 3,4-dichlorobenzaldehyde with 4-fluoro-3-trifluoromethylbenzaldehyde, to give a white solid. $^1$H NMR (d$^6$-DMSO, 300 MHz) δ 2.04 (s, 3H), 3.43–3.80 (m, 8H), 7.21 (dd, J=2.1, 8.4 Hz, 1H), 7.24 (d, J=8.4 Hz, 1H), 7.33 (td, J=2.1, 7.65 Hz, 1H), 7.42 (td, J=1.8,7.65 Hz, 1H), 7.45 (d, J=15.6 Hz, 1H), 7.58 (d, J=15.6Hz, 1H), 7.78 (dd, J=1.8, 8.4 Hz, 1H), 7.96 (dd, J=1.8, 8.4 Hz, 1H), 8.25 (d, J=1.8 Hz, 1H). MS (APCI$^+$) (M+NH$_4$)$^+$ at m/z 530, 532, 534.

Example 85

(5-Indolyl)[2-chloro-4-(E-((4-acetylpiperazin-1-ylcarbonyl)ethenyl)phenyl]sulfide To a stirred solution of 5-iodoindole (255 mg, 1.05 mmol) in 5.0 mL of anhydrous DMF was added the potassium thiolate (457 mg, 1.26 mmol) from Example 65B, followed by $K_2CO_3$ (174 mg, 1.26 mmol), and cuprous iodide (20 mg, 0.11 mmol). The resulting mixture was then heated at 120° C. for overnight. The reaction mixture was then allowed to cool to ambient temperature and poured into water. The aqueous mixture was extracted twice with 25 mL of ethyl acetate. The combined organic layer was then washed with water and brine, dried over $Na_2SO_4$, filtered, concentrated on a rotavap under reduced pressure. The crude product was purified using Gilson Preparative HPLC as described in Example 38B to give the title compound (115 mg, 25% based on the iodide) as a light-brown solid. $^1$H NMR (d$^6$-DMSO, 300 MHz) δ 2.03 (s, 3H), 3.40–3.78 (m, 8H), 6.51 (d, J=8.4 Hz, 1H), 6.53 (s, 1H), 7.23 (dd, J=2.1, 8.4 Hz, 1H), 7.27 (d, J=15.6 Hz, 1H), 7.39 (d, J=15.6 Hz, 1H), 7.41 (dd, J=1.8, 8.4 Hz, 1H), 7.49 (t, J=2.7 Hz, 1 H), 7.56 (d, J=8.4 Hz, 1H), 7.85 (d, J=1.8 Hz, 1H), 7.99 (d, J=1.8 Hz, 1H). MS (APCI$^+$) (M+NH$_4$)$^+$ at m/z440, 442. Anal. Calcd for $C_{23}H_{22}ClN_3O_2S \cdot 0.53 \, CH_2Cl_2$: C, 58.28; H, 4.79; N, 8.66. Found: C, 58.31; H, 4.93; N, 8.65.

Example 86

(5-Benzodioxolyl)[2-chloro-4-(E-((4-acetylpiperazin-1-yl)carbonyl)ethenyl)phenyl]sulfide The title compound was prepared by the procedures described in Example 85 substituting 5-iodoindole with 1-iodo-3,4-methylenedioxybenzene, providing a white solid. $^1$H NMR (CDCl$_3$, 300 MHz) δ 2.14 (s, 3H), 3.48–3.60 (m, 2H), 3.60–3.84 (m, 6H), 6.05 (s, 2H), 6.75 (d, J=8.4 Hz, 1H), 6.80 (d, J=15.3 Hz, 1H), 6.88 (d, J=8.4 Hz, 1H),6.98(d, J=2.1 Hz, 1H), 7.08 (dd, J=2.1, 8.4Hz, 1H), 7.19 (d, J=1.8, 8.4 Hz, 1H), 7.52 (d, J=2.1 Hz, 1H), 7.58 (d, J=15.6 Hz, 1H). MS (APCI$^+$)(M+NH$_4$)$^+$ at m/z 445, 447.

Example 87

(2-Isopropylphenyl)[2-nitro-4-(E-((2-carbomethoxypiperazin-1-yl)carbonyl)ethenyl)phenyl]sulfide Prepared according to the procedures of Example 71, giving a yellow solid. $^1$H NMR (DMSO-d, 300 MHz) δ 1.14 (d, J=6.6 Hz, 6H); 2.52–2.91 (br m, 5H); 3.30–3.40 (m, 1H); 3.68, 3.69 (s, s, 3H); 4.10–4.25 (br m, 1H); 5.00–5.21br m, 1H); 6.60–6.65(m, 1H); 7.29–7.62 (m, 6H); 7.85–7.95 (m, 1H); 8.64–8.68 (m, 1H). MS (APCI) (M+H)$^+$ at m/z 470.

Example 88

(2,3-Dimethoxyphenyl)-[2-chloro-4-(E-[(morpholin-1-yl)carbonyl]ethenyl)phenyl]sulfide The title compound was prepared according to the procedures of Example 1, giving a white solid, m.p. 148–150C. $^1$H NMR (CDCl$_3$, 300 MHz) δ 3.60–3.78 (m, 8H), 3.85 (s, 3H), 3.91 (s, 3H), 6.78 (d, J=16 Hz, 1H), 6.86–6.98 (m, 3H), 7.20 (dd, J=9 Hz, 2 Hz, 1H), 7.54 (d, J=2 Hz, 1H), 7.58 (d, J=16 Hz, 1H). Anal. Calcd. for $C_{21}H_{22}ClNO_4S$: C, 60.06; H, 5.28; N, 3.33. Found: C, 59.72; H, 5.34; N, 2.97.

Example 89

(2-Fluorophenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 2-fluorothiophenol. Yellow solid (40 mg, 78%); $^1$H-NMR (CDCl$_3$, 400 MHz) δ 2.17 (s, 3H), 3.56 (br, m, 2H), 3.77 (br, m, 6H), 6.88 (dd, J=3, 21 Hz, 1H), 6.93 (d, J=39 Hz, 1H), 7.26 (dd, J=3, 21 Hz, 1H), 7.33 (dd, J=3, 19 Hz, 1H), 7.49 (br, d, J=20 Hz, 1H), 7.58 (m, 1H), 7.66 (m, 2H), 8.46 (d, J=4 Hz, 1H). MS (APCI) (M+H)$^+$ at m/z 430. FAB High Resolution MS calculated m/z for $C_{21}H_{21}N_3O_4FS$ (M+H)$^+$: 430.1237. Observed m/z: 430.1246.

Example 90

(2-Bromophenyl)[2-trifluoromethyl-4-(E-((4-(tert-butoxycarbonyl)piperazin-1-yl)carbonyl)ethenyl)phenyl]sulfide The title compound was prepared by the procedures described in Example 1 substituting 2,4-dichlorothiophenol with 2-bromothiophenol, 2-chlorobenzaldehyde with 4-fluoro-3-trifluoromethylbenzaldehyde, and 6-amino-1-hexanol with t-butyl 1-piperazinecarboxylate, to give a white solid. $^1$H NMR (CDCl$_3$, 300 MHz) d 1.48 (s, 9H), 3.49 (br s, 4H), 3.56–3.78 (m, 4H), 6.89 (d, J=15.6 Hz, 1H), 7.10 (d, J=8.4 Hz, 1H), 7.18–7.35 (m, 3H), 7.49 (d, J=8.4 Hz, 1H), 7.65 (d, J=15.6 Hz, 1H), 7.68 (dd, J=2.1, 8.4 Hz, 1H), 7.85 (br s, 1H). MS (APCI$^-$) (M+Cl)$^-$ at m/z 605, 607, 609. Anal. Calcd for $C_{25}H_{26}N_2O_3BrF_3S \cdot 0.03 \, H_2O$: C, 52.50; H, 4.59; N, 4.90. Found: C, 52.54; H, 4.71; N, 4.68.

Example 91

(2-(Pyrrolidin-1-yl phenyl)[2-trifluoromethyl-4-(E-((4-(tert-butoxycarbonyl)piperazin-1-yl)carbonyl)ethenyl)phenyl]sulfide The title compound was prepared by the procedures described in Example 69 substituting the bromide from Example 12 with the bromide from Example 90, to give a white solid. $^1$H NMR (CDCl$_3$, 300 MHz) δ 1.85 (s, 9H), 1.85 (br s, 4H), 3.32–3.55 (m, 8H), 3.55–3.78 (m, 4H), 6.76 (d, J=8.4 Hz, 1H), 6.82 (d, J=15.6 Hz, 1H), 7.23–7.45 (m, 5H), 7.61 (d, J=15.6 Hz, 1H), 7.75 (br s, 1H). MS (APCI$^+$) (M+H)$^+$ at m/z 562.

Example 92

(3-Carboxamidophenyl)[2-nitro-4-(E-((4-acetylpiperazin-1-yl)carbonyl)ethenyl)phenyl]sulfide

Example 92A (3-Carboxyphenyl)[2-nitro-4-(E-((4-acetylpiperazin-1-yl)carbonyl)ethenyl)phenyl]sulfide The title compound was prepared by the procedures described in Example 32B substituting 2,4-dichlorothiophenol with 3-mercaptobenzoic acid.

Example 92B (3-Carboxamidophenyl)[2-nitro-4-(E-((4-acetylpiperazin-1-yl)carbonyl)ethenyl)phenyl]sulfide To a stirred solution of benzoic acid from Example 92A (40 mg, 0.088 mmol) in 1 mL of anhydrous DMF with HOBT (15 mg; 0.097 mmol) was added EDAC (19 mg, 0.097 mmol), followed by ammonium chloride (large excess). The pH of the solution was adjusted to 6 with addition of triethylamine. The resulting mixture was then stirred at ambient temperature for 6 hours. Water was added to quenched the reaction. The product precipitated out after stirring for 30 minutes, which was then isolated by filtration and dried in a vacuum oven to give a light yellow solid (25 mg, 63% yield). $^1$H NMR (d$^6$-DMSO, 300 MHz) δ 2.04 (s, 3H), 3.43–3.82 (m, 8H), 6.84 (d, J=8.7 Hz, 1H), 7.43 (d, J=15.6 Hz, 1H), 7.53 (d, J=15.6 Hz, 1H), 7.56 (d, J=1.8 Hz, 1H), 7.66 (t, J=7.65 Hz, 1H), 8.06 (d, J=7.80 Hz, 1H), 8.12 (s, 2H), 8.67 (d, J=2.1 Hz, 1 H). MS (ESI$^+$) (M+Na)$^+$ at m/z 477.

Example 93

(3-(Hydroxymethyl)phenyl)[2-nitro-4-(E-((4-acetylpiperazin-1yl)-carbonyl)ethenyl)phenyl]sulfide To a stirred solution of benzoic acid from Example 92A (255 mg, 0.56 mmol) in 5 mL of anhydrous THF at 0° C. was added in turn Et$_3$N (102 mL, 0.73 mmol) and ethyl chloroformate (70 mL, 0.73 mmol). After 60 minutes, the reaction mixture was filtered through celite plug into a stirred solution of NaBH$_4$ in water at 0° C. The resulting reaction mixture stirred at 0° C. for 2 hours before it was extracted with EtOAc (2×20 mL). The combined organic layers were washed with 3N HCl, brine, dried over Na$_2$SO$_4$, filtered, concentrated under reduced pressure. The crude product was purified using Gilson Preparative HPLC as described in Example 38B to give the title compound (80 mg, 32% yield) as a light-yellow solid. $^1$H NMR (d$^6$-DMSO, 300 MHz) δ 2.04 (s, 3H), 3.40–3.79 (m, 8H), 4.56 (s, 2H), 5.38 (br s, 1H), 6.85 (d, J=8.7 Hz, 1H), 7.42 (d, J=15.6 Hz, 1H), 7.52 (br s, 3H), 7.57 (br s, 2H), 7.91 (dd, J=2.1, 8.7 Hz, 1H), 8.66 (d, J=2.1 Hz, 1H). MS (APCI$^+$) (M+NH$_4$)$^+$ at m/z 459.

Example 94

Phenyl[2-trifluoromethyl-4-(E-((4-(tert-butoxycarbonyl)piperazin-1-yl )carbonyl)ethenyl)phenyl]sulfide The title compound was obtained as a reductive side product from the reaction mixture described in Example 91, as a colorless oil. $^1$H NMR (CDCl$_3$, 300 MHz) δ 1.49 (s, 9H), 3.43–3.56 br s, 4H), 3.56–3.82 (m, 4H), 6.85 (d, J=15.6 Hz, 1H), 7.06 (d, J=8.4Hz, 1H), 7.37–7.50 (m, 4H), 7.63 (d, J=15.6 Hz, 1H), 7.67 (d, J=8.4 Hz, 1H), 7.76 (d, J=11.7 Hz, 1H), 7.80 (s, 1H). MS (APCI$^-$) (M+Cl)$^-$ at m/z 527.

Example 95

(2-Isopropylphenyl)[2-trifluoromethyl-4-(E-((2-carbomethoxy-4-(tert-butoxycarbonyl)piperazin-1-yl)carbonyl)ethenyl)phenyl]sulfide The title compound was prepared according to +the procedures of Example 71. $^1$H NMR (CDC$_3$, 300 Hz) δ 7.79 (s, 1H), 7.62 (d, 1H, J=15.0 Hz), 7.48 (d, 1H, J=7.2 Hz), 7.43 (m, 2H), 7.38 (d, 1H, J=8.1 Hz), 7.22 (m, 1H), 6.86 (d, 1H, J=15.4 Hz), 6.80 (d, 1H, J=8.4 Hz), 5.30 (br, 1H), 4.62 (br d, 2H, J=14.0 Hz), 3.89 (br m, 1H), 3.76 (s, 3H), 3.49 (dq, 1H, J$_1$=J$_2$=6.9 Hz), 3.12 (m, 2H), 2.94 br, 1H), 1.46 (s, 9H), 1.17 (d, 6H, J=6.6Hz). MS (ESI) m/z −591, −627, −677.

Example 96

(2-Isopropylphenyl)[2-nitro-4-(E-((3(pyridine-4-methylaminocarbonyl)-4-tert-butoxycarbonylpiperazin-1-yl)carbonyl)ethenyl) phenyl]sulfide Prepared according to the procedures of Example 71, giving a yellow solid. $^1$H NMR (DMSO-d$_6$, 300 MHz) δ 1.14 (d, J=6.6 Hz, 6H); 1.38 (s, 9H); 2.83–3.85 (br m, 5H); 4.09–4.51 (br m, 4H); 4.91–5.09 (br m, 1H); 6.64 (d, J=8.5 Hz, 1H); 7.12–7.62 (m, 8H); 7.82–7.96 (m, 1H); 8.26–8.48 (m, 2H); 8.63–8.75 (m, 2H). MS (APCI) (M+H)$^+$at m/z 646. Anal calcd for C$_{34}$H$_{39}$N$_5$S$_1$O$_6$: C, 63.24; H, 6.09; N, 10.84. Found: C, 63.07; H, 6.43; N, 10.54.

Example 97

(2-Ethoxyphenyl)-[2-chloro-4-(E-[(morpholin-1-yl) carbonyl]ethenyl)phenyl]sulfide

Example 97A

2-Ethoxybenzenethiol

To 7.82 g of ethoxybenzene and 7.41 g of tetramethyl-ethylenediamine in 75 mL ether, cooled in an ice bath, a solution of 25.6 mL of a 2.5 M n-butyllithium solution in hexane, was added dropwise under a nitrogen atmosphere. The mixture was stirred for 1 hour at room temperature and then cooled to −65 degrees. Sulfur (2.28 g) was added in portions. The mixture was stirred for 3 hours at room temperature and then cooled in ice. LiAlH$_4$ (0.6 g) was added and the mixture was stirred 1 hour at room temperature. The mixture was again cooled in ice while 5 mL water was added dropwise followed by 15% HCl in water. The aqueous phase was separated and washed with ether. The combined ether layers were washed with HCl, then water. After drying with Na$_2$SO$_4$, the ether was evaporated to give 9.66 g of product. NMR analysis showed 70% pure material with 30% of a diaryl sulfide impurity. This mixture was carried forward to the next step.

Example 97B (2-Ethoxyphenyl)-[2-chloro-4-(E-[(morpholin-1-yl) carbonyl]ethenyl)phenyl]sulfide The title compound was prepared according to the procedures of Example 1, substituting the thiol of Example 97A, giving a white solid, m.p. 125–127C. $^1$H NMR (CDCl$_3$, 300 MHz) δ 1.25 (t, J=7Hz, 3H), 3.60–3.78 (m, 8H), 4.05 (q, J=7 Hz, 2H), 6.76 (d, J=15Hz, 1H), 6.82 (d, J=9H, 1H), 6.94–7.00 (m, 2H), 7.16 (dd, J=9 Hz, 2 Hz, 1H), 7.34–7.45 (m, 2H), 7.54 (d, J=2Hz, 1H), 7.58 (d, J=15 Hz, 1H). Anal. Calcd. for C$_{21}$H$_{22}$ClNO$_3$S: C, 62.44; H, 5.49; N, 3.47. Found: C, 62.14; H, 5.70; N, 3.22.

Example 98

(2-Methoxyphenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 2-methoxythiophenol, giving a yellow solid (40 mg, 77%). 1H-NMR (CDCl$_3$, 400 MHz) δ 2.14 (s, 3H), δ 3.54 (br, m, 2H), δ 3.68 (br, m, 6H), δ 3.79 (s, 3H), δ 6.81 (d, J=21 Hz, 1H), δ 6.89 (d, J=39 Hz, 1H), δ 7.03 (d, J=21 Hz, 1H), δ 7.08 (m, 1H), δ 7.41 (br, d, J=21 Hz, 1H), δ 7.53 (m, 1H), δ 7.60 (m, 1H), δ 7.65 (br, s, 1H), δ 8.42 (br, s, 1H). MS (APCI) (M+H)+ at m/z 442.

Example 99

(2-(Azetidin-1-yl)phenyl)[2-trifluoromethyl-4-(E-((4-(tert-butoxycarbonyl)piperazin-1-yl)carbonyl)ethenyl)phenyl]sulfide The title compound was prepared by the procedures described in Example 69 substituting pyrrolidine with azetidine hydrochloride, and the bromide from Example 12 with bromide from Example 90, giving a white solid. $^1$H NMR (CDCl$_3$, 300 MHz) δ 1.48 (s, 9H), 2.18 (pentet, J=7.43 Hz, 2H), 3.40–3.53 (m, 4H), 3.53–3.77 (m, 4H), 4.02 (t, J=7.43 Hz, 4H), 6.54 (d, J=8.7 Hz, 1H), 6.72 (d, J=8.7 Hz, 1H), 6.78 (tt, J=1.5, 7.35 Hz, 1 H), 6.81 (d, J=15.6 Hz, 1H), 7.29–7.42 (m, 3H), 7.61 (d, J=15.6 Hz, 1H), 7.75 (br s, 1H). MS (APCI$^+$) (M+H)$^+$ at m/z 548.

Example 100

(2-(Piperidin-1-yl)phenyl)[2-trifluoromethyl-4-(E-((4-(tert-butoxycarbonyl)piperazin-1-yl)carbonyl)ethenyl)phenyl]sulfide The title compound was prepared by the procedures described in Example 69 substituting pyrrolidine with piperidine, and the bromide from Example 12 with bromide from Example 90, and isolated as a white solid. $^1$H NMR (CDCl$_3$, 300 MHz) δ 1.48 (s, 9H), 1.54 (br s, 6H), 2.96 (br s, 4H), 3.48 (br s, 4H), 3.55–3.78 (m, 4H), 6.89 (d, J=15.6 Hz, 1H), 6.99 (td, J=1.8, 7.5 Hz, 1H), 7.08 (d, J=8.4 Hz, 1H), 7.19 (dd, J=1.8, 8.1 Hz, 1H), 7.25 (br m, 1H), 7.31 (td, J=1.8, 7.5 Hz, 1H), 7.42 (dd, J=1.8, 8.4 Hz, 1H), 7.65 (d, J=15.6 Hz, 1H), 7.71 (d, J=1.8 Hz, 1 H). MS (APCI$^+$) (M+H)$^+$ at m/z 576.

Example 101

(3-Chloro-2-formylphenyl)[2-chloro-4-(E-((4-acetylpiperazin-1-yl)carbonyl)ethenyl)phenyl]sulfide The title compound was prepared by the procedures described in Example 65B substituting 2,3-dichlorobenzaldehyde with 2,6-dichlorobenzaldehyde, isolated as a white solid. $^1$H NMR (CDCl$_3$, 300 MHz) δ 2.05 (s, 3H), 3.56 (br s, 2H), 3.61–3.86 (m, 6H), 6.68 (q, J=3.0 Hz, 1 H), 6.93 (d, J=15.6 Hz, 1H), 7.23 (d, J=3.0 Hz, 1H), 7.25 (m, 1H), 7.45 (dd, J=2.1, 8.4 Hz, 1H), 7.62 (d, J=8.4 Hz, 1H), 7.67 (d, J=15.6 Hz 1H), 7.69 (d, J=2.1 Hz, 1H). MS (APCI$^+$) (M+H)$^+$ at m/z 463, 465, 467.

Example 102

(2-Trifluoromethylphenyl)[2-trifluoromethyl-4-(E-((4-acetylpiperazin-1-yl)carbonyl)ethenyl)phenyl]sulfide The title compound was prepared according to the procedures of Example 1. $^1$H NMR (CDCl$_3$, 300 MHz) δ 7.84 (s, 1H), 7.80 (m, 1H), 7.66 (d, 1H, J=15.4 Hz), 7.49 (m, 3H), 7.40 (m, 1H), 7.06 (d, 1H, J=8.0 Hz), 6.87 (d, 1H, J=15.4 Hz), 3.62–3.80 (m, 6H), 3.53 (m, 2H), 2.15 (s, 3H). MS (ESI) m/z 503, 525, 1027.

Example 103

(3-Bromophenyl)[2-trifluoromethyl-4E-((4-acetylpiperazin-1-yl)carbonyl)ethenyl)phenyl]sulfide The title compound was prepared according to the procedures of Example 1. $^1$H NMR (CDCl$_3$, 300 MHz) δ 7.83 (s, 1H), 7.66 (d, 1H, J=15.4 Hz), 7.57 (t, 1H, J=1.9 Hz), 7.49 (m, 2H), 7.36 (dt, 1H, J=1.6, 7.8 Hz), 7.24 (m, 1H), 7.18 (d, 1H, J=8.1 Hz), 6.87 (d, 1H, J=15.2 Hz), 3.62–3.82 (m, 6H), 3.54 (m, 2H), 2.15 (s, 3H). MS (ESI) m/z 514, 515, 535, 537.

Example 104

(3,5-Dimethylphenyl([2-trifluoromethyl-4-(E-((4-acetylpiperazin-1-yl)carbonyl)ethenyl)phenyl]sulfide The title compound was prepared according to the procedures of example 1. $^1$H NMR (CDCl$_3$, 300 MHz) δ 7.79 (s, 1H), 7.64 (d, 1H, J=15.1 Hz), 7.42 (d, 1H, J=8.8 Hz), 7.49 (m, 2H), 7.13 (s, 2H), 7.04 (s, 2H), 6.84 (d, 1H, J=15.2 Hz), 3.62–3.82 (m, 6H), 3.54 (m, 2H), 2.32 (s, 6H), 2.15 (s, 3H). MS (ESI) m/z 463, 485, 925, 947.

Example 105

(2-Isopropylphenyl)[2-nitro-4-(E-((3dimethylaminocarbonyl-4-(pyridine-4-carbonyl)piperazin-1-yl)carbonyl)ethenyl)phenyl]sulfide Prepared according to the procedures of Example 71, giving a yellow solid. $^1$H NMR (DMSO-d$_3$, 300 MHz) δ 1.14 (d, J=6.6 Hz, 6H); 2.50–3.83 (br m, 10H); 4.04–4.66 (br m, 3H); 5.32–5.43 (br m, 1H); 6.60–6.69 (m, 1H); 7.15–7.64 (m, 8H); 7.85–7.93 (m, 1H); 8.59–8.72 (m, 3H). MS (APCI) (M+H)$^+$ at m/z 588. Anal calcd for C$_{31}$H$_{33}$N$_5$S$_1$.0.67H$_2$O: C, 62.07; H, 5.77; N, 11.68. Found: C, 62.13; H, 6.01; N, 11.48.

Example 106

(2-Isopropylphenyl)[2-nitro-4-(E-((3-dimethylaminocarbonyl-4-carbomethoxypiperazin-1-yl)carbonylethenyl)phenyl]sulfide Prepared according to the procedures of Example 71, giving a yellow solid. $^1$H NMR (DMSO-d$_6$, 300 MHz) δ 1.14 (d, J=6.6 Hz, 6H); 2.50–3.83 (br m, 14H); 4.16–4.63 (br m, 2H); 4.98 (br s, 1H); 6.60–6.69 (m, I1H); 7.20–7.61 (m, 6H); 7.85–7.93 (m, 1H); 8.59–8.65 (m, 1H). MS (APCI) (M+H)$^+$ at m/z 541.

Example 107

(2-Isopropylphenyl)[2-nitro-4-(E-((3-dimethylaminocarbonyl-4-acetylpiperazin-1-yl)carbonyl)ethenyl)phenyl]sulfide Prepared according to the procedures of Example 71, giving a yellow solid. $^1$H NMR (DMSO-d$_6$, 300 MHz) δ

1.14 (d, J=6.6 Hz, 6H); 1.88, 2.04 (s, s, 3H); 2.50–3.83 (br m, 11H); 4.16–4.59 (br m, 2H); 5.04–5.25 (br m, 1H); 6.60–6.69 (m, 1H); 7.21–7.62 (m, 6H); 7.85–7.93 (m, 1H); 8.58–8.65 (m, 1H). MS (APCI) (M+H)$^+$ at m/z 525. Anal calcd for $C_{27}H_{32}N_4S_1O_5$: C, 61.81; H, 6.15; N, 10.68. Found: C, 61.93; H, 6.75; N, 9.67.

Example 108

(2-Isopropylphenyl)[2-nitro-4-(E-((3-(1-morpholinocarbonyl)-4-tert-butoxycarbonylpiperazin-1-yl)carbonylethenyl) phenyl]sulfide Prepared according to the procedures of Example 71, giving a yellow solid. $^1$H NMR (DMSO-d$_6$, 300 MHz) δ 1.11–1.16 (br m, 6H); 1.35, 1.40 (br s, br s, 9H); 2.67–5.0(br m, 16H); 6.60–6.69 (m, 1H); 7.28–7.62 (m, 6H); 7.87–7.92 (m, 1H); 8.63–8.67 (br m, 1H). MS (APCI) (M+H)$^+$ at m/z 625. Anal calcd for $C_{32}H_{40}N_4S_1O_7$: C, 61.52; H, 6.45; N, 8.97. Found: C, 61.10; H, 6.65; N, 8.60.

Example 109

(2-Isopropylphenyl)[2-nitro-4-(E-((3-(pyridine-4-methylaminocarbonyl)piperazin-1-yl)carbonyl) ethenyl)phenyl]sulfide Prepared according to the procedures of Example 71, giving a yellow solid. $^1$H NMR (DMSO-d$_6$, 300 MHz) δ 1.14 (d, J=6.6 Hz, 6H); 2.504.46 (br m, 10H); 6.63 (d, J=8.5 Hz, 1H); 7.20–7.64 (m, 8H); 7.85–7.93 (m, 1H); 8.43–8.65 (m, 4H). MS (APCI) (M+H)$^+$ at m/z 546. Anal calcd for $C_{29}H_{31}N_5S_1O_4 \cdot 0.46CH_3COOCH_2CH_3$: C, 63.20; H, 5.96; N, 11.95. Found: C, 63.29; H, 6.27; N, 11.97.

Example 110

(2-Isopropylphenyl)[2-nitro-4-(E-(((3-dimethylaminocarbonyl)piperazin-1-yl)carbonyl) ethenyl)phenyl]sulfide Prepared according to the procedures of Example 71, giving a yellow solid. $^1$H NMR (DMSO-d$_6$, 300 MHz) δ 1.14 (d, J=6.6 Hz, 6H); 2.50–3.20 (br m, 4H); 2.82 (s, 3H); 3.04 (s, 3H); 3.26–3.49 (m, 1H); 3.52–3.59 (m, 1H); 4.084.47 (br m, 2H); 6.63 (d, J=8.5 Hz, 1H); 7.31–7.62 (m, 6H); 7.86–7.92 (m, 1H); 8.61 (br m, 1H). MS (APCI) (M+H)$^+$ at m/z 483. Anal calcd for $C_{25}H_{30}N_4S_1O_4 \cdot 0.39CH_3COOCH_2CH_3$: C, 61.71; H, 6.46; N, 10.84. Found: C, 61.96; H, 6.69; N, 10.73.

Example 111

(2-Isopropylphenyl)[2-nitro-4-(E-((3-(benzylaminocarbonyl)4-tert-butoxycarbonylpiperazin-1-yl)carbonyl)ethenyl) phenyl]sulfide Prepared according to the procedures of Example 71, giving a yellow solid. $^1$H NMR (DMSO-d$_6$, 300 MHz) δ 1.14 (d, J=6.6 Hz, 6H); 1.33, 1.42 (br s, br s, 9H); 2.75–4.77 (br m, 10H); 6.60–6.66 (br m, 1H); 7.02–7.94 (br m, 12H); 8.47–8.67 (m, 2H). MS (APCI) (M+H)$^+$ at m/z 645.

Example 112

(2-Isopropylphenyl)[2-nitro-4-(E-((3-(dimethylaminocarbonyl)-4-tert-butoxycarbonylpiperazin-1-yl)carbonyl)ethenyl) phenyl]sulfide Prepared according to the procedures of Example 71, giving a yellow solid. $^1$H NMR (DMSO-d$_6$, 300 MHz) δ 1.14 (d, J=6.6 Hz, 6H); 1.35, 1.40 (br s, br s, 9H) 2.50–4.99 (br m, 14H); 6.60–6.69 (m, 1H); 7.21–7.62 (m, 6H); 7.86–7.92 (m, 1H); 8.59–8.63 (br m, 1H). MS (APCI) (M+H)$^+$ at m/z 583. Anal calcd for $C_{30}H_{38}N_4S_1O_6 \cdot 0.21C_6H_{14}$: C, 62.50; H, 6.87; N, 9.32. Found: C, 62.28; H, 7.15; N, 9.11.

Example 113

(2-Bromophenyl)[2-chloro-4-(E-((3-(5S-hydroxymethyl-2-oxopyrrolidin-1-yl)prop-1-ylamino)carbonyl)ethenyl)phenyl]sulfide (2-Bromophenyl)[2-chloro-4-(2-carboxy-E-ethenyl) phenyl]sulfide was prepared by the procedures described in Example 1 substituting 2,4 dichlorothiophenol with 2-bromothiophenol, 2-chlorobenzaldehyde with 3,4 dichlorobenzaldehyde. 1-(3-aminopropyl)-5-((S)-thexyldimethylsilyloxymethyl)-2-pyrrolidinone (0.2818 g, 0.8959 mmol) was added to a solution of this cinnamic acid (0.3312 g, 0.8959 mmol), 1-[3-(dimethylamino)propyl]-3-ethyl carbodiimide hydrochloride (0.3435 g, 1.79 mmol), and 1-hydroxybenzotriazole hydrate (0.1816 g, 1.34 mmol) in DMF (4.0 mL). After stirring for 12 hours, the reaction mixture was diluted with EtOAc (250 mL), extracted with sat. NH$_4$Cl (1×75 mL), extracted with H$_2$O (2×75 mL), rinsed with brine (75 mL), and dried over Na$_2$SO$_4$. The resultant thexyldimethylsilyl alcohol was purified by flash chromatography (EtOAc) on silica gel (0.4974 g, 83%). Tetrabutylammonium fluoride (0.68 mL of 1.0 M solution in THF) was added dropwise to a solution of this protected alcohol (0.4544 g, 0.682 mmol) in THF (1.7 mL). After 2 hours, the reaction was diluted with EtOAc (50 mL) and extracted with sat. NH$_4$Cl (1×25 mL), extracted with H$_2$O (2×25 mL), rinsed with brine (25 mL), and dried over Na$_2$SO$_4$. Flash chromatography (EtOAc→9:1 CH$_2$Cl$_2$:MeOH) on silica gel yielded the title compound (0.3144 g, 88%). $^1$H-NMR (DMSO-d$_6$, 300 MHz) δ 8.14 (t, J=5.5 Hz, 1H), 7.81 (m, 2H), 7.53 (dd, J=8.3, 1.7 Hz, 1H), 7.44 (dt, J=7.7, 1.5, 1H), 7.40 (dt, J=7.7, 1.8, 1H), 7.39 (d, J=15.6 Hz, 1H), 7.28 (dd, J=7.7, 1.8 Hz, 1H), 7.05 (d, J=8.1 Hz, 1H), 6.67 (d, J=15.6 Hz, 1H), 4.84 (t, J=5.1 Hz, 1H), 2.94–3.62 (m, 8H), 1.54–2.29 (m, 6H), MS(APCI) (M+H)$^+$ at m/z 523, 525, 527, 529.

Example 114

(2-Bromophenyl)[2-chloro-4-(E-((3-(2-oxopyrrolidin-1-yl)prop-1-ylamino)carbonyl) ethenyl)phenyl]sulfide The title compound was prepared by the procedures described in Example 1 substituting 2,4 dichlorothiophenol with 2-bromothiophenol, 2-chlorobenzaldehyde with 3,4 dichlorobenzaldehyde, and 6-amino-1-hexanol with 1-(3-aminopropyl)-2-pyrrolidinone. $^1$H-NMR (DMSO-d$_6$, 300 MHz) δ 8.12 (t, J=5.9 Hz, 1H), 7.81 (m, 2H), 7.52 (dd, J=8.1, 2.0 Hz, 1H), 7.44 (dt, J=7.5, 1.4, 1H), 7.34 (dt, J=7.5, 2.0, 1H), 7.39 (d, J=15.8 Hz, 1H), 7.28 (dd, J=7.6, 1.9 Hz, 1H), 7.05 (d, J=8.1 Hz, 1H), 6.67 (d, J=15.8 Hz, 1H), 4.02 (d, J=0.7 Hz, 1H), 3.29–3.35 (m, 2H), 3.11–3.25 (m, 4H), 2.21 (t, J=8.1 Hz, 1H), 1.94 (m, 2H), 1.64 (m, 2H), MS(APCI) (M+H)$^+$ at m/z 493, 495, 497,499.

Example 115

(2-Bromophenyl)[2-chloro-4-(E-(N-methyl-N-(3-(2-oxopyrrolidin-1-yl)prop-1-yl)amino)carbonyl) ethenyl)phenyl]sulfide The title compound was prepared by the procedures described in Example 1 substituting 2,4 dichlorothiophenol with 2-bromothiophenol, 2-chlorobenzaldehyde with 3,4 dichlorobenzaldehyde, and 6-amino-1-hexanol with 1-(3-methylaminopropyl)-2-pyrrolidinone. $^1$H-NMR (DMSO-$d_6$, 300 MHz) δ 8.06 (d, J=1.5 Hz, 1H),7.80 (dd, J=7.7, 1.1 Hz, 1H), 7.64 (dd, J=8.5, 1.7 Hz,1H), 7.25–7.46 (m, 5H), 7.04 (d, J=8.1, 1.1, 1H), 3.14–5.30 (m, 6H), 3.14 (s, 1H), 2.91 (s, 2H), 2.19 (m, 2H), 1.92 (m, 2H), 1.68 (m, 2H), MS(APCI) (M+H)$^+$ at m/z 507, 509, 511, 513.

Example 116

(2-[2-Methoxy]ethoxyphenyl)-[2-chloro-4-(E-[(morpholin-1-yl)carbonyl]ethenyl)phenyl]sulfide The title compound was prepared according to the procedures of Example 97, substituting 2-methoxyethoxybenzene, giving a white solid. $^1$H NMR (CDCl$_3$, 300 MHz) δ 3.29 (s, 3H), 3.60 (t, J=7 Hz, 2H), 3.60–3.78 (m, 8H), 4.12 (t, J=7 Hz, 2H), 6.78 (d, J=85Hz, 14), 6.82 (d, J=9H, 1H), 6.95–7.03 (m, 2H), 7.18 (dd, J=9 Hz, 2 Hz, 1H), 7.36)7.45 (m, 2J), 7.52 (d, J=2Hz, 1H), 7.57 (d, J=15Hz, 1H). Anal. Calcd. $C_{22}H_{24}ClNO_4S$: C, 60.85; H, 5.57; N, 3.22. Found: C, 60.65; H, 5.59; N, 3.12.

Example 117

(2-Isopropylphenyl)[2-nitro-4-(E-((3-(morpholinocarbonyl)piperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=6.6 Hz, 6H); 2.50–3.40 (br m, 6H); 3.42–3.64 (br m, 87); 4.07–4.44 5(br m, 2H); 4.08–4.47 (br m, 2); 6.64 (d, J=8.5 Hz, 1H); 7.31–7.62 (m, 6H); 7.87–7.92 (m, 1H); 8.61 (br m, 1H). MS (APCI) (M+H)$^+$ at m/z 525. Anal calcd for $C_{27}H_{32}N_4S_1O_5 \cdot 1.57H_2O$: C, 58.64; H, 6.41; N, 10.13. Found: C, 58.69; H, 6.36; N, 9.78.

Example 118

(2-Isopropylphenyl)[2-nitro-4-(E-((4-tert-butoxycarbonylpiperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=7.0 Hz, 6H); 1.41 (s, 9H); 3.30–3.40 (m, 1H); 3.50–3.72 (br m, 8H); 6.64 (d, J=8.5 Hz, 1H); 7.34–7.62 (m, 6H); 7.87–7.92 (dd, J=8.5, 1.5 Hz, 1H); 8.65 (d, J=1.5 Hz, I11). MS (APCI) (M+H)$^+$ m/z 512. Anal calcd for $C_{27}H_{33}N_3S_1O_5$: C, 63.38; H, 6.50; N, 8.21. Found: C, 63.69; H, 6.62; N, 7.87.

Example 119

(2-Isopropylphenyl)[2-nitro-4-(E-((4-methoxycarbonylpiperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=6.8 Hz, 6H); 3.62 (s, 3H); 3.30–3.38 (m, 1H); 3.38–3.72 (br m, 8H); 6.64 (d, J=8.8 Hz, 1H); 7.34–7.62 (m, 6H); 7.87–7.92 (dd, J=8.8, 2.0 Hz, 1H); 8.64 (d, J=2.0 Hz, 1H). MS (APCI) (M+H)$^+$ at m/z 470. Anal calcd for $C_{24}H_{27}N_3S_1O_5 \cdot 0.34C_6H_{14}$: C, 62.77; H, 6.27; N, 8.44. Found: C, 62.70; H, 6.33; N, 8.27.

Example 120

(2-Isopropylphenyl)[2-nitro-4-(E-(4-(pyridine-4-carbonyl)piperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=6.6 Hz, 6H); 3.30–3.40 (m, 1H); 3.52–3.86 (br m, 8H); 6.61–6.66 (br m, 1H); 7.30–7.62 (m, 8H); 7.83–7.96 (br m, 1H); 8.60–8.71 (m, 3H). MS (APCI) (M+H)$^+$ at m/z 517. Anal calcd for $C_{28}H_{28}N_4S_1O_4 \cdot 0.38CH_3COOCH_2CH_3$: C, 64.46; H, 5.69; N, 10.19. Found: C, 64.52; H, 5.94; N, 10.21.

Example 121

(2-Isopropylphenyl)[2-nitro-4-(E-((3-(pyridine-3-methylaminocarbonyl)-4-tert-butoxycarbonylpiperazin-1-ylcarbonyl)ethenyl phenyl]sulfide Yellow solid; $^1$H NMR (DMSO-$d_6$, 300 MHz) δ 1.14 (d, J=6.8 Hz, 6H); 1.31–1.46 (br m, 9H); 3.30–3.41 (m, 1H); 3.15–4.78 (br m, 9H); 6.61–6.67 (br m, 1H); 7.05–7.95 (br m, 9H); 8.20–8.65 (br m, 4H). MS (APCI) (M+H)$^+$ at m/z 646. Anal calcd for $C_{34}H_{39}N_5S_1O_6 \cdot 0.13H_2O$: C, 62.97; H, 6.49; N, 10.79. Found: C, 62.66; H, 6.26; N, 10.60.

Example 122

(2-Isopropylphenyl)[2-nitro-4 E-((3-(pyridine-2-methylaminocarbonyl)piperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=7.0 Hz, 6H); 3.30–3.41 (m, 1H); 2.50–4.46 (br m, 9H); 6.64 (d, J=8.5 Hz, 1H); 7.21–7.93 (br m, 10H); 8.45–8.65 (br m, 3H). MS (APCI) (M+H)$^+$ at m/z 546.

Example 123

(2-Isopropylphenyl)[2-nitro-4-E-((3-(pyridine-3-methylaminocarbonyl)piperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=6.6Hz, 6H); 2.50–4.41 (br m, 10H); 6.61–6.67 (br m, 1H); 7.26–7.70 (br m, 8H); 7.86–7.94 (br m, 1H); 8.40–8.67 (br m, 4H). MS (APCI) (M+H)$^+$ at m/z 546.

Example 124

(4-Hydroxyphenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 4-hydroxythiophenol. Yellow solid (23 mg, 45%); $^1$H-NMR (Pyridine-$d_5$, 500 MHz) δ 2.08 (s, 3H), 3.42 (br, m, 2H), 3.76 (br, m, 6H), 7.01 (d, J=17 Hz, 1H), 7.26 (m, 2H), 7.37 (d, J=31 Hz, 1H), 7.59 (m, 3H), 8.02 (d, J=31 Hz, 1H), 8.60 (d, J=4 Hz, 1H). MS (APCI) (M+H)$^+$ at m/z 428. FAB High Resolution MS calculated m/z for $C_{21}H_{22}N_3O_5S$ (M+H)$^+$: 428.1280. Observed m/z: 428.1296.

Example 125

(3,5-Dichlorophenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 3,5-dichlorothiophenol. Yellow solid (12 mg, 21%); $^1$H-NMR (CDCl$_3$, 400 MHz) δ 2.04 (s, 3H), 3.43 (br, m, 2H), 3.62 (br, m, 6H), 6.82 (d, J=22 Hz, 1H), 6.82 (d, J=38 Hz, 1H), 7.37 (s, 1H), 7.38 (s, 1H), 7.40 (m, 1H), 7.43 (dd, J=3, 21 Hz, 1H), 7.55 (d, J=38 Hz, 1H), 8.29 (d, J=4 Hz, 1H). MS (APCI) (M+H)$^+$ at m/z 480. FAB High Resolution MS calculated m/z for $C_{21}H_{20}N_3O_4Cl_2S$ (M+H)$^+$: 480.0552. Observed m/z: 480.0553.

Example 126

(2-Bromophenyl)[2-chloro-4-(E-((3-(5S-acetoxymethyl-2-oxopyrrolidin-1-yl)prop-1-ylamino)carbonyl)ethenyl)phenyl]sulfide To a solution of the compound of Example 113 (0.0466 g, 0.0889 mmol) in $CH_2Cl_2$ (0.5 mL) was added triethylamine (0.024 mL, 0.18 mmol) and acetic anhydride (0.0088 mL, 0.0933 mmol). After 12 hours, the reaction was diluted with MeOH (1.5 mL) and purified by preparative HPLC to provide the title compound (0.0458 g, 91%). $^1$H-NMR (DMSO-d$_6$, 300 MHz) δ 8.14 (t, J=5.7 Hz, 1H), 7.80 (m, 2H), 7.53 (dd, J=8.5, 1.5 Hz, 1H), 7.45 (dt, J=7.7, 1.5, 1H), 7.35 (dt, J=7.7, 1.8, 1H), 7.39 (d, J=15.6 Hz, 1H), 7.29 (dd, J=7.7, 1.8 Hz, 1H), 7.05 (d, J=8.1 Hz, 1H), 6.67 (d, J=15.6 Hz, 1H), 4.20 (dd, J=11.8, 3.7 Hz, 1H), 4.03 (dd, J 11.8, 4.0 Hz, 1H), 3.85 (m, 1H), 3.45 (m, 2H), 3.15 (m, 2H), 2.95 (m, 2H), 2.00–2.48 (m, 2H), 2.02 (s, 3H), 1.51–1.82 (m, 2H), MS(APCI) (M+H)$^+$ at m/z 565, 567, 569, 571.

Example 127

(2-Bromophenyl)[2-chloro-4-(E-((3-(5S-methoxymethyl-2-oxopyrrolidin-1-yl)prop-1-ylamino)carbonyl)ethenyl)phenyl]sulfide Sodium hydride (0.0088 g, 0.22 mmol, 60% dispersion) was added to a solution of the compound of Example 113 (0.0524 g, 0.1 mmol) in DMF (0.5 mL). After 15 minutes, iodomethane (0.025 mL, 0.4 mmol) was added and the reaction was stirred for 12 hours. The reaction was diluted with EtOAc (7 mL) and extracted with sat. NH$_4$Cl (1×2.5 mL), extracted with H$_2$O (2×2.5 mL), rinsed with brine (2.5mL), dried over Na$_2$SO$_4$, filtered, and concentrated in vacuo. The crude products were diluted with MeOH (1.5 mL) and purified by preparative HPLC to provide the title compound (0.0408 g, 74%). $^1$H-NMR (DMSO-d$_6$, 300 MHz) δ 8.07 (2, 1H), 7.80 (dd, J=7.9, 1.3 Hz, 1H), 7.64 (dd, J=8.3, 1.6 Hz, 1H), 7.23–7.46 (m, 5H), 7.04 (d, J=8.1, 1H), 3.74 (m, 1H), 4.4–3.52 (m, 6H), 3.27 (s, 1.5H), 3.22 (s, 1.5H), 3.14 (s, 1.5H), 2.91 (s, 1.5H), 1.5–2.3 (m, 6H), MS(APCI) (M+H)$^+$ at m/z 551, 553, 555.

Example 128

(2-Bromophenyl)[2-chloro-4-(E-((3-(4R-hydroxymethyl-2-oxopyrrolidin-1-yl)prop-1-ylamino)carbonyl)ethenyl)phenyl]sulfide The title compound was prepared by the procedures described for Example 113 substituting 1-(3-aminopropyl)-5-((S)-thexyldimethylsilyloxymethyl)-2-pyrrolidinone with 1-(3-aminopropyl)-4-((R)-thexyldimethylsilyloxy)-2-pyrrolidinone. $^1$H-NMR (DMSO-d6, 300 MHz) δ 8.13 (t, J=5.5 Hz, 1H), 7.80 (m, 2H), 7.53 (dd, J=8.5, 1.7 Hz, 1H), 7.27–7.44 (m, 4H), 7.05 (d, J=8.1 Hz, 1H), 6.67 (d, J=15.8 Hz, 1H), 5.19 (d, J=3.7 Hz, 1H), 4.28 (br s, 1H),3.10–3.62 (m, 8H), 2.06 (dd, 1H), 1.63 (m, 1H), MS(APCI) (M+H)$^+$ at m/z 509, 511, 513.

Example 129

Phenyl[2-nitro-4-(E-((4-acetylpiperazin-1-yl)carbonyl)ethenyl)phenyl]sulfide

The title compound was prepared by the procedures described in Example 83 substituting 3,4-dimethylthiophenol with thiophenol. Yellow solid (36 mg, 73%); $^1$H-NMR (CDCl$_3$, 400 MHz) δ 2.20 (s, 3H), 3.59 (br, m, 2H), 3.78 (br, m, 6H), 6.92 (d, J=21 Hz, 1H), 6.95 (d, J=39 Hz, 1H), 7.49 (br, d, J=21 Hz, 1H), 7.56 (m, 3H), 7.65 (m, 2H), 7.69 (d, J=38 Hz, 1H), 8.46 (d, J=4 Hz, 1H). MS (APCI) (M+H)$^+$ at m/z 412. FAB High Resolution MS calculated m/z for $C_{21}H_{22}N_3O_4S$ (M+H)$^+$: 412.1331. Observed m/z: 412.1342.

Example 130

(2-Dimethylaminophenyl)[2-nitro-4-(E-((4-acetylpiperazin-1-yl)carbonyl)ethenyl)phenyl]sulfide To a stirred solution of aniline from Example 47 (21 mg, 0.049 mmol) in 1 mL of ethanol was added Me$_2$SO$_4$ (14.0 mL, 0.15 mmol) followed by sat. Na$_2$CO$_3$ (25 mL). The mixture was then refluxed for one day. The reaction mixture was allowed to cool to ambient temperature, partitioned between EtOAc and water. The organic layer was washed with brine, dried over Na$_2$SO$_4$, filtered, concentrated under reduced pressure. The residue was then purified on a Gilson Preparative HPLC as described in Example 38B to give the title compound (10 mg, 45% yield), as a light yellow solid.

Example 131

(3-((2-Hydroxyethyl)aminocarbonyl)phenyl)[2-nitro-4-(E-((4-acetylpiperazin-1-yl)carbonyl)ethenyl)phenyl]sulfide The title compound was prepared by the procedures described in Example 92B, substituting ammonium chloride with ethanolamine, to give a light yellow solid. $^1$H NMR (d$^6$-DMSO, 300 MHz) δ 2.04 (s, 31), 3.30–3.79 (m, 12H), 4.75 (t, J=5.7 Hz, 1H), 6.85 (d, J=8.7 Hz, 1H), 7.42 (d, J=15.6 Hz, 1H), 7.54 (d, J=15.6 Hz, 1H), 7.66 (t, J=7.8 Hz, 1H), 7.79 (d, J=8.1 Hz, 1H), 7.92 (dd, J=2.1, 8.1 Hz, 1H), 8.04 (d, J 8.4 Hz, 1H), 8.11 (s, 1H), 8.62 (t, J=5.7 Hz, 1H), 8.66 (d, J=2.1 Hz, 1H). MS (APCI) (M+Cl)$^-$ at m/z 533, 535.

Example 132

(3-((3-(1-Imidazolyl)propyl)aminocarbonyl)phenyl)[2-nitro-4-(E-((4-acetylpiperazin-1-ylcarbonyl)ethenyl)phenyl]sulfide The title compound was prepared by the procedures described in Example 92B, substituting ammonium chloride with 3-aminopropyl-1-imidazole, as a light yellow solid. $^1$H NMR (d$^6$-DMSO, 300 MHz) d 1.96 (quintet, J=6.98 Hz, 2H), 2.04 (s, 3H), 3.24 (q, J=6.98 Hz, 2H), 3.35–3.95 (m, 8H), 4.02 (t, J=6.98 Hz, 2H), 6.87 (d, J=8.4 Hz, 1H), 6.88 (s, 1H), 7.19 (s, 1 H), 7.41 (d, J=15.6 Hz, 1H), 7.54 (d, J=15.6 Hz, 1H), 7.64 (s, 1H), 7.68 (d, J=7.8 Hz, 1H), 7.79 (dt, J=1.8, 7.8 Hz, 1H), 7.91 (dd, J=1.8, 8.7 Hz, 1H), 8.03 (d, J=7.8 Hz, I1H), 8.09 (t, J=1.8 Hz, 1H), 8.65 (d, J=1.8 Hz, 1H). MS (APCI$^-$) (M+Cl)$^-$ at m/z 597, 599.

Example 133

(3-((2-(1-Morpholinyl)ethyl)aminocarbonyl)phenyl)[2-nitro-4-(E-((4-acetylpiperazin-1-yl)carbonyl)ethenyl)phenyl]sulfide The title compound was prepared by the procedures described in Example 92B, substituting ammonium chloride with 2-aminoethyl-1-morpholine, as a light yellow solid. $^1$H NMR (d$^6$-DMSO, 300 MHz) δ 2.04 (s, 3H), 2.44 (br s, 4H), 3.20–3.80 (m, 16H), 6.87 (d, J=8.4 Hz, 1H), 7.41 (d, J=15.6 Hz, 1H), 7.54 (d, J=15.6 Hz, 1H), 7.68 (d, J=8.4 Hz, 1H), 7.79 (d, J=8.4 Hz, 1H), 7.91 (dd, J=2.1, 8.4 Hz, 1H), 8.02 (d, J=8.4 Hz, 1H), 8.07 (s, 1H), 8.58 (t, J=6.0 Hz, 1H), 8.65 (d, J=2.1 Hz 1H). MS (APCI+) (M+H)$^+$ at m/z 568.

Example 134

(2-Isopropylphenyl)[2-nitro-4-(E-((3-hydroxymethyl-4-tert-butoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 1.41 (s, 9H); 2.62–3.20 (br m, 4H); 3.30–3.40 (m, 1H); 3.72–4.44 (br m, 4H); 4.72–4.98 (br m, 1H); 6.62–6.66 (br m, 1H); 7.25–7.63 (m, 6H); 7.83–7.93 (br m, 1H); 8.57–8.66 (br m, 1H). MS (APCI) (M+H)$^+$ at m/z 542. Anal calcd for C$_{28}$H$_{35}$N$_3$S$_1$O$_6$.0.21C$_6$H$_{14}$: C, 62.78; H, 6.83; N, 7.51. Found: C, 62.65; H, 6.99; N, 7.36.

Example 135

(2-Isopropylphenyl)[2-nitro-4-(E-((4-formylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.1 Hz, 6H); 3.30–3.38 (m, 1H); 3.38–3.77 (br m, 8H); 6.64 (d, J=8.5 Hz, 1H); 7.34–7.62 (m, 6H); 7.88–7.92 (dd, J=8.5, 1.7 Hz, 1H); 8.08 (s, 1H); 8.65 (d, J=1.7 Hz, 1H). MS (APCI) (M+H)$^+$ at m/z 440. Anal calcd for CH$_{23}$H$_{25}$N$_3$S$_1$O$_4$: C, 62.85; H, 5.73; N, 9.56. Found: C, 63.05; H, 5.98; N, 9.47.

Example 136

(2-Isopropylphenyl)[2-nitro-4E-((2-hydroxymethyl-4-tert-butoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.41 (s, 9H); 2.72–3.50 (br m, 4H); 3.30–3.40 (m, 1H); 3.85–4.52 (br m, 4H); 4.74–4.91 (br m, 1H); 6.62–6.66 (br m 1H); 7.28–7.62 (m, 6H); 7.81–7.91 (br m, 1H); 8.57–8.66 (br m, 1H). MS (APCI) (M+H)$^+$ at m/z 542. Anal calcd for C$_{28}$H$_{35}$N$_3$S$_1$O$_6$.0.17C$_6$H$_{14}$: C, 62.65; H, 6.77; N, 7.55. Found: C, 62.54; H, 6.83; N, 7.33.

Example 137

(2-Ethoxyphenyl)-[2-chloro-4-(E-[(3-ethoxycarbonylpiperidin-1-yl)carbonyl]ethenyl)phenyl]sulfide The title compound was prepared according to the procedures of Example 97. $^1$H NMR (CDCl$_3$, 300 MHz) δ 1.25 (t, J=7 Hz, 6H), broad peaks totaling 9 protons at 1.50–1.62, 1.65–1.92, 2.01–2.15, 2.45–2.55, 2.95–3.05, 3.13–3.30, 3.55–3.68, 3.90–4.10, 4.05 (q, J=7Hz, 2H), 4.15 (q, J=7 Hz, 2H), 6.84 (d, J=9 Hz, 1H), 6.80–6.95 (broad, 1H), 6.94–6.99 (m, 2H), 7.18 (dd, J=9 Hz, 2 Hz, 1H), 7.34–7.41 (m, 2H), 7.52 (d, J=15 Hz, 1H), 7.55 (d, J=2 Hz, 1H). Anal Calcd. for C$_{25}$H$_{28}$ClNO$_4$S: C, 63.35; H, 5.95;N, 2.95. Found: C, 63.17; H, 6.02; N, 26.02; N, 2.81.

Example 138

(3-Aminophenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 3-aminothiophenol. Yellow solid (2.9 mg, 5.6%); $^1$H-NMR (CDCl$_3$, 500 MHz) δ 2.20 (s, 3H), 3.60 (br, m, 2H), 3.77 (br, m, 6H), 4.03 (br, s, 2H), 6.85 (dd, J=4, 16 Hz, 1H), 6.90 (m, 3H), 7.04 (d, J=17 Hz, 1H), 7.30 (t, J=16 Hz, 1H), 7.52 (d, J=17 Hz, 1H), 7.68(d, J=31 Hz, 1H), 8.44 (d, J=4 Hz, 1H). MS (APCI) (M+H)$^+$ at m/z 427. FAB High Resolution MS calculated m/z for C$_{21}$H$_{23}$N$_4$O$_4$S (M+H)$^+$: 427.1440. Observed m/z: 427.1440.

Example 139

(4-Aminophenyl)[2-nitro-4-(E-((4-acetylpiperazin-1-ylcarbonyl)ethenyl)phenyl]sulfide The title compound was prepared by the procedures described in Example 83 substituting 3,4-dimethylthiophenol with 4-aminothiophenol. Yellow solid (2.5 mg, 4.9%); $^1$H-NMR (CDCl$_3$, 500 MHz) δ 2.19 (s, 3H), 3.58 (br, m, 2H), 3.76 (br, m, 6H), 4.03 (br, s, 2H), 6.80 (m, 1H), 6.93 (m, 3H), 7.37 (m, 1H), 7.46 (d, J=17 Hz, 1H), 7.67 (d, J=31 Hz, 1H), 8.43 (d, J=3 Hz, 1H). MS (APCI) (M+H)$^+$ at m/z 427. FAB High Resolution MS calculated m/z for C$_{21}$H$_{23}$N$_4$O$_4$S (M+H)$^+$: 427.1440. Observed m/z: 427.1441.

Example 140

(2,4-Dimethylphenyl)[2-nitro-4-(E-((acetylpiperazin-1-yl)carbonyl)ethenyl)phenyl]sulfide The title compound was prepared by the procedures described in Example 83 substituting 3,4-dimethylthiophenol with 2,4-dimethylthiophenol. Yellow solid (40 mg, 76%); $^1$H-NMR (CDCl$_3$, 400 MHz) δ 1.54 (br, s, 2H), 2.14 (s, 3H), 3.53 (br, m, 2H), 3.71 (br, m, 6H), 6.58 (d, J=21 Hz, 1H), 6.76 (d, J=38 Hz, 1H), 7.03 (m, 1H), 7.09 (m, 1H), 7.28 3 (br, d, J=19 Hz, 1H), 7.33 (d, J=20 Hz, 1H), 7.51 (d, J=38 Hz, 1H), 8.30 (d, J=5 Hz, 1H). MS (APCI) (M+H)$^+$ at m/z 440. FAB High Resolution MS calculated m/z for C$_{23}$H$_{26}$N$_3$O$_4$S (M+H)$^+$: 440.1644. Observed m/z: 440.1656.

Example 141

(2.5-Dimethylphenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 2,5-dimethylthiophenol. Yellow solid (34 mg, 64%); $^1$H-NMR (CDCl$_3$, 400 MHz) δ 2.07 (s, 3H), 2.23 (s, 3H), 2.28 (s, 3H), 3.46 (br, m, 2H), 3.64 (br, m, 6H ), 6.65 (d, J=21 Hz , 1H), 6.81 (d, J=39 Hz, 1H), 7.19 (m, 2H), 7.34 (m, 2H), 7.56 (d, J=38 Hz, 1H), 8.35 (d, J=5 Hz, 1H). MS (APCI) (M+H)$^+$ at m/z 440. FAB High Resolution MS calculated m/z for C$_{23}$H$_{26}$N$_3$O$_4$S (M+H)$^+$: 440.1644. Observed m/z: 440.1656.

Example 142

(4-Methoxyphenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 4-methoxythiophenol. Yellow solid (44 mg, 83%); $^1$H-NMR (CDCl$_3$, 400 MHz) δ 2.09 (s, 3H), 3.48 (br, m, 2H), 3.66 (br, m, 6H), 3.83 (s, 3H), 6.79 (d, J=22 Hz, 1H), 6.83 (d, J=40 Hz, 1H), 6.95 (m, 1H), 7.37 (br, d, J=20 Hz, 1H), 7.43 (m, 1H), 7.46 (m, 1H), 7.58

(d, J=38 Hz, 1H), 8.35 (d, J=4 Hz, 1H). MS (APCI) (M+H)⁺ at m/z 442. FAB High Resolution MS calculated m/z for $C_{22}H_{24}N_3O_5S$ (M+H)⁺: 442.1437. Observed m/z: 442.1434.

Example 143

(3-Chlorophenyl)[2-nitro-4-(E-((4-acetylpiperazin-1-yl)carbonyl)ethenyl)phenyl]sulfide The title compound was prepared by the procedures described in Example 83 substituting 3,4-dimethylthiophenol with 3-chlorothiophenol. Yellow solid (43 mg, 80%); ¹H-NMR (CDCl₃, 400 MHz) δ 2.23 (s, 3H), 3.62 (br, m, 2H), 3.80 (br, m, 6H), 6.97 (d, J=21 Hz, 1H), 6.99 (d, 39 Hz, 1H), 7.28 (d, J=19 Hz, 1H), 7.57 (m, 3H), 7.675 (t, J=4 Hz, 1H), 7.73 (d, J=39 Hz, 1H), 8.48 (d, J=4 Hz, 1H). FAB High Resolution MS calculated m/z for $C_{21}H_{21}N_3O_4ClS$ (M+H)⁺: 446.0941. Observed m/z: 446.0953.

Example 144

(2-Chloro-4,5-diaminophenyl)[2-chloro-4-(E-((4-acetylpiperazin-1-yl)carbonyl)ethenyl)phenyl]sulfide

Example 144A (2-Chloro-4-nitro, 5-aminophenyl)[2-chloro-4-(E-((4-acetylpiperazin-1-yl)carbonyl)ethenyl)phenyl]sulfide The title compound was prepared by the procedures described in Example 65B substituting 2,3-dichlorobenzaldehyde with 4,5-dichloro-2-nitroaniline.

Example 144B (2-Chloro-4,5-diaminophenyl)[2-chloro-4-(E-((4-acetylpiperazin-1-yl)carbonyl)ethenyl)phenyl]sulfide To a stirred solution of nitrobenzene from Example 144A (170 mg, 0.34 mmol) in 2 mL of EtOH was added SnCl₂ (325 mg, 1.72 mmol). The mixture was then refluxed under nitrogen atmosphere for 2 hours. The reaction was allowed to cool to ambient temperature, quenched with sat. NaHCO₃, extracted with EtOAc(2×20 mL). The combined organic layer was washed with brine, dried over Na₂SO₄, concentrated in vacuo. The residue was then purified on Gilson preparative HPLC as described in Example 38B to give the title compound (70 mg, 44% yield) as a light yellow solid. ¹H NMR (d⁶-DMSO, 300 MHz) δ 2.04 (s, 3H), 3.42–3.80 (m, 8H), 4.84 (s, 2H), 5.32 (s, 2H), 6.51 (d, J=8.4 Hz, 1H), 6.78 (d, J=8.4 Hz, 2H), 7.26 (d, J=15.6 Hz, 1H), 7.41 (d, J=15.6 Hz, 1H), 7.48 (d, J=8.4 Hz, 1H), 7.95 (d, J=1.8 Hz, 1H). MS (APCI⁺) (M+H)⁺ at m/z 465, 467, 469, 471.

Example 145

(3.4-Diaminophenol)[2-chloro-4-(E-(4-acetylpiperazin-1-ylcarbonyl)ethenyl)phenyl]sulfide The title compound was prepared by the procedures described in Example 144, substituting 4,5-dichloronitroaniline with 5-chloronitroaniline, resulting in a light brown solid. ¹H NMR (d⁶-DMSO, 300 MHz) δ 2.04 (s, 3H), 3.31–3.80 (m, 8H), 4.75 (s, 2H), 5.01 (s, 2H), 6.61 (t, J=4.2 Hz, 3H), 6.68 (s, 1H), 7.26 (d, J=15.6 Hz, 1H), 7.40 (d, J=15.6 Hz, 1H), 7.46 (d, J=8.4Hz, 1H), 7.94(s, 1H). MS (APCI⁺) (M+H)⁺ at m/z431, 433.

Example 146

(6-Chloro-2,3-dihydro-1H-benzimidazol-2-one-5-yl)[2-chloro-4-(E-((4-acetylpiperazin-1-yl)carbonyl)ethenyl)phenyl]sulfide A mixture of dianiline from Example 144 (35 mg, 0.075 mmol) and CDI (13 mg, 0.075 mmol) in THF was stirred at ambient temperature for one day. Solvent was then removed under reduced pressure. The crude product then purified on a Gilson preparative HPLC as described in Example 38B to give the title compound (12 mg, 32% yield) as a white solid. ¹H NMR (d⁶-DMSO, 300 MHz) δ 2.04 (s, 3H), 3.40–3.80 (m, 8H), 6.63 (d, J=8.4 Hz, 1H), 7.11 (d, J=2.4 Hz, 1H), 7.12 (s, 1H), 7.23 (s, 1H), 7.32 (d, J=15.6 Hz, 1H), 7.43 (d, J=15.6 Hz, 1H), 7.50 (d, J=8.4 Hz, 1H), 8.03 (br s, 1H). MS (APCI⁺) (M−CO+H)⁺ at m/z 465, 467.

Example 147

(1-Methylindol-7-yl)[2-chloro-4-((4-acetylpiperazin-1-yl)carbonyl)ethenyl)phenyl]sulfide The title compound was prepared by the procedures described in 85, substituting 5-iodoindole with N-methyl-7-bromoindole, giving a light brown solid. ¹H NMR (CDCl₃, 300 MHz) δ 2.14 (s, 3H), 3.47–3.56 (m, 2H), 3.56–3.83 (m, 6H), 3.96(s, 3H), 6.42 (d, J=8.4 Hz, 1H), 6.55 (d, J3.6 Hz, 1H), 6.76 (d, J=15.6 Hz, 1H), 6.99 (d, J=3.6 Hz, 1H), 7.09 (dd, J=2.1, 8.4 Hz, 1H), 7.15 (t, J=7.65 Hz, 1H), 7.42 (dd, J=0.9, 7.5 Hz, 1H), 7.53 (d, J=1.8 Hz, 1H), 7.55 (dd, J=15.6 Hz, 1H), 7.77 (dd, J=0.9, 7.5 Hz, 1H). MS (APCI⁺) (M+H)⁺ at m/z 454, 456.

Example 148

(2-Hydroxy-4-aminophenyl)[2-chloro-4-(E-((4-acetylpiperazin-1-yl)carbonyl)ethenyl)phenyl]sulfide The title compound was prepared by the procedures described in Example 144, substituting 4,5-dichloronitroaniline with 5-chloronitrophenol, giving a light brown solid. ¹H NMR (d⁶-DMSO, 300 MHz) δ 2.04 (s, 3H), 3.41–3.80 (m,8H), 5.09 (s, 2H), 6.61 (d, J=8.4 Hz, 1H), 6.70 (d, J=7.8 Hz, 1H), 6.79 (s, 1H), 6.80 (dd, J=2.1, 7.8 Hz, 1H), 7.26 (d, J=15.6 Hz, 1H), 7.40 (d, J=15.6 Hz, 1H), 7.46 (d, J=8.4 Hz, 1H), 7.94 (br s, 1H). MS (APCI⁺) (M+H)⁺ at m/z 432, 434.

Example 149

(2-Isopropylphenyl)[2-nitro-4-(E-((4-methylpiperazin-1-yl)carbonyl)ethenyl)phenyl]sulfide Prepared according to the procedures of Example 71, giving a yellow solid. ¹H NMR (DMSO-d₆, 300 MHz) δ 1.14 (d, J=7.0 Hz, 6H); 2.19 (s, 3H); 2.25–2.36 (br m, 4H); 3.30–3.40 (m, 1H); 3.51–3.72 (br m, 4H); 6.63 (d, J=8.5 Hz, 1H); 7.24–7.63 (m, 6H); 7.88–7.92 (dd, J=8.8, 1.8 Hz, 1H); 8.64 (d, J=1.8 Hz, 1H). MS (APCI) (M+H)⁺ at m/z 426. Anal calcd for $C_{23}H_{27}N_3S_1O_3 \cdot 0.26H_2O$: C, 64.19; H, 6.45; N, 9.76. Found: C, 64.21; H, 6.59; N, 9.70.

Example 150

(2-Isopropylphenyl)[2-nitro-4-(E-((4-(pyridine-2-carbonyl)piperazin-1-yl)carbonyl)ethenyl)phenyl]sulfide Prepared according to the procedures of Example 71, giving a yellow solid. ¹H NMR (DMSO-d₆, 300 MHz) δ

1.14 (d, J=6.8 Hz, 6H); 3.30–3.40 (m, 1H); 3.51–3.83 (br m, 8H); 6.61–6.66 (br m, 1H); 7.30–7.65 (m, 8H); 7.83–7.97 (m, 2H); 8.57–8.67 (m, 2H). MS (APCI) (M+H)$^+$ at m/z 517. Anal calcd for $C_{28}H_{28}N_4S_1O_4 \cdot 0.45H_2O$: 64.07; H, 5.53; N, 10.67. Found: C, 64.04; H, 5.77; N, 10.97.

Example 151

(2-Isopropylphenyl)[2-nitro-4-(E-((4-(pyridine-3-carbonyl)piperazin-1-ylcarbonyl)ethenyl)phenyl] sulfide Prepared according to the procedures of Example 71, giving a yellow solid. $^1$H NMR (DMSO-d$_6$, 300 MHz) δ 1.14 (d, J=7.0 Hz, 6H); 3.30–3.40 (m, 1H); 3.52–3.87 (br m, 8H); 6.64 (d, J=8.5 Hz, 1H); 7.30–7.64 (m, 7H); 7.83–7.95 (m, 2H); 8.61–8.70 (m, 3H). MS (APCI) (M+H)$^+$ at m/z 517. Anal calcd for $C_{28}H_{28}N_4S_1O_4 \cdot 0.42H_2O$: C, 64.16; H, 5.55; N, 10.69. Found: C, 64.18; H, 5.64; N, 10.59.

Example 152

(2-Isopropylphenyl)[2-nitro-4-(E-((2-carbomethoxy-4-methoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.1 Hz, 6H); 2.70–3.95 (brim, 4H); 3.30–3.40 (m, 1H); 3.61, 3.61 (s, s, 3H); 3.65, 3.67 (s, s, 3H); 4.16–4.50 (br m, 2H); 5.08–5.39 (br m, 1H); 6.64 (dd, J=8.5, 5.1 Hz, 1 H); 7.30–7.63 (m, 6H); 7.83–7.94 (m, 1H); 8.62–8.67 (m, 1H). MS (APCI) (M+H)$^+$ at m/z 528. Anal calcd for $C_{26}H_{29}N_3S_1O_7 \cdot 0.19C_6H_{14}$: C, 59.94; H, 5.87; N, 7.72. Found: C, 59.87; H, 5.94; N, 7.59.

Example 153

(2-Isopropylphenyl)[2-nitro-4-(E-((2-carboxy-4-methoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 2.70–3.95 (br m, 4H); 3.30–3.40 (m, 1H); 3.61,3.61 (s, s, 3H); 4.16–4.51 (br m, 2H); 5.01–5.28 (br m, 1H); 6.61–6.66 (m, 1H); 7.30–7.63 (m, 6H); 7.83–7.94 (m, 1H); 8.66 (br s, 1H). MS (APCI) (M–H)$^+$ at m/z 512.

Example 154

(2-Isopropylphenyl)[2-nitro-4-(E-((3-carbomethoxy-4-methylpiperazin-1-yl)carbonyl)ethenyl)phenyl] sulfide Prepared according to the procedures of Example 71, giving a yellow solid. $^1$H NMR (DMSO-d$_6$, 300 MHz) δ 1.14 (d, J=7.0 Hz, 6H); 2.25, 2.26 (s, s, 3H); 2.20–3.98 (br m, 8H); 3.57, 3.63 (s, s, 3H); 6.63 (d, J=8.5 Hz, 1H); 7.30–7.63 (m, 6H); 7.91 (dd, J=8.5, 1.5 Hz, 1H); 8.60–8.68 (br m, 1H). MS (APCI) (M–H)$^+$ at m/z 484.

Example 155

(2-Ethoxyphenyl)-[2-chloro-4-(E-[(3-carboxypiperidin-1-yl)carbonyl]ethenyl)phenyl] sulfide The compound of Example 137 was hydrolyzed using an excess of aqueous 10% NaOH in methanol, stirring overnight. The reaction mixture was concentrated in vacuo, water was added, and the solution was extracted with ether. The mixture was acidified; the resultant solid was collected by filtration and dried overnight in a vacuum oven, giving a white solid, m.p. 166–171C. $^1$H-NMR (DMSO 300 MHz) δ 1.17 (t, J=7 Hz, 3H), broad peaks totaling 9 protons at 1.32–1.48, 1.51–1.78, 1.90–2.04, 2.25–2.50, 2.80–2.90, 2.95–3.17, 3.45–3.51, 3.95–4.19, 4.41–4.51, 4.06 (q, J=7 Hz, 1H), 6.80 (d, J=9 Hz, 1H), 7.01 (t, J=7 Hz, 1H), 7.15 (d, J=8 Hz, 1H), 7.26–7.40 (m, 2H), 7.40–7.48 (m, 1H), 7.51 (dd, J=9 Hz, 2 Hz, 1H), 7.99 (d, J=9 Hz, 1H). Anal. Calcd. for $C_{23}H_{24}ClNO_4S$: C, 61.94; H, 5.42; N, 3.14. Found: C, 61.75; H, 5.65; N, 3.15. The resultant acid (303 mg, 0.631 mmol) was dissolved in 3 mL MeOH. A KOH solution (38 mg, 0.595 mmol, of 87.6% KOH) in 1 ml MeOH was added. The resulting solution was concentrated in vacuo, and 5 mL ether was added. The mixture was stirred for one hour to form a powder, which was filtered and dried in the vacuum oven at 60C to yield 307 mg of a solid, water soluble product.

Example 156

(2-Ethoxyphenyl)-[2-chloro-4-(E-[(2-ethoxycarbonylpiperidin-1-yl)carbonyl]ethenyl) phenyl]sulfide The title compound was prepared according to the procedures of Example 97. $^1$H NMR (CDCl$_3$, 300 MHz) δ 1.24 (t, J=7Hz, 3H), 1.28 (t, J=7Hz, 3H), broad peaks totaling 9 protons at 1.35–1.55, 1.65–1.80, 2.25–2.38, 3.33–3.45, 3.95–4.05, 4.15–4.28, 4.60–4.80, 5.44–5.50, 4.05 (q, J=7Hz, 2H), 4.20 (q, J=7Hz, 2H), 6.80–6.98 (m, 4H), 7.12–7.20 (m, 1H)7.35–7.43 (m, 2H), 7.50–7.58 (m, 2H). Anal. Calcd. for $C_{25}H_{28}ClNO_4S$: C, 63.35; H, 5.95; N, 2.95. Found: C,63.51; H, 6.22; N, 2.61.

Example 157

(2-Ethoxyphenyl)[2-trifluoromethyl-4-(E-((1-(tert-butoxycarbonyl)-4-hydroxypyrrolidin-3-ylamino) carbonyl)ethenyl)phenyl]sulfide The title compound was prepared according to the procedures of Example 1. $^1$H NMR (CDCl$_3$, 300 MHz) δ 7.76 (s, 1H), 7.60 (d, 1H, J=15.1 Hz), 7.46 (dd, 1H, J=1.7, 7.5 Hz), 7.38 (m, 2H), 7.01 (d, 1H, J=15.4 Hz), 6.98 (d, 1H, J=7.8 Hz), 6.93 (d, 1H, J=8.3 Hz), 6.42 (d, 1H, J=15.0 Hz), 4.30 (br, 2H), 3.98 (q, 2H, J=7.0 Hz 3.87 (m, 1H), 3.71 (m, 1H), 3.33 (br, 2H), 1.47 (s, 9H), 1.17 (t, 3H, J=7.0 Hz). MS (ESI) m/z –551, –1103. Anal. Calcd for $C_{27}H_{31}F_3N_2O_5S \cdot 0.61$ EtOAc: C, 58.32; H, 5.96; N, 4.62. Found: C, 58.07; H, 5.88; N, 4.76.

Example 158

(2-Ethoxyphenyl)-[2-chloro-4-(E-[(2-carboxypiperidin-1-yl)carbonyl]ethenyl)phenyl] sulfide The compound of Example 156 was hydrolyzed, and the salt formed, according to the procedures of Example 155. m.p. 170–171 C. $^1$H-NMR (DMSO 300 MHz) δ 1.16 (t, J=7Hz, 3H), broad peaks totaling 9 protons at 1.20–1.49, 1.51–1.75, 2.10–2.27, 2.55–2.65, 3.10–3.21, 4.204.29, 4.35–4.45, 5.13–5.25, 4.05 (q, J=7 Hz, 2H), 6.80 (d, J=9Hz, 1H), 6.97–7.07 (m, 1H), 7.15 (d, J=9 Hz, 1H), 7.29–7.57 (m, 5H), 8.02 (s, 1H). Anal. Calcd. for $C_{23}H_{24}ClNO_4S$: C, 61.94; H, 5.42; N, 3.14. Found: C, 61.91; H, 5.48; N, 2.90.

Example 159

(2-Ethoxyphenyl)[2-trifluoromethyl-4-(E-(((pyrrolidin-3-ene-1-yl)carbonyl)ethenyl)phenyl] sulfide The title compound was prepared according to the procedures of Example 1. $^1$H NMR (CDCl$_3$, 300 MHz) δ 7.81 (s, 1H), 7.68 (d, 1H, J=15.4 Hz), 7.35–7.47 (m, 3H), 7.04 (d, 1H, J=8.4 Hz), 6.97 (dd, 1H, J=1.3, 7.5 Hz), 6.91 (d, 1H, J=8.5 Hz), 6.70 (d, 1H, J=15.4 Hz), 5.94 (m, 1H), 5.85 (m, 1H), 4.47 (br, 2H), 4.38 (br, 2H), 3.98 (q, 2H, J 7.0 Hz), 1.19 (t, 3H, J=7.0 Hz). MS (ESI) m/z 420, 839, 861.

Example 160

(2-Ethoxyphenyl)[2-trifluoromethyl-4-(E-((3-(2-oxopyrrolidin-1-yl)prop-1-ylamino)carbonyl)ethenyl)phenyl]sulfide The title compound was prepared according to the procedures of Example 1. $^1$H NMR (CDCl$_3$, 300 MHz) δ 7.78 (s, 1H), 7.54 (d, 1H, J=15.8 Hz), 7.42 (dd, 1H, J=1.7, 7.5 Hz), 7.34–7.39 (m, 2H), 7.13 (br, 1H), 7.03 (d, 1H, J=8.5), 6.97 (dd, 1H, J=1.1, 7.7 Hz), 6.91 (d, 1H, J=8.1 Hz), 6.46 (d, 1H, J=15.8 Hz), 3.98 (q, 2H, J=7.0 Hz), 3.43 (m, 4H), 3.34 (q, 2H, J=6.0 Hz), 2.45 (t, 2H, J=8.1 Hz), 2.08 (m, 2H), 1.75 (m, 2H), 1.18 (t, 3H, J=7.0 Hz). MS (ESI) m/z 493, 515, 985, 1007.

Example 161

(2-Ethoxyphenyl)[2-trifluoromethyl-4-(E-((4-acetylpiperazin-1-yl)carbonyl)ethenyl)phenyl]sulfide The title compound was prepared according to the procedures of Example 1. $^1$H NMR (CDCl$_3$, 300 MHz) δ 7.79 (s, 1H), 7.62 (d, 1H, J=15.6 Hz), 7.44 (dd, 1H, J=1.7, 7.5 Hz), 7.38 (m, 2H), 7.04 (d, 1H, J=8.1), 6.97 (dd, 1H, J=1.4, 7.5 Hz), 6.92 d, 1H, J=8.1 Hz), 6.84 (d, 1H, J=15.6 Hz), 3.98 (q, 2H, J=7.0 Hz), 3.63–78 (m, 6H), 3.53 (m, 2H), 2.14 (s, 3H), 1.19 (t, 3H, J=7.0 Hz). MS (ESI) m/z 479, 501, 957, 979.

Example 162

(2-Ethoxyphenyl)[2-trifluoromethyl-4-(E-((4-(ethoxycarbonyl)piperazin-1-yl)carbonyl)ethenyl)phenyl]sulfide The title compound was prepared according to the procedures of Example 71. $^1$H NMR (CDCl$_3$, 300 MHz) δ 7.79 (d, 1H, J=1.7 Hz), 7.63 (d, 1H, J=15.3 Hz), 7.43 (dd, 1H, J=1.7, 7.7 Hz), 7.38 (m, 2H), 7.04 (d, 1H, J=8.5), 6.97 (dd, 1H, J=1.4, 7.5 Hz), 6.92 (d, 1H, J=8.1 Hz), 6.84 (d, 1H, J=15.3 Hz), 4.18 (q, 2H, J=7.1 Hz), 3.98 (q, 2H, J=6.9 Hz), 3.68 (m, 4H), 3.53 (m, 4H), 1.29 (t, 3H, J=7.1 Hz) 1.19 (t, 3H, J=6.9 Hz). MS (ESI) m/z 509, 531, 1017, 1039.

Example 163

(2-Ethoxyphenyl)[2-trifluoromethyl-4-(E-((4-(2-furlcarbonyl)piperazin-1-yl)carbonyl)ethenyl)phenyl]sulfide The title compound was prepared according to the procedures of Example 71. $^1$H NMR (CDCl$_3$, 300 MHz) δ 7.80 (d, 1H, J=1.5 Hz), 7.66 (d, 1H, J=15.4 Hz), 7.52 (s, 1H), 7.45 (dd, 1H, J=1.6, 7.5 Hz), 7.40 (m, 2H), 7.08 (d, 1H, J=4.0 Hz), 7.04 (d, 1H, J=8.1), 6.98 (dd, 1H, J=1.1, 7.3 Hz), 6.93 (d, 1H, J=8.5 Hz), 6.88 (d, 1H, J=15.4 Hz), 6.52 (dd, 1H, J=1.6, 3.5 Hz), 3.98 (q, 2H, J=7.0 Hz), 3.73–3.90 (m,8H), 1.19 (t, 3H, J=7.0 Hz). MS (ESI) m/z 531, 553, 1061, 1083.

Example 164

(2-Ethoxyphenyl)-[2-chloro-4-(E-[(3-ethoxycarbonylpiperidin-1-yl)carbonyl]ethenyl)phenyl]sulfide The title compound was prepared according to the procedures of Example 97. $^1$H-NMR (CDCl$_3$) δ 1.25 (t, J=7 Hz, 6H), broad peaks totaling 9 protons at 1.65–1.80, 1.95–2.04, 2.51–2.63, 2.90–3.00, 3.15–3.30, 2.95–4.05, 4.42–4.55, 4.14 (q, J=7 Hz, 2H), 4.15 (q, J=7 Hz, 2H), 6.82 (d, J=15 Hz, 1H), 6.84 (d, J=9 Hz, 1H), 6.93–6.99 (m, 2H), 7.17 (dd, J=9 Hz, 2 Hz, 1H), 7.34–7.41 (m, 2H), 7.52 (d, J=15 Hz, 1H), 7.55 (d, J=2 Hz, 1H). Anal. Calcd. for C$_{25}$H$_{28}$ClNO$_4$S: C, 63.35; H, 5.95; N, 2.95. Found: C, 63.09; H, 6.24; N, 2.77.

Example 165

(2-Ethoxyphenyl)-[2-chloro-4-(E-[(4-carboxypiperidin-1-yl)carbonyl]ethenyl)phenyl] sulfide The compound of Example 164 was hydrolyzed, and the salt formed, according to the procedures of Example 155. m.p. 165–166° C. $^1$H-NMR (DMSO 300 MHz) δ 1.25 (t, J=7 Hz, 3H0, 1.35–1.58 (m, 2H), 1.80–1.95 (m, 2H), 2.50–2.60 (m, 1H), 1.78–1.91 (m, 1H), 3.13–3.24 (m, 1H), 4.05 (q, J=7 Hz, 2H), 4.12–4.35 (m, 2H), 6.80 (d, J=9 Hz, 1H), 6.96–7.05 (t, J=8 Hz, 1H), 7.15 (d, J=9 Hz, 1H), 7.28–7.4 (m, 4H), 7.51 (dd, J=9 Hz, 2 Hz, 1H), 8.00 (d, J=2 Hz).

Example 166

(Benzodioxan-6-yl)[2-chloro-4-(E-((4-acetylpiperazin-1-yl)carbonyl)ethenyl)phenyl]sulfide The title compound was prepared by the procedures described in Example 85, substituting 5-iodoindole with 6-iodobenzenedioxane, giving a white solid. $^1$H NMR (CDCl$_3$, 300 MHz) δ 2.14 (s, 3H), 3.44–3.57 (m, 2H), 3.57–3.86 (m, 6H), 4.25–4.35 (m, 4H), 6.75 (d, J=8.4 Hz, 1H), 6.78 (d, J=15.6 Hz, 1H), 6.93 (d, J=8.4 Hz, 1H), 7.03 (dd, J=2.1, 8.4 Hz, 1H), 7.08 (d, J=2.1 Hz, 1H), 7.18 (dd, J=2.1, 8.4 Hz, 1H), 7.51 (d, J=2.1 Hz, 1H), 7.57 (d, J=15.6 Hz, 1H). MS (APCI$^+$) (M+H)$^+$ at m/z 459, 461.

Example 167

(2-Isopropylphenyl)[2-nitro-4-(E-((4-ethoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 1.19 (t, J=7.0 Hz, 3H); 3.30–3.40 (m, 1H); 3.30–3.73 (br m, 8H); 4.06 (q, J=7.0 Hz, 2H); 6.64 (d, J=8.5 Hz, 1H); 7.32–7.63 (m, 6H); 7.90 (dd, J=8.8, 1.8 Hz, 1H); 8.65 (d, J=1.8 Hz, 1H). MS APCI) (M+H)$^+$ at m/z 484. Anal calcd for C$_{25}$H$_{29}$N$_3$S$_1$O$_5$: C, 62.09; H, 6.04; N, 8.69. Found: C, 61.89; H, 6.13; N, 8.51.

Example 168

(2-lsopropylphenyl)[2-nitro-4-(E-((4-isopropoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ

1.14 (d, J=6.8 Hz, 6H); 1.20 (d, J=6.4 Hz, 3H); 3.30–3.40 (m, 1H); 3.32–3.73 (br m, 8H); 4.79 (hept, J=6.1 Hz, 2H); 6.64 (d, J=8.5 Hz, 1H); 7.32–7.63 (m, 6H); 7.89 (dd, J=8.5, 1.7 Hz, 1H); 8.64 (d, J=1.7 Hz, 1H). MS (APCI) (M+H)$^+$ at m/z 498. Anal calcd for $C_{26}H_{31}N_3S_1O_5$: C, 62.76; H, 6.28; N, 8.44. Found: C, 62.57; H, 6.43; N, 8.33.

Example 169

(2-Isopropylphenyl)[2-nitro-4-(E-((4-isobutoxycarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 0.90 (d, J=6.6 Hz, 6H); 1.14 (d, J=7.0 Hz, 6H); 1.88 (hept, J=6.6 Hz, 1H); 3.30–3.40 (m, 1H); 3.30–3.73 (br m, 8H); 3.81 (d, J=6.3 Hz, 2H); 6.64 (d, J=8.5 Hz, 1H); 7.32–7.63 (m, 6H); 7.90 (dd, J=8.5, 1.5 Hz, 1H); 8.65 (d, J=1.5 Hz, 1H). MS (APCI) (M+H)$^+$ at m/z 512. Anal calcd for $C_{27}H_{33}N_3S_1O_5$: C, 63.38; H, 6.50; N, 8.21. Found: C, 63.15; H, 6.55; N, 8.13.

Example 170

(2-Isopropylphenyl)[2-nitro-4-(E-((4-((1-propen-2-oxy)carbonyl)piperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.88 (s, 3H); 3.30–3.40 (m, 1H); 3.30–3.78 (br m, 8H); 4.65 (s, 1H); 4.69 (m, 1H); 6.64 (d, J=8.5 Hz, 1H); 7.32–7.63 (m, 6H); 7.90 (dd, J=8.5, 1.5 Hz, 1H); 8.65 (d, J=1.5 Hz, 1H). MS (APCI) (M+NH$_4$)$^+$ at m/z 513. Anal calcd for $C_{26}H_{29}N_3S_1O_5$: C, 63.01; H, 5.90; N, 8.48. Found: C, 62.98; H, 6.06; N, 8.27.

Example 171

(2-Isopropylphenyl)[2-nitro-4-(E-((4-propionylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.00 (t, J=7.3 Hz, 3H); 1.14 (d, J=7.0 Hz, 6H); 2.35 (q, J=7.5 Hz, 2H); 3.30–3.40 (m, 1H); 3.41–3.76 (br m, 8H); 6.64 (d, J=8.5 Hz, 1H); 7.32–7.63 (m, 6H); 7.90 (dd, J=8.5, 1.5 Hz, 1H); 8.64 (d, J=1.5 Hz, 1H). MS (APCI) (M+NH$_4$)$^+$ at m/z 485. Anal calcd for $C_{25}H_{29}N_3S_1O_4$: C, 64.22; H, 6.25; N, 8.99. Found: C, 64.04; H, 6.44; N, 8.80.

Example 172

(2-Isopropylphenyl)[2-nitro-4-(E-((4-carboxamidopiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 3.30–3.40 (m, 1H); 3.30–3.73 (br m, 8H); 6.10 (s, 2H); 6.64 (d, J=8.5 Hz, 1H); 7.32–7.63 (m, 6H); 7.91 (dd, J=8.5, 1.8 Hz, 1H); 8.65 (d, J=1.8 Hz, 1H). MS (APCI) (M+NH$_2$)$^+$ at m/z 470. Anal calcd for $C_{23}H_{26}N_4S_1O_4 \cdot 0.26 CH_3COOCH_2CH_3$: C, 60.48; H, 5.93; N, 11.73. Found: C, 60.10; H, 5.84; N, 11.90.

Example 173

(2-Isopropylphenyl)[2-nitro-4-(E-((4-methylaminocarbonylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 2.58 (d, J=4.4 Hz, 3H); 3.30–3.40 (m, 1H); 3.28–3.70 (br m, 8H); 6.52 (q, J=4.4 Hz, 1H); 6.64 (d, J=8.5 Hz, 1H); 7.32–7.62 (m, 6H); 7.90 (dd, J=8.5, 1.8 Hz, 1H); 8.64 (d, J=1.8 Hz, 1H). MS (APCI) (M+NH$_4$)$^+$ at m/z 486. Anal calcd for $C_{24}H_{28}N_4S_1O_4 \cdot 0.36 CH_3COOCH_2CH_3$: C, 61.07; H, 6.22; N, 11.19. Found: C, 61.14; H, 6.41; N, 11.19.

Example 174

(2-Isopropylphenyl)[2-nitro-4-(E-((4-(pyrimidin-2-yl)piperazin-1-yl)carbonyl)ethenyl)phenyl]sulfide Prepared according to the procedures of Example 71, giving a yellow solid. $^1$H NMR (DMSO-d$_6$, 300 MHz) δ 1.15 (d, J=6.6 Hz, 6H); 3.30–3.40 (m, 1H); 3.28–3.85 (br m, 8H); 6.64 (d, J=8.5 Hz, 1H); 6.68 (d, J=4.8 Hz, 1H); 7.33–7.63 (m, 6H); 7.92 (dd, J=8.5, 1.8 Hz, 1H); 8.40 (d, J=4.8 Hz, 2H); 8.67 (d, J=1.8 Hz, 1H). MS (APCI) (M+H)$^+$ at m/z 490. Anal calcd for $C_{26}H_{27}N_5S_1O_3$: C, 63.78; H, 5.56; N, 14.30. Found: C, 63.83; H, 5.54; N, 14.11.

Example 175

(2-Isopropylphenyl)[2-nitro-4-(E-((4-hydroxyacetylpiperazin-1-yl)carbonyl)ethenyl)phenyl]sulfide Prepared according to the procedures of Example 71, giving a yellow solid. $^1$H NMR (DMSO-d$_6$, 300 MHz) δ 1.15 (d, J=6.8 Hz, 6H); 3.30–3.40 (m, 1H); 3.28–3.78 br m, 8H); 4.12 (d, J=5.8 Hz, 2H); 4.61–4.69 (br m, 1H); 6.64 (d, J=8.5 Hz, 1H); 7.33–7.63 (m, 6H); 7.90 (dd, J=8.5, 1.8 Hz, 1H); 8.65 (d, J=1.8 Hz, 1H). MS (APCI) (M+H)$^+$ at m/z 470. Anal calcd for $C_{24}H_{27}N_3S_1O_5 \cdot 0.38 CH_3COOCH_2CH_3$: C, 60.93; H, 6.02; N, 8.35. Found: C, 60.95; H, 6.06; N, 8.35.

Example 176

(2-Isopropylphenyl)[2-nitro-4-(E-((4-pyrazine-2-carbonyl)piperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.6 Hz, 6H); 3.30–3.40 (m, 1H); 3.28–3.88 (br m, 8H); 6.61–6.66 (br m, 1H); 7.31–7.63 (m, 6H); 7.85–7.96 (br m, 1H); 8.61–8.92 (m, 4H). MS (APCI) (M+H)$^+$ at m/z 518. Anal calcd for $C_{27}H_{27}N_5S_1O_4 \cdot 0.24 CH_3COOCH_2CH_3$: C, 62.34; H, 5.41; N, 13.01. Found: C, 62.23; H, 5.50; N, 13.10.

Example 177

(2-Isopropylphenyl)[2-trifluoromethyl-4-(E-(((2-carboxypyrrol-3-ene-1-yl)carbonyl)ethenyl)phenyl] sulfide methyl ester The title compound was prepared according to the procedures of Example 71. $^1$H NMR (CDCl$_3$, 300 MHz) δ 7.79 (s, 1H), 7.68 (d, 1H, J=15.4 Hz), 7.48 (d, 1H, J=7.4 Hz), 7.45 (m, 2H), 7.38 (d, 1H, J=8.3 Hz), 7.23 (m, 1H), 6.80 (d, 1H, J=8.5 Hz), 6.70 (d, 1H, J=15.4 Hz), 6.04 (m, 1H), 5.88 (m, 1H), 5.31 (m, 1H), 4.60 (m, 1H), 4.50 (m, 1H), 3.76 (s, 3H), 3.50 (m, 1H), 1.22 (d, 6H, J=7.0 Hz). MS (ESI) m/z 476, 498, 951, 973. Anal. Calcd for $C_{25}H_{24}F_3NO_3S \cdot 0.38$ EtOAc: C, 62.58; H, 5.35; N, 2.75. Found: C, 62.53; H, 5.27; N, 2.76.

Example 178

(2-Isopropylphenyl)[2-nitro-4-(E-((3-hydroxymethyl-4-methylpiperazin-1-yl)carbonyl)ethenyl)phenyl]sulfide Prepared according to the procedures of Example 71, giving a yellow solid. $^1$H NMR (DMSO-d$_6$, 300 MHz) δ

1.14 (d, J=6.8 Hz, 6H); 2.22 (s, 3H); 1.82–4.63 (br m, 9H); 3.30–3.40 (m, 1H); 6.62–6.66 (br m, 1H); 7.25–7.63 (m, 6H); 7.86–7.92 (br m, 1H); 8.57–8.65 (br m, 1H). MS (APCI) (M+H)$^+$ at m/z 456.

Example 179

(2-Isopropylphenyl)[2-trifluoromethyl-4-(E-(((2-carboxypyrrol-3-ene-1-yl)carbonyl)ethenyl)phenyl]sulfide The title compound was prepared according to the procedures of Example 1. $^1$H NMR (CDCl$_3$, 300 MHz) δ 7.79 (s, 1H), 7.72 (d, 1H, J=15.5 Hz), 7.49 (d, 1H, J=7.4 Hz), 7.36–7.46 (m, 3H), 7.23 (m, 1H), 6.82 (d, 1H, J=8.5 Hz), 6.74 (d, 1H, J=15.4 Hz), 6.00 (br, 2H), 4.48 (br, 1H), 4.51 (br, 2H), 3.48 (m, 1H), 1.18 (d, 6H, J=7.0 Hz). MS (ESI) m/z –460, –492, –921.

Example 180

(2-Isopropylphenyl)[2-trifluoromethyl-4-(E-(((2-hydroxymethylpyrrolidin-1-yl)carbonyl)ethenyl)phenyl]sulfide The title compound was prepared according to the procedures of Example 1. $^1$H NMR (CDCl$_3$, 300 MHz) δ 7.79 (s, 1H), 7.68 (d, 1H, J=15.4 Hz), 7.48 (d, 1H, J=7.4 Hz), 7.45 (m, 2H), 7.38 (d, 1H, J=8.3 Hz), 7.23 (m, 1H), 6.80 (d, 1H, J=8.5 Hz), 6.70 (d, 1H, J=15.4 Hz), 5.82 (m, 1H), 5.70 (m, 1H), 4.92 (m, 1H), 4.18 (br s, 2H), 3.76 (s, 3H), 3.78 (d, 1H, J=11.5 Hz), 3.50 (m, 2H), 3.01 (t, 2H, J=7.5 Hz), 2.58 (t, 2H, J=7.6 Hz), 1.19 (d, 6H, J=7.1 Hz). MS (ESI) m/z 450, 472, 921.

Example 181

(2-Isopropylphenyl)[2-nitro-4-(E-((3-methylaminocarbonyl)piperazin-1-yl)carbonyl)ethenyl)phenyl]sulfide Prepared according to the procedures of Example 71, giving a yellow solid. $^1$NMR (DMSO-d$_6$, 300 MHz) δ 1.14 (d, J=7.0 Hz, 6H); 2.60 (d, J=4.4 Hz, 3H); 2.504.45 (br m, 7H); 3.30–3.40 (m, 1H); 6.62–6.66 (br m, 1H); 7.32–7.62 (m, 6H); 7.81–7.92 (m, 2H); 8.59–8.65 (br m, 1H). MS (APCI) (M+H)$^+$ at m/z 469.

Example 182

(2-Isopropylphenyl)[2-nitro-4-(E-(((3-cyclopropylaminocarbonyl)piperazin-1-yl)carbonyl)ethenyl)phenyl]sulfide Prepared according to the procedures of Example 71, giving a yellow solid. $^1$H NMR (DMSO-d$_6$, 300 MHz) δ 0.40–0.62 (br m, 4H); 1.14 (d, J=6.8 Hz, 6H); 2.50–4.41 (br m, 8H); 3.30–3.40 (m, 1H); 6.62–6.67 (br m, 1H); 7.32–7.62 (m, 6H); 7.87–7.92 (m, 2H); 8.59–8.64 (br m, 1H). MS (APCI) (M+H)$^+$ at m/z 495.

Example 183

(2-Isopropylphenyl)[2-nitro-4-(E-((3-carboxamidopiperazin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 2.50–4.42 (br m, 7H); 3.30–3.40 (m, 1H); 6.62–6.67 (br m, 1H); 7.12–7.62 (m, 8H); 7.87–7.92 (m, 1H); 8.60–8.65 br m, 1H). MS (APCI) (M+H)$^+$ at m/z 455.

Example 184

(2-Isopropylphenyl)[2-nitro-4-(E-((3-carbomethoxy-4-oxopiperidin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 2.32–2.55 (br m, 2H); 3.30–3.40 (m, 1H); 3.64,3.76 (s, s, 3H); 3.68–4.58 (br m, 5H); 6.64 (d, J=8.5 Hz, 1H); 7.32–7.63 (m, 6H); 7.88–7.96 (m, 1H); 8.60–8.68 (m, 1H). MS (APCI) (M+H)$^+$ at m/z 483. Anal calcd for C$_{25}$H$_{26}$N$_2$S$_1$O$_6$·0.17C$_6$H$_{14}$: C, 62.86; H, 5.75; N, 5.63. Found: C, 62.81; H, 5.83; N, 5.60.

Example 185

(2-Isopropylphenyl)[2-nitro-4-(E-((3,5-dimethylpiperazin-1-yl)carbonyl)ethenyl)phenyl]sulfide Prepared according to the procedures of Example 71, giving a yellow solid. $^1$H NMR (DMSO-d$_6$, 300 MHz) δ 0.96–1.06 (m, 6H); 1.14 (d, J=6.8 Hz, 6H); 2.07–4.39 (br m, 7H); 6.63 (d, J=8.5 Hz, 1H); 7.30–7.63 (m, 6H); 7.92 (dd, J=8.5, 1.7 Hz, 1H); 8.60 (d, J=1.7 Hz, 1H). MS (APCI) (M+H)$^+$ at m/z 440. Anal calcd for C$_{26}$H$_{29}$N$_3$S$_1$O$_3$: C, 65.58; H, 6.65; N, 9.56. Found: C, 65.36; H, 6.87; N, 9.27.

Example 186

(1-Ethylindol-7-yl)[2-chloro-4-(E-((4-acetylpiperazin-1-yl)carbonyl)ethenyl)phenyl]sulfide The title compound was prepared by the procedures described in Example 85, substituting 5-iodoindole with N-ethyl-7-bromoindole. white solid; $^1$H NMR (CDCl$_3$, 300 MHz) δ 1.30 (t, J=7.05 Hz, 3H), 2.14 (s, 3H), 3.52 (br s, 2H), 3.58–3.84 (m, 6H), 4.42 (q, J=7.05 Hz, 2H), 6.42 (d, J=8.4 Hz, 1H), 6.59 (d, J=3.0 Hz, 1H), 6.76 (d, J=15.6 Hz, 1H), 7.08 (d, J=8.4 Hz, 1H), 7.10 (d, J=3.0 Hz, 1H), 7.16 (t, J=7.65 Hz, 1H), 7.42 (dd, J=0.9, 7.5 Hz, 1H),7.53 (d, J=1.8 Hz, 1H), 7.54 (d, J=15.6 Hz, 1H), 7.78 (dd, J=0.9, 7.5 Hz, 1H). MS (APCI$^+$) (M+H)$^+$ at m/z 468, 470.

Example 187

(3-[2-Methoxy]ethoxyphenyl)-[2-chloro-4-(E-[(morpholin-1-yl)carbonyl]ethenyl)phenyl]sulfide The title compound was prepared according to the procedures of Example 85. $^1$H-NMR (CDCl$_3$ 300 MHz) δ 3.45 (s, 3H), 3.65–3.80 (m, 10H), 4.09–4.13 (m, 2H), 6.82 (broad d, J=15, 1H), 6.88 (d, J=9 Hz, 1H), 6.87 (dd, J=9 Hz, 2 Hz, 1H), 7.03–7.10 (m, 2H), 7.20 (d, J=9 Hz, 1H), 7.31 (t, J=8 Hz, 1H), 7.52 (s, 1H), 7.56 (broad d, J=15, 1H).

Example 188

(2-Bromophenyl)[2-chloro-4-(E-((4,4'-S-dioxythiomorpholin-1-yl)carbonyl)ethenyl)phenyl]sulfide 4-Methylmorpholine N-oxide (0.0935 g, 0.798 mmol) and 4 Å molecular sieves (0.0333 g) were added to a solution of (2-Bromophenyl)[2-chloro-4-(E-((thiomorpholin-1-yl)carbonyl)ethenyl)phenyl]sulfide (0.1230 g, 0.27 mmol; prepared according to the procedures described in Example 1). After 15 minutes, tetrapropylammonium perruthenate (0.0058 g, 0.0166 mmol) was added and after 4 hours had elapsed the starting material was consumed by TLC and the crude products were passed through a plug of silica with 5:2 hexane:ethyl acetate→9:1 $CH_2Cl_2$: MeOH. The mixture was then purified by preparative HPLC to provide the title compound (0.0138 g, 10%). $^1$H-NMR (DMSO-$d_6$, 300 MHz) δ 8.12 (d, J=1.47 Hz, 1H), 7.81 (dd, J=7.9, 1.3, 2H), 7.65 (dd, J=8.0, 1.5 Hz, 1H), 7.47 (d, J=9.0 Hz, 1H), 7.27–7.53 (m, 4H), 7.03 (d, J=9.0 Hz, 1H), 4.12 (br s, 2H), 3.98 (br s, 2H), 3.26 (br s, 2H), 3.19 (br s, 2H), 1.54–2.29 (m, 6H), MS(APCI) (M+H)$^+$ at m/z 486, 488, 490.

Example 189

(2-Bromophenyl)[2-chloro-4-(E-(N-carbomethoxymethyl-N-(3-(2-oxopyrrolidin-1-yl)prop-1-yl)amino)carbonyl)ethenyl)phenyl]sulfide

Example 189A

N-Carbomethoxymethyl-N-(3-(2-oxopyrrolidin-1-yl)prop-1-yl)amine

Methyl bromoacetate (1.35 mL, 14.3 mmol) was added dropwise to a solution of 3-aminopropyl-2-pyrrolidinone (2.0 mL, 14.3 mmol) and diisopropylethylamine (2.7 mL) in $CH_2Cl_2$. The reaction was stirred for 12 hours and was then concentrated in vacuo, and carried forward without further purification.

Example 189B (2-Bromophenyl)[2-chloro-4-(E-(N-carbomethoxymethyl-N-(3-(2-oxopyrrolidin-1-yl)prop-1-yl)amino)carbonyl)ethenyl)phenyl]sulfide The title compound was prepared by the procedures described for Example 113, substituting 2,4 dichlorothiophenol with 2-bromothiophenol, 2-chlorobenzaldehyde with 3,4 dichlorobenzaldehyde, and 1-(3-aminopropyl)-5-((S)-hydroxymethyl)-2-pyrrolidinone with the compound from Example 189A. $^1$H-NMR (DMSO-d6, 300 MHz) δ 8.07 (dd, J=9.4, 1.7 Hz, 1H), 7.81 (m, 1H), 7.64 (m, 1H), 7.24–7.49 (m, 5H), 7.05 (m, 1H), 4.53 (s, 1H), 4.14 (s, 1H), 3.68 (s, 1H), 3.64 (s, 2H), 3.54 (m, 2H), 3.13–3.43 (m, 4H), 2.39 (m, 2H), 1.91 (m, 2H), 1.72 (m, 2H), MS(APCI) (M+H)$^+$ at m/z 565, 567, 569.

Example 190

(2-Bromophenyl)[2-chloro-4-(E-((4-S-oxythiomorpholin-1-yl)carbonyl)ethenyl)phenyl]sulfide The title compound (0.0178 g, 14%) was isolated from the same reaction mixture as described in Example 188. $^1$H-NMR (DMSO-d6, 300 MHz) δ 8.12 (d, J=1.8 Hz, 1H), 7.81 (dd, J=7.9, 1.3 Hz, 1H), 7.65 (dd, J=8.3, 1.7 Hz, 1H), 7.46 (d, J=7.4 Hz, 1H), 7.26–7.48 (m, 4H), 7.04 (d, J=7.4 Hz, 1H), 4.29 (br m, 2H), 3.97 (br m, 1H), 3.61 (br m, 1H), 2.80 (br m, 4H), MS(APCI) (M+H)$^+$ at m/z 470, 472, 474.

Example 191

(2-Methoxy-5-chlorophenyl)[2-nitro-4-(E-((4-acetylpiperazin-1-yl)carbonyl)ethenyl)phenyl]sulfide The title compound was prepared according to the procedures of Example 1. $^1$H NMR (CDCl$_3$, 300 MHz) δ 8.44 (s, 1H), 7.66 (d, 1H, J=15.1 Hz), 7.58 (d, 1H, J=2.6 Hz), 7.48 (dd, 1H, J=2.6, 8.8 Hz), 7.44 (m, 1H), 6.97 (d, 1H, J=8.8 Hz), 6.92 (d, 1H, J=15.5 Hz), 6.82 (d, 1H, J=8.5 Hz), 3.78 (s, 3H), 3.70 (m, 6H), 3.54 (m, 2H), 2.15 (s, 3H). MS (ESI) m/z 476, 498, 951, 973. Anal. Calcd for $C_{22}H_{22}ClN_3O_5S$. 0.48 EtOAc: C, 55.44; H, 5.03; N, 8.11. Found: C, 54.36; H, 4.90; N, 8.50.

Example 192

(2-Isopropylphenyl)[2-nitro-4-(E-((3-acetoxymethyl)piperazin-1-yl)carbonyl)ethenyl)phenyl]sulfide Prepared according to the procedures of Example 71, giving a yellow solid. $^1$H NMR (DMSO-$d_6$, 300 MHz) δ 1.14 (d, J=6.8 Hz, 6H); 2.04 (s, 3H); 3.30–3.40 (m, 1H); 2.50–4.46 (br m, 9H); 6.64 (d, J=8.8 Hz, 1H); 7.30–7.62 (m, 6H); 7.87–7.93 (m, 1H); 8.58–8.63 (br m, 1H). MS (APCI) (M+H)$^+$ at m/z 484. Anal calcd for $C_{25}H_{29}N_3S_1O_3.0.2H_2O$: C, 61.60; H, 6.09; N, 8.62. Found: C, 61.63; H, 6.21; N, 8.41.

Example 193

(2-Isopropylphenyl)[2-nitro-4-(E-((3,5-dimethyl-4-acetyl-piperazin-1-yl)carbonyl)ethenyl)phenyl]sulfide Prepared according to the procedures of Example 71, giving a yellow solid. $^1$H NMR (DMSO-$d_6$, 300 MHz) δ 1.00–1.20 (br m, 6H); 1.15 (d, J=6.8 Hz, 6H); 2.04 s, 3H); 2.76–4.58 (br m, 7H); 6.64 (d, J=8.5 Hz, 1H); 7.32–7.63 (m, 6H); 7.94 (dd, J=8.5, 1.8 Hz, 1H); 8.66 (d, J=1.8 Hz, 1H). MS (APCI) (M+H)$^+$ at m/z 482. Anal calcd for $C_{26}H_{31}N_3S_1O_4.0.3H_2O$: C, 64.13; H, 6.54; N, 8.63. Found: C, 64.15; H, 6.61; N, 8.50.

Example 194

(1-Methylindol-5-yl)[2-chloro-4-(E-((4-acetylpiperazin-1-yl)carbonyl)ethenyl)phenyl]sulfide The title compound was prepared by the procedures described in Example 85, substituting 5-iodoindole with N-methyl-5-bromoindole, giving a white solid. $^1$H NMR (d$^6$-DMSO, 300 MHz) δ 2.04 (s, 3H), 3.40–3.80 (m, 8H), 3.86 (s, 3H), 6.49 (d, J=8.4 Hz, 1H), 6.52 (d, J=3.0 Hz, 1H), 7.27 (d, J=15.6 Hz, 1H), 7.31 (dd, J=2.4, 8.4 Hz, 1H), 7.39 (d, J=15.6 Hz, 1H), 7.41 (dd, J=1.8, 8.4 Hz, 1H), 7.48 (d, J=3.0 Hz, 1H), 7.63 (d, J=8.4 Hz, 1H), 7.85 (d, J=1.8 Hz, 1H), 7.99 (br s, 1H). MS (APCI$^+$) (M+H)$^+$ at m/z 454, 456.

Example 195

(Benzodioxan-6-yl)[2-nitro-4-(E-((4-acetylpiperazin-1-yl)carbonyl)ethenyl)phenyl]sulfide

Example 195A

6-Mercaptobenzodioxane

The title compound was prepared by the procedures described in Example 97A, substituting 2-ethoxybenzene with 6-iodobenzenedioxane.

Example 195B (Benzodioxan-6-yl)[2-nitro-4-(E-((4-acetylpiperazin-1-yl)carbonyl)ethenyl)phenyl]sulfide The title compound was prepared by the procedures described in Example 32, substituting 2,4- dichlorobenzenethiol with 6-mercaptobenzenedioxane, to give a light-yellow solid; $^1$H NMR (d$^6$-DMSO, 300 MHz) δ 2.04 (s, 3H), 3.41–3.80 (m, 8H), 4.28–4.38 (m, 4H), 6.86 (d, J=8.4 Hz, 1H), 7.05 (d, J=8.4 Hz, 1H), 7.10 (dd, J=2.1, 8.4 Hz, 1H), 7.15 (d, J=2.1 Hz, 1H), 7.40 (d, J=15.6 Hz, 1H), 7.53 (d, J=15.6Hz, 1H), 7.91 (dd, J=1.8, 8.4 Hz, 1H), 8.62(d, J=1.8 Hz, 1H). MS (APCI$^+$) (M+H)$^+$ at m/z 470. Anal. Calcd for $C_{23}H_{23}N_3O_6S \cdot 0.17\ H_2O$: C, 58.46; H, 4.98; N, 8.89. Found: C, 58.47; H, 4.88; N. 8.78.

Example 196

(Benzodioxan-6-yl)[2-nitro-4-(E-((3-(2-oxopyrrolidin-1-yl)prop-1-ylamino)carbonyl)ethenyl)phenyl]sulfide The title compound was prepared by the procedures described in Example 32, substituting 2,4-dichlorobenzenethiol with 6-mercaptobenzenedioxane, and 1-acetylpiperazine with 3-aminopropyl-1-pyrrolidin-2-one, giving a light-yellow solid. $^1$H NMR (d$^6$-DMSO, 300 MHz) δ 1.64 (p, J=7.2 Hz, 2H), 1.92 (p, J=7.8 Hz, 2H), 2.21 (t, J=7.8 Hz, 2H), 3.13 (t, J=7.2 Hz, 2H), 3.19 (t, J=7.2 Hz, 2H), 3.38–3.46 (overlapping t, J=7.8 Hz, 2H), 4.27–4.37 (m, 4H), 6.70 (d, J=15.6 Hz, 1H), 6.90 (d, J=8.4 Hz, 1H), 7.05 (d, J=8.4 Hz, 1H), 7.09 (dd, J=2.1, 8.4 Hz, 1H), 7.16 (d, J=2.1 Hz, 1H), 7.46 (d, J=15.6 Hz, 1H), 7.77 (dd, J=2.1, 8.4 Hz, 1H), 8.16 (t, J=6.0 Hz, 1H), 8.41 (d, J=2.1 Hz, 1H). MS (APCI$^+$) (M+H)$^+$ at m/z 484. Anal. Calcd for $C_{24}H_{25}N_3O_6S \cdot 0.51\ CH_2Cl_2 \cdot 0.24\ MeOH$: C, 55.61; H, 5.09; N, 7.86. Found: C, 55.39; H, 5.48; N, 8.26.

Example 197

(Benzodioxan-6-yl)[2-nitro-4-(E-((3-carboethoxypiperidin-1-yl)carbonyl)ethenyl)phenyl]sulfide The title compound was prepared by the procedures described in Example 196 substituting N-(3'-aminopropyl)-2-pyrrolidinone with ethyl nipecotate, giving a yellow solid, mp 73–75° C. $^1$H NMR (CDCl$_3$, 300 MHz) δ 1.26 (t, J=7.0 Hz, 3H), 1.74 (br, 1H), 1.78 (br, 1H), 210 (br, 1H), 2.54 (br, 1H), 2.95–3.70 (br, 2H), 3.90–4.10 (br, 2H), 4.15 (q, J=7.0 Hz, 2H), 4.30–4.40 (m, 4H), 4.65 (br, 1H), 6.90 (d, J=8.5 Hz, 1H), 6.98 (d, J=8.5 Hz, 1H), 7.06 (dd, J=2.0, 8.0 Hz, 1H), 7.10 (d, J=2.0 Hz, 1H), 7.40–7.50 (m, 1H), 7.58 (d, J=15.0 Hz, 1H), 8.40 (d, J=2.0 Hz, 1H). MS (APCI) m/z 499 (M+H)$^+$. Anal. calcd. for $C_{25}H_{26}N_2O_7S$: C, 60.23; H, 5.26; N, 5.62. Found: C, 60.09; H, 5.43; N, 5.47.

Example 198

(Benzodioxan-4-yl)[2-nitro-4-(E-((4-carboethoxypiperidin-1-yl)carbonyl)ethenyl)phenyl]sulfide The title compound was prepared by the procedure described as in example 196 substituting N-(3'-aminopropyl)-2-pyrrolidinone with ethyl isonipecotate, giving a yellow solid, mp 78–88° C. $^1$H NMR (CDCl$_3$, 300 MHz) δ 1.27 (t, J=7.0 Hz, 3H), 1.65 (m, 2H), 2.00 (m, 2H), 2.60 (m, 1H), 2.80–3.50 (br, 2H), 4.15 (br, 1H), 4.16 (q, J=7.0, 2H), 4.34 (m, 4H), 4.54 (br, 1H), 6.90 (d, J=8.0 Hz, 1H), 6.98 (d, J=8.0 Hz, 1H), 7.05 (dd, J=2.0, 8.0 Hz, 1H), 7.10 (d, J=2.0 Hz, 1H), 7.12 (br, 1H), 7.44 (d, J=8.0 Hz, 1H), 7.60 (br, 1H), 8.40 (s, 1H). MS (CI/NH$_3$) m/z 499 (M+H)$^+$. Anal. calcd. for $C_{25}H_{26}N_2O_7S\ 0.03\ H_2O$: C, 60.16; H, 5.26; N. 5.61. Found: C, 60.15; H, 5.65; N, 5.40.

Example 199

(2-Ethoxyphenyl)[2-trifluoromethyl-4-(Z-((4-acetylpiperazin-1-yl)carbonyl)ethenyl)phenyl]sulfide Example 199A (2-Ethoxyphenyl)[2-trifluoromethyl-4-(Z-((4-carbomethoxyethenyl)phenyl]sulfide Bis-(2,2,2-trifluoroethyl)(methoxycarbonylmethyl)phosphonate (1.20 g, 3.77 mmol), and 18-crown-6 (3.56 g, 13.48 mmol) were dissolved in 22 mL of dry THF. The mixture was cooled to −78° C. and KN(SiMe$_3$)$_2$ (0.5 M in THF, 4.04 mmol) was added and stirred for 30 minutes. (2-Ethoxyphenyl)[2-trifluoromethyl-4-formyl phenyl]sulfide (1.10 g, 3.77 mmol, prepared according to the procedure of example 1) in 13 mL of THF was added via cannulation. After 1 hour at that temperature, the cooling bath was removed and the mixture allowed to warm to ambient temperature.

Example 199B (2-Ethoxyphenyl)[2-trifluoromethyl-4-(Z-((4-acetylpiperazin-1-yl)carbonyl)ethenyl)phenyl]sulfide The compound of Example 199A was converted to the corresponding amide according to the procedures of Example 1. $^1$H NMR (CDCl$_3$, 300 MHz) δ 7.64 (d, 1H, J=16.9 Hz), 7.32–7.4 (m, 2H), 6.98 (m, 2H), 6.93 (m, 2H), 6.65 (d, 1H, J=12.1 Hz), 6.08 (d, 1H, J=12.2 Hz), 3.98 (q, 2H, J=7.0 Hz), 3.68 (m, 2H), 3.62 (m, 2H), 3.44–3.54 (m, 4H), 2.11 and 2.05 (s, 3H), 1.20 (t, 3H, J=7.0 Hz). MS (ESI)s m/z 479, 501.

Example 200

(2-Ethoxyphenyl)[2-trifluoromethyl-4-(E-((6-methylpyrid-2-ylamino)carbonyl)ethenyl)phenyl]sulfide The title compound was prepared according to the procedures of Example 1. $^1$H NMR (CDCl$_3$, 300 MHz) δ 8.12 (d, 1H, J=8.1 Hz), 7.78 (s, 1H, J=1.7 Hz), 7.70 (d, 1H, J=15.6 Hz), 7.63 (t, 1H, J=7.8 Hz), 7.46 (dd, 1H, J=1.6, 7.8 Hz), 7.36–7.4 (m, 2H), 7.04 (d, 1H, J=8.1), 6.99 (dd, 1H, J=1.2, 7.6 Hz), 6.92 (m, 2H), 6.50 (d, 1H, J=15.6 Hz), 3.99 (q, 2H, J=6.9 Hz), 2.47 (s, 3H), 1.19 (t, 3H, J=7.0 Hz). MS (ESI)s m/z 459, 481. Anal. Calcd for $C_{24}H_{21}F_3N_2O_2S \cdot 1.1\ H_2O$: C, 60.27; H, 4.89; N, 5.86. Found: C, 60.28; H, 5.05; N, 5.94.

Example 201

(2-Methyl-3-chlorophenyl)[2-nitro-4-(E-((4-acetylpiperazin-1-yl)carbonyl)ethenyl)phenyl]sulfide The title compound was prepared according to the procedures of Example 1. $^1$H NMR (CDCl$_3$, 300 MHz) δ 8.46 (d, 1H, J=1.5 Hz), 7.64 (d, 1H, J=15.4 Hz), 7.56 (d, 1H, J=2.6 Hz), 7.54 (d, 1H, J=2.2 Hz), 7.47 (d, 1H, J=8.5 Hz), 7.27 (m, 1H), 6.92 (d, 1H, J=15.4 Hz), 6.68 (d, 1H, J=8.5 Hz), 3.63–3.78 (m, 6H), 3.53 (m, 2H), 2.45 (s, 3H), 2.15 (s, 3H). MS (ESI) m/z 460, 482, 919. Anal. Calcd for $C_{22}H_{22}Cl_1N_3O_4S$: C, 57.45, H, 4.82, N, 9.14. Found: C, 75.54, 5.08, N, 8.82.

Example 202

(Benzodioxan-6-yl)[2-nitro-4-(E-((3-carboxamidopiperidin-1-yl)carbonyl)ethenyl)phenyl]sulfide The title compound was prepared by the procedures described in Example 196, substituting N-(3'-aminopropyl)-

2-pyrrolidinone with nipecotamide, giving a light yellow solid, mp 243–245° C. $^1$H NMR (CDCl$_3$, 500 MHz) δ 1.38–1.50 (m, 2H), 1.77–2.00 (m, 2H), 2.38 (m, 1H), 2.70 (m, 1H), 3.11 (m, 1H), 4.22 (m, 1H), 4.28–4.30 (m, 2H), 4.32–4.36 (m, 2H), 4.42 (m, 1H), 6.85 (d, J=8.5 Hz, 1H), 7.04–7.16 (m, 2H), 7.35 (s, 1H), 7.40 (d, J=13.0 Hz, 1H), 7.48 (d, J=15.5 Hz, 1H), 7.91 (d, J=8.5 Hz, 1H), 8.58 (s, 1H). MS (APCI) m/z 470 (M+H)$^+$. Anal. calcd. for C$_{23}$H$_{23}$N$_3$O$_6$S.0.37 H$_2$O: C, 58.01; H, 5.03; N, 8.82. Found: C, 58.02; H, 5.13; N, 8.61.

Example 203

(Benzodioxan-6-yl)[2-nitro-4-(E-((2-carboethoxypiperidin-1-yl)carbonyl)ethenyl)phenyl] sulfide The title compound was prepared by the procedures described in Example 196, substituting N-(3'-aminopropyl)-2-pyrrolidinone with ethyl pipecolinate, producing a light yellow solid, mp 74–75° C. $^1$H NMR (CDCl$_3$, 300 MHz) d 1.28 (t, J=7.0 Hz, 3H), 1.32–1.55 (m, 2H), 1.60–1.82 (m, 3H), 2.33 (m, 1H), 3.40 (m, 1H), 3.98 (m, 1H), 4.23 (q, J=6.5 Hz, 2H), 4.32 (q, J=5.0 Hz, 4H), 5.45 (m, 1H), 6.90 (d, J=8.0 Hz, 1H), 6.97 (d, J=8.0 Hz, 1H), 7.0–7.10 (m, 3H), 7.44, (d, H=7.5 Hz, 1H), 7.60 (d, J=15.0 Hz, 1H), 8.38 (m, 1H). MS (APCI) m/z 499 (M+H)$^+$. Anal. calcd. for C$_{25}$H$_{26}$N$_2$O$_7$S.0.11 H$_2$O: C, 59.99; H, 5.28; N, 5.60. Found: C, 59.98; H, 5.42; N, 5.91.

Example 204

(Benzodioxan-6-yl)[2-nitro-4-(E-((4-carboxamidopiperidin-1-yl)carbonyl)ethenyl)phenyl] sulfide The title compound was prepared by the procedures described in Example 196, substituting N-(3'-aminopropyl)-2-pyrrolidinone with isonipecotamide, giving a light yellow solid, mp>230° C. $^1$H NMR (CDCl$_3$, 500 MHz) δ 1.35 (m, 1H), 1.60 (m, 1H), 1.72 (m, 1H), 1.68 (m, 1H), 2.20 (m, 1H), 2.75 (m, 1H), 3.04 (m, 1H), 3.20 (m, 1H), 4.20 (m, 1H), 4.32 (m, 4H), 6.85 (d, J=8.5 Hz, 1H), 7.04 (d, J=8.5 Hz, 1H), 7.09 (dd, J=2.0, 8.5 Hz, 1H), 7.26 (s, 1H), 7.37 (d, J=16.0 Hz, 1H), 7.47 (d, J=16.0 Hz, 1H), 8.58 (d, J=2.0 Hz, 1H). MS (APCI) m/z 470 (M+H)$^+$. Anal. calcd. for C$_{23}$H$_{23}$N$_3$O$_6$S.0.13 H$_2$O: C, 58.55; H, 4.97; N, 8.91. Found: C, 58.41; H, 5.14; N, 9.30.

Example 205

(Benzodioxan-6-yl)[2-nitro-4-(E-((4-tert-butoxycarbonylpiperazin-1-yl)carbonyl)ethenyl) phenyl]sulfide The title compound was prepared by the procedures described in Example 196, substituting N-(3'-aminopropyl)2-pyrrolidinone with Boc-piperazine, giving a light yellow solid, mp 165–167° C. $^1$H NMR (CDCl$_3$, 300 MHz) δ 1.48 (s, 9H), 3.50 (m, 4H), 3.65 (br, m, 4H), 4.32 (m, 4H), 6.89 (d, J=5.0 Hz, 1H), 6.92 (m, 1H), 6.97 (d, J=8.0 Hz, 1H), 7.05 (dd, J=2.0, 8.5 Hz,1H), 7.10 (d, J=2.0 Hz, 1H), 7.45 m, 1H), 7.63 (d, J=15.5 Hz, 1H), 8.40 (m, 1H). MS (APCI) M/z 528 (M+H)$^+$. Anal. calcd. for C$_{26}$H$_{29}$N$_3$O$_7$S: C, 59.19; H, 5.54; N, 7.96. Found: C, 58.85; H, 5.69; N, 8.20.

Example 206

(2-Isopropylphenyl)[2-nitro-4-(E-((syn-3,5-dimethylmorpholin-1-yl)carbonyl)ethenyl)phenyl] sulfide Prepared according to the procedures of Example 71, giving a yellow solid. $^1$H NMR (DMSO-d$_6$, 300 MHz) δ 1.10–1.18 (m, 12H); 2.29–2.39 (m, 1H); 2.67–2.78 (m, 1H); 3.30–3.53 (m, 3H); 4.17–4.38 (m, 2H); 6.63 (d, J=8.8 Hz, 1H); 7.32–7.63 (m, 6H); 7.92 (dd, J=8.8, 1.5 Hz, 1H); 8.66 (d, J=1.8 Hz, 1H). MS (APCI) (M+H)$^+$ at m/z 441. Anal calcd for C$_{24}$H$_{28}$N$_2$S$_1$O$_4$: C, 65.43; H, 6.41; N, 6.36. Found: C, 65.69; H, 6.70; N, 6.17.

Example 207

(2-Isopropylphenyl)[2-nitro-4-(E-((anti-3,5-dimethylmorpholin-1-yl)carbonyl)ethenyl)phenyl] sulfide Prepared according to the procedures of Example 71, giving a yellow solid. $^1$H NMR (DMSO-d$_6$, 300 MHz) δ 1.07–1.12 (m, 6H); 1.15 (d, J=6.6 Hz, 6H); 3.32–3.48 (m, 3H); 3.60–3.83 (br m, 2H); 3.87–3.98 (m, 2H); 6.63 (d, J=8.5 Hz, 1H); 7.32–7.63 (m, 6H); 7.93 (dd, J=8.8, 1.8 Hz, 1H); 8.64 (d, J=1.8 Hz, 1H). MS (APCI) (M+H)$^+$ at m/z 441.

Example 208

(2-Isopropylphenyl)[2-nitro-4-(E-((3-carboethoxypiperazin-1-yl)carbonyl)ethenyl)phenyl] sulfide Prepared according to the procedures of Example 71, giving a yellow solid. $^1$H NMR (DMSO-d$_6$, 300 MHz) δ 1.14 (d, J=6.8 Hz, 6H); 1.08–1.26 (m, 3H); 2.52–3.16 (br m, 4H); 3.25–3.40 (m, 1H); 3.41–4.26 (br m, 5H); 6.61–6.67 (br m, 1H); 7.30–7.62 (m, 6H); 7.87–7.93 (br m, 1H); 8.58–8.64 (br m, 1H). MS (APCI) (M+H)$^+$ at m/z 484. Anal calcd for C$_{25}$H$_{29}$N$_3$S$_1$O$_5$: C, 62.09; H, 6.04; N, 8.69. Found: C, 61.96; H, 6.28; N, 8.49.

Example 209

(2-Isopropylphenyl)[2-nitro-4-(E-((3-isopropoxycarbonylpiperazin-1-yl)carbonyl)ethenyl) phenyl]sulfide Prepared according to the procedures of Example 71, giving a yellow solid. $^1$H NMR (DMSO-d$_6$, 300 MHz) δ 1.07–1.21 (br m, 6H); 1.14 (d, J=7.0 Hz, 6H); 2.52–3.16 (br m, 4H); 3.30–3.40 (m, 1H); 3.41–4.24 (br m, 3H); 4.81–4.97 (m, 1H); 6.61–6.68 (br m, 1H); 7.32–7.63 (m, 6H); 7.87–7.94 (br m, 1H); 8.60–8.66 (br m, 1H). MS (APCI) (M+H)$^+$ at m/z 498. Anal calcd for C$_{26}$H$_{31}$N$_3$S$_1$O$_5$: C, 62.76; H, 6.28; N, 8.44. Found: C, 62.51; H, 6.52; N, 8.14.

Example 210

(2-Isopropylphenyl)[2-nitro-4-(E-((3-(dimethylaminocarbonyl)-4-methylpiperazin-1-yl) carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 2.14 (s, 3H); 2.82, 2.84 (s, s, 3H); 3.12 (s, 3H); 2.12–4.24 (br m, 8H); 6.64 (d, J=8.5 Hz, 1H); 7.32–7.62 (m, 6H); 7.87–7.94 (br m, 1H); 8.60–8.66 (br m, 1H). MS (APCI) (M+H)$^+$ at m/z 497. Anal calcd for C$_{26}$H$_{32}$N$_4$S$_1$O$_4$.042H$_2$O: C, 61.94; H, 6.56; N, 11.11. Found: C, 62,00; H, 6.78; N, 10.89.

Example 211

(2-Isopropylphenyl)[2-nitro-4-(E-((3-carbomethoxy-4-hydroxypiperidin-1-yl)carbonyl)ethenyl)phenyl] sulfide Prepared according to the procedures of Example 71, giving a yellow solid. $^1$H NMR (DMSO-d$_6$, 300 MHz) δ

1.14 (d, J=7.0 Hz, 6H); 1.59–1.75 (br m, 2H); 2.50–3.14 (br m, 1H); 3.30–3.40 (m, 1H); 3.60, 3.61 (s, s, 3H); 4.01–4.44 (br m, 4H); 5.05–5.10 (br m, 1H); 6.63 (d, J=8.5 Hz, 1H); 7.34–7.62 (m, 6H); 7.87–7.94 (br m, 1H); 8.60–8.66 (br m, 1H). MS (APCI) (M+H)$^+$ at m/z 485.

Example 212

(2-Isopropylphenyl)[2-nitro-4-(E-((3-hydroxymethyl-4-hydroxypiperidin-1-yl)carbonyl) ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.49–1.90 (br m, 2H); 2.75–3.14 (br m, 1H); 3.30–3.40 (m, 1H); 3.40–4.23 (br m, 5H); 4.38–4.52 (m, 1H); 4.60–4.73 (m, 1H); 6.61–6.66 (m, 1H); 7.27–7.61 (m, 6H); 7.84–7.93 (br m, 1H); 8.54–8.63 (br m, 1H). MS (APCI) (M+H)$^+$ at m/z 457. Anal calcd for C$_{24}$H$_{28}$N$_2$S$_1$O$_5$.047H$_2$O: C, 61.97; H, 6.27; N, 6.02. Found: C, 62.02; H, 6.49; N, 5.90.

Example 213

(2-Ethoxyphenyl)[2-trifluoromethyl-4-(E-((2-carbomethoxy-4-(methoxycarbonyl)piperazin-1-yl) carbonyl)ethenyl)phenyl]sulfide The title compound was prepared according to the procedures of Example 71. $^1$H NMR (CDCl$_3$, 300 MHz) δ 7.80 (s, 1H), 7.66 (d, 1H, J=15.4 Hz), 7.45 (dd, 1H, J=1.6, 7.5 Hz), 7.48 (m, 2H), 7.01 (d, 1H, J=6.6 Hz), 6.95 (d, 1H, J=6.8 Hz), 6.90 (m, 2H), 5.34 (br s, 1H), 4.66 (m, 2H), 3.76 (s, 3H), 3.73 (s, 3H), 3.18 (m, 1H), 3.00 (m, 3H). MS (ESI) m/z 553, 575.

Example 214

(2-Ethoxyphenyl)[2-trifluoromethyl-4-(E-((2-carbomethoxy-4-methylpiperazin-1-yl)carbonyl) ethenyl)phenyl]sulfide The title compound was prepared according to the procedures of Example 71. $^1$H NMR (CDCl$_3$, 300 MHz) δ 7.79 (s, 1H), 7.64 (d, 1H, J=15.3 Hz), 7.45 (dd, 1H, J=1.7, 7.8 Hz), 7.4–7.35 (m, 2H), 7.01 (d, 1H, J=8.1 Hz), 6.97 (dd, 1H, J=1.2, 7.6 Hz), 6.87–7.91 (m, 2H), 5.36 (br s, 1H), 3.98 (q, 2H, J=6.9 Hz), 3.90 (m, 1H), 3.78 (s, 3H), 3.65 (m, 1H), 3.42 (m, 1H), 2.85 (m, 1H), 2.32 (s, 3H), 2.24 (m, 1H), 2.19 (m, 1H), 1.18 (t, 3H, J=6.9 Hz). MS (ESI) m/z 509, 531.

Example 215

(2-Ethoxyphenyl)[2-trifluoromethyl-4-(E-((2-carboxy-4-(methoxycarbonyl)piperazin-1-yl) carbonyl)ethenyl)phenyl]sulfide The title compound was prepared according to the procedures of Example 71. $^1$H NMR (DMSO-d$_6$, 300 MHz) δ 8.10 (m, 1H), 7.68 (m,1H), 7.42 (m, 2H), 7.30 (m,1H), 7.20 (d, 1H, J=15.6 Hz), 7.10 (d, 1H, J=8.1 Hz), 7.04 (d, 1H, J=8.5 Hz), 6.98 (d, 1H, J=7.5 Hz), 4.65 (br s, 1H), 4.53 (m, 2H), 4.05 (m, 2H), 4.00 (q, 2H, J=6.9 Hz), 3.57 (s, 3H), 1.09 (t, 3H, J=6.9 Hz). MS (ESI) m/z −537, −569.

Example 216

(Indol-6-yl)[2-chloro-4-(E-((4-acetylpiperazin-1-yl) carbonyl)ethenyl)phenyl]sulfide The title compound was prepared by the procedures described in Example 85, substituting 5-iodoindole with 6-bromoindole, isolated as a white solid. $^1$H NMR (d$^6$-DMSO, 300 MHz) δ 2.03 (s, 3H), 3.40–3.77 (m, 8H), 6.52–6.55 (m, 1H), 6.60 (d, J=8.4 Hz, 1H), 7.13 (dd, J=1.8, 8.4 Hz, 1H), 7.27 (d, J=15.6 Hz, 1H), 7.40 (d, J=15.6 Hz, 1H), 7.43 (dd, J=1.8, 8.4 Hz, 1H), 7.51 (t, J=3.0 Hz, 1H), 7.64 (m, 1H), 7.70 (d, J=8.4 Hz, 1H), 7.99 (d, J=1.8 Hz, 1H). MS (APCI$^+$) (M+H)$^+$ at m/z 440, 442.

Example 217

(1-Ethyl-3-(dimethylaminomethyl)indol-7-yl)[2-chloro-4-(E-((4-acetylpiperazin-1-yl)carbonyl) ethenyl)phenyl]sulfide The title compound was prepared by the procedures described in Example 85, substituting 5-iodoindole with 7-bromo-3-N,N-dimethylmethyl-N-ethyl indole, and isolated as a light-brown solid. $^1$H NMR (CDCl$_3$, 300 MHz) δ 1.30 (t, J=7.05 Hz, 3H), 2.14 (s, 3H), 2.41 (s, 6H), 2.93–3.05 (m, 2H), 3.47–3.55 (m, 2H), 3.55–3.87 (m, 6H), 6.42 (d, J=8.4 Hz, 1H), 6.85 (d, J=15.6 Hz, 1H), 7.09 (dd, J=2.1, 8.4 Hz, 1H), 7.17 (d, J=8.4 Hz, 1H), 7.23 (d, J=8.4 Hz, 1H), 7.43 (dd, J=0.9, 7.8 Hz, 1H), 7.52 (d, J=2.1 Hz, 1H), 7.54 (d, J=15.6 Hz, 1H), 7.81 (dd, J=0.9, 7.8 Hz, 1H). MS (ESI$^+$) (M+H)$^+$ at m/z 525, 527.

Example 218

(5-Ethoxybenzodioxan-6-yl)[2-chloro-4-(E-((4-acetylpiperazin-1-yl)carbonyl)ethenyl)phenyl]sulfide The title compound was prepared by the procedures described in Example 85, substituting 5-iodoindole with 6-bromo-5-ethoxybenzodioxane, as a white solid. $^1$H NMR (CDCl$_3$, 300 MHz) δ 1.28 (t, J=7.2 Hz, 3H), 2.14 (s, 3H), 3.54 (br s, 2H), 3.60–3.88 (m, 6H), 4.06 (q, J=7.2 Hz, 2H), 4.33 (s, 4H), 6.70 (d, J=8.4 Hz, 1H), 6.73 (d, J=8.4 Hz, 1H), 6.78 (d, J=15.6 Hz, 1H0, 6.98 (d, J=8.4 Hz, 1H), 7.17 (dd, J=1.8, 8.4 Hz, 1H), 7.50 (d, J=1.8 Hz, 1H), 7.57 (d, J=15.6 Hz, 1H). MS (APCI$^+$) (M+H)$^+$ at m/z 503, 505.

Example 219

(2-Ethyl-4-bromophenyl)[2-nitro-4-(E-((4-acetylpiperazin-1-yl)carbonyl)ethenyl)phenyl]sulfide The title compound was prepared according to the procedures of Example 32. $^1$H NMR (CDCl$_3$, 300 MHz) δ 8.43 (d, 1H, J=2.0 Hz), 7.64 (d, 1H, J=15.6 Hz), 7.58 (d, 1H, J=2.0 Hz), 7.40–7.48 (m, 3H), 6.90 (d, 1H, J=15.2 Hz), 6.90 (d, 1H, J=8.5 Hz), 3.63–3.77 (m, 6H), 3.54 (m, 2H), 2.72 (q, 2H, J=7.5 Hz), 2.15 (s, 3H), 1.18 (t, 3H, J=7.5 Hz). MS (ESI) m/z 518, 520,542, 627. Anal. Calcd for C$_{23}$H$_{24}$Br$_1$N$_3$O$_4$S: C, 53.08; H, 4.60; N, 7.93. Found: C, 53.29, H, 4.67, N, 8.11.

Example 220

(Benzodioxan-6-yl)[2-nitro-4-(E-((2-carboxypiperidin-1-yl)carbonyl)ethenyl)phenyl] sulfide The title compound was prepared by the hydrolysis of the compound of Example 203 under basic conditions (aq. NaOH/EtOH), producing a light yellow solid:, mp 165° C.(dec.). $^1$H NMR (DMSO-d$_6$, 300 MHz) δ 1.15–1.52 (m, 3H), 1.46–1.62 (m, 2H), 2.32 (m, 1H), 2.80 (m, 1H), 3.45(br, 1/2H), 4.00 (br, 1/2H), 4.44 (br, 1/2H), 4.800 (br, 1/2H), 6.83 (d, J=8.0 Hz, 1H), 7.03 (d, J=8.0 Hz, 1H), 7.09 (dd, J=2.0, 14.0 Hz, 1H), 7.15 (d, J=2.0 Hz, 1H), 7.20 (d, J=15.5 Hz. 1H), 7.35 (d, J=15.5 Hz, 1H), 7.73 (m, 1H), 8.52 (m, 1H).

MS (ESI) m/z 469 (M−H)+, 471 (M+H)+. Anal. calcd. for $C_xH_{21}N_{2l}\ O_7SNa\cdot NaOH\cdot 2.7\ H_2O$: C, 47.54; H, 4.75; N, 4.82. Found: C, 47.18; H, 4.36; N, 4.89.

Example 221

(Benzodioxan-6-yl)[2-nitro-4-(E-((4-carboxymethylpiperazin-1-yl)carbonyl)ethenyl)phenyl]sulfide The title compound was prepared by deprotection of Example 205 with TFA in $CH_2Cl_2$. The resultant free amine was treated with tert-butyl bromoacetate and TEA in acetonitrile at room temperature, and followed by deprotection with TEA in $CH_2Cl_2$, giving a light solid, mp 120° C. (dec.). $^1$H NMR (DMSO-$d_6$, 300 MHz) δ 3.20–3.45 (m, 4H), 4.20 (s, 2H), 3.50–3.80 (m, 4H), 4.28–4.46 (m, 4H), 6.86 (d, J=8.5 Hz, 1H), 7.04 (m, J=8.0 Hz, 1H), 7.09 (dd, J=2.0 8.0 Hz, 1H), 7.15 (d, J=2.0 Hz, 1H), 7.40 (d, J=15.5 Hz, 1H), 7.56 (d, J=15.0 Hz, 1H), 7.90 (dd, J=2.0, 8.5 Hz, 1H), 8.63 (m, 1H). MS (ESI) m/z 484 (M−H)+, 486 (M+H)+. Calcd. Anal for $C_{23}H_{21}N_3O_7S\cdot 1.19CF_3COOH\cdot 1.34\ H_2O$: 47.63; H, 4.11; N, 6.89. Found: C, 47.93; H, 4.51; N, 6.49.

Example 222

(3-Morpholinophenyl)[2-nitro-4-(E-((4-acetylpiperazin-1-yl)carbonyl)ethenyl)phenyl]sulfide The title compound was prepared according to the procedures of Example 62, employing the compound of Example 103 as starting material. $^1$H NMR (CDCl$_3$, 300 MHz) δ 7.80 (s, 1H), 7.64 (d, 1H, J=15.4 Hz), 7.43 (m, 1H), 7.32 (t, 1H, J=8.1 Hz), 7.08 (m, 2H), 6.99 (m, 2H), 6.84 (d, 1H, J=15.4 Hz), 3.87 (t, 4H, J=4.8 Hz), 3.63–3.79 (m, 6H), 3.50–3.55 (m, 2H), 3.18 (t, 4H, J=4.8 Hz), 2.10 (s, 3H). MS (ESI) m/z 520, 542, 1061.

Example 223

(5-Ethoxybenzodioxan-8-yl)[2-chloro-4-(E-((4-acetylpiperazin-1-yl)carbonyl)ethenyl)phenyl]sulfide The title compound was prepared by the procedures described in Example 85, substituting 5-iodoindole with 8-bromo-5-ethoxybenzodioxane, giving a white solid. $^1$H NMR (CDCl$_3$, 300 MHz) δ 1.52 (t, J=7.2 Hz, 3H), 2.15 (s, 3H), 3.48–3.59 (m, 2H), 3.59–3.85 (m, 6H), 4.16 (q, J=7.2 Hz, 2H), 4.22–4.30 (m, 2H), 4.30–4.40 (m, 2H), 6.59 (d, J=8.7 Hz, 1H), 6.63 (d, J=8.7 Hz, 1H), 6.78 (d, J=15.6 Hz, 1H), 7.08 (d, J=8.7 Hz, 1H), 7.17 (dd, J=2.1, 8.7 Hz, 1H), 7.51 (d, J=2.1 Hz, 1H), 7.58 (d, J=15.6 Hz, 1H). MS (APCI+) (M+H)+ at m/z 503, 505.

Example 224

(5-Chloro-8-ethoxyquinolin-7-yl)[2-chloro-4-(E-((4-acetylpiperazin-1-yl)carbonyl)ethenyl)phenyl]sulfide The title compound was prepared by the procedures described in Example 85, substituting 5-iodoindole with 5-chloro-8-ethoxy-7-iodoquinoline, giving a white solid. $^1$H NMR (d$^6$-DMSO, 300 MHz) δ 1.37 (t, J=7.2 Hz, 3H), 2.04 (s, 3H), 3.41–3.82 (m, 8H), 4.46 (q, J=7.2 Hz, 2H), 7.29 (s, 1H), 7.37 (d, J=8.4 Hz, 1H), 7.42 (d, J=15.6 Hz, 1H), 7.51 (d, J=15.6 Hz, 1H), 7.68 (dd, J=1.8, 8.4 Hz, 1H), 7.74 (dd, J=3.9, 8.4 Hz, 1H), 8.15 (s, 1H), 8.55 (dd, J=1.8, 8.4 Hz, 1H), 9.05 (dd, J=1.8, 3.9 Hz, 1H). MS (APCI+) (M+H)+ at m/z 530, 532, 534.

Example 225

(2-Isopropylphenyl)[2-nitro-4-(E-((3-carboethoxypiperidin-1-yl)carbonyl)ethenyl)phenyl]sulfide

Example 225A (2-Isopropylphenyl)[2-nitro-4-(E-(carboxy)ethenyl)phenyl]sulfide To a stirred mixture of 4-chloro-3-nitrocinnamic acid (500 mg, 2.2 mmol) in 5 mL of anhydrous DMF with $K_2CO_3$ (911 mg, 6.6 mmol) was added 2-isopropylbenzenethiol (372 mL, 2.2 mmol) in 1 mL of DMF dropwise. The resulting mixture was then heated at 70° C. under nitrogen atmosphere overnight. Water (25 mL) was then added and the reaction mixture was acidified to pH=4 with 3N HCl. The cloudy mixture was extracted with EtOAc (2×20 mL). The combined organic layer was washed with brine, dried over $Na_2SO_4$, concentrated in vacuo to give the title compound as a viscous light-yellow oil, which was used for coupling with further purification.

Example 225B (2-Isopropylphenyl)[2-nitro-4-(E-((3-carboethoxypiperidin-1-yl)carbonyl)ethenyl)phenyl]sulfide The title compound was prepared by the procedures described in Example 92, substituting the benzoic acid with cinnamic acid from 225A, and ammonium chloride with ethyl nipecotate, giving a light-yellow solid. $^1$H NMR (CDCl$_3$, 300 MHz) δ 1.18 (d, J=6.6 Hz, 6H), 1.27 (t, J=7.2 Hz, 3H), 1.69–1.82 (m, 1H), 1.82–1.9 (m, 1H), 1.99–2.20 (m, 1H), 2.45–2.62 (m, 2H), 3.45 (septet, J=6.6 Hz, 1H), 3.56–3.80 (m, 1H), 3.80–4.10 (m, 2H), 4.16 (q, J=7.2 Hz, 2H), 4.65–4.81 (m, 1H), 6.69 (d, J=8.4 Hz, 1H), 7.00 (br s, 1H), 7.31 (dd, J=2.4, 6.9 Hz, 1H), 7.42 (br d, J=8.4 Hz, 1H), 7.51 (d, J=15.6 Hz, 1H), 7.52 (overlapping d, 2H), 7.58 (d, J=15.6 Hz, 1H), 8.43 (s, 1H). MS (APCI+) (M+H)+ at m/z 483.

Example 226

(2-Isopropylphenyl)[2-nitro-4-(E-((3-carboxypiperidin-1-yl)carbonyl)ethenyl)phenyl]sulfide The title compound was prepared by the procedures described in Example 155, substituting the ethyl ester from Example 137 with the ethyl ester from Example 225B, and KOH with NaOH, to give a light-yellow solid. $^1$H NMR (d$^6$-DMSO, 300 MHz) δ 1.15 (d, J=6.9 Hz, 6H), 1.30–1.50 (m, 1H), 1.50–1.80 (m, 2H), 1.88–2.04 (m, 2H), 2.95–3.17 (m, 1H), 3.94–4.06 (m, 1H), 4.06–4.22 (m, 2H), 4.40–4.52 (m, 1H), 6.63 (d, J=8.7 Hz, 1H), 7.33–7.53 (m, 3H), 7.56–7.68 (m, 3H), 7.91 (dd, J=1.8, 8.4 Hz, 1H), 8.63 (d, J=8.4 Hz, 1H). MS (APCI+) (M+H)+ at m/z 455.

Example 227

(2-Isopropylphenyl)[2-nitro-4-(E-(((3-ethanesulfonylaminocarbonyl)piperidin-1-yl)carbonyl)ethenyl)phenyl]sulfide To a stirred solution of free acid (50 mg, 0.11 mmol) from Example 226 in 1 mL of methylene chloride was added ethyl sulfonamide (18 mg, 0.17 mmol), EDAC (25 mg, 0.13 mmol), and DAMP (2.7 mg, 0.022 mmol) sequentially. The mixture was stirred at ambient temperature for 16 hours. The solvent was then removed on a rotavap under reduced pressure and the residue was purified on an Alltech sep-pak, eluting with 1% MeOH in EtOAc to give 30 mg (50% yield) of the title compound as a light yellow solid. $^1$H NMR (CDCl$_3$, 300 MHz) δ 1.18 (d, J=6.3 Hz, 6H), 1.34 (t, J=7.5 Hz, 3H), 1.61–1.74 (m, 2H), 1.84–2.04 (m, 1H), 2.13–2.35 (m, 1H), 2.60–2.75 (m, 2H), 3.44 (p, J=7.5 Hz, 2H), 3.53–3.66 (m, 1H), 3.66–3.85 (m, 2H), 4.00–4.18 (m, 1H), 6.71 (d, J=8.7 Hz, 1H), 6.88 (d, J=15.6 Hz, 1H), 7.31 (dd, J=2.4, 8.4 Hz, 1H), 7.41 (d, J=1.8, 8.4 Hz, 1H), 7.51 (d, J=1.8 Hz, 1H), 7.54 (d, J=8.4 Hz, 1H), 7.67 (d, J=15.6 Hz, 1H), 8.43 (s, 1H). MS (ESI$^+$) (M+H)$^+$ at m/z 546.

Example 228

(2-Isopropylphenyl)[2-nitro-4-(E-(((3-(4-methylpiperazine) sulfonylaminocarbonyl)piperidin-1-yl)carbonyl)ethenyl)phenyl]sulfide The title compound was prepared by the procedures described in Example 228, substituting ethyl sulfonamide with N-methylpiperazine sulfonamide, giving a light yellow solid. $^1$H NMR (CDCl$_3$, 300 MHz) δ 1.18 (d, J=6.5 Hz, 6H), 1.40–2.10 (m, 9H), 2.60 (s, 3H), 2.60–2.76 (m, 4H), 2.90 (br s, 3H), 3.44 (septet, J=6.5 Hz, 1H), 3.52–4.08 (m, 4H), 6.71 (d, J=8.4 Hz, 1H), 6.95 (d, J=15.6 Hz, 1H), 7.31 (d, J=2.1, 8.4 Hz, 1H), 7.43–7.57 (m, 4H), 7.64 (d, J=15.6 Hz, 1H), 8.44 (s, 1H). MS (ESI$^+$) (M+H)$^+$ at m/z 616. Anal. Calcd for C$_{29}$H$_{37}$N$_5$O$_6$S$_2$.1.13 H$_2$O: C, 54.76; H, 6.22; N, 11.01. Found: C, 54.78; H, 6.11; N, 10.87.

Example 229

(2-Isopropylphenyl)[2-nitro-4-(E-(((3-p-toluenesulfonylaminocarbonyl)piperidin-1-yl)carbonyl)ethenyl)phenyl]sulfide The title compound was prepared by the procedures described in Example 228, substituting ethyl sulfonamide with p-toluenesulfonamide, giving a light yellow solid. $^1$H NMR (CDC$_3$, 300 MHz) δ 1.19 (d, J=6.5 Hz, 6H), 1.75–1.94 (m, 2H), 2.05–2.24 (m, 1H), 2.40 (s, 3H), 2.48–2.60 (m, 2H), 3.45 (septet, J=6.5 Hz, 1H), 3.50–3.85 (m, 3H), 3.85–4.12 (m, 1H), 6.72 (d, J=8.4 Hz, 1H), 6.86 (d, J=15.6 Hz, 1H), 7.27–7.34 (m, 2H), 7.43 (dd, J=2.1, 8.4 Hz, 1H), 7.50 (overlapping d, 1H), 7.53 (d, J=8.4 Hz, 2H), 7.55 (d, J=8.4 Hz, 1H), 7.92 (d, J=8.4 Hz, 2H), 8.44 (s, 1H). MS (ESI$^+$) (M+H)$^+$ at m/z 608.

Example 230

(2-isopropylphenyl)[2-nitro-4-(E-((3-methyl-4-acetylpiperazin-1-yl)carbonyl)ethenyl)phenyl]sulfide Prepared according to the procedures of Example 71, giving a yellow solid. $^1$H NMR (DMSO-d6, 300 MHz) δ 0.94–1.18 (m, 3H); 1.14 (d, J=7.0 Hz, 6H); 1.98–2.08 (br m, 3H); 2.69–3.74 (br m, 4H); 4.02–4.65 (br m, 4H); 6.64 (d, J=8.5 Hz, 1H); 7.31–7.63 (m, 6H); 7.88–7.96 (br m, 1H); 8.65 (br s, 1H). MS (APCI) (M+H)$^+$ at m/z 468. Anal calcd for C$_{25}$H$_{29}$N$_3$S$_1$O$_4$.0.1H$_2$O: C, 63.91; H, 6.70; N, 8.94. Found: C, 63.54; H, 6.41; N, 8.67.

Example 231

(2-Hydroxyphenyl)-[2-chloro-4-(E-[(morpholin-1-yl)carbonyl]ethenyl)phenyl]sulfide The title compound was prepared according to the procedures of Example 1, giving a white solid, m.p. 157–158° C. $^1$H-NMR (CDCl$_3$ 300 MHz) δ 3.60–3.76 (m, 8H), 6.42 (s, 1H), 6.57 (d, J=9 hz, 1H), 6.76 (d, J=15 Hz, 1H), 6.99–7.04 (m, 1H), 7.10–7.20 (m, 2H), 7.42–7.55 (m, 4H). Anal. Calcd. for C$_{19}$H$_{18}$ClNO$_3$S: C, 60.71; h, 4.83; N, 3.73. Found: C, 60.48; H, 5.05; N, 3.69.

Example 232

(1-(Carboxymethyl)indol-5-yl)[2-chloro-4-(E-((4-acetylpiperazin-1-yl)carbonyl)ethenyl)phenyl]sulfide To a stirred solution of indole compound from Example 85 (35 mg, 0.080 mmol) in 1 mL of anhydrous DMSO was added crushed KOH (18 mg, 0.32 mmol). After 45 minutes, t-butyl bromoacetate (23.5 mL, 0.16 mmol) was added. The resulting mixture was stirred at ambient temperature for 10 hours. Water was then added and the reaction mixture was acidified with 3 N HCl to pH=3. The title compound (25 mg, 63%) was collected through filtration and dried in a vacuum oven, giving a white solid. $^1$H NMR (d$^6$-DMSO, 300 MHz) δ 2.04 (s, 3H), 3.38–3.80 (m, 8H), 4.59 (s, 2H), 6.45 (d, J=3.0 Hz, 1H), 6.52 (d, J=8.7 Hz, 1H), 7.21 (dd, J=2.1, 8.7 Hz, 1H), 7.25 (d, J=15.6 Hz, 1H), 7.38 (d, J=15.6 Hz, 1H), 7.40 (d, J=3.0 Hz, 1H), 7.47 (d, J=8.4 Hz, 1H), 7.80 (d, J=2.1 Hz, 1H), 7.97 (s, 1H). MS (ESI$^+$) (M−H)$^+$ at m/z 496, 498.

Example 233

(Benzodioxan-6-yl)[2-trifluoromethyl-4-(E-((4-acetylpiperazin-1-yl)carbonyl)ethenyl)phenyl]sulfide The title compound was prepared by the procedures described in Example 84, substituting 2-bromothiophenol with 6-mercaptobenzenedioxane. white solid; $^1$H NMR (CDCl$_3$, 300 MHz) δ 2.15 (s, 3H), 3.46–3.89 (m, 8H), 4.30 (dd, J=2.1, 6.0 Hz, 4H), 6.84 (d, J=15.0 Hz, 1H), 6.92 (d, J=8.4 Hz, 1H), 6.97–7.10 (m, 3H), 7.42 (d, J=8.4 Hz, 1H), 7.64 (d, J=15.0 Hz, 1H), 7.77 (s, 1H). MS (ESI$^+$) m/z 493 (M+H)$^+$.

Example 234

(2-Isopropylphenyl)[2-nitro-4-(E-((3-(2-oxopyrrolidin-1-yl)prop-1-ylamino)carbonyl)ethenyl)phenyl]sulfide Prepared according to the procedures of Example 71, giving a yellow solid. $^1$H NMR (DMSO-d$_6$, 300 MHz) δ 1.14 (d, J=7.1 Hz, 6H); 1.58–1.68 (m, 2H); 1.85–1.97 (m, 2H); 2.18–2.24 (m,2H); 3.10–3.22 (m, 4H); 3.30–3.39 (m, 3H); 6.65–6.72 (m, 2H); 7.32–7.45 (m, 2H); 7.57–7.62 (m, 3H); 7.76 (dd, J=8.8, 2.0 Hz, 1H); 8.11–8.17 (m, 1H); 8.44 (d, J=2.0 Hz, 1H). MS (APCI) (M+H)$^+$ at m/z 468. Anal calcd for C$_{25}$H$_{29}$N$_3$S$_1$O$_4$.0.26CH$_3$COOCH$_2$CH$_3$: C, 63.77; H, 6.39; N, 8.57. Found: C, 63.46; H, 6.37; N, 8.90.

Example 235

(3-(2-Morpholinoethylamino)phenyl)[2-trifluoromethyl-4-(E-((4-acetylpiperazin-1-yl)carbonyl)ethenyl)ethenyl]sulfide The title compound was prepared according to the procedures of Example 62, employing the compound of Example 103 as starting material. $^1$H NMR (CDCl$_3$, 300 MHz) δ 7.78 (d, 1H, J=1.4 Hz), 7.64 (d, 1H, J=15.4 Hz), 7.42 (d, 1H, J=8.8 Hz), 7.21 (t, 1H, J=7.9 Hz), 7.12 (d, 1H, J=8.5 Hz), 6.84 (d, 1H, J=15.4 Hz), 6.82 (m, 1H), 6.76 (t, 1H, J=1.8 Hz), 6.66 (m, 1H), 3.72 (m, 10H), 3.51–3.55 (m, 2H), 3.16 (t, 2H, J=5.9 Hz), 2.64 (t, 2H, J=5.9 Hz), 2.50 (m, 4H), 2.15 (s, 3H). MS (ESI) m/z 563.

Example 236

(2-Pyrrolidin-1-ylphenyl)[2-nitro-4-(E-((4-acetylpiperazin-1-yl)carbonyl)ethenyl)phenyl]sulfide The title compound was prepared according to the procedures of Example 62, employing the compound of Example 103 as starting material. $^1$H NMR (CDCl$_3$, 300 MHz) δ 7.77 (s, 1H), 7.64 (d, 1H, J=15.4 Hz), 7.40 (m, 1H), 7.22 (d, 1H, J=7.8 Hz), 7.10 (d, 1H, J=8.8 Hz), 6.82 (d, 1H, J=15.3 Hz), 6.76 (d, 1H, J=7.8 Hz), 6.70 (t, 1H, J=2.0 Hz), 6.59 (dd, 1H, J=2.4, 8.1 Hz), 3.61–3.79 (m, 6H), 3.51–3.54 (m, 2H), 3.28 (m, 4H), 2.14 (s, 3H), 2.01 (m, 4H). MS (ESI) m/z 504.

Example 237

(3-Bromophenyl)[2-nitro-4-(E-((3-carboethoxypyrrolidin-1-yl)carbonyl)ethenyl)phenyl]sulfide The title compound was prepared according to the procedures of Example 1. $^1$H NMR (CDCl$_3$, 300 MHz) δ 8.40 (d, 1H, J=1.5 Hz), 7.75 (m, 1H), 7.45 (m, 1H), 7.48–7.56 (m, 2H), 7.38 (t, 1H, J=7.9 Hz), 7.00 (br, 1H), 6.87 (d, 1H, J=9.5 Hz), 4.16 (q, 2H, J=7.1 Hz), 3.99 (br, 2H), 3.70 (br, 1H), 3.30 (br, 1H), 3.00 (br, 1H), 2.55 (s, 1H), 2.10 (m, 1H), 1.89 (br, 1H), 1.85 (br, 1H), 1.27 (t, 3H, J=7.0 Hz). MS (ESI) m/z 519, 521. Anal. Calcd for C$_{23}$H$_{23}$BrN$_2$O$_5$S.0.19 H$_2$O: C, 52.84; H, 4.51; N, 5.36. Found: C, 52.85; H, 4.55; N, 5.28.

Example 238

(3-Bromophenyl)[2-nitro-4-(E-((4-carboethoxypyrrolidin-1-yl)carbonyl)ethenyl)phenyl]sulfide The title compound was prepared according to the procedures of Example 1. $^1$H NMR (CDCl$_3$, 300 MHz) δ 8.41 (s, 1H), 7.75 (m, 1H), 7.62–7.67 (m, 2H), 7.53 (m, 1H), 7.48 (d, 1H, J=8.8 Hz), 7.38 (t, 1H, J=7.9 Hz), 6.98 (br, 1H), 6.88 (d, 1H, J=8.5 Hz), 4.18 (q, 2H, J=7.1 Hz), 3.64–78 (br, 4H), 3.55 (br, 4H), 1.29 (t, 3H, J=7.0 Hz). MS (ESI) m/z 520, 522.

Example 239

(2-(Hydroxymethyl)-benzodioxan-6-yl)[2-chloro-4-(E-((4-acetylpiperazin-1-yl)carbonyl)ethenyl)phenyl]sulfide The title compound was prepared by the procedures described in Example 85, substituting 5-iodoindole with a mixture of 2-hydroxymethyl-6-bromobenzodioxane and 2-hydroxymethyl-7-bromobenzodioxane, giving a white solid. $^1$H NMR (CDCl$_3$, 300 MHz, mixture of 3:2 regioisomers) δ 2.15 (s, 3H), 3.46–3.83 (m, 8H), 3.83–4.01 (m, 2H), 4.10–4.42 (m, 4H), 6.75 (d, J=8.4 Hz, 1H), 6.79 (d, J=15.9 Hz, 1H), [6.95 (d), 6.98 (d), J=4.8 Hz, 1H in total], [7.04 (t), 7.07 (t), J=1.5 Hz, 1H in total], [7.10 (d), 7.11 (d), J=2.4 Hz, 1H in total], 7.19 (d, J=8.4 Hz, 1H), 7.53 (s, 1H), 7.58 (d, J=15.6 Hz, 1H). MS (APCI$^+$) (M+H)$^+$ at m/z 489.

Example 240

(Benzodioxan-6-yl)[2-trifluoromethyl-4-(E-((2-oxopyrrolidin-1-yl)prop-1-ylamino)carbonyl)ethenyl)phenyl]sulfide The title compound was prepared by the procedures described in Example 233, substituting 1-acetylpiperazine with 3-aminopropyl-1-pyrrolidin-2-one, giving a white solid. $^1$H NMR (CDCl$_3$, 300 MHz) δ 1.69–1.80 (m, 2H), 2.08 (p, J=7.5 Hz, 2H), 2.44 (t, J=7.5 Hz, 2H), 3.27–3.48 (m, 6H), 4.24–4.34 (m, 4H), 6.44 (d, J=15.6 Hz, 1H), 6.90 (d, J=8.4 Hz, 1H), 7.00 (d, J=8.4 Hz, 1H), 7.01 (dd, J=2.7, 8.4 Hz, 1H), 7.06 (d, J=2.7 Hz, 1H), 7.08 (s, 1H), 7.40 (dd, J=2.1, 8.4 Hz, 1H), 7.53 (d, J=15.6 Hz, 1H), 7.75 (d, J=2.1 Hz, 1H). MS (ESI$^+$) (M+H)$^+$ at m/z 507.

Example 241

(3-(Dimethylaminomethyl)indol-5-yl)[2-chloro-4-(E-((4-acetylpiperazin-1-yl)carbonyl)ethenyl)phenyl]sulfide The title compound was prepared by the procedures described in Example 217, substituting the indole from Example 186 with the indole from Example 85, resulting in a white solid. $^1$H NMR (CDCl$_3$, 300 MHz) δ 1.69–1.80 (m, 2H), 2.08 (p, J=7.5 Hz, 2H), 2.44 (t, J=7.5 Hz, 2H), 3.27–3.48 (m, 6H), 4.24–4.34 (m, 4H), 6.44 (d, J=15.6 Hz, 1H), 6.90 (d, J=8.4 Hz, 1H), 7.00 (d, J=8.4 Hz, 1H), 7.01 (dd, J=2.7, 8.4 Hz, 1H), 7.06 (d, J=2.7 Hz, 1H), 7.08 (s, 1H), 7.40 (dd, J=2.1, 8.4 Hz, 1H), 7.53 (d, J=15.6 Hz, 1H), 7.75 (d, J=2.1 Hz, 1H). MS (ESI$^+$) (M+H)$^+$ at m/z 507.

Example 242

(2-Isopropylphenyl)[2-nitro-4-(E-((2-carboethoxypiperidin-1-yl)carbonyl)ethenyl)phenyl]sulfide The title compound was prepared by the procedures described in Example 225, substituting ethyl nipecotate with ethyl pipecolinate, giving a light-yellow solid. $^1$H NMR (CDCl$_3$, 300 MHz) δ 1.18 (d, J=6.9 Hz, 6H), 1.28 (t, J=7.35 Hz, 3H), 1.34–1.62 (m, 2H), 1.62–1.84 (m, 3H), 2.32 (br d, J=13.2 Hz, 1H), 3.33–3.54 (m, 1H), 3.45 (septet, J=6.9 Hz, 1H), 3.99 (br d, J=13.2 Hz, 1H), 4.21 (q, J=7.35 Hz, 2H), 5.46 (br s, 1H), 6.69 (d, J=8.7 Hz, 1H), 7.01 (d, J=15.6 Hz, 1H), 7.25–7.34 (m, 1H), 7.42 (d, J=8.7 Hz, 1H), 7.46–7.60 (m, 3H), 7.58 (d, J=15.6 Hz, 1H), 8.44 (s, 1H). MS (ESI$^+$) (M+H)$^+$ at m/z 483.

Example 243

(2-Isopropylphenyl)[2-nitro-4-(E-((2-carboxypiperidin-1-yl)carbonyl)ethenyl)phenyl]sulfide The title compound was prepared by the procedures described in Example 226, substituting the ethyl ester from Example 225 with the ethyl ester from Example 242, giving a light-yellow solid. $^1$H NMR (CDCl$_3$, 300 MHz) δ 1.18 (d, J=6.9 Hz, 6H), 1.40–1.89 (m, 5H), 2.34 (br d, J=11.7 Hz, 1H), 3.31–3.51 (m, 1H), 3.44 (septet, J=6.9 Hz, 1H), 4.01 (d, J=11.7 Hz, 1H), 5.42 (br s, 1H), 6.70 (d, J=7.8 Hz, 1H), 6.99 (br d, J=15.6 Hz, 1H), 7.29 (td, J=2.7, 6.9 Hz, 1H), 7.41 (d, J=7.8 Hz, 1H), 7.45–7.58 (m, 3H), 7.64 (d, J=15.6 Hz, 1H), 8.43 (s, 1H). MS (ESI$^+$) (M+H)$^+$ at m/z 455. Anal. Calcd for C$_{24}$H$_{26}$N$_2$O$_5$S.0.08 H$_2$O: C, 63.22; H, 5.78; N, 6.14. Found: C, 63.21; H, 5.65; N, 6.00.

Example 244

(2-Isopropylphenyl)[2-nitro-4-(E-((4-carboethoxypiperidin-1-yl)carbonyl)ethenyl)phenyl]sulfide The title compound was prepared by the procedures described in Example 225, substituting ethyl nipecotate with ethyl isonipecotate, to give a light-yellow solid. $^1$H NMR (CDCl$_3$, 300 MHz) δ 1.18 (d, J=6.9 Hz, 6H), 1.27 (t, J=7.5 Hz, 3H), 1.64–1.86 (m, 2H), 1.94–2.09 (m, 2H), 2.90–3.15 (m, 1H), 3.15–3.39 (m, 1H), 3.44 (septet, J=6.9 Hz, 1H), 3.95–4.14 (m, 1H), 4.16 (q, J=7.5 Hz, 2H), 4.40–4.63 (m, 1H), 6.69 (d, J=8.7 Hz, 1H), 6.98 (d, J=15.6 Hz, 1H), 7.29 (td, J=2.7, 6.9 Hz, 1H), 7.41 (d, J=8.4 Hz, 1H), 7.46–7.60 (m, 3H), 7.58 (d, J=15.6 Hz, 1H), 8.43 (s, 1H). MS (ESI$^+$) (M+H)$^+$ at m/z 483.

Example 245

(2-Isopropylphenyl)[2-nitro-4-(E-((4-carboxypiperidin-1-yl)carbonyl)ethenyl)phenyl]sulfide The title compound was prepared by the procedures described in Example 226, substituting the ethyl ester from Example 225 with the ethyl ester from Example 244, producing a light-yellow solid. $^1$H NMR (CDCl$_3$, 300 MHz) δ 1.18 (d, J=6.9 Hz, 6H), 1.65–1.89 (m, 2H), 1.97–2.14 (m, 2H), 2.59–2.74 (m, 2H), 2.93–3.20 (m, 1H), 3.20–3.42 (m, 1H), 3.44 (septet, J=6.9 Hz, 1H), 3.97–4.18 (m, 1H), 4.40–4.65 (m, 1H), 6.70 (d, J=8.7 Hz, 1H), 6.97 (d, J=15.6 Hz, 1H), 7.30 (td, J=2.7, 6.9 Hz, 1H), 7.41 (d, J=8.7 Hz, 1H), 7.46–7.65 (m, 3H), 7.60 (d, J=15.6 Hz, 1H), 8.43 (s, 1H). MS (ESI$^+$) (M+H)$^+$ at m/z 455.

Example 246

(2-Isopropylphenyl)[2-nitro-4-(E-(((4-p-toluenesulfonylaminocarbonyl)piperidin-1-yl)carbonyl)ethenyl)phenyl]sulfide The title compound was prepared by the procedures described in Example 229, substituting the acid from Example 226 with the acid from Example 245, to give a light-yellow solid; $^1$H NMR (d$^6$-DMSO, 300 MHz) δ 1.14 (d, J=6.9 Hz, 6H), 1.18–1.39 (m, 2H), 1.67–1.79 (m, 2H), 2.39 (s, 3H), 2.60–2.75 (m, 1H), 2.96–3.14 (m, 1H), 3.26–3.42 (m, 1H), 3.34 (septet, J=6.9 Hz, 1H), 4.10–4.42 (m, 2H), 6.62 (d, J=8.4 Hz, 1H), 7.32–7.43 (m, 4H), 7.45 (d, J=15.6 Hz, 1H), 7.58 (d, J=8.4 Hz, 2H), 7.60 (d, J=3.6 Hz, 1H), 7.78 (d, J=8.4 Hz, 2H), 7.87 (dd, J=2.7, 8.4 Hz, 1H), 8.60 (d, J=2.7 Hz, 1H). MS (ESI$^+$) (M+H)$^+$ at m/z 606. Anal. Calcd for C$_{31}$H$_{33}$N$_3$O$_6$S$_2$.0.26 H$_2$O: C, 60.80; H, 5.52; N, 6.86. Found: C, 60.85; H, 5.84; N, 6.61.

Example 247

(2-Isopropylphenyl)[2-nitro-4-(E-((3-carboxy-4-hydroxypiperidin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.53–1.70 (br m, 2H); 2.92–3.52 (br m, 1H); 3.30–3.40 (m, 1H); 3.98–4.44 (br m, 4H); 4.90–5.20 (br m, 1H); 6.63 (d, J=8.5 Hz, 3H); 7.34–7.62 (m, 6H); 7.87–7.94 (br m, 1H); 8.58–8.64 (br m, 1H). MS (APCI) (M+H)$^+$ m/z at 471. Anal calcd for C$_{24}$H$_{26}$N$_2$S$_1$O$_6$: C, 61.26; H, 5.57; N, 5.95. Found: C, 61.05; H, 5.85; N, 5.73.

Example 248

(Benzodioxan-6-yl)[2-trifluoromethyl-4-(E-((3-carboethoxypiperidin-1-yl)carbonyl)ethenyl)phenyl]sulfide The title compound was prepared by the procedures described in Example 240 substituting N-(3'-aminopropyl)-2-pyrrolidinone with ethyl nipecotate, giving a white hygroscopic solid. $^1$H NMR (CDCl$_3$, 300 MHz) δ 1.26 (t, J=7.0 Hz, 3H), 1.54 (m, 1H), 1.65–1.80 (m, 2H), 2.10 (m, 1H), 2.54 (m, 1H), 2.92–3.40 (m, 2H), 3.60–4.10 (m, 2H), 4.14 (q, J=7.0 Hz, 2H), 4.25–4.32 (m, 4H), 6.91 (d, J=7.5 Hz, 1H), 7.00 (dd, J=2.0, 15.0 Hz, 3H), 7.05 (d, J=2.0 Hz, 1H), 7.40 (d, J=8.0, 1H), 7.56 (d, J=15.0 Hz, 1H), 7.76 (s, 1H). MS (Cl/NH$_3$) m/z 522 (M+H)$^+$. Anal. calcd. for C$_{26}$H$_{26}$F$_3$NO$_5$S: C, 59.88; H, 5.02; N, 2.69. Found: C; 59.92; H, 5.39; N, 2.56.

Example 249

(Benzodioxan-6-yl)[2-trifluoromethyl-4-(E-((2-carboethoxypiperidin-1-yl)carbonyl)ethenyl)phenyl]sulfide The title compound was prepared by the procedures described in Example 240 substituting N-(3'-aminopropyl)-2-pyrrolidinone with ethyl pipecolinate. $^1$H NMR (CDCl$_3$, 300 MHz) δ 1.28 (t, J=7.0 Hz, 3H), 1.35–1.54 (m, 2H), 1.64–1.82 (m, 3H), 2.30 (m, 1H), 3.40 (m, 1H), 4.00 (m, 1H), 4.22 (q, J=7.0 Hz, 2H), 4.26–4.34 (m, 4H), 5.48 (m, 1H), 6.91 (d, J=8.5 Hz, 1H), 6.98 (m, 1H), 7.02 (dd, J=2.0, 8.0 Hz, 2H), 7.06 (d, J=2.0 Hz, 1H), 7.41 (d, J=8.0 Hz, 1H), 7.57 (d, J=15.0 Hz, 1H), 7.77 (s, 1H). MS (Cl/NH$_3$) m/z 522 (M+H)$^+$. Anal. calcd for C$_{26}$H$_{26}$F$_3$NO$_5$S: C; 59.88; H, 5.02; N, 2.69. Found: C, 60.25; H, 5.12; N, 2.55.

Example 250

(Benzodioxan-6-yl)[2-nitro-4-(E-((4-carboxypiperidin-1-yl)carbonyl)ethenyl)phenyl]sulfide The title compound was prepared by the hydrolysis of compound 198 under basic condition (aq. NaOH/EtOH), and purified by reversed-phase HPLC. $^1$H NMR (DMSO-d$_6$, 300 MHz) δ 1.44 (m, 2H), 1.78 (m, 2H), 2.04 (m, 2H), 2.82 (m, 1H), 4.02–4.20 (m, 2H), 4.4.20–4.35 (m, 4H), 6.90 (d, J=8.0 Hz, 1H), 6.97 (d, J=8.0 Hz, 1H), 7.05(dd, J=2.0, 8.0 Hz, 1H), 7.10(d, J=2.0 Hz, 1H), 7.15 (br, 1H), 7,44 (m 1H), 7.60 (br, 1H), 8.40 (s, 1H). MS (ESI) m/z 469 (M–1).

Example 251

(Benzodioxan-6-yl)[2-trifluoromethyl-4-(E-((3-carboxypyrrolidin-1-yl)carbonyl)ethenyl)phenyl]sulfide The title compound was prepared according to the procedures of Example 1. $^1$H NMR (CDCl$_3$, 300 MHz) δ 7.75 (s, 1H), 7.60 (d, 1H, J=15.0 Hz) 7.40 (br, 1H), 7.06 (d, 1H, J=2.2 Hz), 6.96–7.02 (m, 3H), 6.90 (d, 1H, J=8.5 Hz), 4.30 (m, 5H), 3.99 (br, 2H), 3.29 (br, 2H), 2.60 (br, 2H), 1.85 (br, 2H). MS (ESI) m/z –492.

Example 252

(Benzodioxan-6-yl)[2-trifluoromethyl-4-(E-((4-carboethoxypiperidin-1-yl)carbonyl)ethenyl)phenyl]sulfide The title compound was prepared by the procedures described in Example 240 substituting N-(3'-aminopropyl)-2-pyrrolidinone with ethyl isonipecotate, giving a white sticky solid. $^1$H NMR (CDCl$_3$, 300 MHz) δ 1.26 (t, J=7.0 Hz, 3H), 1.68–1.80 (m, 2H), 1.98–2.10 (, 2H), 2.54–2.70 (m, 2H), 3.00–3.30 (br, 2H), 4.15 (m, 3H), 4.26–4.34 (m, 4H), 6.90 (d, J=8.0 Hz, 2H), 7.00 (dd, J=2.0, 8.0 Hz, 2H), 7.06 (d, J=2.0 Hz, 1H), 7.41 (m, 1H), 7.50 (br, 1H), 7.75 (s, 1H). MS (Cl/NH3) m/z 522 (M+H)$^+$. Anal. calcd. for C$_{24}$H$_{22}$F$_3$NO$_5$S.0.1 H$_2$O: C, 58.20; H, 4.52; N, 2.83. Found: C, 58.14; H, 4.69; N, 2.76.

Example 253

(Benzodioxan-6-yl)[2-trifluoromethyl-4-(E-((2-carbomethoxy-4-tert-butoxycarbonylpiperazin-1-yl)carbonyl)ethenyl)phenyl]sulfide The title compound was prepared by the procedures described in Example 240 substituting N-(3'-aminopropyl)-2-pyrrolidinone with 1-Boc-3-carbomethoxypiperazine, giving a white solid, mp 85–87° C. $^1$H NMR (CDCl$_3$, 300 MHz) δ 1.46 (s, 9H), 2.90–3.00 (m, 2H), 3.08–3.20 (m, 2H), 3.76 (s, 3H), 3.90 (m, 1H), 4.25–4.34 (m, 4H), 4.58–4.66 (m, 2H), 6.92 (d, J=8.0 Hz, 1H), 6.98 (m, 1H), 7.02 (dd, J=2.0, 8.0 Hz, 2H), 7.06 (d, J=2.0 Hz, 1H), 7.40 (m, 1H), 7.62 (br, 1H), 7.76 (s, 1H). MS (APCI) m/z 609 (M+H)+. Anal. calcd. for $C_{29}H_{31}F_3N_2O_7S$: C, 57.23; H, 5.13; N, 4.60. Found: C, 57.09; H, 5.25; N, 4.37.

Example 254

(Benzodioxan-6-yl)[2-trifluoromethyl-4-(E-((2-carbomethoxy-4-methoxycarbonylpiperazin-1-yl)carbonyl)ethenyl)phenyl]sulfide The title compound was prepared by treating the compound of Example 255 with methyl chloroformate and pyridine in $CH_2Cl_2$ at room temperature, producing a white foam. $^1$H NMR (CDCl$_3$, 300 MHz) δ 3.00 (m, 1H), 3.18 (m, 1H), 3.60 (m, 1H), 3.72 (s, 3H), 3.76 (s, 3H), 3.90 (m, 1H), 4.10 (br, 1H), 4.28–4.34 (m, 4H), 4.64 (m, 1H), 5.32 (m, 1H), 6.85 (d, J=15.5 Hz, 1H), 6.92 (d, J=8.0 Hz, 1H), 6.98 (m, 1H), 7.02 (dd, J=2.0, 8.0 Hz, 1H), 7.08 (d, J=2.0 Hz, 1H), 7.40 (d, J=8.0 Hz, 1H), 7.64 (d, J=15.0 Hz, 1H), 7.77 (s, 1H). MS (Cl/NH$_3$) m/z 567 (M+H)+. Anal. calcd. for $C_{26}H_{25}F_3N_2O_7S$: C, 55.12; H, 4.45; N, 4.94. Found: C, 55.18; H, 4.70; N, 4.68.

Example 255

(Benzodioxan-6-yl)[2-trifluoromethyl-4-(E-((2-carbomethoxypiperazin-1-yl)carbonyl)ethenyl)phenyl]sulfide The title compound was prepared by deprotection of compound 253 with TFA in $CH_2Cl_2$, resulting in a light yellow solid, mp 70–72° C. $^1$H NMR (CDCl$_3$, 300 MHz) δ 2.90 (m, 1H), 3.05 (m, 1H), 3.35 (m, 1H), 3.68 (m, 1H), 3.80 (s, 3H), 4 00 (m, 1H), 4.25–4.34 (m, 4H), 4,70 (br, 1H), 5.46 (m, 1H), 6.84 (d, J=15.5 Hz, 1H), 6.90 (d, J=8.0 Hz, 1H), 6.96–7.04 (m, 2H), 7.06 (m, 1H), 7.40 (d, J=8.0 Hz, 1H), 7.65 (d, J=15.5 Hz, 1H), 7.77 (s, 1H). MS (Cl/NH$_3$) m/z 509 (M+H)+. Anal. calcd. for $C_{24}H_{23}F_3N_2O_5S \cdot 1.55\ H_2O$: C, 53.74; H, 4.90; N, 5.22. Found: C, 54.04; H, 4.59; N, 4.82.

Example 256

(2-Methyl-3-(carboethoxymethyl)indol-5-yl)[2-trifluoromethyl-4-(E-((morpholin-1-yl)carbonyl)ethenyl)phenyl]sulfide Example 256A (4-Bromophenyl)[2-trifluoromethyl-4-(E-((morpholin-1-yl)carbonyl)ethenyl)phenyl]sulfide The bromide was prepared by the procedure described in Example 12, substituting 2-bromothiophenol with 4-bromothiophenol, and 3,4-dichlorobenzaldehyde with 4-fluoro-3-trifluoromethylbenzaldehyde.

Example 256B (4-Hydrazinophenyl)[2-trifluoromethyl-4-(E-((morpholin-1-yl)carbonyl)ethenyl)phenyl]sulfide, benzophenone hydrazone To a stirred solution of above-described bromide (1.0 g, 2.12 mmol) in 10 mL of toluene with Pd(OAc)$_2$ (9.5 mg, 0.04 mmol), BINAP (40 mg, 0.06 mmol), and benzophenone hydrazone (437 mg, 2.12 mmol) was added NaOt-Bu (285 mg, 2.97 mmol). The reaction mixture was bubbled with N$_2$ for 2 minutes before it was heated at 80° C. for 4 hours. The reaction mixture was then allowed to cool to ambient temperature. Ether was then added and the mixture was filtered through celite, washed with diethyl ether. The filtrate was concentrate in vacuo and the residue was purified on a SiO$_2$ flash column chromatography eluting with 10–30% EtOAc/hexanes to give 170 mg (13%) of the title compound as a light brown foamy solid.

Example 256C (2-Methyl-3-(carboethoxymethyl)indol-5-yl)[2-trifluoromethyl-4-(E-((morpholin-1-yl)carbonyl)ethenyl)phenyl]sulfide To a stirred solution of hydrazone (90 mg, 0.15 mmol) in 2 mL of ethanol was added levunilic acid (24 mL, 23 mmol) and p-TsOH (146 mg, 0.75 mmol). The mixture was then refluxed for 2 days. After cooling to ambient temperature, the reaction mixture was partitioned between EtOAc and sat. NaHCO$_3$. The organic layer was then washed with brine, dried over Na$_2$SO$_4$, concentrated in vacuo. The residue was then purified on Gilson preparative HPLC as described in Example 38B to give 6.0 mg (7%) of the title compound as a light-brown solid. $^1$H NMR (CDCl$_3$, 300 MHz) δ 1.20 (t, J=7.4 Hz, 3H), 2.46 (s, 3H), 3.55–3.83 (br m, 8H), 3.67 (s, 2H), 4.12 (q, J=7.4 Hz, 2H), 6.79 (d, J=15.3 Hz, 1H), 6.84 (d, J=8.4 Hz, 1H), 7.23–7.31 (m, 2H), 7.34 (d, J=8.4 Hz, 1H), 7.60 (d, J=15.3 Hz, 1H), 7.76 (s, 1H), 7.80 (s, 1H), 8.04 (s, 1H). MS (ESI+) (M+H)+ at m/z 533.

Example 257

(1-(2-Methoxyethyl)indol-5-yl)[2-chloro-4-(E-((4-acetylpiperazin-1-yl)carbonyl)ethenyl)phenyl]sulfide The title compound was prepared by the procedures described in Example 232, substituting t-butyl bromoacetate with bromoethylmethyl ether. white solid; $^1$H NMR (CDCl$_3$, 300 MHz) δ 2.14 (s, 2H), 3.35 (s, 3H), 3.46–3.56 (m, 2H), 3.56–3.80 (m, 6H), 3.75 (t, J=5.6 Hz, 2H), 4.33 (t, J=5.6 Hz, 2H), 6.54 (d, J=3.3 Hz, 1H), 6.61 (d, J=8.7 Hz, 1H), 6.75 (d, J=15.3 Hz, 1H), 7.09 (dd, J=2.1, 11.7 Hz, 1H), 7.26 (overlapping d, 1H), 7.36 (dd, J=2.1, 8.7 Hz, 1H), 7.44 (d, J=8.7 Hz, 1H), 7.51 (d, J=2.1 Hz, 1H), 7.56 (d, J=15.3 Hz, 1H), 7.88 (d, J=1.5 Hz, 1H). MS (ESI+) (M+H)+ at m/z 498, 500.

Example 258

(2-Isopropylphenyl)[2-nitro-4-(E-((3-acetoxymethyl-4-hydroxypiperidin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 1.51–1.90 (br m, 2H); 1.92–2.06 (m, 3H); 2.50–3.21 (br m, 2H); 3.30–3.40 (m, 1H); 3.40–4.44 (br m, 5H); 4.88–4.97 (br m, 1H); 6.63 (d, J=8.5 Hz, 1H); 7.31–7.62 (m, 6H); 7.87–7.94 (br m, 1H); 8.58–8.64 (br m, 1H). MS (APCI) (M+H)+ at m/z 499. Anal calcd for $C_{26}H_{30}N_2S_1O_6 \cdot 0.29H_2O$: C, 61.98; H, 6.12; N, 5.56. Found: C, 62.00; H, 6.35; N, 5.55.

Example 259

(2-Isopropylphenyl)[2-nitro-4-(E-((3-(dimethylaminocarbonyl)-4-hydroxypiperidin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.54–1.75 (br m, 2H); 2.81, 2.82 (br s, br s, 3H); 3.00, 3.04 (br s, br s, 3H); 2.75–3.60 (br m, 3H); 3.30–3.40 (m, 1H); 3.90–4.28 (br m, 2H); 4.95–5.28 (br m, 1H); 6.61–6.66 (m, 1H); 7.34–7.62 (m, 6H); 7.87–7.94 (br m, 1H); 8.58–8.63 (br m, 1H). MS (ESI) (M+H)$^+$ at m/z 498. Anal calcd for $C_{26}H_{31}N_3S_1O_5 \cdot 0.34H_2O$: C; 61.99; H, 6.34; N, 8.34. Found: C, 61.96; H, 6.37; N, 8.56.

Example 260

(2-Isopropylphenyl)[2-nitro-4-(E-((3-cyanomorpholin-1-yl)carbonyl)ethenyl)phenyl] sulfide Prepared according to the procedures of Example 71, giving a yellow solid. $^1$H NMR (DMSO-d$_6$, 300 MHz) δ 1.14 (d, J=6.8 Hz, 6H); 3.30–3.40 (m, 1H); 3.30–4.16 (br m, 5H); 4.20–4.29 (br m, 1H); 5.07 (t, J=3.5 Hz, 1H); 6.65(d, J=8.8 Hz, 1H); 7.32–7.44 (m, 2H); 7.54–7.62 (m, 4H); 7.91 (dd, J=8.8, 2.0 Hz, 1H); 8.67 (d, J=2.0 Hz, 1H). MS (APCI) (M+H)$^+$ at m/z 438. Anal calcd for $C_{23}H_{23}N_3S_1O_4 \cdot 0.25C_6H_{14}$: C, 64.11; H, 5.82; N, 9.15. Found: C, 63.99; H, 6.00; N, 9.12.

Example 261

(2-Isopropylphenyl)[2-nitro-4-(E-((3-carboethoxymorpholin-1-yl)carbonyl)ethenyl) phenyl]sulfide Prepared according to the procedures of Example 71, giving a yellow solid. $^1$H NMR (DMSO-d$_6$, 300 MHz) δ 1.14 (d, J=7.0 Hz, 6H); 1.12–1.27 (m, 3H); 3.30–3.40 (m, 1H); 3.15–4.33 (br m, 9H); 6.64 (d, J=8.5 Hz, 1H); 7.32–7.42 (m, 2H); 7.50–7.62 (m, 4H); 7.88–7.96 (br m, 1H); 8.65 (br s, 1H). MS (APCI) (M+H)$^+$ at m/z 485. Anal calcd for $C_{25}H_{28}N_2S_1O_6$: C, 61.97; H, 5.82; N, 5.78. Found: C, 61.83; H, 6.07; N, 5.74.

Example 262

(2-Isopropylphenyl)[2-nitro-4-(E-((3-(tetrazol-5-yl) morpholin-1-yl)carbonyl)ethenyl)phenyl]sulfide The compound of Example 260 (160 mg, 0.336), sodium azide (56.6 mg, 0.872 mmol), n-Bu$_3$SnCl and THF were mixed in a reaction tube, flushed with nitrogen and heated to reflux overnight. The mixture was then cooled to ambient temperature and 1N HCl soln. was added. The mixture was extracted with ethyl acetate three times and the combined organics were dried over MgSO$_4$. The mixture was filtered through a short silica gel plug to give 96 mg (56% yield) of the desired material. $^1$H NMR (DMSO-d$_4$, 300 MHz) δ 1.14 (d, J=6.8 Hz, 6H); 2.96–4.62 (br m, 7H); 4.77 (dd, J=10.5, 2.7 Hz, 1H); 6.58–6.67 (m, 1H); 7.32–7.62 (m, 6H); 7.92 (dd, J=8.8, 2.0 Hz, 1H); 8.62–8.67 (br m, 1H). MS (APCI) (M+H)$^+$ at m/z 481. Anal calcd for $C_{23}H_{24}N_6S_1O_4 \cdot 1.2H_2O$: C, 54.93; H, 5.31; N, 16.71. Found: C, 54.97; H, 5.12; N, 16.50.

Example 263

(Benzodioxan-6-yl)[2-trifluoromethyl-4-(E-((4-carboxypiperidin-1-yl)carbonyl)ethenyl)phenyl] sulfide The title compound was prepared by hydrolysis of the compound of Example 252 under basic conditions (aq. NaOH/EtOH), giving a white solid, mp 88° C. (dec.). $^1$H NMR (DMSO-d$_6$, 300 MHz) δ 1.40 (m, 2H), 1.98 (m, 2H), 2.95 (m, 1H), 3.15 (m, 1H), 3.45 (m, 1H), 4.20 (m, 2H), 4.35 (m, 4H), 7.00 (m, 4H), 7.20 (m, 2H), 7.90 (m, 1H), 8.20 (m, 1H), 12.30 (s, 1H). MS (APCI) m/z 494 (M+H)$^+$. Anal. calcd. for $C_{24}H_{22}F_3NO_5S \cdot 0.1 H_2O$: C, 58.20; H, 4.52; N, 2.83. Found: C, 58.14; H, 4.69; N, 2.76.

Example 264

(Benzodioxan-6-yl)[2-trifluoromethyl-4-(E-((2-carboxypiperidin-1-yl)carbonyl)ethenyl)phenyl] sulfide The title compound was prepared by hydrolysis of the compound of Example 249 under basic conditions (aq. NaOH/EtOH), resulting in a white solid, mp 90° C. (dec.). $^1$HNMR (DMSO-d$_6$, 300 MHz) δ 1.15–1.50 (m, 2H), 1.50–1.70 (m, 2H), 2.16 (m, 1H), 2.56 (m, 1H), 3.15 (m, 1H), 4.30 (s, 4H), 4.32 (m, 1H), 5.20 (m, 1H), 7.02 (m, 4H), 7.30–7.52 (m, 2H), 7.84 (m, 1H), 8.15 (s, 1H). MS (APCI) m/z 494 (M+H)$^+$. Anal. calcd. for $C_{24}H_{22}F_3NO_5 \cdot 0.3 H_2O$: C, 57.78; H, 4.57; N, 2.81. Found: C, 57.87; H, 4.5 7; N, 2.76.

Example 265

(Benzodioxan-6-yl)[2-trifluoromethyl-4-(E-((4-carbomethoxypiperazin-1-yl)carbonyl)ethenyl) phenyl]sulfide The title compound was prepared according to the procedures of Example 1. $^1$H NMR (CDCl$_3$, 300 MHz) δ 7.76 (s, 1H), 7.62 (d, 1H, J=15.0 Hz), 7.40 (d, 1H, J=8.6 Hz) 7.06 (d, 1H, J=2.1 Hz), 6.98–7.04 (m, 2H), 6.91 (d, 1H, J=8.4 Hz), 6.84 (d, 1H, J=15.6 Hz), 4.31 (m, 4H), 4.18 (q, 2H, J=7.1 Hz), 3.68 (br, 4H), 3.54 (br s, 4H), 1.29 (t, 3H, J=7.2 Hz). MS (ESI) m/z 523, 545, 1045, 1067.

Example 266

(Benzodioxan-6-yl)[2-trifluoromethyl-4-(E-((3-aza-6,9-dioxaspiro[5.4]decan-1-yl)carbonyl)ethenyl) phenyl]sulfide The title compound was prepared according to the procedures of Example 1. $^1$H NMR (DMSO-d$_6$, 300 MHz) δ 8.13 (s, 1H), 7.84 (d, 1H, J=9.0 Hz), 7.48 (d, 1H, J=15.4 Hz) 7.38 (d, 1H, J=15.4 Hz), 6.98–7.06 (m, 4H), 4.30 (m, 4H), 3.92 (s, 4H), 3.74 (br, 2H), 2.62 (br, 2H), 1.63 (br, 4H). MS (ESI) m/z 508, 1015.

Example 267

(Benzodioxan-6-yl)[2-trifluoro-4-(E-((4-(2-oxo-2,3-dihydro-1H-benzimidizol-1-yl)piperidin-1-yl) carbonyl)ethenyl)phenyl]sulfide The title compound was prepared according to the procedures of Example 1. $^1$H NMR (CDCl$_3$, 300 MHz) δ 8.32 (s, 1H), 7.79 (s, 1H), 7.66 (d, 1H, J=15.4 Hz), 7.44 (d, 1H, J=8.5 Hz), 7.0–7.12 (m, 6H), 6.94 (d, 1H, J=9.9 Hz), 6.90 (d, 1H, J=2.6 Hz), 4.98 (m, 1H), 4.59 (m,1H), 4.20 (m, 5H), 3.31 (br, 1H), 2.83 (br, 1H), 2.40 (m, 2H), 1.98 (m, 2H). MS (ESI) m/z 582, 604, 1163, 1185.

Example 268

(Benzodioxan-6-yl)[2-trifluoromethyl-4-(E-((4-(methylaminocarbonyl)piperidin-1-yl)carbonyl) ethenyl)phenyl]sulfide The title compound was prepared according to the procedures of Example 1. $^1$H NMR (CDCl$_3$, 300 MHz) δ 7.75

(s, 1H), 7.67 (d, 1H, J=15.4 Hz) 7.40 (d, 1H, J=8.1 Hz), 7.06 (d, 1H, J=2.4 Hz), 6.96–7.02 (m, 2H), 6.90 (d, 1H, J=8.2 Hz), 4.28 (m, 4H), 3.95 (br, 2H), 3.50 (m, 1H),2.82 (s, 3), 2.40 (m, 1H), 2.15 (br, 1H), 1.88 (br, 1H), 1.73 (br, 2H). MS (ESI) m/z 507, 529, 1035.

Example 269

(Benzodioxan-6-yl)[2-trifluoromethyl-4-(E-((3-carbomethoxy-4-methoxycarbonylpiperazin-1-yl)carbonyl)ethenyl)phenyl]sulfide The title compound was prepared by the procedures described in Example 240 substituting N-(3'-aminopropyl)-2-pyrrolidinone with 2-carbomethoxy-1-methoxycarbonylpiperazine, producing a light yellow solid, mp 56° C. (dec.). $^1$H NMR (CDCl$_3$, 300 MHz) δ 2.70–3.50 (br, 4H), 3.70 (s, 3H), 3.76 (d, J=9.0 Hz, 3H), 4.00(m, 1H), 4.20 (m, 4H), 4.50–5.00 (br, 2H), 6.91 (d, J=8.5 Hz, 1H), 6.92–7.02 (m, 2H), 7.07 (d, J=2.0 Hz, 1H), 7.25 (m, 1H), 7.40 (m, 1H), 7.60 (m, 1H), 7.72 (s, 1H). MS (APCI) m/z 567 (M+H)$^+$. Anal. calcd. for C$_{26}$H$_{25}$F$_3$N$_2$O$_7$S: C, 55.12; H, 4.45; N, 4.94. Found: C, 55.33; H, 4.74; N, 4.76.

Example 270

(2-Isopropylphenyl)[2-nitro-4-(E-((3-carboxymorpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 3.08–4.33 (br m, 7H); 3.30–3.40 (m, 1H); 6.58–6.68 (m, 1H); 7.32–7.66 (m, 6H); 7.87–7.94 (m, 1H); 8.53–8.65 (m, 1H). MS (APCI) (M+H)$^+$ at m/z 457. Anal calcd for C$_{23}$H$_{24}$N$_2$S$_1$O$_6$: C, 60.51; H, 5.30; N, 6.14. Found: C, 60.33; H, 5.54; N, 5.80.

Example 271

(Benzodioxan-6-yl)[2-trifluoromethyl-4-(E-((2-carboxy-4-methoxycarbonylpiperazin-1-yl)carbonyl)ethenyl)phenyl]sulfide The title compound was prepared by treating the compound of Example 255 with methyl chloroformate and pyridine in CH$_2$Cl$_2$ at room temperature, and followed by hydrolysis under basic conditions (aq. NaOH/EtOH), producing a white solid, mp 102° C. (dec.). $^1$H NMR (DMSO-d$_6$, 300 MHz) δ 2.85 (m, 1H), 3.02 (m, 1H), 3.20 (m, 1H), 3.40 (m, 1H), 3.62 (s, 3H), 3.88 (m, 1H), 4.29 (s, 4H), 4.35 (m, 1H), 5.15 (m, 1H), 6.90–7.10 (m, 3H), 7.30 (d, J=15.0 Hz, 1H), 7.40 (d, J=15.0 Hz, 1H), 7.54 (d, J=15.0 Hz, 1H), 7.82 (m, 1H), 8.15 (m, 1H). MS (ESI) m/z 553 (M+H)$^+$. Anal. calcd. for C$_{25}$H$_{23}$F$_3$N$_2$O$_7$S.0.25 H$_2$O: C, 53.91; H, 4.25; N, 5.03. Found: 53.91; H, 4.35; N, 5.05.

Example 272

(Benzodioxan-6-yl)[2-trifluoromethyl-4-(E-((morpholin-1-yl)carbonyl)ethenyl)phenyl]sulfide The title compound was prepared according to the procedures of Example 1. $^1$H NMR (CDCl$_3$, 300 MHz) δ 7.76 (s, 1H), 7.62 (d, 1H, J=15.6 Hz), 7.40 (dd, 1H, J=1.8, 8.2 Hz), 7.04 (d, 1H, J=2.1 Hz), 6.98–7.03 (m, 2H), 6.91 (d, 1H, J=8.1 Hz), 6.81 (d, 1H, J=15.3 Hz), 4.30 (m, 4H), 3.65–3.74 (br m, 8H). MS (ESI) m/z 452, 474, 925.

Example 273

(Benzodioxan-6-yl)[2-trifluoromethyl-4-(E-((4-(pyrrolidin-1-yl)piperidin-1-yl)carbonyl)ethenyl)phenyl]sulfide The title compound was prepared according to the procedures of Example 1. $^1$H NMR (CDCl$_3$, 300 MHz) δ 7.75 (s, 1H), 7.65 (d, 1H, J=15.3 Hz), 7.40 (dd, 1H, J=1.4, 8.3 Hz), 7.06 (d, 1H, J=2.4 Hz), 6.98–7.02 (m, 2H), 6.90 (d, 1H, J=8.1 Hz), 6.85 (d, 1H, J=15.3 Hz), 4.68 (m,1H), 4.20 (m, 4H), 3.10 (m,1H), 3.14 (m,1H), 2.81 (s, 4H), 2.58 (br, 1H), 2.02 (s, 4H), 1.88 (s, 4H), 1.64 (m,1H). MS (ESI) m/z 519, 1037.

Example 274

(2-Isopropylphenyl)[2-nitro-4-(E-(3-aza-6,9-dioxaspiro[5.4]decan-1-yl)carbonyl)ethenyl)phenyl]sulfide The title compound was prepared according to the procedures of Example 1. $^1$H NMR (CDCl$_3$, 300 MHz) δ 8.44 (s, 1H), 7.50–7.62 (m, 4H), 7.41(d, 1H, J=8.0 Hz), 7.30 (m, 1H), 6.96 (br d, 1H, J=15.6 Hz), 6.69 (d, 1H, J=9.4 Hz), 4.00 (s, 4H), 3.75 (br m, 4H), 3.44 (m, 1H), 1.75 (br s, 4H), 1.18 (d, 6H, J=7.0 Hz). MS (ESI) m/z 439, 937.

Example 275

(2-Isopropylphenyl)[2-nitro-4-(E-((2-(dimethylaminomethyl)piperidin-1-yl)carbonyl)ethenyl)phenyl]sulfide The title compound was prepared according to the procedures of Example 1. $^1$H NMR (CDCl$_3$, 300 MHz) δ 8.40 (d, 1H, J=1.8 Hz), 7.50–7.58 (m,4H), 7.42 (d, 1H, J=8.1 Hz), 7.30 (dd, 1H, J=1.9, 7.0 Hz), 7.00 (d, 1H, J=15.4 Hz), 6.68 (d, 1H, J=8.5 Hz), 5.10 (br, 1H), 3.92 (br, 1H), 3.44 (quintet, 1H, J=6.9 Hz), 3.20 (m,1H), 2.26–2.50 (m, 7H), 1.62–1.85 (m, 7H), 1.48 (m,1H), 1.18 (d, 6H, J=7.0 Hz). MS (ESI) m/z 468.

Example 276

(2-Isopropylphenyl)[2-nitro-4-(E-((piperidin-1-ylamino)carbonyl)ethenyl)phenyl]sulfide The title compound was prepared according to the procedures of Example 1. $^1$H NMR (CDCl$_3$, 300 MHz) δ 8.44 (d, 1H, J=1.8 Hz), 7.66 (d, 1H, J=16.2 Hz), 7.55 (d, 1H, J=7.4 Hz), 7.47–7.51 (m, 3H), 7.30 (m,2H), 6.72 (d, 1H, J=8.5 Hz), 6.37 (s, 1H), 3.48 (m, 2H), 3.10 (m,2H), 2.63 (m,1H), 1.81–1.89 (m,2H), 1.62–1.77 (m,4H), 1.19 (d, 6H, J=7.0 Hz). MS (ESI) m/z 426, 851.

Example 277

(Benzodioxan-6-yl)[2-trifluoromethyl-4-(E-((3-carboxy-4-methoxycarbonylpiperazin-1-yl)carbonyl)ethenyl)phenyl]sulfide The title compound was prepared by hydrolysis of the compound of Example 269 under basic conditions (aq. NaOH/EtOH). $^1$H NMR (DMSO-d$_6$, 300 MHz) δ 2.60–3.30 (m, 3H), 3.40–3.50 (m, 1H), 3.62 (d, J=12.0 Hz 1H),3.80 (m, 1H), 4.25–4.35 (m, 4H), 4.55 (m, 1H), 7.00 (s, 2H), 7.00–7.06 (m, 1H), 7.25 (m,2H), 7.5 (m, 1H), 7.80 (m, 1H), 8.10 (m, 1H). MS (APCI) m/z 553 (M+H)$^+$. Calcd. Anal. C$_{24}$H$_{23}$F$_3$N$_2$O$_5$.1.55 H$_2$O: C, 54.35; H, 4.20; N, 5.07. Found: C, 54.16; H, 4.19; N, 4.96.

Example 278

(2-(Dimethylaminocarbonyl)-benzodioxan-6-yl)[2-chloro-4-(E-((4-acetylpiperazin-1-yl)carbonyl)ethenyl)phenyl]sulfide The title compound was prepared by the procedures described in Example 85, substituting 5-iodoindole with 2-N,N-dimethylcarboxamide-6-bromobenzenedioxane and 3-N,N-dimethylcarboxamide-6-bromobenzenedioxane, giving a white solid. $^1$H NMR (CDCl$_3$, 300 MHz, mixture of regioisomers) δ 1.93 (s, 3H), 2.15 (s, 6H), 3.53 (br s, 2H), 3.59–3.90 (br m, 8H), 4.86–5.01 (m, 1H), 6.74–6.81 (m, 1H), 6.80 (d, J=15.3 Hz, 1H), 6.93 (d, J=8.7 Hz, 1H), 7.02 (d, CDCl$_3$1.8 Hz, 1H), 7.13 (dd, J=1.8, 8.4 Hz, 1H), 7.16–7.25 (m, 1H), 7.54 (s, 1H), 7.58 (d, J=15.6 Hz, 1H). MS (ESI$^+$) (M+Na)$^+$ at m/z 552, 554.

Example 279

(2-Isopropylphenyl)[2-nitro-4-(E-((3-(2-(methoxymethyl)tetrazol-5-yl)piperidin-1-yl)carbonyl)ethenyl)phenyl]sulfide The title compound was prepared by the procedures described in Example 225, substituting ethyl nipecotate with 3-N-methoxymethyltetrazolylpiperidine, to give a light-yellow solid. $^1$H NMR (CDCl$_3$, 300 MHz) δ 1.19 (d, J=6.9 Hz, 6H), 1.62–1.80 (br m, 2H), 1.80–2.20 (br m, 2H), 2.20–2.39 (br m, 2H), 3.12–3.38 (br m, 2H), 3.46 (s, 3H), 4.11 (septet, J=6.9 Hz, 1H), 4.17–4.34 (br m, 1H), 5.79 (s, 2H), 6.70 (br s, 1H), 7.05 (d, J=15.3 Hz, 1H), 7.31 (d, J=7.8 Hz, 1H), 7.35–7.68 (m, 5H), 8.42 (br s, 1H). MS (ESI$^+$) (M+H)$^+$ at m/z 523.

Example 280

(2-Isopropylphenyl)[2-nitro-4-(E-((3-(1-(methoxymethyl)tetrazol-5-yl)piperidin-1-yl)carbonyl)ethenyl)phenyl]sulfide The title compound was prepared by the procedures described in Example 279 and separated from the same reaction mixture via SiO$_2$ flash column chromatography, to give a light-yellow solid. $^1$H NMR (CDCl$_3$, 300 MHz) δ 1.19 (d, J=6.9 Hz, 6H), 1.62–1.80 (br m, 2H), 1.80–2.20 (br m, 2H), 2.20–2.39 (br m, 2H), 3.12–3.38 (br m, 2H), 3.46 (s, 3H), 4.11 (septet, J=6.9 Hz, 1H), 4.17–4.34 (br m, 1H), 5.79 (s, 2H), 6.70 (br s, 1H), 7.05 (d, J=15.3 Hz, 1H), 7.31 (d, J=7.8 Hz, 1H), 7.35–7.68 (m, 5H), 8.42 (br s, 1H). MS (ESI$^+$) (M+H)$^+$ at m/z 523.

Example 281

(1-Methylindol-5-yl)[2-chloro-4-(E-((3-(2-oxopyrrolidin-1-yl)propylamino)carbonyl)ethenyl)phenyl]sulfide

Example 281A

Triisopropylsilyl(1-methylindol-5-yl)sulfide

To a stirred solution of 5-bromo-N-methyl indole (300 mg, 1.43 mmol) in 5 mL of benzene in a sealed tube was added Pd(PPh$_3$)$_4$ (82 mg, 0.072 mmol), followed by KSTIPS (326 mg, 1.43 mmol). The mixture was flushed with N$_2$, the tube was capped, and the reaction mixture refluxed for 2 hours. The reaction mixture was then allowed to cool, partitioned between Et$_2$O and water. The organic layer was washed with brine, dried over Na$_2$SO$_4$, concentrated in vacuo. The residue was purified on a SiO$_2$ flash column chromatography eluting with 5% EtOAc/hexanes to give 400 mg (88%) of the title compound as a colorless oil.

Example 281B

3-Chloro-4-((1-methylindol-5-yl)thio)benzaldehyde

To a stirred solution of thiolsilyl ether (1.0 g, 3.13 mmol) in 5 mL of DMF with 3-chloro-4-fluorobenzaldehyde (500 mg, 3.13 mmol) at ambient temperature was added CsF (5.7 mg, 0.38 mmol). The mixture was stirred overnight before it was poured in water and extracted with Et$_2$O (2×25 mL). The combined organic layer was washed with water and brine, dried over Na$_2$SO$_4$, concentrated in vacuo. The residue was purified on a SiO$_2$ flash column chromatography eluting with 5–10% EtOAc/hexanes to give 650 mg (71%) of the title compound as a white solid.

Example 281C (1-Methylindol-5-yl)[2-chloro-4-(E-((3-(2-oxopyrrolidin-1-yl)propylamino)carbonyl)ethenyl)phenyl]sulfide The title compound was prepared by the procedures described in Example 92, substituting the benzoic acid with cinnamic acid prepared from the above-described aldehyde, and ammonium with 3-aminopropyl-1-pyrrolidin-2-one, to give a white solid. $^1$H NMR (CDCl$_3$, 300 MHz) δ 1.74 (br m, 2H), 2.07 (br m, 2H), 2.44 (br m, 2H), 3.32 (br m, 2H), 3.40 (br m, 4H), 3.85 (s, 3H), 6.36 (d, J=15.3 Hz, 1H), 7.14 (d, J=3.0 Hz, 1H), 7.36 (dd, J=1.5, 9.0 Hz, 1H), 7.41 (d, J=9.0 Hz, 1H), 7.50 (s, 1H), 7.89 (d, J=1.5 Hz, 1H). MS (ESI$^+$) (M+H)$^+$ at m/z 468, 470. Anal. Calcd for C$_{25}$H$_{26}$ClN$_3$O$_2$S.1.37 H$_2$O: C, 60.95; H, 5.88; N, 8.53. Found: C, 60.97; H, 5.98; N, 8.46.

Example 282

(2-Isopropylphenyl)[2-nitro-4-(E-((3-(tetrazol-5-yl)piperidin-1-yl)carbonyl)ethenyl)phenyl]sulfide The compound from Example 279 (75 mg, 0.14 mmol) was dissolved in 1 mL of neat TFA and left at ambient temperature for overnight. The reagent was then removed in vacuo and the residue was evaporated twice with benzene. The crude product was purified using Gilson Preparative HPLC as described in Example 38B to give the title compound as a light-yellow solid (50 mg, 72%); $^1$H NMR (CDCl$_3$, 300 MHz) δ 1.17 (d, J=6.5 Hz, 6H), 1.25–1.39 (m, 1H), 1.69–1.81 (m, 1H), 2.09 (br s, 1H), 2.14–2.30 (m, 1H), 2.57–2.71 (m, 1H), 3.35–3.66 (m, 3H), 3.90–4.03 (m, 1H), 4.66–4.78 (m, 1H), 6.73 (d, J=8.7 Hz, 1H), 6.86 (d, J=15.3 Hz, 1H), 7.32 (dd, J=2.1, 6.9 Hz, 1H), 7.42 (dd, J=2.1, 8.7 Hz, 1H), 7.47–7.57 (m, 3H), 7.76 (d, J=15.3 Hz, 1H), 8.46 (d, J=2.1 Hz, 1H). MS (ESI$^+$) (M+H)$^+$ at m/z 479. Anal. Calcd for C$_{24}$H$_{26}$N$_6$O$_3$S.0.28 H$_2$O: C, 59.61; H, 5.54; N, 17.38. Found: C, 59.71; H, 5.44; N, 16.99.

Example 283

(1-Methylindol-5-yl)[2-chloro-4-(E-((3-carboethoxypiperidin-1-yl)carbonyl)ethenyl)phenyl]sulfide The title compound was prepared by the procedures described in Example 281C, substituting aminopropyl pyrrolidinone with ethyl nipecotate, giving a white solid. $^1$H NMR (CDCl$_3$, 300 MHz) δ 1.26 (t, J=7.5 Hz, 3H), 1.65–1.96 (m, 2H), 2.00–2.20 (m, 1H), 2.04 (s, 1H), 2.54 (br m, 1H), 3.12–3.34 (m, 1H), 3.85 (s, 3H), 3.92–4.07 (m, 1H), 4.07–4.20 (m, 1H), 4.15 (q, J=7.5 Hz, 2H), 4.65–4.90 (m, 1H), 6.53 (d, J=3.0 Hz, 1H), 6.57(d, J=8.1 Hz, 1H), 6.85 (d, J=15.3 Hz, 1H), 7.08 (d, J=8.7 Hz, 1H), 7.14 (d, J=3.0 Hz, 1H), 7.37 (dd, J=1.5, 8.7 Hz, 1H), 7.42 (d, J=8.7 Hz, 1H), 7.51 (s, 1H), 7.51 (d, J=15.3 Hz, 1H), 7.89 (d, J=1.5 Hz, 1H). MS (ESI$^+$) (M+H)$^+$ at m/z 483, 485.

Example 284

(1-Methylindol-5-yl)[2-chloro-4-(E-((3-carboxypiperidin-1-yl)carbonyl)ethenyl)phenyl]sulfide The title compound was prepared by the procedures described in Example 155, substituting the ethyl nipecotate from Example 137 with ethyl ester from Example 283, and KOH with NaOH, to provide a white solid. $^1$H NMR (CDCl$_3$, 300 MHz) δ 1.45–1.69 (m, 1H), 1.69–1.98 (m, 2H), 1.98–2.22 (m, 1H), 2.51–2.70 (m, 1H), 3.05–3.47 (m, 1H), 3.80–4.20 (m, 2H), 3.85 (s, 3H), 4.47–4.68 (m, 1H), 6.53 (d, J=3.0 Hz, 1H), 6.57 (d, J=8.1 Hz, 1H), 6.87 (d, J=15.3 Hz, 1H), 7.08 (d, J=8.1 Hz, 1H), 7.14 (d, J=3.0 Hz, 1H), 7.37 (d, J=9.0 Hz, 1H), 7.42 (d, J=9.0 Hz, 1H), 7.51 (s, 1H), 7.52 (d, J=15.3 Hz, 1H), 7.89 (br s, 1H). MS (ESI$^+$) (M−H+H)$^+$ at m/z 453, 455.

Example 285

(1-Methylindol-5-yl)[2-chloro-4-(E-((4-carboethoxypiperidin-1-yl)carbonyl)ethenyl)phenyl]sulfide The title compound was prepared by the procedures described in Example 281C, substituting aminopropyl pyrrolidinone with ethyl isonipecotate, giving a white solid. $^1$H NMR (CDCl$_3$, 300 MHz) δ 1.26 (t, J=7.5 Hz, 3H), 1.64–1.83 (m, 2H), 1.88–2.08 (m, 2H), 2.48–2.67 (m, 1H), 2.86–3.40 (m, 2H), 3.85 (s, 3H), 3.89–4.24 (m, 1H), 4.15 (q, J=7.5 Hz, 2H), 4.24–4.65 (m, 1H), 6.53 (d, J=3.0 Hz, 1H), 6.58 (d, J=8.1 Hz, 1H), 6.81 (d, J=15.3 Hz, 1H), 7.07 (d, J=8.1 Hz, 1H), 7.14 (d, J=3.0 Hz, 1H), 7.37 (dd, J=1.5, 9.0 Hz, 1H), 7.50 (d, J=9.0 Hz, 1H), 7.50 (d, J=15.3 Hz, 1H), 7.88 (d, J=1.5 Hz, 1H). MS (ESI$^+$) (M+H)$^+$ at m/z 483, 485.

Example 286

(1-Methylindol-5-yl)[2-chloro-4-(E-((4-carboxypiperidin-1-yl)carbonyl)ethenyl)phenyl]sulfide The title compound was prepared by the procedures described in Example 155, substituting the ethyl ester from Example 137 with ethyl ester from Example 285, and KOH with NaOH, giving a white solid. $^1$H NMR (CDCl$_3$, 300 MHz) δ 1.60–1.90 (m, 2H), 1.90–2.10 (m, 2H), 2.57–2.72 (m, 1H), 2.80–3.40 (m, 2H), 3.85 (s, 3H), 3.91–4.20 (m, 1H), 4.30–4.68 (m, 1H), 6.53 (d, J=3.0 Hz, 1H), 6.57 (d, J=8.1 Hz, 1H), 6.80 (d, J=15.3 Hz, 1H), 7.07 (d, J=8.1 Hz, 1H), 7.15 (d, J=3.0 Hz, 1H), 7.37 (dd, J=1.5, 9.0 Hz, 1H), 7.51 (d, J=9.0 Hz, 1H), 7.51 (s, 1H), 7.51 (d, J=15.3 Hz, 1H), 7.89 (br s, 1H). MS (ESI$^+$) (M+H)$^+$ at m/z 455, 457. Anal. Calcd for C$_{24}$H$_{23}$ClN$_2$O$_3$S.0.42 H$_2$O: C, 62.32; H, 5.20; N, 6.06. Found: C, 62.35; H, 5.30; N, 5.87.

Example 287

(2-Isopropylphenyl)[2-nitro-4-(E-((2-(1-methylprrolidin-2-yl)ethylamino)carbonyl)ethenyl)phenyl]sulfide The title compound was prepared according to the procedures of Example 1. $^1$H NMR (CDCl$_3$, 300 MHz) δ 8.44 (d, 1H, J=1.8 Hz), 7.56 (d, 1H, J=3.7 Hz), 7.50–7.58 (m, 3H), 7.43 (DD, 1H, J=1.84, 8.4 Hz), 7.30 (dd, 1H, J=2.2, 6.8 Hz), 6.78 (d, 1H, J=8.5 Hz), 6.52 (d, 1H, J=15.8 Hz), 3.63 (m,2H), 3.42 (m, 3H), 3.00 (m,1H), 3.78 (m,1H), 2.59 (s, 3H), 2.05 (m,1H), 2.00 (m, 5H), 1.18 (d, 6H, J=7.0 Hz). MS (ESI) m/z 454, 490.

Example 288

(2-Isopropylphenyl)[2-nitro-4-(E-((4-pyrrolidin-1-yl)piperidin-1-yl)carbonyl)ethenyl)phenyl]sulfide The title compound was prepared according to the procedures of Example 1. $^1$H NMR (CDCl$_3$, 300 MHz) δ 8.43 (d, 1H, J=1.8 Hz), 7.57 (d, 1H, J=8.5 Hz), 7.51–7.55 (m, 3H), 7.41 (dd, 1H, J=1.84, 8.8 Hz), 7.31 (dd, 1H, J=2.4, 7.5 Hz), 6.92 (d, 1H, J=15.4 Hz), 6.70 (d, 1H, J=8.5 Hz), 4.70 (m, 1H), 4.10 (m,1H), 3.44 (pent, 1H, J=6.8 Hz), 3.16 (m, 1H), 2.80 (br, 4H), 2.55 (br, 1H), 2.03 (m,4H), 1.90 (m, 4H), 1.65 (m, 1H), 1.18 (d, 6H, J=7.0 Hz). MS (ESI) m/z 480, 959.

Example 289

(2-Isopropylphenyl)[2-nitro-4-(E-((4-sulfopiperidin-1-yl)carbonyl)ethenyl)phenyl]sulfide The title compound was prepared according to the procedures of Example 1. $^1$H NMR (DMSO-d$_6$, 300 MHz) δ 8.63 (d, 1H, J=1.8 Hz), 7.92 (dd, 1H, J=1.8, 8.8 Hz), 7.60 (m, 3H), 7.47 (d, 1H, J=14.2 Hz), 7.42 (d, 1H, J=14.2 Hz), 6.62 (d, 1H, J=8.5 Hz), 4.45 (m, 2H), 4.38 (m, 2H), 3.34 (m, 1H), 3.00 (m, 2H), 2.70 (m, 1H), 2.60 (m,2H), 1.14 (d, 6H, J=6.9 Hz). MS (ESI) m/z 491, 981.

Example 290

(2-Isopropylphenyl)[2-nitro-4-(E-((3-hydroxypiperidin-1-yl)carbonyl)ethenyl)phenyl]sulfide The title compound was prepared according to the procedures of Example 1. $^1$H NMR (CDCl$_3$, 300 MHz) δ 8.43 (s, 1H), 7.50–7.62 (m, 4H), 7.41 (d, 1H, J=8.1 Hz), 6.97 (m, 1H), 6.69 (d, 1H, J=8.1 Hz), 3.85 (m, 2H), 3.65 (m, 1H), 3.50 (m,3H), 1.93 (m,2H), 1.65 (m, 2H), 1.18 (d, 6H, J=6.6 Hz). MS (ESI) m/z 427, 449, 853, 875.

Example 291

(Benzodioxan-6-yl)[2-trifluoromethyl-4-(E-((3-((ethanesulfonylamino)carbonyl)piperidin-1-yl)carbonyl)ethenyl)phenyl]sulfide The title compound was prepared by the procedures described in Example 227. The product was purified by reversed-phase HPLC. $^1$H NMR (CDCl$_3$, 300 MHz) δ 1.34 (t, J=7.0 Hz, 2H), 1.44 (t, J=7.0 Hz, 3H), 1.95 (br, 1/2H), 2.20 (br, 1/2H), 2.68 (br, 1H), 3.14 (q, J=7.0 Hz, 2H), 3.45 (m, 1H), 3.65 (m, 1H), 3.93 (m, 1H), 4.30 (m, 4H), 4.50–4.60 (br, 2H), 6.92 (d, J=8.0 Hz, 1H), 6.98–7.04 (m, 3H), 7.06 (m, 1H), 7.40 (d, J=8.0 Hz, 1H), 7.65 (m, 1H), 7.75 (s, 1H). MS (APCI) m/z 585 (M+H)$^+$.

Example 292

(Benzodioxan-6-yl)[2-trifluoromethyl-4-(E-((3-((p-toluenesulfonylamino)carbonyl)piperidin-1-yl)carbonyl)ethenyl)phenyl]sulfide The title compound was prepared by the same procedure described in Example 229. $^1$H NMR (CDCl$_3$, 300 MHz) δ 1.25 (m, 2H), 1.55 (m, 1H), 1.70–2.25 (br, 1H), 2.41 (d, J=13.0 Hz, 3H), 2.55 (br, 1H), 3.50–3.80 (br, 2H), 4.20–4.35 (m, 4H), 4.68–4.75 (m, 2H), 6.90 (d, J=8.0 Hz, 1H), 7.00–7.10 (m, 2H), 7.30 (d, J=8.0 Hz, 1H), 7.81 (d, J=8.0 Hz, 1H), 7.91 (m, 1H). MS (CI/NH$_3$) m/z 647 (M+H)$^+$. Anal. calcd. for C$_{31}$H$_{29}$F$_3$N$_2$O$_6$S$_2$.0.5 H$_2$O: C, 56.78; H, 4.61; N, 4.27. Found: C, 56.86; H, 4.69; N, 4.35.

Example 293

(Benzodioxan-6-yl)[2-trifluoromethyl-4-(E-((4-((ethanesulfonylamino)carbonyl)piperidin-1-yl)carbonyl)ethenyl)phenyl]sulfide The title compound was prepared by the procedures described in Example 227, giving a white foam. $^1$H NMR (CDCl$_3$, 300 MHz) δ 1.35–1.40 (m, 2H), 1.44 (t, J=7.0 Hz, 3H), 1.76 (m, 1H), 2.0 (m, 1H), 2.50–3.20 (br, 1H), 3.15 (q, J=7.0 Hz, 2H), 3.40–3.55 (m, 2H), 4.25–4.32 (m, 4H), 4.52 (br, 2H), 6.90 (d, J=8.0 Hz, 1H), 6.98–7.05 (dd, J=2.0, 8.0 Hz, 2H), 7.06 (d, J=2.0 Hz, 1H), 7.40 (m, 1H), 7.60 (m, 1H), 7.75 (s, 1H), 8.22 (br, 1H). MS (APCI) m/z 585 (M+H)$^+$. Anal. calcd. for C$_{26}$H$_{27}$F$_3$N$_2$O$_6$S$_2$0.8 H$_2$O: C, 52.13; H, 4.81; N, 4.68. Found: C; 52.14; H, 4.80; N, 4.66.

Example 294

(Benzodioxan-6-yl)[2-trifluoromethyl-4-(E-((2-(tetrazol-5-yl)morpholin-1-yl)carbonyl)ethenyl)phenyl]sulfide The corresponding nitrile (160 mg, 0.336 mmol, prepared via the procedures of Example 1), sodium azide (56.6 mg, 0.872 mmol), n-Bu$_3$SnCl and THF were mixed in a reaction tube, flushed with nitrogen and heated to reflux overnight. The mixture was then cooled to ambient temperature, and 1N HCl soln. was added. The mixture was extracted with ethyl acetate three times and the combined organics were dried over MgSO$_4$. The mixture was filtered through a short silica gel plug to give 96 mg (56% yield) of the desired material. $^1$H NMR (DMSO-d$_6$, 500 MHz, 100° C.) δ 7.99 (d, 1H, J=1.7 Hz), 7.79 (dd, 1H, J=2.0, 8.6 Hz), 7.50 (d, 1H, J=15.3 Hz), 7.24 (d, 1H, J=15.6 Hz), 7.14 (d, 1H, J=8.2 Hz), 6.96 (m, 1H), 6.94 (d, 1H, J=2.1 Hz), 6.92 (m, 1H), 4.60 (dd, 1H, J=3.0, 9.8 Hz), 4.50 (br d, 1H, J=12.2 Hz), 4.26 (m, 5H), 4.17 (m, 1H), 4.00 (dt, 1H, J=3.2, 11.6 Hz), 3.72 (td, 1H, J=3.0, 11.0 Hz), 3.43 (br m, 1H), 3.29 (br m, 1H). MS (ESI) m/z −518. Anal. Calcd for C$_{23}$H$_{20}$F$_3$N$_5$O$_4$S. 1.83 HOAc: C, 50.88; H, 4.38; N, 11.13. Found: C, 50.61; H, 4.46; N, 11.4.

Example 295

(2-Isopropylphenyl)[2-nitro-4-(E-((2-butyl,5-(tetrazol-5-yl)morpholin-1-yl)carbonyl)ethenyl)phenyl]sulfide Example 295A 2-Butyl-5-cyanomorpholine The title compound was prepared by the procedures described in Example 260A, substituting ethanolamine with 2-aminohexanol.

Example 295B (2-Isopropylphenyl)[2-nitro-4-(E-((2-butyl-5cyanomorpholin-1-yl)carbonyl)ethenyl)phenyl]sulfide The title compound was prepared by the procedures described in Example 260B, substituting the morpholine from Example 260A with the compound of Example 295A.

Example 295C (2-Isopropylphenyl)[2-nitro-4-(E-((2-butyl-5-(tetrazol-5-yl)morpholin-1-yl)carbonyl)ethenyl)phenyl]sulfide The title compound was prepared by the procedures described in Example 262, substituting the nitrile compound from Example 260 with the compound of Example 295B, giving a light-yellow solid. $^1$H NMR (CDCl$_3$, 300 MHz, 3:2 mixture of diastereomers) δ 0.89 (t, J=7.5 Hz, 1H), 1.01 (br m, 1H), 1.19 (d, J=6.5 Hz, 6H), 1.23–1.43 (m, 4H), 1.68–1.84 (m, 1H), 3.10–3.61 (m, 2H), 3.83–4.17 (m, 2H), 4.40–5.26 (m, 2H), 6.67–6.77 (m, 1H), [6.91 (d), 7.02 (d), J=15.3 Hz, 1H in total], 7.25–7.37 (m, 2H), 7.44–7.60 (m, 3H), [7.67 (d), 7.79 (d), J=15.3 Hz, 1H in total], 8.43–8.50 (m, 1H). MS (ESI$^+$) (M–H)$^+$ at m/z 535.

Example 296

(2-(and 3-)(Hydroxymethyl)-benzodioxan-6-yl)[2-nitro-4-(E-((4-acetylpiperazin-1-yl)carbonyl)ethenyl)phenyl]sulfide Example 296A Triisopropylsilyl (2-(and 3-)hydroxymethylbenzodioxan-6-yl)sulfide The title compound was prepared by the procedures described in Example 281A, substituting 5-bromo-N-methyl indole with a mixture of 6-bromo-2-hydroxymethylbenzenedioxane and 6-bromo-3-hydroxymethylbenzenedioxane.

Example 296B (2-(and 3-)(Hydroxymethyl)-benzodioxan-6-yl)[2-nitro-4-(E-((4-acetylpiperazin-1-yl)carbonyl)ethenyl)phenyl]sulfide The title compound was prepared by the procedures described in Example 281B, substituting 3-chloro-4-fluorobenzaldehyde with 4-chloro-3-nitrocinnamide, giving a light yellow solid. $^1$H NM (CDCl$_3$, 300 MHz, 3:2 mixture of diastereomers) δ [2.11 (s), 2.15 (s), 3H in total], 3.48–3.83 (m, 8H), 3.83–4.04 (m, 2H), 4.20 (dd, J=8.4, 11.4 Hz, 1H), 4.26–4.44 (m, 2H), 6.89 (d, J=5.7 Hz, 1H), 6.92 (s, 1H), 6.97–7.11 (m, 1H), 7.04 (d, J=15.0 Hz, 1H), 7.14 (d, J=2.1 Hz, 1H), 7.46 (br d, J=9.0 Hz, 1H), 7.65 (d, J=15.0 Hz, 1H), 8.41 (d, J=2.1 Hz, 1H). MS (ESI$^+$) (M+H)$^+$ at m/z 500.

Example 297

(2-(and 3-)(Hydroxymethyl)-benzodioxan-6-yl)[2-nitro-4-(E-((3-(2-nitro-4-(E-((3-(2-oxopyrrolidin-1-yl)prop-1-ylamino)carbonyl)ethenyl)phenyl]sulfide The title compound was prepared by the procedures described in Example 296B, substituting the acetylpiperazine 4-chloro-3-nitrocinnamide with 3-aminopropyl-1-pyrrolidin-3-one 4-chloro-3-nitrocinnamide, giving a light-yellow solid. $^1$H NMR (CDCl$_3$, 300 MHz, 3:2 mixture of diastereomers) δ 1.75 (br m, 2H), 2.08 (p, J=7.5 Hz, 2H), 2.45 (t, J=7.5 Hz, 2H), 3.27–3.48 (m, 6H), 3.82–4.03 (m, 2H), 4.13–4.44 (m, 3H), 6.49 (d, J=15.0 Hz, 1H), 6.88 (d, J=8.4 Hz, 1H), [6.99 (d), 7.01 (d), J=8.4 Hz, 1H in total], [7.06 (dd), 7.08 (dd), J=1.5, 2.4 Hz, 1H in total], [7.13 (d), 7.14 (d), J=2.4 Hz, 1H in total], 7.17 (br s, 1H), 7.46 (d, J=8.4 Hz, 1H), 7.54 (d, J=15.0 Hz, 1H), 8.36 (d, J=1.5 Hz, 1H). MS (ESI$^+$) (M+H)$^+$ at m/z 514.

Example 298

(2-(and 3-(Hydroxymethyl)-benzodioxan-6-yl)[2-trifluoromethyl-4-(E-((3-(2-oxopyrrolidin-1-yl)prop-1-ylamino)carbonyl)ethenyl)phenyl]sulfide The title compound was prepared by the procedures described in Example 281, substituting 6-thiolsilyl indole with the thiolsilyl ether described in Example 296A, and 3-chloro4-fluorobenzaldehyde with 4-fluoro-3- trifluoromethylbenzaldehyde, producing a white solid. $^1$H NMR (CDCl$_3$, 300 MHz, 3:2 mixture of diastereomers) δ 1.75 (br m, 2H), 2.09 (br m, 2H), 2.45 (br m, 2H), 3.25–3.60 (m, 6H), 3.80–4.43 (m, 5H), 6.46 (d, J=15.3 Hz, 1H), [6.92 (d), 6.95 (d), J=6.8 Hz, 1H in total], [7.03 (d), 7.04 (d), J=8.1 Hz, 1H in total], 7.06–7.10 (m, 1H), 7.13 (br s, 1H), 7.42 (d, J=8.1 Hz, 1H), 7.54 (d, J=15.3 Hz, 1H), 7.77 (s, 1H). MS (ESI$^+$) (M+H)$^+$ at m/z 537.

Example 299

(3-Hydroxymethyl)-benzodioxan-6-yl)[2-nitro-4-(E-((3-(2-oxopyrrolidin-1-yl)prop-1-ylamino)carbonyl)ethenyl)phenyl]sulfide

Example 299A 3-(Hydroxymethyl)-6-bromo-benzodioxane

To a stirred solution of 5-bromosalicylaldehyde (5.0 g, 24.9 mmol), and epichlorohydrin (5.6 mL, 72.1 mmol) in 20 mL of DMF at 80° C. was added K$_2$CO$_3$ slowly in portions. The resulting mixture was then heated at 90° C. for 3 hours. Reaction was then stopped, water was added, extracted with diethyl ether. The organic extracts were washed with water, brine, dried over Na$_2$SO$_4$, concentrated in vacuo. The residue was purified on a SiO$_2$ flash column chromatography eluting with 15–30% EtOAc/hexanes to give 2.82 g (44%) of the title compound as a colorless oil.

To a stirred solution of the aldehyde (2.82 g, 11 mmol) in 35 mL of CHCl$_3$ was added mCPBA (2.27 g, 13 mmol). The mixture was stirred at ambient temperature for 30 minutes and then heated at 50° C. for 2 hours. The reaction was then quenched with aq. Na$_2$S$_2$O$_5$, extracted with Et$_2$O (2×50 mL). The combined organic layer was washed with aq. NaHCO$_3$, brine, dried over Na$_2$SO$_4$, concentrated in vacuo to give 2.92 g of crude product which was proceeded to the next step without purification.

To a stirred solution of the above-described crude formate (2.92 g) in 5 mL of THF was added 3N aq. NaOH (3.9 mL, 11.7 mmol). The reaction mixture was then heated at 70° C. for 4 hours. The reaction mixture was then partitioned between EtOAc and water. The organic layer was then washed with brine, dried over Na$_2$SO$_4$, concentrated in vacuo to give 2.50 g (93% over two steps) of the title compound.

Example 299B

Triisopropyl (3-(hydroxymethyl)-benzodioxan-6-yl)sulfide

The title compound was prepared by the procedures described in Example 281A, substituting 5-bromo-N-methyl indole with the bromide from Example 299A.

Example 299C (3-Hydroxymethyl)-benzodioxan-6-yl)[2-nitro-4-(E-((3-(2-oxopyrrolidin-1-yl)prop-1-ylamino)carbonyl)ethenyl)phenyl]sulfide The title compound was prepared by the procedures described in Example 297, substituting the mixture of thiolsilyl ethers from Example 296A with the compound of Example 299B, giving a white solid. $^1$H NMR (CDCl$_3$, 300 MHz) δ 1.74 (br m, 2H), 2.08 (t, J=7.5 Hz, 2H), 2.44 (t, J=7.5 Hz, 2H), 3.25–3.53 (m, 6H), 3.88 (dd, J=4.8, 16.8 Hz, 1H), 3.97 (dd, J=4.8, 16.8 Hz, 1H), 4.21 (dd, J=3.1, 12.9 Hz, 1H), 4.26–4.36 (m, 1H), 4.40 (dd, J=2.4, 12.9 Hz, 1H), 6.49 (d, J=15.3 Hz, 1H), 6.88 (d, J=8.7 Hz, 1H), 7.00 (d, J=8.7 Hz, 1H), 7.07 (dd, J=2.4, 8.7 Hz, 1H), 7.14 (d, J=2.4 Hz, 1H), 7.20 (br s, 1H), 7.46 (dd, J=0.9, 8.7 Hz, 1H), 7.54 (d, J=15.3 Hz, 1H), 8.36 (s, 1H). MS (ESI$^+$) (M+H)$^+$ at m/z 514. Anal. Calcd for C$_{25}$H$_{27}$N$_3$O$_7$S.0.82 H$_2$O: C, 56.83; H, 5.46; N, 7.95. Found: C, 56.84; H, 5.18; N, 7.74.

Example 300

(Benzodioxan-6-yl)[2-chloro-4-(E-((3-carboxypiperidin-1-yl)carbonyl)ethenyl)phenyl]sulfide The title compound was prepared by the procedures described in Example 263, substituting 4-fluoro-3-trifluoromethylbenzaldehyde with 3-chloro-4-fluorobenzaldehyde, giving a white solid. $^1$H NMR (CDCl$_3$, 300 MHz) δ 1.64–1.88 (br m, 2H), 1.95–2.09 (br m, 2H), 2.57–2.73 (m, 1H), 2.90–3.17 (m, 1H), 3.17–3.50 (m, 1H), 3.90–4.19 (m, 1H), 4.25–4.36 (m, 4H), 4.39–4.66 (m, 1H), 6.75 (d, J=8.4 Hz, 1H), 6.84 (d, J=15.3 Hz, 1H), 6.93 (d, J=8.7 Hz, 1H), 7.03 (dd, J=2.4, 8.7 Hz, 1H), 7.08 (d, J=2.4 Hz, 1H), 7.18 (d, J=8.4 Hz, 1H), 7.51 (s, 1H), 7.54 (d, J=15.3 Hz, 1H). MS (ESI$^+$) (M+H)$^+$ at m/z 460, 462.

Example 301

(2-(and 3-)(Aminomethyl)-benzodioxan-6-yl)[2-trifluoromethyl-4-(E-((3-(2-oxopyrrolidin-1-yl)prop-1-ylamino)carbonyl)ethenyl)phenyl]sulfide

Example 301A (2-(and 3-)(Mesyloxymethyl)-benzodioxan-6-yl)[2-trifluoromethyl-4-(E-((3-(2-oxopyrrolidin-1-yl)prop-1-ylamino)carbonyl)ethenyl)phenyl]sulfide To a stirred solution of alcohol from Example 298 (200 mg, 0.37 mmol)) in 2 mL of methylene chloride with Et$_3$N (104 mL, 0.74 mmol)) was added methanesulfonyl chloride (35 mL, 0.56 mmol) dropwise. The mixture was then stirred at ambient temperature for one hour. The reaction mixture was then poured into 3N HCl, extracted with EtOAc (2×10 mL). The combined organic layer was washed with aq. NaHCO$_3$, brine, dried over Na$_2$SO$_4$, concentrated in vacuo to give 275 mg of crude product which was proceeded to the next step without purification.

Example 301B (2(and 3-)(Azidomethyl)-benzodioxan-6-yl)[2-trifluoromethyl-4-(E-((3-(2-oxopyrrolidin-1-yl)prop-1-ylamino)carbonyl)ethenyl)phenyl]sulfide To a stirred solution suspension of NaN$_3$ (44 mg, 0.68 mmol) in 1 mL of DMSO was added mesylate (275 mg) in 0.5 mL of DMSO solution. The reaction mixture was then heated at 70° C. for 2 hours, then cooled to room temperature, water was added, extracted with EtOAc (2×10 mL). The combined organic layer was washed with water, brine, dried over Na$_2$SO$_4$, concentrated in vacuo. The residue was purified on a SiO$_2$ flash column chromatography eluting with 5–10% MeOH/EtOAc to give 35 mg (17%, two steps) mg of the title compound as a light brown oil.

Example 301C (2-(and 3-)(Aminomethyl)-benzodioxan-6-yl)[2-trifluoromethyl-4-(E-((3-(2-oxopyrrolidin-1-yl)prop-1-ylamino)carbonyl)ethenyl)phenyl]sulfide To a stirred solution of azide (230 mg, 0.41 mmol) in 1 mL of THF was added PPh$_3$ (118 mg, 0.45 mmol), followed by one drop of water. The mixture was then stirred at room temperature for one hour. The volatile solvent was then removed in vacuo and the crude product was purified using Gilson Preparative HPLC as described in Example 38B to give 25 mg (11%) of the title compound. Light brown oil; $^1$H NMR (CDCl$_3$, 300 MHz, 3:2 mixture of diastereomers) δ 1.74 (br m, 2H), 1.96–2.16 (m, 2H), 2.35–2.50 (m, 2H), 3.23–3.47 (m, 6H), 3.92–4.63 (m, 5H), 6.41–6.55 (m, 1H), 6.83–7.10 (m, 3H), 7.36–7.58 (m, 3H), 7.67–7.67 (m, 2H). MS (ESI$^+$) (M+H)$^+$ at m/z 536. Anal. Calcd for C$_{26}$H$_{28}$F$_3$N$_3$O$_4$S : C, 58.31; H, 5.27; N, 7.85. Found: C, 58.34; H, 5.48; N, 7.78.

Example 302

(2-Isopropylphenyl)[2-nitro-4-(E-((3-(methylaminocarbonyl)morpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.6 Hz, 6H); 2.61 (d, J=4.8 Hz, 3H); 3.14–4.62 (br m, 7H); 3.30–3.40 (m, 1H); 6.63 (d, J=8.8 Hz, 1H); 7.32–7.62 (m, 6H); 7.80–7.97 (m, 2H); 8.66(d, J=1.5 Hz, 1H). MS (APCI) (M+H)$^+$ at m/z 470. Anal calcd for C$_{24}$H$_{27}$N$_3$S$_1$O$_5$.0.8H$_2$O: C, 59.58; H, 5.96; N, 8.68. Found: C, 59.57; H, 5.94; N, 8.72.

Example 303

(2-Isopropylphenyl)[2-nitro-4-(E-((3-hydroxymethyl)morpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 2.70–3.51 (br m, 5H); 3.30–3.40 (m, 1H); 3.83–3.93 (m, 1H); 4.03–4.47 (br m, 2H); 4.74–4.82 (m, 1H); 6.64 (d, J=8.5 Hz, 1H); 7.30–7.62 (m, 6H); 7.86–7.94 (m, 1H); 8.59–8.65 (m, 1H). MS (APCI) (M+H)$^+$ at m/z 443. Anal calcd for C$_{23}$H$_{26}$N$_2$S$_1$O$_5$: C, 62.43; H, 5.92; N, 6.33. Found: C, 62.12; H, 6.20; N, 6.06.

Example 304

(2-Isopropylphenyl)[2-nitro-4-(E-((3-(acetoxymethyl)morpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.1 Hz, 6H); 2.04 (s, 3H); 3.30–3.40 (m, 1H); 2.58–4.41 (br m, 9H); 6.64 (d, J=8.5 Hz, 1H); 7.30–7.62 (m, 6H); 7.90 (dd, J=8.5, 1.8 Hz, 1H); 8.59–8.65 (m, 1H). MS (APCI) (M+H)$^+$ at m/z 485. Anal calcd for C$_{25}$H$_{28}$N$_2$S$_1$O$_6$: C, 61.97; H, 5.82; N, 5.78. Found: C, 61.85; H, 5.84; N, 5.68.

Example 305

(2-Isopropylphenyl)[2-nitro-4-(E-((3-(aminomethylmorpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=7.0 Hz, 6H); 2.61 (d, J=5.5 Hz, 2H); 2.49–3.60 (br m, 5H); 3.82–3.93 (m, 1H); 4.13–4.45 (m, 2H); 6.64 (d, J=8.5 Hz, 1H); 7.32–7.62 (m, 6H); 7.88–7.95 (m, 1H); 8.59–8.67(m, 1H). MS (APCI) (M+H)$^+$ at m/z 442. Anal calcd for C$_{23}$H$_{27}$N$_3$S$_1$O$_4$.0.4H$_2$O: C, 61.55; H, 6.25; N, 9.36. Found: C, 61.60; H, 6.25; N, 9.00.

Example 306

(2-Isopropylphenyl)[2-nitro-4-(E-((3-(acetamidomethyl)morpholin-1-yl)carbonyl)ethenyl)phenyl]sulfide Prepared according to the procedures of Example 71, giving a yellow solid. $^1$H NMR (DMSO-d$_6$, 300 MHz) δ 1.14 (d, J=6.8 Hz, 6H); 1.82 (s, 3H); 2.70–3.50 (br m, 7H); 3.85–3.94 (m, 1H); 4.13–4.40 (m, 2H); 6.64 (d, J=8.5 Hz, 1H); 7.32–7.62 (m, 6H); 7.88–8.06 (m, 1H); 8.59–8.67(m, 1H). MS (APCI) (M+H)$^+$ at m/z 484. Anal calcd for C$_{25}$H$_{29}$N$_3$S$_1$O$_5$.0.27H$_2$O: C, 61.47; H, 6.10; N, 8.60. Found: C, 61.50; H, 6.34; N, 8.53.

Example 307

(Benzodioxan-6-yl)[2-chloro-4-(E-((3-(2-oxopyrrolidin-1-yl)prop-1-ylamino)carbonyl)ethenyl)phenyl)sulfide The title compound was prepared by the procedures described in Example 300 substituting ethyl isonipecotate with N-(3'-aminopropyl)-2-pyrrolidinone. $^1$H NMR (CDCl$_3$, 300 MHz) δ 1.75 (br s, 2H), 2.02–2.34 (m, 2H), 2.40–2.50 (m, 2H), 3.30–3.50 (m, 6H), 4.28–4.33 (m, 4H), 6.40 (br, 1H), 6.75 (d, J=8.0 Hz, 1H), 6.93 (d, J=8.5 Hz, 1H), 7.02 (dd, J=2.0, 8.0 Hz, 1H), 7.08 (d, J=2.0 Hz, 1H), 7.18 (d, J=8.5 Hz, 1H), 7.45 (m, 1H), 7.50 (s, 1H). MS (ESI) m/z 473 (M+H)$^+$. Anal. calcd. for C$_{24}$H$_{25}$ClN$_2$O$_4$S.0.5 H2O: C, 59.81; H, 5.44; N, 5.81. Found: C, 59.76; H, 5.80; N, 5.43.

Example 308

(Benzodioxan-6-yl)[2-chloro-4-(E-((3-carboethoxypiperidin-1-yl)carbonyl)ethenyl)phenyl]sulfide The title compound was prepared by the procedures described in Example 300 substituting ethyl isonipecotate with ethyl nipecotate. $^1$H NMR (CDCl$_3$, 300 MHz) δ 1.25 (t, J=7.0 Hz, 3H), 1.60–1.90 (br, 2H), 2.10 (br, 1H), 2.52 (br, 1H), 3.00–3.50 (br, 2H), 3.80 (br, 1H), 4.10–4.20 (m, 4H), 4.28–4.35 (m, 4H), 6.74 (d, J=8.0 Hz, 1H), 6.92 (d, J=8.0 Hz, 1H), 7.02 (dd, J=2.0, 8.0 Hz, 1H), 7.08 (d, J=2.0 Hz, 1H), 7.18 (m, 1H), 7.50–7.03 (m, 3H). MS (ESI) m/z 488 (M+H)$^+$. Anal. calcd. for C$_{25}$H$_{26}$ClNO$_5$SNa.0.5 H$_2$O: C, 60.42; H, 5.48; N, 2.82. Found: C, 60.61; H, 5.51; N, 2.42.

Example 309

(Benzodioxan-6-yl)[2-chloro-4-(E-((2-carboethoxypiperidin-1-yl)carbonyl)ethenyl)phenyl]sulfide The title compound was prepared by the same procedure described in Example 300 substituting ethyl isonipecotate with ethyl pipecolinate. $^1$H NMR (CDCl$_3$, 300 MHz) δ 1.30 (t, J=7.0 Hz, 3H), 1.30–1.50 (br,3H), 1.55–1.85 (br, 3H), 2.30 (m, 1H), 4.00 (m, 1H), 4.20 (m, 2H), 4.30 (m, 4H), 5.44 (br, 1H), 6.85 (d, J=8.0 Hz, 1H), 6.90 (d, J=8.0 Hz, 1H), 7.00 (dd, J=2.0, 8.0 Hz, 1H), 7.07 (d, J=2.0 Hz, 1H), 7.10–7.20 (m, 2H), 7.22 (m, 1H), 7.50 (s, 1H). MS (ESI) m/z 488 (M+H)$^+$. Anal. calcd. for C$_{25}$H$_{26}$ClNO$_5$S: C, 61.53; H, 5.37; N, 2.87. Found: C, 61.86; H, 5.63; N, 2.56.

Example 310

(2-Methoxyphenyl)-[2,3-dichloro-4-(E-[(morpholin-1-yl)carbonyl]ethenyl)phenyl]sulfide Example 310A 2,3-Dichloro-4-trifluoromethanesulfonyloxy-benzaldehyde 2,3-Dichloro-4-hydroxy-benzaldehyde (9.10 g, J. Med. Chem. 19 (4), 534, 1994) was dissolved in 45 mL pyridine at room temperature. The solution was placed in an ice bath and immediately, 15.63 g of trifluoromethanesulfonic anhydride was added slowly. [Note: If the pyridine solution is cooled to zero before addition of triflic anhydride the aldehyde crystallizes out and the mixture cannot be stirred.] After the addition was completed the dark mixture was stirred for 1 hour at room temperature. It was then poured into a stirred mixture of ice water, 100 mL of concentrated HCl and ether. [Note: Not everything is soluble in this mixture] The ether layer was separated, dried over sodium sulfate, and the solvent removed. Warm heptane was added to this residue, and any insoluble material was filtered. The solution was concentrated to give 8.74 g (57% yield) of product as an orange oil which solidified in the refrigerator.

Example 310B 2,3-Dichloro-4-(2-methoxyphenylthio)-benzaldehyde 2,3-Dichloro-4-trifluoromethanesufonyloxy-benzaldehyde (2.50 g) was dissolved in 6 mL acetonitrile. 2-Methoxybenzenethiol (2.55 g of 70% pure material, 50% excess) was added. With cooling 2.50 g diisopropylethylamine was added slowly. The solution was removed from the ice bath, whereon a solid formed. The solution was warmed in a 50 C waterbath for 5 minutes. More acetonitrile (5 mL) was added and the mixture was cooled in ice, and then filtered to get 2.047 g of product, m.p. 137–139C.

Example 310C 2.3-Dichloro-4-(2-methoxyphenythio)-cinnamic acid

A mixture of 2,3-dichloro-4-(2-methoxyphenylthio)-benzaldehyde (2.03 g), 1.44 g malonic acid, 5 mL pyridine, and 0.100 g piperidine was heated to 115 degrees for 1.5 hours. The mixture was cooled, and ice and HCl were added. The resulting solid was: filtered, washed with water and dissolved in tetrahydrofuran. This solution was dried over sodium sulfate, the solvent removed and ether added to give 1.733 g of product, m.p. 187–188 C.

Example 310D (2-Methoxyphenyl)-[2,3-dichloro-4-(E-[(morpholin-1-yl)carbonyl]ethenyl)phenyl]sulfide The title compound was prepared according to the procedure of Example 1, substituting the cinnamic acid of Example 310C for Example 1B, giving a white solid, m.p. 161–162 C. $^1$H-NMR (CDCl$_3$ 300 MHz) δ3.83 (s, 3H), 6.55 (d, J=9 Hz, 1H), 6.70 (broad d, J=15 Hz, 1H), 6.99–7.05 (m, 2H), 7.26 (d, J=9 Hz, 1H), 7.43–7.50 (m, 2H), 8.07 (broad d, J=15 Hz, 1H) Anal. Calcd. for C$_{20}$H$_{19}$Cl$_2$NO$_3$S: C, 56.61; H, 4.51; N, 3.30. Found: C, 56.75; H, 4.57; N, 2.61.

Example 311

(2-Methoxyphenyl)-[2,3-dimethyl-4-(E-[(morpholin-1-yl)carbonyl]ethenyl)phenyl]sulfide The title compound was prepared according to the procedures of Example 310. $^1$H-NMR (CDCl$_3$ 300 MHz) δ 2.39 (s, 3H), 2.42 (s, 3H), 3.60–3.80 (m, 8H), 3.90 (s, 3H), 6.69 (d, J=15 Hz, 1H), 6.82–6.94 (m, 3H), 7.05 (d, J=9 Hz, 1H), 7.20–7.30 (m, 2H), 8.06 (d, J=15 Hz, 1H). Anal. Calcd. for C$_{22}$H$_{25}$NO$_3$S: C, 68.91; H, 6.57; N, 3.65. Found: C, 68.75; H, 6.67; N, 3.24.

Example 312

(2-Isopropylphenyl)[2-nitro-4-(E-((indol-5-ylaminoncarbonyl)ethenyl)phenyl]sulfide The title compound was prepared according to the procedures of Example 1. $^1$H NMR (DMSO-d$_6$, 300 MHz) δ 11.04 (s, 1H), 10.10 (s, 1H), 8.52 (d, 1H, J=1.5 Hz), 8.02 (s, 1H), 7.81 (dd, 1H, J=1.8, 8.5 Hz), 7.53–6.63 (m, 4H7.39 (m, 1H), 7.25–7.35 (m, 3H), 6.94 (d, 1H, J=15.8 Hz), 7.72 (d, 1H, J=8.5 Hz), 6.40 (m, 1H), 3.33 (m, 1H), 1.16 (d, 6H, J=6.6 Hz). MS (ESI) m/z 458, 480, 915. Anal. Calcd for C$_{26}$H$_{23}$N$_3$O$_3$S.0.22 H$_2$O: C, 67.67; H, 5.12; N, 9.10. Found: C, 67.68; H, 5.19; N, 9.08.

Example 313

(Benzodioxan-6-yl)[2-chloro-4-(E-((3-carboxylpiperidin-1-yl)carbonyl)ethenyl)phenyl] sulfide The title compound was prepared by hydrolysis of the compound of Example 308 under basic condition (aq. NaOH/EtOH). $^1$H NMR (DMSO-d$_6$, 300 MHz) δ 1.10–1.40 (m, 2H), 1.60 (m, 1H), 1.76–1.96 (m, 3H), 2.88 (m, 1H), 3.98 (m, 1H), 3.98 (m, 1H), 4.30 (m, 4H), 6.72 (d, J=8.0 Hz, 1H), 7.02 (m, 3H), 7.30 (m, 2H), 7.48 (m, 1H), 7.92 (m, 1H), MS (ESI) m/z 458 (M+H)$^+$. Anal. calcd. for C$_{23}$H$_{21}$ClNO$_5$SNa: C, 55.76; H, 4.58; N, 2.83. Found: C, 55.76; H, 4.78; N, 2.63.

Example 314

(Benzodioxan-6-yl)[2-chloro-4-(E-((3-(tetrazol-5-yl) piperidin-1-yl)carbonyl)ethenyl)phenyl]sulfide The title compound was prepared by the procedures described in Example 282, producing a white solid. $^1$H NMR (CDCl$_3$, 300 MHz) δ 1.66–1.80 (m, 2H), 2.10–2.30 (m, 2H), 2.64 (m, 1H), 3.55 (m, 2H), 3.98 (m, 1H), 4.25 (m, 1H), 4.30–4.36 (m, 4H), 6.72 (dd, J=3.0, 12.0 Hz, 2H), 6.93 (d, J=8.0 Hz, 1H), 7.03 (dd, d=2.0, 8.0 Hz, 1H), 7.09 (d, J=2.0 Hz, 1H), 7.20 (d, J=8.5 Hz, 1H), 7.52 (s, 1H), 7.70 (d, J=15.0 Hz, 1H). MS (ESI) m/z 484 (M+H)$^+$. Anal. calcd. for C$_{23}$H$_{22}$ClN$_5$O$_3$S.0.38 H$_2$O: C, 56.28; H 4.67; N, 14.27. Found: C, 56.46; H, 4.58; N, 13.94.

Example 315

(Benzodioxan-6-yl)[2-chloro-4-(E-((4-(tert-butoxycarbonyl)piperazin-1-yl)carbonyl)ethenyl) phenyl]sulfide The title compound was prepared by the procedures described in Example 300 substituting ethyl isonipecotate with 1-Boc-piperazine. $^1$H NMR (CDCl$_3$, 300 MHz) δ 1.50 (s, 9H), 3.50 (br, s 4H), 3.70 (br, 4H), 4.28–4.35 (m, 4H), 6.74 (d, J=8.0 Hz, 1H), 6.82 (m, 1H), 6.92 (d, J=8.0 Hz, 1H), 7.02 (dd, J=2.0, 8.0 Hz, 1H), 7.17 (d, J=2.0 Hz, 1H), 7.28 (d, J=8.0 Hz, 1H), 7.50 (s, 2H), 7.58 (m, 1H). MS (ESI) m/z 517 (M+H)$^+$. Anal. calcd. for C$_{26}$H$_{29}$ClN$_2$O$_5$S.0.1 H$_2$O: C, 60.19; H, 5.67; N, 5.40. Found: C, 60.20; H, 5.97; N, 5.11.

Example 316

(Benzodioxan-6-yl)[2-chloro-4-(E-((2-carboxypiperidin-1-yl)carbonyl)ethenyl)phenyl] sulfide The title compound was prepared by hydrolysis of the compound of Example 309 under basic conditions (aq. NaOH/EtOH). $^1$H NMR (DMSO-d$_{6, 300}$ MHz) δ 1.10–1.40 (m, 3H), 1.45–1.60 (m, 2H), 2.25–2.45 (m, 2H), 2.55–2.80 (m, 1H), 4.30 (m, 4H), 4.50 (m, 1H), 6.70 (d, J=8.0 Hz, 1H), 7.00 (m, 3H),7.10 (m, 1H), 7.25 (d, J=16.0 Hz, 1H), 7.48 (d, J=8.0 15.5 Hz, 1H), 7.90 (d, J=15.5 Hz, 1H). MS (ESI) m/z 458 (M+H)$^+$. Anal. calcd. for C$_{23}$H$_{21}$ClNO$_5$SNa.1.3 H$_2$O: C, 54.69; H, 4.73; N, 2.45. Found: C, 54.67; H, 4.71; N, 2.77.

Example 317

(Benzodioxan-6-yl)[2-chloro-4-(E-((3-(tetrazol-5-yl)morpholin-1-yl)carbonyl)ethenyl)phenyl]sulfide The title compound was prepared by the procedures described in Example 262. $^1$H NMR (CDCl$_3$, 300 MHz) δ 1.50–1.70 (m, 2H), 3.15 (br, 1H), 3.70–3.90 (m, 2H), 4.25–4.35 (m, 4H), 4.55 (m, 1H), 5.04 (br, 1H), 6.72 (d, J=8.0 Hz, 1H), 6.93 (d, J=8.0 Hz, 1H), 7.03 (dd, J=2.0, 8.0 Hz, 1H), 7.07 (d, J=2.0 Hz, 1H), 7.20–7.30 (m, 2H), 7.50 (m, 1H), 7.65 (m, 1H). MS (ESI) m/z 486 (M+H)$^+$. Anal. calcd. for C$_{22}$H$_{20}$ClN$_5$O$_4$S.H$_2$O: C, 52.43; H, 4.40; N, 13.90. Found: C, 52.34; H, 4.35; 13.62.

Example 318

(Benzodioxan-6-yl)[2-chloro-4-(E-((4-(methylaminocarbonyl)piperazin-1-yl)carbonyl)ethenyl)phenyl]sulfide The title compound was prepared by deprotection of the of Example 315 compound using anhydrous TFA in dichloromethane, followed by treatment with methyl isocyanate. $^1$H NMR (CDCl$_3$, 300 MHz) δ 2.88 (s, 3H), 3.50 (br, 4H), 3.72 (br, 4H), 4.30 (m, 4H), 6.74 (d, J=8.0 Hz, 1H), 6.82 (d, J=15.0 Hz, 1H), 6.92 (d, J=8.0 Hz, 1H), 7.03 (dd, J=2.0, 8.0 Hz, 1H), 7.08 (d, J=2.0 Hz, 1H), 7.20 (d, J=8.0 Hz, 1H), 7.50 (s, 1H), 7.60 (m, 1H). MS (ESI) m/z 474 (M+H)$^+$. Anal. calcd. for C$_{23}$H$_{24}$ClN$_3$O$_4$S: C, 57.63; H, 5.17; N, 8.77. Found: C, 57.53; H, 5.02; N, 8.58.

Example 319

(2-Methoxyphenyl)-[2,3-dichloro-4-(E-[(4-carboxypiperidin-1-yl)carbonyl]ethenyl)phenyl]sulfide The title compound was prepared according to the procedures of Example 310. $^1$H-NMR (CDCl$_3$ 300 MHz) δ 1.66–1.83 (m, 2H), 1.95–2.09 (m, 2H), 2.57–2.69 (m, 1H), 2.94–3.08 (m, 1), 3.15–3.31 (m, 1H), 3.72 (s, 3H), 3.90–4.05 (m, 1H), 4.41–4.55 (m, 1H), 6.55 (d, J=9 Hz, 1H), 6.73 (d, J=15 Hz, 1H), 7.00–7.05 (m, 2H), 7.27 (d, J=8Hz, 1H), 7.44–7.50 (m, 2H), 7.92 (d, J=5 Hz, 1H). Anal. Calcd. for C$_{22}$H$_{21}$Cl$_2$NO$_4$S: C, 56.66; H, 4.54; N, 3.00. Found: C, 56,89; H, 4.84; N, 2.64.

Example 320

(Benzodioxan-6-yl)[2-chloro-4-(E-((4-(tetrazol-5-yl)piperidin-1-yl)carbonyl)ethenyl)phenyl]sulfide The title compound was prepared by the procedures described in Example 314 substituting 3-(tetrazol-5-yl)piperidine with 4-(tetrazol-5-yl)piperidine. The crude reaction product was purified by reversed-phase HPLC. $^1$H NMR (DMSO-d$_6$, 300 MHz) δ 1.22 (m, 1H), 1.55–1.75 (m, 2H), 2.06 (m, 1H), 2.45 (m, 1H), 4.22 (m, 4H), 4.30 (m, 4H), 6.70 (m, 1H), 7.00 (dd, J=2.0, 8.0 Hz, 2H), 7.25–7.40 (m, 4H), 7.50 (m, 1H). MS (ESI) m/z 484 (M+H)$^+$.

Example 321

(2-Methoxyphenyl)-[3-chloro-4-(E-[(morpholin-1-yl)carbonyl]ethenyl)phenyl]sulfide The title compound was prepared according to the procedures of Example 1, giving a white solid, m.p. 124–125 C $^1$H-NMR (CDCl$_3$ 300 MHz) δ 3.60–3.80 (m, 8H), 3.85 (s, 3H), 6.80 (d, J=15 Hz, 1H), 6.95–7.01 (m, 2H), 7.05 (dd, J=9 Hz, 2 Hz, 1H), 7.15 (d, J=2Hz, 1H), 7.35–7.48 (m, 3H), 7.75 (d, J=15 Hz, 1H). Anal. Calcd. for C$_{20}$H$_{20}$ClNO$_3$S: C, 61.61; H, 5.17; N, 3.59. Found: C, 61.43; H, 5.30; N, 3.73.

Example 322

(2-Isopropylphenyl)[2-nitro-4-(E-((4-oxopiperidin-1-yl)carbonyl)ethenyl)phenyl]sulfide The title compound was prepared according to the procedures of Example 1. $^1$H NMR (CDCl$_3$, 300 MHz) δ 8.45 (s, 1H), 7.50–7.57 (m, 3H), 7.42(br d, 1H, J=8.1 Hz), 7.30 (m, 1H), 7.02 (br, 1H), 6.72 (d, 1H, J=8.4 Hz), 4.01 (br s, 4H), 3.44 (quintet, 1H, J=6.8 Hz), 2.56 (br m, 4H), 1.18 (d, 6H, J=7.1 Hz). MS (ESI) m/z 425, 457. Anal. Calcd for C$_{23}$H$_{24}$N$_2$O$_4$S : C, 65.07; H, 5.70; N, 6.60. Found: C, 64.92; H, 5.67; N, 6.62.

Example 323

(Benzodioxan-6-yl)[2-trifluoromethyl-4-(E-((3-R-carboethoxypiperidin-1-yl)carbonyl)ethenyl)phenyl]sulfide The title compound was prepared by the procedures described in Example 248, substituting ethyl (±)nipecotate with ethyl nipecotate tartrate, giving a white solid. $^1$H NMR (CDCl$_3$, 300 MHz) δ 1.26 (t, J=7.4 Hz, 3H), 1.46–1.67 (m, 1H), 1.67–1.98 (m, 2H), 1.98–2.23 (m, 1H), 2.46–2.63 (m, 1H), 3.10–3.42 (m, 1H), 3.53–4.13 (m, 2H), 4.16 (q, J=7.4 Hz, 2H), 4.25–4.40 (m, 4H), 4.60–4.88 (m, 1H), 6.91 (d, J=8.4 Hz, 1H), 6.93 (d, J=15.3 Hz, 1H), 6.97–7.05 (m, 2H), 7.07 (d, J=2.7 Hz, 1H), 7.42 (d, J=8.4 Hz, 1H), 7.59 (d, J=15.3 Hz, 1H), 7.77 (s, 1H). MS (ESI$^+$) (M+H)$^+$ at m/z 522.

Example 324

(Benzodioxan-6-yl)[2-trifluoromethyl-4-(E-((3-R-carboxypiperidin-1-yl)carbonyl)ethenyl)phenyl]sulfide The title compound was prepared by the procedures described in Example 251, substituting the ethyl ester from Example 248 with ethyl ester from Example 323, giving a white solid. $^1$H NMR (CDCl$_3$, 300 MHz) δ 1.48–1.71 (m, 1H), 1.71–2.01 (m, 2H), 2.01–2.20 (m, 1H), 2.53–2.70 (m, 1H), 3.18–3.54 (m, 1H), 3.86–4.20 (m, 2H), 4.20–4.33 (m, 4H), 4.45–4.75 (m, 1H), 6.90 (d, J=8.7 Hz, 1H), 6.95–7.04 (m, 3H), 7.06 (d, J=2.4 Hz, 1H), 7.35–7.45 (br m, 1H), 7.60 (d, J=15.3 Hz, 1H), 7.75 (s, 1H). MS (ESI$^+$) (M+H)$^+$ at m/z 494.

Example 325

(Benzodioxan-6-yl)[2,3-dichloro-4-(E-((3-(2-oxopyrrolidin-1-yl)prop-1-ylamino)carbonyl)ethenyl)phenyl]sulfide The title compound was prepared by the procedures described in Example 240, substituting 4-fluoro-3-trifluoromethylbenzaldehyde with 2,3-dichloro-4-trifluoromethanesulfoxybenzaldehyde, giving a white solid. $^1$H NMR (CDCl$_3$, 300 MHz) δ 1.71–1.82 (m, 2H), 2.08 (p, J=7.5 Hz, 2H), 2.46 (t, J=7.5 Hz, 2H), 3.2603.50 (m, 6H), 4.23–4.36 (m, 4H), 6.36 (t, J=15.6 Hz, 1H), 6.60 (d, J=8.7 Hz, 1H), 6.44 (d, J=8.7 Hz, 1H), 7.03 (dd, J=2.4, 8.7 Hz, 1H), 7.09 (d, J=2.4 Hz, 1H), 7.31 (d, J=8.7 Hz, 1H), 7.94 (d, J=15.6 Hz, 1H). MS (ESI$^+$) (M+H)$^+$ at m/z 507, 509, 511. Anal. Calcd for C$_{24}$H$_{24}$Cl$_2$N$_2$O$_4$S.1.87 H$_2$O: C, 53.27; H, 5.17; N, 5.18. Found: C, 53.30; H, 5.17; N, 4.83.

Example 326

(Benzodioxan-6-yl)[2,3-dichloro-4-(E-((4-acetylpiperazin-1-yl)carbonyl)ethenyl)phenyl]sulfide The title compound was prepared by the procedures described in Example 325, substituting aminopropyl pyrrolidinone with 1-acetylpiperazine white solid; $^1$H NMR (CDCl$_3$, 300 MHz) δ 2.17 (s, 3H), 3.50–3.94 (m, 8H), 4.26–4.40 (m, 4H), 6.61 (d, J=8.7 Hz, 1H), 6.71 (d, J=15.6 Hz, 1H), 6.95 (d, J=8.4 Hz, 1H), 7.04 (dd, J=2.4, 8.4 Hz, 1H), 7.09 (d, J=2.4 Hz, 1H), 7.30 (d, J=8.7 Hz, 1H), 7.99 (d, J=15.6 Hz, 1H). MS (ESI$^+$) (M+Na)$^+$ at m/z 515, 517, 519. Anal. Calcd for C$_{23}$H$_{22}$Cl$_2$N$_2$O$_4$S.0.52 CH$_2$Cl$_2$: C, 52.55; H, 4.32; N, 5.21. Found: C, 52.63; H, 4.16; N, 4.82.

Example 327

(Benzodioxan-6-yl)[2,3-dichloro-4-(E-((3-carboethoxypiperidin-1-yl)carbonyl)ethenyl)phenyl] sulfide The title compound was prepared by the procedures described in Example 325, substituting aminopropyl pyrrolidinone with ethyl nipecotate, giving a white solid. $^1$H NMR (CDCl$_3$, 300 MHz) δ 1.26 (t, J=7.0 Hz, 3H), 1.66–1.96 (m, 2H), 1.96–2.21 (m, 1H), 2.44–2.60 (m, 1H), 2.85–3.40 (m, 2H), 3.50–3.70 (m, 1H), 3.80–4.10 (m, 2H), 4.15 (q, J=7.0 Hz, 2H), 4.26–4.40 (m, 4H), 6.66 (d, J=8.7 Hz, 1H), 6.74 (d, J=15.3 Hz, 1H), 6.95 (d, J=8.4 Hz, 1H), 7.03 (dd, J=2.4, 8.4 Hz, 1H), 7.09 (d, J=2.4 Hz, 1H), 7.25–7.38 (m, 1H), 7.93 (d, J=15.3 Hz, 1H). MS (ESI$^+$) (M+Na)$^+$ at m/z 544, 546, 548.

Example 328

(Benzodioxan-6-yl)[2,3-dichloro-4-(E-((4-carboethoxypiperidin-1-yl)carbonyl)ethenyl)phenyl] sulfide The title compound was prepared by the procedures described in Example 325, substituting aminopropyl pyrrolidinone with ethyl isonipecotate, giving a white solid. $^1$H NMR (CDCl$_3$, 300 MHz) δ 1.26 (t, J=7.2 Hz, 3H), 1.69 (td, J 3.9, 10.8 Hz, 1H), 1.74 (td, J=3.9, 10.8 Hz, 1H), 1.82–2.05 (m, 2H), 2.50–2.63 (m, 1H), 2.84–3.31 (m, 2H), 3.81–4.06 (m, 1H), 4.15 (q, J=7.2 Hz, 2H), 4.24–4.34 (m, 4H), 4.34–4.59 (m, 1H), 6.61 (d, J=8.7 Hz, 1H), 6.74 (d, J=15.6 Hz, 1H), 6.94 (d, J=8.7 Hz, 1H), 7.03 (dd, J=2.7, 8.7 Hz, 1H), 7.08 (d, J=2.7 Hz, 1H), 7.29 (d, J=8.7 Hz, 1H), 7.90 (d, J=15.6 Hz, 1H). MS (ESI$^+$) (M+H)$^+$ at m/z 522, 524, 526. Anal. Calcd for C$_{25}$H$_{25}$Cl$_2$NO$_5$S: C, 57.48; H, 4.82; N, 2.68. Found: C, 57.82; H, 4.96; N, 2.28.

Example 329

(Benzodioxan-6-yl)[2,3-dichloro-4-(E-((3-carboxypiperidin-1-yl)carbonyl)ethenyl)phenyl] sulfide The title compound was prepared by the procedures described in Example 155, substituting the ethyl ester from Example 137 with the ethyl ester from Example 327, and KOH with NaOH, providing a white solid. $^1$H NMR (CDCl$_3$, 300 MHz) δ 1.70–2.0 (m, 2H), 2.0–2.20 (m, 1H), 2.54–2.68 (m, 1H), 3.03–3.46 (m, 2H), 3.80–4.11 (m, 2H), 4.27–4.40 (m, 4H), 4.50–4.70 (m, 1H), 6.60 (d, J=8.9 Hz, 1H), 6.79 (d, J=15.3 Hz, 1H), 6.94 (d, J=8.5 Hz, 1H), 7.03 (dd, J=2.1, 8.5 Hz, 1H), 7.08 (d, J=2.1 Hz, 1H), 7.30 (d, J=8.9 Hz, 1H), 7.93 (d, J=15.3 Hz, 1H). MS (ESI$^+$) (M–2H)$^+$ at m/z 492, 494, 496. Anal. Calcd for C$_{23}$H$_{21}$Cl$_2$NO$_5$S.0.73 H$_2$O: C, 54.43; H, 4.46; N, 2.76. Found: C, 54.43; H, 4.39; N, 2.49.

Example 330

(Benzodioxan-6-yl)[2,3-dichloro-4-(E-((4-carboxypiperidin-1-yl)carbonyl)ethenyl)phenyl] sulfide The title compound was prepared by the procedures described in Example 155, substituting the ethyl ester from Example 137 with the ethyl ester from Example 328, and KOH with NaOH, to produce a white solid. $^1$H NMR (d$^6$-DMSO, 300 MHz) δ 1.33–1.55 (m, 2H), 1.62–1.78 (m, 2H), 1.93–2.07 (m, 1H), 2.90 (brt, J=10.5 Hz, 1H), 3.16 (brt, J=10.5 Hz, 1H), 3.96 (br d, J=13.5 Hz, 1H), 4.09 (br d, J=13.5 Hz, 1H), 4.26–4.42 (m, 4H), 6.60 (d, J=9.0 Hz, 1H), 7.04–7.08 (m, 2H), 7.13 (d, J=1.5 Hz, 1H), 7.22 (d, J=15.3 Hz, 1H), 7.70 (d, J=15.3 Hz, 1H), 7.86 (d, J=9.0 Hz, 1H). MS (ESI$^+$) (M+H)$^+$ at m/z 516, 518, 520. Anal. Calcd for C$_{23}$H$_{20}$Cl$_2$N$_1$NaO$_5$S.0.36 Et$_2$O: C, 54.06; H, 4.38; N, 2.58. Found: C, 53.99; H, 4.37; N, 2.22.

Example 331

(2-Isopropylphenyl)[2,3-dichloro-4-(E-((3-(2-oxopyrrolidin-1-yl)propylamino)carbonyl)ethenyl) phenyl]sulfide The title compound was prepared by the procedures described in Example 325, substituting 6-mercaptobenzodioxane with 2-isopropylbenzenethiol, to give a white solid. $^1$H NMR (CDCl$_3$, 300 MHz) δ 1.19 (d, J=7.2 Hz, 6H), 1.76 (p, J=5.8 Hz, 2H), 2.08 (p, J=7.65 Hz, 2H), 2.46 (t, J=7.65 Hz, 2H), 3.32 (q, J=5.8 Hz, 3.36–3.51 (m, 5H), 6.35 (d, J=15.3 Hz, 1H), 6.40 (d, J=8.7 Hz, 1H), 7.10 (brt, J=7.5 Hz, 1H), 7.20–7.30 (m, 2H), 7.42–7.53 (m, 2H), 7.94 (d, J 15.3 Hz, 1H). MS (ESI$^+$) (M+H)$^+$ at m/z 491, 493, 495. Anal. Calcd for C$_{25}$H$_{28}$Cl$_2$N$_2$O$_2$S.0.7 CH$_2$Cl$_2$: C, 56.03; H, 5.38; N, 5.08. Found: C, 56.06; H, 5.22; N, 5.01.

Example 332

(2-Isopropylphenyl)[2,3-dichloro-4-(E-((4-acetylpiperazin-1-yl)carbonyl)ethenyl)phenyl]sulfide The title compound was prepared by the procedures described in Example 326, substituting 6-mercaptobenzodioxane with 2-isopropylbenzenethiol, providing a white solid. $^1$H NMR (CDCl$_3$, 300 MHz) δ 1.19 (d, J=7.2 Hz, 6H), 2.17 (s, 3H), 3.46 (septet, J=7.2 Hz, 1H), 3.50–3.90(m, 8H), 6.41 (d, J=8.7 Hz, 1H), 6.71 (d, J=15.3 Hz, 1H), 7.21–7.35 (m, 2H), 7.44–7.57 (m, 3H), 7.99 (d, J=15.3 Hz, 1H) MS (ESI$^+$) (M+H)$^+$ at m/z 477, 479, 481. Anal. Calcd for C$_{24}$H$_{26}$Cl$_2$N$_2$O$_2$S.0.32 CH$_2$Cl$_2$: C, 57.89; H, 5.32; N, 5.55. Found: C, 57.85; H, 5.25; N, 5.74.

Example 333

(2-Isopropylphenyl)[2,3-dichloro-4-(E-((3-carboethoxypiperidin-1-yl)carbonyl)ethenyl)phenyl] sulfide The title compound was prepared by the procedures described in Example 327, substituting 6-mercaptobenzodioxane with 2-isopropylbenzenethiol, giving a white solid. $^1$H NMR (CDCl$_3$, 300 MHz) δ 1.20 (d, J=7.2 Hz, 6H), 1.20–1.35 (m, 5H), 1.65–1.93 (m, 1H), 1.93–2.16 (m, 1H), 2.43–2.58 (m, 1H), 3.06–3.35 (m, 1H), 3.47 (septet, J=7.2 Hz, 1H), 3.77–4.23 (m, 4H), 4.50–4.77 (m, 1H), 6.41 (d, J=8.4 Hz, 1H), 6.80 (d, J=15.3 Hz, 1H), 7.18–7.32 (m, 2H), 7.40–7.55 (m, 2H), 7.93 (d, J=15.3 Hz, 1H). MS (ESI$^+$) (M+H)$^+$ at m/z 506, 508, 510.

Example 334

(2-Isopropylphenyl)[2,3-dichloro-4-(E-((4-carboethoxypiperidin-1-yl)carbonyl)ethenyl)phenyl] sulfide The title compound was prepared by the procedures described in Example 328, substituting 6-mercaptobenzodioxane with 2-isopropylbenzenethiol, to give a white solid. $^1$H NMR (CDCl$_3$, 300 MHz) δ 1.19 (d, J=7.2 Hz, 6H), 1.26 (t, J=7.05 Hz, 3H), 1.69 (td, J=3.9, 10.8 Hz, 1H), 1.74 (td, J=3.9, 10.8 Hz, 1H), 1.88–2.06 (m, 2H), 2.50–2.63 (m, 1H), 2.84–3.08 (m, 1H), 3.08–3.32 (m, 1H), 3.47 (septet, J=7.2 Hz, 1H), 3.86–4.06 (m, 1H), 4.15 (q, J=7.05 Hz, 2H), 4.37–4.61 (m, 1 H), 6.40 (d, J=8.7 Hz, 1H), 6.73 (d, J=15.6 Hz, 1H), 7.22–7.35 (m, 2H), 7.44–7.57 (m, 3H), 7.92 (d, J=15.6 Hz, 1H). MS (ESI$^+$) (M+H)$^+$ at m/z 506, 508, 510. Anal. Calcd for C$_{26}$H$_{29}$Cl$_2$NO$_3$S.0.01 H$_2$O: C, 61.64; H, 5.77; N, 2.76. Found: C, 61.64; H, 5.90: N, 2.70.

Example 335

(2-Isopropylphenyl)[2,3-dichloro-4-(E-((3-carboxypiperidin-1-yl) carbonyl)ethenyl)phenyl] sulfide The title compound was prepared by the procedures described in Example 329, substituting 6-mercaptobenzodioxane with 2-isopropylbenzenethiol, giving a white solid. $^1$H NMR (CDCl$_3$, 300 MHz) δ 1.19 (d, J=7.2 Hz, 1H), 1.43–1.67 (m, 1H), 1.67–1.97 (m, 2H), 1.97–2.19 (m, 1H), 2.52–2.64 (m, 1H), 3.04–3.38 (m, 1H), 3.47 (septet, J=7.2 Hz, 1H), 3.75–4.10 (m, 2H), 4.44–4.70 (m, 1H), 6.40 (d, J=8.4 Hz 1H), 6.79 (d, J=15.3 Hz, 1H), 7.18–7.29 (m, 2H), 7.41–7.53 (m, 3H), 7.93 (d, J=15.3 Hz, 1H). MS (ESI$^+$) (M+H)$^+$ at m/z 478, 480, 482. Anal. Calcd for C$_{24}$H$_{25}$Cl$_2$NO$_3$S.0.05 H$_2$O.0.01 EtOH: C, 60.13; H, 5.29; N, 2.92. Found: C, 60.14; H, 5.11; N, 2.52.

Example 336

(2-Isopropylphenyl)[2,3-dichloro-4-(E-((4carboxypiperidin-1-yl)carbonyl)ethenyl)phenyl] sulfide The title compound was prepared by the procedures described in Example 330, substituting 6-mercaptobenzodioxane with 2-isopropylbenzenethiol, giving a white solid. $^1$H NMR (d$^6$-DMSO, 300 MHz) δ 1.16 (d, J=7.2 Hz, 6H), 1.33–1.53 (m, 2H), 1.64–1.78 (m, 2H), 1.97–2.10 (m, 1H), 2.88 (brt, J=10.5 Hz, 1H), 3.15 (brt, J=10.5 Hz, 1H), 3.97 (br d, J=13.2 Hz, 1H), 4.11 (br d, J=13.2 Hz, 1H), 6.41 (d, J=9.0 Hz, 1H), 7.22 (d, J=15.6 Hz, 1H), 7.31–7.42 (m, 1H), 7.53 (d, J=7.8 Hz, 1H), 7.56–7.64 (m, 2H), 7.71 (d, J=15.6 Hz, 1H), 7.85 (d, J=9.0 Hz, 1H). MS (ESI$^+$) (M+H)$^+$ at m/z 478, 480, 482. Anal. Calcd for C$_{24}$H$_{24}$Cl$_2$NNaO$_3$S.0.95 H$_2$O: C, 55.70; H, 5.04; N, 2.71. Found: C, 55.69; H, 4.90; N, 2.57.

Example 337

(1-Methylindol-5-yl)[2,3-dichloro-4-(E-((3-carboethoxypiperidin-1-yl)carbonyl)ethenyl)phenyl] sulfide The title compound was prepared by the procedures described in Example 283, substituting 4-fluoro-3-chlorobenzaldehyde with 2,3-dichloro-4-trifluoromethanesulfoxybenzaldehyde, giving a white solid. $^1$H NMR (CDCl$_3$, 300 MHz) δ 1.23 (t, J=7.5 Hz, 3H), 1.46–1.67 (m, 1H), 1.67–1.95 (m, 2H), 1.95–2.17 (m, 1H), 2.43–2.60 (m, 1H), 3.02–3.42 (m, 1H), 3.67–3.92 (m, 2H), 3.86 (s, 3H), 4.13 (q, J=7.5 Hz, 2H), 4.59–4.80 (m, 1H), 6.46 (d, J=8.7 Hz, 1H), 6.54 (d, J=3.0 Hz, 1H), 6.77 (d, J=15.3 Hz, 1H), 7.15 (d, J=3.0 Hz, 1H), 7.19 (d, J=8.7 Hz, 1 H), 7.37 (d, J=8.7 Hz, 1H), 7.42 (d, J=8.7 Hz, 1H), 7.89 (s, 1H), 7.92 (d, J=15.3 Hz, 1H). MS (ESI$^+$) (M+H)$^+$ at m/z 517, 519, 521.

Example 338

(1-Methylindol-5-yl)[2,3-dichloro-4-(E-((3-carboxypiperidin-1-yl) carbonyl)ethenyl)phenyl] sulfide The title compound was prepared by the procedures described in Example 155, substituting the ethyl ester from Example 137 with ethyl ester from Example 337, and KOH with NaOH, to give a white solid. $^1$H NMR (d$^6$-DMSO, 300 MHz) δ 1.29–1.45 (m, 1H), 1.45–1.78 (m, 2H), 1.78–2.02 (m, 1H), 2.20–2.40 (m, 1H), 2.82 (brt, J=10.5 Hz, 1H), 3.08 (brt, J=10.5 Hz, 1H), 3.80–4.07 (m, 2H), 3.86 (s, 3H), 4.38 4.50 (m, 1H), 6.42 (d, J=8.4 Hz, 1H), 6.54 (d, J=3.0 Hz, 1H), 7.19 (d, J=15.3 Hz, 1H), 7.32 (dd, J=1.8, 8.7 Hz, 1H), 7.48 (d, J=3.0 Hz, 1H), 7.64 (d, J=8.7 Hz, 1H), 7.67–7.77 (m, 2H), 7.87 (d, J=1.8 Hz, 1H). MS (ESI$^+$) (M+H)$^+$ at m/z 489,491,493. Anal. Calcd for C$_{24}$H$_{22}$Cl$_2$N$_2$O$_3$S.0.56 CH$_2$Cl$_2$: C, 54.94; H, 4.34; N, 5.22. C, 54.89; H, 4.44; N, 5.32.

Example 339

(1-Methylindol-5-yl)[2,3-dichloro-4-(E-((4-carboethoxypiperidin-1-yl)carbonyl)ethenyl)phenyl] sulfide The title compound was prepared by the procedures described in Example 285, substituting 4-fluoro-3-chlorobenzaldehyde with 2,3-dichloro-4-trifluoromethanesulfoxybenzaldehyde, providing a white solid. $^1$H NMR (CDCl$_3$, 300 MHz) δ 1.25 (t, J=7.2 Hz, 3H), 1.62–1.79 (m, 2H), 1.87–2.04 (m, 2H), 2.41–2.63 (m, 1H), 2.85–3.41 (m, 2H), 3.85 (s, 3H), 3.87–4.10 (m, 1H), 4.15 (q, J=7.2 Hz, 2H), 4.32–4.60 (m, 1H), 6.46 (d, J=8.7 Hz, 1H), 6.54 (d, J=3.0 Hz, 1H), 6.71 (d, J=15.3 Hz, 1H), ,7.15 (d, J=3.0 Hz, 1H), 7.17 (d, J=8.7 Hz, 1H), 7.36 (dd, J=2.4, 8.4 Hz, 1H), 7.42 (d, J=8.4 Hz, 1H), 7.88 (d, J=2.4 Hz, 1 H), 7.90 (d, J=15.3 Hz, 1H). MS (ESI$^+$) (M+H)$^+$ at m/z 517, 519, 521. Anal. Calcd for C$_{26}$H$_{26}$Cl$_2$N$_2$O$_3$S.0.12 H$_2$O: C, 60.10; H, 5.09; N, 5.39. Found: C, 60.09; H, 5.21; N, 5.54.

Example 340

(1-Methylindol-5-yl)[2,3-dichloro-4-(E-((4-carboxypiperidin-1-yl)carbonyl)ethenyl)phenyl] sulfide The title compound was prepared by the procedures described in Example 155, substituting the ethyl ester from Example 137 with ethyl ester from Example 339, and KOH with NaOH, to give a white solid. $^1$H NMR (d$^6$-DMSO, 300 MHz) δ 1.31–1.53 (m, 2H), 1.62–1.76 (m, 2H), 1.94–2.09 (m, 1H), 2.88 (brt, J=10.5 Hz, 1H), 3.13 (m, J=10.5 Hz, 1H), 3.86 (s, 3H), 3.93 (br d, J=13.2 Hz, 1 H), 4.09 (br d, J=13.2 Hz, 1H), 6.41 (d, J=8.7 Hz, 1H), 6.53 (dd, J=0.9,3.0 Hz, 1H), 7.04 (d, J=15.3 Hz, 1H), 7.32 (dd, J=2.1, 8.7 Hz, 1H), 7.48

(d, J=3.0 Hz, 1 H), 7.64 (d, J=8.7 Hz, 1H), 7.69 (d, J=15.3 Hz, 1H), 7.73 (d, J=8.7 Hz, 1H), 7.88 (d, J=2.1 Hz, 1H). MS (ESI$^+$) (M+H)$^+$ at m/z 489, 491, 493. Anal. Calcd for $C_{24}H_{21}Cl_2N_2NaO_3S$.0 H20: C, 56.37; H, 4.14; N, 5.48. Found: C, 56.44; H, 4.38; N, 5.20.

An alternative method for preparing Example 340 is given below.

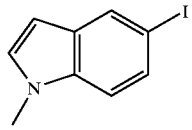

Example 340A

1-Methyl-5-iodoindole

To a solution of 5-iodoindole (75 g, 0.31 mol) in dry THF (750 mL), at −78° C. was added sodium hydride (60% in mineral oil, 14.85 g, 0.37 mol) in one portion. The suspension was stirred at −78° C. for 1 hour after which iodomethane (28.8 mL, 0.46 mol) was added. The reaction mixture was stirred overnight with a slow elevation of temperature to room temperature (no more dry ice was added). Ether (600 mL) and hexane (1.2 L) were added and the mixture was washed with brine (1.6 L) and water (1.5 L), dried over $Na_2SO_4$ and filtered. The solution was concentrated and the residual brown solid was recrystallized from hexane to give the title compound (66 g). The impure fraction from the mother liquor was flash chromatographed (8% EtOAc in hexane) to give an additional quantity of desired product (12.5 g, combined yield of 99%). MS (DCI/NH$_3$) m/e 258 (M+H)$^+$.

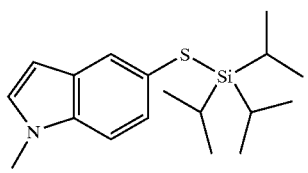

Example 340B

1-Methyl-S-triisopropylsilyl-5-indolethiol

Potassium hydride (35% in mineral oil, 12.03 g, 0.105 mol) was charged to a 250 mL round-bottom flask and was washed with dry THF (2×50 mL). The resultant KH powder was then suspended in dry THF (75 mL), and cooled to 5° C. Triisopropylsilylthiol (20.0 g, 0.1 05 mol) was slowly added via syringe over a period of 15 minutes. Vigorous escape of hydrogen gas was observed with addition of the thiol. The suspension was stirred at 5° C. for 1 hour and became homogenous. After another hour stirring at room temperature, this solution was cannulated to a THF solution (100 mL) containing Example 340A (24.5 g, 95.5 mmol) and tetrakis(triphenylphosphine)palladium(0) (2.2 g, 1.91 mmol). The yellow suspension was stirred at 70° C. for 1 hour. After cooling, ether and hexane were added, and the mixture was washed with brine, dried (Na$_2$SO$_4$) and concentrated. The residual oil was purified by flash chromatography (silica gel, 3% EtOAc in hexane) to give the title compound (26.7 g, 88%). MS (DCI/NH$_3$) m/e 320 (M+H)$^+$.

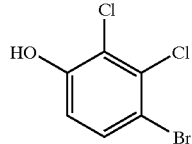

Example 340C

4-Bromo-2,3-dichlorophenol

To a solution of 2,3-dichlorophenol (200 g, 1.227 mol) in dichloromethane (800 mL), at 0° C. was added dropwise bromine (196.1 g, 1.227 mol) from a dropping funnel within 1 hour. The red solution was stirred overnight (0° C.-rt), and washed with 10% NaHSO$_3$. The organic phase was dried over Na$_2$SO$_4$, and concentrated. The residual white solid was recrystallized from hexane to give example 340C as white needles (207 g, 70%). MS (DCI/NH$_3$) m/e 241 (M+H)$^+$.

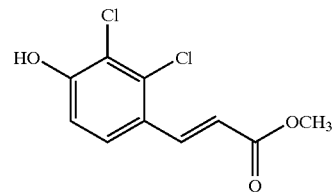

Example 340D

Methyl 2,3-dichloro-4-hydroxyphenylacrylate

A 1 L round-bottom flask was charged with Example 340C (48.4 g, 0.2 mol), Pd$_2$(dba)$_3$ (4.6 g, 5 mmol), (Tol)$_3$P (4.66 g, 15.2 mmol), and purged with nitrogen. Dry DMF (300 mL), methyl acrylate (51.66 g, 0.6 mol) and triethylamine (84 mL, 0.6 mol) were then added. The reaction mixture was purged with nitrogen and stirred at 100° C. (oil bath) for 16 hours. After cooling to room temperature, white crystalline material formed. Ethyl acetate (500 mL) and brine (not saturated, 800 mL) were added, and stirred. The white crystalline material dissolved. A little insoluble black solid (Pd) was filtered off. To the solution was then added, with stirring, saturated NaCl solution (2 L) and hexane (500 mL). The mixture was stirred for 1 hour. The formed yellowish solid was collected by filtration, washed with water (400 mL), acetonitrile (50 mL) and 1:1 ethyl acetate/hexane (500 mL), and dried to give pure desired compound (44.99g, 91%). MS (DCI/NH$_3$) m/e 247 (M+H)$^+$.

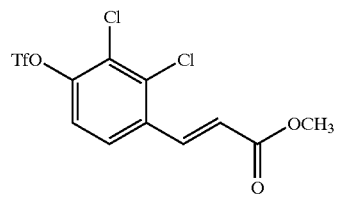

Example 340E

Methyl 2,3-dichloro-4-trifluoromethane sulfonyloxyphenylacrylate

To a suspension of Example 340D (18.62 g, 75.4 mmol) in pyridine (150 mL) at 5° C. was added trifluoromethylsulfonyl anhydride (25.53 g, 90 mmol) very slowly. The suspension was stirred at 5° C. for 1 hour and became homogeneous. The solution was kept at 5° C. for 2 hours and at room temperature for 20 minutes. Ether (700 mL) was added and the mixture was washed 10% HCl (700 mL)/brine (300 mL), 10% HCl (100 mL)/brine (900 mL), and brine (500 mL). The organic phase was dried (Na$_2$SO$_4$) and concentrated to give the title compound (24.86 g, 87%). MS (DCI/NH$_3$) m/e 379 (M+H)$^+$.

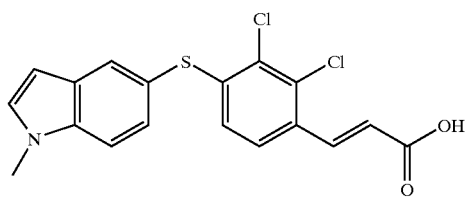

Example 340F (1-Methylindol-5-yl)[2,3-dichloro-4-(E-(carboxyethenyl)phenyl]sulfide To a solution of Example 340B (38.5 g, 0.12 mol) and Example 340E (30.3 g, 0.08 mol) in dry N-methylpyrrolidinone (300 mL) was added CsF (18.2 g, 0.12 mol) at 5° C. under nitrogen atmosphere. After 1 hour stirring at the same temperature, the cooling bath was removed, and the mixture was stirred at room temperature for 0.5 hour. Ethyl acetate (800 mL) was added, and the mixture was washed with brine and water, and concentrated. The residual oil was separated by flash chromatography (20% EtOAc/hexane) to give a yellow solid (30 g).

This yellow solid was dissolved in THF (150 mL), and was added a solution of LiOH (4.0 g, 0.16 mol) in H$_2$O (50 mL). The mixture was stirred at room temperature for 1 hour and more water (100 mL) was added to form a transparent solution. After overnight stirring the solution was acidified with 10% aq. HCl. The mixture was concentrated under reduced pressure to about 100 mL. The formed solid material was collected by filtration, washed with water (200 mL), acetonitrile (30 mL), 1:1 ether/hexane, and dried to give the title compound (22.3 g, overall 74%). MS (DCI/NH$_3$) m/e 378 (M+H)$^+$.

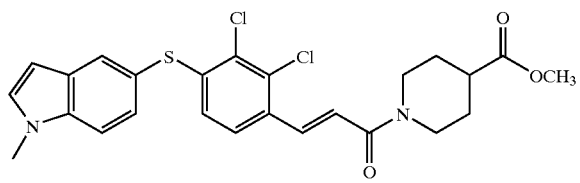

Example 340G (1-Methylindol-5-yl)[2,3-dichloro-4-(E-((4-carboethoxypiperidin-1-yl)carbonyl)ethenyl)phenyl] sulfide To a solution of Example 340F (9.5 g, 25.1 mmol) and methyl isonipecotate (7.19 g, 50.2 mmol) in DMF (70 mL) was added EDC (9.64 g, 50.2 mmol), HOBt (6.78 g, 50.2 mmol) and triethylamine (7.0 mL, 50.2 mmol). The reaction mixture was stirred at room temperature for 15 hours. Ethyl acetate (800 mL) was added, and the mixture was washed with brine, and concentrated. The residue was purified by flash chromatography (60% EtOAc in hexane) to give example 340G as white powder (10.86 g, 94%). MS (ESI$^+$) m/z 503 (M+H)$^+$.

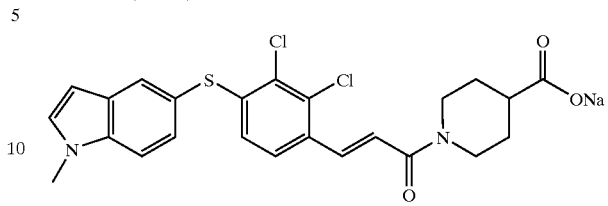

Example 340H (1-Methylindol-5-yl)[2,3-dichloro-4-(E-((4-carboxypiperidin-1-yl)carbonyl)ethenyl)phenyl] sulfide, sodium salt To a suspension of Example 340G (11.8 g, 23.6 mmol) in THF (150 mL) was added a solution of lithium hydroxide monohydrate (1.98 g, 47.2 mmol) in H$_2$O (30 mL). The mixture was stirred at room temperature overnight. Water (120 mL) was added and the formed transparent solution was stirred for another hour before 10% HCl (30 mL) was added. The mixture was concentrated under reduced pressure to about 120 mL. The formed solid material was collected by filtration, washed with water, acetonitrile, and dried to give a white solid (11.0 g).

10.50 grams of the solid was suspended in methanol (60 mL), and was treated with a solution NaOH (0.859 g) in methanol (20 mL). After all of the solid material went into solution, the solvent was removed under reduced pressure. The residual yellow oil was triturated with ether, and dried to give the title compound as a yellow powder (11.33 g, 95%).

Example 341

(2-Ethoxyphenyl)-[2,3-dichloro-4-(E-[(4-carboxypiperidin-1-yl)carbonyl)ethenyl)phenyl] sulfide The title compound was prepared according to the procedures of Example 310, substituting 2-methoxybenzenethiol prepared according to the procedures of Example 97A. $^1$H-NMR (CD$_3$OD, 300 MHz) Potassium salt δ 1.20 (t, J=7 Hz, 3H), 1.55–1.72 (m, 2H), 1.88–1.98 (m, 2H), 2,32 (m, 1H), 2.88 (t, J=12 Hz, 1H), 3.20 (t, J=12 Hz, 1H), (q, J=7 Hz, 2H), 4.14 (d, J=12 Hz, 1H), 4.48, (d, J=12 Hz, 1H), 6.64 9d, J=9 Hz, 1H), 7.00–7.15 (m, 3H), 7.44–7.50 (m, 2H), 7.56 (d, J=9 Hz, 1H), 7.90 (d, J=15 Hz, 1H) Anal. Calcd. for C$_{23}$H$_{22}$KC$_2$NO$_4$S.0.5 H$_2$: C, 52.37, H, 4.39, N, 2.66. Found: C, 52,23; H 4.56; N, 2.49.

Example 342

(2-Ethoxyphenyl)-[2,3-dichloro-4-(E-[(morpholin-1-yl)carbonyl)ethenyl)phenyl]sulfide The title compound was prepared according to the procedures of Example 310, substituting 2-methoxybenzenethiol with 2-ethoxybenzenethiol prepared according to the procedures of Example 97A. $^1$H-NMR (CDCl$_3$ 300 MHz) δ 1.25 (t, J=7 Hz, 3H), 3.55–3.80 (m, 8H), 4.05 (q, J=7 Hz, 2H), 6.63 (d, J=9 Hz, 1H), 6.71 (d, J=15 Hz, 1H), 6.95–7.03 (m, 2H), 7.26 (d, J=9 Hz, 1H), 7.39–7.50 (m, 2H), 7.99 (d, J=15 Hz, 1H) Anal. Calcd. for $C_{21}H_{21}Cl_2NO_3S$: C, 57.54; H 4.82; N, 3.20. Found: C, 57.55; H, 4.77; N, 3.14.

Example 343

(2-Ethoxyphenyl[2,3-dichloro-4-(E-[(3-carboxypiperidin-1-yl)carbonyl)ethenylphenyl] sulfide The title compound was prepared according to the procedures of Example 310, substituting 2-methoxybenzenethiol with 2-ethoxybenzenethiol prepared according to the procedures of Example 97A. $^1$H-NMR (CD$_3$OD 300 MHz) δ 1.20 (t, J=7 Hz, 3H), broad peaks totaling 9 protons at 1.4–1.95, 2.0–2.14, 2.22–2.35, 2.75–3.134.10–4.34, 4.69–4.76, 4.05 (q, J=7 Hz, 2H), 6.64 (d, J=9 Hz, 1H), 7.03 (t, J=8 Hz, 1H), 7.10 (d, J=9 Hz, 1H), 7.22 (d, J=15 Hz, 1H), 7.45–7.50 (m, 2H), 7.62 (d, J=9 Hz, 1H), 7.80 (d, J=15 Hz, 1H), The acid (303 mg, 0.63 mmol) was dissolved in 3 mL of methanol. A solution of KOH (0.60 mmol) in 1mL of methanol was added. The resultant solution was stirred for 5 minutes and concentrated in vacuo. Ether (5 mL) was added, and the mixture was stirred for 1 hour. The resultant powder was collected by filtration and dried under vacuum at 60C to give 307 mg of a solid, water-soluble product. Anal. Calcd. for $C_{23}H_{22}KC_{12}NO_4S.0.5 H_2O$; C, 52.37; H, 4.39; N, 2.66. Found: C, 52.20; H, 4.65, N, 3.04.

Example 344

(2-Isopropylphenyl)[2-nitro-4-(E-((3-carboethoxypyrrolidin-1-yl)carbonyl)ethenyl) phenyl]sulfide Prepared according to the procedures of Example 71, giving a yellow solid. $^1$H NMR (DMSO-d$_6$, 300 MHz) δ 1.14 (d, J=7.0 Hz, 6H); 1.20 (t, J=7.0 Hz, 3H); 1.92–2.30 (m, 2H); 3.10–4.01 (m, 6H); 4.06–4.17 (m, 2H); 6.64 (d, J=8.5 Hz, 1H); 7.06–7.17 (m, 1H), 7.34–7.62 (m, 5H); 7.88–7.96 (m, 1H); 8.62 (dd, J=1.5, 8.5 Hz, 1H). MS (APCI) (M+H)$^+$ at m/z 469. Anal calcd for $C_{25}H_{28}N_2S_1O_5$: C, 64.08; H, 6.02; N, 5.98. Found: C, 64.12; H, 5.98; N, 5.89.

Example 345

(2-Isopropylphenyl)[2-nitro-4-(E-((3-carboxypyrrolidin-1-yl)carbonyl)ethenyl)phenyl] sulfide Prepared according to the procedures of Example 71, giving a yellow solid. $^1$H NMR (DMSO-d$_6$, 300 MHz) δ 1.14 (d, J=6.8 Hz, 6H); 1.92–2.24 (m, 2H); 3.01–3.92 (m, 6H); 6.64 (dd, J=1.7, 8.5 Hz, 1H); 7.04–7.16 (m, 1H), 7.33–7.61 (m, 5H), 7.87–7.95 (m, 1H); 8.61 (dd, J=1.7, 8.5 Hz, 1H). MS (APCI) (M+H)$^+$ at m/z 441. Anal calcd for $C_{21}H_{24}N_2S_1O_5$: C, 62.71; H, 5.49; N, 6.36. Found: C, 62.47; H, 5.39; N, 6.09.

Example 346

(2-Isopropylphenyl)[2,3-difluoro-4-(E-((3-carboethoxypiperidin-1-yl)carbonyl)ethenyl)phenyl] sulfide Prepared according to the procedures of Example 71, giving a yellow solid. $^1$H NMR (DMSO-d$_6$, 300 MHz) δ 1.18 (d, J=7.0 Hz, 6H); 1.10–1.22 (m, 3H); 1.30–2.07(br m, 4H); 2.50–3.45 (br m, 3H); 3.554.47 (br m, 5H); 6.62–6.72 (m, 1H); 7.23–7.73 (m, 7H). MS (APCI) (M+H)$^+$ at m/z 474.

Example 347

(2-Isopropylphenyl)[2,3difluoro-4-(E-((3-carboxypiperidin-1-yl)carbonyl)ethenyl)phenyl] sulfide Prepared according to the procedures of Example 71, giving a yellow solid. $^1$H NMR (DMSO-d$_6$, 300 MHz) δ 1.18 (d, J=7.0 Hz, 6H); 1.30–2.03 (br m, 4H); 2.25–3.50 (br m, 4H); 3.87–4.51 (br m, 2H); 6.62–6.72 (m, 1H); 7.23–7.73 (m, 7H). MS (APCI) (M+H)$^+$ at m/z 446.

Example 348

(2-Isopropylphenyl)[2,3-difluoro-4-(E-((4-carboxypiperidin-1-yl)carbonyl)ethenyl)phenyl] sulfide Prepared according to the procedures of Example 71, giving a yellow solid. $^1$H NMR (DMSO-d$_6$, 300 MHz) δ 1.18 (d, J=6.8 Hz, 6H); 1.30–1.91 (br m, 4H); 2.50–3.50 (br m, 4H); 4.02–4.34 (br m, 2H); 6.62–6.72 (m, 1H), 7.23–7.73 (m, 7H). MS (APCI) (M+H)$^+$ at m/z 446.

Example 349

(Benzodioxan-6-yl)[2-trifluoromethyl-4-(E-((3-ethoxycarbonylpyrrolidin-1-yl)carbonyl)ethenyl) phenyl]sulfide The title compound was prepared according to the procedures of Example 1. $^1$H NMR (CDCl$_3$, 300 MHz) δ 7.77 (s, 1H), 7.62 (d, 1H, J=15.4 Hz) 7.42 (d, 1H, J=8.5 Hz), 7.06 (d, 1H, J=2.1 Hz), 6.98–7.04 (m, 2H), 6.91 (d, 1H, J=8.1 Hz), 6.68 (dd, 1H, J=3.3, 15.3 Hz), 4.30 (m, 4H), 4.19 (q, 2H, J=7.0 Hz), 3.56–3.92 (m, 4H), 3.06–3.24 (m, 1H), 2.10–2.35 (m, 2H), 1.28 and 1.29 (two t, 3H, J=7.2 Hz). MS (ESI) m/z 508, 1015.

Example 350

(Benzodioxan-6-yl)[2-trifluoromethyl-4-(E-((3-carboxypyrrolidin-1-yl)carbonyl)ethenyl)phenyl] sulfide The title compound was prepared by hydrolysis of the compound of Example 349 according to standard procedures. $^1$H NMR (DMSO-d$_6$, 300 MHz) δ 8.10 (d, 1H, J=9.9 Hz), 7.84 (t, 1H, J=7.8 Hz), 7.46 (d, 1H, J=15.3 Hz), 7.10 (d, 1H, J=15.3 Hz), 6.97–7.06 (m, 4H), 4.30 (m, 4H), 3.50 (br, overlapped with water residue peak), 3.00 (m, 1H), 2.10 (m, 1H), 2.00 (m, 1H). MS (ESI) m/z –478, –957.

Example 351

(2-Methoxyphenyl)[2-chloro-3-trifluoromethyl4-(E-((4-carboethoxypiperidin-1-yl)carbonyl)ethenyl) phenyl]sulfide

Example 351A

3-Chloro-4-hydroxy-2-(trifluoromethyl) benzaldehyde

Chloroform (6.7 g, 2.0 eq.) was added dropwise to a stirred mixture of Ca(OH)$_2$ (8.95 g, 120 mmol.), K$_2$CO$_3$ (13.5 g, 98 mmol.), 2-chloro-3-(trifluoromethyl)phenol (50. g, 22 mmol.), and H$_2$O (50 mL) at 60°–70° over 2 hours. The reaction mixture was cooled, and acidified with conc. HCl. The product was extracted into EtOAc and dried over Na$_2$SO$_4$. Solvent was evaporated, the crude product was separated and purified through a silica column, eluting with hexane and EtOAc (3:2) to give 580 mg (10%) of the title compound.

Example 351B (2-Methoxyphenyl)[2-chloro-3-trifluoromethyl-4-(E-carboxyethenyl)phenyl]sulfide The title compound was prepared according to the procedures described in Example 310, substituting the compound of Example 351 A for 4-hydroxy-2,3-dichlorobenzaldehyde.

Example 351C (2-Methoxyphenyl)[2-chloro-3-trifluoromethyl-4-(E-((4-carboethoxypiperidin-1-yl)carbonyl)ethenyl)phenyl]sulfide To the acyl chloride (37 mg, 0.1 mmol) prepared from the compound of Example 351B, as a solution in CH$_2$Cl$_2$ was added 1.2 eq. of ethyl isonipecotate and 1.2 eq. of Hunig's base. The mixture was stirred at room temperature for 20 min., ~90% of the solvent was removed in vacuo, and the resultant solution was loaded on a silica column to elute with hexane and EtOAc (3:2) to give 51 mg (98%) of the title compound. $^1$H-NMR (CDCl3, 300 MHz) δ 1.25 (t, J=7.5 Hz, 3H), 1.65–1.78 (m, 2H), 1.92–2.02 (br, 2H), 2.51–2.60 (m, 1H), 2.93–3.24 (br, 2H), 3.82 (s, 3H), 3.88–3.96 (m, 1H), 4.15 (q,J=7.5 Hz, 2H), 4.40–4.50 (br, 1H), 6.48 (d, J=115 Hz, 1H), 6.72 (d, J=9 Hz, 1H), 7.02 (d, J=7.5 Hz, 2H), 7.12 (d, J=9 Hz, 1H), 7.49 (t, J=9 Hz, (qq, J=4.5 Hz, 1H). MS (DCI/NH$_3$) m/e 528 (M+H)$^+$.

Example 352

(2-Methoxyphenyl)[2-chloro-3-trifluoromethyl-4-(E-((4-carboxypiperidin-1-yl)carbonyl)ethenyl)phenyl]sulfide The compound of Example 351 was hydrolyzed by aq. NaOH in EtOH at rt. to give 90% yield of the title compound. $^1$H NMR(DMSO, 300 MHz) δ 1.37–1.52 (br. 2H), 1.78–1.86 (br. 2H), 2.45–2.55 (m, 1H), 2.83 (t, J=12 Hz, 1H), 3.17 (t, J=13.5 Hz, 1H), 3.80 (s, 3H), 4.07 (d, J=12 Hz, 1H), 4.26 (d, J=13.5 Hz, 1H), 6.75 (d, J=9 Hz, 1H), 6.98 (d, J=15 Hz, 1H), 7.1 1(t, J=9 Hz, 1H), 7.26 (d, J=9 Hz, 1H), 7.53 (d, J=(d, J=7.5 Hz 1H), 7.62 (d, J=9 Hz, 2H), 7.70 (qq, J=4.5 Hz, 1H). MS (DCI/NH$_3$) m/e 500(M+H)$^+$.

Example 353

(2-Methoxyphenyl)[2-chloro-3-trifluoromethyl4-(E4-(morpholin-1-yl)carbonyl)ethenyl)phenyl]sulfide Prepared according to the procedures of Example 351, giving 50 mg (91%) of the title compound. $^1$H-NMR (CDCl$_3$, 300 MHz) δ 3.56–3.62 (br m, 2H), 3.67–3.77 (br m, 6H), 3.85 (s, 31H), 6.45 (d, J=15 Hz, 11t), 6.73 (d, J=9 Hz, 1H), 7.03 (d, J=9 Hz, 2H), 7.09 (t, J=9 Hz, 1H), 7.52 (d, J=9 Hz, 2H), 2.93 (qq, J=6 Hz, 1H). MS (DCI/NH$_3$) m/z 458 (M+H)$^+$.

Example 354

(Benzodioxan-6-yl)[4-(E-((4-carboxypiperidin-1-yl)carbonyl)ethenyl)naphthyl]sulfide The methods of Example 310 and 311 were used to convert 4-hydroxy-2-naphthaldehyde and 6-benzodioxanethiol to the desired product as a yellow solid. $^1$H NMR (DMS-d$_6$, 300 MHz) δ 1.50 (br s, 2H), 1.83–1.92 (m, 2H), 2.5–2.6 (m, 1H), 2.85–2.95 (m, 1H), 3.18–3.29 (m, 1H), 4.22 (br s, SH), 4.30–4.38 (m, 1H), 6.87–6.92 (m, 3H), 7.38 (d, J=15 Hz, 1H), 7.45 (d, J=7.5 Hz, 1H), 7.64–7.70 (m, 2H), 7.93 (d, J=7.5 Hz, 1H), 8.20–8.45 (m, J=3H). MS(ESI$^+$) m/z 476 (M+H)$^+$. Anal calcd for C$_{27}$H$_{25}$NO$_5$S0.67H$_2$O: C, 66.50; H, 5.44; N, 2.87. Found: C, 66.56; H, 5.81; N, 2.49.

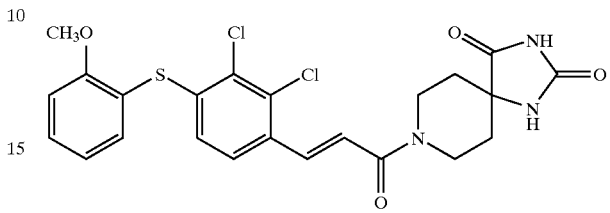

Example 355

(2-Methoxyphenyl)[2,3-dichloro-4-(E-((4-spirohydantoin-5-yl)piperidin-1-yl)carbonyl)ethenyl)phenyl]sulfide The title compound was prepared from Example 310C, using the procedures described in Example 340 and substituting methyl isonipecotate with piperidine-4-spiro-5'-hydantoin, which was prepared according to a literature method (Wysong, C., et al, *J. Org. Chem.* 1996, 7650). $^1$H NMR (300 MHz, DMSO-d$_6$) δ 1.65 (m, 2H), 1.75 (m, 2H), 3.05 (m, 1H), 3.50 (m, 1H), 4,12 (m, 1H), 4.20 (m, 1H), 6.56 (d, J=6.5 Hz, 1H), 7.10 (t, J=8.0 Hz, 1H), 7.22 (d, J=8.0 Hz, 1H), 7.28 (d, J=15.6 Hz, 1H), 7.49 (dd, J=8.0, 1.7 Hz, 1H), 7.56 (t, J=8.2 Hz, 1H), 7.76 (d, J=15.6 Hz, 1H), 7.84(d, J=8.6 Hz, 1H), 8.58 (s, 1H), 10.73(s, 1H). MS (ESI$^-$) m/z 504 (M–H)$^-$.

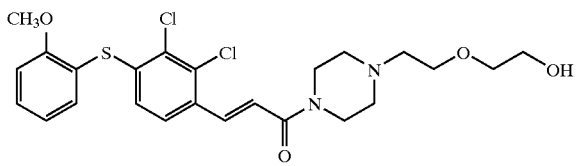

Example 356

(2-Methoxyphenyl)[2,3-dichloro-4-(E-(4-(2-(2-hydroxyethoxy)ethyl)piperazin-1-yl)carbonyl)ethenyl)phenyl]sulfide The title compound was prepared from Example 310C by the procedures described in Example 340 and substituting methyl isonipecotate with N-[2-(2-hydroxyethoxy)ethyl]piperazine. $^1$H NMR (300 MHz, DMSO-d$_6$) δ 3.10 (m, 2H), 3.50 (m, 4H), 4.50 (m, 2H), 4.70 (s, 1H), 6.57 (d, J=8.5 Hz, 1H), 7.09 (t, J=8.0 Hz, 1H), 7.23 (d, J=8.0 Hz, 1H), 7.26 (d, J=15.5 Hz, 1H), 7.49 (dd, J=7.8, 1.7 Hz, 1H), 7.57 (t, J=8.2 Hz, 1H), 7.78 (d, J=15.6 Hz, 1H), 7.80 (d, J=7.8 Hz, 1H). MS (ESI$^-$) m/z 545 (M–H)$^-$.

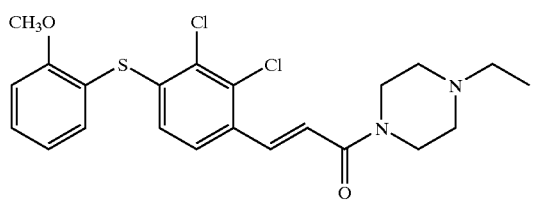

Example 357

(2-Methoxyphenyl)[2,3-dichloro-4-(E-((4-ethylpiperazin-1-yl)carbonyl)ethenyl)phenyl]sulfide The title compound was prepared from Example 310C by the procedures described in Example 340 and substituting methyl isonipecotate with 1-ethylpiperazine. $^1$H NMR (300 MHz, CDCl$_3$) δ 1.09 (t, J=7.1 Hz, 3H), 2.42 (q, J=7.1 Hz, 2H), 2.47 (m, 4H), 3.60 (m, 2H), 3.75 (m, 2H), 3.82 (s, 3H), 6.56 (d, J=8.5 Hz, 1H), 6.74(d, J=15.3 Hz, 1H) 7.02 (m, 2H), 7.26 (d, J=8.5 Hz, 1H), 7.46 (m, 2H), 7.94 (d, J=15.5 Hz, 1H). MS (ESI$^+$) m/z 451 (M+H)$^+$.

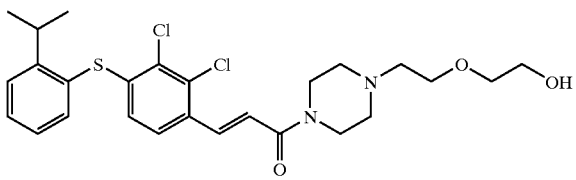

Example 358

(2-Isopropylphenyl)[2,3-dichloro-4-(E-((4-(2-(2-hydroxyethoxy)ethyl)piperazin-1-yl)carbonyl)ethenyl)phenyl]sulfide The title compound was prepared from the cinnamide acid of Example 331, using the procedures described in Example 340 and substituting methyl isonipecotate with N-[2-(2-hydroxyethoxy)ethyl]piperazine. $^1$H NMR (300 MHz, DMSO-d$_6$) δ 1.18 (d, 6H), 3.0 (m, 3H), 3.30 (m, 2H), 3.50 (m, 10H), 3.80 (m, 2H), 4.50 (t, 1H), 6.45 (d, 1H), 7.30 (d, 1H), 7.35 (dd, 1H), 7.55 (d, 1H), 7.60 (m, 2H), 7.75 (d, 1H), 7.80 (d, 1H). MS (ESI$^+$) m/z 523 (M+H)$^+$.

Example 359

(Benzodioxan-6-yl)[2,3-bis(trifluoromethyl)-4-(E-((4-carboxypiperidin-1-yl)carbonyl)ethenyl)phenyl]sulfide

Example 359A

1-Methyl-2,3-bis(trifluoromethyl)-7-oxabicyclo[2.2.1]hepta-2,5-diene

Hexafluoro-2-butyne (21.0 g, 0.13 mol) was transferred into a reaction bottle and treated with 2-methylfuran (12.86 g, 0.157 mol). This resulting mixture bottle was sealed and heated for 15 hours at 120° C. After cooling, the excess 2-methylfuran was rotoevaporated in vacuo at room temperature, to give the crude title product (29 g, 92%), which was used directly.

Example 359B

4-Methyl-2,3-bis(trifluoromethyl)phenol

A mixture of Example 359A (12.0 g, 0.05 mol) and boron trifluoride-diethyl ether complex (150 mL) was stirred at room temperature overnight, then neutralized carefully with 20% aqueous potassium carbonate, then the mixture was extracted with ether. The ether layer was dried over MgSO$_4$ and evaporated under reduced pressure to afford 10.4 g (85%) of the title compound.

Example 359C

4-[4-Bromobenzene sufonyloxy-2,3-bis(trifluoromethyl)]benzylbromide

The phenol compound of Example 359B (10 g, 0.04 mol) was treated with 4-bromobenzenesulfonyl chloride (11.0 g, 0.043 mol) and Hunig's base (5.56 g, 0.043 mol) in CH$_2$Cl$_2$ (150 mL). The solution was washed with water, brine and dried over MgSO$_4$. After evaporating the solvent, N-bromosuccinimide (7.3 g, 0.04 mol) and benzoyl peroxide (200 mg) were added and the mixture was suspended in CCl$_4$ (100 mL). The resulting mixture was refluxed for 13 hours. When the reaction was cooled, the white solid was filtered and washed with CCl$_4$ to afford the crude title compound. This crude product was used for the next step without further purification.

Example 359D

4-Hydroxy-2,3-bis(trifluoromethyl)benzaldehyde

The crude product of Example 359C was dissolved in 60 mL of DMSO and 20 mL of CH$_2$Cl$_2$, and 12 g of trimethylamine N-oxide added. The resulting mixture was stirred at rt for 2.5 hours. The reaction mixture was poured into an ice cold 50% saturated aqueous NaCl solution (200 mL) and extracted with ether (3×100 mL). The combined organic layer was washed with brine and dried over Na$_2$SO$_4$. After evaporation of solvent, the product was purified by column chromatography, eluted with hexane:EtOAc (3:2) to provide 3.0 g of the title compound, plus 4.0 g of recovered 4-[4-bromobenzenesulfonyloxy-2,3-bis(trifluoromethyl)] toluene.

Example 359E (Benzodioxan-6-yl)-[2,3-bis(trifluoromethyl)4-(E-carboethenyl)phenyl]sulfide The title compound was prepared according to the procedures described in Example 330, substituting the compound of Example 359D for 4-hydrox-2,3-dichlorobenzaldehyde.

Example 359F (Benzodioxan-6-yl)[2,3-bis(trifluoromethyl)-4-(E-((4-carboxypiperidin-1-yl)carbonyl)ethenyl)phenyl]sulfide The title compound was prepared from Example 359E by the procedures described in Example 10, giving a white solid. $^1$H NMR (CD$_3$OD, 300 MHz) δ 1.65(br s, 2H), 1.93–2.04 (m, 2H), 2.57–2.65 (m, 1H), 2.95–3.05 (m, 1H), 3.25 (m, 1H), 4.12 (m, 1H), 4.28 (m, 4H), 4.41 (m, 1H), 6.92–7.03 (m, 4H), 7.25 (d, J=9 Hz, 1H), 7.72 (d, J=9 Hz, 1H), 7.72–7.81 (m, 1H). MS (ESI) m/e 562 (M+H)$^+$. Anal calcd for C$_{25}$H$_{21}$NO$_5$F$_6$S: C, 53.48; H, 3.77; N, 2.49. Found: C, 53.42; H, 3.69; N, 2.25.

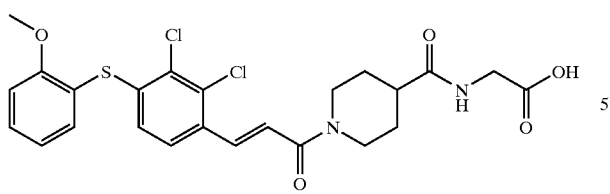

Example 360

(2-Methoxyphenyl)[2,3-dichloro-4-(E-((4-(carboxymethylamino)carbonyl-piperidin-1-yl)carbonyl)ethenyl)phenyl]sulfide

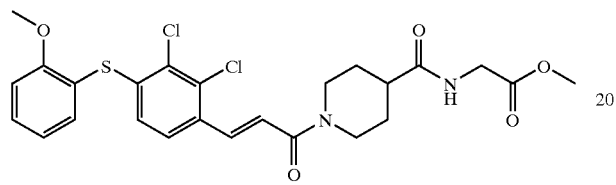

Example 360A (2-Methoxyphenyl)[2,3-dichloro-4-(E-((4-(methylaminomethylcarboxylate)carbonyl-piperidin-1-yl)carbonyl)ethenyl)phenyl]sulfide The title compound was prepared by the procedure described in Example 363 using glycine methyl ester as the coupling substrate. HPLC (Supelco C-18 column, water:acetonitrile 50:90–90:50, 9 minute elution, flow rate 1.5 mL/min, rt=6.11 minutes MS (APCI) m/e 537 (M+H)$^+$; $^1$H NMR (300 MHz, DMSO-$d_6$) δ 1.46(m, 3H), 1.78(br d, 2H), 2.79(m, 1H), 3.15(m, 1H), 3.62(s, 3H), 3.80(s, 3H), 3.83(d, 2H), 4.20(m, 1H), 4.40(m, 1H), 6.58(d, 1H), 7.09(t, 1H), 7.22(d, 1H), 7.25(dd, 1H), 7.48(d, 1H), 7.56(t, 1H), 7.72(d, 1H), 7.81(d, 1H), 8.28(t, 1H). Anal calcd for $C_{25}H_{26}Cl_2N_2O_5S$·1.3 $H_2O$; C, 53.54; H, 5.14; N, 4.99. Found: C, 53.49; H, 4.88; N, 4.75.

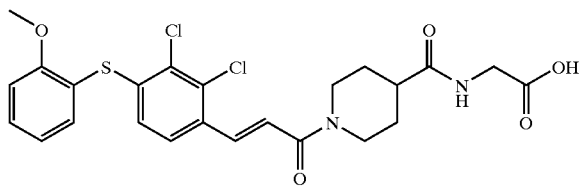

Example 360B (2-Methoxyphenyl)[2,3-dichloro-4-(E-((4-(carboxymethylamino)carbonyl-piperidin-1-yl)carbonyl)ethenyl)phenyl]sulfide The title compound was hydrolyzed as described in Example 340H. HPLC (Supelco C-18 column, water:acetonitrile 90:0–0:90, 30 minute elution, flow rate 0.8 mL/min) rt 26.14 minutes. $^1$H NMR (300 MHz, DMSO-$d_6$) δ 1.46 (m, 2H), 1.75 (m, 2H), 2.73 (m, 1H), 3.12 (m, 1H), 3.70 (m, 2H), 3.79 (s, 3H), 4.02 (m, 1H), 4.20 (m, 1H), 4.41 (m, 1H), 6.65 (d, 1H), 7.09 (dt, 1H), 7.22 (d, 1H), 7.25 (dd, 1H), 7.48 (dd, 1H), 7.58 (m, 1H), 7.72 (d, 1H), 7.82 (d, 1H), 8.11 (m, 1H). MS (APCI) m/e 523 (M+H)$^+$.

Example 361

(2-Methoxyphenyl)[2,3-bis(trifluoromethyl)-4-(E-((4carboxymethylpiperazin-1-yl)carbonyl)ethenyl)phenyl]sulfide The title compound was prepared according to the procedures of Example 22, employing the compound of Example 359D as starting material, to give a white solid. $^1$H NMR (CD$_3$OD, 300 MHz) δ 3.07–3.12 (m, 4H), 3.48 (s, 2H), 3.74 (s, 3H), 3.89 (br s, 4H), 6.99–7.18 (m, 4H), 7.53 (d, J=9 Hz, 2H), 7.72 (d, J=9 Hz, 1H), 7.78–7.88 (m, 1H). MS (ESI) m/z 549 (M+H)$^+$. Anal calcd for $C_{26}H_{26}F_6N_2O_4S$·0.9HAc: C, 51.43, H 4.28, N, 4.65. Found: C, 51.48, H, 4.12, N,4.45.

Example 362

(2-Methoxyphenyl)[2,3-bis(trifluoromethyl)4-(E-((4-N-(2-hydroxyethyl)piperazin-1-yl)carbonyl)ethenyl)phenyl]sulfide The title compound was prepared by the procedures described in Example 356, employing the compound of Example 359D as starting material to give an oil. $^1$H NMR (CDCl$_3$, 300 MHz) δ 2.68 (br s, 6H), 3.71 (br s, 4H), 3.80 (br s, 5H), 6.55 (d, J=15 Hz, 1H), 6.93–7.02 (m, 2H), 7.10 (d, J=9 Hz, 1H), 7.35 (d, J=9Hz, 1H), 7.41–7.50 (m, 2H), 7.82 (qq, J=15 Hz, 1H). MS (ESI) m/z 535 (M+H)$^+$. Anal calcd for $C_{24}H_{24}F_6N_2O_3S$·HCl: C,50.49; H, 4.41; N, 4.91. Found: C, 50.72; H1 4.70; N, 4.55.

Example 363

(1-Methylindol-5-yl)[2,3-dichloro-4-(E-((4-(carbo-2,3-dihydroxypropylamino)piperidin-1-yl)carbonyl)ethenyl)phenyl]sulfide To a solution of Example 340H (100 mg, 0.2 mmol) and 3-amino-1,2-propanediol (37.4 mg, 0.41 mmol) in DMF (3 mL) was added EDC (78 mg, 0.41 mmol), HOBt (55 mg, 0.41 mmol) and triethylamine (0.057 mL, 0.41 mmol). The reaction mixture was stirred at room temperature for 15 hours. Ethyl acetate (60 mL) was added, and the mixture was washed with brine. The aqueous phase was extracted with 10% MeOH in methylene chloride. The combined organic phases were concentrated to dry. The residual material was triturated with water, filtered, washed with water, acetonitrile and ethyl acetate, and dried to give example 363 (92 mg, 80%). $^1$HNMR (300 MHz, DMSO-$d_6$) δ 1.44 (m, 1H), 1.72 (m, 1H), 2.41 (m, 1H), 2.70 (t, 1H), 3.00 (m, 2H), 3.20 (m, 2H), 3.27 (m, 2H), 3.50 (m, 2H), 3.90 (s, 3H), 4.18 (br d, 1H), 4.40 (br d, 1H), 4.50 (t, 1H), 4.77 (d, 1H), 6.40 (d, 1H), 6.58 (d, 1H), 7.19 (d, 1H), 7.35 (d, 1H), 7.5 0(d, 1H), 7.66 (d, 1H), 7.70 (m, 2H), 7.80 (t, 1H), 7.88 (s, 1H). MS (ESI$^+$) m/z 562 (M+H)$^+$. Anal. calcd for $C_{27}H_{29}Cl_2N_3SO_4$·0.25H$_2$O: C, 57.19; H, 5.24; N, 7.41. Found: C, 57.07; H, 5.22; N, 7.13.

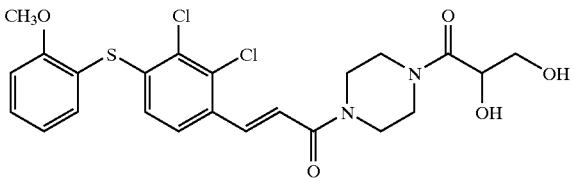

364

(2-Methoxyphenyl)[2,3-dichloro-4-(E-(4-(2,3-dihydroxypropionyl)piperazin-1-yl)carbonyl)ethenyl)phenyl]sulfide

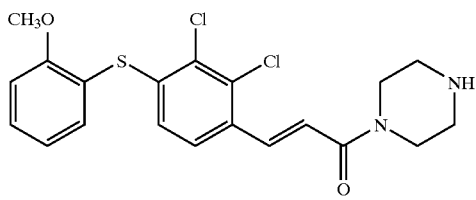

Example 364A (2-Methoxyphenyl)[2,3-dichloro-4-(E-((piperazin-1-yl)carbonyl)ethenyl)phenyl]sulfide The title compound was prepared by the procedures described in Example 340G substituting methyl isonipecotate with piperazine. MS (DCI/NH$_3$) m/e 423 (M+H)$^+$.

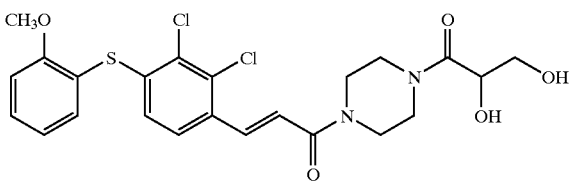

Example 364B (2-Methoxyphenyl)[2,3-dichloro-4-(E-(4-(2,3-dihydroxypropiony)piperazin-1-yl)carbonyl)ethenyl)phenyl]sulfide The title compound was prepared by the procedures described in Example 340, substituting methyl isonipecotate with Example 364A and substituting Example 340G with DL-glyceric acid Ca salt. $^1$H NMR (300 MHz, DMSO-d$_6$) δ 3.2–3.8 (m, 12H), 4.38 (t, 1H), 6.58 (d, 1H), 7.10 (t, 1H), 7.27 (d, 1H), 7.28 (d, 1H), 7.50 (d, 1H), 7.60 (t, 1H), 7.79 (d, 1H), 7.83 (d, 1H). MS ESI$^+$ m/z 511 M+H)$^+$.

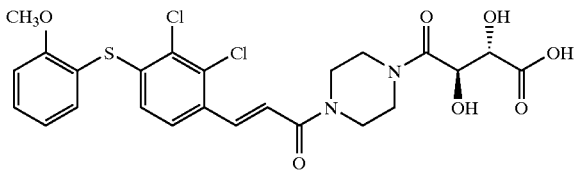

Example 365

(2-Methoxyphenyl)[2,3-dichloro-4-(E-(4-(2,3-dihydroxy-3-carboxypropionyl)piperazin-1-yl)carbonyl)ethenyl)phenyl]sulfide The title compound was prepared by the procedures described in Example 340 substituting methyl isonipecotate with Example 364A and substituting Example 340G with meso-tartaric acid. $^1$H NMR (300 MHz, CDCl$_3$) δ 3.70 (m, 8H), 4.33 (br s, 1H), 4.72 (br s, 1H), 6.58 (d, 1H), 6.77 (d, 1H), 7.03 (m, 2H), 7.25(d, 1H), 7.50 (d, 1H), 7.52 (d, 1H), 8.00 (d, 1H). MS (ESI$^+$) m/z 555 (M+H)$^+$.

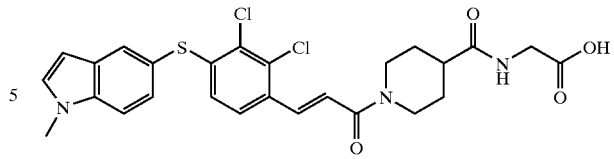

Example 366

(1-Methylindol-5-yl)[2,3-dichloro-4-(E-((4(4-(carboxymethylamino)carbonyl-piperidin-1-yl)carbonyl)ethenyl)phenyl]sulfide The title compound was prepared by the procedures described in Example 363 substituting 3-amino-1,2-propanediol with glycine methyl ester hydrochloride followed by hydrolysis. $^1$H NMR (300 MHz, DMSO-d$_6$) δ 1.42 (m, 2H), 1.75 (m, 2H), 2.45 (m, 1H), 2.78 (m, 1H), 3.10 (m, 1H), 3.72 (d, 2H), 3.90 (s, 3H), 4.18 (br, d, 1H), 4.40 (br d, 1H), 6.42 (d, 1H), 6.57 (d, 1H), 7.18 (d, 1H), 7.32 (d, 1H), 7.50 (d, 1H), 7.65 (d, 1H), 7.67 (d, 1H), 7.70 (m, 1H), 7.88 (s, 1H), 8.18 (t, 1H). MS (ESI$^+$) m/z 546 (M+H)$^+$. Anal. calcd for C$_{26}$H$_{25}$N$_3$Cl$_2$SO$_4$: C, 57.15; H, 4.61; N, 7.69. Found: C, 57.17; H, 4.64; N, 7.39.

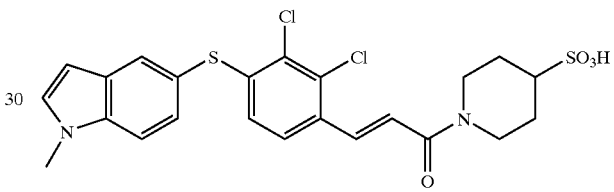

Example 367

(1-Methylindol-5-yl)[2,3-dichloro-4-(E-((4-sulfopiperidin-1-yl)carbonyl)ethenyl)phenyl]sulfide The title compound was prepared from Example 340F, by the procedures described in Example 340G, substituting methyl isonipecotate with piperadine-4-sulfonic acid. $^1$H NMR (300 MHz, DMSO-d$_6$) δ 1.40 (m, 2H), 1.90 (m, 2H), 3.03 (m, 1H), 4.10 (m, 3H), 4.42 (br d, 1H), 6.40 (d, J=8.8 Hz, 1H), 6.53 (d, J=3.1 Hz, 1H), 7.15 (d, J=15.3 Hz, 1H), 7.33 (dd, J=8.5, 1.7 Hz, 1H), 7.48 (d, J=3.1 Hz, 1H), 7.65 (d, J=8.5 Hz, 1H), 7.67 (d, J=15.2 Hz, 1H), 7.74 (d, J=8.8 Hz, 1H), 7.87 (d, J=1.5 Hz). MS (ESI$^+$) m/z 525 (M+H)$^+$. Anal. calcd for C$_{23}$H$_{22}$N$_2$Cl$_2$S$_2$O$_4$·0.8 TFA: C, 47.91; H, 3.73; N, 4.54. Found: C, 47.71; H, 3.84; N, 4.73.

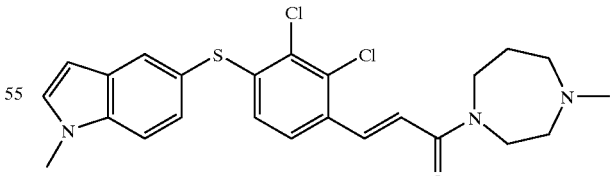

Example 368

(1-Methylindol-5-yl)[2,3-dichloro-4-(E-(4-methylhomopiperazin-1-yl)carbonyl)ethenyl)phenyl]sulfide The title compound was prepared by the procedures described in Example 340G substituting methyl isonipecotate with N-methyl homopiperazine. ¹H NMR (300 MHz, DMSO-d₆) δ 2.06 (m, 2H), 2.81 (m, 2H), 3.17 (m, 2H), 3.55 (m 3H), 3.70 (s, 3H), 3.86 (s, 3H), 4.05 (m, 1H), 6.42 (dd, J=8.4,3.3 Hz, 1H), 6.54 (d, J=3.0 Hz, 1H), 7.08 (dd, J=15.4, 7.5 Hz, 1H), 7.35 (dd, J=8.8,2.0 Hz, 1H), 7.49 (d, J=3.0 Hz, 1H), 7.65 (d, J=8.5 Hz, 1H), 7.73 (d, J=8.8 Hz, 1H), 7.80 (d, J=15.2 Hz, 1H), 7.88 (d, J=2.0 Hz, 1H). MS (ESI⁺) m/z 474 (M+H)⁺. Anal. calcd for C₂₆H₂₆N₃Cl₂SF₃O₃.0.75 TFA: C, 49.01; H, 4.00; N, 6.23. Found: C, 48.71; H, 4.09; N, 6.13.

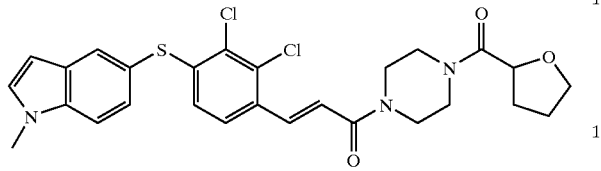

Example 369

(1-Methylindol-5-yl)[2,3-dichloro-4-(E-(4-tetrahydrofuroylpiperazin-1-yl)carbonyl)ethenyl)phenyl]sulfide The title compound was prepared by the procedures described in Example 340G substituting methyl isonipecotate with 1-tetrahydrofuroylpiperazine. ¹H NMR (300 MHz, DMSO-d₆) δ 1.80 (m, 2H), 2.00 (m, 2H), 3.50 (m, 8H), 3.75 (m, 2H), 3.88 (s, 3H), 4.68 (t, 1H), 6.42 (d, 1H), 6.57 (d, 1H), 7.19 (d, 1H), 7.32 (d, 1H), 7.48 (d, 1H), 7.65 (d, 1H), 7.70 (d, 1H), 7.75 (d, 1H), 7.87 (s, 1H). MS (ESI⁺) m/z 544 (M+H)⁺. Anal calcd for C₂₇H₂₇N₃Cl₂SO₃: C, 59.56; H, 4.99; N, 7.71. Found: C, 59.40; H, 4.94; N, 7.61.

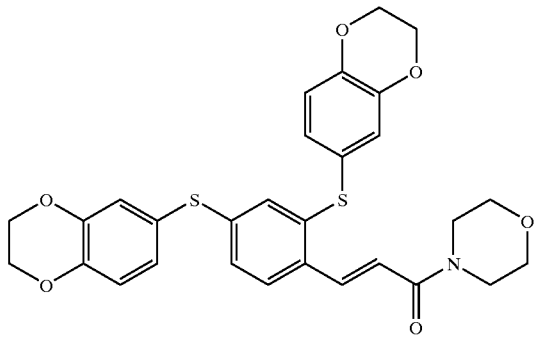

Example 370

(Benzodioxan-6-yl)[2-(Benzodioxan-6-sulfanyl)-4-(E-((4-morpholino)carbonyl)ethenyl)phenyl]sulfide Example 370A (E)-Morpholino 2,4-difluorocinnamide The title compound was processed as reported in Example 1C substituting morpholine (1.04 mL, 11.9 mmol) for the amine and trans-2,4-difluorocinnamic acid (1.00 g, 5.4 mmol) for the carboxylic acid. The title compound was obtained as an off-white foam (1.4 g, 100%). ¹H NMR (DMSO-d₆, 300 MHz) d 8.04 (dd, J=15.26, 8.82 Hz, 1H), 7.53 (d, J=14.91 Hz, 1H), 7.38–7.30 (m, 1H), 3.61–3.48 (m, 8H). MS (APCI) m/z 254 (M+H)⁺.

Example 370B

Morpholinyl-(E)-2,4-bis(1,4-benzodioxane-6-mercaptan)cinnamic amide

Example 370A (233 mg, 1.00 mmol) was combined with cesium carbonate (652 mg, 2.00 mmol), 1,4-benzodioxane-6-thiol (370 mg, 2.20 mmol), and DMF (5 mL). The mixture was processed as reported in Example 1A to provide the title compound (220 mg, 40%) as a white foam. ¹H NMR (DMSO-d⁶, 300 MHz) δ 7.83 (d, J=15.20 Hz, 1H), 7.80 (d, J=8.20 Hz, 1H), 7.17 (d, J=15.3 Hz, 1H), 7.02 (dd, J=8.5, 2.0 Hz, 1H), 6.87–6.75 (m, 6H), 6.48 (s, 1H), 4.33–4.25 (m, 8H), 3.61–3.48 (m, 8H). MS (APCI) m/z 550 (M+H)⁺.

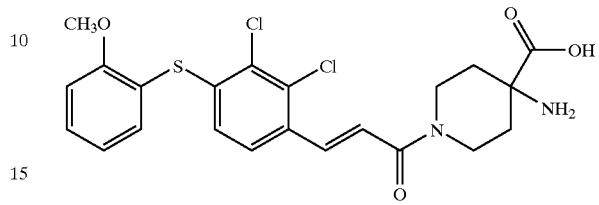

Example 371

(2-Methoxyphenyl)[2,3-dichloro-4-(E-((4-amino-4-carboxypiperidin-1-yl)carbonyl)ethenyl)phenyl]sulfide To a suspension of Example 355 (700 mg, 1.4 mmol) in DME (10 mL) was added a solution of (BOC)₂O (1.51 g, 6.9 mmol) in DME (5 mL), triethylamine (0.23 mL, 1.7 mmol) and DMAP (9 mg, 0.07 mmol). The reaction mixture was stirred at room temperature overnight. Additional triethylamine (0.23 mL) and DMAP (30 mg) were added, and the mixture was heated at 60° C. for 6 hours. After aqueous work up, the crude product was suspended in DME (5 mL) and water (5 mL) containing 200 mg of NaOH. The suspension was stirred for 5 hours at room temperature, and separated by HPLC to give the title compound (300 mg, 45%). ¹H NMR (300 MHz, DMSO-d₆) δ 1.78 (m, 2H), 2.10 (m, 2H), 3.60 (m, 2H), 3.80 (s, 3H), 3.86 (m, 2H), 6.58 (d, 1H), 7.10 (d, 1H), 7.25 (d, 1H), 7.28 (d, 1H), 7.50 (d, 1H), 7.58 (t, 1H), 7.77 (d, 1H), 7.80 (d, 1H), 8.50 (br s, 2H). MS (ESI⁺) m/z 481 (M+H)⁺. Anal calcd for C₂₂H₂₂N₂Cl₂SO₄.0.75 H₂O: C, 47.34; H. 4.06; N, 4.60. Found: C, 47.31; H, 4.05; N, 4.43.

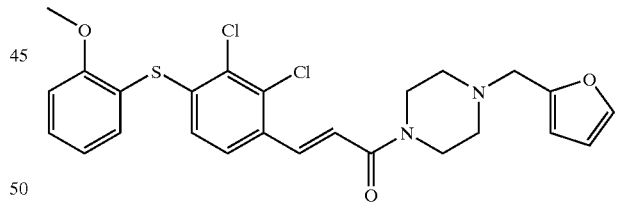

Example 372

(2-Methoxyphenyl)[2,3-dichloro-4-((4-furoylpiperazin-1-yl)carbonyl)ethenyl)phenyl]sulfide To a solution of Example 364A (100 mg, 0.24 mmol) and 2-furfural (30 mg, 0.24. mmol) in dichloroethane (2 mL) was added NaBH(OAc)₃ (142 mg, 0.67 mmol) under nitrogen atmosphere. The mixture was stirred for 16 hours at room temperature. Dichloromethane (20 mL) was added and the mixture was washed with 5% NaHCO₃, then with brine, and the organic phase was separated and concentrated. The residual solid was chromatographed by flash chromatography (5% MeOH/CH₂CL₂) and desired fractions were combined, concentrated and dried to afford the title compound as an off-white solid (84 mg, 69%). HPLC (Supelco C-18 column, water:acetonitrile 100:0–0:100, 15 minute elution, flow rate 1.5 mL/min) rt 11.90 minutes. $^1$H NMR (300 MHz, DMSO-d$_6$) δ 2.39 (m, 4H), 3.52 (s, 2H), 3.55 (m, 2H), 3.63 (m, 2H), 3.79 (s, 3H), 6,29 (d, 1H), 6.40 (m, 1H), 6.57 (d, 1H), 7.08 (dt, 1H), 7.21 (d, 1H), 7.23 (dd, 1H), 7.48 (dd, 1H), 7.57 (m, 2H), 7.72 (d, 1H), 7.80 (d, 1H). MS (ESI) m/e 503 (M+H)$^+$.

Example 375

(2-Methoxyphenyl)[2,3-bis(trifluoromethyl)-4-(E-((4-carboxypiperidin-1-yl)carbonyl)ethenyl)phenyl]sulfide The title compound was prepared by the procedures described in Example 352, employing the compound of Example 359D to give a white solid. $^1$H NMR(CD$_3$OD, 300 MHz) δ 1.65 (br s, 2H), 1.94–2.03 (m, 2H), 2.57–2.67 (m, 1H), 2.95–3.05 (m, 1H), 3.23–3.32 (m, 1H), 3.75 (s, 3H), 4.12 (br s, 1H), 4.40 (br s, 1H), 7.00 (d, J=15 Hz, 1H), 7.03–7.20 (m, 3H), 7.47–7.53 (m, 2H), 7.68 (d, J=9 Hz, 1H), 7.77 (qq, J=15 Hz, 1H). MS (ESI) m/z 534 (M+H)+. Anal calcd for C$_{24}$H$_{21}$NF$_6$O$_4$S: C, 54.03; H, 3.97; N, 2.63. Found: C, 54.11; H, 4.04; N, 1.76.

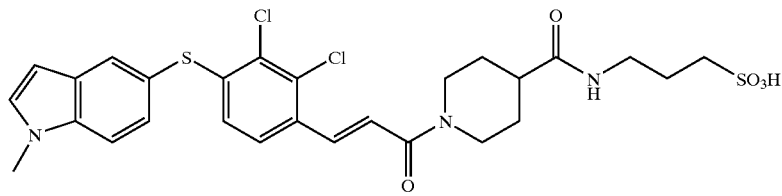

Example 373

(1-Methylindol-5-yl)[2,3-dichloro-4-(E-(4-(carbo-3-sulfopropylamino)piperadin-1-yl)carbonyl)ethenyl)phenyl]sulfide The title compound was prepared from Example 340H by the procedures described in Example 363 substituting 3-amino-1,2-propanediol with 3-amino-1-propanesulfonic acid. $^1$H NMR (300 MHz, DMSO-d$_6$) δ 1.40 (m, 2H), 1.70 (m, 4H), 2.38 (m, 1H), 2.42 (m, 2H), 2.70 (m, 1H), 3.05 (m, 3H), 3.86 (s, 3H), 4.18 (br d, 1H), 4.40 (br d, 1H), 6.40 (d, 1H), 6.55 (d, 1H), 7.20 (d, 1H), 7.35 (d, 1H), 7.50 (d, 1H), 7.65 (d, 1H), 7.70 (d, 1H), 7.77 (d, 1H), 7.87 (d, 1H). MS (ESI$^+$) m/z 610 (M+H)$^+$. Anal calcd for C$_{27}$H$_{29}$N$_3$Cl$_2$S$_2$O$_5$.1.5 TFA: C, 46.10; H, 3.93; N, 5.38. Found: C, 46.52; H, 4.03; N, 5.66.

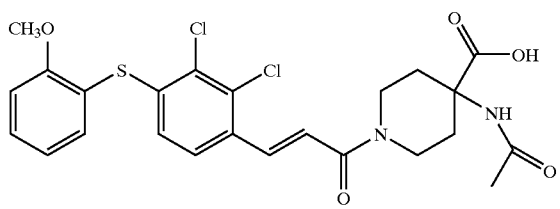

Example 374

(2-Methoxyphenyl)[2,3dichloro-4-(E-(4-acetylamino-4-carboxypiperidin-1-yl)carbonyl)ethenyl)phenyl]sulfide To a suspension of Example 371 (90 mg, 0.187 mmol) and triethylamine (0.08 mL, 0.57 mmol) in DMF (3 mL) was added acetyl chloride (0.1 mL) at room temperature. The mixture was stirred for 3 hours. Ethyl acetate (60 mL) was added, and the mixture was washed with brine. The organic phase was dried, filtered and concentrated. The residue was separated by HPLC (C-18, CH$_3$CN/H$_2$O) to give example 374 (56 mg, 57%). $^1$H NMR (300MHz, DMSO-d$_6$) δ 1.78 (m, 2H), 1.82 (s, 3H), 1.98 (m, 2H), 3.05 (t, 1H), 3.38 (t, 1H), 3.80 (s, 3H), 4.00 (br d, 1H), 4.12 (br d, 1H), 6.58 (d, 1H), 7.08 (t, 1H), 7.23 (d, 1H), 7.25 (d, 1H), 7.50 (d, 1H), 7.58 (t, 1H), 7.78 (d, 1H), 7.80 (d, 1H), 8.18 (s, 1H). MS (ESI$^+$) m/z 523 (M+H)$^+$. Anal calcd for C$_{24}$H$_{24}$N$_2$Cl$_2$SO$_5$.0.35TFA: C, 52.80; H, 4.40; N, 5.05. Found: C, 52.74; H, 4.42; N, 5.11.

Example 376

(2-Methoxyphenyl) 5-[8-(E-((4-aminocarbonyl)piperidin-1-yl)carbonyl)ethenyl)quinolinyl]sulfide

Example 376A

5-Chloro-8-(trifluoromethanesulfonyloxy)quinoline

5-Chloro-8-hydroxyquinoline was treated as described in Example 340E to provide the title compound. $^1$H NMR (DMSO-d$_6$, 300 MHz) δ 7.59 (7.5 Hz, 1H), 7.65–7.69 (m,2H), 8.63 (dd, J$_1$=9 Hz, J$_2$=1.5 Hz, 1H), 9.21 (dd, J$_1$=6 Hz, J$_2$32 1.5 Hz, 1H). MS (APCI–NH$_3$) m/e 312, 314 (M+H)$^+$.

Example 376B

5-Chloro-8-[E-(methoxycarbony)ethenyl]quinoline

The method of Example 340D was used, substituting the product from Example 376A for Example 340C. Thus, Example 376A (6.23 g, 20.0 mmol) was converted to the title compound (2.22 g, 45%). $^1$H NMR (DMSO-d$_6$, 300 MHz) δ 3.78 (s, 3H), 6.98 (d, J=16.5 Hz, 1H), 7.78–7.83 (m, 1H), 7.88 (d, J=9 Hz, 1H), 8.32 (d, J=9 Hz, 1H), 8.65 (dd, J$_1$=9 Hz, J$_2$=1.5 Hz, 1H), 8.85 (d, J=16.5 Hz, 1H), 9.12 (dd, J$_1$=4.5 Hz, J$_2$=1.5 Hz, 1H). MS (APCI–NH$_3$) m/e 248, 250 (M+H)$^+$.

Example 376C (2-Methoxyphenyl)5-[8-(E-(methoxycarbonyl)ethenyl)quinolinyl]sulfide The method of Example 340F was used, substituting the product from Example 376B for Example 340E. Thus, Example 376B (2.19 g, 8.84 mmol) was converted to the title compound (1.07 g,36%). $^1$H NMR (DMSO-d$_6$, 300 MHz) δ 3.83 (s, 3H), 6.80 (d, J=16.5 Hz, 1H), 6.86–6.99 (m, 2H), 7.16 (d, J=6 Hz, 1H), 7.33–7.38 (m, 1H), 7.44 (d, J=7.5 Hz, 1H), 7.67–7.72 (m,1H), 8.22 (d, J=7.5 Hz, 1H), 8.63 (dd, $J_1$=9 Hz, $J_2$=1.5 Hz, 1H), 8.82 (d, J=16.5 Hz, 1H), 9.07 (dd, $J_1$=6 Hz, $J_2$=1.5 Hz), 12.48 (s, 1H). MS (APCI–NH$_3$) m/e 338 (M+H)$^+$.

Example 376C (2-Methoxyphenyl)5-[8-(E-((4-(aminocarbonyl) piperidin-1-yl)carbonyl)ethenyl)quinolinyl]sulfide The method of Example 340G was used, substituting the product from Example 376B for Example 340F, and substituting 4-piperidinecarboxamide for methyl isonipecotate. $^1$H NMR (DMSO-d$_6$, 300 MHz) δ 1.71–2.82 (m, 2H), 2.96–2.03 (m, 2H), 2.44–2.52 (m, 1H), 2.81–2.94 and 3.16–3.30 (m, 1H), 3.37–3.54 (m, 2H), 3.88 (s, 3H), 4.17–4.34 and 4.60–4.80 (m, 1H), 5.72 (s, 2H), 6.82 (t, 4.5 Hz, 1H), 6.90 (dd, $J_1$=4.5 Hz, $J_2$=0.75 Hz, 1H), 6.93 (d, 6 Hz, 1H), 7.23–7.28 (m, 1H), 7.40 (d, J=9 Hz, 1H), 7.47–7.50 (m, 1H), 7.51 (d, J=6 Hz, 1H), 7.82 (d, J=4.5 Hz, 1H), 8.57 (d, J9 Hz, 1H), 8.74 (dd, $J_1$=4.5 Hz, $J_2$=0.75 Hz, 1H), 9.00 (m, 1H).

Example 377

(2-Methoxyphenyl)[2-trifluoromethyl-4-(E-((4-carboxypiperidin-1-yl)carbonyl)ethenyl)phenyl] sulfide

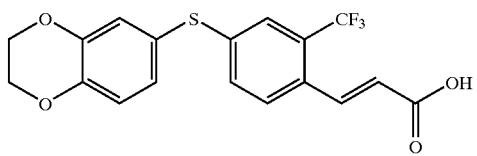

Example 377A

2-Trifluoromethyl-4-(thiobenzodioxan-6-yl)cinnamic acid

A solution of commercially available 4-fluoro-2-(trifluoromethyl)cinnamic acid (5 g, 21.4 mmol) in ethyl acetate (200 mL) under nitrogen at ambient temperature was treated with a solution of diazomethane in diethyl ether to a persistent yellow color, stirred an additional ten minutes, then quenched by dropwise addition of glacial acetic acid. The resultant clear solution was washed with saturated NaHCO$_3$, brine, dried (MgSO$_4$), filtered through a plug of silica, rinsed with ethyl acetate and concentrated to give 5.4 grams of a yellow oil. A solution of this methyl ester (2.5 g, 10 mmol) and 6-mercaptobenzodioxane (1.9 g, 11 mmol) in 40 mL of dimethylformamide was treated with cesium carbonate (3.9 g, 12 mmol), and stirred at room temperature for 20 hours. The resultant orange heterogeneous solution was diluted with diethyl ether and water, washed with 1 M NaOH, distilled water, brine, dried (MgSO$_4$), filtered through a plug of silica, concentrated and then flash chromatographed with 20% ethyl acetate/hexane followed by 33% ethyl acetate/hexane to give 2.8 g of a light yellow syrup. A solution of this diaryl sulfide ester (2.8 g, 7.1 mmol) in THF (21 mL) and distilled water (7 mL) was treated with lithium hydroxide hydrate (450 mg, 10.7 mmol) and stirred 67 hours at ambient temperature. The resultant solution was diluted with distilled water, washed with an diethyl ether, acidified to pH 1–2 with 3 M H$_2$SO$_4$, extracted with diethyl ether, washed with brine, dried (MgSO$_4$) and concentrated to give 2.7 g (7.1 mmol) of the title compound as an off-white powder (71%). $^1$H NMR (300 MHz, d6-DMSO) δ 7.97 (d, 1H), 7.72 (dq, 1H), 7.47 (d, 1H), 7.31 (dd, 1H), 7.05 (m, 3H), 6.58 (d, 1H), 4.3 (m, 4H). MS (APCI–NH$_3$) m/e 383 (M+H)$^+$, 400 (M+NH$_4$)$^+$.

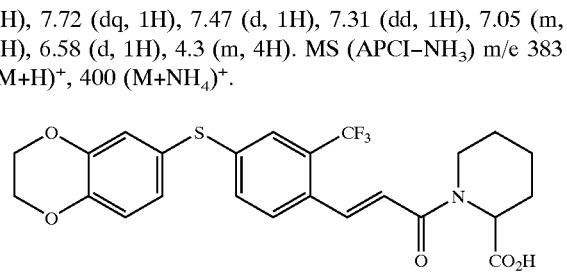

Example 377B (Benzodioxan-6-yl)[3-trifluoromethyl-4-(E-((2-carboxypiperidin-1-yl)carbonyl)ethenyl)phenyl] sulfide Example 377A (382 mg, 1 mmol) was coupled with (d,1)-ethyl pipecolinate according to the procedure of Example 340G. The derived ethyl ester was hydrolyzed using the method of Example 340H to give 280 mg of the title compound as a light yellow foam (84%). Analytical HPLC: 4.6×250 mm C18 column, 0.8 mL/min, 254 nm, CH$_3$CN:H$_2$O with 0.1% TFA, 0:100 (0 minutes), ramp to 90:10 (0–10 minutes), 90:10 (10–18 minutes), ramp to 0:100 (18–20 minutes), rt 11.29 minutes (98.2 area %). $^1$H NMR (300 MHz, d6-DMSO) δ 8.07 (t, 1H), 7.65 (dq, 1H), 7.38 (m, 3H), 7.03 (m, 3H), 5.15 (m, 1H), 4.4 (m, 1H), 4.29 (m, 4H), 4.1 (m, 1H), 3.2 (m, 1H), 2.2 (m, 1H), 1.68 (m, 2H), 1.3 (m, 2H). MS (APCl-NH$_3$) m/e 494 (M+H)$^+$, 511 (M+NH$_4$)$^+$.

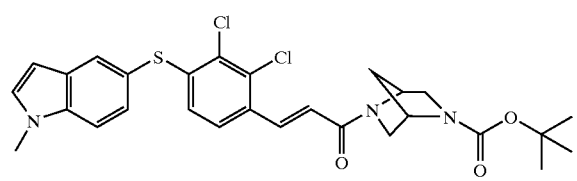

Example 378

(1-Methylindol-5-yl)[2,3-dichloro-4-(E-(((1S,4S)-5-tert-butyloxycarbonyl-2,5-diazabicyclo(2.2.1) heptan-2-yl)carbonyl)ethenyl)phenyl]sulfide The title compound was prepared by the procedures described in Example 340 substituting methyl isonipecotate with t-butyl (1S,4S)-(−)2,5-diazabicyclo(2.2.1)heptane-2-carboxylate. $^1$H NMR (300 MHz, DMSO-d$_6$) δ 1.40 (s, 9H), 1.82 (m, 2H), 3.17 (m, 1H), 3.30 (m, 2H), 3.58 (m, 1H), 3.82 (s, 3H), 4.05 (m, 1H), 4.40 (m, 1H), 4.75 (br s, 1H), 4.92 (br s, 1H), 6.42 (dd, 1H), 6.58 (d, 1H), 6.75 (d, 1H), 7.05 (d, 1H) 7.35 (d, 1H), 7.50 (d, 1H), 7.65 (d, 1H), 7.68 (d, 1H), 7.78 (t, 1H), 7.77 (s, 1H). MS (ES$^+$) m/z 558 (M+H)$^+$. Anal calcd for C$_{28}$H$_{29}$N$_3$Cl$_2$SO$_3$: C, 60.21; H, 5.23; N, 7.52. Found: C, 60.23 H, 5.36; N, 7.41.

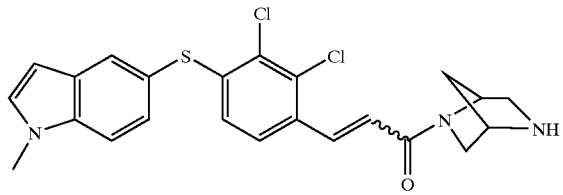

Example 379

(1-Methylindol-5-yl)[2,3dichloro-4-(E/Z-((1S,4S)-2,
5-diazabicyclo(2.2.1)heptan-2-yl)carbonyl)ethenyl)-
2,3-dichlorophenyl]sulfide To a solution of Example 378 (820 mg, 1.47 mmol) in CH$_2$Cl$_2$(20 mL) was added trifluoroacetic acid (2mL) at 0° C. The yellow solution was stirred at the same temperature for 2 hours. More CH$_2$Cl$_2$ (50 mL) was added and the solution was poured into water (100 mL) containing NaHCO$_3$ (4.5 g). The insoluble material was collected by filtration, washed with water and methanol. The CH$_2$Cl$_2$ solution was concentrated, and the residual solid was filtered, washed with water, methanol and CH$_2$Cl$_2$. The combined solid was dried to give the title compound (650 mg, 95%). $^1$H NMR (300 MHz, DMSO-d$_6$) δ 1.70 (m, 2H), 2.90 (m, 1H), 3.50.(m, 4H), 3.88 (s, 3H), 4.85 (m, 1H), 6.45 (d, 1H), 6.60 (dd, 1H), 6.77 (d, 1H), 7.05 (dd, 1H), 7.25 (s, 1H), 7.35 (dd, 1H), 7.65 (d, 1H), 7.70 (d, 1H), 7.80 (d, 1H). MS (ESI$^+$) m/z 458(M+H)$^+$.

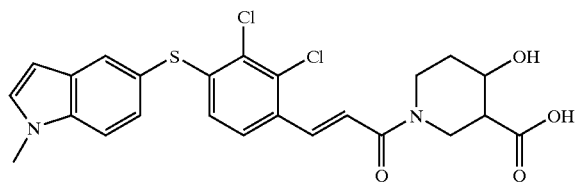

Example 380

(1-Methylindol-5-yl)[2,3-dichloro-4-(E-(4-hydroxy-
3-carboxypiperidin-1-yl)carbonyl)ethenyl)phenyl]
sulfide To a suspension of Example 340G (300 mg, 0.794 mmol) and methyl 4-oxo-3-piperidine carboxylate hydrochloride (307 mg, 1.59 mmol) in DMF (10 mL) was added EDC (305 mg, 1.59 mmol), HOBt (215 mg, 1.59 mmol) and triethylamine (0.443 mL, 1.59 mmol), HOBt (215 mg, 1.59 mmol) and triethylamine (0.443 mL, 1.59 mmol). The suspension was stirred at room temperature overnight. Ethyl acetate (100 mL) was added and the mixture was washed with brine, water and was concentrated. The residual oil was separated by flash chromatography (60% EtOAc in hexane) to give a white solid (220 mg).

180 mg of this solid was dissolved in THF (10 mL). A solution of lithium hydroxide monohydrate (29 mg, 0.68 mmol) in water (10 mL) was added. The mixture was stirred at room temperature 2 hours, NaBH$_4$ (50 mg) was then added. After 4 hours stirring, the solution was acidified and concentrated to 5 mL. The formed white solid was collected by filtration, washed with water, acetonitrile, and dried to give the title compound (92 mg). 1H NMR (300 MHz, DMSO-d$_6$) δ 1.60 (m, 2H), 3.00 (m, 1H), 3.40 (m, 1H), 3.85(1H, 4.05 (m, 1H), 4.20 (m, 1H), 4.35 (m, 1H), 5.00 (m, 1H), 6.42 (d, 1H), 6.58 (d, 1H), 7.20 (dd, 1H), 7.35 (d, 1H), 7.50 (d, 1H), 7.6–7.8 (m, 3H), 7.90 (s, 1H). MS (ESI$^+$) m/z 505 (M+H)$^+$. Anal calcd for C$_{24}$H$_{22}$N$_2$Cl$_2$SO$_4$: C, 57.03; H, 4.38; N, 5.54. Found: C, 56.77; H, 4.17; N, 5.34.

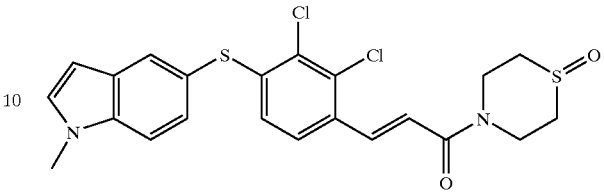

Example 381

(1-Methylindol-5-yl)[2,3-dichloro-4-(E-(S-
oxothiomorpholin-1-yl)carbonyl)ethenyl)phenyl]
sulfide The title compound was prepared by the procedures described in Example 340 substituting methyl isonipecotate with thiomorpholine S-oxide. $^1$H NMR (300 MHz, CDCl$_3$) δ 2.70 (m, 2H), 2.85 (m, 2H), 3.85 (s, 3H), 3.90 (m, 2H), 4.20 (m, 1H), 4.60 (m, 1H), 6.45 (d, 1H), 6.55 (d, 1H), 6.70 (d, 1H), 7.18 (d, 1H), 7.20 (d, 1H), 7.38 (d, 1H), 7.41 (d, 1H), 7.77 (s, 1H), 7.98 (d, 1H). MS (ESI$^+$) m/z 479 (M+H)$^+$.

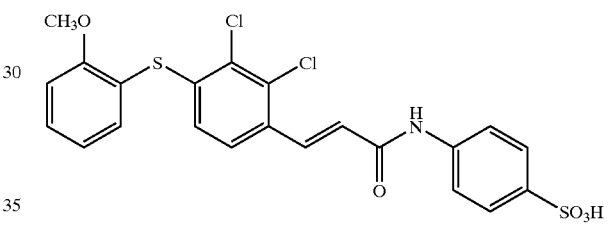

Example 382

(2-Methoxyphenyl)[2,3-dichloro-4-(E-((4-
sulfophenylamino)carbonyl)ethenyl)phenyl]sulfide The title compound was prepared by the procedures described in Example 1C substituting Example 1B with (2-methoxy)[2,3-dichloro-4(E-(2-carboxyethenyl)phenyl] sulfide and substituting 6-amino-1-hexanol with sulfanilic acid. $^1$H NMR (300 MHz, DMSO-d$_6$) δ 3.82 (s, 3H), 6.65 (d, 1H), 6.82 (d, 1H), 7.12 (t, 1H), 7.25 (d, 1H), 7.5–7.7 (m, 7H), 7.85 (d, 1H), 10.40 (s, 1H). MS (ESI$^+$) m/z 510 (M+H)$^+$. Anal calcd for C$_{22}$H$_{17}$Cl$_2$NS$_2$O$_5$.0.65TFA: C, 50.80; H, 3.25; N, 2.55. Found: C, 50.75; H, 3.43; N, 2.65.

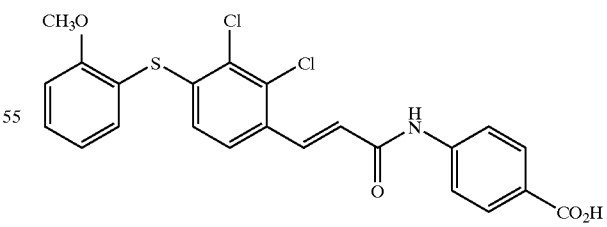

Example 383

(2-Methoxyphenyl)[2,3-dichloro-4-(E-((4-
carboxyphenylamino)carbonyl)ethenyl)phenyl]
sulfide The title compound was prepared by the procedures described in Example 1C substituting Example 1B with (2-methoxy)[2,3-dichloro-4-(E-(2-carboxyethenyl)phenyl] sulfide and substituting 6-amino-1-hexanol with 4-aminobenzoic acid. ¹H NMR (300 MHz, DMSO-d₆) δ 3.82 (s, 3H), 6.65 (d, 1H), 6.82 (d, 1H), 7.10 (t, 1H), 7.30 (d, 1H), 7.60 (m, 3H), 7.82 (t, 3H), 7.90 (d, 1H), 7.92 (d, 1H), 10.65 (s, 1H), 12.75 (s, 1H). MS (ESI⁺) m/z 474 (M+H)⁺.

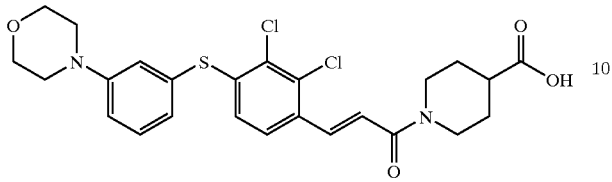

Example 384

[3-(4-Morpholino)phenyl][2,3-dichloro-4-(E-((4carboxypiperidin-1-yl)carbonyl)ethenyl)phenyl] sulfide

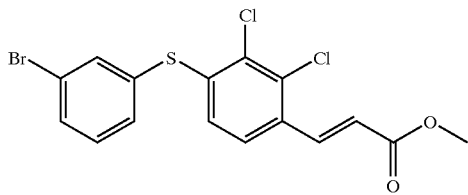

Example 384A (3-Bromophenyl)[2,3-dichloro-4-(E-[methoxycarbonyl]ethenyl)phenyl]sulfide To a solution of the resultant compound from Example 340E (12.0 g, 31.7 mmol) in N-methylpyrrolidinone (63 mL) at 0° C. (under dry N₂) was added 3-bromothiophenol (4.0 mL, 7.3 g, 38.8 mmol) and a solution of lithium tert-butoxide (3.1 g, 38.8 mmol), and the resulting solution was stirred for 3 hours at 0° C. The reaction was diluted with 500 mL EtOAc and extracted sequentially with 100 mL water, 3×60 mL of 1 N aq. NaOH, then 2×100 mL brine. The organic phase was dried over Na₂SO4, filtered, and concentrated in vacuo to produce the crude title compound (9.2 g). ¹H NMR (DMSO-d₆, 300 MHz) δ 3.75 (s, 3H), 6.67 (d, J=15 Hz, 1H), 6.83 (d, J=9 Hz, 1H), 7.46–7.59 (m, 2H), 7.72–7.76 (m, 2H), 7.80 (t, J=2.5 Hz, 1H), 7.85 (d, J=9 Hz, 1H) 7.88 (d, J=15 Hz, 1H); MS (APCI) m/e 419 (M+H)⁺.

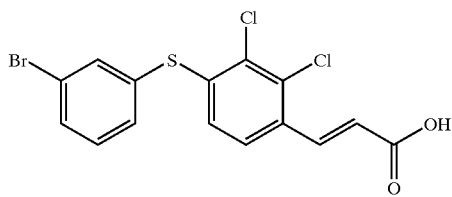

Example 384B (3-Bromophenyl)[2,3-dichloro-4-(E-carboxyethenyl) phenyl]sulfide Using the procedure for Example 340H, Example 348A was hydrolyzed to the title compound. ¹H NMR (DMSO-d₆, 300 MHz) δ 6.56 (d, J=16.5 Hz, 1H), 6.84 (d, J=9 Hz, 1H), 7.45–7.58 (m, 2H), 7.72 (m, 1H), 7.77–7.86 (m, 4H), 12.75 (br s, 1H); (ESI) m/e 401, 403 (M−H)⁻.

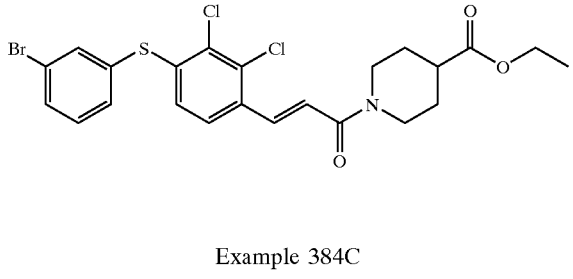

Example 384C 3-bromophenyl)[2,3-dichloro-4-(E-[(4-ethoxycarbonylpiperidin-1-yl)carbonyl]ethenyl) phenyl]sulfide The title compound (750 mg, 58%) was prepared from Example 384B (1.0 g, 2.48 mmol), using the procedures described in Example 340G substituting methyl isonipecotate with ethyl isonipecotate. ¹H NMR (300 MHz, DMSO-d₆) δ 1.18 (t, J=7.5 Hz, 3H), 1.38–1.56 (m, 2H), 1.82–1.92 (m, 2H), 2.50–2.69 (m, 1H), 2.80–2.93 (m, 1H), 3.14–3.27 (m, 1H), 4.07 (t, J=7.5 Hz, 2H), 4.10–4.35 (m, 2H), 6.92 (d, J=9 Hz, 1H), 7.30 (d, J=15 Hz, 1H), 7.43–7.52 (m, 2H), 7.67–7.77 (m, 3H), 7.92 (d, J=9 Hz, 1H).

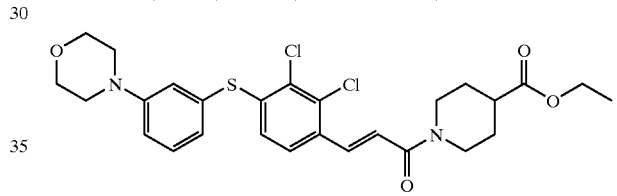

Example 384D

[3-(4-Morpholino)phenyl][2,3-dichloro-4-(E-((4-ethoxycarbonylpiperidin-1-yl)carbonyl)ethenyl) phenyl]sulfide The procedure of D. W.; Wolfe, J. P.; Buchwald, S. L. *J. Am. Chem. Soc.* 1998, 120, 9722–9723, was adapted. To a stirred solution of Example 384D (180 mg, 0.331 mmol) in ethylene glycol dimethyl ether (1 mL) containing 1-(N,N-dimethylamino)-1'-(dicyclohexylphophino)biphenyl (7 mg, 5 mol %), Pd₂(dba)₃ (8 mg, 2.5 mol %), and morpholine (0.058 mL, 0.663 mmol) was added powdered K₃PO₄ (141 mg, 0.663 mmol). The reaction mixture was bubbled with N₂ for 5 minutes and heated at 90° C. in sealed tube for 18 hours. Then the solvent was removed under reduced pressure and residue was diluted with methylene chloride (1 mL). The title compound (90 mg, 50%) was isolated by flash chromatography on silica gel eluting with 20% acetone-hexane. ¹H NMR (DMSO-d₆, 300 MHz) δ 1.18 (t, J=7.5 Hz, 3H), 1.35–1.55 (m, 2H), 1.79–1.91 (m, 2H), 2.58–2.69 (m, 1H), 2.70–2.94 (m, 2H), 3.16 (t, J=4.5 Hz, 2H), 3.15 (t, J=5 Hz, 4H), 3.73 (t, J=4.5 Hz, 4H), 3.78 (t, J=5 Hz, 2H), 4.08 (q, J=7.5 Hz, 2H), 4.11–4.36 (m, 2H), 6.70 (d, J=8.25 Hz, 1H), 6.97 (m, 1H), 7.10–7.27 (m, 2H), 7.24.(d, J=15 Hz, 1H), 7.39 (m, 1H), 7.73 (d, J=15 Hz, 1H), 7.86 (d, J=8.25 Hz, 1H); MS (ESI) m/e 549, 551 (M+H)⁺.

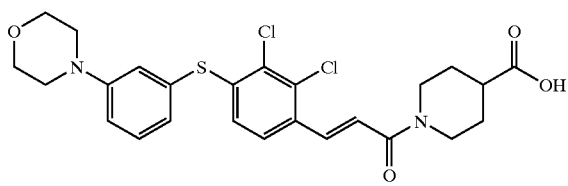

Example 384E

[3-(4-Morpholino)phenyl][2,3-dichloro-4-(E-((4-carboxypiperidin-1-yl)carbonyl]ethenyl)phenyl] sulfide The title compound (38 mg, 67%) was prepared from Example 384D (60 mg, 0.11 mmol) using the procedures described in Example 340H. $^1$H NMR (DMSO-$d_6$, 400 MHz) δ 1.37–1.55 (m, 2H), 1.81–1.90 (m, 2H), 2.52–2.58 (m, 1H), 2.80–2.94 (m, 1H), 3.10–3.15 (m, 3H), 3.67–3.75 (m, 3H), 3.76–3.99(m, 3H), 4.04–4.16 (M, 1H), 4.22–4.33 (m, 1H),6.71 (d, J=8 Hz, 1H), 6.96 (d, J=7 Hz, 1H), 7.07 (m, 1H), 7.12 (s, 1H), 7.24 (d, J=15 Hz, 1H), 7.38 (t, j=7 Hz, 1H), 7.73 (d, J=15 Hz, 1H), 7.85 (d, J=8 Hz, 1H). MS (ESI) m/e 521, 523 (M+H)$^+$, 519, 521 (M−H)$^-$.

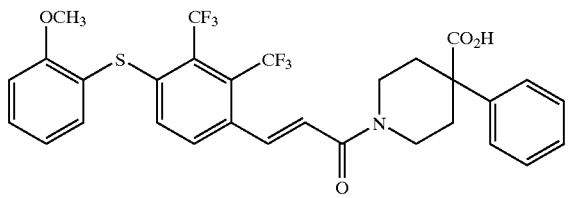

Example 385

(2-Methoxyphenyl)[2,3-bis(trifluoromethyl)-4-(E-((4-phenylcarboxypiperidin-1-yl)carbonyl]ethenyl) phenyl]sulfide

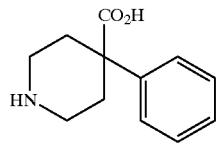

Example 385A

4-Phenylpiperidine-4-carboxylic acid

4-Cyano-4-phenylpiperidine hydrochloride (2.0 g, 0.11 mol) was dissolved in 8 mL of conc. $H_2SO_4$ and 4mL of $H_2O$, then the solution was heated at reflux for 4 hours. The solution was cooled and then NaOH was added to precipitate a white solid. The solid was collected, then dissolved in methanol, and the solution was filtered and concentrated to obtain a white solid. This dried solid was used without purification for Example 385B.

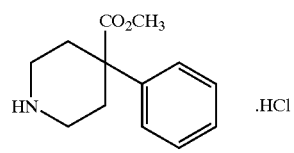

Example 385B

Methyl 4-phenylpiperidine-4-carboxylate hydrochloride

Dissolved the 4-phenylpiperidinecarboxylic acid in 10 mL of methanol and added 2 mL of thionyl chloride dropwise at room temperature. The resulting mixture was stirred overnight at room temperature. Evaporated solvent in vacuo, added toluene and evaporated excess thionyl chloride in vacuo. This white powder salt was used for next step without further purification.

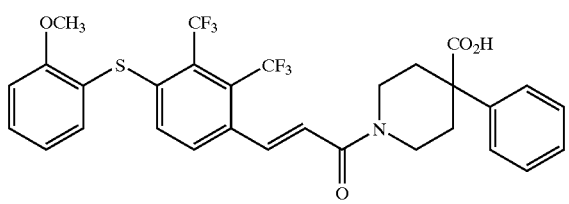

Example 385C (2-Methoxyphenyl)[2,3-bis(trifluoromethyl)-4-(E-((4-phenylcarboxypiperidin-1-yl)carbonyl)ethenyl) phenyl]sulfide The methyl ester of the title compound was prepared by the procedures described in Example 356, employing the compound of Example 359D as starting material, to give an oil. The resultant methyl ester was hydrolyzed with aq. NaOH in methanol at 60° C. for 4 hours to give a white solid. $^1$H NMR (CD$_3$OD, 300 MHz) δ 1.88 (br t, J=13.5 Hz, 2H), 2.59(br d, J=13.5 Hz, 2H), 3.13(br t, J=13.5 Hz, 1H), 3.75 (s, 3H), 3.44 (br t, J=13.5 Hz, 1H), 4.12 (br d, J=13.5 Hz, 1H), 4.42(br d, J=13.5 Hz, 1H), 6.35 (d, J=15 Hz, 1H), 7.0–7.46 (m, 7H), 7.43–7.55 (m, 3H), 7.62–7.85 (m, 2H); MS(ESI) m/z 610(M+H)$^+$. Anal calcd for $C_{30}H_{25}F_6NO_4S\cdot H_2O$: C, 57.49; H, 4.13; N, 2.20. Found: C, 57.12; H, 3.93; N, 1.77.

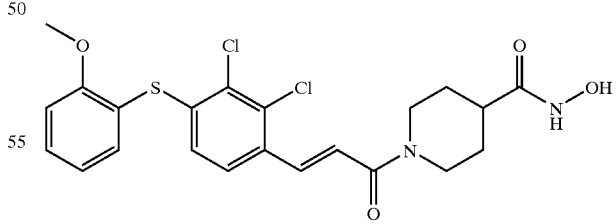

Example 386

(2-Methoxyphenyl)[2,3-dichloro-4-(E-(((4-hydroxylaminocarbonyl)piperidin-1-yl)carbonyl) ethenyl)phenyl]sulfide To a suspension of Example 319 (300 mg, 0.64 mmol) in CH$_2$Cl$_2$ (10 mL) was added oxalyl chloride (67 μL) and 2 drops of DMF. The yellow suspension was stirred at room temperature for 2 hours to give an orange solution which was then concentrated under reduced pressure, and dried under vacuum. An aliquot of the resulting acid chloride solution (2 mL) was added to a solution containing o-trimethylsilyloxyamine (101 mg, 0.96 mmol), Hunig's base (122 µL, 0.7 mmol) and DMAP (2 mg) in CH$_2$Cl$_2$ (3 mL). After the solution was stirred at room temperature for 1 hour, TBAF (1.0 M solution in THF, 1.5 mL) was then added. The brown solution was stirred at room temperature for another hour, then it was purified by HPLC (Zorbax, C-18) to give the title compound as a white solid (71 mg). $^1$H NMR (300 MHz, DMSO-d6) δ 1.50 (m, 2H), 1.70 (m, 2H), 2.28 (m, 1H), 2.70 (m, 1H), 3.09 (m, 1H), 3.79 (s, 3H), 4.23 (m, 1H), 4.45 (m, 1H), 6.55 (d, J=8.8 Hz, 1H), 7.08 (t, J=7.4 Hz, 1H), 7.25 (m, 2H), 7.48 (d, J=7.2 Hz, 1H), 7.54 (t, J=8.2 Hz, 1H), 7.73 (d, J=15.3 Hz 1H), 7.82 (d, J=8.8 Hz, 1H), 8.55 (br s, 1H), 10.46 (s, 1H). MS (ESI$^+$) m/z 481 (M+H)$^+$.

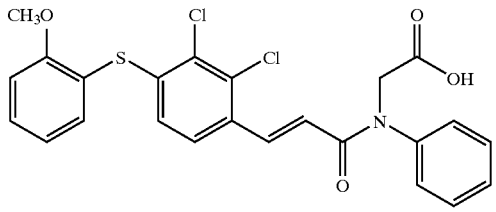

Example 387

(2-Methoxyphenyl)[2,3-dichloro-4-(E-((N-carboxymethyl-N-phenylamino)carbonyl)ethenyl) phenyl]sulfide The title compound was prepared by the procedures described in Example 1C substituting Example 1B with (2-methoxy)[2,3-dichloro-4-(E-(2-carboxyethenyl)phenyl] sulfide and substituting 6-amino-1-hexanol with N-phenylglycine ethyl ester followed by hydrolysis. $^1$H NMR (300 MHz, DMSO-d$_6$) δ 3.76 (s, 3H), 4.40 (s, 2H), 6.35 (d, J=15.5 Hz, 1H), 6.46 (d, J=8.4 Hz, 1H), 7.05 (t, J=7.3 Hz, 1H), 7.22 (m, 2H), 7.35 (t, J=7.5 Hz, 3H), 7.44 (t, J=7.2 Hz, 3H), 7.55 (t, J=7.4 Hz, 1H), 7.76 (d, J=15.4 Hz, 1H); MS (ESI$^+$) m/z 488,490 (M+H)$^+$. Anal. calcd for C$_{24}$H$_{19}$NCl$_2$O$_4$S: C, 59.02; H, 3.92; N, 2.87. Found: C, 58.71; H, 4.10; N, 2.58.

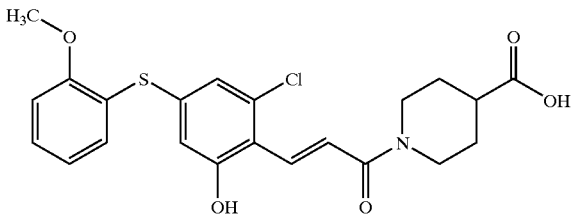

Example 388

(2-Methoxyphenyl)[3-chloro-6-hydroxy-4-(E-((3-carboxypiperidin-1-yl)carbonyl)ethenyl)phenyl] sulfide

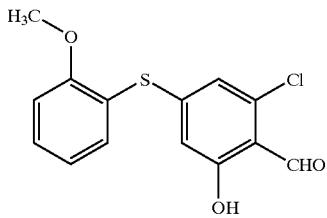

Example 388A (2-Methoxyphenyl) ((3-chloro-6-hydroxy-4-formyl) phenyl)sulfide

2-Methoxyphenyl (3.5 mL, 28.9 mmol) and 2,4-dichoro-6-hydroxybenzaldehyde (5.00 g, 26.3 mmol) were processed as described in Example 1 to provide the title disulfide (6.71 g, 87%) as a pale yellow solid. $^1$H NMR (DMSO-d$_6$, 300 MHz) δ 10.18 (s, 1H), 7.61 (dd, J=7.4 Hz, J=1.7 Hz, 1H), 7.56 (dd, J=7.7 Hz, J=1.9 Hz, 1H), 7.25 (d, J7.3 Hz, 1H), 7.11 (dt, J=7.7 Hz, J=1.5 Hz, 1H), 6.69 (d, J=1.8 Hz, 1H), 6.38 (d, J=1.5 Hz, 1H), 3.80 (s, 3H); MS (APCI) m/z 294 (M+H)$^+$.

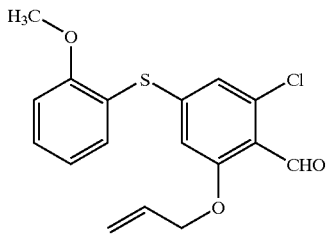

Example 388B (2-Methoxyphenyl)(3-chloro-6-allyloxy-4-benzaldehyde)sulfide

Allyl bromide (2.0 mL, 22.8 mmol) was added to a stirred solution of Example 388A (6.71 g, 22.8 mmol), cesium carbonate (14.86 g, 45.6 mmol), and DMF (45 mL). After 21 hours, the pale yellow solution was diluted with 1 N aqueous HCl (100 mL) and extracted with Et$_2$O (2×75 mL). The ether extracts were combined, dried (MgSO$_4$), filtered, and concentrated to a yellow solid (7.20 g, 94%). $^1$H NMR (DMSO-d$_6$, 300 MHz) δ 10.28 (s, 1H), 7.58 (dd, J=8.4 Hz, J=1.7 Hz, 1H), 7.52 (dd, J=7.8 Hz, J=1.7 Hz, 1H), 7.23 (d, J=8.1 Hz, J=1.0 Hz, 1H), 7.08 (dt, J=7.8 Hz, J=1.4 Hz, 1H), 6.82 (d, J=1.7 Hz, 1H), 6.52 (d, J=1.7 Hz, 1H), 5.97 (m, 1H), 5.33 (d, J=17.3 Hz, 1H), 5.28 (d, J=10.8 Hz, 1H), 4.61 (m, 2H), 3.80 (s, 3H); MS (APCI m/z 335 (M+H)$^+$.

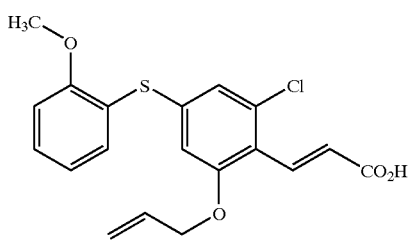

Example 388C

(2-Methoxyphenyl)[3-chloro-6-allyloxy-4-((carboxy)ethenyl)phenyl]sulfide

Example 388B was processed as detailed in Example 1B. $^1$H NMR (DMSO-d$_6$, 300 MHz) δ 7.77 (d, J=16.3 Hz, 1H), 7.51 (dd, J=7.4 Hz, J=1.7 Hz, 1H), 7.43 (dd, J=7.4 Hz, J=1.7 Hz, 1H), 7.19 (dd, J=8.1 Hz, J=1.0 Hz, 1H), 7.05 (dt, J=7.4 Hz, J=1.4 Hz, 1H), 6.82 (d, J=1.3 Hz, 1H), 6.72 (d, J=15.9 Hz, 1H), 6.66 (d, J=1.7 Hz, 1H), 6.00 (m, 1H), 5.30 (d, J=9.8 Hz, 1H), 5.26 (d, J=3.1 Hz, 1H), 4.63 (m, 2H), 3.80 (s, 3H). MS (APCI) m/z 377 (M+H$^+$) 394 (M+NH$_4^+$).

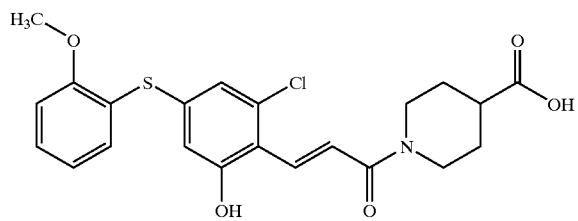

Example 388D

(2-Methoxyphenyl)[3-chloro-6-hydroxy-4-(E-((3-carboxypiperidin-1-yl)carbonyl)ethenyl)phenyl]sulfide

The allyl group of Example 388C was removed as reported in the literature (Honda, M.; Morita, H.; Nagakura, I. J. Org. Chem. 1997, 62, 8932.) and the carboxylic acid was converted to the amide as reported in Example 165 to provide the title compound as a white solid. $^1$H NMR (DMSO-d$_6$, 300 MHz) δ 7.73 (d, J=16.3 Hz, 1H), 7.51 (d, J=7.4 Hz, 1H), 7.43 (d, J=7.4 Hz, 1H), 7.19 (d, J=7.9 Hz, 1H), 7.05 (dt, J=7.8 Hz, J=1.1 Hz, 1H), 6.70 (d, J=1.8 Hz, 1H), 6.59 (d, J=6.59 Hz, 1H), 4.30 (m, 1H), 3.95 (m, 2H), 3.80 (s, 3H), 2.85 (m, 2H), 1.87 (m, 2H), 1.45 (m,2H). MS (APCI) m/z 448 (M+H$^+$).

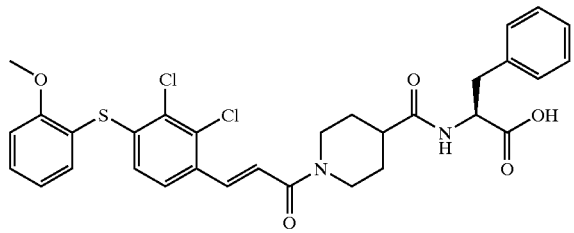

Example 389

(2-Methoxyphenyl)[2,3-dichloro-4-(E-(4-((1-(2-phenyl-1-carboxyethyl)amino)carbonyl)piperidin-1-yl)carbonyl)ethenyl)phenyl]sulfide

The methyl ester of the title compound was prepared by the procedure described in Example 363 using L-phenylalanine methyl ester as the coupling substrate. The methyl ester was the n hydrolyzed as described in Example 340 to provide the title compound. HPLC (Supelco C-18 column, water:acetonitrile 100:0–0:100, 20 minute elution, flow rate 1.5 mL/min, RT=13.97 minutes; $^1$H NMR (300 MHz, DMSO-d6) δ 1.45 (m, 2H), 1.56 (m, 1H), 1.68 (m, 1H), 2.41 (m, 1H), 2.71 (m, 1H), 2.83 (m, 2H), 3.08 (m, 2H), 3.79 (s, 3H), 4.12 (m, 1H), 4.30 (m, 1H), 4.41 (m, 7H), 6.55 (d, 1H), 7.09 (t, 1H), 7.22 (m, 6H), 7.48 (dd, 1H), 7.57 (m, 1H), 7.72 (d, 1H), 7.81 (d, 1H), 8.11 (m, 1H), 12.64 (br s, 1H); MS (ESI) m/e 613 (M+H)$^+$.

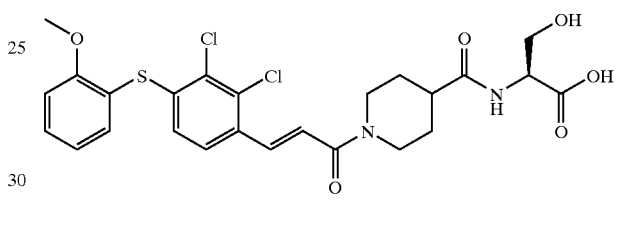

Example 390

(2-Methoxyphenyl)[2,3-dichloro-4-(E-(4-((1-(2-hydroxy-1-carboxyethyl)amino)carbonyl)piperidin-1-yl)carbonyl)ethenyl)phenyl]sulfide

The methyl ester of the title compound was prepared by the procedure described in Example 363 using L-serine methyl ester as the coupling substrate. The methyl ester was then hydrolyzed as described in Example 340 to give the title compound. HPLC (Supelco C-18 column, water:acetonitrile 100:0–0:100, 20 minute elution, flow rate 1.5 mL/min, RT=11.79 minutes; $^1$H NMR (300 MHz, DMSO-d$_6$) δ 1.48 (m, 2H), 1.72 (m, 2H), 2.55 (m, 2H), 2.71 (m, 1H), 3.10 (m, 1H), 3.62 (m, 2H), 3.79 (s, 3H), 4.22 (m, 4.41 (m, 1H), 6.55 (d, 1H), 7.09 (t, 1H), 7.34 (m, 2H), 7.48 (m, 1H), 7.57 (m, 1H), 7.71 (d, 1H), 7.81 (d, 1H), 7.96 (br d, 1H); MS (ESI) m/e 553 (M+H)$^+$.

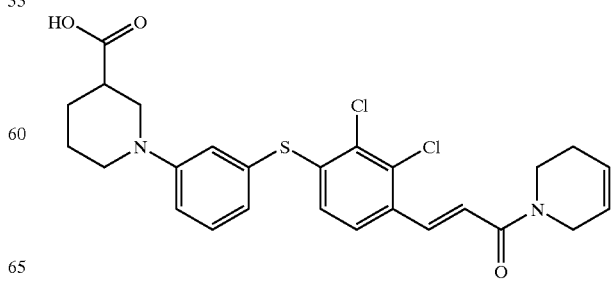

Example 391

(3-(1-(3-Carboxypiperidinyl)phenyl)[2,3-dichloro-4-(E-((1,2,5,6-tetrahydropyridin-1-yl)carbonyl)ethenyl)phenyl]sulfide

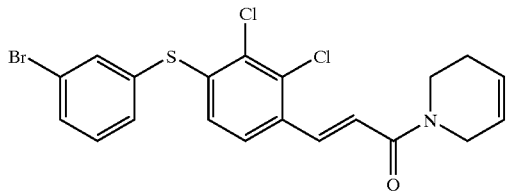

Example 391A (3-bromophenyl)[2,3-dichloro-4-(E-[(1,2,3,6-tetrahydropyridin-1-yl)carbonyl]ethenyl)phenyl]sulfide The title compound (1.2 g, 103%) was prepared from Example 384B (1.00 g, 2.48 mmol), using the procedures described in Example 340G substituting methyl isonipecotate with 1,2,3,6-tetrahydropyridine.

Example 391B

[3-(3-ethoxycarbonylpiperidine)][2,3-dichloro-4-(E-[(1,2,3,6-tetrahydropyridin-1-yl)carbonyl]ethenyl)phenyl]sulfide

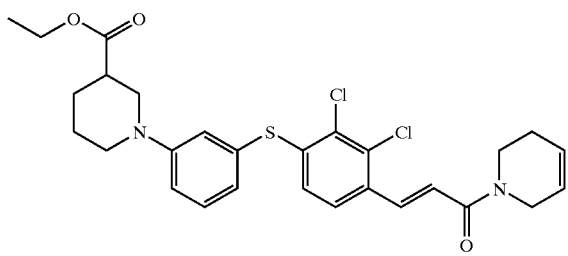

The title compound (50 mg, 46%) was prepared by the procedures described in Example 384D, substituting morpholine with ethyl nipecotate. $^1$H NMR (300 MHz, DMSO-$d_6$) δ 1.17 (t, J=6.8 Hz, 3H), 1.5–1.76 (m, 3H), 1.82–1.95 (m, 1H), 2.06–2.19 (m, 2H), 2.56–2.67 (m, 1H) 2.84–2.96 (m, 1H), 3.06–3.13 (m, 1H), 3.43–3.52 (m, 1H), 3.61–3.74 (m, 2H), 3.99–4.18 (m, 4H), 5.66–5.91 (m, 2H), 6.73 (d, J=9 Hz, 1H), 6.92 (d, J=7.5 Hz, 1H), 7.06–7.12 (m, 2H), 7.31–7.39 (m, 2H), 7.75 (d, J=15 Hz, 1H), 7.80–7.91 (m, 1H); MS (ESI) m/e 545, 547 (M+H)$^+$.

Example 391C

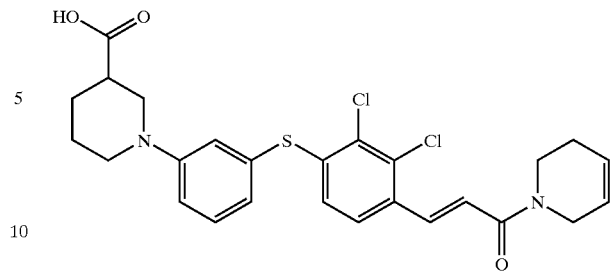

[3-(3-carboxylpiperidine)][2,3-dichloro-4-(E-[(1,2,3,6-tetrahydropyridin)-1-yl)carbonyl]ethenyl)phenyl]sulfide The title compound (20 mg, 49%) was prepared from Example 391B (43 mg, 0.08 mmol) using the procedures described in Example 340H. $^1$H NMR (DMSO-$d_6$, 500 MHz) δ 1.51–1.64 (m, 2H), 1.68–1.73 (m, 1H), 1.87–1.94 (m, 1H), 2.07–2.19 (m, 2H), 2.51–2.57 (m, 1H), 2.83–2.89 (m, 1H); 2.99–3.04 (m, 1H), 3.61–3.73 (m, 4H), 4.02 (br s, 1H), 4.15 (br s, 1H), 5.67–5.76 (m, 1H), 5.79–5.90 (m, 1H), 6.72 (d, J=7.5 Hz, 1H), 6.92 (J=6.25 Hz, 1H), 7.10–7.13 (m, 2H), 7.14–7.30 (m, 1H), 7.36 (t, J=7.5 Hz, 1H), 7.74 (d, J=15 Hz, 1H), 7.80–7.90 (m, 1H); MS (ESI) m/e 517, 519 (M+H)$^+$.

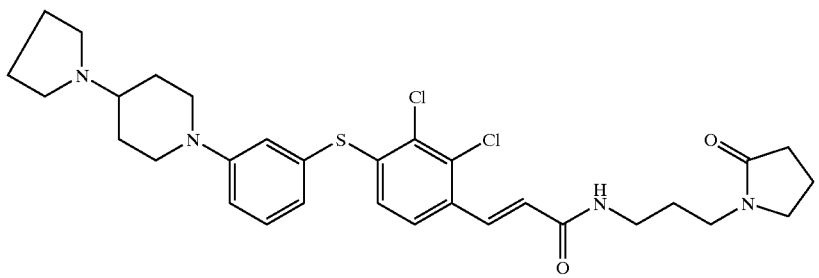

Example 392

(3-(4-Pyrrolidin-1-yl)piperidin-1-yl)phenyl)[2,3-dichloro-4-(E-(((3-(2-oxopyrrolidin-1-yl)propylamino)carbonyl)ethenyl)phenyl]sulfide

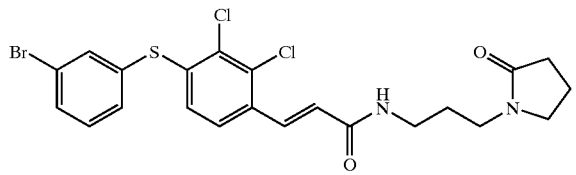

Example 392A (3-bromophenyl)[2,3dichloro-4-(E-(((3-(2-oxopyrolidin-1-yl)propylamino)carbonyl)ethenyl)phenyl]sulfide The title compound (1.25 g, 95%) was prepared from Example 384D (1.00 g, 2.475 mmol), using the procedures described in Example 340G substituting methyl isonipecotate with 3-aminopropylpyrrolidine. MS (ESI) m/e 529, $(M+H)^+$, 527, $(M-H)^-$.

Example 392B (3-(4-Pyrrolidin-1-yl)piperidin-1-yl)phenyl)[2,3-dichloro-4-(E-(((3-(2-oxopyrolidin-1-yl)propylamino)carbonyl)ethenyl)phenyl]sulfide

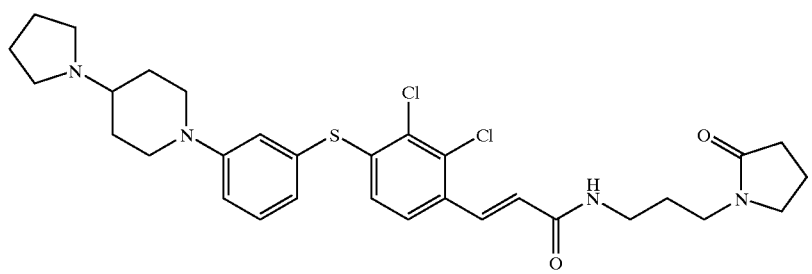

The title compound (32 mg, 27%) was prepared from Example 392A as described in Example 384D, substituting morpholine with 4-(1-pyrrolidinyl)piperidine. $^1$H NMR (500 MHz, DMSO-d$_6$) δ 1.60–1.67 (m, 4H), 1.84–2.90 (m, 5H), 2.91–2.03 (m, 1H), 2.04–2.11 (m, 3H), 2.20 (t, J=7.5 Hz, 2H) (br t, J=12.5 Hz, 2H), 3.00–3.16 (m, XH), 3.21 (t, J=7.5 Hz, XH), 3.33(m, 1H), 3.46–3.64 (m, 1H), 3.87 (br d, J=10 Hz, 2H), 6.59 (d, J=15 Hz, 1H), 6.80 (d, J=8.75 Hz, 1H), 6.94 (d, J=7.5 Hz, 1H), 7.12–7.18 (m, 2H), 7.33 (t, J=7.5 Hz, 1H), 7.57 (d, J=8.75 Hz, 1H), 7.68 (d, J=15 Hz, 1H), 8.24 (t, J=5 Hz, 1H); MS (ESI) m/e 601, 603, $(M+H)^+$; 599, 601 $(M-H)^-$.

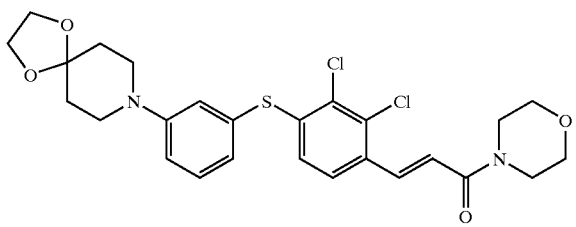

Example 393

[3-(4-(Spiro-2,2-dioxolanyl)piperidin-1-yl)phenyl][2,3-dichloro-4-(E-((4-morpholinyl)carbonyl)ethenyl)phenyl]sulfide

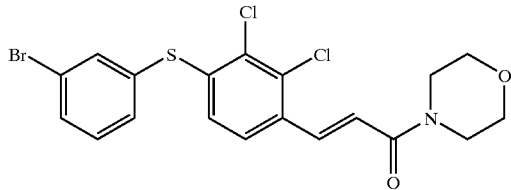

Example 393A (3-bromophenyl)[2,3dichloro-4-(E-((4-morpholino)carbonyl)ethenyl)phenyl]sulfide The title compound (980 mg, 84%) was prepared from Example 384B (1.00 g, 2.48 mmol), using the procedures described in Example 340G substituting methyl isonipecotate with morpholine. $^1$H NMR (400 MHz, DMSO-d$_6$) 3.53–3.63 (m, 6H), 3.68 (br s, 2H), 6.93 (d, J=8 Hz, 1H), 7.27 (d, J=15 Hz, 1H), 7.44–7.52 (m, 2H), 7.67–7.74 (m, 2H), 7.78 (d, J=15 Hz, 1H), 7.80 (d, J=8 Hz, 1H); MS (ESI) m/e 474 $(M+H)^+$.

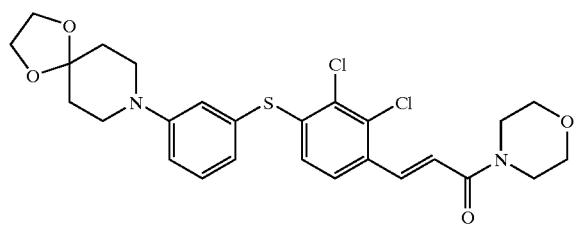

Example 393B

[3-(4-(Spiro-2,2-dioxolanyl)piperidin-1-yl)phenyl]
[2,3-dichloro-4-(E-((4-morpholinyl)carbonyl)
ethenyl)phenyl]sulfide

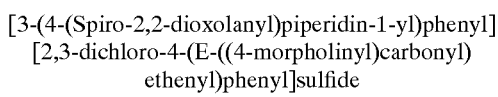

The title compound (32 mg, 27%) was prepared from Example 393A as described in Example 384D, substituting morpholine with 1,4-dioxa-8-azaspiro[4,5]decane. $^1$H NMR (500 MHz, DMSO-d$_6$) δ 1.68 (t, J=5 Hz, 4H), 3.52–3.60 (m, 7H), 3.66 (br s, 2H), 3.91 (s, 4H), 6.71 (d, J=8.75 Hz, 1H), 6.91 (m, 1H), 7.11–7.13 (m, 2H), 7.22 (d, J=15 Hz, 1H), 7.35 (m, 1H), 7.76 (d, J=15 Hz, 1H), 7.85 (d, J=8.75 Hz, 1H); MS (ESI) m/e 535, 537 (M+H)$^+$.

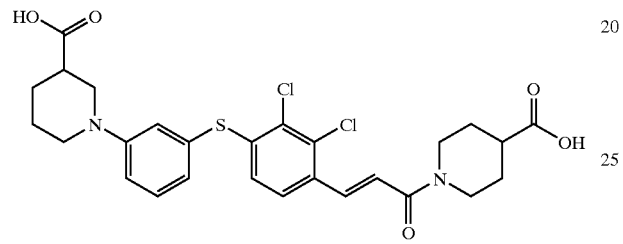

Example 394

[3-(3-Carboxylpiperidin-1-yl)phenyl][2,3-dichloro-4-(E-[(4-carboxypiperidin-1-yl)carbonyl]ethenyl)
phenyl]sulfide The title compound (51 mg, 41%) was prepared from Example 384C as described in Example 384D, substituting morpholine with ethyl nipecotate followed by hydrolysis with LiOH as described in Example 340H. $^1$H NMR (400 MHz, DMSO-d$_6$) δ 1.39–1.60 (m, 4H), 1.67–1.76 (m, 1H), 1.82–1.96 (m, 3H), 2.52–2.59 (m, 3H), 2.81–2.93 (m, 2H), 2.99–3.07 (m, 1H), 3.14–3.25 (m, 1H), 3.47–3.54 (m, 1H), 3.69 (dd, J$_1$=4 Hz, J$_2$=12 Hz, 1H), 4.05–4.17 (m, 1H), 4.24–4.34 (m, 1H), 6.72 (d, J=8 Hz, 1H), 6.92 (d, J=8 Hz, 1H), 7.11 (m, 2H), 7.23 (d, J=15 Hz, 1H), 7.34–7.40 (m, 1H), 7.73 (d, J=15 Hz, 1H), 7.85 (d, J=8 Hz, 1H); MS (ESI) m/e 563,565 (M+H)$^+$.

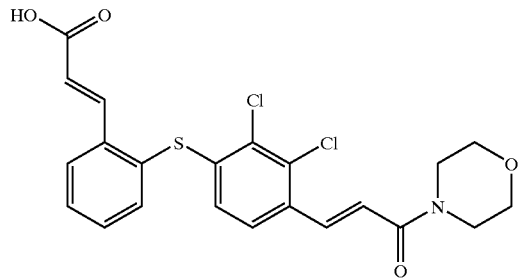

Example 395

(2-(2-Carboxy)ethenyl)phenyl)[2,3-dichloro-4-(E-((4-morpholinyl)carbonyl)ethenyl)phenyl]sulfide

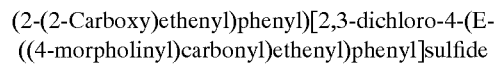

Example 395A (2-(2-Tert-butyloxycarbonyl)ethenyl)phenyl)[2,3-dichloro-4-(E-((4-morpholinyl)carbonyl)ethenyl)
phenyl]sulfide A solution of Example 4-((2E)-3-{4-[(2-bromophenyl)sulfanyl]-2,3-dichlorophenyl}-2 propenoyl)morpholine (50 mg, 0.11 mmol), tris(benzylidineacetone)dipalladium[0] (5.1 mg, 0.0056 mmol), and tri-o-tolylphosphine (11 mg, 0.035 mmol) in 0.2 mL DMF was degassed with nitrogen gas for 10 minutes, then triethylamine (50 μL, 36 mg, 0.36 mmol) and tert-butyl acrylate (50 μL, 44 mg, 0.34 mmol) were added to the solution, and the vessel was sealed under nitrogen and heated in a 100° C. oil bath for 17 hours. The reaction was concentrated under hi-vacuum, and the residue was partially purified by preparative TLC eluting with 10% acetone-CH$_2$Cl$_2$ to provide 42 mg (0.080 mmol, 73%) of the title compound as a crude material. The compound was further purified by preparative HPLC (30–100% MeCN in 0.1% aqueous TFA, 40 minute elution, C-18 reverse-phase Sorbax 10 mm column, producing 26 mg (0.051 mmol, 47%) of the title compound as a glass. $^1$H NMR (300 MHz, CDCl$_3$) δ 1.47 (s, 9H), 2.3–2.7 (v br s, 5H), 3.54–3.90 (2 br m, 8H), 6.32 (d, J=16 Hz, 1H), 6.46 (d, J=8 Hz, 1H), 6.69 (br d, J=15 Hz, 1H), 7.24 (br d, partially overlapped with CHCl$_3$, approx. 1H), 7.40–7.54 (m, 2H), 7.59 (dd, J=2,8 Hz, 1H), 7.75 (dd, J=2,8 Hz, 1H), 7.94 (br d, J=15 Hz, 1H), 7.98 (d, J=16 Hz, 1H); MS (ESI) m/e 520, 522 (M+H)$^+$.

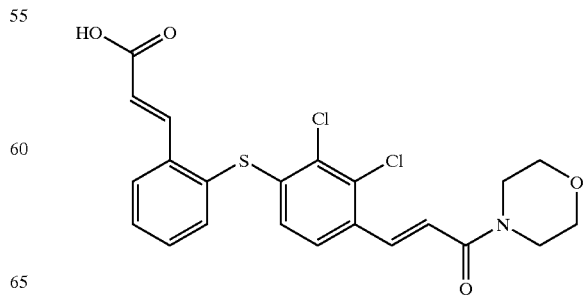

Example 395B (2-(2-Carboxy)ethenyl)phenyl)[2,3-dichloro-4-(E-((4-morpholinyl)carbonyl)ethenyl)phenyl]sulfide Example 395A (26 mg, 0.050 mmol) was dissolved in 1 mL chloroform and 1 mL TFA and the solution was stirred at ambient temperature for 1 hour. $^1$H NMR (300 MHz, CDCl$_3$) δ 3.55–3.85 (2 br m, 9H), 6.42 (d, J=16 Hz, 1H), 6.47 (d, J=8 Hz, 1H), 6.69 (d, J=15 Hz, 1H), 7.24 (d, partially overlapped with CHCl$_3$, approx. 1H), 7.43–7.56 (m, 2H), 7.78 (dd, J=2,8 Hz, 2H), 7.93 (d, J=15 Hz, 1H), 8.23 (d, J=16 Hz, 1H); MS (ESI) m/e 464, 466 (M+H)$^+$.

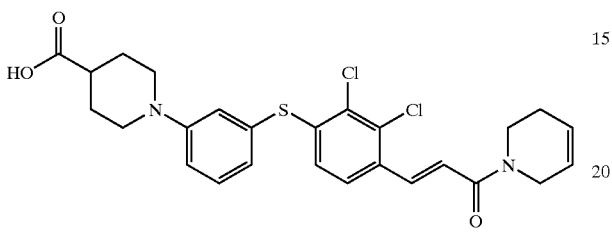

Example 396

[3-(4-Carboxylpiperidin-1-yl)phenyl][2,3-dichloro-4-(E-[(1,2,3,6-tetrahydropyridin-1-yl)carbonyl]ethenyl)phenyl]sulfide The title compound (22 mg, 58%) was prepared from Example 391A as described in Example 384D, substituting morpholine with ethyl isonipecotate followed by hydrolysis with LiOH as described in Example 340H. $^1$H NMR (400 MHz, DMSO-d$_6$) δ 1.59–1.70 (m, 2H), 1.87–1.93 (m, 2H), 2.07–2.19 (m, 2H), 2.39–2.47 (m, 1H), 2.80–2.90 (m, 2H), 4.03 (br s, 1H), 4.16 (br s, 1H), 5.68–5.76 (m, 1H), 5.79–5.90 (m, 1H), 6.72 (d, J=8 Hz, 1H), 6.93 (d, J=7 Hz, 1H), 7.13 (m, 2H), 7.17–7.3 (m, 1H), 7.36 (t, J=7 Hz, 1H), 7.75 (d, J=15 Hz, 1H), 7.80–7.90 (m, 1H); MS (ESI) m/e 517, 519 (M+H)$^+$.

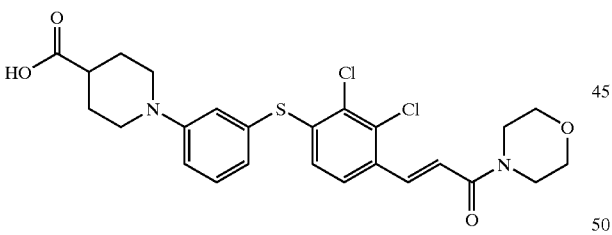

Example 397

[3-(4-Carboxylpiperidinyl)phenyl][2,3-dichloro-4E-[(4morpholinyl)carbonyl]ethenyl)phenyl]sulfide The title compound (39 mg, 79%) was prepared from Example 393A as described in Example 384D, substituting morpholine with ethyl isonipecotate followed by hydrolysis with LiOH as described in Example 340H. $^1$H NMR (400 MHz, DMSO-d$_6$) δ 1.56–1.68 (m, 2H), 1.86–1.92 (m, 2H), 2,38–2.46 (m, 1H), 2.77–2.86 (m, 2H), 3.52–3.61 (m, 6H), 3.65–3.72 (m, 4H), 6.71 (d, J=8 Hz, 1H), 6.91)d, J=7 Hz, 1H), 7.10 (m, 2H), 7.21 (d, J=15 Hz, 1H), 7.34 (t, J=8 Hz, 1H), 7.76 (d, J=15 Hz, 1H), 7.83 (d, J=8 Hz, 1H); MS (ESI) m/e 521, 523 (M+H)$^+$.

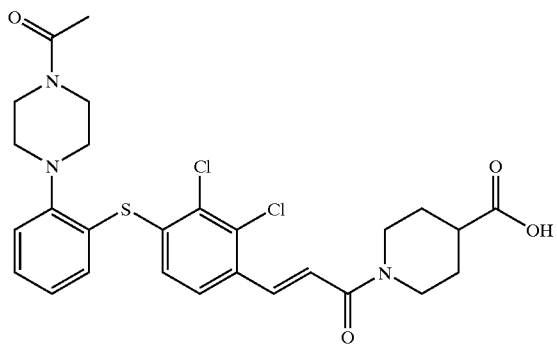

Example 398

[2-(4-Acetylpiperazin-1-yl)phenyl][2,3-dichloro-4-(E-[(4-carboxypiperidin-1-yl)carbonyl]ethenyl)phenyl]sulfide The title compound (19 mg, 83%) was prepared from Example 384C as described in Example 384D, substituting morpholine with 4-acetylpiperazine, followed by hydrolysis with LiOH as described in Example 340H. $^1$H NMR (300 MHz, DMSO-d$_6$) δ 1.38–1.54 (m, 2H), 1.82–11.92 (m, 2H), 2.00 (s, 3H), 2.51–2.60 (m, 1H), 2.87–3.00 (m, 5H), 3.13–3.27 (m, 1H), 3.36–3.46 (m, 4H), 4.06–4.18 (m, 1H), 4.22–4.36 (m, 1H), 6.91 (d, J=7.5 Hz, 1H), 7.10–7.17 (m, 1H), 7.20–7.25 (m, 2H), 7.28 (d, J=15 Hz, 1H), 7.39–7.45 (m, 1H), 7.77 (d, J=15 Hz, 1H), 7.89 (d, J=7.5 Hz, 1H); MS (ESI) m/e 562, 564 (M+H)$^+$.

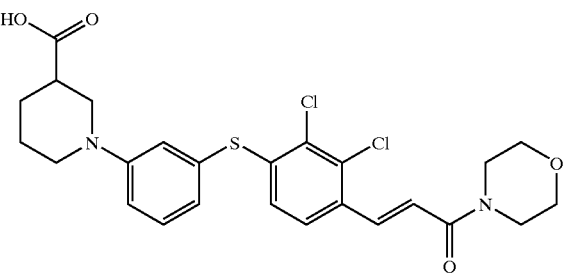

Example 399

[3-(3-Carboxypiperidin-1-yl)phenyl][2,3-dichloro-4-(E-[(4-morpholinyl)carbonyl]ethenyl)phenyl]sulfide The title compound (30 mg, 60%) was prepared from Example 393A as described in Example 384D, substituting morpholine with ethyl nipecotate followed by hydrolysis with LiOH as described in Example 340H. $^1$H NMR (400 MHz, DMSO-d$_6$) δ 1.51–1.60 (m, 1H), 1.66–1.72 (m, 1H), 1.87–1.94 (m, 1H), 2.79–2.87 (m, 1H), 2.96–3.02 (m, 1H), 3.44–3.72 (m, 12H), 6.71 (d, J=8 Hz, 1H), 6.90 (d, J=7 Hz, 1H), 7.09 (m,2H), 7.21 (d, J=15 Hz, 1H), 7.32–7.38 (m,1H), 7.76 (d, J=15 Hz, 1H), 7.84 (d, J=8 Hz, 1H); MS (ESI) m/e 521, 523 (M+H)$^+$.

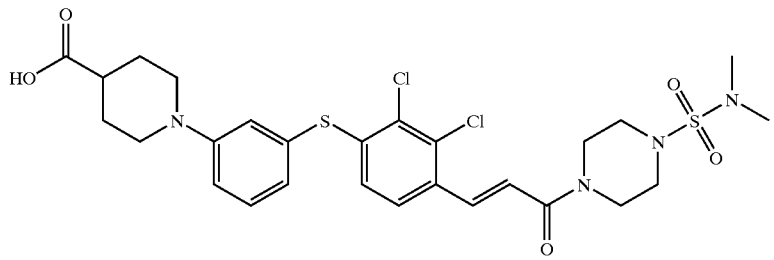

Example 400

[3-(4-Carboxypiperidin-1-yl)phenyl][2,3-dichloro-4-(E-[(4(dimethylaminosulfamoyl)piperazin-1-yl)carbonyl]ethenyl)phenyl]sulfide

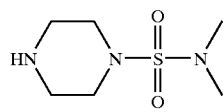

Example 400A

N,N-Dimethyl piperazinylsulfamide

To a solution of tert-butyl 1-piperazinecarboxylate (2.5 g. 13.42 mmol) in tetrahydrofuran (21.5 ml, 0.25 M) at 0° C. was added triethylamine (2.25 mL, 16.11 mmol) followed by dimethylsulfamoyl chloride (1.73 mL, 16.11 mmol). The reaction mixture was stirred at 0° C. for 1 hour, diluted with ethyl acetate (100 mL) and washed with saturated NaHCO$_3$ solution (2×30 mL), followed by brine (2×30 mL). The dried (Na$_2$SO$_4$) organic layer was evaporated to dryness under reduced pressure and the residue obtained was treated with 10% trifluoroacetic acid in methylene chloride (20 mL) at ambient temperature. After 48 hours, methylene chloride was evaporated in vacuo to obtain a colorless syrup. This crude material was made basic (1 N NaOH, 50 mL), and the mixture was extracted sequentially with ethyl acetate (2×20 mL) and methylene chloride (2×30 mL). The combined organic layers were dried (Na$_2$SO$_4$) and evaporated to dryness under reduced pressure to obtain the title compound in quantitative yield. $^1$H NMR (300 MHz, DMSO-d$_6$) δ 2.77 (s, 3H), 2.79 (s, 3H), 3.12–3.20 (m, 7H), 3.3 (m,1H), 8.86 (br s, 1H); MS (ESI) m/e 194 (M+H)$^+$.

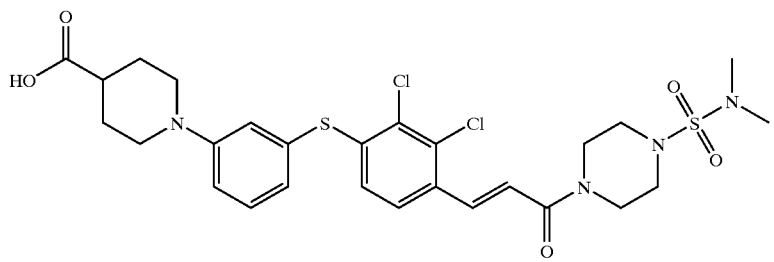

Example 400B

[3-(4-Carboxypiperidin-1-yl)phenyl][2,3-dichloro-4-(E-[(4-(dimethylaminosulfamoyl)piperazin-1-ylcarbonyl]ethenyl)phenyl]sulfide The title compound was prepared from Example 384B as described in Example 340G, substituting methy isonipecotate with Example 400A, followed by amination with ethyl isonipecotate as described in Example 396. $^1$H NMR (500 MHz, MeOH-d$_4$) δ 2.79–2.88 (m, 2H), 2.01–2.08 (m, 2H), 2.48–2.53 (m, 1H), 2.84 (s, 6H), 2.91–2.99 (m, 2H), 3.24–3.29 (m, 2H), 3.66–3.73 (m, 2H), 3.77 (m, 6H), 6.80 (d, J=7.5 Hz, 1H), 7.05(d, J=7.5 Hz, 1H), 7.11 (d, J=15 Hz, 1H), 7.16–7.22 (m, 2H), 7.39 (t, J=7.5 Hz, 1H), 7.62 (d, J=7.5 Hz, 1H), 7.95 (d, J=15 Hz, 1H); MS (ESI) m/e 625, 627 (M–H)$^-$.

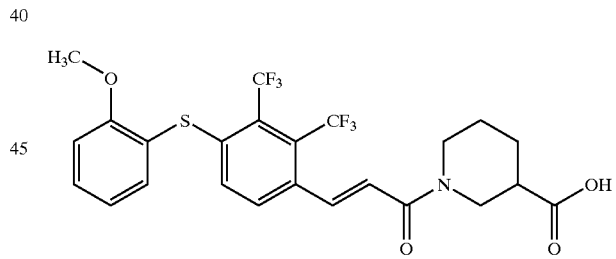

Example 401

(2-Methoxyphenyl)[2,3-bis(trifluoromethyl)-4-(E-((3-carboxypiperidin-1-yl)carbonyl)ethenyl)phenyl] sulfide

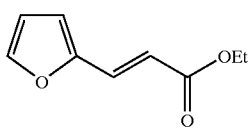

Example 401A

Ethyl 2-Furylacrylate

Ethyl iodide (64 mL, 0.796 mol) was added to furylacrylic acid (100 g, 0.724 mol), diisopropylethyl amine (140 mL, 0.796 mmol), in acetonitrile (1100 mL), and the mixture was heated to 60° C. After 18 h, the dark solution was cooled to room temperature and concentrated in vacuo. The resulting brown sludge was diluted with Et$_2$O (500 mL), washed with 1 N aqueous HCl (2×250 mL), washed with 0.2 N aqueous NaOH (2×250 mL), washed with saturated aqueous NaHCO$_3$ (1×250 mL), dried (MgSO$_4$), filtered, and concentrated to a black oil (114 g, 95%). $^1$H NMR (DMSO-d$_6$, 300 MHz) δ 7.84 (d, J=1.7 Hz, 1H), 7.46 (d, J=15.6 Hz, 1H), 6.97 (d, J=3.4 Hz, 1H), 6.33 (dd, J=3.4 Hz, J=1.7 Hz, 1H), 6.22 (d, J=15.9 Hz, 1H), 4.17 (q, J=7.1 Hz, 2H), 1.24 (t, J=7.1 Hz, 3H); MS (APCI) m/z 167 (M+H)$^+$.

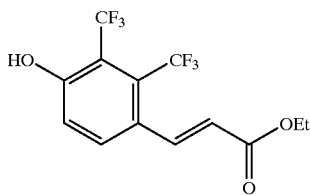

Example 401B

Ethyl E-2,3-bis(trifluoromethyl)-4-hydroxycinnamate

A solution of Example 401A (20 g, 0.12 mol) in tetrahydrofuran (40 mL) at –50° C. in a 600 mL Parr stirred reactor was treated with hexafluoroacetylene (24.4 g, 0.15 mol), the reactor sealed and heated to 110° C. for 22 hours, allowed to slowly cool to room temperature, and then concentrated to a brown oil (36 g). This oil was then treated with boron trifluoride etherate (33 mL, 0.275 mol) at room temperature for 17 hours, additional boron trifluoride etherate (16 mL, 0.135 mol) added, stirred six hours, cooled to 0° C., diethyl ether (200 mL) added, followed by slow addition of 150 mL of 2M potassium carbonate (vigorous gas evolution). This mixture was diluted with additional diethyl ether, layers separated, organic layer washed with brine, dried (MgSO$_4$) and concentrated to give 39 grams of a brown semi-solid. This semi-solid was diluted with 75 mL of dichloromethane and then flash chromatographed on silica gel with 10–50% ethyl acetate/hexane to provide the title compound (22.8 g, 58%). mp 138–140° C.; $^1$H NMR (300 MHz, d6 DMSO) δ 11.64 (bs, 1H), 7.95 (d, 1H), 7.78 (dq, 1H), 7.33 (d, 1H), 6.47 (d, 1H), 4.21 (q, 2H), 1.26 (t, 3H); MS (APCI-NH$_3$) m/e 329 (M+H)$^+$, 346 (M+NH$_4$)$^+$, 327 (M–H)$^-$. Analytical HPLC: 4.6×250 mm Zorbax C18 column, 1.5 mL/min, 254 nm, CH$_3$CN:H$_2$O with 0.1% TFA, 0:100 ramp to 90:10 (0–10 min), 90:10 (10–18 min), ramp to 0:100 (18–20 min), Rt=10.6 min (98.3 area %).

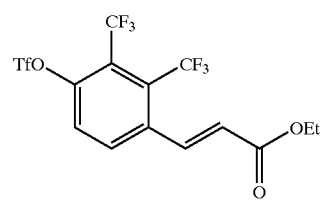

Example 401C

Ethyl E4-(trifluoromethanesulfonyl)-2,3-bis(trifluoromethyl)cinnamate

Triflic anhydride (670 μL 3.97 mmol) was added to a mixture of Example 401B (1.00 g, 3.05 mmol) and pyridine (6.5 mL). After 2 hours, the dark solution was diluted with Et$_2$O (75 mL), washed with 1 N aqueous HCl (2×50 mL), washed with saturated aqueous NaHCO$_3$ (1×75 mL), dried (MgSO$_4$), filtered, and concentrated to a dark amber oil (1.35 g, 96%). $^1$H NMR (DMSO-d$_6$, 300 MHz) δ 8.33 (d, J=8.8 Hz, 1H), 8.11 (d, J=8.8 Hz, 1H), 7.87–7.78 (m, 1H), 6.67 (d, J=16.0 Hz, 1H), 4.24 (q, J=7.1 Hz, 2H), 1.27 (t, 7.1 Hz, 3H); MS (APCI) m/z 478 (M+NH$_4$)$^+$, 495 (M+Cl)$^-$.

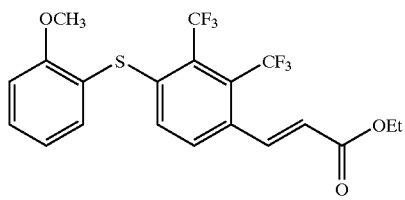

Example 401D (2-Methoxyphenyl)[2,3-bis(trifluoromethyl)-4-(E-(ethoxycarbonyl)ethenyl)phenyl]sulfide 2-Methoxythiophenol (524 μL, 4.30 mmol) was added to Example 401C (1.69 g, 3.90 mmol), cesium carbonate (3.18 g, 9.75 mmol), and DMF (8 mL)., After 15 hours, the dark solution was diluted with Et$_2$O (100 mL), washed with water (1×50 mL), washed with 1 N aqueous HCl (2×100 mL), washed with saturated aqueous NaHCO$_3$ (1×100 mL), dried (MgSO$_4$), filtered, and concentrated to a dark oil. Flash silica gel column chromatography (85:15 hexane:ethyl acetate) provided the ethyl ester (1.16 g, 66%) as a yellow oil. The ester (858 mg) was subsequently hydrolyzed as previously detailed in Example 155 to provide the title compound (670 mg, 84%) as a white solid. 1H NMR (DMSO-d$_6$, 300 MHz) δ 7.89 (d, J=8.8 Hz, 1H), 7.74–7.67 (m, 1H), 7.55 (dd, J=7.5 Hz J=1.7 Hz, 1H), 7.50 (dd, J=9.9 Hz, J=1.7 Hz, 1H), 7.20 (d, J=8.4 Hz, 1H), 7.19 (t, J=7.1 Hz, 1H), 7.07 (dt, J=7.5 Hz, J=1.3 Hz, 1H), 6.44 (d, J=15.6 Hz, 1H), 3.75 (s, 3H). MS (APCI) m/z 421 (M–H$^+$).

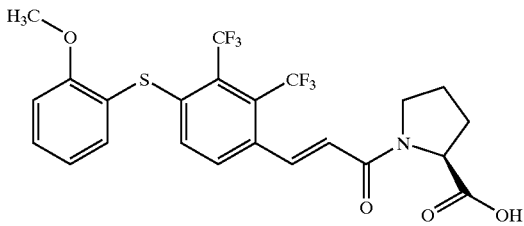

Example 402

(2-Methoxyphenyl)[2,3-bis(trifluoromethyl)-4-(E-((2-carboxypyrrolidin-1-yl)carbonyl)ethenyl)phenyl] sulfide Example 401D was processed as reported in Example 401E, substituting L-proline methyl ester hydrochloride for the amine. $^1$H NMR (DMSO-d$_6$, 300 MHz) δ 7.98 (d, J=8.2 Hz, 1H), 7.64 (m, 1H), 7.53 (d, J=8.2 Hz, 1H), 7.50 (t, J=7.4 Hz, 1H), 7.21 (d, 1H), 7.19 (d, 1H), 7.07 (t,J=7.8 Hz, 1H), 6.95 (d, J=15.0 Hz, 1H), 4.34 (m, 1H), 3.70 (m, 2H), 3.76 (s, 3H), 2.08 (m, 2H), 1.91 (m, 2H); MS (APCI) m/z 520 (M+H$^+$). Anal. calcd for C$_{23}$H$_{19}$F$_6$NO$_4$S: C, 53.18; H, 3.69; N, 2.70. Found: C, 52.88; H, 3.86; N, 2.43.

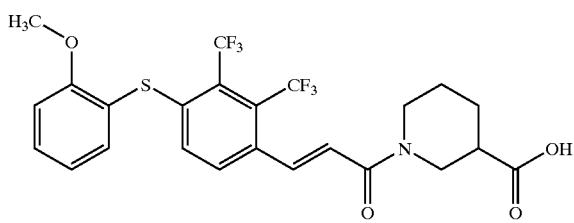

Example 401E (2-Methoxyphenyl)[2,3-bis(trifluoromethyl)-4-(E-((3-carboxypiperidin-1-yl)carbonyl)ethenyl)phenyl] sulfide Example 401D was processed as detailed in Examples 137 and 155 to provide the title compound (168 mg, 86%) as a white solid. $^1$H NMR (DMSO-d$_6$, 300 MHz) δ 7.95 (d, 1H), 7.57 (m, 1H), 7.50 (t, 1H), 7.46 (d, 1H), 7.20 (d, 1H), 7.15 (d, 1H), 7.14 (d, 1H), 7.06 (t, 1H), 4.4 (m, 1H), 4.01 (m, 2H), 3.75 (s, 3H), 1.93 (m, 2H), 1.63 (m, 2H), 1.42 (m, 2H). MS (APCI) m/z 534 (M+H$^+$). Anal. calcd for C$_{24}$H$_{21}$F$_6$NO$_4$S+0.75M H$_2$O: C, 52.70; H, 4.15; N, 2.56. Found: C, 53.01; H, 3.78; N 2.17.

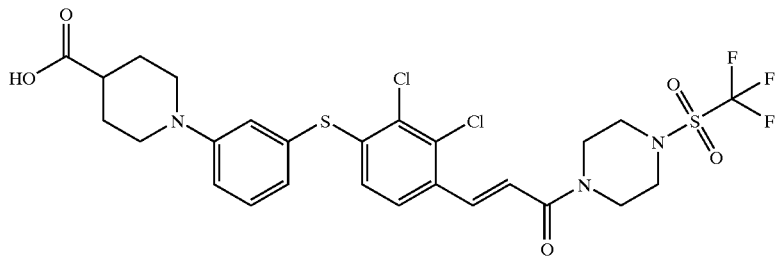

Example 403

[3-(4-Carboxypiperidin-1-yl)phenyl][2,3-dichloro-4-(E-((4-((trifluoromethylsulfonyl)piperazin-1-yl)carbonyl)ethenyl)phenyl]sulfide

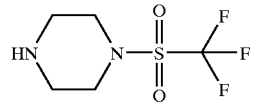

Example 403A

Piperazine-1-trifluoromethylsulfonamide

The title compound (1.65 g, 72%) was prepared as described in Example 400A, substituting dimethylsulfamoyl chloride with trifluoromethanesulfonyl chloride (1.26 ml, 11.81 mmol). MS (ESI) m/e 219 (M+H)$^+$.

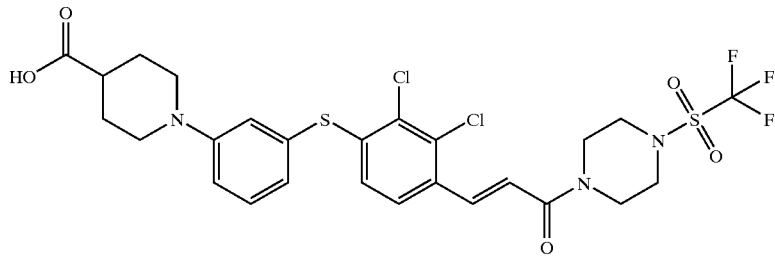

Example 403B

[3-(4-Carboxypiperidin-1-yl)phenyl][2,3-dichloro-4-(E-((4-((trifluoromethylsulfonyl)piperazin-1-yl)carbonyl)ethenyl)phenyl]sulfide Example 403B (51 mg, 38%) was prepared from Example 384B as described in Example 340G, substituting methy isonipecotate with Example 403A followed by amination with ethyl isonipecotate as described in Example 396. $^1$H NMR (500 MHz, DMSO-d$_6$) δ 1.56–1.66 (m, 2H), 2.84–2.91 (m, 2H), 2,37–2.45 (m, 1H), 2.77–2.86 (m, 2H), 3.63–3.70 )m, 7H), 3.72–3.85 (m, 3H), 6.72 (d, J=8.75 Hz, 1H), 6.90 (d, J=7.5 Hz, 1H), 7.09 (m, 1H), 7.11 (s, 1H), 7.21 (d, J=15 Hz, 1H), 7.34 (t, J=7.5 Hz, 1H), 7.76 (d, J=15 Hz, 1H), 7.81 (d, J=8.75 Hz, 1H); MS (ESI) m/e 650, 652 (M–H)$^-$.

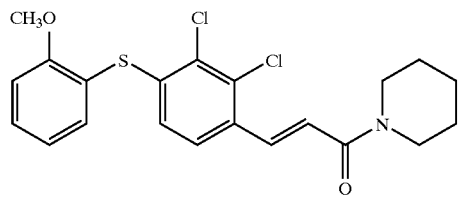

Example 404

(2-Methoxyphenyl)[2,3-dichloro-4-(E-(piperidin-1-ylcarbonyl)ethenyl)phenyl]sulfide The title compound was prepared by procedures described in Example 1C substituting Example 1 B with (2-methoxy)[2,3-dichloro-4-(E-(2-carboxyethenyl)phenyl]sulfide and substituting 6-amino-1-hexanol with piperidine. $^1$H NMR (300 MHz, DMSO-d$_6$) δ 1.48 (m, 4H1), 1.59 (m, 2H), 3.55 (m, 4H), 3.79 (s, 3H), 6.55 (d, J=8.4 Hz, 1H), 7.08 (t, J=7.4 Hz, 1H), 7.21 (d, J=6.0 Hz, 1H), 7.25 (s, 1H), 7.48 (dd, J=7.8, 1.7 Hz, 1H), 7.56 (m, 1H), 7.72 (d, J=15.6 Hz, 1H), 7.82 (d, J=8.5 Hz, 1H); MS (ESI$^+$) m/z 422, 424 (M+H)$^+$. Anal. calcd for C$_{21}$H$_{21}$NCl$_2$SO$_2$: C, 59.72; H, 5.01; N, 3.32. Found: C, 59.52; H, 4.94; N, 3.05.

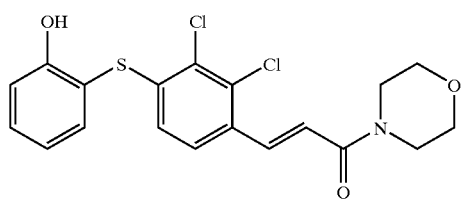

Example 405

(2-Hydroxyphenyl)[2,3-dichloro-4-(E-((4-morpholino)carbonyl)ethenyl)phenyl]sulfide

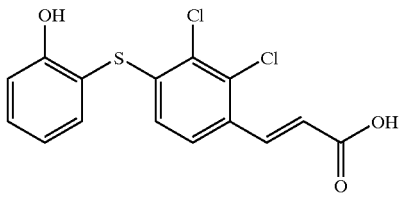

Example 405A (2-Hydroxyphenyl)[2,3-dichloro-4-(E-(carboxy)ethenyl)phenyl]sulfide Boron tribromide (84 mL of a 1.0M solution in CH$_2$Cl$_2$) was added to a suspension of Example 310C in CH$_2$Cl$_2$ (85 mL) at 0° C. After addition was completed, the ice-water bath was removed, and the homogeneous dark solution was stirred for 2 hours before the mixture was poured into 1 N aqueous HCl (100 mL) and ice (100 g), and extracted with EtOAc (3×100 mL). ). The organic layers were combined, washed with brine (1×50 mL), dried (MgSO$_4$), filtered, and concentrated to a white solid (11.3 g). $^1$H NMR (DMSO-d$_6$, 300 MHz) δ 10.26 (s, 1H), 7.82 (d, J15.6, 1H), 7.74 (d, J=8.5 Hz, 1H), 7.44 (dt, J=7.8 Hz, J=1.7 Hz, 1H), 7.41 (dd, J=7.4 Hz, J=1.7 Hz, 1H), 7.05 (dd, J=8.4 Hz, J=1.3 Hz, 1H), 6.94 (dt, J=7.8 Hz, J=1.4 Hz, 1H), 6.52 (d, J=8.2 Hz, 1H), 6.50 (d, J=16.0 Hz, 1H); MS (APCI) m/z 339 (M–H)$^-$, 375 (M+Cl)$^-$.

Example 405B (2-Hydroxyphenyl)[2,3-dichloro-4-(E-((4-morpholino)carbonyl)ethenyl)phenyl]sulfide Example 405A (11.3 g) was processed as reported in Example 310D to provide the title product (8.47 g, 62%) as a white solid. $^1$H NMR (DMSO-d$_6$, 300 MHz) δ 10.24 (s, 1H), 7.81 (d, J=8.9, 1H), 7.77 (d, J=14.9 Hz, 1H), 7.44 (dt, J=6.4 Hz, J=1.7 Hz, 1H), 7.39 (dd, J=8.2 Hz, J=1.7 Hz, 1H), 7.05 (dd, J=8.1 Hz, J=1.0 Hz, 1H), 6.94 (dt, J=7.8 Hz, J=1.0 Hz, 1H), 6.52 (d, J=8.8 Hz, 1H), 6.53 (d, J=8.8 Hz, 1H); MS (APCI) m/z 410 (M+H)⁺, 446 (M+Cl)⁻.

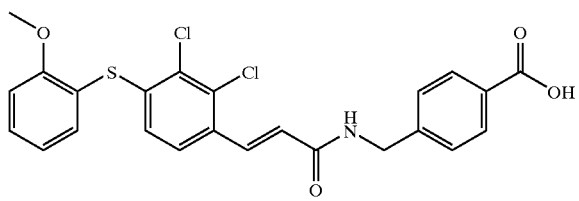

Example 406

(2-Methoxyphenyl)[2,3-dichloro-4-(E-((((4-carboxyphenyl)methyl)amino)carbonyl)ethenyl) phenyl]sulfide The title compound was prepared by the procedures described in Example 1C substituting Example 1B with (2-methoxy)[2,3-dichloro-4-(E-(2-carboxyethenyl)phenyl] sulfide and substituting 6-amino-1-hexanol with methyl 4-(aminomethyl)benzoate hydrochloride followed by hydrolysis. ¹H NMR (300 MHz, DMSO-d₆) δ3.79 (s, 3H), 4.46 (s, 2H), 6.60 (d, J=8.1 Hz, 1H), 6.66 (d, J=15.6 Hz, 1H), 7.08 (t, J=8.4 Hz, 1H), 7.25 (d, J=8.5 Hz, 1H), 7.39 (d, J=8.5 Hz, 2H), 7.51 (m, 3H), 7.75 (d, J=15.6 Hz, 1H), 7.90 (d, J=8.4 Hz, 2H), 8.83 (t, J=5.7 Hz, 1H), 12.90 (brs, 1H); MS (ESI⁺) m/z 488,490 (M+H)⁺. Anal. calcd for $C_{24}H_{19}NCl_2O_4S$: C, 59.02; H, 3.92; N, 2.87. Found: C, 58.97; H, 4.07; N, 2.71.

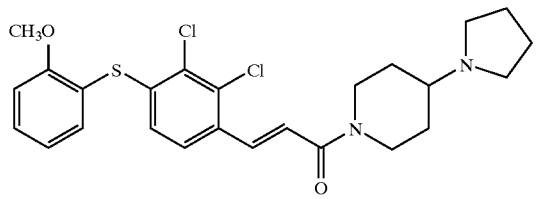

Example 407

(2-Methoxyphenyl)[2,3-dichloro-4-(E-(((4-pyrrolidin-1-yl)piperidin-1-yl)carbonyl)ethenyl) phenyl]sulfide The title compound was prepared by the procedures described in Example 1C substituting Example 1B with (2-methoxy)[2,3-dichloro-4-(E-(2-carboxyethenyl)phenyl] sulfide and substituting 6-amino-1-hexanol with 4-(pyrrolidinyl)piperidine. ¹H NMR (300 MHz, DMSO-d₆) δ 1.48 (m, 2H), 1.84 (m, 2H), 2.00 (m, 2H), 2.10 (m, 2H), 2.65 (m, 1H), 3.10 (m, 3H), 3.35 (m, 1H), 3.50 (m, 1H), 3.80 (s, 3H), 4.38 (m, 2H), 4.52 (m, 1H), 6.56 (d, J=8.5 Hz, 1H), 7.08 (t, J=7.8 Hz, 1H), 7.22 (d, J=7.8 Hz, 1H), 7.26 (d, J=15.2 Hz, 1H), 7.48 (dd, J=7.8, 1.7 Hz, 1H), 7.57 (t, J=8.2 Hz, 1H), 7.76 (d, J=15.3 Hz, 1H), 7.82 (d, J=7.8 Hz, 1H); MS (ESI⁺) m/z 491, 493 (M+H)⁺. Anal. calcd for $C_{25}H_{28}N_2Cl_2O_2S$ 1.8 TFA: C, 49.30; H, 4.31; N, 4.02. Found: C, 49.08; H, 4.31; N, 3.97.

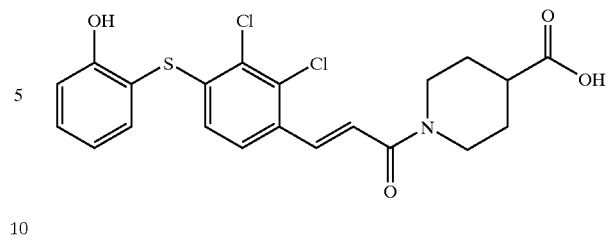

Example 408

(2-Hydroxyphenyl)[2,3-dichloro-4-(E-((4-carboxypiperidin-1-yl)carbonyl)ethenyl)phenyl] sulfide Example 405A (119 mg) was processed as detailed in Example 165 to provide the title compound as a white solid (43 mg, 28%). ¹H NMR (DMSO-d₆, 300 MHz) δ 10.23 (s, 1H), 7.81 (d, J=8.8, 1H), 7.72 (d, J=15.2 Hz, 1H), 7.42 (dt, J=7.8 Hz, J=1.7 Hz, 1H), 7.39 (dd, 7.1 Hz, J=1.7 Hz, 1H), 7.21 (d, J=15.3 Hz, 1H), 7.05 (dd, J=8.2 Hz, J=1.0 Hz, 1H), 6.93 (dt, J=7.4 Hz, J=1.0 Hz, 1H), 6.53 (d, J=8.5 Hz, 1H), 4.25 (m, 1H), 4.03 (m, 2H), 2.85 (m, 2H), 1.87 (m, 2H), 1.44 (m, 2H). MS (APCI) m/z 452 (M+H⁺), 450 (M−H⁺), 486 (M+Cl⁻). Anal. calcd for $C_{21}H_{19}Cl_2NO_4S+0.25M\ H_2O$: C, 55.21; H, 4.30; N, 3.07. Found: C, 55.26; H, 4.29; N, 2.72.

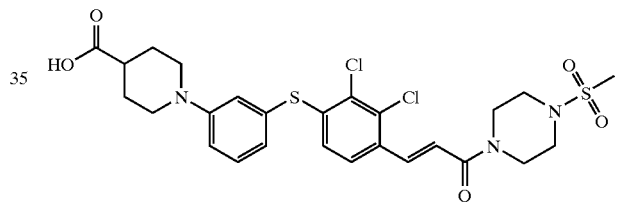

Example 409

[3-(4-Carboxypiperidin-1-yl)phenyl][2,3-dichloro-4-(E-((4-((methylsulfonyl)piperazin-1-yl)carbonyl) ethenyl)phenyl]sulfide

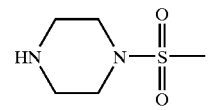

Example 409A

Piperazine methylsulfonamide

The title compound (1.65 g, 72%) was prepared as described in Example 400A, substituting dimethylsulfamoyl chloride with methanesulfonyl chloride (1.26 ml, 11.81 mmol).

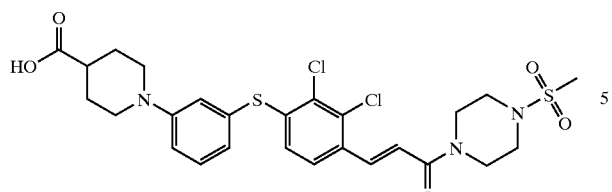

Example 409B

[3-(4-Carboxypiperidin-1-yl)phenyl][2,3-dichloro-4-(E-((4-((methylsulfonyl)piperazin-1-yl)carbonyl)ethenyl)phenyl]sulfide Example 409B (48 mg, 72%) was prepared from Example 384B as described in Example 340G, substituting methy isonipecotate with Example 409A followed by amination with ethyl isonipecotate as described in Example 396. $^1$H NMR (300 MHz, DMSO-d$_6$) δ 1.55–1.71 (m, 2H), 1.83–1.94 (m, 2H), 2.36–2.48 (m, 1H), 2.77–2.86 (m, 2H), 2.88 (s, 3H), 3.10–3.18 (m, 4H), 3.66–3.84 (m, 6H), 6.73 (d, J=8 Hz, 1H), 6.93 (d, J=7.5 Hz, 1H), 7.11 (m, 1H), 7.13 (s, 1H), 7.25 (d, J=15 Hz, 1H) 7.32–7.41 (m, 1H), 7.78 (d, J=15 Hz, 1H), 7.85 (d, J=8 Hz, 1H); MS (ESI) m/e 598, 600 (M+H)$^+$; 596, 598 (M–H).

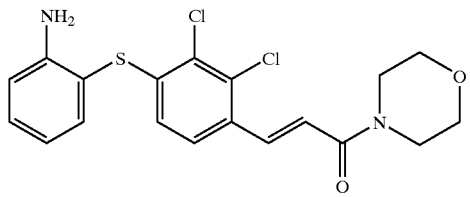

Example 410

(2-Aminophenyl)[2,3-dichloro-4-(E-((4-morpholinyl)carbonyl)ethenyl)phenyl]sulfide

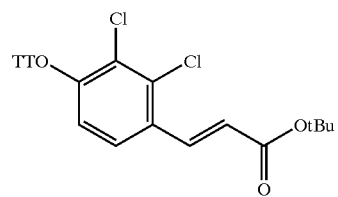

Example 410A tert-Butyl 2,3-dichloro-4-((trifluoromethyl)sulfonyloxy)cinnamate

The title compound was constructed according to the procedure for Example 340D and 340E, substituting methyl acrylate with tert-butyl acrylate. $^1$H NMR (300 MHz, DMSO-d$_6$) δ 8.11 (d, 1H), 7.78 (d, 1H), 7.72 (d, 1H), 6.72 (d, 1H), 1.5 (s, 9H); MS (APCI-NH$_3$) m/e 456 (M+Cl)$^-$.

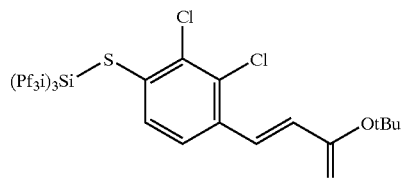

Example 410B tert-Butyl 2,3-dichloro-4-((triisopropylsilyl)thio)cinnamate

Sodium hydride (3.05 g of 60% dispersion, 76 mmol) that had been rinsed with dry tetrahydrofuran (2×), was suspended in 128 mL of THF, cooled to −5° C., and slowly treated with triisopropylsilyl thiol (12.2 mL, 57 mmol), maintaining an internal temperature below 4° C., stirred at 0° C. for 1.5 hours, then added to a second flask containing Example 410A (20 g, 47.4 mmol) and tetrakistriphenylphosphine palladium (4.4 g, 3.8 mmol) in 95 mL of THF. The reaction was heated at reflux for 8 hours, then allowed to cool to ambient temperature and concentrated. The resultant slurry was diluted with ethyl acetate, filtered through celite, washed with brine, dried (Na$_2$SO$_4$) and concentrated. The resultant black residue was flash chromatographed on silica gel with 2.5–5% acetone/hexane to provide the title compound (18.2 g, 83%).

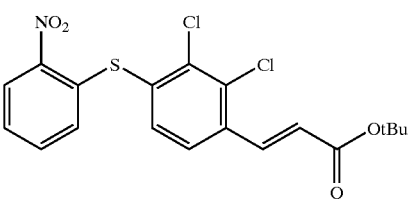

Example 410C (2-Nitrophenyl)[2,3-dichloro-4-(E-((tert-butyloxycarbonyl)ethenyl)phenyl]sulfide A solution of Example 410B in toluene (40 mL) was treated with cesium fluoride (600 mg, 4 mmol) followed by 2-fluoronitrobenzene (5.03 mL, 47.4 mmol), then heated at reflux for 2 h, then allowed to cool and the mixture was concentrated under reduced pressure. The resultant dark brown slurry was diluted with ethyl acetate, washed with water (2×), 1 M NaOH,(2×), water (2×), dried (Na$_2$SO$_4$) and concentrated. The 21.2 grams of crude product was flash chromatographed on silica gel with 10% acetone/hexane to provide the title compound (8.92 g, 53%). $^1$H NMR (300 MHz, DMSO-d$_6$) δ 8.17 (dd, 1H), 7.95 (d, 1H), 7.83 (d, 1H), 7.78 (m, 1H), 7.48 (m, 1H), 7.3 (dd, 1H), 7.17 (d, 1H), 6.6 (d, 1H), 1.5 (s, 3H); MS (APCI-NH$_3$) m/e 427 (M+H)$^+$.

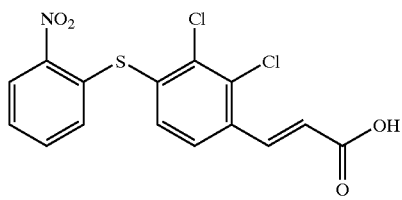

Example 410D (2-Nitrophenyl)[2,3-dichloro-4-(E-((carboxy)ethenyl)phenyl]sulfide

A solution of Example 410C (3.2 g, 7.5 mmol) in dichloromethane (12 mL) at room temperature was treated with trifluoroacetic acid (4 mL), stirred 30 minutes, and concentrated to give the title compound (2.8 g, 100%) as an off-white solid. $^1$H NMR (300 MHz, DMSO-$d_6$) δ 8.16 (dd, 1H), 7.94 (d, 1H), 7.86 (d, 1H), 7.76 (m, 1H), 7.48 (m, 1H), 7.29 (dd, 1H), 7.11 (d, 1H), 6.61 (d, 1H); MS (APCI–NH$_3$) m/e 371 (M+H)$^+$.

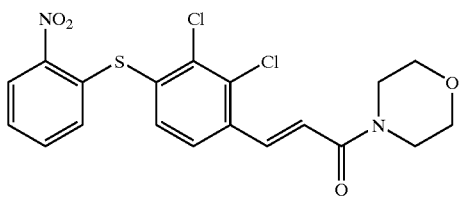

Example 410E (2-Nitrophenyl)[2,3-dichloro-4-(E-((4-morpholinyl)carbonyl)ethenyl)phenyl]sulfide A solution of Example 410D (2.7 g, 7.29 mmol) in dimethylformamide (32 mL) was treated with hydroxybenzotriazole hydrate (1.2 g, 8.0 mmol), morpholine (1.4 mL, 16 mmol) and then 1-(3-dimethylaminopropyl)-3-ethylcarbodiimide hydrochloride (1.53 g, 8.0 mmol), stirred at room temperature for 64 hours. The heterogeneous mixture was filtered, the white solid washed with water, and then dried in a vacuum oven at 50° C. for 24 hours to provide 2.8 g (88%) of the title compound as a white powder. mp 210–213° C.; $^1$H NMR (300 MHz, d6 DMSO) δ 8.15 (dd, 1H), 8.03(d, 1H), 7.82 (d, 1H), 7.74 (m, 1H), 7.45 (m, 1H), 7.32 (d, 1H), 7.2 (m, 2H), 3.7 (m, 2H), 3.6 (m, 6H); MS (APCI–NH$_3$) m/e 440 (M+H)$^+$.

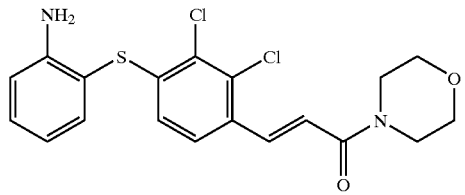

Example 410F (2-Aminophenyl)[2,3dichloro-(E-((4-morpholinyl)carbonyl)ethenyl)phenyl]sulfide A solution of iron powder (1.3 g, 22.8 mmol) and ammonium chloride (292 mg, 5.46 mmol) in ethanol (9 mL) and distilled water (9 mL) at 105° C. was treated with example 410F (2 g, 4.55 mmol) in ethanol (20 mL), stirred for one hour and then allowed to cool to room temperature. The resultant heterogeneous black mixture was filtered through a plug of Celite, rinsed through with ethyl acetate (100 mL), the filtrate washed with 1 M potassium carbonate, brine, dried (Na$_2$SO$_4$) and concentrated to give 1.9 g (1 00%) of the title compound as an off-white powder. mp 230–240° C. (dec); $^1$H NMR (300 MHz, d6 DMSO) δ 7.9 (d, 1H), 7.8 (d, 1H), 7.2 (d, 1H), 6.95 (dt, 1H), 6.84 (m, 2H), 6.68 (d, 1H), 6.58 (dt, 1H), 5.05 (bs, 2H), 3.7 (m, 2H), 3.6 (m, 6H); MS (APCI–NH$_3$) m/e 410 (M+H)$^+$; Analytical HPLC: 4.6×250 mm Zorbax C18 column, 1.5 mL/min 254 nm, CH$_3$CN:H$_2$O with 0.1% TFA, 0:100 ramp to 90:10 (0–10 min), 90:10 (10–18 min), ramp to 0:100 (18–20 min), Rt=9.2 min.

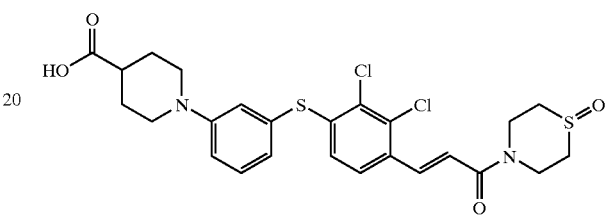

Example 411

(3-(4-carboxypiperidine-1-yl)phenyl)[2,3-dichloro-4-(E-((S-oxothiomorpholin-1-yl)carbonyl)ethenyl)phenyl]sulfide

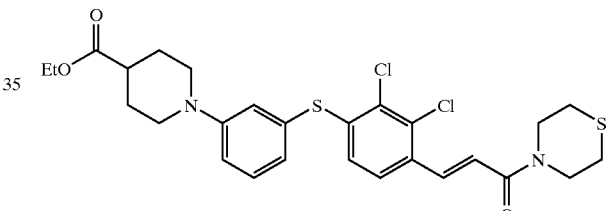

Example 411A

[3-(4-Ethoxycarbonyl)piperidin-1-yl)phenyl][2,3dichloro-4-(E-(thiomorpholin-yl)carbonyl)ethenyl)phenyl]sulfide The title compound was prepared by the procedures described in Example 397B substituting morpholine with thiomorpholine. MS (APCI$^+$) m/z 565, 567 (M+H)$^+$.

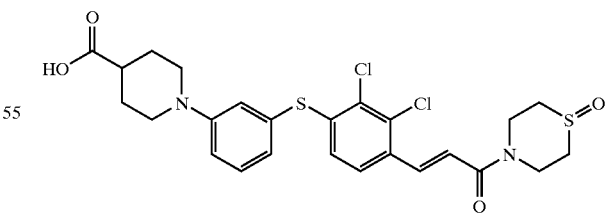

Example 411B (3-(4-carboxypiperidin-1-yl)phenyl)[2,3-dichloro-4-(E-((S-oxothiomorpholin-1-yl)carbonyl)ethenyl)phenyl]sulfide To a solution of Example 411A (107 mg, 0.189 mmol) in CH$_2$Cl$_2$ (6 mL) was added mCPBA (80%, 41 mg, 0.189 mmol) at 0° C. After stirring at the same temperature for 2 hours, THF (2 mL) was added. The solution was concentrated to 1 mL, and was diluted with THF to 3 mL. Lithium hydroxide monohydrate (24 mg) in water (1 mL) was then added. The mixture was stirred at room temperature for 3 hours. The formed transparent solution was separated by HPLC (Zorbax C-18) to give the title compound (68 mg). $^1$H NMR (300 MHz, DMSO-d$_6$) δ 1.64 (m, 2H), 1.90 (m, 2H), 2.41 (m, 1H), 2.86 (m, 4H), 3.62 (m, 2H), 3.95 (m, 1H), 4.18 (m, 1H), 4.3 (m, 4H), 6.71 (d, J=8.4 Hz, 1H), 6.93 (d, J=7.5 Hz, 1H), 7.12 (d, J=7.5 Hz, 1H), 7.13 (s, 1H), 7.28 (d, J=15.3 Hz, 1H), 7.36 (t, J=8.8 Hz, 1H), 7.80 (d, J=15.3 Hz, 1H), 7.88 (d, J=8.8 Hz, 1H); MS (APCI$^+$) m/z 553,555 (M+H)$^+$. Anal. calcd for $C_{25}H_{26}N_2Cl_2S_2O_4$2 TFA: C, 44.57; H, 3.61; N, 3.58. Found: C, 44.34; H, 3.76; N, 3.51.

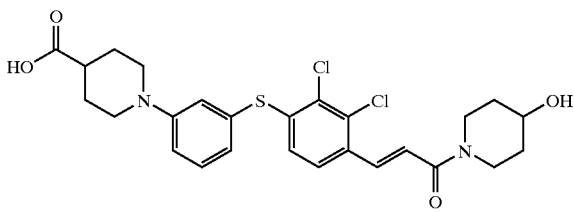

Example 412

[3-(4-Carboxypiperidin-1-yl)phenyl][2,3-dichloro-4-(E-((4-hydroxypiperidin-1-yl)carbonyl)ethenyl)phenyl]sulfide

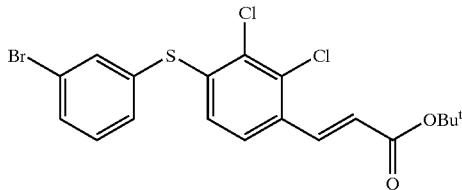

Example 412A (3-Bromophenyl)[2,3-dichloro-4-(E-((tert-butyloxycarbonyl)ethenyl)phenyl]sulfide To a solution of Example 384B (2.35 g, 5.82 mmol) in THF (23 mL) at 5° C. was added tert-butyl trichloroacetimidate (2.6 mL, 14.54 mmol) and boron trifluoride-etherate (2.35 mL, 18.54 mmol). The solution was stirred at the same temperature for 10 minutes, and was then warmed to room temperature for 5 hours. The yellow solution was poured into aq. NaHCO$_3$ solution, and the mixture was extracted with ethyl acetate. The combined organic phases were washed with water, dried over anhydrous MgsSO$_4$, and concentrated. The residual white solid was dissolved in CH$_2$Cl$_2$ and was precipitated by adding hexane. The formed suspension was filtered through silica gel, and washed with The solution was concentrated and was further purified by flash chromatography (silica gel, 1:20 EtOAc/hexane) to give the title compound (2.50 g, 94%). MS (APCI$^+$) m/z 461 (M+H)$^+$.

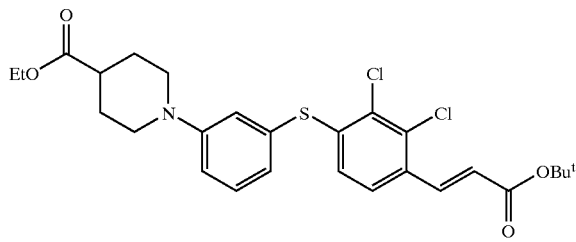

Example 412B (3-(4-carboethoxypiperidin-1-yl)phenyl)[2,3-dichloro-4-(E-(carbo-t-butoxyethenyl)phenyl]sulfide A pressure tube was charged with Example 412A (589 mg, 1.28 mmol), Pd$_2$(dba)$_3$(30 mg, 0.032 mmol), 2-dicyclohexylphosphanyl-2'-dimethylaminobiphenyl (26 mg, 0.064 mmol), and anhydrous K$_3$PO$_4$ (382 mg, 1.8 mmol), and was purged with nitrogen. DME (4 mL) and ethyl isonipecotate (242 mg, 1.54 mmol) were added via syringe, and the mixture was purged with nitrogen again. The red reaction mixture was stirred at room temperature for 0.5 hours and at 95° C. for 15 hours. After the reaction mixture was cooled, it was diluted with ethyl acetate, and washed with brine. The aqueous phase was extracted with ethyl acetate. The combined ethyl acetate solution was concentrated and the residual oil was separated by flash chromatography (silica gel, 1:6 EtOAc/hexane) to give the title compound (523 mg, 76%). MS (APCI$^+$) m/z 536 (M+H)$^+$.

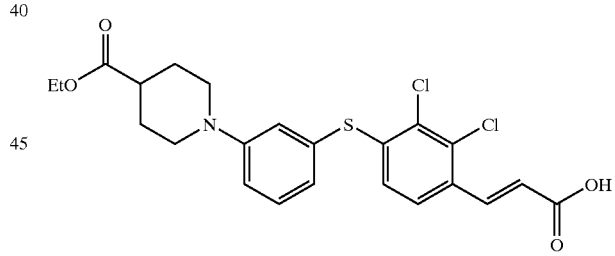

Example 412C

[3-(4-(Ethoxycarbonyl)piperidin-1-yl)phenyl][2,3-dichloro-4-(E-(carboxy)ethenyl)phenyl]sulfide To a solution of Example 412B (510 mg, 0.95 mmol) in CH$_2$Cl$_2$ (8 mL) at 0° C. was added trifluoroacetic acid (1.6 mL). The yellow solution was stirred at 0° C. for 1 hour, and was warmed to room temperature for 3 hours. After diluting with CH$_2$Cl$_2$, the solution was poured into aq. NaHCO$_3$ solution. The inorganic phase was acidified to pH 5, and was extracted with 10% MeOH in $CH_2Cl_2$. The combined organic phases were washed with water, concentrated under vacuum and dried to give the title compound (472 mg, 100%). MS (APCI$^+$) m/z 480 (M+H)$^+$.

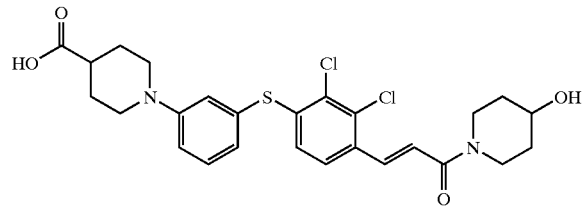

Example 412D

[3-(4-carboxypiperidin-1-yl)phenyl][2,3-dichloro-4-(E-((4-hydroxypiperidine-1-yl)carbonyl)ethenyl)phenyl]sulfide To a suspension of Example 412C (150 mg, 0.31 mmol) in DMF (3 mL) was added 4-hydroxypiperidine (63 mg, 0.62 mmol), 1-(3-dimethylaminopropyl)-3-ethylcarbodimide (120 mg, 0.62 mmol), HOBt (84 mg, 0.62 mmol) and triethylamine (87 µL, 0.62 mmol) at room temperature. The mixture was stirred at the same temperature for 15 hours. Ethyl acetate was added, the mixture was washed with brine, water, and was concentrated. The residual oil was dissolved in THF (3 mL), and was added lithium hydroxide monohydrate (26 mg, 0.62 mmol) in water (1.5 mL). After stirring for 15 hours, the solution was separated by HPLC (Zorbax C-18) to give the title compound (132 mg, 55%). $^1$H NMR (300 MHz, DMSO-d$_6$) δ 1.32 (m, 2H), 1.65 (m, 2H), 1.75 (m, 2H), 1.92 (m, 2H), 2.43 (m, 1H), 2.86 (t, J =10.6 Hz, 2H), 3.15 (m, 1H), 3.32 (m, 1H), 3.71 (m, 3H), 3.95 (m, 2H), 6.73 (d, J=8.5 Hz, 1H), 6.94 (d, J=7.2 Hz, 1H), 7.13 (d, J=7.8 Hz, 1H), 7.13 (s, 1H), 7.24 (d, J=15.2 Hz, 1H), 7.37 (t, J=8.1 Hz, 1H), 7.72 (d, J=15.2 Hz, 1H), 7.85 (d, J=8.5 Hz, 1H); MS (ESI$^+$) m/z 535, 537 (M+H)$^+$. Anal. calcd for $C_{26}H_{28}N_2Cl_2SO_4$ 0.25 TFA: C, 56.43; H, 5.05; N, 4.97. Found: C, 56.37; H, 5.00; N, 4.91.

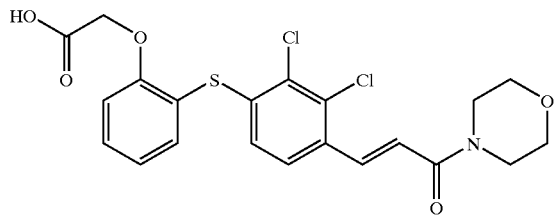

Example 413

(2-Glycoxyphenyl)[2,3-dichloro-4-(E-((4-morpholino)carbonyl)ethenyl)phenyl]sulfide Diethyl azodicarboxylate (270 µL, 1.47 mmol) was added to a suspension of Example 405 (400 mg, 0.95 mmol), triphenylphosphine (386 mg, 1.47 mmol), and THF (2.0 mL). After 16 hours, the dark orange solution was diluted with EtOAc (40 mL), washed with 1 N aqueous HCl (1×20 mL), washed with 0.2 N aqueous NaOH (1×20 mL), washed with brine (1×20 mL), dried (MgSO$_4$), filtered, and concentrated. Flash silica gel column chromatography (9:1 hexane-:ethyl acetate) provided a mix of desired ester and triphenyl phosphine oxide. The mixture (200 mg) was combined with lithium hydroxide, monohydrate (34 mg, 0.81 mmol), THF (0.5 mL), and $H_2O$ (0.5 mL). After 21 hours, the cloudy solution was diluted with 0.2 N aqueous NaOH (30 mL), washed with $CH_2Cl_2$ (2×15 mL), combined with 1 N aqueous HCl until pH<2, and extracted with EtOAc (2×20 mL). The EtOAc extracts were combined, washed with brine (1×20 mL), dried (MgSO$_4$), filtered, and concentrated to a white solid (87 mg, 47%). $^1$H NMR (DMSO-d$_6$, 300 MHz) δ 7.80 (d, J=7.8, 1H), 7.77 (d, J=15.3 Hz, 1H), 7.51 (dt, J=8.1 Hz, J=2.0 Hz, 1H), 7.48 (d, J=8.1 Hz, 1H), 7.22 (d, J=15.3 Hz, 1H), 7.09 (d, J=7.8 Hz, 1H), 7.08 (dt, J=7.1 Hz, J=1.0 Hz, 1H), 6.71 (d, J=8.9 Hz, 1H), 4.77 (s, 2H), 3.66 (s, 2H), 3.58 (s, 6H); MS (APCI) m/z 468 (M+H)$^+$; 466 (M–H)$^-$, 502 (M+Cl)$^-$. Anal. calcd for $C_{21}H_{19}Cl_2NO_5S$: C, 53.85; H, 4.09; N, 2.99. Found: C, 54.07; H, 4.28; N, 2.69.

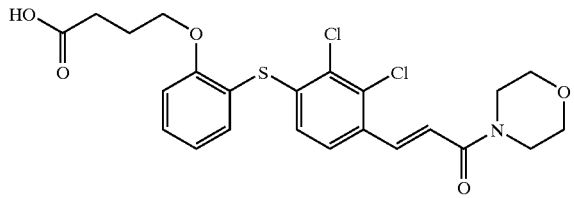

Example 414

(2-(4-Butyroxy)phenyl)[2,3-dichloro-4-(E-((4-morpholino)carbonyl)ethenyl)phenyl]sulfide Ethyl 4-bromobutyrate was added to a mixture of Example 405 (300 mg, 0.731 mmol), cesium carbonate (358 mg, 1.10 mmol), and DMF (1.5 mL). After 16 hours, the pale milky solution was diluted with EtOAc (30 mL), washed with 1 N aqueous HCl (2×25 mL), washed with brine (1×25 mL), dried (MgSO$_4$), filtered, and concentrated to a white solid (326 mg, 85%) as the ethyl ester. The ethyl ester (312 mg, 0.595 mmol), THF (1.5 mL), and $H_2O$ (1.5 mL) were combined with lithium hydroxide, monohydrate (63 mg, 1.50 mmol). After 18 hours, the clear solution was poured into 1 N aqueous HCl (25 mL) and extracted with EtOAc (2×25 mL). The organic layers were combined, dried (MgSO$_4$), filtered, and concentrated to a white solid (247 mg, 85%). $^1$H NMR (DMSO-d$_6$, 300 MHz) δ 7.79 (d, J=8.5, 1H), 7.77 (d, J=15.6 Hz, 1H), 7.51 (dt, J=7.5 Hz, J=1.7 Hz, 1H), 7.48 (dd, J=7.5 Hz, J=1.0 Hz, 1H), 7.20 (d, J=14.9 Hz, 1H), 7.19 (d, J=9.5 Hz, 1H), 7.06 (t, J=7.5 Hz, 1H), 6.63 (d, J=8.5 Hz, 1H), 4.01 (t, J=6.1 Hz, 2H), 3.65 (s, 2H), 3.58 (s, 6H), 2.10 (t, J=7.4 Hz, 2H), 1.75 (m, 2H); MS (APCI) m/z 496 (M+H)$^+$.

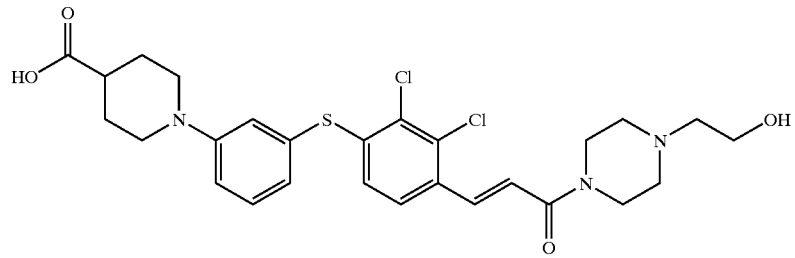

Example 415

[3-(4-Carboxypiperidin-1-yl)phenyl][2,3-dichloro-4-(E-((4-hydroxyethylpiperazin-1-5 yl)carbonyl)ethenyl)phenyl]sulfide The title compound was prepared by the procedures described in Example 412 substituting 4-hydroxypiperidine with 1-hydroxyethylpiperazine. $^1$H NMR (300 MHz, DMSO-d$_6$) δ 1.70 (m, 2H), 1.94 (m, 2H), 2.98 (m, 2H), 3.05 (m, 2H), 3.18 (m, 2H), 3.54 (m, 2H), 3.65 (m, 3H), 3.78 (m, 2H), 6.77 (d, J=8.8 Hz, 1H), 7.03 (d, J=6.8 Hz, 1H), 7.28 (d, J=14.9 Hz, 1H), 7.29 (m, 2H), 7.42 (t, J=7.8 Hz, 1H), 7.78 (d, J=15.3 Hz, 1H), 7.86 (d, J=8.8 Hz, 1H); MS (ESI$^+$) m/z 564, 566 (M+H)$^+$.

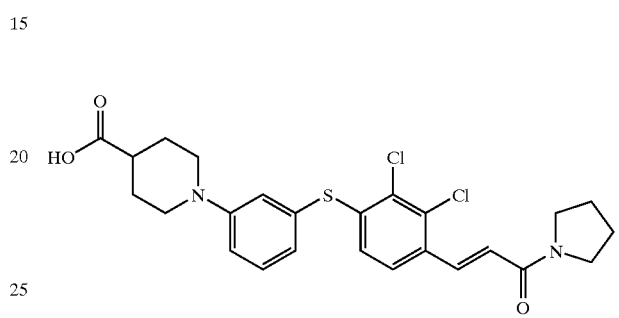

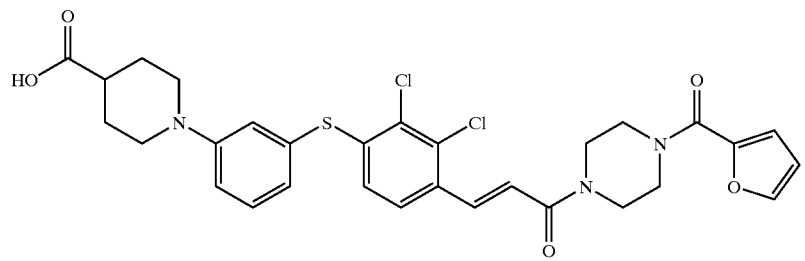

Example 416

[3-(4-Carboxypiperidin-1-yl)phenyl][2,3-dichloro-4-(E-((4-furoylpiperazin-1-yl)carbonyl)ethenyl)phenyl]sulfide The title compound was prepared by the procedures described in Example 412 substituting 4-hydroxypiperidine with 1-furoylpiperazine. $^1$H NMR (300 MHz, DMSO-d$_6$) δ 1.64 (m, 2H), 1.91 (m, 2H), 2.43 (m, 1H), 2.87 (m, 2H), 3.70 (m, 10H), 6.43 (m, 1H), 6.72 (d, J=8.5 Hz, 1H), 6.94 (d, J=7.8 Hz, 1H), 7.03 (d, J=3.3 Hz, 1H), 7.13 (d, J=7.8 Hz, 1H), 7.14 (s, 1H), 7.26 (d, J=15.2 Hz, 1H), 7.36 (t, J=7.5 Hz, 1H), 7.77 (d, J=15.2 Hz, 1H), 7.86 (m, 2H); MS (ESI$^+$) m/z 614, 616 (M+H)$^+$. Anal. calcd for $C_{30}H_{29}N_3Cl_2SO_5$ 1.5 TFA: C, 50.45; H, 3.91; N, 5.35. Found: C, 50.53; H, 3.96; N, 5.35.

Example 417

[3-(4-Carboxypiperidin-1-yl)phenyl][2,3-dichloro4-(E-((pyrrolidin-1-yl)carbonyl)ethenyl)phenyl]sulfide The title compound was prepared by the procedures described in Example 412 substituting 4-hydroxypiperidine with pyrrolidine. $^1$H NMR (300 MHz, DMSO-d$_6$) δ 1.63 (m, 2H), 1.79 (m, 2H), 1.88 (m, 4H), 2.43 (m, 1H), 2.82 (m, 2H), 3.39 (t, J=6.7 Hz, 2H), 3.59 (t, J=6.8 Hz, 2H), 3.68 (m, 2H), 6.71 (d, J=8.5 Hz, 1H), 6.92 (d, J=7.5 Hz, 1H), 6.96 (d, J=15.3 Hz, 1H), 7.12 (d, J=6.8 Hz, 1H), 7.13 (s, 1H), 7.35 (t, J=8.8 Hz, 1H), 7.72 (d, J=15.3 Hz, 1H), 7.80 (d, J=8.5 Hz); MS (ESI$^+$) m/z 505, 507 (M+H)$^+$. Anal. calcd for $C_{25}H_{26}N_2Cl_2SO_3$ 0.8 TFA: C, 53.54; H, 4.53; N, 4.69. Found: C, 53.74; H, 4.40; N, 4.64.

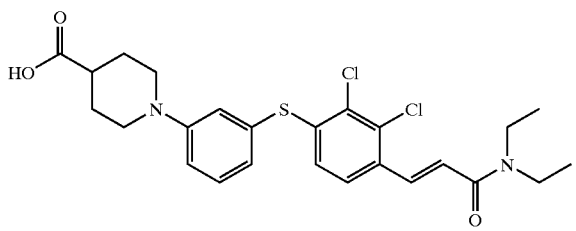

Example 418

[3-(4-Carboxypiperidin-1-yl)phenyl][2,3-dichloro-4-(E-((diethylaminocarbonyl)ethenyl)phenyl]sulfide The title compound was prepared by the procedures described in Example 412 substituting 4-hydroxypiperidine with diethylamine. $^1$H NMR (300 MHz, DMSO-d$_6$) δ 1.06(t, J=6.7 Hz, 3H), 1.11 (t, J=6.7 Hz, 3H), 1.63 (m, 2H), 1.88 (m, 2H), 2.43 (m, 1H), 2.82 (m, 2H), 3.35 (q, J=6.7 Hz, 2H), 3.47 (q, J=6.7 Hz, 2H), 3.70 (m, 2H), 6.68 (d, J=8.5 Hz, 1H), 6.92 (d, J=7.5 Hz, 1H), 7.07 (d, J=15.2 Hz, 1H), 7.12 (d, J=8.6 Hz, 1H), 7.13 (s, 1H), 7.35 (t, J=8.8 Hz, 1H), 7.75 (d, J=15.3 Hz, 1H), 7.84 (d, J=8.5 Hz, 1H); MS (ESI$^+$) m/z 507 (M+H)$^+$. Anal. calcd for C$_{25}$H$_{28}$N$_2$Cl$_2$SO$_3$ 0.2 TFA: C, 57.53; H, 5.36; N, 5.28. Found: C, 57.68; H, 5.38; N, 5.33.

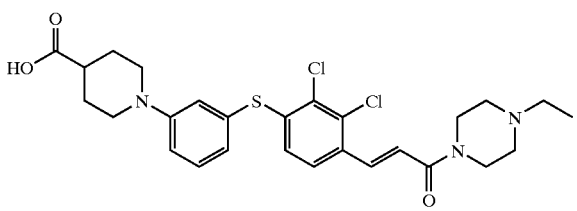

Example 419

[3-(4-Carboxypiperidin-1-yl)phenyl][2,3-dichloro-4-(E-((4-ethylpiperazin-yl)carbonyl)ethenyl)phenyl]sulfide The title compound was prepared by the procedures described in Example 412 substituting 4-hydroxypiperidine with 1-ethylpiperazine. $^1$H NMR (300 MHz, DMSO-d$_6$) δ 1.22 (t, J=7.5 Hz, 3H), 1.63 (m, 2H), 1.87 (m, 2H), 2.42 (m, 1H), 2.81 (t, J=10.5 Hz, 2H), 3.00 (m, 2H), 3.15 (m, 2H), 3.40 (m, 1H), 3.51 (m, 2H), 3.67 (m, 2H), 4.50 (m, 2H), 6.73 (d, J=8.8 Hz, 1H), 6.89 (d, J=7.8 Hz, 1H), 7.11 (m, 2H), 7.28 (d, J=15.2 Hz, 1H), 7.36 (m, 1H), 7.80(d, J=15.2Hz, 1H), 7.86(d, J=8.5 Hz); MS (APCI$^+$) m/z 548, 550 (M+H)$^+$. Anal. calcd for C$_{27}$H$_{31}$N$_3$Cl$_2$SO$_3$ 2.2 TFA: C, 47.18; H, 4.19; N, 5.26. Found: C, 47.27; H, 4.27; N, 5.30.

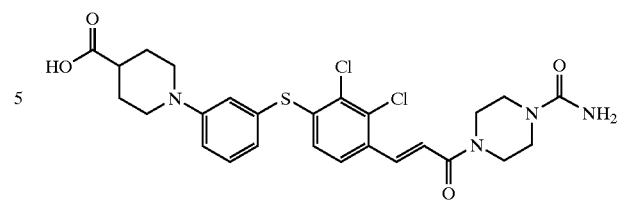

Example 420

[3-(4-Carboxypiperidin-1-yl)phenyl][2,3-dichloro-4-(E-((4-(aminocarbonyl)piperidin-1-yl)carbonyl)ethenyl)phenyl]sulfide The title compound was prepared by the procedures described in Example 412 substituting 4-hydroxypiperidine with isonipecotamide. $^1$H NMR (300 MHz, DMSO-d$_6$) δ 1.45 (m, 2H), 1.63 (m, 2H), 1.73 (m, 2H), 1.87 (m, 2H), 2.43 (m, 2H), 2.78) m, 2H), 3.10 (m, 2H), 3.7 (m, 3H), 4.30 (m, 1H), 4.40 (m, 1H), 6.70 (d, J=8.5 Hz, 1H), 6.78 (s, 1H), 6.92 (d, J=7.5 Hz, 1H), 7.12 (m, 2H), 7.25 (d, J=15.2 Hz, 1H), 7.27 (s, 1H), 7.35 (m, 1H), 7.73 (d, J=15.2 Hz, 1H), 7.86 (d, j=8.6 Hz, 1H); MS (APCI$^+$) m/z 562 (M+H)$^+$. Anal. calcd for C$_{27}$H$_{29}$N$_3$Cl$_2$SO$_4$ 0.2 TFA: C, 56.23; H, 5.03; N, 7.18. Found: C, 56.41; H, 4.96; N, 6.98.

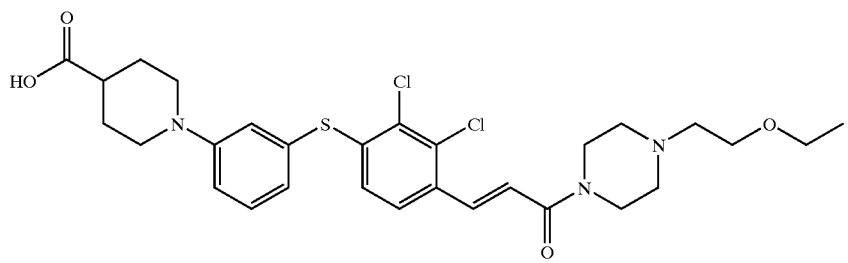

Example 421

[3-(4-Carboxypiperidin-1-yl)phenyl][2,3-dichloro-4-(E-((4-(2-(ethoxyethyl)piperidin-1-yl)carbonyl)ethenyl)phenyl]sulfide The title compound was prepared by the procedures described in Example 412 substituting 4-hydroxypiperidine with 1-(2-ethoxyethyl)piperazine. $^1$H NMR (300 MHz, DMSO-d$_6$) δ 1.15 (t, J=6.8 Hz, 3H), 1.63 (m, 2H), 1.90 (m, 2H), 2.42 (m, 1H), 2.81 (t, J=10.2 Hz, 2H), 3.09(m, 2H), 3.32 (m, 2H), 3.50 (q, J=6.8 Hz, 2H), 3.51 (m, 2H), 3.68 (m, 4H), 4.45 (m, 2H), 6.73 (d, J=8.6 Hz, 1H), 6.91 (d, J=7.5 Hz, 1H), 7.11 (m, 2H), 7.26 (d, J=15.3 Hz, 1H), 7.36 (m, 1H), 7.80 (d, J=15.2 Hz, 1H), 7.83 (d, J=8.5 Hz, 1H); MS (APCI$^+$) m/z 592 (M+H)$^+$. Anal. calcd for C$_{29}$H$_{35}$N$_3$Cl$_2$SO$_4$ 2.5 TFA: C, 46.53; H, 4.31; N, 4.79. Found: C, 46.51; H, 4.31; N, 4,77.

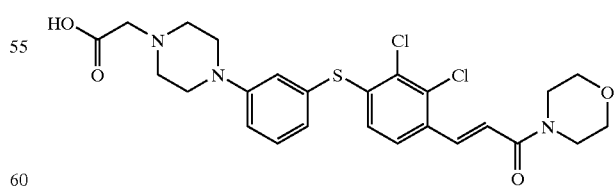

Example 422

[3-((4-Carboxymethyl)piperazin-1-yl)phenyl][(2,3-dichloro-4(E-(4-morpholinyl)carbonyl)ethenyl)phenyl]sulfide The title compound (24 mg, 42%) was prepared from Example 393A as described in Example 384D, substituting morpholine with 1-((ethoxycarbonyl)methyl)piperazine, followed by hydrolysis with LiOH as described in Example 340H. $^1$H NMR (300 MHz, MeOH-$d_4$) δ 3.54 (s, 8H), 3.69 (s, 8H), 4.11 (s, 2H), 6.77 (d, J=8.5 Hz, 1H), 7.06 (d, J=15 Hz, 1H), 7.08 (m, 1H), 7.42 (t, J=7.5 Hz, 1H), 7.59 (d, J=8.25 Hz, 1H), 7.93 (d, J=15 Hz, 1H); MS (ESI) m/e 536, 538 (M+H)$^+$.

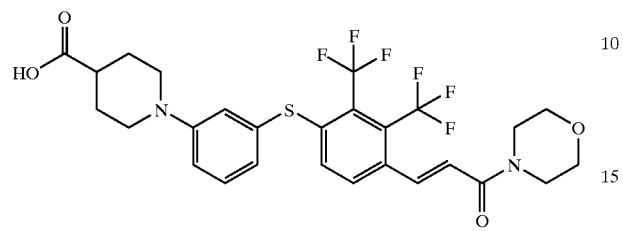

Example 423

[3-(4-Carboxypiperidin-1-yl)phenyl][2,3-bis(trifluoromethyl)4-(E-((4-morpholino)carbonyl)ethenyl)phenyl]sulfide

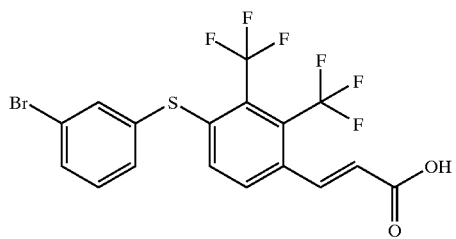

Example 423A

[3-Bromophenyl][2,3-bis(trifluoromethyl)-4-(E-(2-carboxy)ethenyl)phenyl]sulfide

The title compound was prepared from Example 401C using the procedures described in Example 384A, followed by hydrolysis with LiOH as given in Example 340H.

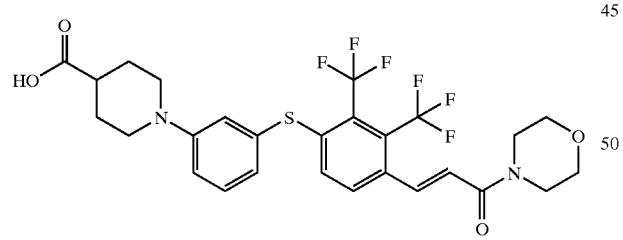

[3-(4-Carboxypiperidin-1-yl)phenyl][2,3-bis(trifluoromethyl)-4-(E-((4-morpholino)carbonyl)ethenyl)phenyl]sulfide The title compound was prepared from Example 423A as described in Example 340G, substituting methy isonipecotate with morpholine, followed by amination with ethyl isonipecotate as described in Example 396, and subsequent hydrolysis according to the procedure of Example 340H. $^1$H NMR (400 MHz, DMSO-$d_6$) δ 1.5–1.64 (m, 2H), 1.67–1.75 (m, 1H), 1.87–1.96 (m, 1H), 2.49–2.57 (m, 2H), 2.82–2.91 (m, 1H), 2.99–3.06 (m, 1H), 3.46–3.54 (m, 2H), 3.54–3.62 (m, 5H), 3.63–3.72 (m, 3H), 6.87 (d, J=8 Hz, 1H), 7.06–7.13 (m, 2H), 7.16 (d, J=15 Hz, 1H), 7.25–7.36 (m, 2H), 7.66 (dd, J$_1$=15 Hz, J$_2$=4 Hz, 1H), 8.00 (d, J=8 Hz, 1H); MS (ESI) m/e 589 (M+H)$^+$.

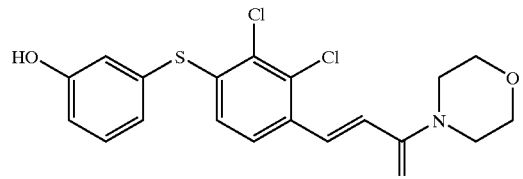

Example 424

(3-Hydroxyphenyl)[2,3-dichloro-4-(E-((4-morpholino)carbonyl)ethenyl)phenyl]sulfide Example 310B was processed as described in Examples 310 and 405, substituting 3-methoxythiophenol for the thiol. $^1$H NMR (DMSO-$d_6$, 300 MHz) δ 9.88 (s, 1H), 7.86 (d, J=8.8, 1H), 7.77 (d, J=14.9 Hz, 1H), 7.33 (dt, J=7.4 Hz, J=1.0 Hz, 1H), 7.24 (d, J=14.8 Hz, 1H), 6.96 (dd, J=8.8 Hz, J=1.0 Hz, 1H), 6.90 (dd, J=8.8 Hz, J=1.0 Hz, 1H), 6.89 (s, 1H), 6.79 (d, J=8.5 Hz, 1H), 3.67 (s, 2H), 3.58 (s, 6H); MS (APCI) m/z 410 (M+H)$^+$, 427 (M+NH$_4$)$^+$; 408 (M–H)$^-$, 446 (M+Cl)$^-$. Anal. calcd for C$_{19}$H$_{17}$Cl$_2$NO$_3$S.0.25H$_2$O: C, 55.01; H, 4.25; N, 3.38. Found: C, 55.15; H, 4.25; N, 3.51.

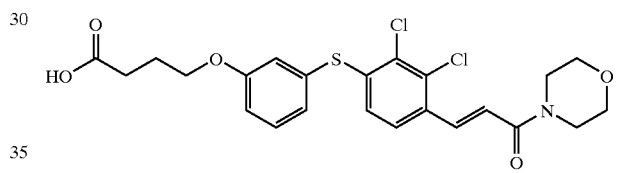

Example 425

[3-(4-Butyroxy)phenyl][2,3-dichloro-4-(E-((4-molpholino)carbonyl)ethenyl)phenyl]sulfide Example 424 was processed as described in Example 414 to provide the title compound as a white solid. $^1$H NMR (DMSO-$d_6$, 300 MHz) δ 7.86 (d, J=8.8 Hz, 1H), 7.77 (d, J=15.3 Hz, 1H), 7.43 (dt, J=7.5 Hz, J=1.7 Hz, 1H), 7.24 (d, J=15.2 Hz, 1H), 7.11 (s, 1H), 6.79 (d, J=8.4 Hz, 1H), 6.73 (d, J=8.5 Hz, 1H), 4.02 (t, J=6.5 Hz, 2H), 3.67 (s, 2H), 3.58 (s, 6H), 2.37 (t, J=7.5 Hz, 2H), 1.95 (m, 2H); MS (APCI) m/z 410 (M+H$^+$), 494 (M–H)$^-$, 530 (M+Cl)$^-$.

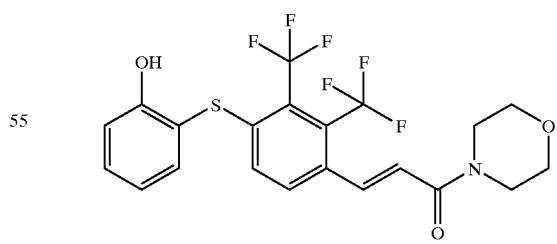

Example 426

(2-Hydroxyphenyl)[2,3-bis(trifluoromethyl)-4-(E-((4-morpholino)carbonyl)ethenyl)phenyl]sulfide Example 401D was processed as described in Example 405 to provide the title compound as a white solid. $^1$H NMR (DMSO-d$_6$, 300 MHz) δ 10.26 (s, 1H), 7.96 (d, J=8.5, 1H), 7.67 (m, 1H), 7.46 (dd, J=7.4 Hz, J=1.3 Hz, 1H), 7.38 (dt, J=7.5 Hz, J=1.3 Hz, 1H), 7.16 (d, J=15.2 Hz 1H), 7.13 (d, J=8.5 Hz, 1H), 7.00 (d, J=8.2 Hz, 1H), 6.90 (t, J=7.4 Hz, 2H), 3.65 (s, 2H), 3.57 (s, 6H). MS (APCI) m/z 478 (M+H)$^+$, 495 (M+NH$_4$)$^+$; 476 (M−H)$^−$, 512 (M+Cl)$^−$.

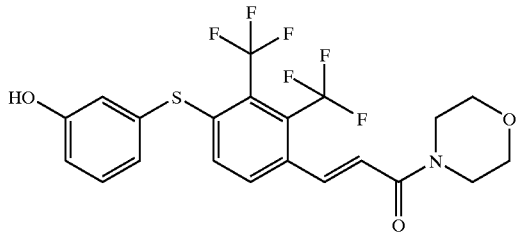

Example 427

(3-Hydroxyphenyl)[2,3-bis(trifluoromethyl)-4-(E-((4-morpholino)carbonyl)ethenyl)phenyl]sulfide Example 401C was processed as described in Example 401D, substituting 3-methoxythiophenol for the thiol, and in Example 405 to provide the title compound as a white solid. $^1$H NMR (DMSO-d$_6$, 300 MHz) δ 9.86 (s, 1H), 8.02 (d, J=8.8, 1H), 7.67 (m, 1H), 7.35 (d, J=9.5 Hz, 1H), 7.30 (dt, J=7.8 Hz, J=0.7 Hz, 1H), 7.19 (d, J=15.2 Hz 1H), 6.95 (d, J=8.8 Hz, 1H), 6.88 (d, J=7.5 Hz, 1H), 6.85 (s, 1H), 3.67 (s, 2H), 3.58 (s, 6H). MS (APCI) m/z 478 (M+H$^+$), 495 (M+NH4$^+$), 476 (M−H$^+$), 512 (M+Cl$^−$).

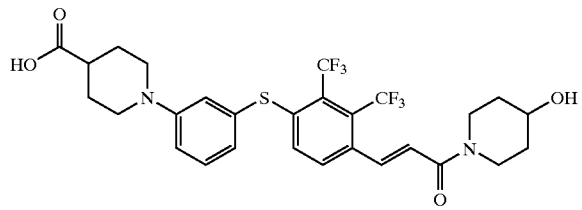

Example 428

[3-(4-Carboxypiperidin-1-yl)phenyl][2,3-bis(trifluoromethyl)-4-(E-((4-hydroxypiperidin-1-yl)carbonyl)ethenyl)phenyl]sulfide The title compound was prepared by the procedures described in Example 412 substituting Example 384B with Example 423A. $^1$H NMR (300 MHz, DMSO-d$_6$) δ 1.31 (m, 2H), 1.63 (m, 2H), 1.71 (m, 2H), 1.91 (m, 2H), 2.42 (m, 1H), 2.82 (t, J=10.5 Hz, 2H), 3.16 (m, 1H), 3.31 (m, 1H), 3.70 (m, 3H), 3.93 (m, 2H), 6.88 (d, J=7.1 Hz, 1H), 7.10 (d, J=8.5 Hz, 1H), 7.14 (t, J=7.1 Hz, 1H), 7.23 (d, J=8.8 Hz, 1H), 7.28 (d, J=8.2 Hz, 1H), 7.34 (d, J=8.2 Hz, 1H), 7.60 (dq, J=15.2, 4.5 Hz, 1H), 8.01 (d, J=8.8 Hz, 1H); MS (APCI$^+$) m/z 603 (M+H)$^+$. Anal. calcd for C$_{28}$H$_{28}$F$_6$N$_2$O$_4$S 1.15 TFA: C, 49.60; H, 4.00; N, 3.82. Found: C, 49.65; H, 3.80; N, 3.81.

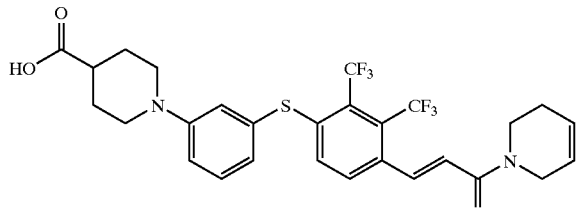

Example 429

[3-(4-Carboxypiperidin-1-yl)phenyl][2,3-bis(trifluoromethyl)-4-(E-((1,2,5,6-tetrahydropyridin-1-yl)carbonyl)ethenyl)phenyl]sulfide The title compound was prepared by the procedures described in Example 412 substituting Example 384B with Example 423A, and substituting 4-hydroxypiperidine with 1,2,5,6-tetrahydropyridine. $^1$H NMR (300 MHz, DMSO-d$_6$) δ 1.63 (m, 2H), 1.90 (m, 2H), 2.12 (m, 2H), 2.43 (m, 1H), 2.81 (t, J=10.5 Hz, 2H), 3.75 (m, 4H), 4.01 ((s, 1H), 4.15 (s, 1H), 5.73 (m, 1H), 5.84 (m, 1H), 6.87 (d, J=7.5 Hz, 1H), 7.10 (m, 2H), 7.30 (m, 3H), 7.62 (m, 1H), 8.01 (t, J=6.5 Hz, 1H); MS (APCI$^+$) m/z 585 (M+H)$^+$. Anal. calcd for C$_{28}$H$_{26}$F$_6$N$_2$O$_3$S 0.1 TFA: C, 56.83; H, 4.41; N, 4.70. Found: C, 56.91; H, 4.44; N, 4.60.

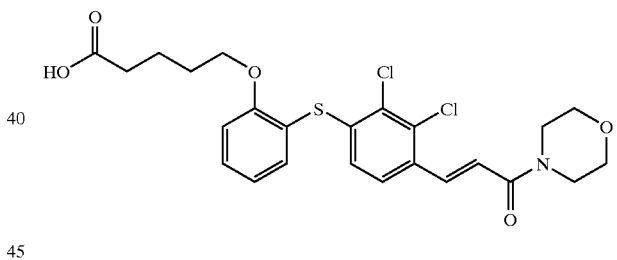

Example 430

[2-((4-Carboxy)butyloxy)phenyl][2,3-dichloro-4-(E-((4-morpholino)carbonyl)ethenyl)phenyl]sulfide Example 405 was processed as described in Example 414, substituting ethyl 5-bromovalerate for the alkyl halide. $^1$H NMR (DMSO-d$_6$, 300 MHz) δ 7.79 (d, J=8.5, 1H), 7.77 (d, J=15.3 Hz, 1H), 7.51 (dt, J=8.2 Hz, J=1.7 Hz, 1H), 7.48 (dd, J=7.5 Hz, J=1.7 Hz, 1H), 7.20 (dd, J=7.5 Hz, J=1.7 Hz, 1H), 7.20 (d, J=15.6 Hz, 1H), 7.05 (dt, J=7.5 Hz, J=1.0 Hz, 1H), 6.63 (d, J=8.5 Hz, 1H), 3.99 (t, J=6.1 Hz, 2H), 3.65 (s, 2H), 3.58 (s, 6H), 2.10 (t, J=7.1 Hz, 2H), 1.56 (m, 2H), 1.39 (m, 2H). MS (APCI) m/z 510 (M+H)$^+$. Anal. calcd for C$_{24}$H$_{25}$Cl$_2$NO$_5$S.0.75 H$_2$O: C, 55.02; H, 5.10; N, 2.67. Found: C, 54.72; H, 4.82; N, 2.77.

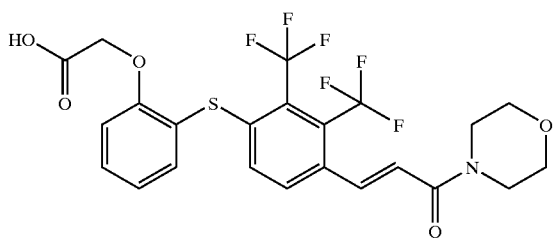

Example 431

(2-Glycoxyphenyl)[2,3-bis(trifluoromethyl)-4-(E-((4-morpholino)carbonyl)ethenyl)phenyl]sulfide Example 426 was processed as detailed in Example 414, substituting ethyl bromoacetate for the alkyl bromide. $^1$H NMR (DMSO-$d_6$, 300 MHz) δ 7.94 (d, J=8.4, 1H), 7.66 (m, 1H), 7.50 (m, 1H), 7.47 (d, J=7.4 Hz, 1H), 7.28 (d, J=8.5 Hz, 1H), 7.16 (d, J=14.9 Hz, 1H), 7.07 (m, 2H), 4.74 (s, 2H), 3.65 (s, 2H), 3.57 (s, 6H); MS (APCI) m/z 536 (M+H)$^+$, 553 (M+NH$_4$)$^+$; 534 (M−H)$^+$. Anal. calcd for $C_{23}H_{19}F_6NO_5S$: C, 51.59; H, 3.58; N, 2.62. Found: C, 51.31; H, 3.63; N, 2.33.

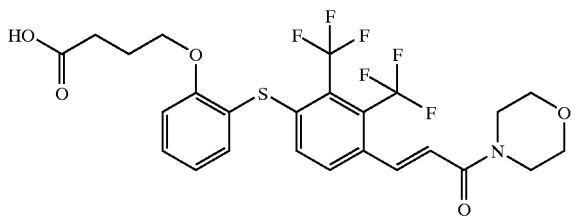

Example 432

(2-(4-Butyroxy)phenyl)[2,3-bis(trifluoromethyl)-4-(E-((4-morpholino)carbonyl)ethenyl)phenyl]sulfide Example 426 was processed as described in Example 414 to provide the title compound as a white solid. $^1$H NMR (DMSO-$d_6$, 300 MHz) δ 7.92 (d, J=8.5, 1H), 7.65 (m, 1H), 7.59 (d, J=7.8 Hz, J=1.7 Hz, 1H), 7.50 (t, J=8.2 Hz, 1H), 7.15 (d, J=8.2 Hz, 1H), 7.12 (d, J=15.6 Hz, 1H), 7.09 (d, J=8.8 Hz, 1H), 7.07 (t, J=7.2 Hz, 1H), 3.92 (t, J=6.1 Hz, 2H), 3.65 (s, 2H), 3.57 (s, 6H), 1.99 (t, J=7.1 Hz, 2H), 1.63 (m, 2H); MS (APCI) m/z 562 (M−H)$^−$, 598 (M+Cl)$^−$.

Example 433

[3-(4-Carboxypiperidin-1-yl)phenyl][2,3-ditrifluoromethyl)-4-(E-((bis-(2-ethoxyethyl)amino)carbonyl)ethenyl)phenyl]sulfide The title compound was prepared by the procedures described in Example 412 substituting Example 384B with Example 423A, and substituting 4-hydroxypiperidine with bis(2-ethoxyethyl)amine. $^1$H NMR (300 MHz, DMSO-$d_6$) δ 0.99 (t, J=6.8 Hz, 3H), 1.09 (t, J=6.8 Hz, 3H), 1.63 (m, 2H), 1.90 (m, 2H), 2.44 (m, 1H), 2.82 (t, J=10.8 Hz, 2H), 3.40 (m, 4H), 3.50 (m, 6H), 3.68 (m, 4H), 6.88 (d, J=7.5 Hz, 1H), 7.11 (m, 3H), 7.32 (m, 2H), 7.62 (dq, J=15.2, 4.5 Hz, 1H), 7.94 (d, J=8.5 Hz, 1H); MS (APCI$^+$) m/z 663 (M+H)$^+$. Anal. calcd for $C_{31}H_{36}F_6N_2O_5S$ 0.7 TFA: C, 52.41; H, 4.98; N, 3.77. Found: C, 52.38; H, 4.94; N, 3.68.

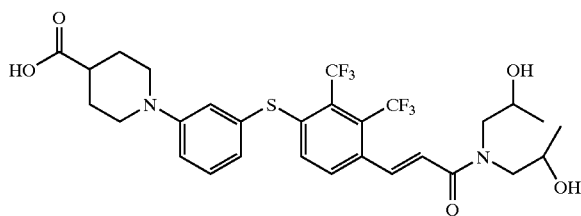

Example 434

[3-(4-Carboxypiperidin-1-yl)phenyl][2,3-bis-(trifluoromethyl)-4-(E-((bis-(2-hydroxypropyl)amino)carbonyl)ethenyl)phenyl]sulfide The title compound was prepared by the procedures described in Example 412 substituting Example 384B with Example 423A, and substituting 4-hydroxypiperidine with diisopropanolamine. $^1$H NMR (300 MHz, DMSO-$d_6$) δ 1.04 (m, 6H), 1.63 (m, 2H), 1.90 (m, 2H), 2.42 (m, 1H), 2.83 (t, J=10.5 Hz, 2H), 3.04 (m, 1H), 3.26 (m, 1H), 3.45 (m, 2H), 3.67 (m, 2H), 3.75 (m, 1H), 3.90 (m, 1H), 6.90 (d, J=7.5 Hz, 1H), 7.11 (m, 3H), 7.28 (d, J=8.5 Hz, 1H), 7.33 (t, J=8.2 Hz, 1H), 7.63 (m, 1H), 7.95 (dd, J=8.5, 2.1 Hz, 1H); MS (APCI$^+$) m/z 635 (M+H)$^+$. Anal. calcd for $C_{29}H_{32}F_6N_2O_5S$ 1.5 TFA: C, 47.71; H, 4.19; N, 3.48. Found: C, 47.52; H, 4.28; N, 3.40.

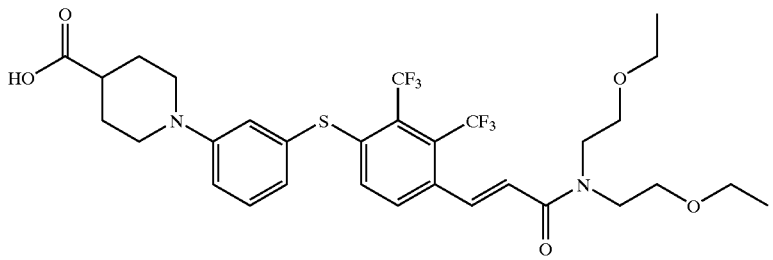

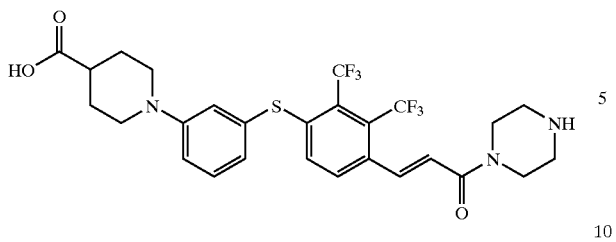

Example 435

[3-(4-Carboxypiperidin-1-yl)phenyl][2,3-bis-(trifluoromethyl)4-(E-((piperazin-1-yl)carbonyl)ethenyl)phenyl]sulfide The title compound was prepared by the procedures described in Example 412 substituting Example 384B with Example 423A, and substituting 4-hydroxypiperidine with 1-(1,2,3,4-tetrahydrofuroyl)piperazine. $^1$H NMR (300 MHz, DMSO-d$_6$) δ 1.62 (m, 2H), 1.88 (m, 2H), 2.43 (m, 1H), 2.82 (t, J=10.5 Hz, 2H), 3.15 (br s, 4H), 3.71 (m, 2H), 3.75 (m, 2H), 3.86 (m, 2H), 6.87 (d, J=7.5 Hz, 1H), 7.10 (d, J=8.5 Hz, 1H), 7.12 (d, J=7.5 Hz, 1H), 7.20 (d, J=15.2 Hz, 1H), 7.28 (d, J=8.5 Hz, 1H), 7.35 (d, J=7.8 Hz, 1H), 7.70 (dt, J=15.2, 4.5 Hz, 1H), 7.98 (d, J=8.5 Hz, 1H), 8.85 (br s, 1H); MS (APCI$^+$) m/z 588 (M+H)$^+$. Anal. calcd for C$_{27}$H$_{27}$F$_6$N$_3$O$_3$S 3.3 TFA: C, 41.87; H, 3.17; N, 4.36. Found: C, 41.78; H, 3.26; N, 4.43.

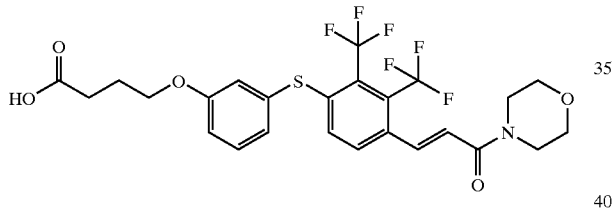

Example 436

(3-(4-Butyroxy)phenyl)[2,3-bis(trifluoromethyl)-4-(E-((4-morpholino)carbonyl)ethenyl)phenyl]sulfide Example 427 was processed as described in Example 414 to provide the title compound as a white solid. $^1$H NMR (DMSO-d$_6$, 300 MHz) δ 8.02 (d, J=8.5, 1H), 7.65 (m, 1H), 7.40 (t, J=7.8 Hz, 1H), 7.33 (d, J=8.8 Hz, 1H), 7.19 (d, J=14.9 Hz, 1H), 7.09 (m, 3H), 4.02 (t, J=6.4 Hz, 2H), 3.67 (s, 2H), 3.58 (s, 6H), 2.37 (t, J=7.1 Hz, 2H), 1.95 (m, 2H); MS (APCI) m/z 564 (M+H)$^+$; 562 (M−H)$^−$, 598 (M+Cl)$^−$.

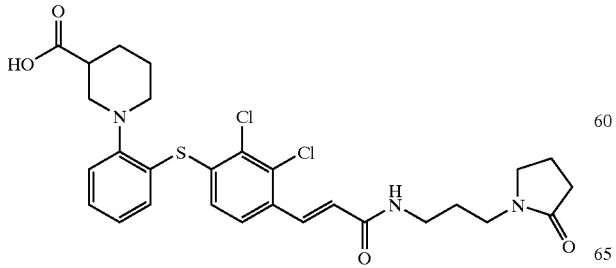

Example 437

[2-(3-Carboxypiperidin-1-yl)phenyl][2,3-dichloro-4-(E-[(3-(2-oxopyrrolidin-1-yl)propylaminocarbonyl)ethenyl)phenyl]sulfide

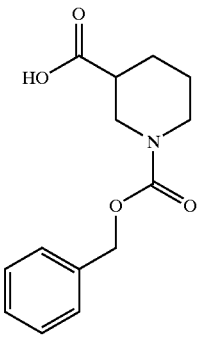

Example 437A

N-Benzyloxycarbonyl nipecotic acid

To a solution of nipecotic acid 10 g, 63.6 mmol) in 1 N NaOH (2.5 g in 64 mL water, 63.6 mmol) at 0° C. was alternately added benzyloxycarbonyl chloride (10.9 mL, 76.5 mmol) in diethyl ether (50 mL) and 1 N NaOH (5 g in 128 mL water, 127.2 mmol) in five portions. The reaction mixture was stirred at 0° C. for 2 hours, and at ambient temperature for 24 hours. Then this was made acidic with 10% HCl and the solid formed was filtered and dried (vacuum oven, 45° C.) to obtain the title compound (18.9 g, 113%). MS (ESI) m/e 264 (M+H)$^+$.

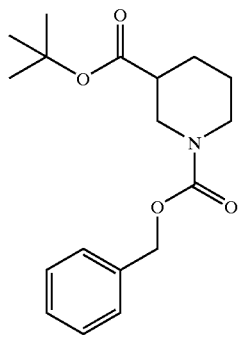

Example 437B tert-Butyl N-benzyoxycarbonyl nipecotate

A solution of Example A (18 g, 62 mmol) in THF (250 mL, 0.25 M) was treated with trichloroacetimidate (28 mL, 15.5 mmol) and BF$_3$.Et$_2$O (18 mL, 1 mL/g) at ambient temperature. After 18 hours the reaction mixture was quenched with solid NaHCO$_3$ followed by water and stirred vigorously. Then the solvent was removed, and partitioned with ethyl acetate (250 mL). The organic layer was separated and washed with brine (3×80 mL), dried (Na$_2$SO$_4$) and evaporated to dryness under reduced pressure to obtain the crude product. The title compound (19.2 g, 96%) was obtained by flash chromatography on silica gel eluting with 20% acetone:hexane. MS (ESI) m/e 320 (M+H)$^+$.

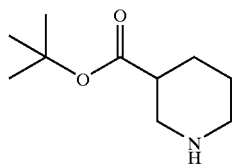

Example 437C tert-Butyl nipecotate

Example 437B (19 g, 59.5 mmol) was treated with 10% Pd on carbon (2 g, 10 wt %) in ethanol (237 mL, 0.25 M) to obtain the title compound (10.4 g, 94%).

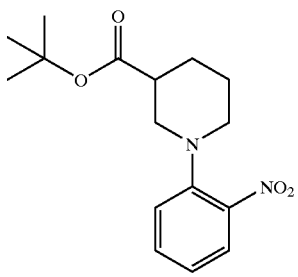

Example 437D

2-Nitro-(3-(tert-butyloxycarbonyl)piperidin-1-yl) benzene

To a solution of Example 437C (10.4 g, 56.1 mmol) in toluene (112 mL) was added 2-fluoronitrobenzene (6.0 ml, 56 mmol) and CsF (852 mg, 5.6 mmol). The reaction mixture was stirred under reflux conditions for 18 hours, and allowed to cool to ambient temperature. The mixture was diluted with ethyl acetate (100 ml), washed with 10% HCl (2×50 ml), followed by brine (3×100 ml), then dried (Na$_2$SO$_4$) and evaporated in vacuo to obtain the title compound (16.5 g, 94%). MS (ESI) m/e 367 (M+H)$^+$.

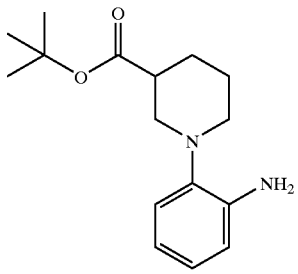

Example 437E

2-Amino-(3-(tert-butyloxycarbonyl)piperidin-1-yl) benzene

Example 437E (16.4 g, 53.5 mmol) was treated with 10% Pd on carbon (1.65 g, 10 wt %) in ethanol (215 ml, 0.5 M) at ambient temperature for 2 hours. The reaction mixture was filtered through celite and the filtrate was evaporated to dryness under reduced pressure to obtain the title compound (13.45 g, 91%). MS (ESI) m/e 277 (M+H)$^+$.

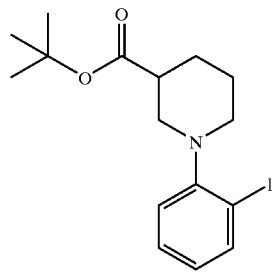

Example 437F

2-Iodo-(3-(tert-butyloxycarbonyl)piperidin-1-yl) benzene

Example 437E was dissolved in 3 N H$_2$SO$_4$ (195 mL, 0.25 M), cooled to 0° C. and treated with NaNO$_2$ (3.35 g, 48.6 mmol) in water (20 mL). After 30 minutes at 0° C. potassium iodide (12.01 g, 72.8 mmol) and urea (583 mg, 9.7 mmol) in water (10 mL) were added and stirred for 1 hour. The reaction mixture was quenched with 10% NaHCO$_3$ (50 mL) and partitioned with ethyl acetate (450 mL). The organic layer was separated and washed with 10% NaHCO$_3$ (2×100 mL), brine (2×100 mL), dried (Na$_2$SO$_4$) and evaporated to dryness under reduced pressure. The title compound (17.2 g, 91%) was obtained by flash chromatography on silica gel eluting with 10% acetone:hexane. 1H NMR (400 MHz, DMSO-d$_6$) δ 1.39 (s, 9H), 6.85 (tt, J$_1$=1.5 Hz, J$_2$=7.5 Hz, 1H), 7.14 (dd, J$_1$=1.5 Hz, J$_2$=7.5 Hz, 1H), 7.37 (tt, J$_1$=1.5 Hz, J$_2$=7.5 Hz, 1H), 7.84 (dd, J$_1$=1.5 Hz, J$_2$=7.5 Hz, 1H); MS (ESI) m/e 388 (M+H)$^+$.

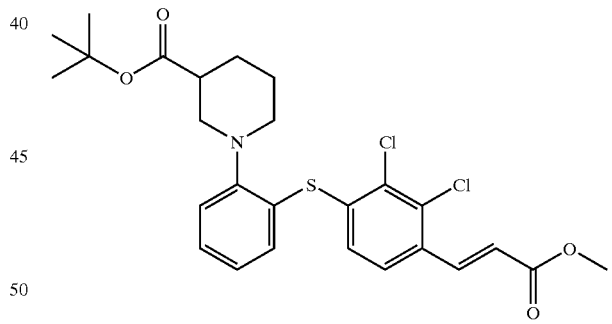

Example 437G

[2-(3-tert-Butyloxycarbonyl)piperidin-1-yl)phenyl] [2,3-dichloro-4-(E-(2-methoxycarbonyl)ethenyl) phenyl]sulfide Example 437F was converted to the corresponding triisopropylsilyl thiol analogue by the method described for the preparation of Example 340B. Then this intermediate was reacted with Example 340E (2.94 g, 7.75 mmol) at −20° C. as described in Example 340F to obtain the title compound (2.5 g, 63%). MS (ESI) m/e 522, 524 (M+H)$^+$.

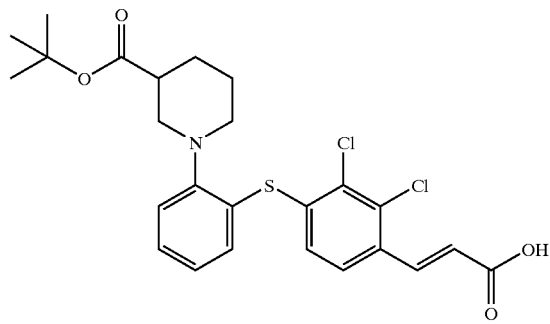

Example 437H

[2-(3-tert-Butyloxycarbonyl)piperidin-1-yl)phenyl]
[2,3-dichloro-4-(E-(2-carboxy)ethenyl)phenyl]
sulfide Using the procedure for Example 340H, Example 437H was hydrolyzed to the title compound. MS (ESI) m/e 508, 510 (M+H)⁺.

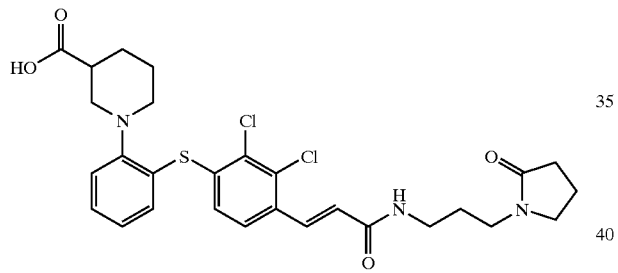

Example 437I

[2-(3-Carboxypiperidin-1-yl)phenyl][2,3-dichloro-4-(E-[(3-(2-oxopyrrolidin-1-yl)propylaminocarbonyl)ethenyl)phenyl]sulfide The title compound (66 mg) was prepared from Example 437H (90 mg, 0.177 mmol), using the procedures described in Example 340G substituting methyl isonipecotate with 3-aminopropyl-2-pyrrolidinone followed by treatment with 20% TFA in methylene chloride as described in Example 412C. ¹H NMR (500 MHz, DMSO-$d_6$) δ 1.27–2.43 (m, 2H), 2.60–2.72 (m, 3H), 2.84 (m, 3H), 2.17–2.30 (m, 3H), 2.62–2.73 (m, 2H), 3.08–3.23 (m, 5H), 3.29–3.38 (m, 3H), 6.62 (d, J=15 Hz, 1H), 6.92 (d, J=8.5 Hz, 1H), 7.12 (t, J=7.5 Hz, 1H), 7.41 (m, 1H), 7.58 (d, J=8.75 Hz, 1H), 7.70 (d, J=15 Hz, 1H), 8.21 (t, J=5 Hz, 1H); MS (ESI) m/e 576, 578 (M+H)⁺.

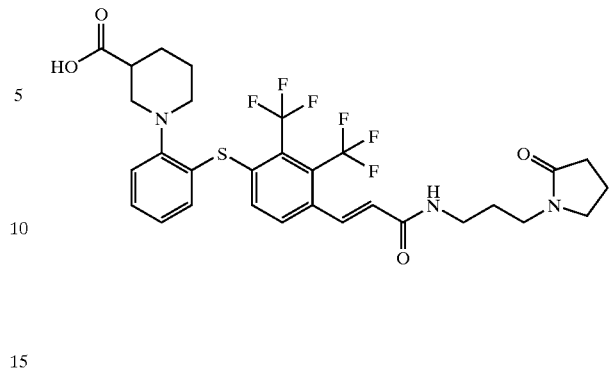

Example 438

[2-(3-Carboxypiperidin-1-yl)phenyl][2,3-bis(trifluoromethyl)-4-(E-[(3-(2-oxoprrolidin-1-yl)propylamino)carbonyl)ethenyl)phenyl]sulfide

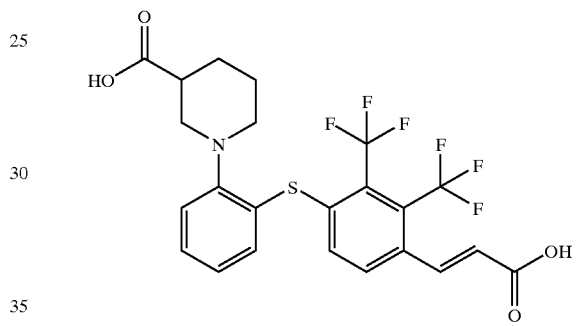

Example 438A

[2-(3-tert-Butyloxycarbonyl)piperidin-1-yl)phenyl]
[2,3-bis(trifluoromethyl)-4-(E-(2-carboxy)ethenyl)
phenyl]sulfide The title compound (445 mg, 71%) was prepared from the reaction of Example 401C (500 mg, 1.08 mmol) with Example 437F, using the procedures described in Example 437G followed by hydrolysis as described in Example 340G. MS (ESI) m/e 604 (M+H)⁺.

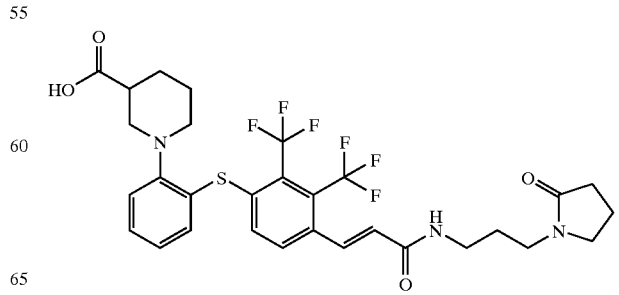

Example 438B

[2-(3-Carboxypiperidin-1-yl)phenyl][2,3-bis
(trifluoromethyl)-4-(E-[(3-(2-oxopyrrolidin-1-yl)
propylaminocarbonyl)ethenyl)phenyl]sulfide The title compound was prepared from Example 438A (110 mg, 0.191 mmol), using the procedures described in Example 340G substituting methyl isonipecotate with 3-aminopropyl-2-pyrrolidinone followed by treatment with 20% TFA in methylene chloride as described in Example 412C. $^1$H NMR (500 MHz, DMSO-d$_6$) δ 1.11–1.21 (m, 1H), 1.28–1.38 (m, 1H), 1.60–1.70 (m, 3H), 1.79–1.86 (m, 1H), 1.87–1.94 (m, 2H), 2.05–2.12 (m, 1H), 2.00 (t, J=7.5 Hz, 2H), 2.58–2.66 (m, 2H), 2.96–3.01 (m, 1H), 3.11–3.18 (m, 2H), 3.19 (t, J=6.25 Hz, 2H), 3.26 (m, 1H), 3.32 (t, J=6.25 Hz, 2H), 6.46 (d, J=15 Hz, 1H), 7.15 (t, J=7.5 Hz, 1H), 7.33 (m, 2H), 7.43 (m, 1H), 7.62 (m, 1H), 7.75 (d, J=7.5 Hz, 1H), 8.22 (t, J=5 Hz, 1H); MS (ESI) m/e 644 (M+H)$^+$.

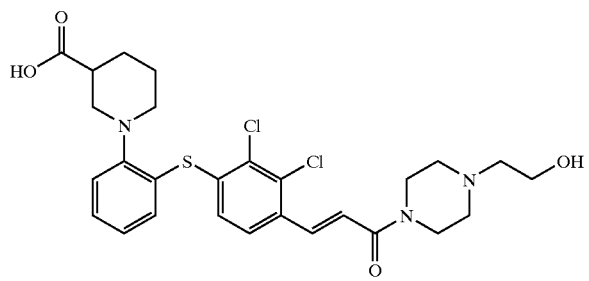

Example 439

[2-(3-Carboxypiperidin-1-yl)phenyl][2,3-dichloro-4-
(E-((4-(2-hydroxyethyl)piperazin-1-yl)carbonyl)
ethenyl)phenyl]sulfide The title compound was prepared from Example 437H (90 mg, 0.177 mmol), using the procedures described in Example 340G substituting methyl isonipecotate with 1-(2-hydroxyethyl)piperazine followed by treatment with 20% TFA in methylene chloride as described in Example 412C. $^1$H NMR (500 MHz, DMSO-d$_6$) δ 1.31–1.45 (m, 2H), 1.67–1.74 (m, 1H), 1.86–1.92 (m, 1H), 2.24–2.31 (m, 1H), 2.66 (t, J=10 Hz, 1H), 2.73 (t, J=10 Hz, 1H), 3.02–3.24 (m, 5H), 3.33–3.38 (m, 1H), 3.52 (m, 3H), 3.75 (t, J=5 Hz, 2H), 4.31–4.60 (m, 3H), 6.90 (d, J=9 Hz, 1H), 7.11 (t, J=7.5 Hz, 1H), 7.21 (d, J=7.5 Hz, 1H), 7.25 (d, J=7.5 Hz, 1H), 7.30 (d, J=15 Hz, 1H), 7.42 (t, J=7.5 Hz, 1H), 7.83 (d, J=15 Hz, 1H), 7.85 (d, 9 Hz, 1H); MS (ESI) m/e 564, 566 (M+H)$^+$.

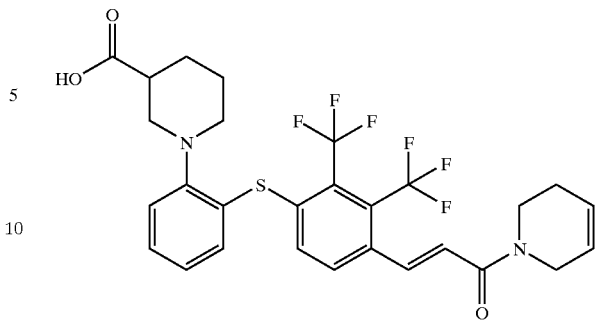

Example 440

[2-(3-Carboxypiperidin-1-yl)phenyl][2,3-bis
(trifluoromethyl)-4-(E-((1,2,5,6-tetrahydropyridin-1-
yl)carbonyl)ethenyl)phenyl]sulfide The title compound was prepared from Example 438A (110 mg, 0.191 mmol), using the procedures described in Example 340G substituting methyl isonipecotate with 1,2,5,6-tetrahydropyridine followed by treatment with 20% TFA in methylene chloride as described in Example 412C. $^1$H NMR (500 MHz, DMSO-d$_6$) δ 1.19–1.27 (m, 1H), 1.30–1.40 (m, 1H), 1.64–1.70 (m, 1H), 1.80–1.86 (m, 1H), 2.04–2.18 (m, 2H), 2.60 (t, J=10 Hz, 1H), 2.68 (t, J=10 Hz, 1H), 3.03 (br d, J=10 Hz, 1H), 3.23 (brd, J=10 Hz, 1H), 3.60–3.74 (m, 2H), 3.91–4.20 (m, 3H), 5.68–5.74 (m, 1H), 5.80–5.90 (m, 1H), 7.06–7.19 (m, 2H), 7.20–7.28 (m, 2H), 7.36 (m, 1H), 7.44 (t, J=7.5 Hz, 1H), 7.62–7.71 (m, 1H), 7.94–8.04 (m, 1H); MS (ESI) m/e 585 (M+H)$^+$.

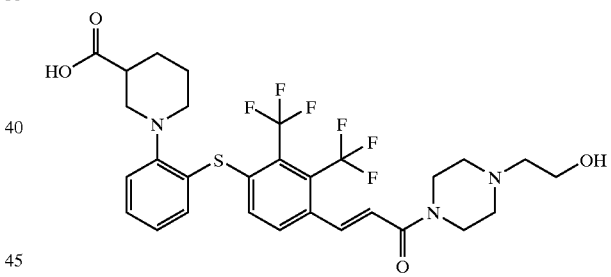

Example 441

[2-(3-Carboxypiperidin-1-yl)phenyl][2,3-bis
(trifluoromethyl)-4-(E-((4-(2-hydroxyethyl)
piperazin-1-yl)carbonyl)ethenyl)phenyl]sulfide The title compound was prepared from Example 438A (110 mg, 0.191 mmol), using the procedures described in Example 340G substituting methyl isonipecotate with 1-(2-hydroxyethyl)piperazine followed by treatment with 20% TFA in methylene chloride as described in Example 412C. $^1$H NMR (500 MHz, DMSO-d$_6$) δ 1.17–1.27 (m, 1H), 1.17–1.27 (m, 1H), 1.31–1.41 (m, 1H), 1.64–1.71 (m, 1H), 1.80–1.88 (m, 1H), 2.07–2.15 (m, 1H), 2.61 (t, J=10 Hz, 1H), 2.09 (t, J=10 Hz, 1H), 2.91–3.13 (m, 3H), 3.18–3.28 (m, 3H), 3.44–3.58 (m, 3H), 3.75 (t, J=5 Hz, 2H), 4.29–4.58 (m, 3H), 7.15 (d, J=7.5 Hz, 1H), 7.19 (d, J=10 Hz, 1H), 7.28 (d, J=7.5 Hz, 2H), 7.37 (d, J=7.5 Hz, 1H), 7.45 (t, J=7.5 Hz, 1H), 7.69–7.77 (m, 1H), 7.98 (d, J=7.5 Hz, 1H), 9.77 (br s, 1H); MS (ESI) m/e 632 (M+H)$^+$.

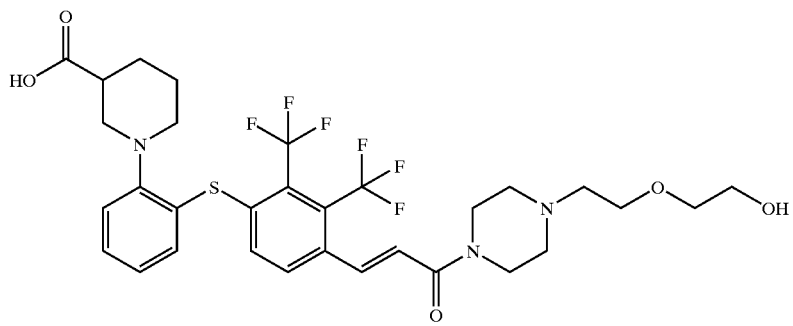

Example 442

[2-(3-Carboxypiperidin-1-yl)phenyl][2,3-bis(trifluoromethyl)-4-(E-((4-(2-(hydroxyethoxy)ethyl)piperazin-1-yl)carbonyl)ethenyl)phenyl]sulfide The title compound was prepared from Example 438A (110 mg, 0.191 mmol), using the procedures described in Example 340G substituting methyl isonipecotate with 1-[2-(2-hydroxyethoxy)ethyl]piperazine followed by treatment with 20% TFA in methylene chloride as described in Example 412C. $^1$H NMR (500 MHz, DMSO-d$_6$) δ 1.17–1.27 (m, 1H), 1.31–1.40 (m, 1H), 1.64–1.70 (m, 1H), 1.80–1.86 (m, 1H), 2.08–2.16 (m, 1H), 2.61 (t, J=10 Hz, 1H), 2.68 (t, J=10 Hz, 1H), 3.03 (br d J=10 Hz, 1H), 3.06–3.18 (m, 2H), 3.25 (br d, J=10 Hz, 1H), 3.33 (m, 2H), 3.42–3.51 (m, 2H), 3.53–3.60 (m, 2H), 3.70–3.80 (m, 5H), 4.32–4.56 (m, 3H), 7.13–7.21 (m, 2H), 7.27 (d, J=9 Hz, 2H), 7.35 (d, J=7.5 Hz, 1H), 7.44 (t, J=7.5 Hz, 1H), 7.68–7.77 (m, 1H), 7.44–8.01 (m, 1H), 9.81 (br s, 1H); MS (ESI) m/e 676 (M+H)$^+$.

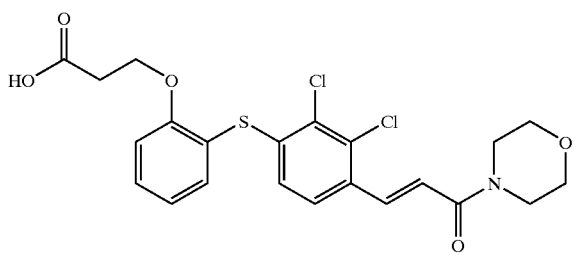

Example 443

(3-(3-Propioxy)phenyl)[2,3-dichloro-4-(E-((4-morpholino)carbonyl)ethenyl)phenyl]sulfide β-Propiolactone (50 μL, 0.75 mmol) was added to a mixture of Example 405 (308 mg, 0.75 mmol), potassium tert-butoxide (750 mL, 1M in THF), and THF (1.0 mL). After 18 hours, the reaction was diluted with EtOAc, washed with 1M aqueous HCl, washed with brine, dried (MgSO$_4$), filtered, and concentrated. Purification by preparative HPLC provided the title compound (72 mg, 20%) as a white solid. $^1$H NMR (DMSO-d$_6$, 300 MHz) δ 7.80 (d, J=8.4 Hz, 1H), 7.78 (d, J=15.8 Hz, 1H), 7.52 (dt, J=8.8 Hz, J=1.7 Hz, 1H), 7.46 (dd, J=7.8 Hz, J=17 Hz, 1H), 7.23 (d, J=9.1 Hz, 1H), 7.22 (d, J=15.3 Hz, 1H), 7.08 (t, J=7.4 Hz, 1H), 6.58 (d, J=8.5 Hz, 1H), 4.22 (m, 2H), 4.05 (m, 2H), 3.66 (s, 2H), 3.58 (s, 6H); MS (APCI) m/z 482 (M+H)$^+$; 480 (M−H)$^-$.

Compounds that antagonize the interaction between ICAM-1 and LFA-1 can be identified, and their activities quantitated, using both biochemical and cell-based adhesion assays. A primary biochemical assay measures the ability of the compound in question to block the interaction between the integrin LFA-1 and its adhesion partner ICAM-1, as described below:

ICAM-1/LFA-1 Biochemical Interaction Assay

In the biochemical assay, 100 μL of anti-LFA-1 antibody (ICOS Corporation) at a concentration of 5 μg/mL in Dulbecco's phosphate-buffered saline (D-PBS) is used to coat wells of a 96-well microtiter plate overnight at 4° C. The wells are then washed twice with wash buffer (D-PBS w/o Ca$^{++}$ or Mg$^{++}$, 0.05% Tween 20) and blocked by addition of 200 μL of D-PBS, 5% fish skin gelatin. Recombinant LFA-1 (100 μL of 0.7 μg/mL, ICOS Corporation) in D-PBS is then added to each well. Incubation continues for 1 hour at room temperature and the wells are washed twice with wash buffer. Serial dilutions of compounds being assayed as ICAM-1/LFA-1 antagonists, prepared as 10 mM stock solutions in dimethyl sulfoxide (DMSO), are diluted in D-PBS, 2 mM MgCl$_2$, 1% fish skin gelatin and 50 μL of each dilution added to duplicate wells. This is followed by addition of 50 μL of 0.8 μg/mL biotinylated recombinant ICAM-1/Ig (ICOS Corporation) to the wells and the plates are incubated at room temperature for 1 hour. The wells are then washed twice with wash buffer and 100 μL of Europium-labeled Streptavidin (Wallac Oy) diluted 1:100 in Delfia assay buffer (Wallac Oy) are added to the wells. Incubation proceeds for 1 hour at room temperature. The wells are washed eight times with wash buffer and 100 μL of enhancement solution (Wallac Oy, cat. No. 1244-105) are added to each well. Incubation proceeds for 5 minutes with constant mixing. Time-resolved fluorimetry measurements are made using the Victor 1420 Multilabel Counter (Wallac Oy) and the percent inhibition of each candidate compound is calculated using the following equation:

$$\% \text{inhibition} = 100 \times \left\{ 1 - \frac{\text{average } OD \text{ w/ compound minus background}}{\text{average } OD \text{ w/o compound minus background}} \right\}$$

where "background" refers to wells that are not coated with anti-LFA-1 antibody.

Compounds of the present invention exhibit inhibitory activity in the above assay. % inhibition at 4 μM was demonstrated.

Biologically relevant activity of the compounds in this invention is confirmed using a cell-based adhesion assay, which measures their ability to block the adherence of JY-8 cells (a human EBV-transformed B cell line expressing LFA-1 on its surface) to immobilized ICAM-1, as follows:

ICAM-1/JY-8 Cell Adhesion Assay

For measurement of inhibitory activity in the cell-based adhesion assay, 96-well microtiter plates are coated with 70 μL of recombinant ICAM-1/Ig (ICOS Corporation) at a concentration of 5 μg/mL in D-PBS w/o Ca$^{++}$ or Mg$^{++}$ overnight at 4° C. The wells are then washed twice with D-PBS and blocked by addition of 200 μL of D-PBS, 5% fish skin gelatin by incubation for 1 hour at room temperature. Fluorescent tagged JY-8 cells (a human EBV-transformed B cell line expressing LFA-1 on its surface; 50 μL at 2×10$^6$ cells/mL in RPMI 1640/1% fetal bovine serum) are added to the wells. Microtiter plates are incubated for 45 minutes at room temperature and the wells are washed gently once with RPMI-1640/1% fetal bovine serum. Fluorescent intensity is measured in a fluorescent plate reader with an excitation wavelength at 485 nM and an emission wavelength at 530 nM. The percent inhibition of a candidate compound at a given concentration is calculated using the following equation:

$$\%\text{inhibition} = 100 \times \left\{1 - \frac{\text{average OD w/ compound}}{\text{average OD w/o compound}}\right\}$$

and these concentration/inhibition data are used to generate dose response curves, from which IC$_{50}$ values are derived.

Compounds of the present invention exhibit blocking activity in the above assay. Inhibition at 4 μM was demonstrated.

Compounds of the present invention have been demonstrated to act via interaction with the integrin LFA-1, specifically by binding to the interaction domain (I-domain), which is known to be critical for the adhesion of LFA-1 to a variety of cell adhesion molecules. As such, it is expected that these compounds should block the interaction of LFA-1 with other CAMs. This has in fact been demonstrated for the case of ICAM-3. Compounds of the present invention may be evaluated for their ability to block the adhesion of JY-8 cells (a human EBV-transformed B cell line expressing LFA-1 on its surface) to immobilized ICAM-3, as follows:

ICAM-3/JY-8 Cell Adhesion Assay

For measurement of inhibitory activity in the cell-based adhesion assay, 96-well microtiter plates are coated with 50 μL of recombinant ICAM-3/Ig (ICOS Corporation) at a concentration of 10 μg/mL in D-PBS w/o Ca$^{++}$ or Mg$^{++}$ overnight at 4° C. The wells are then washed twice with D-PBS, blocked by addition of 100 μL of D-PBS, 1% bovine serum albumin (BSA) by incubation for 1 hour at room temperature, and washed once with RPMI-1640/5% heat-inactivated fetal bovine serum (adhesion buffer). Dilutions of compounds to be assayed for ICAM-3/LFA-1 antagonistic activity are prepared in adhesion buffer from 10 mM stock solutions in DMSO and 100 μL are added to duplicate wells. JY-8 cells (a human EBV-transformed B cell line expressing LFA-1 on its surface; 100 μL at 0.75×10$^6$ cells/ml in adhesion buffer) are then added to the wells. Microtiter plates are incubated for 30 minutes at room temperature; the adherent cells are then fixed with 50 μL of 14% glutaraldehyde/D-PBS and incubated for an additional 90 minutes. The wells are washed gently with dH$_2$O; 50 μL of dH$_2$O is added, followed by 50 μL of 1% crystal violet. After 5 minutes the plates are washed 3× with dH$_2$O; 75 μL of dH$_2$O and 225 μL of 95% EtOH are added to each well to extract the crystal violet from the cells. Absorbance is measured at 570 nM in an ELISA plate reader. The percent inhibition of a candidate compound is calculated using the following equation:

$$\%\text{inhibition} = 100 \times \left\{1 - \frac{\text{average OD w/ compound}}{\text{average OD w/o compound}}\right\}$$

Compounds of the present invention exhibit blocking activity in the above assay. 100% inhibition at 0.6 μM was demonstrated.

Additional JY-8 (ICAM/LFA-1) Cell Adhesion Assay Protocol

Reagents
  ICAM-1/Ig, ICOS
  D-PBS, Dulbecco's w/o Ca & Mg
  D-PBS, Dulbecco's w/Ca & Mg
  Blocking Solution: 1% non-fat dried milk in PBS w/o Ca & Mg
  RPMI 1640 media
  RPMI 1640 media with 1% FBS (RPMI-1% FBS)
  RPMI 1640 media with 50% FBS (RPMI-50% FBS)
  1 mM Calcein AM, Molecular Probes, cat. C-1430 or C-3099
  DMSO
  JY-8 cells Procedure
1. Coat plate (70 μL/well) with 5 ug/mL in D-PBS w/Ca & Mg of ICAM-1/Ig. Cover and incubate overnight at 4° C.
2. Make compound and control dilutions using RPMI-1% FBS and RPMI-50% FBS as the diluents.
3. Decant ICAM-1/Ig coated plate(s), and wash 3× with D-PBS w/o Ca & Mg.
4. Block entire plate(s) with 150 μL/well of Blocking solution. Cover and incubate for approximately 1 hour at room temperature.
5. Count the number of viable JY-8 cells using standard methodology. Need approximately 10–15×10E6 cells per 96 mw tray.
6. Wash cells 1× in RPMI 1640 media without serum—centrifuging for 5 minutes at approximately 1400 rpm. Remove supernate and resuspend cell pellet to 5×10E6 cells per mL in RPMI 1640 media without serum.
7. Add 2 μL of 1 nM Calcein AM for every 1 mL of cell suspension. Mix. Incubate for 30–60 minutes at 37 degrees C. in a CO2 incubator (keeping cap of centrifuge tube loose for gas exchange).
8. Add approximately 10 mL of RPMI-1% FBS, aliquot into two equal pools and centrifuge for 5 minutes at 1400 rpm.
9. Remove supernate from each pool and resuspend each cell pellet to 2×10E6 cell per mL with RPMI-1% FBS or RPMI-50% FBS.
10. Decant blocked 96 mw plate(s) and wash 3× with D-PBS w/o Ca & Mg.
11. Add 50 μL/well of each compound dilution or control. Add 50 μL of Calcein labeled JY-8 cells to all wells. Centrifuge plate(s) briefly (2–5 seconds) at 100–150 rpm. Cover and incubate for 30–60 minutes at 37 degrees C.
12. Gently wash wells 1× with approximately 150 μL per well of PBS w/Ca & Mg. Remove all liquid from wells.
13. Read absorbence using reader with an excitation of 485/20 and an emission of 530/25.

14. Calculate % inhibition using the following equation:

$$\%\text{inhibition} = 100 \times \left\{ 1 - \frac{\text{average } OD \text{ w/ compound}}{\text{average } OD \text{ w/o compound}} \right\}$$

The ability of the compounds of this invention to treat arthritis can be demonstrated in a murine collagen-induced arthritis model according to the method of Kakimoto, et al., *Cell Immunol* 142: 326–337, 1992, in a rat collagen-induced arthritis model according to the method of Knoerzer, et al., *Toxicol Pathol* 25:13–19, 1997, in a rat adjuvant arthritis model according to the method of Halloran, et al., *Arthritis Rheum* 39: 810–819, 1996, in a rat streptococcal cell wall-induced arthritis model according to the method of Schimmer, et al., *J Immunol* 160: 1466–1477, 1998, or in a SCID-mouse human rheumatoid arthritis model according to the method of Oppenheimer-Marks et al., *J Clin Invest* 101: 1261–1272, 1998.

The ability of the compounds of this invention to treat Lyme arthritis can be demonstrated according to the method of Gross et al., *Science* 281, 703–706, 1998.

The ability of compounds of this invention to treat asthma can be demonstrated in a murine allergic asthma model according to the method of Wegner et al., *Science* 247:456–459, 1990, or in a murine non-allergic asthma model according to the method of Bloemen et al., *Am J Respir Crit Care Med* 153:521–529, 1996.

The ability of compounds of this invention to treat inflammatory lung injury can be demonstrated in a murine oxygen-induced lung injury model according to the method of Wegner et al., *Lung* 170:267–279, 1992, in a murine immune complex-induced lung injury model according to the method of Mulligan et al., *J Immunol* 154:1350–1363, 1995, or in a murine acid-induced lung injury model according to the method of Nagase, et al., *Am J Respir Crit Care Med* 154:504–510, 1996.

The ability of compounds of this invention to treat inflammatory bowel disease can be demonstrated in a rabbit chemical-induced colitis model according to the method of Bennet et al., *J Pharmacol Exp Ther* 280:988–1000, 1997.

The ability of compounds of this invention to treat autoimmune diabetes can be demonstrated in an NOD mouse model according to the method of Hasagawa et al., *Int Immunol* 6:831–838, 1994, or in a murine streptozotocin-induced diabetes model according to the method of Herrold et al., *Cell Immunol* 157:489–500, 1994.

The ability of compounds of this invention to treat inflammatory liver injury can de demonstrated in a murine liver injury model according to the method of Tanaka et al., *J Immunol* 151:5088–5095, 1993.

The ability of compounds of this invention to treat inflammatory glomerular injury can be demonstrated in a rat nephrotoxic serum nephritis model according to the method of Kawasaki, et al., *J Immunol* 150:1074–1083, 1993.

The ability of compounds of this invention to treat radiation-induced enteritis can be demonstrated in a rat abdominal irradiation model according to the method of Panes et al., *Gastroenterology* 108: 1761–1769, 1995.

The ability of compounds of this invention to treat radiation pneumonitis can be demonstrated in a murine pulmonary irradiation model according to the method of Hallahan et al., *Proc Natl Acad Sci USA* 94:6432–6437, 1997.

The ability of compounds of this invention to treat reperfusion injury can be demonstrated in the isolated rat heart according to the method of Tamiya et al., *Immunopharmacology* 29(1): 53–63, 1995, or in the anesthetized dog according to the model of Hartman et al., *Cardiovasc Res* 30(1): 47–54, 1995.

The ability of compounds of this invention to treat pulmonary reperfusion injury can be demonstrated in a rat lung allograft reperfusion injury model according to the method of DeMeester et al., *Transplantation* 62(10): 1477–1485, 1996, or in a rabbit pulmonary edema model according to the method of Horgan et al., *Am J Physiol* 261(5): H1578–H1584, 1991.

The ability of compounds of this invention to treat stroke can be demonstrated in a rabbit cerebral embolism stroke model according the method of Bowes et al., *Exp Neurol* 119(2): 215–219, 1993, in a rat middle cerebral artery ischemia-reperfusion model according to the method of Chopp et al., *Stroke* 25(4): 869–875, 1994, or in a rabbit reversible spinal cord ischemia model according to the method of Clark et al., *Neurosurg* 7(4): 623–627, 1991.

The ability of compounds of this invention to treat peripheral artery occlusion can be demonstrated in a rat skeletal muscle ischemia/reperfusion model according to the method of Gute et al., *Mol Cell Biochem* 179: 169–187, 1998.

The ability of compounds of this invention to treat graft rejection can be demonstrated in a murine cardiac allograft rejection model according to the method of Isobe et al., *Science* 255: 1125–1127, 1992, in a murine thyroid gland kidney capsule model according to the method of Talento et al., *Transplantation* 55: 418–422, 1993, in a cynomolgus monkey renal allograft model according to the method of Cosimi et al., *J Immunol* 144: 4604–4612, 1990, in a rat nerve allograft model according to the method of Nakao et al., *Muscle Nerve* 18: 93–102, 1995, in a murine skin allograft model according to the method of Gorczynski and Wojcik, *J Immunol* 152 : 2011–2019, 1994, in a murine corneal allograft model according to the method of He et al., *Opthalmol Vis Sci* 35: 3218–3225, 1994, or in a xenogeneic pancreatic islet cell transplantation model according to the method of Zeng et al., *Transplantation* 58:681–689, 1994.

The ability of compounds of this invention to treat graft-vs.-host disease (GVHD) can be demonstrated in a murine lethal GVHD model according to the method of Harning et al., *Transplantation* 52:842–845, 1991.

The ability of compounds of this invention to treat cancers can be demonstrated in a human lymphoma metastasis model (in mice) according to the method of Aoudjit et al., *J Immunol* 161:2333–2338, 1998.

What is claimed is:

1. A compound of formula I

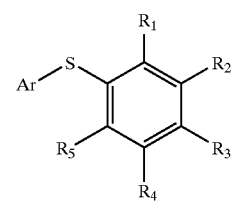

or a pharmaceutically-acceptable salt or prodrug thereof,
where $R_1$, $R_2$, $R_4$, and $R_5$ are each independently selected from
  a. hydrogen,
  b. halogen,
  c. alkyl,
  d. haloalkyl,
  e. alkoxy,
  f. cyano,
  g. nitro, h. carboxaldehyde,
i. heterocyclylsulfanyl,
j. "cis-cinnamide", and
k. "trans-cinnamide",
where "cis-cinnamide" and "trans-cinnamide" are defined as

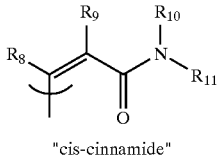 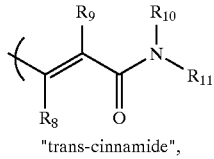

"cis-cinnamide"  "trans-cinnamide", where $R_8$ and $R_9$ are each independently selected from
a. hydrogen,
b. alkyl,
c. carboxy alkyl,
d. monoalkylaminocarbonyl alkyl, and
e. dialkylaminocarbonyl alkyl,
where $R_3$ is a "cis-cinnamide" or a "trans-cinnamide", and at least one of $R_1$, $R_8$, and $R_9$ are hydrogen.
and $R_{10}$ and $R_1$ are each independently selected from
a. hydrogen,
b. alkyl,
c. cycloalkyl,
d. alkoxycarbonylalkyl,
e. hydroxyalkyl,
f. substituted aryl,
g. unsubstituted heterocyclyl,
h. unsubstituted heterocyclylalkyl,
i. heterocyclylamino,
j. substituted heterocyclyl,
k. substituted heterocyclylalkyl,
l. unsubstituted aryl,
m. arylalkyl,
n. carboxyalkyl, and
o. alkoxyalkyl,
or $R_{10}$ and $R_{11}$ are taken together with N to form an unsubstituted heterocyclyl or substituted heterocyclyl group, substituted by at least one substituent, each substitutent independently selected from
1) alkyl
2) alkoxy,
3) alkoxyalkyl,
4) cycloalkyl,
5) aryl,
6) heterocyclyl,
7) heterocyclylcarbonyl,
8) heterocyclylalkylaminocarbonyl,
9) hydroxy,
10) hydroxyalkyl,
11) hydroxyalkoxyalkyl,
12) carboxy,
13) carboxyalkyl,
14) carboxycarbonyl,
15) carboxaldehyde,
16) alkoxycarbonyl,
17) arylalkoxycarbonyl,
18) aminoalkyl,
19) aminoalkanoyl,
20) carboxamido,
21) alkoxycarbonylalkyl,
22) carboxamidoalkyl,
23) cyano,
24) unsubstituted tetrazolyl,
25) substituted tetrazolyl,
26) alkanoyl,
27) hydroxyalkanoyl,
28) alkanoyloxy,
29) alkanoylamino,
30) alkanoyloxyalkyl,
31) alkanoylaminoalkyl,
32) sulfonate,
33) alkylsulfonyl,
34) alkylsulfonylaminocarbonyl,
35) arylsulfonylaminocarbonyl,
36) heterocyclylsulfonylaminocarbonyl,
37) alkenoxycarbonyl,
38) alkoxycarbonylalkylaminocarbonyl,
39) aryl(carboxy)alkylaminocarbonyl,
40) carboxyalkylaminocarbonyl,
41) heterocyclylalkyl,
42) hydroxyalkylaminocarbonyl,
43) hydroxyaminocarbonyl,
44) hydroxy(carboxy)alkylaminocarbonyl,
45) hydroxy(carboxy)alkylcarbonyl, and
46) sulfoalkylaminocarbonyl,
and where Ar is a substituted aryl or substituted heteroaryl group, substituted by at least one substituent, each substituent independently selected from
a. halogen,
b. alkyl,
c. aryl,
d. haloalkyl,
e. hydroxy,
f. alkoxy,
g. alkoxyalkyl,
h. alkoxycarbonyl,
i. alkoxyalkoxy,
j. hydroxyalkyl,
k. aminoalkyl,
l. alkyl(alkoxycarbonylalkyl)aminoalkyl,
m. unsubstituted heterocyclyl,
n. substituted heterocyclyl,
o. unsubstituted heterocyclylalkyl,
p. substituted heterocyclylalkyl,
q. carboxaldehyde,
r. carboxaldehyde hydrazone,
s. carboxamide,
t. alkoxycarbonylalkyl,
u. carboxy,
v. carboxyalkyl,
w. carboxyalkoxy,
x. carboxythioalkoxy,
y. carboxycycloalkoxy,
z. alkylsulfanyl,
aa. hydroxycarbonylalkyl(carboxyalkyl),
bb. hydroxyalkylaminocarbonyl,
cc. cyano,
dd. amino,
ee. heterocyclylalkylamino,
ff. carboxyalkylamino,
gg. carboxyalkenyl,
hh. alkoxycarbonylalkenyl
ii. heterocyclylalkylaminocarbonyl, and
jj. "trans-cinnamide",
wherein the heterocyclyl is chosen from 4-, 5-, 6- and 7-membered rings containing 1–3 heteroatoms independently selected from nitrogen, oxygen and sulfur; the 4- and 5-membered rings have zero to two double bonds and the 6- and 7-membered rings have zero to three double bonds, the heterocyclyl being optionally substituted with alkyl, halogen, hydroxy or alkoxy substituents, further wherein the heterocyclyl optionally comprises a group chosen from:
  (i) bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring, and another monocyclic heterocyclic ring;
  (ii) bridged bicyclic groups where a monocyclic heterocyclic group is bridged by an alkylene group optionally selected from

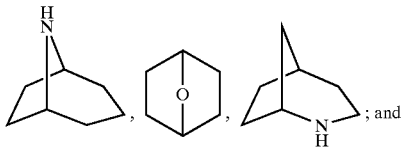

(iii) compounds of the formula

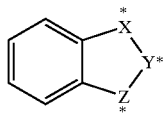

where X* and Z* are independently selected from —CH$_2$—, —CH$_2$NH—, —CH$_2$O—, —NH— and —O—, with the proviso that at least one of X* and Z* is not —CH$_2$—, and Y* is selected from —C(O)— and —C(R")$_2$)$_v$—, where R" is hydrogen or alkyl of one to four carbons, and v is 1–3, subject to the provisos that:
  i) at least one of R$_1$ or R$_3$ is a "cis-cinnamide" or a "trans-cinnamide", as defined above, and
  ii) when R$_3$ is a "cis-cinnamide" or a "trans-cinnamide," and R$_8$ is alkyl, then
    (A) at least one of R$_1$, R$_2$, R$_4$, and R$_5$ is other than hydrogen when Ar is an unsubstituted aryl group, or
    (B) Ar is a substituted aryl group, when all of R$_1$, R$_2$, R$_4$, and R$_5$ are hydrogen.

2. A compound according to claim 1 where Ar is a substituted aryl or substituted heteroaryl group selected from phenyl, 1,3-benzimidazol-2-one, 1,4-benzodioxane, 1,3-benzodioxole, 1-benzopyr-2-en-4-one, indole, isatin, 1,3-quinazolin-4-one, and quinoline.

3. A compound according to claim 1 selected from:

(2,4-Dichlorophenyl)[2-chloro-4-(E-((2-hydroxyethyl-amino)carbonyl)ethenyl)phenyl]sulfide;
(2,4-Dichlorophenyl)[2-chloro-4-(E-((6-hydroxyhexyl-amino)carbonyl)ethenyl)phenyl]sulfide;
(2,4-Dichlorophenyl)[2-chloro-4-(E-((bis-(2-hydroxyethyl)amino)carbonyl)ethenyl)phenyl]sulfide;
(2,4-Dichlorophenyl)[2-chloro-4-(E-((3-(2-oxopyrrolidin-1-yl)propylamino)carbonyl)ethenyl)phenyl]sulfide;
(2,4-Dichlorophenyl)[2-chloro-4-(E-((1-morpholinyl)carbonyl)ethenyl)phenyl]sulfide;
(2,4-Dichlorophenyl)[2-chloro-4-(E-((4-methylpiperazin-1-yl)carbonyl)ethenyl)phenyl]sulfide;
(2,4-Dichlorophenyl)[2-chloro-4-(E-((4-acetylpiperazin-1-yl)carbonyl)ethenyl)phenyl]sulfide;
(2,4-Dichlorophenyl)[2-chloro-4-(E-((4-(2-pyridyl)piperazin-1-yl)carbonyl)ethenyl)phenyl]sulfide;
(2-(Hydroxymethyl)phenyl)[2-chloro-4-(E-((1-morpholinyl)carbonyl)ethenyl)phenyl]sulfide;
(2-Bromophenyl)[2-chloro-4-(E-((1-morpholinyl)carbonyl)ethenyl)phenyl]sulfide;
(2,4-Dichlorophenyl)[2-chloro-4-(E-((4-(2-hydroxyethyl)piperazin-1-yl)carbonyl)ethenyl)phenyl]sulfide;
(2,4-Dichlorophenyl)[2-chloro-4-(E-((4-(2-hydroxyethoxyethyl)piperazin-1-yl)carbonyl)ethenyl)phenyl]sulfide;
(2-Bromophenyl)[2-chloro-4-(E-((3-(hydroxymethyl)piperidin-1-yl)carbonyl)ethenyl)phenyl]sulfide;
(2-Bromophenyl)[2-chloro-4-(E-((2-(hydroxymethyl)piperidin-1-yl)carbonyl)ethenyl)phenyl]sulfide;
(2-Bromophenyl)[2-chloro-4-(E-((3-acetamidopyrrolidin-1-yl)carbonyl)ethenyl)phenyl]sulfide;
(2-Bromophenyl)[2-chloro-4-(E-((4-hydroxypiperidin-1-yl)carbonyl)ethenyl)phenyl]sulfide;
(2-Bromophenyl)[2-chloro-4-(E-((piperidin-1-yl)carbonyl)ethenyl)phenyl]sulfide;
(2,4-Dichlorophenyl)[2-chloro-4-(E-((3-carboxypiperidin-1-yl)carbonyl)ethenyl)phenyl]sulfide;
(2,4-Dichlorophenyl)[2-chloro-4-(E-((4-carboxypiperidin-1-yl)carbonyl)ethenyl)phenyl]sulfide;
(2-Bromophenyl)[2-chloro-4-(E-((4-acetylhomopiperazin-1-yl)carbonyl)ethenyl)phenyl]sulfide;
(2-Bromophenyl)[2-chloro-4-(E-((thiomorpholin-1-yl)carbonyl)ethenyl)phenyl]sulfide;
(2-Bromophenyl)[2-chloro-4-(E-((4-(2-oxo-2,3-dihydro-1H-benzimidazol-1-yl)piperidin-1-yl)carbonyl)ethenyl)phenyl]sulfide;
(2-Bromophenyl)[2-chloro-4-(E-((2-tetrahydroisoquinolinyl)carbonyl)ethenyl)phenyl]sulfide;
(2-Methylphenyl)[2-trifluoromethyl-4-(E-((4-acetylpiperazin-1-yl)carbonyl)ethenyl)phenyl]sulfide;
(2-Methylphenyl)[2-trifluoromethyl-4-(E-((1-morpholinyl)carbonyl)ethenyl)phenyl]sulfide;
(2-Methylphenyl)[2-trifluoromethyl-4-(E-((2-(1-morpholinyl)ethylamino)carbonyl)ethenyl)phenyl]sulfide;
(2-Methylphenyl)[2-trifluoromethyl-4-(E-((4-phenylpiperazin-1-yl)carbonyl)ethenyl)phenyl]sulfide;
(2-Methylphenyl)[2-trifluoromethyl-4-(E-((3-(2-oxopyrrolidin-1-yl)propylamino)carbonyl)ethenyl)phenyl]sulfide;
(2-Methylphenyl)[2-trifluoromethyl-4-(E-((cyclopropylamino)carbonyl)ethenyl)phenyl]sulfide;
(2,4-Dichlorophenyl)[2-nitro-4-(E-((4-acetylpiperazin-1-yl)carbonyl)ethenyl)phenyl]sulfide;
(2,4-Dichlorophenyl)[2-nitro-4-(E-((3-(2-oxopyrrolidin-1-yl)propylamino)carbonyl)ethenyl)phenyl]sulfide;
(2,3-Dichlorophenyl)[2-nitro-4-(E-((4-acetylpiperazin-1-yl)carbonyl)ethenyl)phenyl]sulfide;
(4-Bromophenyl)[2-nitro-4-(E-((4-acetylpiperazin-1-yl)carbonyl)ethenyl)phenyl]sulfide;
(4-Methylphenyl)[2-nitro-4-(E-((4-acetylpiperazin-1-yl)carbonyl)ethenyl)phenyl]sulfide;
(2,4-Dichlorophenyl)[2-nitro-4-(E-((4-(tert-butoxycarbonyl)piperazin-1-yl)carbonyl)ethenyl)phenyl]sulfide;
(2,4-Dichlorophenyl)[2-nitro-4-(E-((4-(2-furoylcarbonyl)piperazin-1-yl)carbonyl)ethenyl)phenyl]sulfide;
(2,4-Dichlorophenyl)[2-nitro-4-(E-((4-(methanesulfonyl)piperazin-1-yl)carbonyl)ethenyl)phenyl]sulfide;
(2,4-Dichlorophenyl)[2-nitro-4-(E-((4-(diethylamino-carbonylmethyl)piperazin-1-yl)carbonyl)ethenyl)phenyl]sulfide;
(2,4-Dichlorophenyl)[2-nitro-4-(E-((4-(diethylamino-carbonyl)piperazin-1-yl)carbonyl)ethenyl)phenyl]sulfide;

(2,4-Dichlorophenyl)[2-nitro-4-(E-((4-(tert-butoxycarbonylmethyl)piperazin-1-yl)carbonyl)ethenyl)phenyl]sulfide;
(2,4-Dichlorophenyl)[2-nitro-4-(E-((4-(carboxycarbonyl)piperazin-1-yl)carbonyl)ethenyl)phenyl]sulfide;
(2,4-Dichlorophenyl)[2-nitro-4-(E-((4-(carboxymethyl)piperazin-1-yl)carbonyl)ethenyl)phenyl]sulfide;
(2-Methylphenyl)[2-nitro-4-(E-((4-acetylpiperazin-1-yl)carbonyl)ethenyl)phenyl]sulfide;
(2-Chlorophenyl)[2-nitro-4-(E-((4-acetylpiperazin-1-yl)carbonyl)ethenyl)phenyl]sulfide;
(2-Aminophenyl)[2-nitro-4-(E-((4-acetylpiperazin-1-yl)carbonyl)ethenyl)phenyl]sulfide;
(2-Hydroxymethylphenyl)[2-nitro-4-(E-((4-acetylpiperazin-1-yl)carbonyl)ethenyl)phenyl]sulfide;
(2-Ethylphenyl)[2-nitro-4-(E-((4-acetylpiperazin-1-yl)carbonyl)ethenyl)phenyl]sulfide;
(2-isop-Propylphenyl)[2-nitro-4-(E-((4-acetylpiperazin-1-yl carbonyl)ethenyl)phenyl]sulfide;
(2-tert-Butylphenyl)[2-nitro-4-(E-((4-acetylpiperazin-1-yl)carbonyl)ethenyl)phenyl]sulfide;
(2-Chlorophenyl)[2-chloro-4-(E-((4-acetylpiperazin-1-yl)carbonyl))2-propenyl)phenyl]sulfide;
(2-(1-Morpholinylmethyl)phenyl)[2-chloro-4-(E-((1-morpholinyl)carbonyl)ethenyl)phenyl]sulfide;
(2-(4-(1,3-Benzodioxolyl-5-methyl)piperazin-1-ylmethyl)phenyl)[2-chloro-4-(E-((1-morpholinyl)carbonyl)ethenyl)phenyl]sulfide;
(2-(4-(iso-Propylaminocarbonylmethyl)piperazin-1-ylmethyl)phenyl)[2-chloro-4-(E-((1-morpholinyl)carbonyl)ethenyl)phenyl]sulfide;
(2-((N-Ethoxycarbonylmethyl-N-methyl)aminomethyl)phenyl)[2-chloro-4-(E-((1-morpholinyl)carbonyl)ethenyl)phenyl]sulfide;
(2-Formylphenyl)[2-chloro-4-(E-((1-morpholinyl)carbonyl)ethenyl)phenyl]sulfide;
(2-(4-Formylpiperazin-1-ylmethyl)phenyl)[2-chloro-4-(E-((1-morpholinyl)carbonyl)ethenyl)phenyl]sulfide;
(2-(E-((1-Morpholinyl)carbonyl)ethenyl)phenyl)[2-chloro-4-(E-((1-morpholinyl)carbonyl)ethenyl)phenyl]sulfide;
(2-Formylphenyl)[2-nitro-4-(E-((4-acetylpiperazin-1-yl)carbonyl)ethenyl)phenyl]sulfide;
(2-Formylphenyl)[2-chloro-4-(E-((1-morpholinyl)carbonyl)ethenyl)phenyl]sulfide, N,N-dimethyl hydrazone;
(2-((3-(1-Morpholinyl)propyl)-1-amino)phenyl)[2-chloro-4-(E-((1-morpholinyl)carbonyl)ethenyl)phenyl]sulfide;
(2,4-Dichlorophenyl)[2-bromo-4-(E-((3-(2-oxopyrrolidin-1-yl)propylamino)carbonyl)ethenyl)phenyl]sulfide;
(2,4-Dichlorophenyl)[2-formyl-4-(E-((1-morpholinyl)carbonyl)ethenyl)phenyl]sulfide;
(2-Chloro-6-formylphenyl)[2-chloro-4-(E-((4-acetylpiperazin-1-yl)carbonyl)ethenyl)phenyl]sulfide;
(2-Cyanophenyl)[2-chloro-4-(E-((4-acetylpiperazin-1-yl)carbonyl)ethenyl)phenyl]sulfide;
(2-Isopropylphenyl)[2-cyano-4-(E-((morpholin-1-yl)carbonyl)ethenyl)phenyl]sulfide;
(2-Bromophenyl)[2-nitro-4-(E-((4-acetylpiperazin-1-yl)carbonyl)ethenyl)phenyl]sulfide;
(2-(Pyrrolidin-1-yl)phenyl)[2-chloro-4-(E-((morpholin-1-yl)carbonyl)ethenyl)phenyl]sulfide;
(2-Methoxyphenyl)[2-chloro-4-(E-[(morpholin-1-yl)carbonyl]ethenyl)phenyl]sulfide;
(2-Isopropylphenyl)[2-nitro-4-(E-((3-carbomethoxy-piperazin-1-yl)carbonyl)ethenyl)phenyl]sulfide;
(2-Methylphenyl)[2-nitro-4-(E-((3-carboxamido-4-carbobenzoxypiperazin-1-yl)carbonyl)ethenyl)phenyl]sulfide;
(2-Isopropylphenyl)[2-nitro-4-(E-((2-carbomethoxy-4-tert-butoxycarbonylpiperazin-1-yl)carbonyl)ethenyl)phenyl]sulfide;
(2-Isopropylphenyl)[2-nitro-4-(E-((2-carboxy-4-tert-butoxycarbonylpiperazin-1-yl)carbonyl)ethenyl)phenyl]sulfide;
(2-Isopropylphenyl)[2-trifluoromethyl-4-(E-((4-acetylpiperazin-1-yl)carbonyl)ethenyl)phenyl]sulfide;
(2-Isopropylphenyl)[2-trifluoromethyl-4-(E-((morpholin-1-yl)carbonyl)ethenyl)phenyl]sulfide;
(2-Isopropylphenyl)[2-trifluoromethyl-4-(E-((3-(2-oxopyrrolidin-1-yl)prop-1-ylamino)carbonyl)ethenyl)phenyl]sulfide;
(2-Isopropylphenyl)[2-trifluoromethyl-4-(E-((cyclobutylamino)carbonyl)ethenyl)phenyl]sulfide;
(2-Isopropylphenyl)[2-trifluoromethyl-4-(E-((cyclopentylamino)carbonyl)ethenyl)phenyl]sulfide;
(2-Isopropylphenyl)[2-trifluoromethyl-4-(E-((5-hydroxypent-1-ylamino)carbonyl)ethenyl)phenyl]sulfide;
(2-Isopropylphenyl)[2-nitro-4-(E-((3-carbomethoxy-4-acetylpiperazin-1-yl)carbonyl)ethenyl)phenyl]sulfide;
(2-Biphenyl)[2-chloro-4-(E-((morpholin-1-yl)carbonyl)ethenyl)phenyl]sulfide;
(3,4-Dimethylphenyl)[2-nitro-4-(E-((4-acetylpiperazin-1-yl)carbonyl)ethenyl)phenyl]sulfide;
(2-Bromophenyl)[2-trifluoromethyl-4-(E-((4-acetylpiperazin-1-yl)carbonyl)ethenyl)phenyl]sulfide;
(5-Indolyl)[2-chloro-4-(E-((4-acetylpiperazin-1-yl)carbonyl)ethenyl)phenyl]sulfide;
(5-Benzodioxolyl)[2-chloro-4-(E-((4-acetylpiperazin-1-yl)carbonyl)ethenyl)phenyl]sulfide;
(2-Isopropylphenyl)[2-nitro-4-(E-((2-carbomethoxy-piperazin-1-yl)carbonyl)ethenyl)phenyl]sulfide;
(2,3-Dimethoxyphenyl)-[2-chloro-4-(E-[(morpholin-1-yl)carbonyl]ethenyl)phenyl]sulfide;
(2-Fluorophenyl)[2-nitro-4-(E-((4-acetylpiperazin-1-yl)carbonylethenyl)phenyl]sulfide;
(2-Bromophenyl)[2-trifluoromethyl-4-(E-((4-(tert-butoxycarbonyl)piperazin-1-yl)carbonyl)ethenyl)phenyl]sulfide;
(2-(Pyrrolidin-1-yl)phenyl)[2-trifluoromethyl-4-(E-((4-(tert-butoxycarbonyl)piperazin-1-yl)carbonyl)ethenyl)phenyl]sulfide;
(3-Carboxamidophenyl)[2-nitro-4-(E-((4-acetylpiperazin-1-yl)carbonyl)ethenyl)phenyl]sulfide;
(3-(Hydroxymethyl)phenyl)[2-nitro-4-(E-((4-acetylpiperazin-1-yl)carbonyl)ethenyl)phenyl]sulfide;
(2-Isopropylphenyl)[2-trifluoromethyl-4-(E-((2-carbomethoxy-4-(tert-butoxycarbonyl)piperazin-1-yl)carbonyl)ethenyl)phenyl]sulfide;
(2-Isopropylphenyl)[2-nitro-4-(E-((3-(pyridine-4-methylaminocarbonyl)-4-tert-butoxycarbonylpiperazin-1-yl)carbonyl)ethenyl)phenyl]sulfide;
(2-Ethoxyphenyl)-[2-chloro-4-(E-[(morpholin-1-yl)carbonyl]ethenyl)phenyl]sulfide;
(2-Methoxyphenyl)[2-nitro-4-(E-((4-acetylpiperazin-1-yl)carbonyl)ethenyl)phenyl]sulfide;
(2-(Azetidin-1-yl)phenyl)[2-trifluoromethyl-4-(E-((4-(tert-butoxycarbonyl)piperazin-1-yl)carbonyl)ethenyl)phenyl]sulfide;
(2-(Piperidin-1-yl)phenyl)[2-trifluoromethyl-4-(E-((4-(tert-butoxycarbonyl)piperazin-1-yl)carbonyl)ethenyl)phenyl]sulfide;
(3-Chloro-2-formylphenyl)[2-chloro-4-(E-((4-acetylpiperazin-1-yl)carbonyl)ethenyl)phenyl]sulfide;
(2-Trifluoromethylphenyl)[2-trifluoromethyl-4-(E-((4-acetylpiperazin-1-yl)carbonyl)ethenyl)phenyl]sulfide;

(3-Bromophenyl)[2-trifluoromethyl-4-(E-((4-acetylpiperazin-1-yl)carbonyl)ethenyl)phenyl]sulfide;
(3,5-Dimethylphenyl)[2-trifluoromethyl-4-(E-((4-acetylpiperazin-1-yl)carbonyl)ethenyl)phenyl]sulfide;
(2-Isopropylphenyl)[2-nitro-4-(E-((3-dimethylamino-carbonyl-4-(pyridine-4-carbonyl)piperazin-1-yl)carbonyl)ethenyl)phenyl]sulfide;
(2-Isopropylphenyl)[2-nitro-4-(E-((3-dimethylamino-carbonyl-4-carbomethoxypiperazin-1-yl)carbonyl)ethenyl)phenyl]sulfide;
(2-Isopropylphenyl)[2-nitro-4-(E-((3-dimethylamino-carbonyl-4-acetylpiperazin-1-yl)carbonyl)ethenyl)phenyl]sulfide;
(2-Isopropylphenyl)[2-nitro-4-(E-((3-(1-morpholino-carbonyl)-4-tert-butoxycarbonylpiperazin-1-yl)carbonyl)ethenyl)phenyl]sulfide;
(2-isopropylphenyl)[2-nitro-4-(E-((3-(pyridine-4-methylaminocarbonyl)piperazin-1-yl)carbonyl)ethenyl)phenyl]sulfide;
(2-Isopropylphenyl)[2-nitro-4-(E-(((3-dimethylamino-carbonyl)piperazin-1-yl)carbonyl)ethenyl)phenyl]sulfide;
(2-Isopropylphenyl)[2-nitro-4-(E-((3-(benzylamino-carbonyl)-4-tert-butoxycarbonylpiperazin-1-yl)carbonyl)ethenyl)phenyl]sulfide;
(2-Isopropylphenyl)[2-nitro-4-(E-((3-(dimethylamino-carbonyl)-4-tert-butoxycarbonylpiperazin-1-yl)carbonyl)ethenyl)phenyl]sulfide;
(2-Bromophenyl)[2-chloro-4-(E-((3-(5S-hydroxymethyl-2-oxopyrrolidin-1-yl)prop-1-ylamino)carbonyl)ethenyl)phenyl]sulfide;
(2-Bromophenyl)[2-chloro-4-(E-((3-(2-oxopyrrolidin-1-yl)prop-1-ylamino)carbonyl)ethenyl)phenyl]sulfide;
(2-Bromophenyl)[2-chloro-4-(E-(N-methyl-N-(3-(2-oxyopyrrolidin-1-yl)prop-1-yl)amino)carbonyl)ethenyl)phenyl]sulfide;
(2-[2-Methoxy]ethoxyphenyl)-[2-chloro-4-(E-[(morpholin-1-yl)carbonyl]ethenyl)phenyl]sulfide;
(2-Isopropylphenyl)[2-nitro-4-(E-((3-(morpholinocarbonyl)piperazin-1-yl)carbonyl)ethenyl)phenyl]sulfide;
(2-Isopropylphenyl)[2-nitro-4-(E-((4-tert-butoxy-carbonylpiperazin-1-yl)carbonyl)ethenyl)phenyl]sulfide;
(2-Isopropylphenyl)[2-nitro-4-(E-((4-methoxycarbonyl-piperazin-1-yl)carbonyl)ethenyl)phenyl]sulfide;
(2-Isopropylphenyl)[2-nitro-4-(E-(4-(pyridine-4-carbonyl)piperazin-1-yl)carbonyl)ethenyl)phenyl]sulfide;
(2-Isopropylphenyl)[2-nitro-4-(E-((3-(pyridine-3-methylaminocarbonyl)-4-tert-butoxycarbonylpiperazin-1-yl)carbonyl)ethenyl)phenyl]sulfide;
(2-Isopropylphenyl)[2-nitro-4-(E-((3-(pyridine-2-methylaminocarbonyl)piperazin-1-yl)carbonyl)ethenyl)phenyl]sulfide;
(2-Isopropylphenyl)[2-nitro-4-(E-((3-(pyridine-3-methylaminocarbonyl)piperazin-1-yl)carbonyl)ethenyl)phenyl]sulfide;
(4-Hydroxyphenyl)[2-nitro-4-(E-((4-acetylpiperazin-1-l)carbonyl)ethenyl)phenyl]sulfide;
(3,5-Dichlorophenyl)[2-nitro-4-(E-((4-acetylpiperazin-1-yl)carbonyl)ethenyl)phenyl]sulfide;
(2-Bromophenyl)[2-chloro-4-(E-((3-(5S-acetoxymethyl-2-oxopyrrolidin-1-yl)prop-1-ylamino)carbonyl)ethenyl)phenyl]sulfide;
(2-Bromophenyl)[2-chloro-4-(E-((3-(5S-methoxymethyl-2-oxopyrrolidin-1-yl)prop-1-ylamino)carbonyl)ethenyl)phenyl]sulfide;
(2-Bromophenyl)[2-chloro-4-(E-((3-(4R-hydroxy-2-oxopyrrolidin-1-yl)prop-1-ylamino)carbonyl)ethenyl)phenyl]sulfide;
(2-Dimethylaminophenyl)[2-nitro-4-(E-((4-acetylpiperazin-1-yl)carbonyl)ethenyl)phenyl]sulfide;
(3-((2-Hydroxyethyl)aminocarbonyl)phenyl)[2-nitro-4-(E-((4-acetylpiperazin-1-yl)carbonyl)ethenyl)phenyl]sulfide;
(3-((3-(1-Imidazolyl)propyl)aminocarbonyl)phenyl)[2-nitro-4-(E-((4-acetylpiperazin-1-yl)carbonyl)ethenyl)phenyl]sulfide;
(3-((2(1-Morpholinyl)ethyl)aminocarbonyl)phenyl)[2-nitro-4-(E-((4-acetylpiperazin-1-yl)carbonyl)ethenyl)phenyl]sulfide;
(2-isopropylphenyl)[2-nitro-4-(E-((3-hydroxymethyl-4-tert-butoxycarbonylpiperazin-1-yl)carbonyl)ethenyl)phenyl]sulfide;
(2-Isopropylphenyl)[2-nitro-4-(E-((4-formylpiperazin-1-yl)carbonyl)ethenyl)phenyl]sulfide;
(2-Isopropylphenyl)[2-nitro-4-(E-((2-hydroxymethyl-4-tert-butoxycarbonylpiperazin-1-yl)carbonyl)ethenyl)phenyl]sulfide;
(2-Ethoxyphenyl)-[2-chloro-4(E-[(3-ethoxycarbonyl-piperidin-1-yl)carbonyl]ethenyl)phenyl]sulfide;
(3-Aminophenyl)[2-nitro-4-(E-((4-acetylpiperazin-1-yl)carbonyl)ethenyl)phenyl]sulfide;
(4-Aminophenyl)[2-nitro-4-(E-((4-acetylpiperazin-1-yl)carbonyl)ethenyl)phenyl]sulfide;
(2,4-Dimethylphenyl)[2-nitro-4-(E-((4-acetylpiperazin-1-yl)carbonyl)ethenyl)phenyl]sulfide;
(2,5-Dimethylphenyl)[2-nitro-4-(E-((4-acetylpiperazin-1-yl)carbonyl)ethenyl)phenyl]sulfide;
(4-Methoxyphenyl)[2-nitro-4-(E-((4-acetylpiperazin-1-yl)carbonyl)ethenyl)phenyl]sulfide;
(3-Chlorophenyl)[2-nitro-4-(E-((4-acetylpiperazin-1-yl)carbonyl)ethenyl)phenyl]sulfide;
(2-Chloro-4,5-diaminophenyl)[2-chloro-4-(E-((4-acetylpiperazin-1-yl)carbonyl)ethenyl)phenyl]sulfide;
(3,4-Diaminophenyl)[2-chloro-4-(E-((4-acetylpiperazin-1-yl)carbonyl)ethenyl)phenyl]sulfide;
(6-Chloro-2-oxo-2,3-dihydro-1H-benzimidazol-5-yl)[2-chloro-4-(E-((4-acetylpiperazin-1-yl)carbonyl)ethenyl)phenyl]sulfide;
(1-Methylindol-7-yl)[2-chloro-4-(E-((4-acetylpiperazin-1-yl)carbonyl)ethenyl)phenyl]sulfide;
(2-Hydroxy-4-aminophenyl)[2-chloro-4-(E-((4-acetylpiperazin-1-yl)carbonyl)ethenyl)phenyl]sulfide;
(2-Isopropylphenyl)[2-nitro-4-(E-((4-methylpiperazin-1-yl)carbonyl)ethenyl)phenyl]sulfide;
(2-Isopropylphenyl)[2-nitro-4-(E-((4-(pyridine-2-carbonyl)piperazin-1-yl)carbonyl)ethenyl)phenyl]sulfide;
(2-Isopropylphenyl)[2-nitro-4-(E-((4-(pyridine-3-carbonyl)piperazin-1-yl)carbonyl)ethenyl)phenyl]sulfide;
(2-isopropylphenyl)[2-nitro-4-(E-((2-carbomethoxy-4-methoxycarbonylpiperazin-1-yl)carbonyl)ethenyl)phenyl]sulfide;
(2-Isopropylphenyl)[2-nitro-4-(E-((2-carboxy-4-methoxycarbonylpiperazin-1-yl)carbonyl)ethenyl)phenyl]sulfide;
(2-Isopropylphenyl)[2-nitro-4-(E-((3-carbomethoxy-4-methylpiperazin-1-yl)carbonyl)ethenyl)phenyl]sulfide;
(2-Ethoxyphenyl)-[2-chloro-4-(E-[(3-carboxypiperidin-1-yl)carbonyl]ethenyl)phenyl]sulfide;
(2-Ethoxyphenyl)-[2-chloro-4-(E-[(2-ethoxycarbonyl-piperidin-1-yl)carbonyl]ethenyl)phenyl]sulfide;
(2-Ethoxyphenyl)[2-trifluoromethyl-4-(E-((1-(tert-butoxycarbonyl)-4-hydroxypyrrolidin-3-ylamino)carbonyl)ethenyl)phenyl]sulfide;

(2-Ethoxyphenyl)-[2-chloro-4(E-[(2-carboxypiperidin-1-yl)carbonyl]ethenyl)phenyl]sulfide;
(2-Ethoxyphenyl)[2-trifluoromethyl-4-(E-(((pyrrolidin-3-ene-1-yl)carbonyl)ethenyl)phenyl]sulfide;
(2-Ethoxyphenyl)[2-trifluoromethyl-4-(E-((3-(2-oxopyrrolidin-1-yl)prop-1-ylamino)carbonyl)ethenyl)phenyl]sulfide;
(2-Ethoxyphenyl)[2-trifluoromethyl-4-(E-((4-acetylpiperazin-1-yl)carbonyl)ethenyl)phenyl]sulfide;
(2-Ethoxyphenyl)[2-trifluoromethyl-4-(E-((4-(ethoxycarbonyl)piperazin-1-yl)carbonyl)ethenyl)phenyl]sulfide;
(2-Ethoxyphenyl)[2-trifluoromethyl-4-(E-((4-(2-furylcarbonyl)piperazin-1-yl)carbonyl)ethenyl)phenyl]sulfide;
(2-Ethoxyphenyl)-[2-chloro-4-(E-[(3-ethoxycarbonyl-piperidin-1-yl)carbonyl]ethenyl)phenyl]sulfide;
(2-Ethoxyphenyl)-[2-chloro-4-(E-[(4-carboxypiperidin-1-yl)carbonyl]ethenyl)phenyl]sulfide;
(Benzodioxan-6-yl)[2-chloro-4-(E-((4-acetylpiperazin-1-yl)carbonyl)ethenyl)phenyl]sulfide;
(2-Isopropylphenyl)[2-nitro-4-(E-((4-ethoxycarbonyl-piperazin-1-yl)carbonyl)ethenyl)phenyl]sulfide;
(2-Isopropylphenyl)[2-nitro-4-(E-((4-isopropoxycarbonyl-piperazin-1-yl)carbonyl)ethenyl)phenyl]sulfide;
(2-Isopropylphenyl)[2-nitro-4-(E-((4-isobutoxycarbonyl-piperazin-1-yl)carbonyl)ethenyl)phenyl]sulfide;
(2-Isopropylphenyl)[2-nitro-4-(E-((4-((1-propen-2oxy)carbonyl)piperazin-1-yl)carbonyl)ethenyl)phenyl]sulfide;
(2-Isopropylphenyl)[2-nitro-4-(E-((4-propionylpiperazin-1-yl)carbonyl)ethenyl)phenyl]sulfide;
(2-Isopropylphenyl)[2-nitro-4-(E-((4-carboxamido-piperazin-1-yl)carbonyl)ethenyl)phenyl]sulfide;
(2-Isopropylphenyl)[2-nitro-4-(E-((4-methylamino-carbonylpiperazin-1-yl)carbonyl)ethenyl)phenyl]sulfide;
(2-Isopropylphenyl)[2-nitro-4-(E-((4-(pyrimidin-2-y)piperazin-1-yl)carbonyl)ethenyl)phenyl]sulfide;
(2-Isopropylphenyl)[2-nitro-4-(E-((4-hydroxyacetyl-piperazin-1-yl)carbonyl)ethenyl)phenyl]sulfide;
(2-Isopropylphenyl)[2-nitro-4-(E-((4-(pyrazine-2-carbonyl)piperazin-1-yl)carbonyl)ethenyl)phenyl]sulfide;
(2-Isopropylphenyl)[2-trifluoromethyl-4-(E-(((2-carboxypyrrol-3-ene-1-yl)carbonyl)ethenyl)phenyl]sulfide methyl ester;
(2-Isopropylphenyl)[2-nitro-4-(E-((3-hydroxymethyl-4-methylpiperazin-1-yl)carbonyl)ethenyl)phenyl]sulfide;
(2-Isopropylphenyl)[2-trifluoromethyl-4-(E-(((2-carboxypyrrol-3-ene-1-yl)carbonyl)ethenyl)phenyl]sulfide;
(2-Isopropylphenyl)[2-trifluoromethyl-4-(E-(((2-hydroxymethylpyrrolidin-1-yl)carbonyl)ethenyl)phenyl]sulfide;
(2-Isopropylphenyl)[2-nitro-4-(E-((3-methylamino-carbonyl)piperazin-1-yl)carbonyl)ethenyl)phenyl]sulfide;
(2-Isopropylphenyl)[2-nitro-4-(E-(((3-cyclopropyl-aminocarbonyl)piperazin-1-yl)carbonyl)ethenyl)phenyl]sulfide;
(2-Isopropylphenyl)[2-nitro-4-(E-((3-carboxamido-piperazin-1-yl)carbonyl)ethenyl)phenyl]sulfide;
(2-Isopropylphenyl)[2-nitro-4-(E-((3-carbomethoxy-4-oxopiperidin-1-yl)carbonyl)ethenyl)phenyl]sulfide;
(2-Isopropylphenyl)[2-nitro-4-(E-((3,5-dimethylpiperazin-1-yl)carbonyl)ethenyl)phenyl]sulfide;
(1-Ethylindol-7-yl)[2-chloro-4-(E-((4-acetylpiperazin-1-yl)carbonyl)ethenyl)phenyl]sulfide;
(3-[2-Methoxy]ethoxyphenyl)-[2-chloro-4-(E-[(morpholin-1-yl)carbonyl]ethenyl)phenyl]sulfide;
(2-Bromophenyl)[2-chloro-4-(E-((4,4'-S-dioxythio-morpholin-1-yl)carbonyl)ethenyl)phenyl]sulfide;
(2-Bromophenyl)[2-chloro-4-(E-(N-carbomethoxymethyl-N-(3-(2-oxopyrrolidin-1-yl)prop-1-yl)amino)carbonyl)ethenyl)phenyl]sulfide;
(2-Bromophenyl)[2-chloro-4-(E-((4-S-oxythiomorpholin-1-yl)carbonyl)ethenyl)phenyl]sulfide;
(2-Methoxy-5-chlorophenyl)[2-nitro-4-(E-((4-acetylpiperazin-1-yl)carbonyl)ethenyl)phenyl]sulfide;
(2-Isopropylphenyl)[2-nitro-4-(E-((3-acetoxymethyl)piperazin-1-yl)carbonyl)ethenyl)phenyl]sulfide;
(2-Isopropylphenyl)[2-nitro-4-(E-((3,5-dimethyl-4-acetyl-piperazin-1-yl)carbonyl)ethenyl)phenyl]sulfide;
(1-Methylindol-5-yl)[2-chloro-4-(E-((4-acetylpiperazin-1-yl)carbonyl)ethenyl)phenyl]sulfide;
(Benzodioxan-6-yl)[2-nitro-4-(E-((4-acetylpiperazin-1-yl)carbonyl)ethenyl)phenyl]sulfide;
(Benzodioxan-6-yl)[2-nitro-4-(E-((3-(2-oxopyrrolidin-1-yl)prop-1-ylamino)carbonyl)ethenyl)phenyl]sulfide;
(Benzodioxan-6-yl)[2-nitro-4-(E-((3-carboethoxypiperidin-1-yl)carbonyl)ethenyl)phenyl]sulfide;
(Benzodioxan-6-yl)[2-nitro-4-(E-((4-carboethoxypiperidin-1-yl)carbonyl)ethenyl)phenyl]sulfide;
(2-Ethoxyphenyl)[2-trifluoromethyl-4-(Z-((4-acetylpiperazin-1-yl)carbonyl)ethenyl)phenyl]sulfide;
(2-Ethoxyphenyl)[2-trifluoromethyl-4-(E-((6-methylpyrid-2-ylamino)carbonyl)ethenyl)phenyl]sulfide;
(2-Methyl-3-chlorophenyl)[2-nitro-4-(E-((4-acetylpiperazin-1-yl)carbonyl)ethenyl)phenyl]sulfide;
(Benzodioxan-6-yl)[2-nitro-4-(E-((3-carboxamido-piperidin-1-yl)carbonyl)ethenyl)phenyl]sulfide;
(Benzodioxan-6-yl)[2-nitro-4-(E-((2-carboethoxypiperidin-1-yl)carbonyl)ethenyl)phenyl]sulfide;
(Benzodioxan-6-yl)[2-nitro-4-(E-((4-carboxamido-piperidin-1-yl)carbony)ethenyl)phenyl]sulfide;
(Benzodioxan-6-yl)[2-nitro-4-(E-((4-tert-butoxy-carbonylpiperazin-1-yl)carbonyl)ethenyl)phenyl]sulfide;
(2-isopropylphenyl)[2-nitro-4-(E-((syn-3,5-dimethylmorpholin-1-yl)carbonyl)ethenyl)phenyl]sulfide;
(2-Isopropylphenyl)[2-nitro-4-(E-((anti-3,5-dimethylmorpholin-1-yl)carbonyl)ethenyl)phenyl]sulfide;
(2-Isopropylphenyl)[2-nitro-4-(E-((3-carboethoxy-piperazin-1-yl)carbonyl)ethenyl)phenyl]sulfide;
(2-Isopropylphenyl)[2-nitro-4-(E-((3-isopropoxy-carbonylpiperazin-1-yl)carbonyl)ethenyl)phenyl]sulfide;
(2-Isopropylphenyl)[2-nitro-4-(E-((3-(dimethylamino-carbonyl)-4-methylpiperazin-1-yl)carbonyl)ethenyl)phenyl]sulfide;
(2-Isopropylphenyl)[2-nitro-4-(E-((3-carbomethoxy-4-hydroxypiperidin-1-yl)carbonyl)ethenyl)phenyl]sulfide;
(2-Isopropylphenyl)[2-nitro-4-(E-((3-hydroxymethyl-4-hydroxypiperidin-1-yl)carbonyl)ethenyl)phenyl]sulfide;

(2-Ethoxyphenyl)[2-trifluoromethyl-4-(E-((2-carbomethoxy-4-(methoxycarbonyl)piperazin-1-yl)carbonyl)ethenyl)phenyl]sulfide;

(2-Ethoxyphenyl)[2-trifluoromethyl-4-(E-((2-carbomethoxy-4-methyl piperazin-1-yl)carbonyl)ethenyl)phenyl]sulfide;

(2-Ethoxyphenyl)[2-trifluoromethyl-4-(E-((2-carboxy-4-(methoxycarbonyl)piperazin-1-yl)carbonyl)ethenyl)phenyl]sulfide;

(Indol-6-yl)[2-chloro-4-(E-((4-acetylpiperazin-1-yl)carbonyl)ethenyl)phenyl]sulfide;

(1-Ethyl-3-(dimethylaminomethyl)indol-7-yl)[2-chloro-4-(E-((4-acetylpiperazin-1-yl)carbonyl)ethenyl)phenyl]sulfide;

(5-Ethoxybenzodioxan-6-yl)[2-chloro-4-(E-((4-acetylpiperazin-1-yl)carbonyl)ethenyl)phenyl]sulfide;

(2-Ethyl-4-bromophenyl)[2-nitro-4-(E-((4-acetylpiperazin-1-yl)carbonyl)ethenyl)phenyl]sulfide;

(Benzodioxan-6-yl)[2-nitro-4-(E-((2-carboxypiperidin-1-yl)carbonyl)ethenyl)phenyl]sulfide;

(Benzodioxan-6-yl)[2-nitro-4-(E-((4-carboxymethyl-piperazin-1-yl)carbonyl)ethenyl)phenyl]sulfide;

(3-Morpholinophenyl)[2-nitro-4-(E-((4-acetylpiperazin-1-yl)carbonyl)ethenyl)phenyl]sulfide;

(5-Ethoxybenzodioxan-8-yl)[2-chloro-4-(E-((4-acetylpiperazin-1-yl)carbonyl)ethenyl)phenyl]sulfide;

(5-Chloro-8-ethoxyquinolin-7-yl)[2-chloro-4-(E-((4-acetylpiperazin-1-yl)carbonyl)ethenyl)phenyl]sulfide;

(2-Isopropylphenyl)[2-nitro-4-(E-((3-carboethoxypiperidin-1-yl)carbonyl)ethenyl)phenyl]sulfide;

(2-Isopropylphenyl)[2-nitro-4-(E((3-carboxypiperidin-1-yl)carbonyl)ethenyl)phenyl]sulfide;

(2-Isopropylphenyl)[2-nitro-4-(E-(((3-ethanesulfonyl-aminocarbonyl)piperidin-1-yl)carbonyl)ethenyl)phenyl]sulfide;

(2-Isopropylphenyl)[2-nitro-4-(E-(((3-(4-methylpiperazine)sulfonylaminocarbonyl)piperidin-1-yl)carbonyl)ethenyl)phenyl]sulfide;

(2-Isopropylphenyl)[2-nitro-4-(E-(((3-p-toluenesulfonyl-aminocarbonyl)piperidin-1-yl)carbonyl)ethenyl)phenyl]sulfide;

(2-Isopropylphenyl)[2-nitro-4-(E-((3-methyl-4-acetylpiperazin-1-yl)carbonyl)ethenyl)phenyl]sulfide;

(2-Hydroxyphenyl)-[2-chloro-4-(E-[(morpholin-1-yl)carbonyl]ethenyl)phenyl]sulfide;

(1-(Carboxymethyl)indol-5-yl)[2-chloro-4-(E-((4-acetylpiperazin-1-yl)carbonyl)ethenyl)phenyl]sulfide;

(Benzodioxan-6-yl)[2-trifluoromethyl-4-(E-((4-acetylpiperazin-1-yl)carbonyl)ethenyl)phenyl]sulfide;

(2-Isopropylphenyl)[2-nitro-4-(E-((3-(2-oxopyrrolidin-1-yl)prop-1-ylamino)carbonyl)ethenyl)phenyl]sulfide;

(3-(2-Morpholinoethylamino)phenyl)[2-trifluoromethyl-4-(E-((4-acetylpiperazin-1-yl)carbonyl)ethenyl)phenyl]sulfide;

(2-Pyrrolidin-1-ylphenyl)[2-nitro-4-(E-((4-acetylpiperazin-1-yl)carbonyl)ethenyl)phenyl]sulfide;

(3-Bromophenyl)[2-nitro-4-(E-((3-carboethoxypyrrolidin-1-yl)carbonyl)ethenyl)phenyl]sulfide;

(3-Bromophenyl)[2-nitro-4-(E-((4-carboethoxypyrrolidin-1-yl)carbonyl)ethenyl)phenyl]sulfide;

(2-(Hydroxymethyl)-benzodioxan-6-yl)[2-chloro-4-(E-((4-acetylpiperazin-1-yl)carbonyl)ethenyl)phenyl]sulfide;

(Benzodioxan-6-yl)[2-trifluoromethyl-4-(E-((3-(2-oxopyrrolidin-1-yl)prop-1-ylamino)carbonyl)ethenyl)phenyl]sulfide;

(3-(Dimethylaminomethyl)indol-5-yl)[2-chloro-4-(E-((4-acetylpiperazin-1-yl)carbonyl)ethenyl)phenyl]sulfide;

(2-Isopropylphenyl)[2-nitro-4-(E-((2-carboethoxypiperidin-1-yl)carbonyl)ethenyl)phenyl]sulfide;

(2-Isopropylphenyl)[2-nitro-4-(E-((2-carboxypiperidin-1-yl)carbonyl)ethenyl)phenyl]sulfide;

(2-Isopropylphenyl)[2-nitro-4-(E-((4-carboethoxypiperidin-1-yl)carbonyl)ethenyl)phenyl]sulfide;

(2-Isopropylphenyl)[2-nitro-4-(E-((4-carboxypiperidin-1-yl)carbonyl)ethenyl)phenyl]sulfide;

(2-Isopropylphenyl)[2-nitro-4-(E-(((4-p-toluenesulfonyl-aminocarbonyl)piperidin-1-yl)carbonyl)ethenyl)phenyl]sulfide;

(2-Isopropylphenyl)[2-nitro-4-(E-((3-carboxy-4-hydroxypiperidin-1-yl)carbonyl)ethenyl)phenyl]sulfide;

(Benzodioxan-6-yl)[2-trifluoromethyl-4-(E-((3-carboethoxypiperidin-1-yl)carbonyl)ethenyl)phenyl]sulfide;

(Benzodioxan-6-yl)[2-trifluoromethyl-4-(E-((2-carboethoxypiperidin-1-yl)carbonyl)ethenyl)phenyl]sulfide;

(Benzodioxan-6-yl)[2-nitro-4-(E-((4-carboxypiperidin-1-yl)carbonyl)ethenyl)phenyl]sulfide;

(Benzodioxan-6-yl)[2-trifluoromethyl-4-(E-((3-carboxypyrrolidin-1-yl)carbonyl)ethenyl)phenyl]sulfide;

(Benzodioxan-6-yl)[2-trifluoromethyl-4-(E-((4-carboethoxypiperidin-1-yl)carbonyl)ethenyl)phenyl]sulfide;

(Benzodioxan-6-yl)[2-trifluoromethyl-4-(E-((2-carbomethoxy-4-tert-butoxycarbonylpiperazin-1-yl)carbonyl)ethenyl)phenyl]sulfide;

(Benzodioxan-6-yl)[2-trifluoromethyl-4-(E-((2-carbomethoxy-4-methoxycarbonylpiperazin-1-yl)carbonyl)ethenyl)phenyl]sulfide;

(Benzodioxan-6-yl)[2-trifluoromethyl-4-(E-((2-carbomethoxypiperazin-1-yl)carbonyl)ethenyl)phenyl]sulfide;

(2-Methyl-3-(carboethoxymethyl)indol-5-yl)[2-trifluoromethyl-4-(E-((morpholin-1-yl)carbonyl)ethenyl)phenyl)sulfide;

(1-(2-Methoxyethyl)indol-5-yl)[2-chloro-4-(E-((4-acetylpiperazin-1-yl)carbonyl)ethenyl)phenyl]sulfide;

(2-Isopropylphenyl)[2-nitro-4-(E-((3-acetoxymethyl-4-hydroxypiperidin-1-yl)carbonyl)ethenyl)phenyl]sulfide;

(2-Isopropylphenyl)[2-nitro-4-(E-((3-(dimethylamino-carbonyl)-4-hydroxypiperidin-1-yl)carbonyl)ethenyl)phenyl]sulfide;

(2-Isopropylphenyl)[2-nitro-4-(E-((3-cyanomorpholin-1-yl)carbonyl)ethenyl)phenyl]sulfide;

(2-Isopropylphenyl)[2-nitro-4-(E-((3-carboethoxy-morpholin-1-yl)carbonyl)ethenyl)phenyl]sulfide;

(2-Isopropylphenyl)[2-nitro-4-(E-((3-(tetrazol-5-yl)morpholin-1-yl)carbonyl)ethenyl)phenyl]sulfide;

(Benzodioxan-6-yl)[2-trifluoromethyl-4-(E-((4-carboxypiperidin-1-yl)carbonyl)ethenyl)phenyl]sulfide;

(Benzodioxan-6-yl)[2-trifluoromethyl-4-(E-((2-carboxypiperidin-1-yl)carbonyl)ethenyl)phenyl]sulfide;

(Benzodioxan-6-yl)[2-trifluoromethyl-4-(E-((4-carbomethoxypiperazin-1-yl)carbonyl)ethenyl)phenyl]sulfide;

(Benzodioxan-6-yl)[2-trifluoromethyl-4-(E-((3-aza-6,9-dioxaspiro[5.4]decan-1-yl)carbonyl)ethenyl)phenyl]sulfide;

(Benzodioxan-6-yl)[2-trifluoro-4-(E-((4-(2-oxo-2,3-dihydro-1H-benzimidazole-1-yl)piperidin-1-yl)carbonyl)ethenyl)phenyl]sulfide;

(Benzodioxan-6-yl)[2-trifluoromethyl-4-(E-((4-(methylaminocarbonyl)piperidin-1-yl)carbonyl)ethenyl)phenyl]sulfide;

(Benzodioxan-6-yl)[2-trifluoromethyl-4-(E-((3-carbomethoxy-4-methoxycarbonylpiperazin-1-yl)carbonyl)ethenyl)phenyl]sulfide;
(2-Isopropylphenyl)[2-nitro-4-(E-((3-carboxymorpholin-1-yl)carbonyl)ethenyl)phenyl]sulfide;
(Benzodioxan-6-yl)[2-trifluoromethyl-4-(E-((2-carboxy-4-methoxycarbonylpiperazin-1-yl)carbonyl)ethenyl)phenyl]sulfide;
(Benzodioxan-6-yl)[2-trifluoromethyl-4-(E-((morpholin-1-yl)carbonyl)ethenyl)phenyl]sulfide;
(Benzodioxan-6-yl)[2-trifluoromethyl-4-(E-((4-(pyrrolidin-1-yl)piperidin-1-yl)carbonyl)ethenyl)phenyl]sulfide;
(2-Isopropylphenyl)[2-nitro-4-(E-((3-aza-6,9-dioxaspiro[5.4]decan-1-yl)carbonyl)ethenyl)phenyl]sulfide;
(2-Isopropylphenyl)[2-nitro-4-(E-((2-(dimethylaminomethyl)piperidin-1-yl)carbonyl)ethenyl)phenyl]sulfide;
(2-Isopropylphenyl)[2-nitro-4-(E-((piperidin-1-ylamino)carbonyl)ethenyl)phenyl]sulfide;
(Benzodioxan-6-yl)[2-trifluoromethyl-4-(E-((3-carboxy-4-methoxycarbonylpiperazin-1-yl)carbonyl)ethenyl)phenyl]sulfide;
(2-(Dimethylaminocarbonyl)-benzodioxan-6-yl)[2-chloro-4-(E-((4-acetylpiperazin-1-yl)carbonyl)ethenyl)phenyl]sulfide;
(2-Isopropylphenyl)[2-nitro-4-(E-((3-(2-(methoxymethyl)tetrazol-5-yl)piperidin-1-yl)carbonyl)ethenyl)phenyl]sulfide;
(2-Isopropylphenyl)[2-nitro-4-(E-((3-(1-(methoxymethyl)tetrazol-5-yl)piperidin-1-yl)carbonyl)ethenyl)phenyl]sulfide;
(1-Methylindol-5-yl)[2-chloro-4-(E-((3-(2-oxopyrrolidin-1-yl)propylamino)carbonyl)ethenyl)phenyl]sulfide;
(2-Isopropylphenyl)[2-nitro-4-(E-((3-(tetrazol-5-yl)piperidin-1-yl)carbonyl)ethenyl)phenyl]sulfide;
(1-Methylindol-5-yl)[2-chloro-4-(E-((3-carboethoxypiperidin-1-yl)carbonyl)ethenyl)phenyl]sulfide;
(1-Methylindol-5-yl)[2-chloro-4-(E-((3-carboxypiperidin-1-yl)carbonyl)ethenyl)phenyl]sulfide;
(1-Methylindol-5-yl)[2-chloro-4-(E-((4-carboethoxypiperidin-1-yl)carbonyl)ethenyl)phenyl]sulfide;
(1-Methylindol-5-yl)[2-chloro-4-(E-((4-carboxypiperidin-1-yl)carbonyl)ethenyl)phenyl]sulfide;
(2-Isopropylphenyl)[2-nitro-4-(E-((2-(1-methylpyrrolidin-2-yl)ethylamino)carbonyl)ethenyl)phenyl]sulfide;
(2-Isopropylphenyl)[2-nitro-4-(E-((4-(pyrrolidin-1-yl)piperidin-1-yl)carbonyl)ethenyl)phenyl]sulfide;
(2-Isopropylphenyl)[2-nitro-4-(E-((4-sulfopiperidin-1-yl)carbonyl)ethenyl)phenyl]sulfide;
(2-Isopropylphenyl)[2-nitro-4-(E-((3-hydroxypiperidin-1-yl)carbonyl)ethenyl)phenyl]sulfide;
(Benzodioxan-6-yl)[2-trifluoromethyl-4-(E-((3-((ethanesulfonylamino)carbonyl)piperidin-1-yl)carbonylethenyl)phenyl]sulfide;
(Benzodioxan-6-yl)[2-trifluoromethyl-4-(E-((3-((p-toluenesulfonylamino)carbonyl)piperidin-1-yl)carbonyl)ethenyl)phenyl]sulfide;
(Benzodioxan-6-yl)[2-trifluoromethyl-4-(E-((4-((ethanesulfonylamino)carbonyl)piperidin-1-yl)carbonyl)ethenyl)phenyl]sulfide;
(Benzodioxan-6-yl)[2-trifluoromethyl-4-(E-((2-(tetrazol-5yl)morpholin-1-yl)carbonyl)ethenyl)phenyl]sulfide;
(2-Isopropylphenyl)[2-nitro-4-(E-((2-butyl-5-(tetrazol-5yl)morpholin-1-yl)carbonyl)ethenyl)phenyl]sulfide;
(2-(and 3-)(Hydroxymethyl)-benzodioxan-6-yl)[2-nitro-4-(E-((4-acetylpiperazin-1-yl)carbonyl)ethenyl)phenyl]sulfide;
(2-(and 3-)(Hydroxymethyl)-benzodioxan-6-yl)[2-nitro-4-(E-((3-(2-oxopyrrolidin-1-yl)prop-1-ylamino)carbonyl)ethenyl)phenyl]sulfide;
(2-(and 3-)(Hydroxymethyl)-benzodioxan-6-yl)[2-trifluoromethyl-4-(E-((3(2-oxopyrrolidin-1-yl)prop-1-ylamino)carbonyl)ethenyl)phenyl]sulfide;
(3-Hydroxymethyl)-benzodioxan-6-yl)[2-nitro-4-(E-((3-(2-oxopyrrolidin-1-yl)prop-1-ylamino)carbonyl)ethenyl)phenyl]sulfide;
(Benzodioxan-6-yl)[2-chloro-4-(E-((3-carboxypiperidin-1-ylcarbonyl)ethenyl)phenyl]sulfide;
(2-(and 3-)(Aminomethyl)-benzodioxan-6-yl)[2-trifluoromethyl-4(E-((3-(2-oxopyrrolidin-1-yl)prop-1-ylamino)carbonyl)ethenyl)phenyl]sulfide;
(2-Isopropylphenyl)[2-nitro-4-(E-((3-(methylaminocarbonyl)morpholin-1-yl)carbonyl)ethenyl)phenyl]sulfide;
(2-Isopropylphenyl)[2-nitro-4-(E-((3-(hydroxymethyl)morpholin-1-yl)carbonyl)ethenyl)phenyl]sulfide;
(2-Isopropylphenyl)[2-nitro-4-(E-((3-(acetoxymethyl)morpholin-1-yl)carbonyl)ethenyl)phenyl]sulfide;
(2-Isopropylphenyl)[2-nitro-4-(E-((3-(aminomethyl)morpholin-1-yl)carbonyl)ethenyl)phenyl]sulfide;
(2-Isopropylphenyl)[2-nitro-4-(E-((3-(acetamidomethyl)morpholin-1-yl)carbonyl)ethenyl)phenyl]sulfide;
(Benzodioxan-6-yl)[2-chloro-4-(E-((3-(2-oxopyrrolidin-1-yl)prop-1-ylamino)carbonyl)ethenyl)phenyl]sulfide;
(Benzodioxan-6-yl)[2-chloro-4-(E-((3-carboethoxy-piperidin-1-yl)carbonyl)ethenyl)phenyl]sulfide;
(Benzodioxan-6-yl)[2-chloro-4-(E-((2-carboethoxy-piperidin-1-yl)carbonyl)ethenyl)phenyl]sulfide;
(2-Methoxyphenyl)-[2,3-dichloro-4-(E-[(morpholin-1-yl)carbonyl]ethenyl)phenyl]sulfide;
(2-Methoxyphenyl-[2,3-dimethyl-4-(E-[(morpholin-1-yl)carbonylethenyl)phenyl]sulfide;
(2-Isopropylphenyl)[2-nitro-4-(E-((indol-5-ylamino)carbonyl)ethenyl)phenyl]sulfide;
(Benzodioxan-6-yl)[2-chloro-4-(E-((3-carboxypiperidin-1-yl)carbonyl)ethenyl)phenyl]sulfide;
(Benzodioxan-6-yl)[2-chloro-4-(E-((3-(tetrazol-5-yl)piperidin-1-yl)carbonyl)ethenyl)phenyl]sulfide;
(Benzodioxan-6-yl)[2-chloro-4-(E-((4-(tert-butoxycarbonyl)piperazin-1-yl)carbonyl)ethenyl)phenyl]sulfide;
(Benzodioxan-6-yl)[2-chloro-4-(E-((2-carboxypiperidin-1-yl)carbonyl)ethenyl)phenyl]sulfide;
(Benzodioxan-6-yl)[2-chloro-4-(E-((3-(tetrazol-5-yl)morpholin-1-yl)carbonyl)ethenyl)phenyl]sulfide;
(Benzodioxan-6-yl)[2-chloro-4-(E-((4-(methylaminocarbonyl)piperazin-1-yl)carbonyl)ethenyl)phenyl]sulfide;
(2-Methoxyphenyl)-[2,3-dichloro-4-(E-[(4-carboxypiperidin-1-yl)carbonyl]ethenyl)phenyl]sulfide;
(Benzodioxan-6-yl)[2-chloro-4-(E-((4-(tetrazol-5-yl)piperidin-1-yl)carbonyl)ethenyl)phenyl]sulfide;
(2-Methoxyphenyl)-[3-chloro-4-(E-[(morpholin-1-yl)carbonyl]ethenyl)phenyl]sulfide;
(2-Isopropylphenyl)[2-nitro-4-(E-((4-oxopiperidin-1-yl)carbonyl)ethenyl)phenyl]sulfide;
(Benzodioxan-6-yl)[2-trifluoromethyl-4-(E-((3-R-carboethoxypiperidin-1-yl)carbonyl)ethenyl)phenyl]sulfide;
(Benzodioxan-6-yl)[2-trifluoromethyl-4-(E-((3-R-carboxypiperidin-1-yl)carbonyl)ethenyl)phenyl]sulfide;
(Benzodioxan-6-yl)[2,3-dichloro-4-(E-((3-(2-oxopyrrolidin-1-yl)prop-1-ylamino)carbonyl)ethenyl)phenyl]sulfide;

(Benzodioxan-6-yl)[2,3-dichloro-4-(E-((4-acetylpiperazin-1-yl)carbonyl)ethenyl)phenyl]sulfide;
(Benzodioxan-6-yl)[2,3-dichloro-4-(E-((3-carboethoxypiperidin-1-yl)carbonyl)ethenyl)phenyl]sulfide;
(Benzodioxan-6-yl)[2,3-dichloro-4-(E-((4-carboethoxypiperidin-1-yl)carbonyl)ethenyl)phenyl]sulfide;
(Benzodioxan-6-yl)[2,3-dichloro-4-(E-((3-carboxypiperidin-1-yl)carbonyl)ethenyl)phenyl]sulfide;
(Benzodioxan-6-yl)[2,3-dichloro-4-(E-((4-carboxypiperidin-1-yl)carbonyl)ethenyl)phenyl]sulfide;
(2-Isopropylphenyl)[2,3-dichloro-4-(E-((3-(2-oxopyrrolidin-1-yl)propylamino)carbonyl)ethenyl)phenyl]sulfide;
(2-Isopropylphenyl)[2,3-dichloro-4-(E-((4-acetylpiperazin-1-yl)carbonyl)ethenyl)phenyl]sulfide;
(2-Isopropylphenyl)[2,3-dichloro-4-(E-((3-carboethoxypiperidin-1-yl)carbonyl)ethenyl)phenyl]sulfide;
(2-Isopropylphenyl)[2,3-dichloro-4-(E-((4-carboethoxypiperidin-1-yl)carbonyl)ethenyl)phenyl]sulfide;
(2-Isopropylphenyl)[2,3-dichloro-4-(E-((3-carboxypiperidin-1-yl)carbonyl)ethenyl)phenyl]sulfide;
(2-Isopropylphenyl)[2,3-dichloro-4-(E-((4-carboxypiperidin-1-yl)carbonyl)ethenyl)phenyl]sulfide;
(1-Methylindol-5-yl)[2,3-dichloro-4-(E-((3-carboethoxypiperidin-1-yl)carbonyl)ethenyl)phenyl]sulfide;
(1-Methylindol-5-yl)[2,3-dichloro-4-(E-((3-carboxypiperidin-1-yl)carbonyl)ethenyl)phenyl]sulfide;
(1-Methylindol-5-yl)[2,3-dichloro-4-(E-((4-carboethoxypiperidin-1-yl)carbonyl)ethenyl)phenyl]sulfide;
(1-Methylindol-5-yl)[2,3-dichloro-4-(E-((4-carboxypiperidin-1-yl)carbonyl)ethenyl)phenyl]sulfide;
(2-Ethoxyphenyl)-[2,3-dichloro-4-(E-[(4-carboxypiperidin-1-yl)carbonyl]ethenyl)phenyl]sulfide;
(2-Ethoxyphenyl)-[2,3-dichloro-4-(E-[(morpholin-1-yl)carbonyl]ethenyl)phenyl]sulfide;
(2-Ethoxyphenyl)-[2,3-dichloro-4-(E-[(3-carboxypiperidin-1-yl)carbonyl]ethenyl)phenyl]sulfide;
(2-Isopropylphenyl)[2-nitro-4-(E-((3-carboethoxypyrrolidin-1-yl)carbonyl)ethenyl)phenyl]sulfide;
(2-Isopropylphenyl)[2-nitro-4-(E-((3-carboxypyrrolidin-1-yl)carbonyl)ethenyl)phenyl]sulfide;
(2-Isopropylphenyl)[2,3-difluoro-4-(E-((3-carboethoxypiperidin-1-yl)carbonyl)ethenyl)phenyl]sulfide;
(2-Isopropylphenyl)[2,3-difluoro-4-(E-((3-carboxypiperidin-1-yl)carbonyl)ethenyl)phenyl]sulfide;
(2-Isopropylphenyl)[2,3-difluoro-4-(E-((4-carboxypiperidin-1-yl)carbonyl)ethenyl)phenyl]sulfide;
(Benzodioxan-6-yl)[2-trifluoromethyl-4-(E-((3-ethoxycarbonylpyrrolidin-1-yl)carbonyl)ethenyl)phenyl]sulfide;
(Benzodioxan-6-yl)[2-trifluoromethyl-4-(E-((3-carboxypyrrolidin-1-yl)carbonyl)ethenyl)phenyl]sulfide;
(2-Methoxyphenyl)[2-chloro-3-trifluoromethyl-4-(E-((4-carboethoxypiperidin-1-yl)carbonyl)ethenyl)phenyl]sulfide;
(2-Methoxyphenyl)[2-chloro-3-trifluoromethyl-4-(E-((4-carboxypiperidin-1-yl)carbonyl)ethenyl)phenyl]sulfide;
(2-Methoxyphenyl)[2-chloro-3-trifluoromethyl-4-(E-((morpholin-1-yl)carbonyl)ethenyl)phenyl]sulfide;
(2-Methoxyphenyl)[2,3-dichloro-4-(E-((4,2,4-dioxo-1,3,8-triazaspiro[4.5])-piperidin-1-yl)carbonyl)ethenyl)phenyl]sulfide;
(2-Methoxyphenyl)[2,3-dichloro-4-(E-((4-ethylpiperazin-1-yl)carbonyl)ethenyl)phenyl]sulfide;
(2-Isopropylphenyl)[2,3-dichloro-4-(E-((4-(2-(2-hydroxyethoxy)ethyl)piperazin-1-yl)carbonyl)ethenyl)phenyl]sulfide;
(Benzodioxan-6-yl)[2,3-bis(trifluoromethyl)-4-(E-((4-carboxypiperidin-1-yl)carbonyl)ethenyl)phenyl]sulfide;
(2-Methoxyphenyl)[2,3-dichloro-4-(E-((4-(carboxy-methylamino)carbonyl-piperidin-1-yl)carbonyl)ethenyl)phenyl]sulfide;
(2-Methoxyphenyl)[2,3-bis(trifluoromethyl)-4-(E-((4-carboxymethylpiperazin-1-yl)carbonyl)ethenyl)phenyl]sulfide;
(2-Methoxyphenyl)[2,3-bis(trifluoromethyl)-4-(E-((4-N-(2-hydroxyethyl)piperazin-1-yl)carbonyl)ethenyl)phenyl]sulfide;
(1-Methylindol-5-yl)[2,3-dichloro-4-(E-((4-(carbo-2,3-dihydroxypropylamino)piperidin-1-yl)carbonyl)ethenyl)phenyl]sulfide;
(2-Methoxyphenyl)[2,3-dichloro-4-(E-(4-(2,3-dihydroxypropionyl)piperazin-1-yl)carbonyl)ethenyl)phenyl]sulfide;
(2-Methoxyphenyl)[2,3-dichloro-4-(E-(4-(2,3-dihydroxy-3-carboxypropionyl)piperazin-1-yl)carbonyl)ethenyl)phenyl]sulfide;
(1-Methylindol-5-yl)[2,3-dichloro-4-(E-((4-(carboxymethylamino)carbonyl-piperidin-1-yl)carbonyl)ethenyl)phenyl]sulfide;
(1-Methylindol-5-yl)[2,3-dichloro-4-(E-((4-sulfopiperidin-1-yl)carbonyl)ethenyl)phenyl]sulfide;
(1-Methylindol-5-yl)[2,3-dichloro-4-(E-(4-methylhomopiperazin-1-ylcarbonyl)ethenyl)phenyl]sulfide;
(1-Methylindol-5-yl)[2,3-dichloro-4-(E-(4-tetrahydrofuroylpiperazin-1-yl)carbonyl)ethenyl)phenyl]sulfide;
(Benzodioxan-6-yl)[2-(benzodioxan-6-sulfanyl)-4-(E-((4-morpholino)carbonyl)ethenyl)phenyl]sulfide;
(2-Methoxyphenyl)[2,3-dichloro-4-(E-((4-amino-4-carboxypiperidin-1-yl)carbonyl)ethenyl)phenyl]sulfide;
(2-Methoxyphenyl)[2,3-dichloro-4-(4-furoylpiperazin-1-yl)carbonyl)ethenyl)phenyl]sulfide;
(1-Methylindol-5-yl)[2,3-dichloro-4-(E-(4-(carbo-3-sulfopropylamino)piperadin-1-yl)carbonyl)ethenyl)phenyl]sulfide;
(2-Methoxyphenyl)[2,3-dichloro-4-(E-(4-acetylamino-4-carboxypiperidin-1-ylcarbonyl)ethenyl)phenyl]sulfide;
(2-Methoxyphenyl)[2,3-bis(trifluoromethyl)-4-(E-((4-carboxypiperidin-1-yl)carbonyl)ethenyl)phenyl]sulfide;
(2-Methoxyphenyl)[2-trifluoromethyl-4-(E-((4-carboxypiperidin-1-yl)carbonyl)ethenyl)phenyl]sulfide;
(1-Methylindol-5-yl)[2,3-dichloro-4-(E-(((1S,4S)-5-tert-butyloxycarbonyl-2,5-diazabicyclo(2.2.1)heptan-2-yl)carbonyl)ethenyl)phenyl]sulfide;
(1-Methylindol-5-yl)[2,3-dichloro-4-(E/Z-((1S,4S)-2,5-diazabicyclo(2.2.1)heptan-2-ylcarbonyl)ethenyl)phenyl]sulfide;
(1-Methylindol-5-yl)[2,3-dichloro-4-(E-(4-hydroxy-3-carboxypiperidin-1-ylcarbonyl)ethenyl)phenyl]sulfide;
(1-Methylindol-5-yl)[2,3-dichloro-4-(E-(S-oxothiomorpholin-1-ylcarbonyl)ethenyl)phenyl]sulfide;
(2-Methoxyphenyl)[2,3-dichloro-4-(E-((4-sulfophenyl-amino)carbonyl)ethenyl)phenyl]sulfide;
(2-Methoxyphenyl)[2,3-dichloro-4-(E-((4-carboxyphenyl-amino)carbonyl)ethenyl)phenyl]sulfide;

[3-(4-Morpholino)phenyl][2,3-dichloro-4-(E-[(4-carboxypiperidin-1-yl)carbonyl]ethenyl)phenyl]sulfide;

(2-Methoxyphenyl)[2,3-bis(trifluoromethyl)-4-(E-((4-phenylcarboxypiperidin-1-yl)carbonyl)ethenyl)phenyl]sulfide;

(2-Methoxyphenyl)[2,3-dichloro-4-(E-(((4-hydroxyl-aminocarbonyl)piperidin-1-yl)carbonyl)ethenyl)phenyl]sulfide;

(2-Methoxyphenyl)[2,3-dichloro-4-(E-((N-carboxymethyl-N-phenylamino)carbonyl)ethenyl)phenyl]sulfide;

(2-Methoxyphenyl)[2,3-dichloro-4-(E-(4-((1-(2-phenyl-1-carboxyethyl)amino)carbonyl)piperidin-1-yl)carbonyl)ethenyl)phenyl]sulfide;

(2-Methoxyphenyl)[2,3-dichloro-4-(E-(4-((1-(2-hydroxy-1-carboxyethyl)amino)carbonyl)piperidin-1-yl)carbonyl)ethenyl)phenyl]sulfide;

(3-(1-(3-Carboxypiperidinyl)phenyl)[2,3-dichloro-4-(E-((1,2,5,6-tetrahydropyridin-1-yl)carbonyl)ethenyl)phenyl]sulfide;

(3-(4-Pyrrolidin-1-yl)piperidin-1-yl)phenyl)[2,3-dichloro-4-(E-(((3-(2-oxopyrrolidin-1-yl)propylamino)carbonyl)ethenyl)phenyl]sulfide;

[3-(4-(Spiro-2,2-dioxolanyl)piperidin-1-yl)phenyl][2,3-dichloro-4-(E-((4-morpholinyl)carbonyl)ethenyl)phenyl]sulfide;

[3-(3-Carboxylpiperidin-1-yl)phenyl][2,3-dichloro-4-(E-[(4-carboxypiperidin-1-yl)carbonyl]ethenyl)phenyl]sulfide;

(2-(2-Carboxy)ethenyl)phenyl)[2,3-dichloro-4-(E-((4-morpholinyl)carbonyl)ethenyl)phenyl]sulfide;

[3-(4-Carboxylpiperidin-1-yl)phenyl][2,3-dichloro-4-(E-[(1,2,3,6-tetrahydropyridin-1-yl)carbonyl]ethenyl)phenyl]sulfide;

[3-(4-Carboxylpiperidinyl)phenyl][2,3-dichloro-4-(E-[(4-morpholinyl)carbonyl]ethenyl)phenyl]sulfide;

[2-(4-Acetylpiperazin-1-yl)phenyl][2,3-dichloro-4-(E-[(4-carboxypiperidin-1-yl)carbonyl]ethenyl)phenyl]sulfide;

3-(3-Carboxypiperidin-1-yl)phenyl)[2,3-dichloro-4-(E-[(4-morpholinyl)carbonyl]ethenyl)phenyl]sulfide;

(2-Methoxyphenyl)[2,3-bis(trifluoromethyl)-4-(E-((3-carboxypiperidin-1-yl)carbonyl)ethenyl)phenyl]sulfide;

(2-Methoxyphenyl)[2,3-bis(trifluoromethyl)-4-(E-((2-carboxypyrrolidin-1-yl)carbonyl)ethenyl)phenyl]sulfide;

[3-(4-Carboxypiperidin-1-yl)phenyl][2,3-dichloro-4-(E-((4-((trifluoromethylsulfonyl)piperazin-1-yl)carbonyl)ethenyl)phenyl]sulfide;

(2-Methoxyphenyl)[2,3-dichloro-4-(E-(piperidin-1-ylcarbonyl)ethenyl)phenyl]sulfide;

(2-Hydroxyphenyl)[2,3-dichloro-4-(E-((4-morpholino)carbonyl)ethenyl)phenyl]sulfide;

(2-Methoxyphenyl)[2,3-dichloro-4-(E-((((4-carboxyphenyl)methyl)amino)carbonyl)ethenyl)phenyl]sulfide;

(2-Methoxyphenyl)[2,3-dichloro-4-(E-(((4-pyrrolidin-1-yl)piperidin-1-yl)carbonyl)ethenyl)phenyl]sulfide;

(2-Hydroxyphenyl)[2,3-dichloro-4-(E-((4-carboxy-piperidin-1-yl)carbonyl)ethenyl)phenyl]sulfide;

[3-(4-Carboxypiperidin-1-yl)phenyl][2,3-dichloro-4-(E-((4-((methylsulfonyl)piperazin-1-yl)carbonyl)ethenyl)phenyl]sulfide;

(2-Aminophenyl)[2,3-dichloro-4-(E-((4-morpholinyl)carbonyl)ethenyl)phenyl]sulfide;

(3-(4-carboxypiperidin-1-yl)phenyl)[2,3-dichloro-4-(E-((S-oxothiomorpholin-1-yl)carbonyl)ethenyl)phenyl]sulfide;

[3-(4-Carboxypiperidin-1-yl)phenyl][2,3-dichloro-4-(E-((4-hydroxypiperidin-1-yl)carbonyl)ethenyl)phenyl]sulfide;

(2-Glycoxyphenyl)[2,3-dichloro-4-(E-((4-morpholino)carbonyl)ethenyl)phenyl]sulfide;

(2-(4-Butyroxy)phenyl)[2,3-dichloro-4-(E-((4-morpholino)carbonyl)ethenyl)phenyl]sulfide;

[3-(4-Carboxypiperidin-1-yl)phenyl][2,3-dichloro-4-(E-((4-hydroxyethylpiperazin-1-yl)carbonyl)ethenyl)phenyl]sulfide;

[3-(4-Carboxypiperidin-1-yl)phenyl][2,3-dichloro-4-(E-((4-furoylpiperazin-1-yl)carbonyl)ethenyl)phenyl]sulfide;

[3-(4-Carboxypiperidin-1-yl)phenyl][2,3-dichloro-4-(E-((pyrrolidin-1-yl)carbonyl)ethenyl)phenyl]sulfide;

[3-(4-Carboxypiperidin-1-yl)phenyl][2,3-dichloro-4-(E-((diethylaminocarbonyl)ethenyl)phenyl]sulfide;

[3-(4-Carboxypiperidin-1-yl)phenyl][2,3-dichloro-4-(E-((4-ethylpiperazin-1-yl)carbonyl)ethenyl)phenyl]sulfide;

[3-(4-Carboxypiperidin-1-yl)phenyl][2,3-dichloro-4-(E-((4-(aminocarbonyl)piperidin-1-yl)carbonyl)ethenyl)phenyl]sulfide;

[3-(4-Carboxypiperidin-1-yl)phenyl][2,3-dichloro-4-(E-((4-(2-(ethoxyethyl)piperidin-1-yl)carbonyl)ethenyl)phenyl]sulfide;

[3-((4-Carboxymethyl)piperazin-1-yl)phenyl][(2,3-dichloro-4-(E-(4-morpholinyl)carbonyl)ethenyl)phenyl]sulfide;

[3-(4-Carboxypiperidin-1-yl)phenyl][2,3-bis(trifluoromethyl)-4-(E-((4-morpholino)carbonyl)ethenyl)phenyl]sulfide;

(3-Hydroxyphenyl)[2,3-dichloro-4-(E-((4-morpholino)carbonyl)ethenyl)phenyl]sulfide;

[3-(4-Butyroxy)phenyl][2,3-dichloro-4-(E-((4-morpholino)carbonyl)ethenyl)phenyl]sulfide;

(2-Hydroxyphenyl)[2,3-bis(trifluoromethyl)-4-(E-((4-morpholino)carbonyl)ethenyl)phenyl]sulfide;

(3-Hydroxyphenyl)[2,3-bis(trifluoromethyl)-4-(E-((4-morpholino)carbonyl)ethenyl)phenyl]sulfide;

[3-(4-Carboxypiperidin-1-yl)phenyl][2,3-bis(trifluoromethyl-4-(E-((4-hydroxypiperidin-1-yl)carbonyl)ethenyl)phenyl]sulfide;

[3-(4-Carboxypiperidin-1-yl)phenyl][2,3-bis(trifluoromethyl-4-(E-((1,2,5,6-tetrahydropyridin-1-yl)carbonyl)ethenyl)phenyl]sulfide;

[2-((4-Carboxy)butyloxy)phenyl][2,3-dichloro-4-(E-((4-morpholino)carbonyl)ethenyl)phenyl]sulfide;

(2-Glycoxyphenyl)[2,3-bis(trifluoromethyl)-4-(E-((4-morpholino)carbonyl)ethenyl)phenyl]sulfide;

(2-(4-Butyroxy)phenyl)[2,3-bis(trifluoromethyl)-4-(E-((4-morpholino)carbonyl)ethenyl)phenyl]sulfide;

[3-(4-Carboxypiperidin-1-yl)phenyl][2,3-bis(trifluoromethyl)-4-(E-((bis-(2-ethoxyethyl)amino)carbonyl)ethenyl)phenyl]sulfide;

[3-(4-Carboxypiperidin-1-yl)phenyl][2,3-bis-(trifluoromethyl)-4-(E-((bis-(2-hydroxypropyl)amino)carbonyl)ethenyl)phenyl]sulfide;

[3-(4-Carboxypiperidin-1-yl)phenyl][2,3-bis-(trifluoromethyl)-4-(E-((piperazin-1-yl)carbonyl)ethenyl)phenyl]sulfide;

(3-(4-Butyroxy)phenyl)[2,3-bis(trifluoromethyl)-4-(E-((4-morpholino)carbonyl)ethenyl)phenyl]sulfide;

[2-(3-Carboxypiperidin-1-yl)phenyl][2,3-dichloro-4-(E-[(3-(2-oxopyrrolidin-1-yl)propylaminocarbonyl)ethenyl)phenyl]sulfide;

[2-(3-Carboxypiperidin-1-yl)phenyl][2,3-bis(trifluoromethyl)-4-(E-[(3-(2-oxopyrrolidin-1-yl)propylaminocarbonyl)ethenyl)phenyl]sulfide;

[2-(3-Carboxypiperidin-1-yl)phenyl][2,3-dichloro-4-(E-((4-(2-hydroxyethyl)piperazin-1-yl)carbonyl)ethenyl)phenyl]sulfide;

[2-(3-Carboxypiperidin-1-yl)phenyl][2,3-bis(trifluoromethyl)-4-(E-(((1,2,5,6-tetrahydropyridin-1-yl)carbonyl)ethenyl)phenyl]sulfide;

[2-(3-Carboxypiperidin-1-yl)phenyl][2,3-bis(trifluoromethyl)-4-(E-((4-(2-hydroxyethyl)piperazin-1-yl)carbonyl)ethenyl)phenyl]sulfide;
[2-(3-Carboxypiperidin-1-yl)phenyl][2,3-bis(trifluoromethyl)-4-(E-((4-(2-(hydroxyethoxy)ethyl)piperazin-1-yl)carbonyl)ethenyl)phenyl]sulfide; and
(3-(3-Propioxy)phenyl)[2,3-dichloro-4-(E-((4-morpholino)carbonyl)ethenyl)phenyl]sulfide.

4. A compound according to claim 1 selected from the group consisting of:

(2-Formylphenyl)[2-nitro-4-(E-((4-acetylpiperazin-1-yl)carbonyl)ethenyl)phenyl]sulfide;
(2-Ethoxyphenyl)[2-chloro-4-(E-[(morpholin-1-yl)carbonyl]ethenyl)phenyl]sulfide;
(2-Isopropylphenyl)[2-nitro-4-(E-((3-dimethylaminocarbonyl-4-acetylpiperazin-1-yl)carbonyl)ethenyl)phenyl]sulfide;
(2-Isopropylphenyl)[2-nitro-4-(E-((4-methoxycarbonyl-piperazin-1-yl)carbonyl)ethenyl)phenyl]sulfide;
(2-Ethoxyphenyl)[2-trifluoromethyl-4-(E-((2-carboxy-4-(methoxycarbonyl)piperazin-1-yl)carbonyl)ethenyl)phenyl]sulfide;
(2-Ethyl-4-bromophenyl)[2-nitro-4-(E-((4-acetylpiperazin-1-yl)carbonyl)ethenyl)phenyl]sulfide;
(3-Morpholinophenyl)[2-nitro-4-(E-((4-acetylpiperazin-1-yl)carbonyl)ethenyl)phenyl]sulfide;
(2-Isopropylphenyl)[2-nitro-4-(E-((3-carboethoxypiperidin-1-yl)carbonyl)ethenyl)phenyl]sulfide;
(2-Isopropylphenyl)[2-nitro-4-(E-((3-(2-oxopyrrolidin-1-yl)prop-1-ylamino)carbonyl)ethenyl)phenyl]sulfide;
(2-(Hydroxymethyl)-benzodioxan-6-yl)[2-chloro-4-(E-((4-acetylpiperazin-1-yl)carbonyl)ethenyl)phenyl]sulfide;
(Benzodioxan-6-yl)[2-trifluoromethyl-4-(E-((3-carboxypyrrolidin-1-yl)carbonyl)ethenyl)phenyl]sulfide;
(Benzodioxan-6-yl)[2-trifluoromethyl-4-(E-((4-carboethoxypiperidin-1-yl)carbonyl)ethenyl)phenyl]sulfide;
(Benzodioxan-6-yl)[2-trifluoromethyl-4-(E-((2-carbomethoxy-4-methoxycarbonylpiperazin-1-yl)carbonyl)ethenyl)phenyl]sulfide;
(Benzodioxan-6-yl)[2-trifluoromethyl-4-(E-((2-carbomethoxypiperazin-1-yl)carbonyl)ethenyl)phenyl]sulfide;
(Benzodioxan-6-yl)[2-chloro-4-(E-((4-(methylaminocarbonyl)piperazin-1-yl)carbonyl)ethenyl)phenyl]sulfide;
(2-Methoxyphenyl)-[2,3-dichloro-4-(E-[(4-carboxypiperidin-1-yl)carbonyl]ethenyl)phenyl]sulfide;
(Benzodioxan-6-yl)[2-trifluoromethyl-4-(E-((3-R-carboethoxypiperidin-1-yl)carbonyl)ethenyl)phenyl]sulfide;
(Benzodioxan-6-yl)[2,3-dichloro-4-(E-((3-(2-oxopyrrolidin-1-yl)prop-1-ylamino)carbonyl)ethenyl)phenyl]sulfide;
(Benzodioxan-6-yl)[2,3-dichloro-4-(E-((4-acetylpiperazin-1-yl)carbonyl)ethenyl)phenyl]sulfide;
(Benzodioxan-6-yl)[2,3-dichloro-4-(E-((3-carboethoxypiperidin-1-yl)carbonyl)ethenyl)phenyl]sulfide;
(Benzodioxan-6-yl)[2,3-dichloro-4-(E-((4-carboethoxypiperidin-1-yl)carbonyl)ethenyl)phenyl]sulfide;
(Benzodioxan-6-yl)[2,3-dichloro-4-(E-((3-carboxypiperidin-1-yl)carbonyl)ethenyl)phenyl]sulfide;
(Benzodioxan-6-yl)[2,3-dichloro-4-(E-((4-carboxypiperidin-1-yl)carbonyl)ethenyl)phenyl]sulfide;
(2-Isopropylphenyl)[2,3-dichloro-4-(E-((4-acetylpiperazin-1-yl)carbonyl)ethenyl)phenyl]sulfide;
(2-Isopropylphenyl)[2,3-dichloro-4-(E-((3-carboethoxypiperidin-1-yl)carbonyl)ethenyl)phenyl]sulfide;
(2-Isopropylphenyl)[2,3-dichloro-4-(E-((3-carboxypiperidin-1-yl)carbonyl)ethenyl)phenyl]sulfide;
(2-Isopropylphenyl)[2,3-dichloro-4-(E-((4-carboxypiperidin-1-yl)carbonyl)ethenyl)phenyl]sulfide;
(2-Methoxyphenyl)[2,3-dichloro-4-(E-((4-(carboxymethylamino)carbonyl-piperidin-1-yl)carbonyl)ethenyl)phenyl]sulfide;
(2-Methoxyphenyl)[2,3-bis(trifluoromethyl)-4-(E-((4-carboxymethylpiperazin-1-yl)carbonyl)ethenyl)phenyl]sulfide; and
(2-Methoxyphenyl)[2,3-bis(trifluoromethyl)-4-(E-((4-N-(2-hydroxyethyl)piperazin-1-yl)carbonyl)ethenyl)phenyl]sulfide.

5. A compound according to claim 1 where Ar is benzodioxan or substituted benzodioxan.

6. A compound according to claim 1 where $R_{10}$ and $R_{11}$ are each independently selected from hydrogen, alkyl, cycloalkyl, alkoxycarbonylalkyl, hydroxyalkyl, and heterocyclylalkyl.

7. A compound according to claim 1 where $R_{10}$ and $R_{11}$ are taken together with N to form an unsubstituted heterocyclyl or substituted heterocyclyl group.

* * * * *